(12) United States Patent
Bakthavatchalam et al.

(10) Patent No.: US 7,304,059 B2
(45) Date of Patent: Dec. 4, 2007

(54) SUBSTITUTED QUINAZOLIN-4-YLAMINE ANALOGUES

(75) Inventors: Rajagopal Bakthavatchalam, Madison, CT (US); Charles A. Blum, Westbrook, CT (US); Harry Brielmann, Guilford, CT (US); Timothy M. Caldwell, Guilford, CT (US); Stéphane De Lombaert, Madison, CT (US); Kevin J. Hodgetts, Killingworth, CT (US); Xiaozhang Zheng, Branford, CT (US); Taeyoung Yoon, Newton, MA (US)

(73) Assignee: Neurogen Corporation, Branford, CT (US)

( * ) Notice: Subject to any disclaimer, the term of this patent is extended or adjusted under 35 U.S.C. 154(b) by 0 days.

(21) Appl. No.: 11/345,926

(22) Filed: Feb. 1, 2006

(65) Prior Publication Data

US 2006/0173003 A1 Aug. 3, 2006

Related U.S. Application Data

(62) Division of application No. 10/347,210, filed on Jan. 17, 2003, now Pat. No. 7,074,799.

(60) Provisional application No. 60/350,527, filed on Jan. 22, 2002, provisional application No. 60/349,920, filed on Jan. 17, 2002.

(51) Int. Cl.
C07D 403/12 (2006.01)
C07D 403/14 (2006.01)
A61K 31/517 (2006.01)

(52) U.S. Cl. .............. 514/233.8; 514/266.2; 514/266.21; 514/266.22; 514/266.23; 514/266.24; 514/266.4; 544/116; 544/284; 544/292

(58) Field of Classification Search ............... 544/116, 544/284, 292; 514/233.8, 266.2, 266.21, 514/266.22, 266.23, 266.24, 266.4
See application file for complete search history.

(56) References Cited

U.S. PATENT DOCUMENTS

| | | | |
|---|---|---|---|
| 4,424,205 A | 1/1984 | LaHann et al. |
| 4,681,897 A | 7/1987 | Brand |
| 4,812,446 A | 3/1989 | Brand |
| 5,021,450 A | 6/1991 | Blumberg |
| 5,064,833 A | 11/1991 | Ife et al. |
| 5,290,816 A | 3/1994 | Blumberg |
| 5,420,135 A | 5/1995 | Brown et al. |
| 5,580,870 A | 12/1996 | Barker et al. |
| 5,616,582 A | 4/1997 | Barker |
| 5,654,307 A | 8/1997 | Bridges et al. |
| 5,747,498 A | 5/1998 | Schnur et al. |
| 5,801,183 A | 9/1998 | Keana et al. |
| 5,814,630 A | 9/1998 | Barker et al. |
| 5,840,720 A | 11/1998 | Chen |
| 5,866,572 A | 2/1999 | Barker et al. |
| 5,939,421 A | 8/1999 | Palanki et al. |
| 5,962,532 A | 10/1999 | Campbell et al. |
| 6,030,969 A | 2/2000 | Bhagwat et al. |
| 6,084,095 A | 7/2000 | Bridges et al. |
| 6,169,091 B1 | 1/2001 | Cockerill et al. |
| 6,174,889 B1 | 1/2001 | Cockerill et al. |
| 6,207,669 B1 | 3/2001 | Cockerill et al. |
| 6,225,318 B1 | 5/2001 | Sobolov-Jaynes et al. |
| 6,248,771 B1 | 6/2001 | Shenoy et al. |
| 6,248,788 B1 | 6/2001 | Robbins et al. |
| 6,251,912 B1 | 6/2001 | Wissner et al. |
| 6,391,874 B1 | 5/2002 | Cockerill et al. |
| 6,399,602 B1 | 6/2002 | Barker et al. |
| 6,437,147 B1 | 8/2002 | Andersen et al. |
| 6,476,076 B1 | 11/2002 | Lee et al. |
| 6,482,611 B1 | 11/2002 | Cortright et al. |
| 6,723,730 B2 | 4/2004 | Bakthavatchalam et al. |
| 2003/0133951 A1 | 7/2003 | Coe et al. |

FOREIGN PATENT DOCUMENTS

| | | |
|---|---|---|
| CN | 1469874 A | 1/2004 |
| EP | 1 229 025 | 8/2002 |
| WO | WO-89/05297 | 6/1989 |
| WO | WO-95/19774 | 8/1995 |
| WO | WO-96/09294 | 3/1996 |
| WO | WO-96/15118 | 5/1996 |
| WO | WO-96/40142 | 12/1996 |
| WO | WO-97/13771 | 4/1997 |
| WO | WO-98/02434 | 1/1998 |
| WO | WO-98/02437 | 1/1998 |
| WO | WO-95/15758 | 6/1998 |

(Continued)

OTHER PUBLICATIONS

Szallasi et al. {Journal of Medicinal Chemistry, (2004), vol. 47, No. 11, 2717-2723}.*

(Continued)

Primary Examiner—Kahsay Habte
(74) Attorney, Agent, or Firm—Edwards Angell Palmer & Dodge LLP; Peter F. Corless; Mark D. Russett

(57) ABSTRACT

Substituted quinazolin-4-ylamine analogues are provided. Such compounds are ligands that may be used to modulate specific receptor activity in vivo or in vitro, and are particularly useful in the treatment of conditions associated with pathological receptor activation in humans, domesticated companion animals and livestock animals. Pharmaceutical compositions and methods for using them to treat such disorders are provided, as are methods for using such ligands for receptor localization studies.

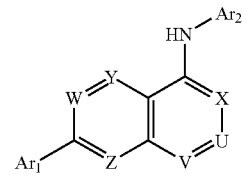

58 Claims, No Drawings

FOREIGN PATENT DOCUMENTS

| | | |
|---|---|---|
| WO | WO-98/23613 | 6/1998 |
| WO | WO-98/46605 | 10/1998 |
| WO | WO-99/00115 | 1/1999 |
| WO | WO-99/35146 | 7/1999 |
| WO | WO-00/23444 | 4/2000 |
| WO | WO-01/04111 | 1/2001 |
| WO | WO-01/25218 A1 | 4/2001 |
| WO | WO-01/85158 A2 | 11/2001 |
| WO | WO-02/16317 A1 | 2/2002 |
| WO | WO-02/16318 A1 | 2/2002 |
| WO | WO-02/16319 A1 | 2/2002 |
| WO | WO-02/22601 | 3/2002 |
| WO | WO-02/22602 A2 | 3/2002 |
| WO | WO-02/22603 A1 | 3/2002 |
| WO | WO-02/22604 A1 | 3/2002 |
| WO | WO-02/22605 A1 | 3/2002 |
| WO | WO-02/22606 A1 | 3/2002 |
| WO | WO-02/22607 A1 | 3/2002 |
| WO | WO-02/22608 A1 | 3/2002 |
| WO | WO-02/072536 A1 | 9/2002 |
| WO | WO-02/076946 A2 | 10/2002 |
| WO | WO-02/076946 A3 | 10/2002 |
| WO | WO-02/090326 A1 | 11/2002 |
| WO | WO-03/014064 | 2/2003 |

OTHER PUBLICATIONS

Nagy et al. {European Journal of Pharmacology 500 (2004), 351-369}.*

Wu et al., "Multiple Sensory and Functional Effects of Non-Phenolic Aminodimethylene Nonivamide: An Approach to Capsaicin Antagonist," Gen. Pharmac. 27:151-158 (1996).

Urban et al., "In vivo pharmacology of SDZ 249-665, a novel, non-pungent capsaicin analogue," Pain 89:65-74 (2000).

Ohkubo et al., "The Selective Capsaicin Antagonist Capsazepine Abolishes the Antinociceptive Action of Eugnol and Guaiacol," J. Dent. Res. 76:848-851 (1997).

Santos et al., "Ruthenium red and capsazepine antinociceptive effect in formalin and capsaicin models of pain in mice," Neurosecience Lettes 235:73-76 (1997).

Kwak et al., "A Capsaicin-Receptor Antagonist, Capsazepine, Reduces Inflammation-Induced Hyperalgesic Responses in the Rat: Evidence For An Endogenous Capsaicin-Like Substance," Neuroscience 86:619-626 (1998).

Szallasi et al., "Vanilloid (Capsaicin) Receptors and Mechanisms," Pharmacological Reviews 1:159-211 (1999).

Bevan et al., "Capsazepine: a competitive antagonist of the sensory neurones excitant capsaicin," Br. J. Pharmacol. 107:544-552 (1992).

Dickenson et al., "Selective antagonism of capsaicin by capsazepine: evidence for a spinal receptor site in capsaicin-induced antinociception," Br. J. Pharmacol. 104:1045-1049 (1991).

Caterina et al., "Impaired Nociception and Pain Sensation in Mice Lacking the Capsaicin Receptor," Science 288:306-313 (2000).

Szallasi et al., "Vanilloid Receptor Ligands," Drugs and Aging 18:561-573 (2001).

Liu et al., "Capsazepine, a vanilloid receptor antagonist, inhibits nicotinic acetylcholine receptors in rat trigeminal ganglia," Neuroscience Letters 228:29-32 (1997).

Abbadie et al. (1994) J. Neurosci. 14(10):5865-5871.

Aguayo and White (1992) Brain Research 570:61-67.

Bennett and Xie (1988) Pain 33:87-107.

Bertorelli et al. (1999) Br. J. Pharmacol. 128(6):1252-1258.

Carpenter et al. (1979) J. Biol. Chem. 254:4884-4891.

Chaplan et al. (1994) J. Neurosci. Methods 53:55-63.

Field et al. (1997) Br. J. Pharmacol. 121(8):1513-1522.

Fitzgerald et al. (1988) Toxicology 49(2-3):433-9.

Hargreaves et al. (1988) Pain 32(1):77-88.

Joshi, et al. (1987) Indian J. Chem., Sect. B. 26B(6):602-4.

Koch et al. (1996) Analgesia 2(3):157-164.

Liu et al. (1997) Neuroscience Letters 228:29.

Malinowski (1988) Bull. Soc. Chim. Belg. 97:51.

Menozzi, et al. (1987 J. Heterocyclic Chem. 24: 1669-1675.

Mitchell, (1992) Synthesis 803-815.

Miyaura and Suzuki (1995) Chemical Reviews 95:2457.

Nellmann et al. (2001) Toxicology 163(1):29-38.

Sakamoto, et al. (1985) Chem. Pharm. Bull. 33:565-571.

Stein et al. (1998) Pharmacol. Biochem. Behav. 31(2):455-51.

Szallasi et al. (1992) J. Pharmacol. Exp. Ther. 262:883-888.

Szallasi et al. (1993) J. Pharmacol. Exp. Ther. 266:678-683.

Tal and Eliav (1998) Pain 64(3):511-518.

Torssell et al. (1957) Arkiv Kemi 10:497.

International search Report for International Application PCT/US03/01563.

Temple et al. (1968) J. Medicinal Chem 11:1216-1218.

Thomas, Karen C. et al., "Transient Receptor Potential Vanilloid 1 Agonists Cause Endoplasmic Reticulum Stress and Cell Death in Human Lung Cells," *The Journal of Pharmacology and Experimental Therapeutics* 321(3), 830-838 (2007).

Bolcskei, Kata et al., "Investigation of the role of TRPV1 receptors in acute and chronic nociceptive processes using gene-deficient mice," *Pain* 117, 368-376 (2005).

Helyes, Zsuzsanna et al., "Role of transient receptor potential vanilloid 1 receptors in endotoxin-induced airway inflammation in the mouse," *Am J Physiol Lung Cell Mol Physiol.* 292 (5):L1173-81 (2007).

Banvolgyi, Agnes et al., "Evidence for a novel protective role of the vanilloid TRPV1 receptor in a cutaneous contact allergic dermatitis model, " *J Neuroimmunol.* 169, 86-96 (2005).

Johansen, M.E. et al., "TRPV1 Antagonists Elevate Cell Surface Populations of Receptor Protein and Exacerbate TRPV1-Mediated Toxicities in Human Lung Epithelial Cells", Toxicological Sciences 89(1), 278-286 (2006) (Advance Access publication Aug. 24, 2005).

* cited by examiner

SUBSTITUTED QUINAZOLIN-4-YLAMINE ANALOGUES

CROSS-REFERENCE TO RELATED APPLICATION(S)

This application is a divisional of patent application U.S. Ser. No. 10/347,210, filed on Jan. 17, 2003 now U.S. Pat. No. 7,074,799, which application claims priority to U.S. Provisional Patent Application 60/349,920, filed Jan. 17, 2002, and U.S. Provisional Patent Application 60/350,527, filed Jan. 22, 2002, each of which is incorporated by reference.

FIELD OF THE INVENTION

This invention relates generally to substituted quinazolin-4-ylamine analogues that are modulators of capsaicin receptors, and to the use of such compounds for treating conditions related to capsaicin receptor activation. The invention further relates to the use such compounds as probes for the detection and localization of capsaicin receptors.

BACKGROUND OF THE INVENTION

Pain perception, or nociception, is mediated by the peripheral terminals of a group of specialized sensory neurons, termed "nociceptors." A wide variety of physical and chemical stimuli induce activation of such neurons in mammals, leading to recognition of a potentially harmful stimulus. Inappropriate or excessive activation of nociceptors, however, can result in debilitating acute or chronic pain.

Neuropathic pain involves pain signal transmission in the absence of stimulus, and typically results from damage to the nervous system. In most instances, such pain is thought to occur because of sensitization in the peripheral and central nervous systems following initial damage to the peripheral system (e.g., via direct injury or systemic disease). Neuropathic pain is typically burning, shooting and unrelenting in its intensity and can sometimes be more debilitating that the initial injury or disease process that induced it.

Existing treatments for neuropathic pain are largely ineffective. Opiates, such as morphine, are potent analgesics, but their usefulness is limited because of adverse side effects, such as physical addictiveness and withdrawal properties, as well as respiratory depression, mood changes, and decreased intestinal motility with concomitant constipation, nausea, vomiting, and alterations in the endocrine and autonomic nervous systems. In addition, neuropathic pain is frequently non-responsive or only partially responsive to conventional opioid analgesic regimens. Treatments employing the N-methyl-D-aspartate antagonist ketamine or the alpha(2)-adrenergic agonist clonidine can reduce acute or chronic pain, and permit a reduction in opioid consumption, but these agents are often poorly tolerated due to side effects.

Topical treatment with capsaicin has been used to treat chronic and acute pain, including neuropathic pain. Capsaicin is a pungent substance derived from the plants of the Solanaceae family (which includes hot chili peppers) and appears to act selectively on the small diameter afferent nerve fibers (A-delta and C fibers) that are believed to mediate pain. The response to capsaicin is characterized by persistent activation of nociceptors in peripheral tissues, followed by eventual desensitization of peripheral nociceptors to one or more stimuli. From studies in animals, capsaicin appears to trigger C fiber membrane depolarization by opening cation selective channels for calcium and sodium. Capsaicin responses in isolated sensory neurons show dose-dependence.

Such responses are also evoked by structural analogues of capsaicin that share a common vanilloid moiety. One such analogue is resiniferatoxin (RTX), a natural product of *Euphorbia* plants. The term vanilloid receptor (VR) was coined to describe the neuronal membrane recognition site for capsaicin and such related irritant compounds. The capsaicin response is competitively inhibited (and thereby antagonized) by another capsaicin analog, capsazepine, and is also inhibited by the non-selective cation channel blocker ruthenium red. These antagonists bind to VR with no more than moderate affinity (typically with $K_i$ values of no lower than 140 μM).

Recently, rat and human receptors for capsaicin were cloned from dorsal root ganglion cells. Such receptors have also been referred to as VR1, and the terms "VR1" and "capsaicin receptor" are used interchangeably herein to refer to rat and/or human receptors of this type, as well as mammalian homologs. The role of VR1 in pain sensation has been confirmed using mice lacking this receptor, which exhibit no vanilloid-evoked pain behavior, and impaired responses to heat and inflammation. The capsaicin receptor is a nonselective cation channel with a threshold for opening that is lowered in response to elevated temperatures, low pH, and capsaicin receptor agonists. For example, the channel usually opens at temperatures higher than about 45° C. Opening of the capsaicin receptor channel is generally followed by the release of inflammatory peptides from neurons expressing the receptor and other nearby neurons, increasing the pain response. After initial activation by capsaicin, the capsaicin receptor undergoes a rapid desensitization via phosphorylation by cAMP-dependent protein kinase.

Because of their ability to thus desensitize nociceptors in peripheral tissues, VR1 agonist vanilloid compounds have been used as topical anesthetics. However, agonist application may itself cause burning pain, which limits this therapeutic use.

Thus, compounds that interact with VR1 but do not elicit the initial painful sensation of VR1 agonist vanilloid compounds, are desirable for the treatment of chronic and acute pain, including neuropathic pain. Antagonists of this receptor are particularly desirable for the treatment of pain, as well as conditions such as tear gas exposure, itch and urinary incontinence. The present invention fulfills this need, and provides further related advantages.

SUMMARY OF THE INVENTION

The present invention provides capsaicin receptor modulators that modulate, preferably inhibit, capsaicin receptor activation. Within certain aspects, compounds provided herein are characterized by the formula:

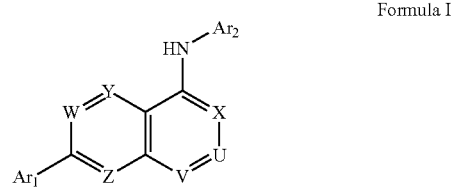

Formula I or a pharmaceutically acceptable salt thereof.

Within Formula I, V and X are each independently N or $CR_1$, with the proviso that at least one of V and X is N; U is N or $CR_2$, with the proviso that if V and X are N, then U is $CR_2$. W, Y and Z are each independently N or $CR_1$. $R_1$ is independently selected at each occurrence from hydrogen, halogen, hydroxy, cyano, amino, $C_1$–$C_8$alkyl, halo$C_1$–$C_8$alkyl, $C_1$–$C_8$alkoxy, halo$C_1$–$C_8$alkoxy and mono- and di-($C_1$–$C_8$alkyl)amino.

$R_2$ is: (i) hydrogen, halogen, cyano or —COOH; (ii) $C_2$–$C_8$alkoxycarbonyl, $C_1$–$C_8$alkanoyl, $C_2$–$C_8$alkanone, $C_1$–$C_8$alkanoyloxy, $C_1$–$C_8$carbonate or $C_1$–$C_8$carbamate, each of which is unsubstituted or substituted with from 1 to 9 substituents independently selected from $R_b$ or $R_d$; or (iii) a group of the formula —$R_c$-M-A-$R_y$, wherein: $R_c$ is $C_0$–$C_3$alkyl; M is a bond, $N(R_z)O$, S, $SO_2$, —$C(=O)_pN(R_z)$, $N(R_z)C(=O)_p$, $SO_2N(R_z)$, or $N(R_z)SO_2$, wherein p is 0 or 1; A is a bond or $C_1$–$C_8$alkyl optionally substituted with from 1 to 3 substituents independently chosen from $R_b$ or $R_d$; and $R_y$ and Rz are independently (a) hydrogen, $C_1$–$C_8$alkyl, $C_2$–$C_8$alkanone, $C_2$–$C_8$alkyl ether, $C_2$–$C_8$alkenyl, a 4- to 10-membered carbocycle or heterocycle, or (b) joined to $R_c$ to form a 4- to 10-membered carbocycle or heterocycle, wherein each $R_y$ and $R_z$ is independently unsubstituted or substituted with from 1 to 9 substituents independently selected from $R_b$ or $R_d$; or $R_y$ and $R_z$ are joined to form a 4- to 10-membered heterocycle that is unsubstituted or substituted with from 1 to 9 substituents independently selected from $R_b$ or $R_d$.

$R_b$ is independently chosen at each occurrence from hydroxy, halogen, amino, aminocarbonyl, amido, cyano, nitro, oxo, $C_1$–$C_8$alkyl, $C_1$–$C_8$alkoxy, $C_1$–$C_8$alkylthio, $C_1$–$C_8$alkyl ether, hydroxy$C_1$–$C_8$alkyl, halo$C_1$–$C_8$alkyl, phenyl, phenyl($C_1$–$C_8$alkyl), mono- and di-($C_1$–$C_6$alkyl)amino, $(SO_2)C_1$–$C_8$alkyl, 5- to 7-membered heterocycle and (5- to 7-membered heterocycle)($C_1$–$C_8$alkyl).

$R_d$ is independently selected at each occurrence from hydroxy, halogen, amino, aminocarbonyl, amido, cyano, nitro, $C_1$–$C_8$alkyl, $C_1$–$C_8$alkylthio, hydroxy$C_1$–$C_8$alkyl, halo$C_1$–$C_8$alkyl, phenyl, phenyl($C_1$–$C_8$alkyl), mono- and di-($C_1$–$C_6$alkyl)amino, $(SO_2)C_1$–$C_8$alkyl, 5- to 7-membered heterocycle and (5- to 7-membered heterocycle)($C_1$–$C_8$alkyl).

$Ar_1$ and $Ar_2$ are independently selected from 5- to 10-membered aromatic carbocycles and heterocycles, each of which is unsubstituted or substituted with from 1 to 3 substituents independently selected from groups of the formula $LR_a$. L is independently selected at each occurrence from a bond, —O—, —C(=O)—, —OC(=O)—, —C(=O)O—, —O—C(=O)O—, —$S(O)_m$—, —$NR_x$—, —C(=O)$NHR_x$—, —$NHR_xC(=O)$—, —$NR_xS(O)_m$—, —$S(O)_mNR_x$— and —$N[S(O)_mR_x]S(O)_m$—; wherein m is independently selected at each occurrence from 0, 1 and 2; and $R_x$ is independently selected at each occurrence from hydrogen and $C_1$–$C_8$alkyl. $R_a$ is independently selected at each occurrence from: (i) hydrogen, halogen, cyano and nitro; and (ii) $C_1$–$C_8$alkyl, $C_2$–$C_8$alkenyl, $C_2$–$C_8$alkynyl, $C_2$–$C_8$alkyl ether, 3- to 10-membered heterocycles, mono- and di-($C_1$–$C_8$alkyl)amino and (3- to 10-membered heterocycle)$C_1$–$C_6$alkyl, each of which is optionally substituted with from 1 to 9 substituents independently selected from $R_b$. Within certain compounds of Formula I, $Ar_2$ is a 5- to 7-membered aromatic heterocycle, optionally substituted as described above.

Within further aspects, compounds provided herein are characterized by the formula:

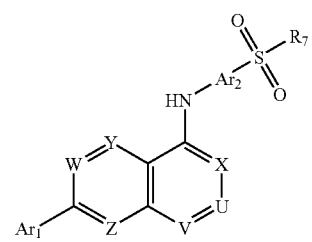

Formula II or a pharmaceutically acceptable salt thereof. Within Formula II, U, V, W, X, Y and Z are as described above. $Ar_1$ and $Ar_2$ of Formula II are each independently chosen from phenyl and 5- and 6-membered aromatic heterocycles, optionally substituted with from 1 to 3 substituents independently selected from groups of the formula $LR_a$, as described above. $R_7$ of Formula II is. $C_1$–$C_8$alkyl, $C_2$–$C_8$alkenyl, $C_2$–$C_8$alkynyl, mono- or di-($C_1$–$C_8$alkyl)amino or a 3- to 10-membered heterocycle, each of which is optionally substituted with from 1 to 5 substituents independently selected from hydroxy, halogen, $C_1$–$C_6$alkyl, $C_1$–$C_8$alkoxy, $C_2$–$C_8$alkyl ether, halo$C_1$–$C_8$alkyl and halo$C_1$–$C_8$alkoxy.

Within still further aspects, compounds provided herein are substituted 2-aminoalkyl-quinazoline-4ylamine analogues of Formula III:

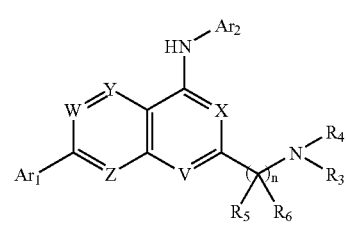

Formula III or a pharmaceutically acceptable salt or prodrug thereof, wherein:

V, X, W, Y and Z are as described above;

$Ar_1$ and $Ar_2$ are independently selected from phenyl and 5- to 7-membered aromatic heterocycles, each of which is unsubstituted or substituted with from 1 to 3 substituents independently selected from groups of the formula $LR_a$ as described above;

$R_3$ and $R_4$ are:
  (i) each independently selected from:
    (a) hydrogen;
    (b) $C_1$–$C_8$alkyl, $C_2$–$C_8$alkenyl, $C_2$–$C_8$alkynyl, $C_1$–$C_8$alkoxy, $C_3$–$C_8$alkanone, $C_2$–$C_8$alkanoyl, $C_2$–$C_8$alkyl ether, $C_6$–$C_{10}$aryl$C_0$–$C_8$alkyl, 5- to 10-membered heterocycle$C_0$–$C_8$alkyl and —$(SO_2)$$C_1$–$C_8$alkyl, each of which is optionally substituted with from 1 to 9 substituents independently selected from $R_b$; and
    (c) groups that are joined to an $R_5$ or $R_6$ to form a 4- to 10-membered heterocyclic group that is unsubstituted or substituted with from 1 to 6 substituents independently selected from $R_b$; or
  (ii) joined to form, with the N to which they are bound, a 4- to 10-membered heterocyclic group that is unsubstituted or substituted with from 1 to 6 substituents independently selected from $R_b$, $C_1$–$C_8$alkanoyl, 4- to 7-membered heterocycloalkyl$C_0$–$C_4$alkyl, and mono- and di-($C_1$–$C_6$alkyl)amino$C_1$–$C_6$alkyl;

$R_5$ and $R_6$ are, independently at each occurrence:
(i) each independently selected from:
  (a) hydrogen or hydroxy;
  (b) $C_1$–$C_8$alkyl, unsubstituted or substituted with 1 or 2 substituents independently selected from $R_b$; and
  (c) groups that are joined to $R_3$ or $R_4$ to form a 4- to 10-membered heterocyclic group that is unsubstituted or substituted with from 1 to 6 substituents independently selected from $R_b$;
(ii) taken together to form a keto group; or
(iii) joined to form a 3- to 7-membered carbocyclic or heterocyclic ring, unsubstituted or substituted with from 1 to 4 substituents selected from $R_b$;

$R_b$ is as described above; and n is 1, 2 or 3.

Within certain additional aspects, the compounds provided herein are substituted 2-hydroxyalkyl-quinazoline-4ylamine analogues of Formula IV:

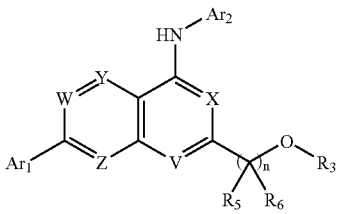

Formula IV or a pharmaceutically acceptable salt or prodrug thereof, wherein:

V, X, W, Y and Z are as described above;

$Ar_1$ and $Ar_2$ are independently selected from phenyl and 5- to 7-membered aromatic heterocycles, each of which is unsubstituted or substituted with from 1 to 3 substituents independently selected from groups of the formula $LR_a$ as described above;

$R_3$ is selected from:
(i) hydrogen;
(ii) $C_1$–$C_8$alkyl, $C_2$–$C_8$alkenyl, $C_2$–$C_8$alkynyl, $C_2$–$C_8$alkyl ether, $C_6$–$C_{10}$aryl$C_0$–$C_8$alkyl, and 5- to 10-membered heterocycle$C_0$–$C_8$alkyl, each of which is optionally substituted with from 1 to 9 substituents independently selected from $R_b$; and
(iii) groups that are joined to an $R_5$ or $R_6$ to form a 4- to 10-membered heterocyclic group that is unsubstituted or substituted with from 1 to 6 substituents independently selected from $R_b$;

$R_5$ and $R_6$ are, independently at each occurrence:
(i) each independently selected from:
  (a) hydrogen or hydroxy;
  (b) $C_1$–$C_8$alkyl, unsubstituted or substituted with 1 or 2 substituents independently selected from $R_b$; and
  (c) groups that are joined to $R_3$ to form a 5- to 10-membered heterocyclic group that is unsubstituted or substituted with from 1 to 6 substituents independently selected from $R_b$; or
(ii) joined to form a 3- to 7-membered carbocyclic or heterocyclic ring, unsubstituted or substituted with from 1 to 4 substituents selected from $R_b$;

$R_b$ is as described above; and n is 1, 2 or 3.

Within certain aspects, compounds as described herein exhibit a $K_i$ of no greater than 1 micromolar, 100 nanomolar, 10 nanomolar or 1 nanomolar in a capsaicin receptor binding assay and/or have an $IC_{50}$ value of no greater than 1 micromolar, 100 nanomolar, 10 nanomolar or 1 nanomolar in an assay for determination of capsaicin receptor antagonist activity. Preferred compounds generally include those with higher potency (i.e., lower $K_i$ or lower $IC_{50}$).

Within certain aspects, compounds as described herein are labeled with a detectable marker (e.g., radiolabeled or fluorescein conjugated).

The present invention further provides, within other aspects, pharmaceutical compositions comprising at least one compound or salt as described herein in combination with a physiologically acceptable carrier or excipient.

Within further aspects, methods are provided for reducing calcium conductance of a cellular capsaicin receptor, comprising contacting a cell (e.g., neuronal) expressing a capsaicin receptor with an effective amount of at least one compound or salt as described herein. Such contact may occur in vivo or in vitro.

Methods are further provided, within other aspects, for inhibiting binding of vanilloid ligand to a capsaicin receptor. Within certain such aspects, the inhibition takes place in vitro. Such methods comprise contacting a capsaicin receptor with at least one compound or salt as described herein, under conditions and in an amount sufficient to detectably inhibit vanilloid ligand binding to the capsaicin receptor. Within other such aspects, the capsaicin receptor is in a patient. Such methods comprise contacting cells expressing a capsaicin receptor in a patient with at least one compound or salt as described herein in an amount sufficient to detectably inhibit vanilloid ligand binding to cells expressing a cloned capsaicin receptor in vitro, and thereby inhibiting binding of vanilloid ligand to the capsaicin receptor in the patient.

The present invention provides, within further aspects, methods for treating a condition responsive to capsaicin receptor modulation in a patient, comprising administering to the patient a capsaicin receptor modulatory effective amount of at least one compound or salt as described herein.

Within other aspects, methods are provided for treating pain in a patient, comprising administering to a patient suffering from pain a capsaicin receptor modulatory amount of at least one compound or salt as described herein.

Methods are further provided, within other aspects, for treating itch, urinary incontinence, cough and/or hiccup in a patient, comprising administering to a patient suffering from one or more of the foregoing conditions a capsaicin receptor modulatory amount of at least one compound or salt as described herein.

The present invention further provides methods for promoting weight loss in an obese patient, comprising administering to an obese patient a capsaicin receptor modulatory amount of at least one compound or salt as described herein.

Within further aspects, the present invention provides methods for determining the presence or absence of capsaicin receptor in a sample, comprising: (a) contacting a sample with a compound as described herein under conditions that permit binding of the compound to capsaicin receptor; and (b) detecting a level of the compound bound to capsaicin receptor.

The present invention further provides packaged pharmaceutical preparation, comprising: (a) a pharmaceutical composition as described herein in a container; and (b) instructions for using the composition to treat one or more conditions responsive to capsaicin receptor modulation, such as pain, itch, urinary incontinence, cough, hiccup, and/or obesity.

In yet another aspect, the invention provides methods of preparing the compounds disclosed herein, including the intermediates.

These and other aspects of the present invention will become apparent upon reference to the following detailed description.

DETAILED DESCRIPTION

As noted above, the present invention provides capsaicin receptor modulators comprising substituted quinazolin-4-ylamine analogues. Such modulators may be used in vitro or in vivo, to modulate (preferably inhibit) capsaicin receptor activity in a variety of contexts.

Certain compounds of Formula I include those in which:

V, X, W, Y and Z are each independently N or $CR_1$, with the proviso that at least one of V and X is N;

U is N or $CR_2$, with the proviso that if V and X are N, then U is $CR_2$;

$R_1$ is independently selected at each occurrence from hydrogen, halogen, hydroxy, amino, $C_1$–$C_8$alkyl, halo$C_1$–$C_8$alkyl, $C_1$–$C_8$alkoxy, halo$C_1$–$C_8$alkoxy and mono- and di-($C_1$–$C_8$alkyl)amino;

$R_2$ is: (i) hydrogen, halogen or cyano;
(ii). $C_2$–$C_8$alkanoyl or $C_3$–$C_8$alkanone, each of which is unsubstituted or substituted with from 1 to 9 substituents independently selected from $R_d$; or
(iii) a group of the formula —$R_c$-M-A-$R_y$, wherein:
  $R_c$ is $C_0$–$C_3$alkyl;
  M is a bond, S, $SO_2$, $(C=O)_pN(R_z)$, $N(R_z)(C=O)_p$, $SO_2N(R_z)$, or $N(R_z)SO_2$, wherein p is 0 or 1;
  A is a bond or $C_1$–$C_8$alkyl, optionally substituted with from 1 to 3 substituents independently selected from $R_d$; and
  $R_y$ and $R_z$, if present, are:
    (a) independently hydrogen, $C_1$–$C_8$alkyl, $C_2$–$C_8$alkanone, $C_2$–$C_8$alkenyl, a 4- to 10-membered carbocycle, or joined to $R_c$ to form a 4- to 10-membered carbocycle, wherein each $R_y$ and $R_z$ is independently unsubstituted or substituted with from 1 to 9 substituents independently selected from $R_d$; or
    (b) joined to form a 4- to 10-membered heterocycle that is unsubstituted or substituted with from 1 to 9 substituents independently selected from $R_d$;
  wherein $R_d$ is independently selected at each occurrence from hydroxy, halogen, amino, aminocarbonyl, amido, cyano, nitro, $C_1$–$C_8$alkyl, $C_1$–$C_8$alkylthio, hydroxy$C_1$–$C_8$alkyl, halo$C_1$–$C_8$alkyl, phenyl, phenyl($C_1$–$C_8$alkyl), mono- and di-($C_1$–$C_6$alkyl)amino, $(SO_2)C_1$–$C_8$alkyl, 5- to 7-membered heterocycle and (5- to 7-membered heterocycle)($C_1$–$C_8$alkyl);

$Ar_2$ is a 5- to 7-membered aromatic heterocycle, optionally substituted with from 1 to 3 substituents independently selected from groups of the formula $LR_a$;

$Ar_1$ is a 5- to 10-membered aromatic carbocycle or heterocycle, optionally substituted with from 1 to 3 substituents independently selected from groups of the formula $LR_a$;

L is independently selected at each occurrence from a bond, —O—, —C(=O)—, —OC(=O)—, —C(=O)O—, —O—C(=O)O—, —S(O)$_m$—, —NR$_x$—, —C(=O) NHR$_x$—, —NHR$_x$C(=O)—, —NR$_x$S(O)$_m$—, —S(O)$_m$ NR$_x$— and —N[S(O)$_m$R$_x$]S(O)$_m$—; wherein m is independently selected at each occurrence from 0, 1 and 2; and $R_x$ is independently selected at each occurrence from hydrogen and $C_1$–$C_8$alkyl;

$R_a$ is independently selected at each occurrence from:
(i) hydrogen, halogen, cyano and nitro; and
(ii) $C_1$–$C_8$alkyl, $C_2$–$C_8$alkenyl, $C_2$–$C_8$alkynyl, $C_2$–$C_8$alkyl ether, 3- to 10-membered heterocycles, mono- and di-($C_1$–$C_8$alkyl)amino and (3- to 10-membered heterocycle)$C_1$–$C_6$alkyl, each of which is unsubstituted or substituted with from 1 to 9 substituents independently selected from $R_b$; and $R_b$ is independently chosen at each occurrence from hydroxy, halogen, amino, aminocarbonyl, amido, cyano, nitro, $C_1$–$C_8$alkyl, $C_1$–$C_8$alkoxy, $C_1$–$C_8$alkylthio, $C_1$–$C_8$alkyl ether, hydroxy$C_1$–$C_8$alkyl, halo$C_1$–$C_8$alkyl, phenyl, phenyl($C_1$–$C_8$alkyl), mono- and di-($C_1$–$C_6$alkyl) amino, $(SO_2)C_1$–$C_8$alkyl, 5- to 7-membered heterocycle and (5- to 7-membered heterocycle)($C_1$–$C_8$alkyl).

Such compounds are referred to herein as compounds of Formula Ib.

Within certain compounds of Formula Ib, $Ar_2$ is selected from pyridyl, pyridazinyl, pyrimidinyl, pyrazinyl, pyrrolyl, imidazolyl, pyrazolyl, oxazolyl, isoxazolyl, thiazolyl, isothiazolyl and thiadiazolyl, each of which is unsubstituted or substituted with 1 or 2 substituents selected from halogen, cyano, $C_1$–$C_6$alkyl, halo$C_1$–$C_6$alkyl, hydroxy$C_1$–$C_6$alkyl, $C_1$–$C_6$alkyl ether, $C_1$–$C_6$alkanoyl, amino, mono- and di-($C_1$–$C_6$alkyl)amino. In certain embodiments, $Ar_2$ is pyridyl, isoxazolyl, thiadiazolyl or pyrazolyl, each of which is unsubstituted or substituted with halogen, $C_1$–$C_4$alkyl or halo$C_1$–$C_4$alkyl. For example, $Ar_1$ and $Ar_2$ may each be pyridyl, substituted with 1 substituent independently chosen from halogen, $C_1$–$C_4$alkyl, $C_1$–$C_4$haloalkyl, and $C_1$–$C_4$alkoxy.

Within certain compounds of Formula Ib, U is $CR_2$, and $R_2$ is:
(i) hydrogen or halogen; or
(ii) $C_1$–$C_6$alkyl, —(CH$_2$)$_n$NH$_2$, —(CH$_2$)$_n$NH ($C_1$–$C_8$alkyl), —(CH$_2$)$_n$N($C_1$–$C_8$alkyl)$_2$, —(CH$_2$)$_n$(5- to 8-membered heterocycloalkyl), or —(CH$_2$)$_n$OH, each of which is unsubstituted or substituted with from 1 to 4 substituents independently chosen from halogen, cyano, hydroxy, amino, mono- and di-($C_1$–$C_6$alkyl) amino, $C_1$–$C_6$alkyl, and halo$C_1$–$C_6$alkyl.

Certain compounds of Formula II include those in which:

V, X, W, Y and Z are each independently N or $CR_1$, with the proviso that at least one of V and X is N;

U is N or $CR_2$, with the proviso that if V and X are N, then U is $CR_2$;

$R_1$ is independently selected at each occurrence from hydrogen, halogen, hydroxy, amino, $C_1$–$C_8$alkyl, halo$C_1$–$C_8$alkyl, $C_1$–$C_8$alkoxy, halo$C_1$–$C_8$alkoxy and mono- and di-($C_1$–$C_8$alkyl)amino;

$R_2$ is: (i) hydrogen, halogen or cyano;
(ii) $C_2$–$C_8$alkanoyl or $C_3$–$C_8$alkanone, each of which is unsubstituted or substituted with from 1 to 9 substituents independently selected from $R_d$; or
(iii) a group of the formula —$R_c$-M-A-$R_y$, wherein:
  $R_c$ is $C_0$–$C_3$alkyl;
  M is a bond, S, $SO_2$, $(C=O)_pN(R_z)$, $N(R_z)(C=O)_p$, $SO_2N(R_z)$, or $N(R_z)SO_2$, wherein p is 0 or 1;
  A is a bond or $C_1$–$C_8$alkyl, optionally substituted with from 1 to 3 substituents independently selected from $R_d$; and
  $R_y$ and $R_z$, if present, are:
    (a) independently hydrogen, $C_1$–$C_8$alkyl, $C_2$–$C_8$alkanone, $C_2$–$C_8$alkenyl, a 4- to 10-membered carbocycle, or joined to $R_c$ to form a 4- to 10-membered carbocycle, wherein each $R_y$ and $R_z$ is independently unsubstituted or substituted with from 1 to 9 substituents independently selected from $R_d$; or (b) joined to form a 4- to, 10-membered heterocycle that is unsubstituted or substituted with from 1 to 9 substituents independently selected from $R_d$;

wherein $R_d$ is independently selected at each occurrence from hydroxy, halogen, amino, aminocarbonyl, amido, cyano, nitro, $C_1$–$C_8$alkyl, $C_1$–$C_8$alkylthio, hydroxy$C_1$–$C_8$alkyl, halo$C_1$–$C_8$alkyl, phenyl, phenyl($C_1$–$C_8$alkyl), mono- and di-($C_1$–$C_6$alkyl)amino, $(SO_2)C_1$–$C_8$alkyl, 5- to 7-membered heterocycle and (5- to 7-membered heterocycle)($C_1$–$C_8$alkyl);

$Ar_1$ and $Ar_2$ are independently chosen from phenyl and 5- and 6-membered aromatic heterocycles, optionally substituted with from 1 to 3 substituents independently selected from groups of the formula $LR_a$;

L is independently selected at each occurrence from a bond, —O—, —C(=O)—, —OC(=O)—, —C(=O)O—, —O—C(=O)O—, —S(O)$_m$—, —NR$_x$—, —C(=O)NHR$_x$—, —NHR$_x$C(=O)—, —NR$_x$S(O)$_m$—, —S(O)$_m$NR$_x$— and —N[S(O)$_m$R$_x$]S(O)$_m$—; wherein m is independently selected at each occurrence from 0, 1 and 2; and $R_x$ is independently selected at each occurrence from hydrogen and $C_1$–$C_8$alkyl;

$R_a$ is independently selected at each occurrence from:
(i) hydrogen, halogen, cyano and nitro; and
(ii) $C_1$–$C_8$alkyl; $C_2$–$C_8$alkenyl, $C_2$–$C_8$alkynyl, $C_2$–$C_8$alkyl ether, 3- to 10-membered heterocycles, mono- and di-($C_1$–$C_8$alkyl)amino and (3- to 10-membered heterocycle)$C_1$–$C_6$alkyl, each of which is unsubstituted or substituted with from 1 to 9 substituents independently selected from $R_b$;

$R_b$ is independently chosen at each occurrence from hydroxy, halogen, amino, aminocarbonyl, amido, cyano, nitro, $C_1$–$C_8$alkyl, $C_1$–$C_8$alkoxy, $C_1$–$C_8$alkylthio, $C_1$–$C_8$alkyl ether, hydroxy$C_1$–$C_8$alkyl, halo$C_1$–$C_8$alkyl, phenyl, phenyl($C_1$–$C_8$alkyl), mono- and di-($C_1$–$C_6$alkyl)amino, $(SO_2)C_1$–$C_8$alkyl, 5- to 7-membered heterocycle and (5- to 7-membered heterocycle)($C_1$–$C_8$alkyl); and $R_7$ is $C_1$–$C_8$alkyl, $C_2$–$C_8$alkenyl, $C_2$–$C_8$alkynyl, mono- or di-($C_1$–$C_8$alkyl)amino or a 3- to 10-membered heterocycle, each of which is optionally substituted with from 1 to 5 substituents independently selected from hydroxy, halogen, $C_1$–$C_6$alkyl, $C_1$–$C_8$alkoxy, $C_2$–$C_8$alkyl ether, halo$C_1$–$C_8$alkyl and halo$C_1$–$C_8$alkoxy.

Such compounds are referred to herein as compounds of Formula IIb.

Within certain compounds of Formula IIb, $Ar_2$ is phenyl or pyridyl, each of which is optionally substituted with 1 or 2 substituents selected from halogen, cyano, $C_1$–$C_6$alkyl and halo$C_1$–$C_6$alkyl. In certain embodiments, $Ar_2$ is phenyl, optionally substituted with halogen, $C_1$–$C_4$alkyl or halo$C_1$–$C_4$alkyl.

Within certain compounds of Formula IIb, U is $CR_2$, and $R_2$ is:
(i) hydrogen or halogen; or
(ii) $C_1$–$C_6$alkyl, —(CH$_2$)$_n$NH$_2$, —(CH$_2$)$_n$NH($C_1$–$C_8$alkyl), —(CH$_2$)$_n$N($C_1$–$C_8$alkyl)$_2$, —(CH$_2$)$_n$(5- to 8-membered heterocycloalkyl) or —(CH$_2$)$_n$OH, each of which is unsubstituted or substituted with from 1 to 4 substituents independently chosen from halogen, cyano, hydroxy, amino, mono- and di-($C_1$–$C_6$alkyl)amino, $C_1$–$C_6$alkyl and halo$C_1$–$C_6$alkyl.

Within certain compounds of Formula IIb, $R_7$ comprises a nitrogen atom directly bonded to the $SO_2$. In certain embodiments, $R_7$ is amino, mono- or di($C_1$–$C_6$alkyl)amino, morpholinyl, piperidinyl, piperazinyl or pyrrolidinyl, each of which is unsubstituted or substituted with from 1 to 3 substituents independently chosen from halogen, $C_1$–$C_6$alkyl and halo$C_1$–$C_6$alkyl. In other embodiments, $R_7$ is $C_1$–$C_6$alkyl, halo$C_1$–$C_6$alkyl, morpholinyl, piperidinyl, piperazinyl or pyrrolidinyl, optionally substituted with from 1 to 5 substituents independently selected from $C_1$–$C_6$alkyl, $C_1$–$C_6$alkoxy, $C_1$–$C_6$alkyl ether, halo$C_1$–$C_6$alkyl and halo$C_1$–$C_6$alkoxy.

Certain compounds of Formula III include those in which:
V, X, W, Y and Z are each independently N or $CR_1$, with the proviso that at least one of V and X is N;
$R_1$ is independently selected at each occurrence from hydrogen, halogen, hydroxy, cyano, amino, $C_1$–$C_8$alkyl, halo$C_1$–$C_8$alkyl, $C_1$–$C_8$alkoxy, halo$C_1$–$C_8$alkoxy and mono- and di-($C_1$–$C_6$alkyl)amino;
$Ar_1$ and $Ar_2$ are independently selected from phenyl and 5- to 7-membered aromatic heterocycles, each of which is unsubstituted or substituted with from 1 to 3 substituents independently selected from groups of the formula $LR_a$;
L is independently selected at each occurrence from a bond, —O—, —C(=O)—, —OC(=O)—, —C(=O)O—, —O—C(=O)O—, —S(O)$_m$—, —NR$_x$—, —C(=O)NHR$_x$—, —NHR$_x$C(=O)—, —NR$_x$S(O)$_m$—, —S(O)$_m$NR$_x$— and —N[S(O)$_m$R$_x$]S(O)$_m$—; wherein m is independently selected at each occurrence from 0, 1 and 2; and $R_x$ is independently selected at each occurrence from hydrogen and $C_1$–$C_8$alkyl;
$R_a$ is independently selected at each occurrence from:
(i) hydrogen, halogen, cyano and nitro; and
(ii) $C_1$–$C_8$alkyl, $C_2$–$C_8$alkenyl, $C_2$–$C_8$alkynyl, $C_2$–$C_8$alkyl ether, 3- to 10-membered heterocycles, and (3- to 10-membered heterocycle)$C_1$–$C_6$alkyl, each of which is unsubstituted or substituted with from 1 to 9 substituents independently selected from $R_b$;
$R_3$ and $R_4$ are:
(i) each independently selected from:
(a) hydrogen;
(b) $C_1$–$C_8$alkyl, $C_2$–$C_8$alkenyl, $C_2$–$C_8$alkynyl, $C_1$–$C_8$alkoxy, $C_3$–$C_8$alkanone, $C_2$–$C_8$alkanoyl, $C_2$–$C_8$alkyl ether, $C_6$–$C_{10}$aryl$C_0$–$C_8$alkyl, 5- to 10-membered heterocycle$C_0$–$C_8$alkyl and —(SO$_2$)$C_1$–$C_8$alkyl, each of which is optionally substituted with from 1 to 9 substituents independently selected from $R_b$; and
(c) groups that are joined to an $R_5$ or $R_6$ to form a 4- to 10-membered heterocyclic group that is unsubstituted or substituted with from 1 to 6 substituents independently selected from $R_b$; or
(ii) joined to form, with the N to which they are bound, a 4- to 10-membered heterocyclic group that is unsubstituted or substituted with from 1 to 6 substituents independently selected from $R_b$, $C_1$–$C_8$alkanoyl, 4- to 7-membered heterocycloalkyl$C_0$–$C_4$alkyl, and mono- and di-($C_1$–$C_6$alkyl)amino$C_1$–$C_6$alkyl;
$R_5$ and $R_6$ are, independently at each occurrence:
(i) each independently selected from:
(a) hydrogen or hydroxy;
(b) $C_1$–$C_8$alkyl, unsubstituted or substituted with 1 or 2 substituents independently selected from $R_b$; and
(c) groups that are joined to $R_3$ or $R_4$ to form a 4- to 10-membered heterocyclic group that is unsubstituted or substituted with from 1 to 6 substituents independently selected from $R_b$;

(ii) taken together to form a keto group; or (iii) joined to form a 3- to 7-membered carbocyclic or heterocyclic ring, unsubstituted or substituted with from 1 to 4 substituents selected from $R_b$;

$R_b$ is independently chosen at each occurrence from hydroxy, halogen, amino, aminocarbonyl, amido, cyano, nitro, $C_1$–$C_8$alkyl, $C_1$–$C_8$alkoxy, $C_1$–$C_8$alkylthio, $C_1$–$C_8$alkyl ether, hydroxy$C_1$–$C_8$alkyl, halo$C_1$–$C_8$alkyl, phenyl, phenyl($C_1$–$C_8$alkyl), mono- and di-($C_1$–$C_6$alkyl)amino, $(SO_2)C_1$–$C_8$alkyl, 5- to 7-membered heterocycle and (5- to 7-membered heterocycle)($C_1$–$C_8$alkyl); and n is 1, 2 or 3.

Such compounds are referred to herein as compounds of Formula IIIb.

In certain compounds of Formula IIIb, $Ar_1$ and $Ar_2$ are independently selected from phenyl and 6-membered aromatic heterocycles, each of which is substituted with 0, 1 or 2 substituents. In certain embodiments, (i) $Ar_1$ is phenyl or pyridyl, each of which is unsubstituted or substituted with 1 or 2 substituents selected from halogen, hydroxy, cyano, amino, nitro, mono- and di-($C_1$–$C_6$alkyl)amino, $C_1$–$C_6$alkyl, halo$C_1$–$C_6$alkyl, $C_1$–$C_6$alkoxy and halo$C_1$–$C_6$alkoxy; and (ii) $Ar_2$ is phenyl or pyridyl, each of which is unsubstituted or substituted with 1 or 2 substituents independently selected from halogen, hydroxy, cyano, amino, mono- and di-($C_1$–$C_6$alkyl)amino, $C_1$–$C_6$alkyl, halo$C_1$–$C_6$alkyl, $C_1$–$C_6$alkoxy, halo$C_1$–$C_6$alkoxy, $C_2$–$C_6$alkyl ether, $C_1$–$C_6$alkanoyl, —$(SO_2)R_2$, —$NR_xS(O)_m$—, and —N(S$(O_m)_2$; wherein m is 1 or 2, $R_x$ is hydrogen or $C_1$–$C_6$alkyl, and $R_2$ is $C_1$–$C_6$alkyl, halo$C_1$–$C_6$alkyl, amino, mono- or di-($C_1$–$C_6$alkyl)amino or a 5- to 10-membered, N-linked heterocyclic group, each of which $R_2$ is optionally substituted with $R_b$. For example, in some embodiments, (i) $Ar_1$ is pyridyl, unsubstituted or substituted with halogen, $C_1$–$C_4$alkyl or halo$C_1$–$C_4$alkyl; and (ii) $Ar_2$ is phenyl or pyridyl, each of which is unsubstituted or substituted with halogen, cyano, $C_1$–$C_4$alkyl, halo$C_1$–$C_4$alkyl, $C_2$–$C_4$alkyl ether, $C_1$–$C_4$alkanoyl or —$(SO_2)R_a$, wherein $R_a$ is $C_1$–$C_4$alkyl or halo$C_1$–$C_4$alkyl. Certain such compounds are those in which (i) $Ar_1$ is pyridin-2-yl, 3-methyl-pyridin-2-yl, 3-trifluoromethyl-pyridin-2-yl or 3-halo-pyridin-2-yl; and (ii) $Ar_2$ is phenyl, 2-pyridyl or 3-pyridyl, each of which is substituted at the 4-position with trifluoromethanesulfonyl, propanesulfonyl, propane-2-sulfonyl, t-butyl, trifluoromethyl or 2,2,2-trifluoro-1-methyl-ethyl.

In certain compounds of Formula IIIb, $R_3$ and $R_4$ are each independently: (i) hydrogen; or (ii) $C_1$–$C_8$alkyl, $C_2$–$C_8$alkenyl, phenyl$C_0$–$C_4$alkyl, indanyl$C_0$–$C_4$alkyl, 5- to 6-membered heteroaryl$C_0$–$C_4$alkyl, or 4- to 7-membered heterocycloalkyl$C_0$–$C_4$alkyl, each of which is unsubstituted or substituted with from 1 to 4 substituents independently selected from hydroxy, halogen, amino, $C_1$–$C_6$alkyl, halo$C_1$–$C_6$alkyl, $C_1$–$C_6$alkoxy and halo$C_1$–$C_6$alkoxy. In certain embodiments, $R_3$ and $R_4$ are each independently: (i) hydrogen; or (ii) $C_1$–$C_6$alkyl, $C_2$–$C_6$alkenyl, 5- to 7-membered heterocyclo$C_0$–$C_4$alkyl, $C_2$–$C_6$alkyl ether, indanyl, benzyl, 1-phenyl-ethyl, 1-phenyl-propyl and 2-phenyl-ethyl, each of which is unsubstituted or substituted with from 1 to 3 substituents independently selected from hydroxy, halogen and $C_1$–$C_4$alkyl. For example, one of $R_3$ and $R_4$ may be pyridyl$C_0$–$C_4$alkyl, pyrimidyl$C_0$–$C_4$alkyl, imidazolyl$C_0$–$C_4$alkyl or tetrazolyl$C_0$–$C_4$alkyl, each of which is substituted with 0, 1 or 2 substituents.

In other compounds of Formula IIb, $R_3$ and $R_4$ are joined to form a 5 to 10-membered heterocyclic group that is substituted with from 0 to 4 substituents. In certain embodiments, the heterocyclic group is substituted with at least one substituent selected from hydroxy, halogen $C_1$–$C_4$alkyl, halo$C_1$–$C_4$alkyl, $C_1$–$C_4$alkoxy, halo$C_1$–$C_4$alkoxy, $C_1$–$C_4$alkanoyl, and aminocarbonyl. In certain embodiments, the heterocyclic group comprises an aromatic ring. One heterocyclic group is 3,4-dihydro-1H-isoquinolin-2-yl, substituted with 0, 1 or 2 substituents. In other embodiments, the heterocyclic group is a 5- to 10-membered heterocycloalkyl, substituted with from 0 to 4 substituents. For example, the heterocycloalkyl may be piperadinyl, piperazinyl, pyrrolidinyl, azepanyl, azocinyl, decahydroquinolinyl or 1,4-dioxa-8-aza-spiro[4.5]dec-8-yl, each of which is unsubstituted or substituted with from 1 to 4 substituents independently selected from halogen, hydroxy, $C_1$–$C_4$alkyl, $C_1$–$C_4$alkoxy, halo$C_1$–$C_4$alkyl, halo$C_1$–$C_4$alkoxy, $C_1$–$C_4$alkanoyl and $C_1$–$C_4$alkoxycarbonyl. Still further heterocyclic groups include morpholino, thiomorpholino or 1,1-dioxo-thiomorpholin-4-yl, each of which is unsubstituted or substituted with from 1 to 4 substituents independently selected from halogen, hydroxy, $C_1$–$C_4$alkyl, $C_1$–$C_4$alkoxy, halo$C_1$–$C_4$alkyl, halo$C_1$–$C_4$alkoxy, $C_1$–$C_4$alkanoyl and $C_1$–$C_4$alkoxycarbonyl. Within certain compounds of Formula III in which $R_3$ and $R_4$ are joined to form a 5 to 10-membered heterocyclic group, the heterocyclic group is substituted with from 1 to 4 substituents independently selected from methyl and ethyl.

Within certain compounds of Formula IIIb, each $R_5$ and $R_6$ is independently selected from hydrogen and $C_1$–$C_6$alkyl. In certain such compounds, $R_5$ and $R_6$ are hydrogen.

Within certain compounds of Formula IIIb, n is 1.

Representative compounds of Formula IIIb include compounds wherein:

(i) V and X are N;

(ii) $Ar_1$ is pyridyl, unsubstituted or substituted with halogen, $C_1$–$C_4$alkyl or halo$C_1$–$C_4$alkyl;

(iii) $Ar_2$ is phenyl or pyridyl, unsubstituted or substituted with $C_1$–$C_4$alkyl, halo$C_1$–$C_4$alkyl or a group of the formula —$(SO_2)R_2$, wherein $R_2$ is $C_1$–$C_4$alkyl or halo$C_1$–$C_4$alkyl;

(iv) $R_3$ and $R_4$ are each independently selected from $C_1$–$C_6$alkyl, $C_2$–$C_6$alkenyl, $C_2$–$C_6$alkyl ether, 5- to 10-membered heteroaryl$C_0$–$C_4$alkyl, phenyl$C_0$–$C_4$alkyl and indanyl, each of which is substituted with 0, 1 or 2 substituents independently selected from hydroxy, halogen, $C_1$–$C_4$alkyl and halo$C_1$–$C_4$alkyl; and (v) n is 1.

Yet other compounds of Formula IIIb include compounds wherein:

(i) V and X are N;

(ii) $Ar_1$ is pyridyl, unsubstituted or substituted with halogen, $C_1$–$C_4$alkyl or halo$C_1$–$C_4$alkyl;

(iii) $Ar_2$ is phenyl or pyridyl, unsubstituted or substituted with $C_1$–$C_4$alkyl, halo$C_1$–$C_4$alkyl or a group of the formula —$(SO_2)R_2$, wherein $R_2$ is $C_1$–$C_4$alkyl or halo$C_1$–$C_4$alkyl;

(iv) $R_3$ and $R_4$ are joined to form a 5- to 10-membered heterocyclic group that is unsubstituted or substituted with from 1 to 3 substituents; and (v) n is 1.

Preferred compounds of Formulas Ib, IIb and IIIb have an $IC_{50}$ value of 100 nanomolar or less, 10 nanomolar or less or 1 nanomolar or less in a capsaicin receptor calcium mobilization assay.

In another aspect, the invention provides pharmaceutical compositions, comprising at least one compound or salt according to Formula Ib, IIb or IIIb in combination with a physiologically acceptable carrier or excipient.

Within each of the methods described herein, the VR1 modulator(s) employed may satisfy one or more of the following formulas: I, II, III, IV, Ia, IIa, IIIa, IVa, Ib, IIb, IIIb or IVb. Certain such modulators satisfy Formula I, in which:

V, X, W, Y and Z are each independently N or $CR_1$, with the proviso that at least one of V and X is N;

U is N or $CR_2$, with the proviso that if V and X are N, then U is $CR_2$;

$R_1$ is independently selected at each occurrence from hydrogen, halogen, hydroxy, cyano, amino, $C_1$–$C_8$alkyl, halo$C_1$–$C_8$alkyl, $C_1$–$C_8$alkoxy, halo$C_1$–$C_8$alkoxy and mono- and di-($C_1$–$C_8$alkyl)amino;

$R_2$ is: (i) hydrogen, halogen or cyano;
  (ii) $C_2$–$C_8$alkanoyl or $C_3$–$C_8$alkanone, each of which is unsubstituted or substituted with from 1 to 9 substituents independently selected from $R_d$; or
  (iii) a group of the formula —$R_c$-M-A-$R_y$, wherein:
    $R_c$ is $C_0$–$C_3$alkyl;
    M is a bond, $N(R_z)S$, $SO_2$, $(C=O)_pN(R_z)$, $N(R_z)(C=O)_p$, $SO_2N(R_z)$, or $N(R_z)SO_2$, wherein p is 0 or 1;
    A is a bond or $C_1$–$C_8$alkyl, optionally substituted with from 1 to 3 substituents independently selected from $R_d$; and
    $R_y$ and $R_z$, if present, are:
      (a) independently hydrogen, $C_1$–$C_8$alkyl, $C_2$–$C_8$alkenyl, $C_2$–$C_8$alkynyl, $C_6$–$C_{10}$aryl$C_0$–$C_8$alkyl, a 4- to 10-membered carbocycle, or joined to $R_c$ to form a 4- to 10-membered carbocycle, wherein each $R_y$ and $R_z$ is independently unsubstituted or substituted with from 1 to 9 substituents independently selected from $R_d$; or
      (b) joined to form a 4- to 10-membered heterocycle that is unsubstituted or substituted with from 1 to 9 substituents independently selected from $R_d$;
    wherein $R_d$ is independently selected at each occurrence from hydroxy, halogen, amino, aminocarbonyl, amido, cyano, nitro, $C_1$–$C_8$alkyl, $C_1$–$C_8$alkylthio, hydroxy$C_1$–$C_8$alkyl, halo$C_1$–$C_8$alkyl, phenyl, phenyl($C_1$–$C_8$alkyl), mono- and di-($C_1$–$C_6$alkyl)amino, $(SO_2)C_1$–$C_8$alkyl, 5- to 7-membered heterocycle and (5- to 7-membered heterocycle)($C_1$–$C_8$alkyl);

$Ar_1$ and $Ar_2$ are independently selected from 5- to 10-membered aromatic carbocycles and heterocycles, each of which is unsubstituted or substituted with from 1 to 3 substituents independently selected from groups of the formula $LR_a$;

L is independently selected at each occurrence from a bond, —O—, —C(=O)—, —OC(=O)—, —C(=O)O—, —O—C(=O)O—, —S(O)$_m$—, —$NR_x$—, —C(=O)$NHR_x$—, —$NHR_xC(=O)$—, $NR_xS(O)_m$—, $S(O)_mNR_x$, and —N[S(O)$_mR_x$]S(O)$_m$—; wherein m is independently selected at each occurrence from 0, 1 and 2; and $R_x$ is independently selected at each occurrence from hydrogen and $C_1$–$C_8$alkyl;

$R_a$ is independently selected at each occurrence from:
  (i) hydrogen, halogen, cyano and nitro; and
  (ii) $C_1$–$C_8$alkyl, $C_2$–$C_8$alkenyl, $C_2$–$C_8$alkynyl, $C_2$–$C_8$alkyl ether, 3- to 10-membered heterocycles, mono- and di-($C_1$–$C_8$alkyl)amino and (3- to 10-membered heterocycle)$C_1$–$C_6$alkyl, each of which is unsubstituted or substituted with from 1 to 9 substituents independently selected from $R_b$; and $R_b$ is independently chosen at each occurrence from hydroxy, halogen, amino, aminocarbonyl, amido, cyano, nitro, $C_1$–$C_8$alkyl, $C_1$–$C_8$alkoxy, $C_1$–$C_8$alkylthio, $C_1$–$C_8$alkyl ether, hydroxy$C_1$–$C_8$alkyl, halo$C_1$–$C_8$alkyl, phenyl, phenyl($C_1$–$C_8$alkyl), mono- and di-($C_1$–$C_6$alkyl)amino, $(SO_2)C_1$–$C_8$alkyl, 5- to 7-membered heterocycle and (5- to 7-membered heterocycle)($C_1$–$C_8$alkyl).

Terminology

Compounds are generally described herein using standard nomenclature. For compounds having asymmetric centers, it should be understood that (unless otherwise specified) all of the optical isomers and mixtures thereof are encompassed. In addition, compounds with carbon-carbon double bonds may occur in Z- and E-forms, with all isomeric forms of the compounds being included in the present invention unless otherwise specified. Where a compound exists in various tautomeric forms, a recited compound is not limited to any one specific tautomer, but rather is intended to encompass all tautomeric forms. Certain compounds are described herein using a general formula that includes variables (e.g., $R_1$, n, $Ar_1$). Unless otherwise specified, each variable within such a formula is defined independently of any other variable, and any variable that occurs more than one time in a formula is defined independently at each occurrence.

The term "quinazolin-4-ylamine analogue," as used herein, encompasses all compounds that satisfy one or more of Formulas I–IV herein, as well as pharmaceutically acceptable salts and hydrates of such compounds. Such compounds include analogues in which the quinazoline core is modified in the number and/or placement of ring nitrogen atoms, as well as analogues in which varied substituents, as described in more detail below, are attached to such a core structure. In other words, compounds that are pyrido[2,3-d]pyrimidine-4-ylamines, pyrido[3,2-d]pyrimidin-4-ylamines, isoquinolin-1-ylamines and phthalazin-1-ylamines are within the scope of quinazolin-4ylamine analogues.

As used herein, the term "alkyl" refers to a straight chain, branched chain or cyclic saturated aliphatic hydrocarbon. An alkyl group may be bonded to an atom within a molecule of interest via any chemically suitable portion. Alkyl groups include groups having from 1 to 8 carbon atoms ($C_1$–$C_8$alkyl), from 1 to 6 carbon atoms ($C_1$–$C_6$alkyl) and from 1 to 4 carbon atoms ($C_1$–$C_4$alkyl), such as methyl, ethyl, propyl, isopropyl, n-butyl, sec-butyl, tert-butyl, pentyl, 2-pentyl, isopentyl, neopentyl, hexyl, 2-hexyl, 3-hexyl, 3-methylpentyl, cyclopropyl, cyclopropylmethyl, cyclopentyl, cyclopentylmethyl, cyclohexyl, cycloheptyl and norbornyl. "$C_0$–$C_4$alkyl" refers to a bond or a $C_1$–$C_4$alkyl group; "$C_0$–$C_8$alkyl" refers to a bond or a $C_1$–$C_8$alkyl group.

Similarly, "alkenyl" refers to straight or branched chain alkene groups or cycloalkene groups. Within an alkenyl group, one or more unsaturated carbon-carbon double bonds are present. Alkenyl groups include $C_2$–$C_8$alkenyl, $C_2$–$C_6$alkenyl and $C_2$–$C_4$alkenyl groups, which have from 2 to 8, 2 to 6 or 2 to 4 carbon atoms, respectively, such as ethenyl, allyl or isopropenyl. "Alkynyl" refers to straight or branched chain alkyne groups, which have, one or more unsaturated carbon-carbon bonds, at least one of which is a triple bond. Alkynyl groups include $C_2$–$C_8$alkynyl, $C_2$–$C_6$alkynyl and $C_2$–$C_4$alkynyl groups, which have from 2 to 8, 2 to 6 or 2 to 4 carbon atoms, respectively.

By "alkoxy," as used herein, is meant an alkyl, alkenyl or alkynyl group as described above attached via an oxygen bridge. Alkoxy groups include $C_1$–$C_8$alkoxy, $C_1$–$C_6$alkoxy and $C_1$–$C_4$alkoxy groups, which have from 1 to 8, 1 to 6 or 1 to 4 carbon atoms, respectively. Alkoxy groups include, for example, methoxy, ethoxy, propoxy, isopropoxy, n-butoxy, sec-butoxy, tert-butoxy, n-pentoxy, 2-pentoxy, 3-pentoxy, isopentoxy, neopentoxy, hexoxy, 2-hexoxy, 3-hexoxy, and 3-methylpentoxy.

The term "alkanoyl" refers to an acyl group in a linear, branched or cyclic arrangement (e.g., —(C=O)-alkyl). Alkanoyl groups include $C_2$–$C_8$alkanoyl, $C_2$–$C_6$alkanoyl and $C_2$–$C_4$alkanoyl groups, which have from 2 to 8, 2 to 6 or 2 to 4 carbon atoms, respectively. "$C_1$alkanoyl" refers to —(C=O)—H, which (along with $C_2$–$C_8$alkanoyl) is encompassed by the term "$C_1$–$C_8$alkanoyl."

An "alkanone" is a ketone group in which carbon atoms are in a linear, branched or cyclic alkyl arrangement. "$C_3$–$C_8$alkanone," "$C_3$–$C_6$alkanone" and "$C_3$–$C_4$alkanone" refer to an alkanone having from 3 to 8, 6 or 4 carbon atoms, respectively. By way of example, a $C_3$ alkanone group has the structure —$CH_2$—(C=O)—$CH_3$.

Similarly, "alkyl ether" refers to a linear or branched ether substituent linked via a carbon-carbon bond. Alkyl ether groups include $C_2$–$C_8$alkyl ether, $C_2$–$C_6$alkyl ether and $C_2$–$C_4$alkyl ether groups, which have 2 to 8, 6 or 4 carbon atoms, respectively. By way of example, a $C_2$ alkyl ether group has the structure —$CH_2$—O—$CH_3$.

The term "alkoxycarbonyl" refers to an alkoxy group linked via a carbonyl (i.e., a group having the general structure —C(=O)—O-alkyl). Alkoxycarbonyl groups include $C_2$–$C_8$, $C_2$–$C_6$ and $C_2$–$C_4$alkoxycarbonyl groups, which have from 2 to 8, 6 or 4 carbon atoms, respectively. "$C_1$alkoxycarbonyl" refers to —C(=O)—OH, which is encompassed by the term "$C_1$–$C_8$alkoxycarbonyl."

"Alkanoyloxy," as used herein, refers to an alkanoyl group linked via an oxygen bridge (i.e., a, group having the general structure —O—C(=O)-alkyl). Alkanoyloxy groups include $C_2$–$C_8$, $C_2$–$C_6$ and $C_2$–$C_4$alkanoyloxy groups, which have from 2 to 8, 6 or 4 carbon atoms, respectively. "$C_1$alkanoyloxy" refers to O—C(=O)—H, which is encompassed by the term "$C_1$–$C_8$alkanoyloxy."

The term "$C_1$–$C_8$carbonate" refers to an alkoxycarbonyl group linked via an oxygen bridge. In other words, a carbonate group has the general structure —O—C(=O)—O-alkyl. $C_1$–$C_6$carbonate groups are generally preferred, with $C_1$–$C_4$carbonate groups particularly preferred.

The term "$C_1$–$C_8$carbamate," as used herein, refers to a group having the general structure —N—C(=O)—O-alkyl. $C_1$–$C_6$carbamate groups, i.e., where the alkyl group is a $C_1$–$C_6$ alkyl, are generally preferred, with $C_1$–$C_4$carbamate groups particularly preferred.

Alkylamino refers to a secondary or tertiary amine having the general structure —NH-alkyl or —N(alkyl)(alkyl), wherein each alkyl may be the same or different. Such groups include, for example, mono- and di-($C_1$–$C_8$alkyl) amino groups, in which each alkyl may be the same or different and may contain from 1 to 8 carbon atoms, as well as mono- and di-($C_1$–$C_6$alkyl)amino groups and mono- and di-($C_1$–$C_4$alkyl)amino groups. Alkylaminoalkyl refers to an alkylamino group linked via an alkyl group (i.e., a group having the general structure -alkyl-NH-alkyl or -alkyl-N(alkyl)(alkyl)). Such groups include, for example, mono- and di-($C_1$–$C_8$alkyl)amino$C_1$–$C_8$alkyl, mono- and di-($C_1$–$C_6$alkyl)amino$C_1$–$C_6$alkyl and mono- and di-($C_1$–$C_4$alkyl)amino$C_1$–$C_4$alkyl, in which each alkyl may be the same or different.

The term "aminocarbonyl" refers to an amide group (i.e., —C(=O)$NH_2$).

The term "halogen" includes fluorine, chlorine, bromine and iodine. A "haloalkyl" is a branched, straight-chain or cyclic alkyl group, substituted with 1 or more halogen atoms (e.g., "halo$C_1$–$C_8$alkyl" groups have from 1 to 8 carbon atoms; "halo$C_1$–$C_6$alkyl" groups have from 1 to 6 carbon atoms). Examples of haloalkyl groups include, but are not limited to, mono-, di- or tri-fluoromethyl; mono-, di- or tri-chloromethyl; mono-, di-, tri-, tetra- or penta-fluoroethyl; and mono-, di-, tri-, tetra- or penta-chloroethyl. Typical haloalkyl groups are trifluoromethyl and difluoromethyl. Within certain compounds provided herein, not more than 5 or 3 haloalkyl groups are present. The term "haloalkoxy" refers to a haloalkyl group as defined above attached via an oxygen bridge. "Halo$C_1$–$C_8$alkoxy" groups have 1 to 8 carbon atoms.

A dash ("-") that is not between two letters or symbols is used to indicate a point of attachment for a substituent. For example, —$CONH_2$ is attached through the carbon atom.

A "heteroatom," as used herein, is oxygen, sulfur or nitrogen.

A "carbocycle" or "carbocyclic group" comprises at least one ring formed entirely by carbon-carbon bonds (referred to herein as a carbocyclic ring), and does not contain a heterocyclic ring. Unless otherwise specified, each carbocyclic ring within a carbocycle may be saturated, partially saturated or aromatic. A carbocycle generally has from 1 to 3 fused, pendant or spiro rings, carbocycles within certain embodiments have one ring or two fused rings. Typically, each ring contains from 3 to 8 ring members (i.e., $C_3$–$C_8$); $C_5$–$C_7$ rings are recited in certain embodiments. Carbocycles comprising fused, pendant or spiro rings typically contain from 9 to 14 ring members. Certain representative carbocycles are cycloalkyl (i.e., groups that comprise saturated and/or partially saturated rings, such as cyclopropyl, cyclobutyl, cyclopentyl, cyclohexyl, cycloheptyl, cyclooctyl, adamantyl, decahydro-naphthalenyl, octahydro-indenyl, and partially saturated variants of any of the foregoing, such as cyclohexenyl), as well as aromatic groups (i.e., groups that contain at least one aromatic carbocyclic ring, such as phenyl, benzyl, naphthyl, phenoxyl, benzoxyl, phenylethanonyl, fluorenyl, indanyl and 1,2,3,4-tetrahydro-naphthyl. Carbon atoms present within a carbocyclic ring may, of course, be further bonded to zero, one or two hydrogen atoms and/or any of a variety of ring substituents, such as hydroxy, halogen, cyano, nitro, $C_1$–$C_8$alkyl, $C_2$–$C_8$alkenyl, $C_2$-$C$alkynyl, $C_1$–$C_8$alkoxy, $C_2$–$C_8$alkyl ether, $C_3$–$C_8$alkanone, $C_1$–$C_8$alkylthio, amino, mono- or di-($C_1$–$C_8$alkyl)amino, $C_3$–$C_7$cycloalkyl$C_0$–$C_4$alkyl, halo$C_1$–$C_8$alkyl, halo$C_1$–$C_8$alkoxy, amino$C_1$–$C_8$alkyl, hydroxy$C_1$–$C_8$alkyl, $C_1$–$C_8$alkanoyl, $C_1$–$C_8$alkoxycarbonyl, —COOH, —C(=O)$NH_2$, mono- or di-($C_1$–$C_8$alkyl)carboxamido, —$S(O_2)NH_2$, and/or mono- or di-($C_1$–$C_8$alkyl) sulfonamido.

Certain carbocycles recited herein include $C_6$–$C_{10}$aryl$C_0$–$C_8$alkyl groups (i.e., groups in which a carbocyclic group comprising at least one aromatic ring is linked via a direct bond or a $C_1$–$C_8$alkyl group). Such groups include, for example, phenyl and indanyl, as well as groups in which either of the foregoing is linked via $C_1$–$C_8$alkyl, preferably via $C_1$–$C_4$alkyl. Phenyl groups linked via a direct bond or alkyl group may be designated phenyl$C_0$–$C_8$alkyl (e.g., benzyl, 1-phenyl-ethyl, 1-phenyl-propyl and 2-phenyl-ethyl).

A "heterocycle" or "heterocyclic group" has from 1 to 3 fused, pendant or spiro rings, at least one of which is a heterocyclic ring (i.e., one or more ring atoms is a heteroatom, with the remaining ring atoms being carbon). Typically, a heterocyclic ring comprises 1–4 heteroatoms; within certain embodiments each heterocyclic ring has 1 or 2 heteroatoms per ring. Each heterocyclic ring generally contains from 3 to 8 ring members (rings having from 5 to 7 ring members are recited in certain embodiments), and heterocycles comprising fused, pendant; or spiro rings typically contain from 9 to 14 ring members. Heterocycles may be optionally substituted at nitrogen and/or carbon atoms with a variety of substituents, such as those described above for carbocycles. Unless otherwise specified, a heterocycle may be a heterocycloalkyl group (i.e., each ring is saturated or partially saturated) or a heteroaryl group (i.e., at least one ring within the group is aromatic). A heterocyclic group may generally be linked via any ring or substituent atom, provided that a stable compound results. N-linked heterocyclic groups are linked via a component nitrogen atom. A "heterocycle$C_0$–$C_8$alkyl" is a heterocyclic group linked via a direct bond or $C_1$–$C_8$alkyl group. A (3- to 10-membered heterocycle)$C_1$–$C_6$alkyl is a heterocyclic group having from 3 to, 10 ring members linked via a $C_1$–$C_6$alkyl group Heterocyclic groups include, for example, acridinyl, azepanyl, azocinyl, benzimidazolyl, benzimidazolinyl, benzisothiazolyl, benzisoxazolyl, benzofuranyl, benzothiofuranyl, benzothiophenyl, benzoxazolyl, benzothiazolyl, benzotriazolylcarbazolyl, benztetrazolyl, NH-carbazolyl, carbolinyl, chromanyl, chromenyl, cinnolinyl, decahydroquinolinyl, dihydrofuro[2,3-b]tetrahydrofuran, dihydroisoquinolinyl, dihydrotetrahydrofuranyl, 1,4-dioxa-8-aza-spiro[4.5]dec-8-yl, dithiazinyl, furanyl, furazanyl, imidazolinyl, imidazolidinyl, imidazolyl, indazolyl, indolenyl, indolinyl, indolizinyl, indolyl, isobenzofuranyl, isochromanyl, isoindazolyl, isoindolinyl, isoindolyl, isothiazolyl, isoxazolyl, isoquinolinyl, morpholinyl, naphthyridinyl, octahydroisoquinolinyl, oxadiazolyl, oxazolidinyl, oxazolyl, phenanthridinyl, phenanthrolinyl, phenazinyl, phenothiazinyl, phenoxathiinyl, phenoxazinyl, phthalazinyl, piperazinyl, piperidinyl, piperidinyl, piperidonyl, pteridinyl, purinyl, pyranyl, pyrazinyl, pyrazolidinyl, pyrazolinyl, pyrazolyl, pyridazinyl, pyridoimidazolyl, pyridooxazolyl, pyridothiazolyl, pyridyl, pyrimidyl, pyrrolidinyl, pyrrolidonyl, pyrrolinyl, pyrrolyl, quinazolinyl, quinolinyl, quinoxalinyl, quinuclidinyl, tetrahydroisoquinolinyl, tetrahydroquinolinyl, tetrazolyl, thiadiazinyl, thiadiazolyl, thianthrenyl, thiazolyl, thienothiazolyl, thienooxazolyl, thienoimidazolyl, thienyl, thiophenyl, thiomorpholinyl and variants thereof in which the sulfur atom is oxidized, triazinyl, xanthenyl and any of the foregoing that are substituted with from 1 to 4 substituents as described above.

Certain heterocyclic groups are 3- to 10-membered or 5- to 10-membered groups that contain 1 heterocyclic ring or 2 fused or spiro rings, optionally substituted as described above. ($C_3$–$C_{10}$)heterocycloalkyls include, for example, piperidinyl, piperazinyl, pyrrolidinyl, azepanyl, 1,4-dioxa-8-aza-spiro[4.5]dec-8-yl, morpholino, thiomorpholino, and 1,1-dioxo-thiomorpholin-4-yl, as well as groups in which each of the foregoing is substituted with from 1 to 6 (preferably from 1 to 4) substituents in dependently selected from halogen, hydroxy, $C_1$–$C_4$alkyl, $C_1$–$C_4$alkoxy, halo$C_1$–$C_4$alkyl, halo$C_1$–$C_4$alkoxy, $C_1$–$C_4$alkylcarbonyl and $C_1$–$C_4$alkoxycarbonyl. In certain embodiments, a heterocycloalkyl may be a 4- to 7-membered heterocycloalkyl$C_0$–$C_4$alkyl group. Such groups comprise a 4- to 7-membered heterocycloalkyl group as described above, linked via a direct bond or a $C_1$–$C_4$ alkyl group.

Certain aromatic heterocycles include 5- to 10-membered heteroaryl$C_0$–$C_8$alkyl groups (i.e., groups in which the heterocyclic group comprising at least one aromatic ring is linked via a direct bond or a $C_1$–$C_8$alkyl group). Such groups include, for example, the heteroaryl groups recited above, as well as groups in which any of the foregoing is linked via $C_1$–$C_8$alkyl, $C_1$–$C_6$alkyl or $C_1$–$C_4$alkyl. Representative aromatic heterocycles are azocinyl, pyridyl, pyrimidyl, imidazolyl, tetrazolyl and 3,4-dihydro-1H-isoquinolin-2-yl, as well as groups in which each of the foregoing is linked via $C_1$–$C_4$alkyl.

A "substituent," as used herein, refers to a molecular moiety that is covalently bonded to an atom within a molecule of interest. For example, a "ring substituent" may be a moiety such as a halogen, alkyl group, haloalkyl group or other group discussed herein that is covalently bonded to an atom (preferably a carbon or nitrogen atom) that is a ring member. The term "substitution" refers to replacing a hydrogen atom in a molecular structure with a substituent as described above, such that the valence on the designated atom is not exceeded, and such that a chemically stable compound (i.e., a compound that can be isolated, characterized, and tested for biological activity) results from the substitution.

Groups that are "optionally substituted" are unsubstituted or are substituted by other than hydrogen at one or more available positions, typically 1, 2, 3, 4 or 5 positions, by one or more suitable groups (which may be the same or different). Such optional substituents include, for example, hydroxy; halogen, cyano, nitro, $C_1$–$C_8$alkyl, $C_2$–$C_8$alkenyl, $C_2$–$C_8$alkynyl, $C_1$–$C_8$alkoxy, $C_2$–$C_8$alkyl ether, $C_3$–$C_8$alkanone, $C_1$–$C_8$alkylthio, amino, mono- or di-($C_1$–$C_8$alkyl)amino, halo$C_1$–$C_8$alkyl, halo$C_1$–$C_8$alkoxy, $C_1$–$C_8$alkanoyl, $C_1$–$C_8$alkanoyloxy, $C_1$–$C_8$alkoxycarbonyl, —COOH, —CONH$_2$, mono- or di-($C_1$–$C_8$alkyl)carboxamido, —SO$_2$NH$_2$, and/or mono or di($C_1$–$C_8$alkyl)sulfonamido, as well as carbocyclic and heterocyclic groups. Certain optionally substituted groups are substituted with from 0 to 3 independently selected substituents.

The terms "VR1," "type 1 vanilloid receptor" and "capsaicin receptor" are used interchangeably herein. Unless otherwise specified, these terms encompass both rat and human VR1 receptors (e.g., GenBank Accession Numbers AF327067, AJ277028 and NM_018727; sequences of certain human VR1 cDNAs are provided in SEQ ID NOs:1–3, and the encoded amino acid sequences shown in SEQ ID NOs:4 and 5, of U.S. Pat. No. 6,482,611), as well as homologs thereof found in other species.

A "VR1 modulator," also referred to herein as a "modulator," is a compound that modulates VR1 activation and/or VR1-mediated signal transduction. A VR1 modulator may be a VR1 agonist or antagonist although, for certain purposes described herein, a VR1 modulator preferably inhibits VR1 activation resulting from binding of a vanilloid ligand agonist (e.g., capsaicin or a capsaicin analogue such as olvanil or resiniferatoxin) to VR1. A modulator binds with "high affinity" if the $K_i$ at VR1 is less than 1 micromolar, preferably less than 100 nanomolar, 10 nanomolar or 1 nanomolar. A representative assay for determining $K_i$ at VR1 is provided in Example 5, herein. A modulator is considered an antagonist if it detectably inhibits vanilloid ligand binding to VR1 and/or VR1-mediated signal transduction (using, for example, the representative assay provided in Example 6); in general, such an antagonist inhibits VR1 activation with a IC$_{50}$ value of less than 1 micromolar, preferably less than 100 nanomolar, and more preferably less than 10 nanomolar or 1 nanomolar within the assay provided in Example 6. VR1 antagonists include neutral antagonists and inverse agonists. Preferred modulators do not substantially inhibit activity of human epidermal growth factor (EGF) receptor tyrosine kinase (i.e., IC$_{50}$ in an EGF receptor assay is greater than 1 micromolar, preferably greater than 100 micromolar or 10 micromolar). More preferably, a modulator does not detectably inhibit EGF receptor activity. Assays for detecting an inhibitory effect on EGF receptor are well known in the art, and include those described by Carpenter et al. (1979) *J. Biol. Chem.* 254:4884, as well as U.S. Pat. Nos. 5,654,301 and 6,169,091.

An "inverse agonist" of VR1 is a compound that inhibits the activity of vanilloid ligand at VR1, and reduces the activity of VR1 below its basal activity level in the absence of added vanilloid ligand. Inverse agonists of VR1 may also inhibit binding of vanilloid ligand to VR1. The ability of a compound to inhibit the binding of vanilloid ligand to VR1 may be measured by a binding assay, such as the binding assay given in Example 5. The basal activity of VR1, as well as the reduction in VR1 activity due to the presence of VR1 antagonist, may be determined from a calcium mobilization assay, such as the assay of Example 6.

A "neutral antagonist" of VR1 is a compound that inhibits the activity of vanilloid ligand at VR1, but does not significantly change the basal activity of the receptor (i.e., within a calcium mobilization assay as described in Example 6 performed in the absence of vanilloid ligand, VR1 activity is reduced by no more than 10%, more preferably by no more than 5%, and even more preferably by no more than 2%; most preferably, there is no detectable reduction in activity. Neutral antagonists of VR1 may inhibit the binding of vanilloid ligand to VR1.

As used herein an "agonist" of VR1 is a compound that elevates the activity of the receptor above the basal activity level of the receptor.

A "vanilloid ligand" is capsaicin or any capsaicin analogue that comprises a phenyl ring with two oxygen atoms bound to adjacent ring carbons, and that binds to VR1 with a $K_i$ (determined as described herein) that is no greater than 10 µM. Vanilloid ligand agonists include capsaicin, olvanil, N-arachidonoyl-dopamine and resiniferatoxin (RTX). Vanilloid ligand antagonists include capsazepine and iodo-resiniferatoxin.

A "prodrug" is a compound that may not fully satisfy the structural requirements of the compounds provided herein, but is modified in vivo, following administration to a patient, to produce a quinazolin-4-ylamine analogue. For example, a prodrug may be an acylated derivative of a compound as provided herein. Prodrugs include compounds wherein hydroxy, amine or sulfhydryl groups are bonded to any group that, when administered to a mammalian subject, cleaves to form a free hydroxyl, amino, or sulfhydryl group, respectively. Examples of prodrugs include, but are not limited to, acetate, formate and benzoate derivatives of alcohol and amine functional groups within the compounds provided herein.

A "patient" is any individual treated with a VR1 modulator as provided herein. Patients include humans, as well as other animals such as companion animals (e.g., dogs and cats) and livestock. Patients may be experiencing one or more symptoms of a condition responsive to capsaicin receptor modulation (e.g., pain, exposure to vanilloid ligand, itch, urinary incontinence, respiratory disorders, cough and/or hiccup), or may be free of such symptom(s) (i.e., treatment may be prophylactic).

VR1 Modulators

As noted above, the present invention provides VR1 modulators (i.e., compounds that modulate VR1-mediated signal transduction; preferably compounds that also detectably bind to VR1). VR1 modulators may be used to modulate VR1 activity in a variety of contexts, including in the treatment of (i) pain (e.g., neuropathic or peripheral nerve-mediated pain), (ii) exposure to capsaicin, (iii) exposure to acid, heat, light, tear gas air pollutants, pepper spray or related agents, (iv) respiratory conditions such as asthma or chronic obstructive pulmonary disease, (v) itch, (vi) urinary incontinence, (vii) cough or hiccup and/or (viii) obesity. VR1 modulators may also be used within a variety of in vitro assays (e.g., assays for receptor activity), as probes for detection and localization of VR1 and as standards in assays of ligand binding and VR1-mediated signal transduction.

VR1 modulators provided herein are substituted quinazolin-4-ylamine analogues that detectably modulate the binding of capsaicin to VR1 at nanomolar (i.e., submicromolar) concentrations, preferably at subnanomolar concentrations, more preferably at concentrations below 100 picomolar, or even below 20 picomolar. Such modulators are preferably not capsaicin analogs (i.e., they do not comprise a phenyl ring with two oxygen atoms bound to adjacent ring carbons). Preferred modulators are VR1 antagonists and have no detectable agonist activity in the assay described in Example 6. In certain embodiments, such modulators further bind with high affinity to VR1, and do not substantially inhibit activity of human EGF receptor tyrosine kinase.

The present invention is based, in part, on the discovery that small molecules having the general Formula I (as well as pharmaceutically acceptable salts, hydrates and prodrugs thereof). modulate VR1 activity. In certain embodiments, no more than 2 of W, Y and Z are N. Representative quinazoline-4-ylamine analogues include, but are not limited to, compounds in which U, V, W, X, Y and Z are as indicated for any one of the embodiments listed in Table I.

TABLE I

Representative Quinazoline-4-ylamine Analogue Core Structures

| U | V | X | W | Y | Z |
|---|---|---|---|---|---|
| CR$_2$ | N | CH | CH | CH | CH |
| CR$_2$ | CH | N | CH | CH | CH |
| CR$_2$ | N | N | CH | CH | CH |
| N | CH | N | CH | CH | CH |
| CR$_2$ | N | CH | CH | N | CH |
| CR$_2$ | CH | N | CH | N | CH |
| CR$_2$ | N | N | CH | N | CH |
| N | CH | N | CH | N | CH |
| CR$_2$ | N | CH | CH | CH | N |
| CR$_2$ | CH | N | CH | CH | N |
| CR$_2$ | N | N | CH | CH | N |
| N | CH | N | CH | CH | N |
| CR$_2$ | N | CH | N | CH | CH |
| CR$_2$ | CH | N | N | CH | CH |
| CR$_2$ | N | N | N | CH | CH |
| N | CH | N | N | CH | CH |
| CR$_2$ | N | CH | N | CH | N |
| CR$_2$ | CH | N | N | CH | N |
| CR$_2$ | N | N | N | CH | N |
| N | CH | N | N | CH | N |
| CR$_2$ | N | CH | CH | N | N |
| CR$_2$ | CH | N | CH | N | N |
| CR$_2$ | N | N | CH | N | N |
| N | CH | N | CH | N | N |

Within Formulas I–IV, $R_1$ is preferably hydrogen, $C_1$–$C_4$alkyl or halo$C_1$–$C_4$alkyl, with hydrogen particularly preferred. Further, V and X may both be N. Within certain such embodiments, one of W, Y and Z is N and the others are CH, or all three of W, Y and Z are CH.

In certain embodiments, $R_2$ in Formulas I and II, if present, is hydrogen, amino, hydroxy, halogen, or optionally substituted —(CH$_2$)$_n$NH$_2$, —(CH$_2$)$_n$NH(C$_1$–C$_8$alkyl), —(CH$_2$)$_n$N(C$_1$–C$_8$alkyl)$_2$, —(CH$_2$)$_n$(5- to 8-membered heterocycloalkyl), or —(CH$_2$)$_n$OH. Optionally substituted groups include, for example, unsubstituted groups and groups substituted on the alkyl portion with from 1 to 4 substituents independently chosen from halogen, cyano, hydroxy, amino, mono- and di-($C_1$–$C_6$alkyl)amino, $C_1$–$C_6$alkyl, and halo$C_1$–$C_6$alkyl. Heterocycloalkyl groups include those in which the heterocycloalkyl comprises a nitrogen or oxygen atom directly linked to the —($CH_2$)$_n$.

Within certain embodiments, $Ar_1$ and $Ar_2$ in compounds of Formulas I-IV are independently selected from 5- to 7-membered aromatic carbocycles and heterocycles, optionally substituted. For example, $Ar_1$ and $Ar_2$ may be independently selected from phenyl and 6-membered aromatic heterocycles, each of which is substituted with 0, 1 or 2 substituents. In certain embodiments, $Ar_1$ is phenyl or pyridyl, each of which is unsubstituted or substituted with, 1, 2 or 3 substituents as described above; preferably such substituents, if any, are independently selected from halogen, hydroxy, cyano, amino, nitro, mono- and di-($C_1$–$C_6$alkyl)amino, $C_1$–$C_6$alkyl, halo$C_1$–$C_6$alkyl, $C_1$–$C_6$alkoxy and halo$C_1$–$C_6$alkoxy. For example, $Ar_1$ may contain one substituent selected from halogen, $C_1$–$C_6$alkyl, $C_1$–$C_6$alkoxy, halo$C_1$–$C_6$alkyl and halo$C_1$–$C_6$alkoxy. If one or more $Ar_1$ substituents is present, at least one such substituent is preferably located in the ortho position (e.g., $Ar_1$ may be phenyl substituted at the 2-position, or 2-pyridyl substituted at the 3-position). $Ar_1$ groups include, but are not limited to, pyridin-2-yl, 3-methyl-pyridin-2-yl, 3-trifluoromethyl-pyridin-2-yl and 3-halo-pyridin-2-yl.

$Ar_2$, within certain embodiments, is phenyl or pyridyl, each of which is unsubstituted or substituted with 1 or 2 substituents as described above. In certain embodiments, one such substituent is located in the para position of a 6-membered $Ar_2$; in Formula II the —$SO_2$—$R_7$ is preferably in the para position, and in Formulas I, III and IV one of the optional substituents is preferably located in that position. Optional $Ar_2$ substituents are as described above and include, for example, groups in which $R_a$ is independently selected at each occurrence from: (i) hydrogen, halogen, cyano and nitro; and (ii) $C_1$–$C_8$alkyl, $C_2$–$C_8$alkenyl, $C_2$–$C_8$alkynyl and 3- to 10-membered heterocycles, each of which is optionally substituted with from 1 to 9 substituents independently selected from hydroxy, halogen, $C_1$–$C_6$alkyl and halo$C_1$–$C_6$alkyl. Preferred $R_a$ moieties include halogen, hydroxy, cyano, amino, mono- and di-($C_1$–$C_6$alkyl)amino, $C_1$–$C_6$alkyl, halo$C_1$–$C_6$alkyl, $C_1$–$C_6$alkoxy, halo$C_1$–$C_6$alkoxy, $C_2$–$C_6$alkyl ether, $C_1$–$C_6$alkanoyl, —($SO_2$)$R_a$, —$NR_xS(O)_m$, and —$N(S(O)_m)_2$; wherein m is 1 or 2, $R_x$ is hydrogen or $C_1$–$C_6$alkyl, and $R_a$ is $C_1$–$C_6$alkyl, halo$C_1$–$C_6$alkyl, or a 5- to 10-membered, N-linked heterocyclic group, each of which $R_a$ is optionally substituted with from 1 to 4 substituents independently chosen from $R_b$. Preferred $Ar_2$ substituents include $C_1$–$C_4$alkyl, halo$C_1$–$C_4$alkyl and groups of the formula —($SO_2$)$R_a$, wherein $R_a$ is $C_1$–$C_4$alkyl or halo$C_1$–$C_4$alkyl. $Ar_2$ groups include phenyl, pyridyl, pyridazinyl, pyrimidinyl, pyrazinyl, pyrrolyl, imidazolyl, pyrazolyl, oxazolyl, isoxazolyl, thiazolyl, isothiazolyl and thiadiazolyl, each of which is optionally substituted with 1 or 2 substituents independently selected from halogen, cyano, $C_1$–$C_6$alkyl, halo$C_1$–$C_6$alkyl, $C_1$–$C_6$alkoxy, halo$C_1$–$C_6$alkoxy, —$SO_2$—$R_a$ and —$SO_2NR_x$—$R_a$. Preferred $Ar_2$ groups are phenyl, pyridyl, isoxazolyl, thiadiazolyl and pyrazolyl, optionally substituted with halogen, $C_1$–$C_4$alkyl or halo$C_1$–$C_4$alkyl. Within certain embodiments, $Ar_2$ is phenyl or pyridyl, each of which is optionally substituted with 1 or 2 substituents independently chosen from halogen, cyano, $C_1$–$C_4$alkyl, halo$C_1$–$C_4$alkyl, $C_2$–$C_4$alkyl ether, $C_1$–$C_4$alkanoyl and groups of the formula $SO_2)R_a$, wherein $R_a$ is $C_1$–$C_6$alkyl or halo$C_1$–$C_6$alkyl. $Ar_2$ groups include, but are not limited to, phenyl, 2-pyridyl and 3-pyridyl, each of which is substituted at the 4-position with halogen, cyano, methyl, ethyl, propyl, isopropyl, t-butyl, trifluoromethyl, 2,2,2-trifluoroethyl, 2,2,2-trifluoro-1-methyl-ethyl, methanesulfonyl, ethanesulfonyl, propanesulfonyl, propane-2-sulfonyl, trifluoromethanesulfonyl or 2,2,2-trifluoroethanesulfonyl.

Within certain embodiments of compounds of Formula II, $Ar_2$ is phenyl or pyridyl, optionally substituted with 1 or 2 substituents independently chosen from halogen, cyano, $C_1$–$C_6$alkyl, and halo$C_1$–$C_6$alkyl; and $Ar_1$ is phenyl or pyridyl, optionally substituted with halogen, $C_1$–$C_6$alkyl, halo$C_1$–$C_6$alkyl, $C_1$–$C_6$alkoxy or halo$C_1$–$C_6$alkoxy. Within Formula II, the carbon atom of $Ar_2$ that is linked to the $SO_2$ is preferably separated from the carbon atom linked to the N by at least one, and preferably two, ring atoms. In other words, for embodiments in which $Ar_2$ is phenyl, the $SO_2$ is preferably located at the para (4) position. In certain embodiments, $R_7$ is $C_1$–$C_6$alkyl, halo$C_1$–$C_6$alkyl, amino, mono or di($C_1$–$C_6$alkyl)amino or a nonaromatic heterocycle (e.g., morpholinyl, piperidinyl, piperazinyl or pyrrolidinyl), optionally substituted as described above.

Within certain embodiments, $R_3$ and $R_4$ of Formula III are each independently selected from (i) hydrogen or (ii) $C_1$–$C_8$alkyl, $C_2$–$C_8$alkenyl, $C_2$–$C_8$alkynyl, $C_3$–$C_8$alkanone, $C_1$–$C_8$alkanoyl, $C_2$–$C_8$alkyl ether, $C_6$–$C_{10}$aryl$C_0$–$C_8$alkyl, 5- to 10-membered heterocycle$C_0$–$C_8$alkyl and —($SO_2$) $C_1$–$C_8$alkyl, each of which is optionally substituted with from 1 to 9 substituents independently selected from $R_b$. Within other embodiments, $R_3$ and $R_4$ are each independently selected from (i) hydrogen and (ii) $C_1$–$C_8$alkyl, $C_2$–$C_8$alkenyl, phenyl$C_0$–$C_4$alkyl, indanyl$C_0$–$C_4$alkyl, 5- to 6-membered heteroaryl$C_0$–$C_4$alkyl and 4- to 7-membered heterocycloalkyl$C_0$–$C_4$alkyl, each of which is optionally substituted with from 1 to 4 substituents independently selected from hydroxy, halogen, amino, $C_1$–$C_6$alkyl, halo$C_1$–$C_6$alkyl, $C_1$–$C_6$alkoxy and halo$C_1$–$C_6$alkoxy. Representative $R_3$ and $R_4$ groups include $C_1$–$C_6$alkyl, $C_2$–$C_6$alkenyl, 5- to 7-membered heterocyclo$C_0$–$C_4$alkyl, $C_2$–$C_6$alkyl ether, indanyl, benzyl, 1-phenyl-ethyl, 1-phenyl-propyl and 2-phenyl-ethyl, each of which is unsubstituted or substituted with from 1 to 3 substituents independently selected from hydroxy, halogen and $C_1$–$C_4$alkyl. For example, at least one of $R_3$ and $R_4$ may be pyridyl$C_0$–$C_4$alkyl, pyrimidyl$C_0$–$C_4$alkyl, imidazolyl$C_0$–$C_4$alkyl or tetrazolyl$C_0$–$C_4$alkyl, each of which is substituted with 0, 1 or 2 substituents. Alternatively, $R_3$ and/or $R_4$ may be joined to an $R_5$ or $R_6$ group (along with the N to which $R_3$ and $R_4$ are bound and any carbon atoms between the N and $R_5$ or $R_6$) to form an optionally substituted heterocycle, such as a 5- to 10-membered mono- or bi-cyclic group.

Within other embodiments, $R_3$ and/or $R_4$ of Formula Emi may form an optionally substituted heterocycle. For example, $R_3$ and $R_4$ may be joined to form, with the N to which they are bound, an optionally substituted heterocycle; or $R_3$ or $R_4$ may be joined to an $R_5$ or $R_6$ moiety to from an optionally substituted heterocycle. In either case, the resulting heterocycle may be, for example, a 4- or 5- to 10-membered, mono- or bi-cyclic group substituted with from 0 to 4 substituents (e.g., from 1 to 4 substituents or 0, 1 or 2 substituents). In certain embodiments, each substituent is independently selected from hydroxy, halogen, $C_1$–$C_4$alkyl, halo$C_1$–$C_4$alkyl, $C_1$–$C_4$alkoxy, halo$C_1$–$C_4$alkoxy, $C_1$–$C_4$alkanoyl, $C_1$–$C_4$alkoxycarbonyl, aminocarbonyl, heterocycle$C_0$–$C_8$alkyl and heterocycle$C_1$–$C_8$alkoxycarbonyl. In certain embodiments, such substituents are lower alkyl groups such as methyl and/or ethyl.

A heterocyclic group that comprises $R_3$ and/or $R_4$ may be a heteroaryl group, which comprises an aromatic ring (e.g., optionally substituted acridinyl, benzimidazolinyl, benzimidazolyl, benzotriazolyl, carbazolyl, cinnolinyl, indazolyl, indolinyl, indolyl, isoquinolinyl, quinoxalinyl, naphthyridinyl, phenanthridinyl, phenazinyl, phenothiazinyl, phenoxazinyl, phthalazinyl, pteridinyl, purinyl, quinolinyl, quinoxalinyl, quinazolinyl, tetrahydroisoquinolinyl or tetrahydroquinolinyl). One such heteroaryl is 3,4-dihydro-1H-isoquinolin-2-yl. Alternatively, the heterocycle may be an optionally substituted heterocycloalkyl group, such as azepanyl, azocinyl, decahydroquinolinyl, 1,4-dioxa-8-azaspiro[4.5]dec-8-yl, imidazolidinyl, imidazolinyl, morpholino, piperadinyl, piperazinyl, pyridazinyl, pyrazolidinyl, pyrazolinyl, pyrrolidinyl, pyrrolinyl, thiomorpholino or 1,1-dioxo-thiomorpholin-4-yl. Representative heterocycles that may be formed from $R_3$ and $R_4$ include, but are not limited to, optionally substituted azepane, azocane, dihydroisoquinoline, imidazole, morpholine, octahydroquinoline, piperazine, piperidine and pyrrolidine. Representative heterocycles that may be formed from $R_3$ or $R_4$, in combination with an $R_5$ or $R_6$, include (but are not limited to) optionally substituted piperadine and pyrrolidine $R_5$ and $R_6$ of Formula III, within certain embodiments, are independently (at each occurrence) hydrogen or optionally substituted $C_1$–$C_6$alkyl; in addition, or alternatively, any $R_5$ or $R_6$ may be joined with any other $R_5$ or $R_6$ to form an optionally substituted 5- to 7-membered cycloalkyl, or (as discussed above) joined with $R_3$ or $R_4$ to form an optionally substituted heterocycle.

Within Formula IV, $R_3$ may be (in certain embodiments) (i) hydrogen or (ii) $C_1$–$C_8$alkyl, $C_2$–$C_8$alkenyl, $C_2$–$C_8$alkynyl, $C_3$–$C_8$alkanone, $C_2$–$C_8$alkyl ether, $C_6$–$C_{10}$aryl$C_0$–$C_8$alkyl, or 5- to 10-membered heterocycle$C_0$–$C_8$alkyl, each of which is optionally substituted with from 1 to 9 substituents independently selected from $R_b$. Within other embodiments, $R_3$ of Formula IV is (i) hydrogen or (ii) $C_1$–$C_6$alkyl, $C_2$–$C_6$alkyl ether, phenyl$C_0$–$C_4$alkyl, 5- to 6-membered heteroaryl$C_0$–$C_4$alkyl, or 4- to 7-membered heterocycloalkyl$C_0$–$C_4$alkyl, each of which is optionally substituted with from 1 to 4 substituents independently selected from hydroxy, halogen, amino, $C_1$–$C_6$alkyl, halo$C_1$–$C_6$alkyl, $C_1$–$C_6$alkoxy and halo$C_1$–$C_6$alkoxy. Representative $R_3$ groups include hydrogen, $C_1$–$C_4$alkyl, $C_1$–$C_4$alkyl ether and benzyl, each of which is unsubstituted or substituted with from 1 to 3 substituents independently selected from hydroxy, halogen and $C_1$–$C_4$alkyl. Alternatively, $R_3$ may be joined to an $R_5$ or $R_6$ group (along with the O to which $R_3$ is bound and any carbon atoms between the O and $R_5$ or $R_6$) to form an optionally substituted heterocycle, such as a 5- to 10-membered mono- or bi-cyclic group. The resulting heterocycle may, for example, be substituted with from 0 to 4 (e.g., 0, 1 or 2) substituents independently chosen from hydroxy, halogen, $C_1$–$C_4$alkyl, halo$C_1$–$C_4$alkyl, $C_1$–$C_4$alkoxy, halo$C_1$–$C_4$alkoxy, $C_1C_4$alkanoyl, $C_1$–$C_4$alkoxycarbonyl, aminocarbonyl, heterocycle$C_0$–$C_8$alkyl and heterocycle$C_1$–$C_8$alkoxycarbonyl.

$R_5$ and $R_6$, within certain embodiments of Formula IV, are independently (at each occurrence) hydrogen or optionally substituted $C_1$–$C_6$alkyl; in addition, or alternatively, any $R_5$ or $R_6$ may be joined with any other $R_5$ or $R_6$ to form an optionally substituted 5- to 7-membered cycloalkyl, or (as discussed above) joined with $R_3$ to form an optionally substituted heterocycle. In certain such embodiments, each $R_5$ and $R_6$ is hydrogen. n may be 1, 2 or 3, with 1 preferred in certain embodiments.

Certain preferred compounds satisfy at least one of Formulas Ia, IIa, IIIa or IVa, in which the variables are as defined above for Formulas I, II, III and IV, respectively:

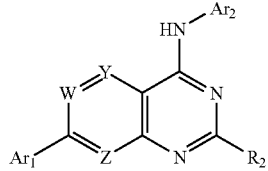

Formula Ia

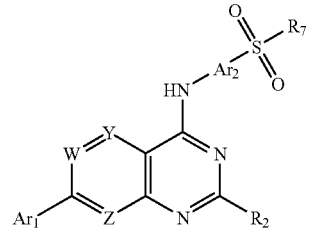

Formula IIa

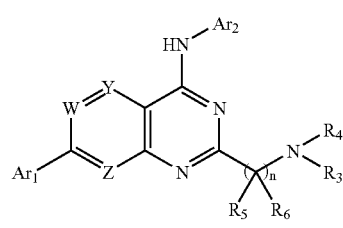

Formula IIIa

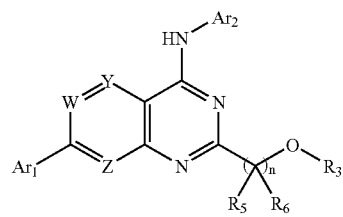

Formula IVa

Representative compounds of Formulas I–IV include, but are not limited to, those specifically described in Examples 1–3. It will be apparent that the specific compounds recited therein are representative only, and are not intended to limit the scope of the present invention. Further, as noted above, all compounds of the present invention may be present as a hydrate, free base or a pharmaceutically acceptable acid addition salt.

Substituted quinazolin-4-ylamine analogues provided herein detectably alter (modulate) vanilloid ligand-induced VR1 activity, as determined using a standard in vitro VR1 ligand binding assay and/or a functional assay such as a calcium mobilization assay, dorsal root ganglion assay or in vivo pain relief assay. References herein to a "VR1 ligand binding assay" are intended to refer to a standard in vitro receptor binding assay such as that provided in Example 5, and a "calcium mobilization assay" (also referred to herein as a "signal transduction assay") may be performed using the method of Example 6. Briefly, to assess VR1 binding, a competition assay may be performed in which a VR1 preparation is incubated with labeled (e.g., $^{125}$I) VR1 agonist and unlabeled test compound. Within the assays provided herein, the VR1 used is preferably a mammalian VR1, more preferably a human or rat VR1. The receptor may be recombinantly expressed or naturally expressed. The VR1 preparation may be, for example, a membrane preparation from HEK293 or CHO cells that recombinantly express human VR1 (such as a VR1 sequence provided in U.S. Pat. No. 6,482,611).

Incubation with a compound that detectably modulates vanilloid ligand binding to VR1 will result in a decrease or increase in the amount of label bound to the VR1 preparation, relative to the amount of label bound in the absence of the compound. Preferably, such a compound will exhibit a $K_i$ at VR1 of less than 1 micromolar, more preferably less than 500 nM, 100 nM, 20 nM, 10 nM or 1 nM within a VR1 ligand binding assay performed as described in Example 5. In general, compounds that decrease the amount of label bound to the VR1 preparation within such an assay are preferred.

As noted above, compounds that are VR1 antagonists are preferred within certain embodiments. Such compounds exhibit $IC_{50}$ values of 1 micromolar or less, preferably about 100 nanomolar or less, 10 nanomolar or less or 1 nanomolar or less within a standard in vitro VR1-mediated calcium mobilization assay, as provided in Example 6. Briefly, cells expressing capsaicin receptor are contacted with a compound of interest and with an indicator of intracellular calcium concentration (e.g., a membrane permeable calcium sensitivity dye such as Fluo-3 or Fura-2 (both of which are available, for example, from Molecular Probes, Eugene, Oreg.), each of which produce a fluorescent signal when bound to $Ca^{++}$). Such contact is preferably carried out by one or more incubations of the cells in buffer or culture medium comprising either or both of the compound and the indicator in solution. Contact is maintained for an amount of time sufficient to allow the dye to enter the cells (e.g., 1–2 hours). Cells are washed or filtered to remove excess dye and are then contacted with a vanilloid receptor agonist (e.g., capsaicin, RTX or olvanil), typically at a concentration equal to the $IC_{50}$ concentration, and a fluorescence response is measured. When cells are contacted with a compound that is a VR1 antagonist, and with a vanilloid receptor agonist, the fluorescence response is generally reduced by at least 20%, preferably at least 50% and more preferably at least 80%, as compared to cells that are contacted with the agonist in the absence of test compound. Alternatively, or in addition, compounds may be evaluated for activity using a cultured dorsal root ganglion assay as provided in Example 9 and/or an in vivo pain relief assay as provided in Example 10. Compounds provided herein preferably have a statistically significant specific effect on VR1 activity within one or more such functional assays.

Within certain embodiments, modulators provided herein do not substantially modulate ligand binding to other cell surface receptors, such as EGF receptor tyrosine kinase or the nicotinic acetylcholine receptor. In other words, such modulators do not substantially inhibit activity of a cell surface receptor such as the human epidermal growth factor (EGF) receptor tyrosine kinase or the nicotinic acetylcholine receptor (e.g., the $IC_{50}$ or $IC_{40}$ at such a receptor is preferably greater than 1 micromolar, and most preferably greater than 10 micromolar). Preferably, a modulator does not detectably inhibit EGF receptor activity or nicotinic acetylcholine receptor activity at a concentration of 0.5 micromolar, 1 micromolar or more preferably 10 micromolar. Assays for determining EGF receptor inhibition are well known in the art, and include those described by Carpenter et al. (1979) *J. Biol. Chem.* 254:4884, as well as U.S. Pat. Nos. 5,654,307 and 6,169,091, and WO 95/19774. Assays for determining nicotinic acetylcholine receptor inhibition (e.g., as $IC_{40}$) are also well known in the art, and include those described by Liu and Simon (1997) *Neuroscience Letters* 228:29.

Preferred compounds of the present invention are non-sedating. In other words, a dose of such compounds that is twice the minimum dose sufficient to provide analgesia in an animal model for determining pain relief (such as a model provided in Example 10, herein) causes only transient (i.e., lasting for no more than ½ the time that pain relief lasts) or preferably no statistically significant sedation in an animal model assay of sedation (using the method described by Fitzgerald et al. (1988) Toxicology 49(2–3):433–9). Preferably, a dose that is five times the minimum dose sufficient to provide analgesia does not produce statistically significant sedation. More preferably, a compound provided herein does not produce sedation at intravenous doses of less than 25 mg/kg (preferably less than 10 mg/kg) or at oral doses of less than 140 mg/kg (preferably less than 50 mg/kg, more preferably less than 30 mg/kg).

If desired, compounds provided herein may be evaluated for certain pharmacological properties including, but not limited to, oral bioavailability (preferred compounds are orally bioavailable to an extent allowing for therapeutically effective concentrations of the compound to be achieved at oral doses of less than 140 mg/kg, preferably less than 50 mg/kg, more preferably less than 30 mg/kg, even more preferably less than 10 mg/kg, still more preferably less than 1 mg/kg and most preferably less than 0.1 mg/kg), toxicity (a preferred compound is nontoxic when a capsaicin receptor modulatory amount is administered to a subject), side effects (a preferred compound produces side effects comparable to placebo when a therapeutically effective amount of the compound is administered to a subject), serum protein binding and in vitro and in vivo half-life (a preferred compound exhibits an in vitro half-life that is equal to an in vivo half-life allowing for Q.I.D dosing, preferably T.I.D. dosing, more preferably B.I.D. dosing, and most preferably once-a-day dosing). In addition, differential penetration of the blood brain barrier may be desirable for compounds used to treat pain by modulating CNS VR1 activity such that total daily oral doses as described above provide such modulation to a therapeutically effective extent, while low brain levels of compounds used to treat peripheral nerve mediated pain may be preferred (i.e., such doses do not provide brain (e.g., CSF) levels of the compound sufficient to significantly modulate VR1 activity). Routine assays that are well known in the art may be used to assess these properties, and identify superior compounds for a particular use. For example, assays used to predict bioavailability include transport across human intestinal cell monolayers, including Caco-2 cell monolayers. Penetration of the blood brain barrier of a compound in humans may be predicted from the brain levels of the compound in laboratory animals given the compound (e.g., intravenously). Serum protein binding may be predicted from albumin binding assays. Compound half-life is inversely proportional to the frequency of dosage of a compound. In vitro half-lives of compounds may be predicted from assays of microsomal half-life as described within Example 7, herein.

Toxicity and side effects may be assessed using any standard method. In general, the term "nontoxic" as used herein shall be understood in a relative sense and is intended to refer to any substance that has been approved by the United States Food and Drug Administration ("FDA") for administration to mammals (preferably humans) or, in keeping with established criteria is susceptible to approval by the FDA for administration to mammals (preferably humans). Toxicity may be also evaluated using the assay detecting an effect on cellular ATP production provided in Example 8. Other assays that may be used include bacterial reverse mutation assays, such as an Ames test, as well as standard teratogenicity and tumorogenicity assays. Preferably, administration of compounds provided herein at certain doses (i.e., doses yielding therapeutically effective in vivo concentrations or preferably doses of 0.01, 0.05. 0.1, 0.5, 1, 5, 10, 40, or 50 mg/kg administered parenterally or orally) does not result in prolongation of heart QT intervals (i.e., as determined by electrocardiography in guinea pigs, minipigs or dogs). When administered daily for five or preferably ten days, such doses also do not cause liver enlargement resulting in an increase of liver to body weight ratio of more than 100%, preferably not more than 75% and more preferably not more than 50% over matched controls in laboratory rodents (e.g., mice or rats). Such doses also preferably do not cause liver enlargement resulting in an increase of liver to body weight ratio of more than 50%, preferably not more than 25%, and more preferably not more than 10% over matched untreated controls in dogs or other non-rodent mammals.

Preferred compounds also do not promote substantial release of liver enzymes (e.g., ALT, LDH, or AST) from hepatocytes in vivo. Preferably the above doses do not elevate serum levels of such enzymes by more than 100%, preferably not by more than 75% and more preferably not by more than 50% over matched untreated controls in vivo in laboratory rodents. Similarly, concentrations (in culture media or other such solutions that are contacted and incubated with cells in vitro) equivalent to two-fold, preferably five-fold, and most preferably ten-fold the minimum in vivo therapeutic concentration do not cause detectable release of any of such liver enzymes from hepatocytes in vitro into culture medium above baseline levels seen in media from untreated cells.

Preferred compounds further do not exhibit significant activity as sodium ion channel blockers, exhibiting less than 15 percent inhibition, and more preferably less than 10 percent inhibition, of sodium channel specific ligand (e.g., batrachotoxin, tetrodotoxin or saxitoxin) binding when present at a concentration of 4 µM or less. Assays for sodium channel specific ligand binding are well known in the art. In addition, preferred compounds do not exhibit significant androgen antagonist activity (e.g., in vivo, in a Hershberger assay, or in vitro, in an assay such as that described by Nellemann et al. (2001) Toxicology 163(1):29–38). Preferred compounds exhibit less than a 15% inhibition, more preferably less than a 10% inhibition, and most preferably less than 5% inhibition of androgen receptor activation in the in vitro assay when present at concentrations of 4 µM or less. By significant activity is meant results varying from control at the p<0.1 level or more preferably at the p<0.05 level of significance as measured using a standard parametric assay of statistical significance such as a student's T test.

For detection purposes, as discussed in more detail below, compounds provided herein may be isotopically-labeled or radiolabeled. Accordingly, compounds recited in Formula I may have one or more atoms replaced by an atom of the same element having an atomic mass or mass number different from the atomic mass or mass number usually found in nature. Examples of isotopes that can be present in the compounds provided herein include isotopes of hydrogen, carbon, nitrogen, oxygen, phosphorous, fluorine and chlorine, such as $^2$H, $^3$H, $^{11}$C, $^{13}$C, $^{14}$C, $^{15}$N, $^{18}$O, $^{17}$O, $^{31}$P, $^{32}$P, $^{35}$S, $^{18}$F and $^{36}$Cl. In addition, substitution with heavy isotopes such as deuterium (i.e., $^2$H) can afford certain therapeutic advantages resulting from greater metabolic stability, for example increased in vivo half-life or reduced dosage requirements and, hence, may be preferred in some circumstances.

Preparation of VR1 Modulators

Substituted quinazolin-4-ylamine analogues may generally be prepared using standard synthetic methods. In general, starting materials are commercially available from suppliers such as Sigma-Aldrich Corp. (St. Louis, Mo.), or may be synthesized from commercially available precursors using established protocols. By way of example, a synthetic route similar to that shown in any of Schemes 1–23 may be used, together with synthetic methods known in the art of synthetic organic chemistry, or variations thereon as appreciated by those skilled in the art. "R," in the following schemes, refers to any group consistent with the description of the compounds provided herein.

In the Schemes that follow, the term "catalyst" refers to a suitable transition metal catalyst such as, but not limited to, tetrakis(triphenylphosphine)palladium(0) or palladium(II) acetate. In addition, the catalytic systems may include ligands such as, but not limited to, 2-(Dicyclohexylphosphino)biphenyl and tri-tert-butylphosphine, and may also include a base such as $K_3PO_4$, $Na_2CO_3$ or sodium or potassium tert-butoxide. Transition metal-catalyzed reactions can be carried out at ambient or elevated temperatures using various inert solvents including, but not limited to, toluene, dioxane, DMF, N-methylpyrrolidinone, ethyleneglycol dimethyl ether, diglyme and acetonitrile. When used in conjunction with suitable metallo-aryl reagents, transition metal-catalyzed (hetero)aryl-aryl coupling reactions can be used to prepare the compounds encompassed in general structures 1C, 2A and 2F, 3C, 5A and 5H, 14C, 15A, 16D, 18D, 19C, 20C and 22C. Commonly employed reagent/catalyst pairs include aryl boronic acid/palladium(0) (Suzuki reaction; Miyaura and Suzuki (1995) Chemical Reviews 95:2457) and aryl trialkylstannane/palladium(0) (Stille reaction; T. N. Mitchell, Synthesis (1992) 803), arylzinc/palladium(0) and aryl Grignard/nickel(II).

The term "reduce" refers to the process of reducing a nitro functionality to an amino functionality. This transformation can be carried out in a number of ways well known to those skilled in the art of organic synthesis including, but not limited to, catalytic hydrogenation, reduction with $SnCl_2$ and reduction with titanium trichloride. For an overview of reduction methods see: Hudlicky, M. (1996) Reductions in Organic Chemistry, ACS Monograph 188.

The term "activate" refers to a synthetic transformation in which a carbonyl of an amide moiety is converted to a suitable leaving group (L). Such a transformation can be used, for example, to prepare compounds of general structure 1F, 2E, 2G, 5F, 11A, 14I, 15G, 16L, 17H, 19I, 20I, 21C and 23H. Reagents suitable for carrying out this transformation are well known to those skilled in the art of organic synthesis and include, but are not limited to, $SOCl_2$, $POCl_3$ and triflic anhydride.

The term "oxidize" refers to a synthetic transformation wherein a methyl group is converted to a carboxylic acid functionality. Such a transformation can be used, for example, to prepare compounds such as 10E, 11-C, 14E, 19E and 22D. Various reagents familiar to those skilled in the art of organic synthesis may be used to carry out this transformation including, but not limited to, $KMnO_4$ in basic media (e.g., NaOH solution or aqueous pyridine) and $K_2Cr_2O_7$ in acidic media (e.g., $H_2SO_4$).

The term "cyclize" refers to a synthetic transformation in which ortho-amino-benzoic acids, ortho-amino-benzoic esters, and ortho-amino-benzonitriles are converted to the corresponding 3H-Quinazolin-4-ones. Methods for effecting the cyclization of ortho-amino-benzonitriles include, but are not limited to, reaction with refluxing formic acid containing sodium acetate. Methods for effecting the cyclization of ortho-amino-benzoic acids include, but are not limited to, reaction with formamide at elevated temperatures or reaction with formamidine acetate in an inert solvent, also at elevated temperatures. Methods for effecting the cyclization of ortho-amino-benzoic esters include, but are not limited to, reaction with formamidine acetate at elevated temperature in an inert solvent.

In Scheme 8, "$H_2N$-Prot" refers to a protected amino functionality, such as 4-methoxybenzylamine, and "deprotect" refers to a chemical method by which such a protecting group can be removed. For an overview of protection and deprotection methods as used by those skilled in the art of organic synthesis, see: Greene, T. and Wuts, P. *Protective Groups in Organic Synthesis*, 3rd ed., John Wiley and Sons, 1999.

In Scheme 9, the term "nucleophile" refers to a primary or secondary amine, or an alkoxide.

In Scheme 19, the term "deprotection" refers to the process of cleaving the C—O bond of a benzylic ether to give a "deprotected" alcohol using various methods familiar to those who are skilled in the art of organic synthesis. This is exemplified in Scheme 19 in which compounds of general structure 19I can be converted to deprotected alcohols of general structure 19J. Methods to effect this transformation include, but are not limited to, hydrogenolysis using hydrogen gas and an appropriate catalyst system such as palladium on carbon or Raney nickel. For an overview of protection and deprotection methods as used by those skilled in the art of organic synthesis, see: Greene, T. and Wuts, P. *Protective Groups in Organic Synthesis*, 3rd ed., John Wiley and Sons, 1999.

The term "demethylation" refers to the cleavage of the Me-O bond in a methyl ether functionality as exemplified by the conversion on 16D to 16E. This transformation can be carried out in a variety of ways familiar to those skilled in the art of organic synthesis including, but not limited to, treatment with HBr, treatment with Lewis acid/nucleophile combinations, Trimethylsilyl iodide, etc.

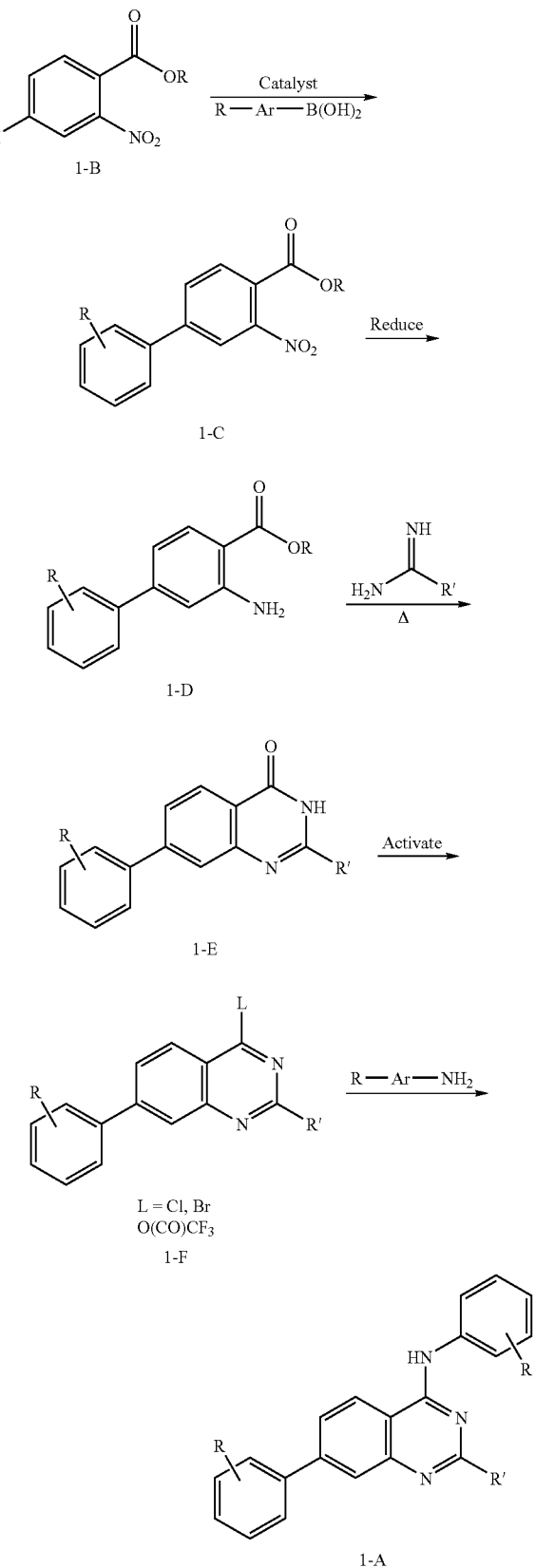

Scheme 2
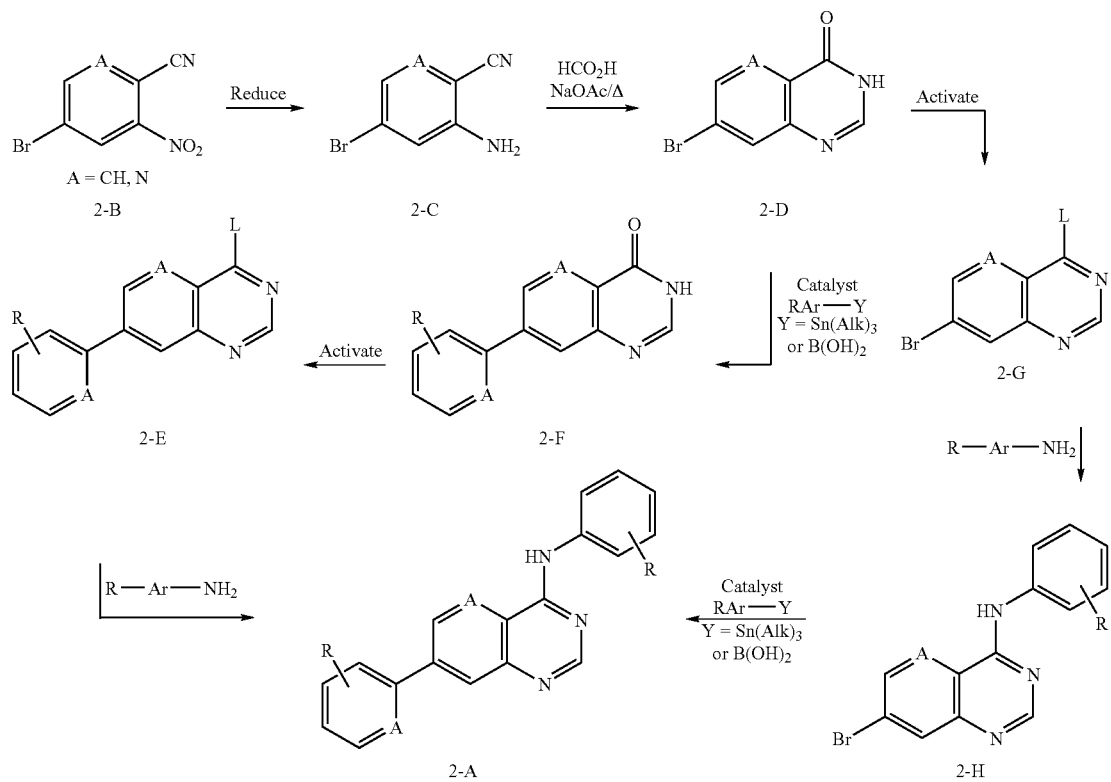
Scheme 3
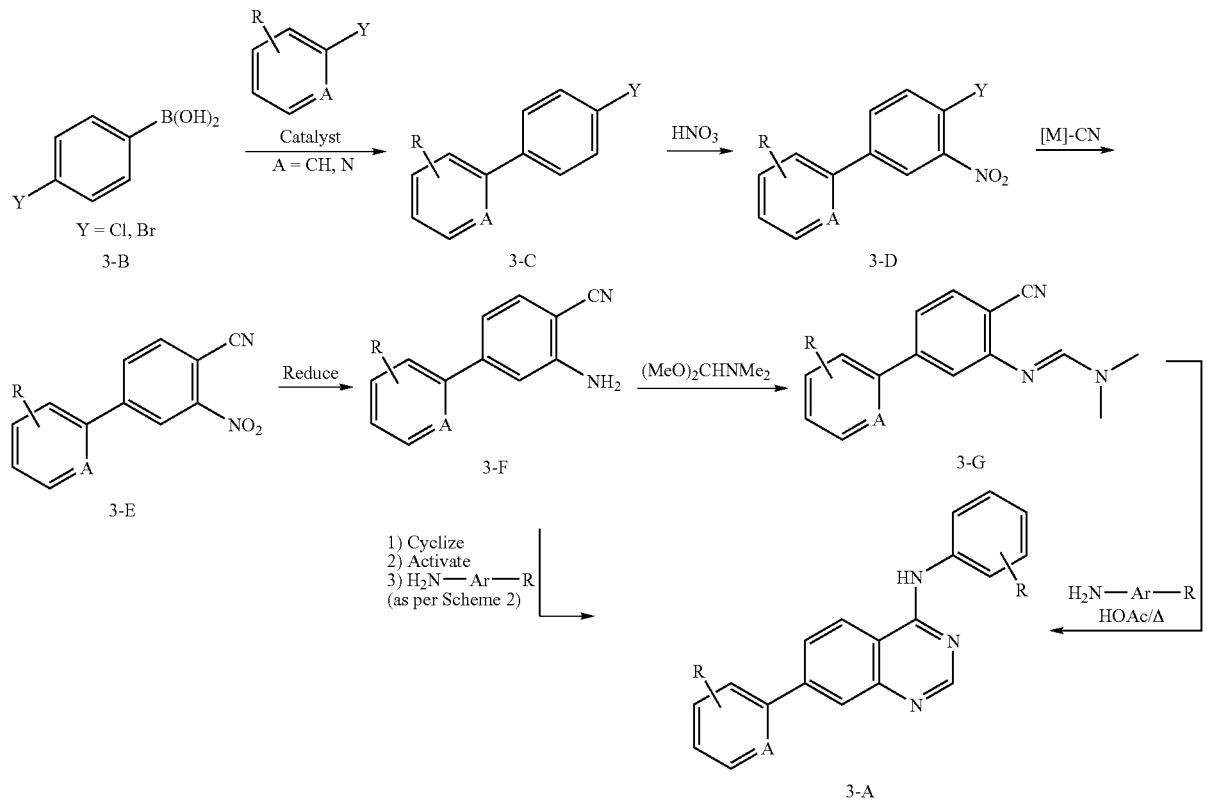

Scheme 4
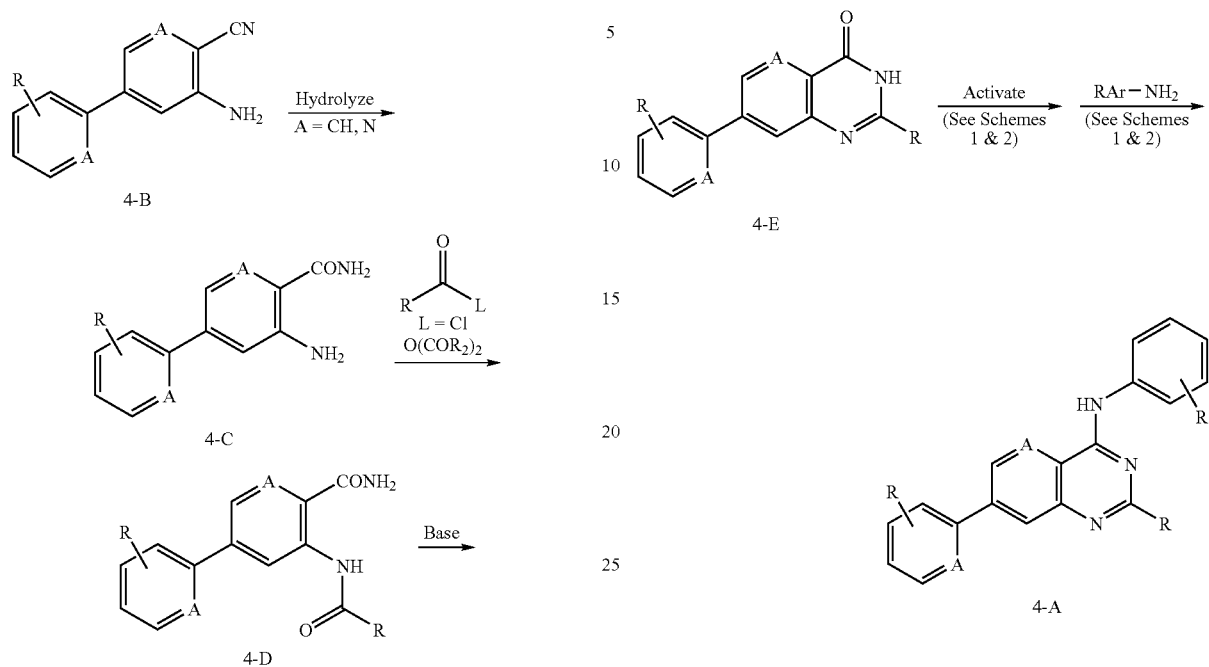
Scheme 5
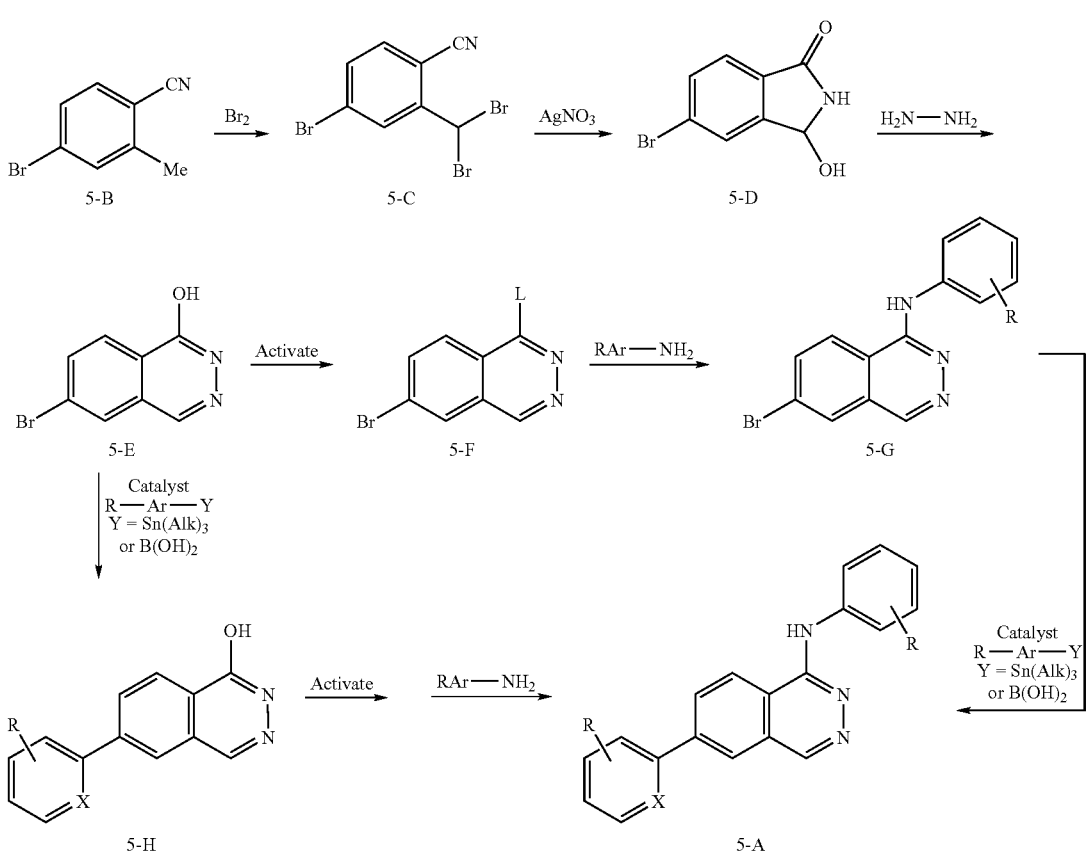

Scheme 6
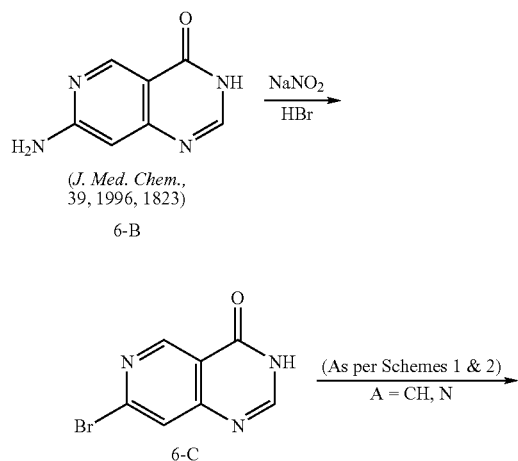
(*J. Med. Chem.*, 39, 1996, 1823)
Scheme 7
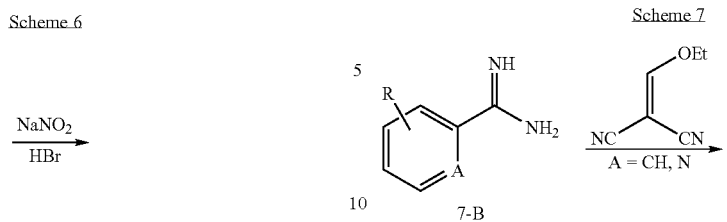
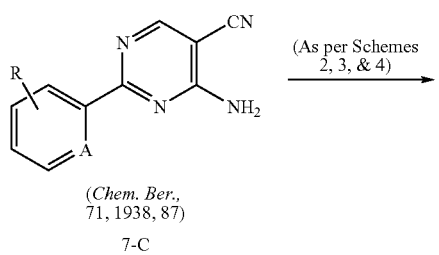
(*Chem. Ber.*, 71, 1938, 87)
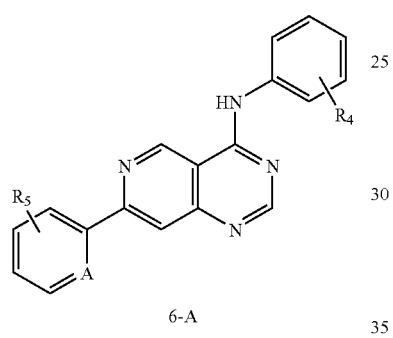
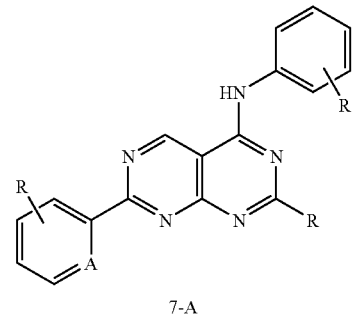
Scheme 8
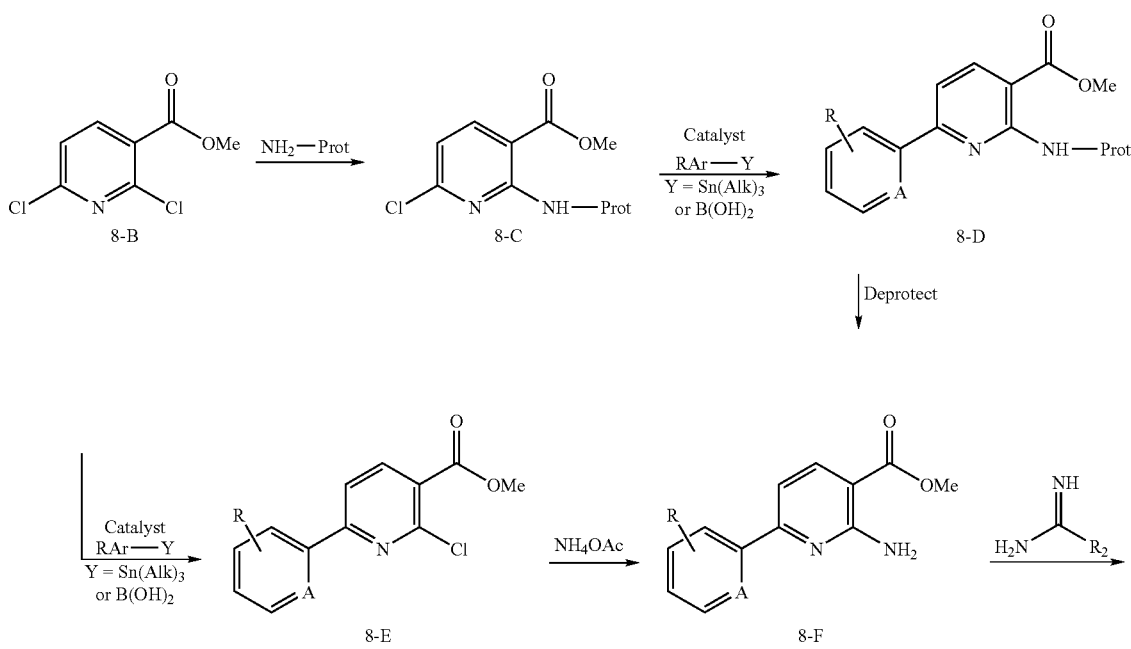

-continued
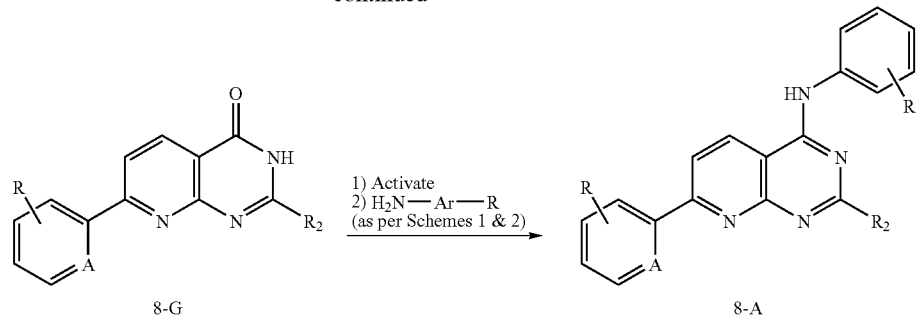
8-G → 8-A
1) Activate
2) $H_2N\text{—}Ar\text{—}R$ (as per Schemes 1 & 2)
Scheme 9
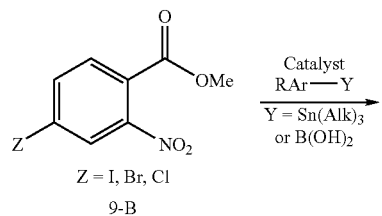
$Z = I, Br, Cl$
9-B
Catalyst
$RAr\text{—}Y$
$Y = Sn(Alk)_3$ or $B(OH)_2$
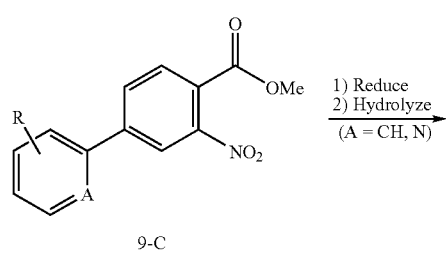
9-C
1) Reduce
2) Hydrolyze
$(A = CH, N)$
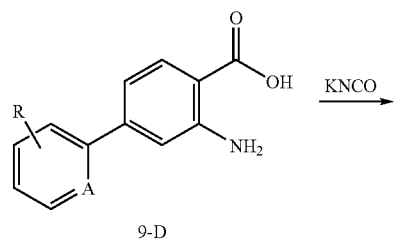
9-D
KNCO →
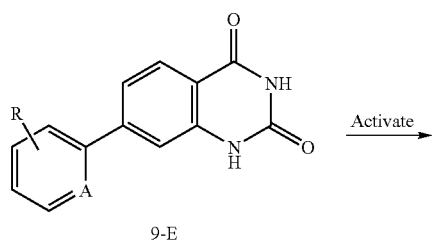
9-E
Activate →
-continued
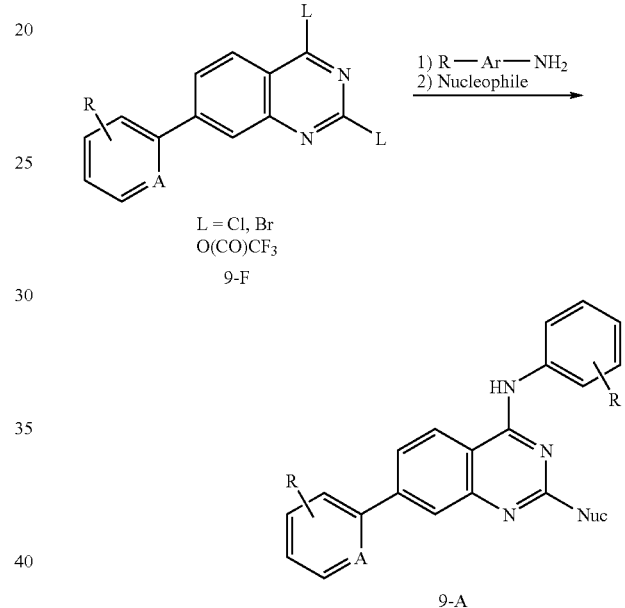
9-F
$L = Cl, Br$
$O(CO)CF_3$
1) $R\text{—}Ar\text{—}NH_2$
2) Nucleophile
9-A
Scheme 10
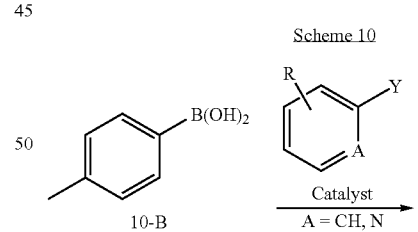
10-B
Catalyst
$A = CH, N$
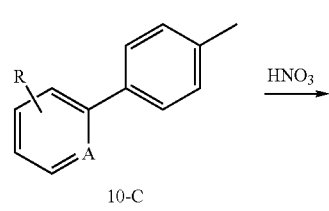
10-C
$HNO_3$ →

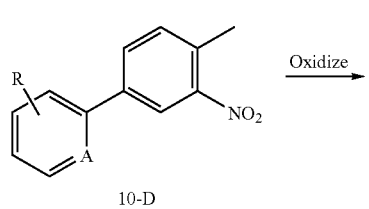
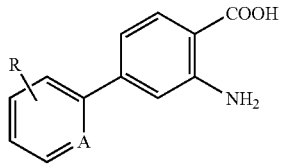
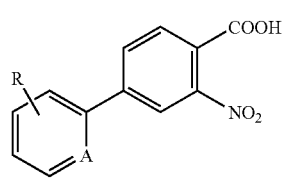
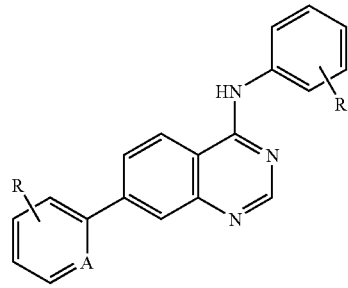
Scheme 11
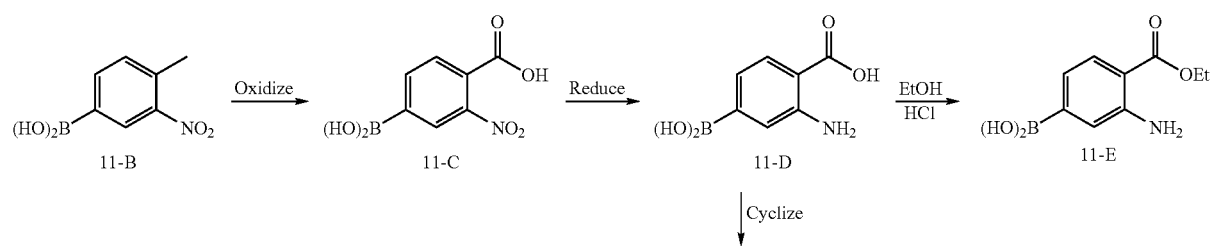
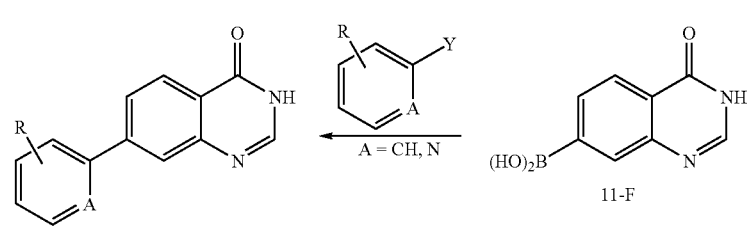
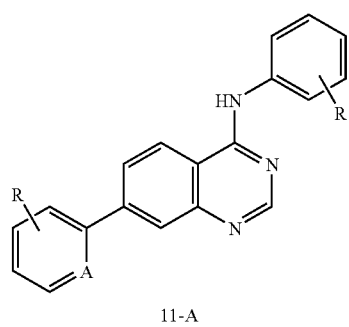

Scheme 12
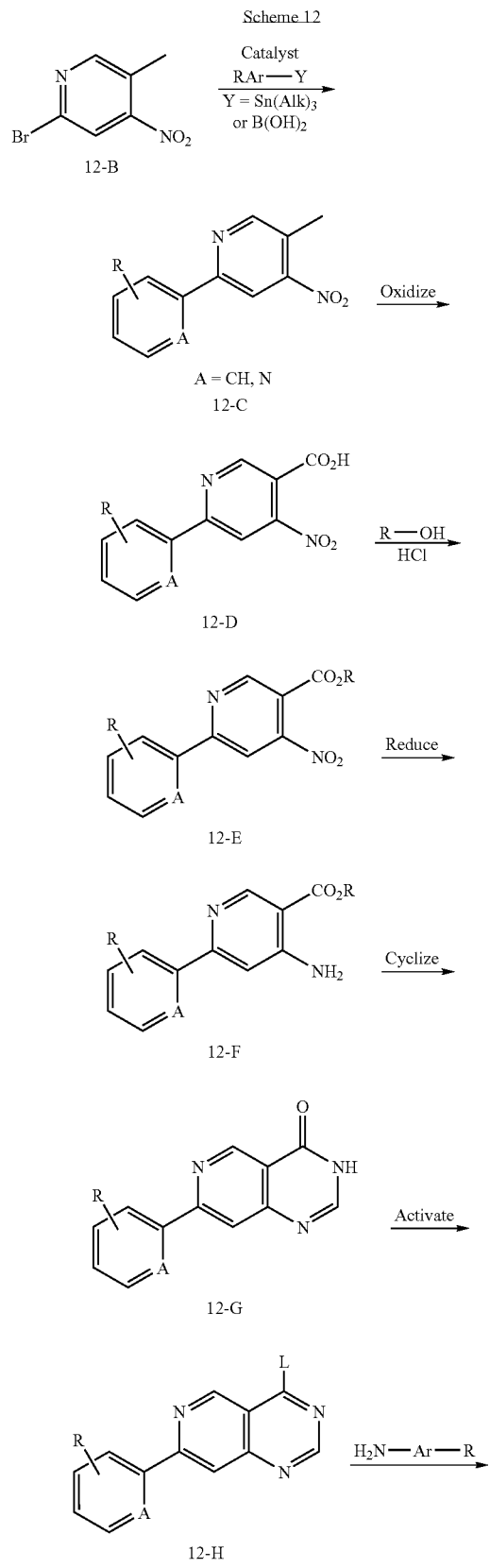
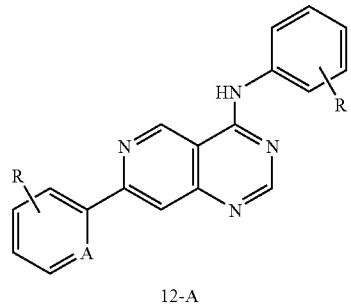
12-A
Scheme 13
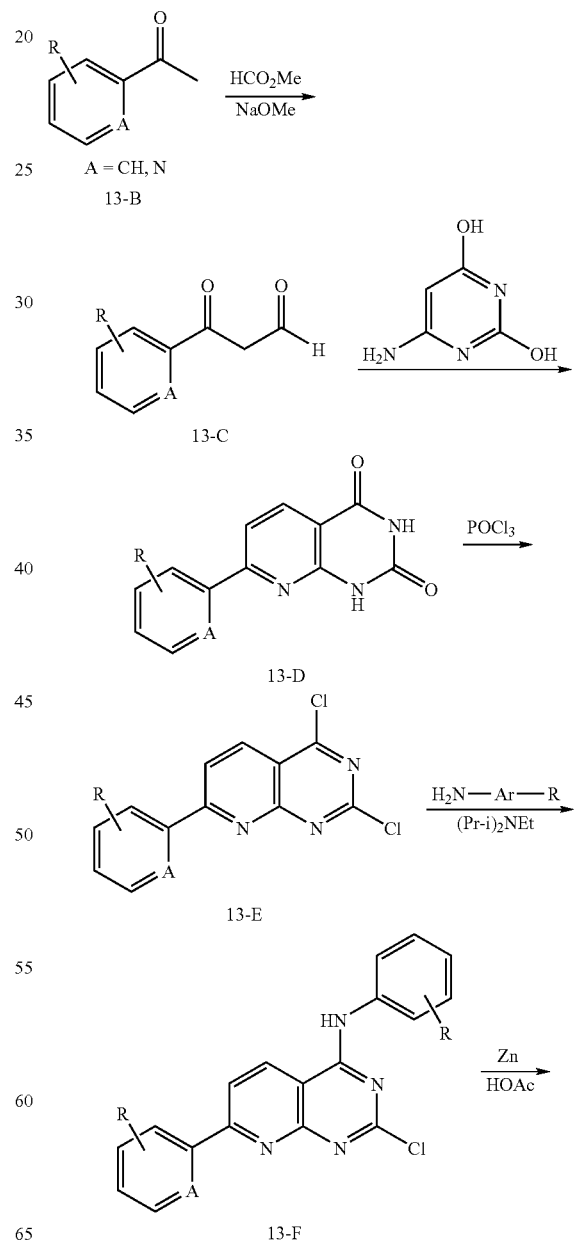

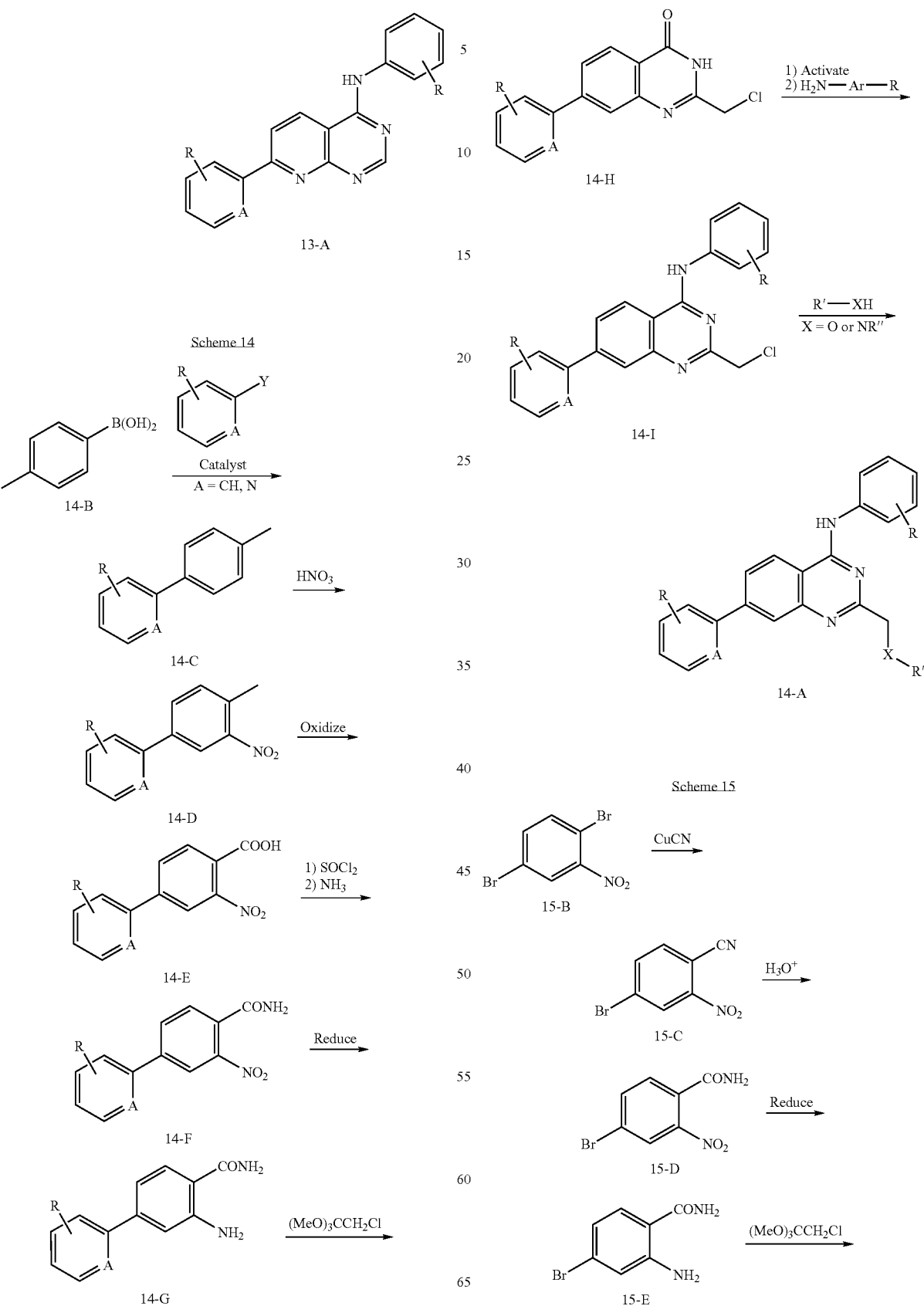

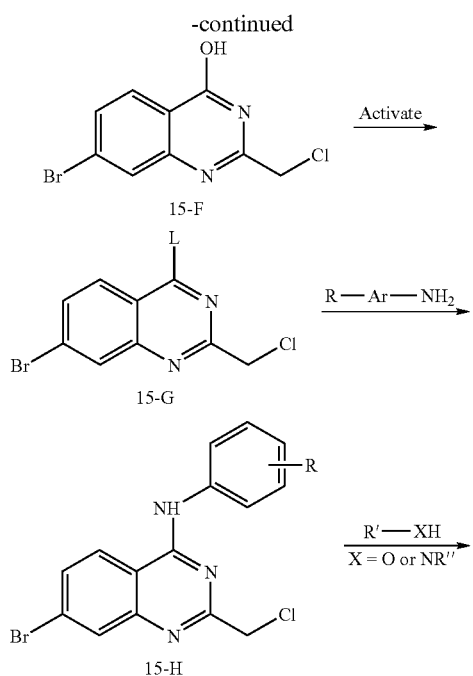
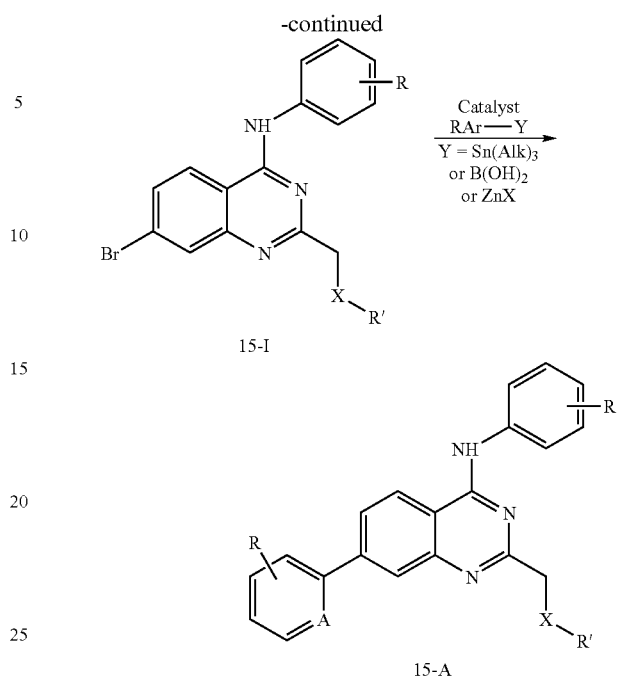
Scheme 16
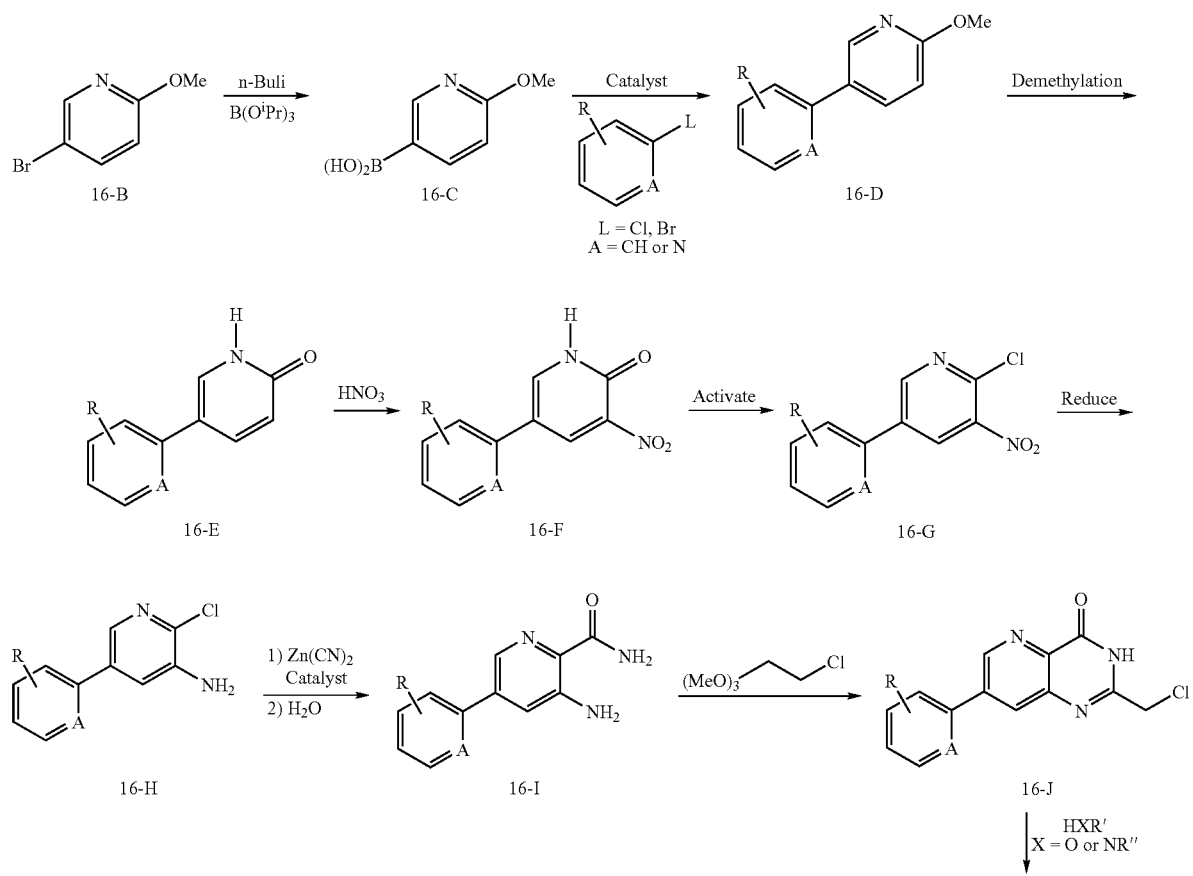

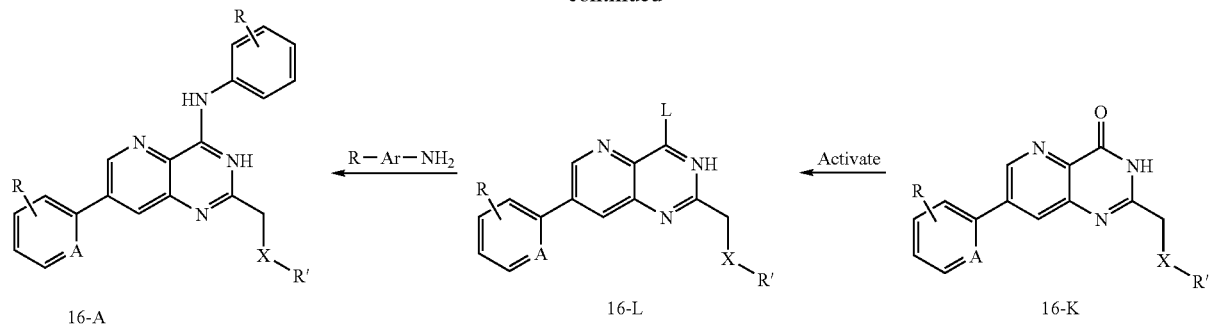
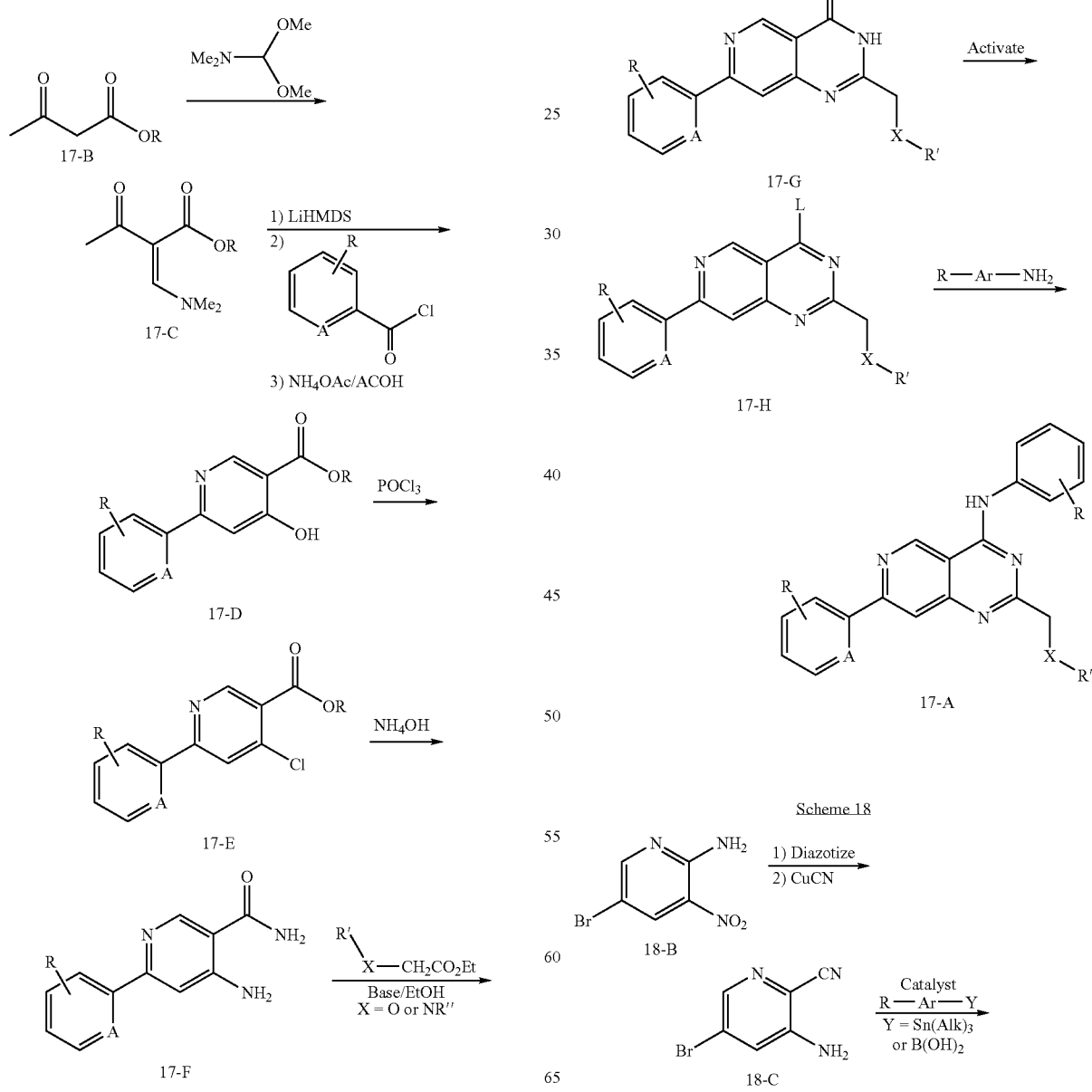

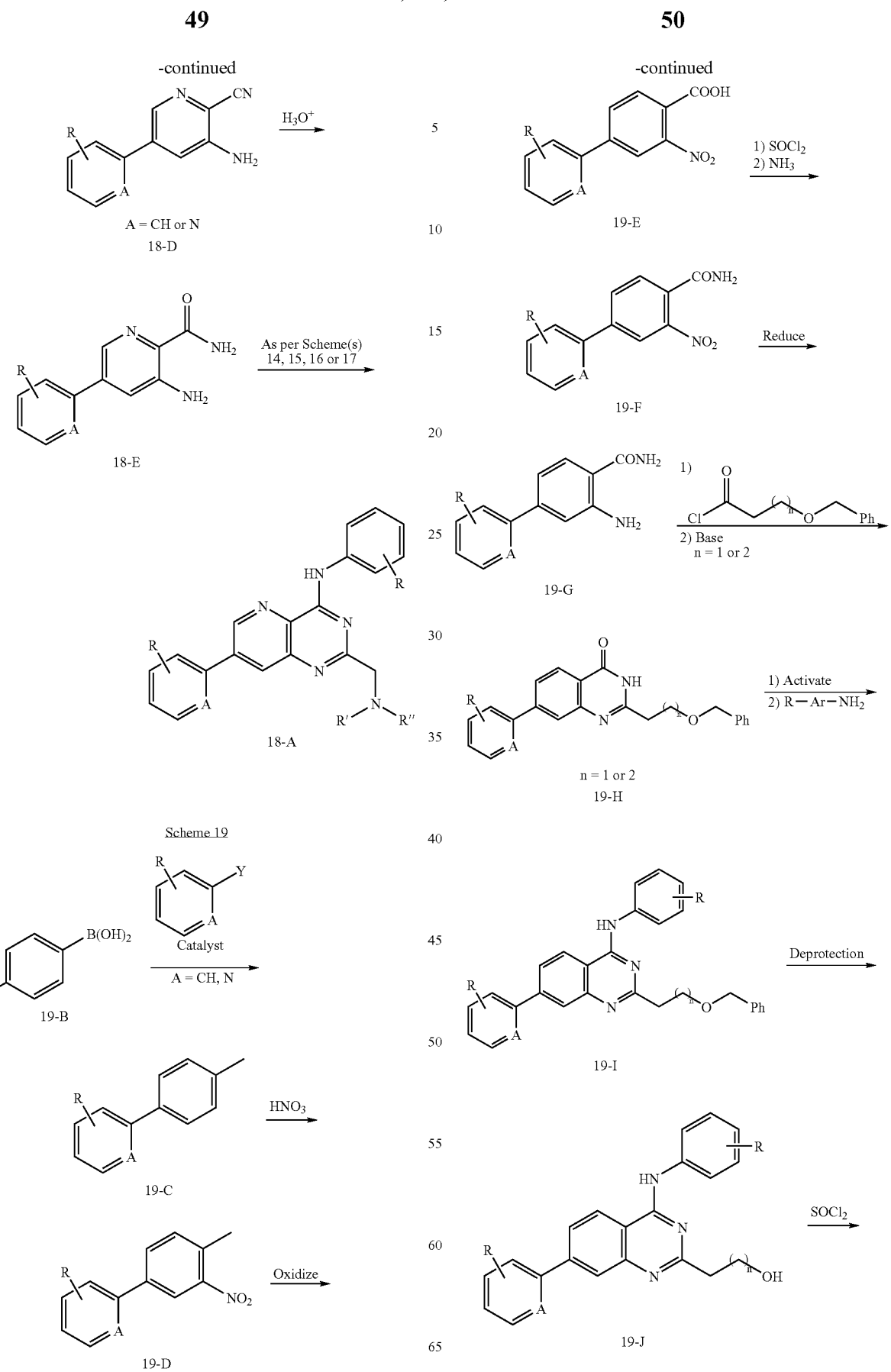

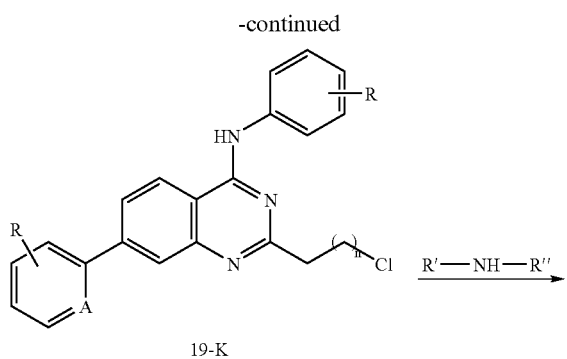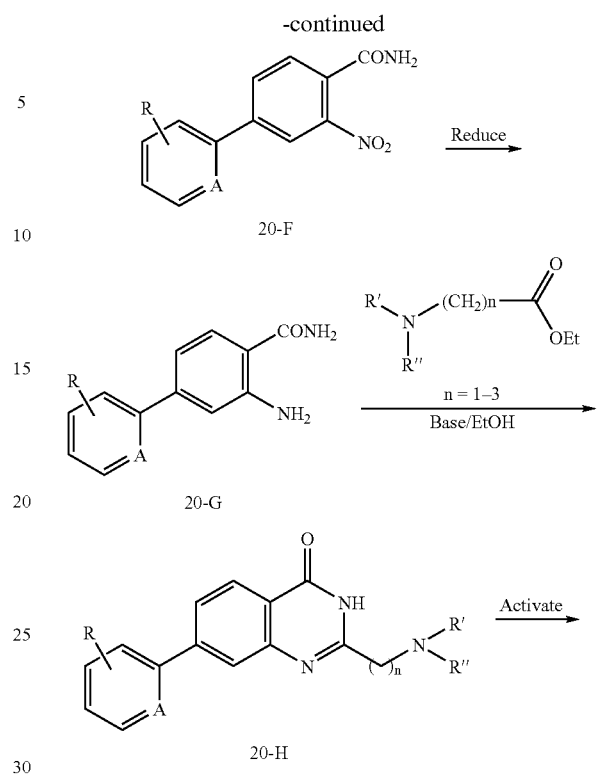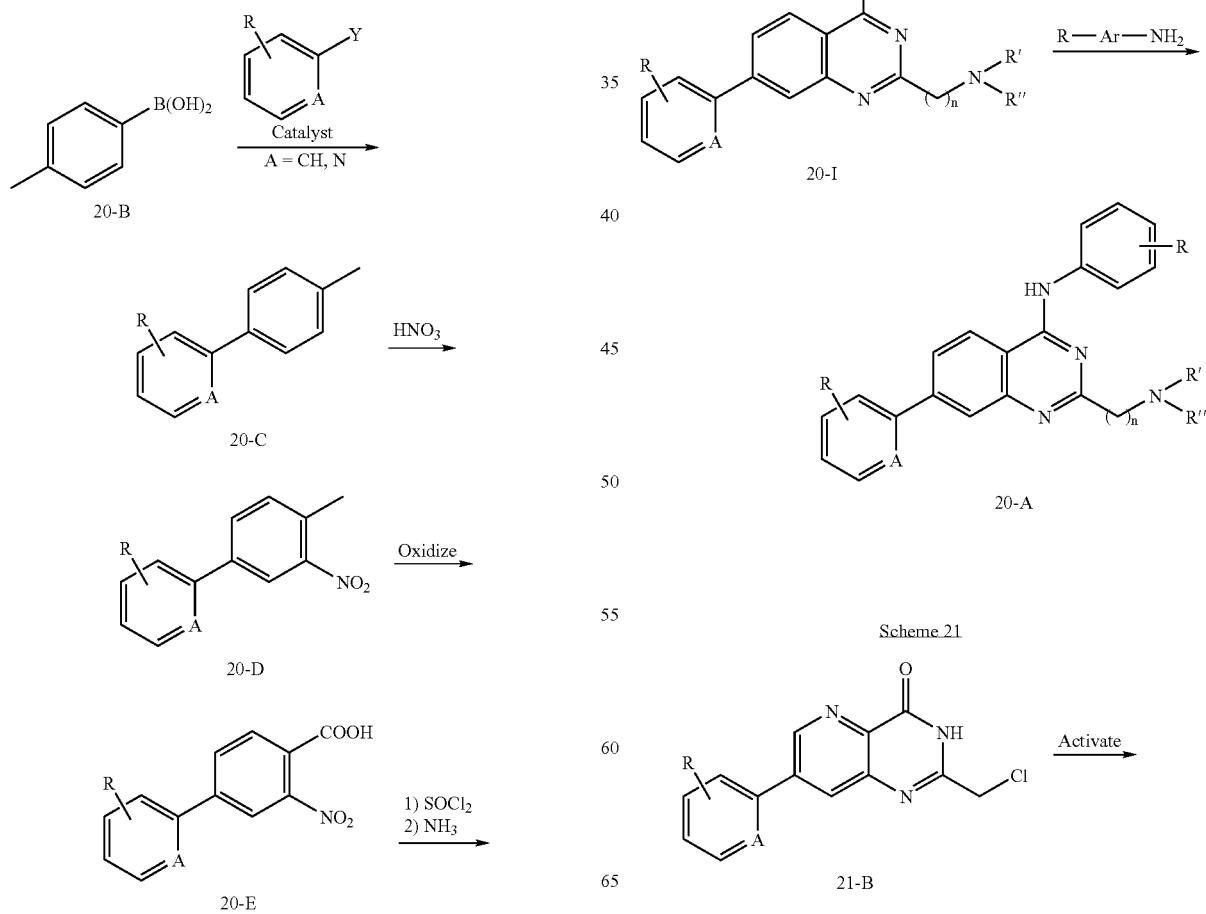

-continued
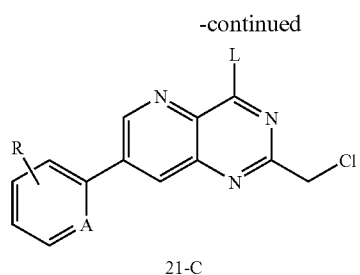
21-C
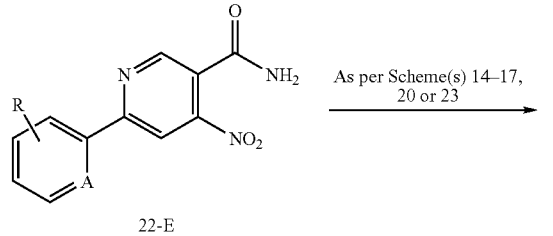
22-E
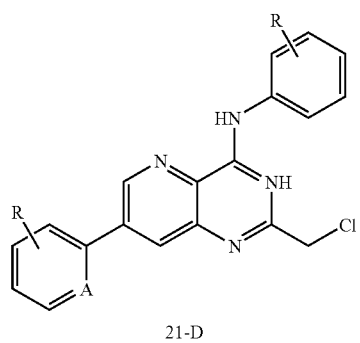
21-D
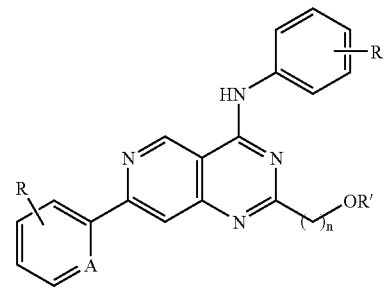
22-A
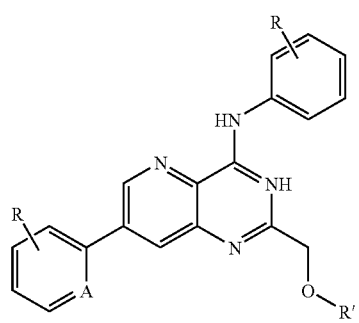
21-A
Scheme 23
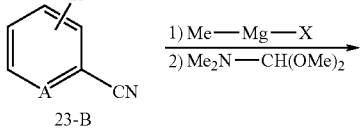
23-B
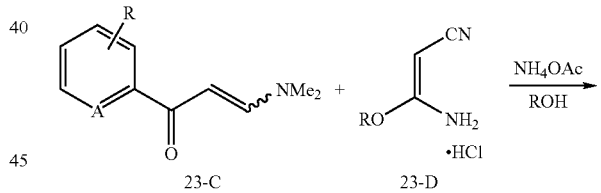
23-C    23-D
Scheme 22
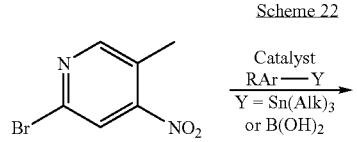
Eur. J. Med. Chem.
-Chim. Ther.,
1977, 12(6), 541-7
22-B
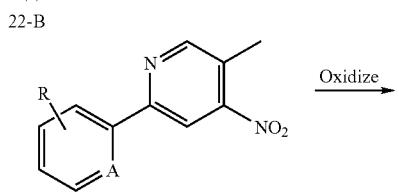
A = CH, N
22-C
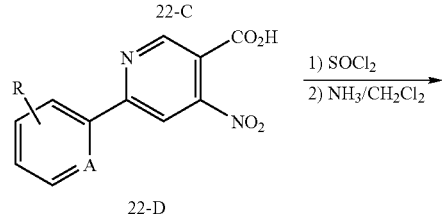
22-D
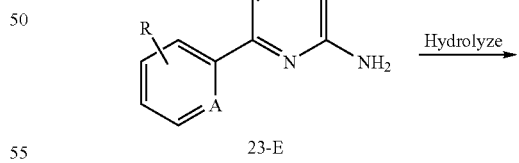
23-E
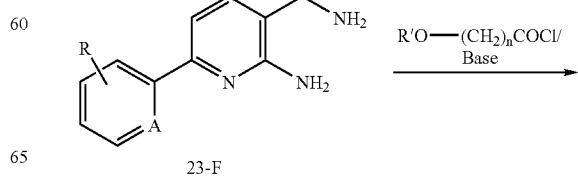
23-F

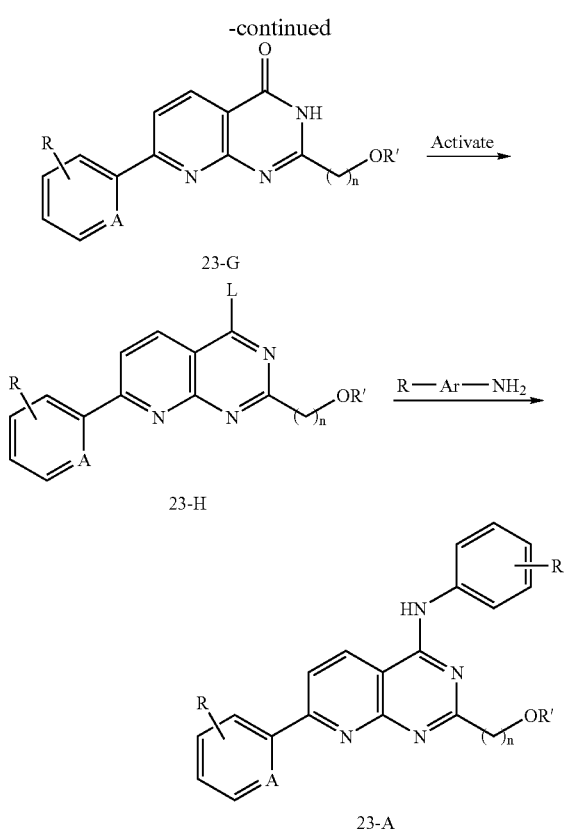

In certain embodiments, a VR1 modulator may contain one or more asymmetric carbon atoms, so that the compound can exist in different stereoisomeric forms. Such forms can be, for example, racemates or optically active forms. As noted above, all stereoisomers are encompassed by the present invention. Nonetheless, it may be desirable to obtain single enantiomers (i.e., optically active forms). Standard methods for preparing single enantiomers include asymmetric synthesis and resolution of the racemates. Resolution of the racemates can be accomplished, for example, by conventional methods such as crystallization in the presence of a resolving agent, or chromatography using, for example a chiral HPLC column.

As noted above, the present invention encompasses pharmaceutically acceptable salts of the compounds described herein. As used herein, a "pharmaceutically acceptable salt" is an acid or base salt that is generally considered in the art to be suitable for use in contact with the tissues of human beings or animals without excessive toxicity, irritation, allergic response, or other problem or complication. Such salts include mineral and organic acid salts of basic residues such as amines, as well as alkali or organic salts of acidic residues such as carboxylic acids. Specific pharmaceutical salts include, but are not limited to, salts of acids such as hydrochloric, phosphoric, hydrobromic, malic, glycolic, fumaric, sulfuric, sulfamic, sulfanilic, formic, toluenesulfonic, methanesulfonic, benzene sulfonic, ethane disulfonic, 2-hydroxyethylsulfonic, nitric, benzoic, 2-acetoxybenzoic, citric, tartaric, lactic, stearic, salicylic, glutamic, ascorbic, pamoic, succinic, fumaric, maleic, propionic, hydroxymaleic, hydroiodic, phenylacetic, alkanoic such as acetic, HOOC—$(CH_2)_n$—COOH where n is 0–4, and the like. Similarly, pharmaceutically acceptable cations include, but are not limited to sodium, potassium, calcium, aluminum, lithium and ammonium. Those of ordinary skill in the art will recognize further pharmaceutically acceptable salts for the compounds provided herein, including those listed by *Remington's Pharmaceutical Sciences*, 17th ed., Mack Publishing Company, Easton, Pa., p. 1418 (1985). Accordingly, the present disclosure should be construed to include all pharmaceutically acceptable salts of the compounds specifically recited.

A wide variety of synthetic procedures are available for the preparation of pharmaceutically acceptable salts. In general, a pharmaceutically acceptable salt can be synthesized from a parent compound that contains a basic or acidic moiety by any conventional chemical method. Briefly, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred.

Prodrugs of the compounds provided herein may be prepared by modifying functional groups present in the compounds in such a way that the modifications are cleaved to the parent compounds. Prodrugs include compounds wherein hydroxy, amine or sulfhydryl groups are bonded to any group that, when administered to a mammalian subject, cleaves to form a free hydroxyl, amino, or sulfhydryl group, respectively. Examples of prodrugs include, but are not limited to, acetate, formate and benzoate derivatives of alcohol and amine functional groups within the compounds provided herein. Preferred prodrugs include acylated derivatives. Those of ordinary skill in the art will recognize various synthetic methods that may be employed to prepare prodrugs of the compounds provided herein.

Compounds may be radiolabeled by carrying out their synthesis using precursors comprising at least one atom that is a radioisotope. Each radioisotope is preferably carbon (e.g., $^{14}C$), hydrogen (e.g., $^{3}H$), sulfur (e.g., $^{35}S$), or iodine (e.g., $^{125}I$). Tritium labeled compounds may also be prepared catalytically via platinum-catalyzed exchange in tritiated acetic acid, acid-catalyzed exchange in tritiated trifluoroacetic acid, or heterogeneous-catalyzed exchange with tritium gas using the compound as substrate. In addition, certain precursors may be subjected to tritium-halogen exchange with tritium gas, tritium gas reduction of unsaturated bonds, or reduction using sodium borotritide, as appropriate. Preparation of radiolabeled compounds may be conveniently performed by a radioisotope supplier specializing in custom synthesis of radiolabeled probe compounds.

Pharmaceutical Compostions

The present invention also provides pharmaceutical compositions comprising one or more VR1 modulators, together with at least one physiologically acceptable carrier or excipient. Pharmaceutical compositions may comprise, for example, one or more of water, buffers (e.g., neutral buffered saline or phosphate buffered saline), ethanol, mineral oil, vegetable oil, dimethylsulfoxide, carbohydrates (e.g., glucose, mannose, sucrose or dextrans), mannitol, proteins, adjuvants, polypeptides or amino acids such as glycine, antioxidants, chelating agents such as EDTA or glutathione and/or preservatives. As noted above, other active ingredients may (but need not) be included in the pharmaceutical compositions provided herein.

Pharmaceutical compositions may be formulated for any appropriate manner of administration, including, for example, topical, oral, nasal, rectal or parenteral administration. The term parenteral as used herein includes subcutaneous, intradermal, intravascular (e.g., intravenous), intramuscular, spinal, intracranial, intrathecal and intraperitoneal injection, as well as any similar injection or infusion technique. In certain embodiments, compositions in a form suitable for oral use are preferred. Such forms include, for example, tablets, troches, lozenges, aqueous or oily suspensions, dispersible powders or granules, emulsion, hard or soft capsules, or syrups or elixirs. Within yet other embodiments, compositions of the present invention may be formulated as a lyophilizate. Formulation for topical administration may be preferred for certain conditions (e.g., in the treatment of skin conditions such as burns or itch).

Compositions intended for oral use may further comprise one or more components such as sweetening agents, flavoring agents, coloring agents and/or preserving agents in order to provide appealing and palatable preparations. Tablets contain the active ingredient in admixture with physiologically acceptable excipients that are suitable for the manufacture of tablets. Such excipients include, for example, inert diluents (e.g., calcium carbonate, sodium carbonate, lactose, calcium phosphate or sodium phosphate), granulating and disintegrating agents (e.g., corn starch or alginic acid), binding agents (e.g., starch, gelatin or acacia) and lubricating agents (e.g., magnesium stearate, stearic acid or talc). The tablets may be uncoated or they may be coated by known techniques to delay disintegration and absorption in the gastrointestinal tract and thereby provide a sustained action over a longer period. For example, a time delay material such as glyceryl monosterate or glyceryl distearate may be employed.

Formulations for oral use may also be presented as hard gelatin capsules wherein the active ingredient is mixed with an inert solid diluent (e.g., calcium carbonate, calcium phosphate or kaolin), or as soft gelatin capsules wherein the active ingredient is mixed with water or an oil medium (e.g., peanut oil, liquid paraffin or olive oil).

Aqueous suspensions contain the active material(s) in admixture with excipients suitable for the manufacture of aqueous suspensions. Such excipients include suspending agents (e.g., sodium carboxymethylcellulose, methylcellulose, hydropropylmethylcellulose, sodium alginate, polyvinylpyrrolidone, gum tragacanth and gum acacia); and dispersing or wetting agents (e.g., naturally-occurring phosphatides such as lecithin, condensation products of an alkylene oxide with fatty acids such as polyoxyethylene stearate, condensation products of ethylene oxide with long chain aliphatic alcohols such as heptadecaethyleneoxycetanol, condensation products of ethylene oxide with partial esters derived from fatty acids and a hexitol such as polyoxyethylene sorbitol monooleate, or condensation products of ethylene oxide with partial esters derived from fatty acids and hexitol anhydrides such as polyethylene sorbitan monooleate). Aqueous suspensions may also comprise one or more preservatives, for example ethyl, or n-propyl p-hydroxybenzoate, one or more coloring agents, one or more flavoring agents, and one or more sweetening agents, such as sucrose or saccharin.

Oily suspensions may be formulated by suspending the active ingredients in a vegetable oil (e.g., arachis oil, olive oil, sesame oil or coconut oil) or in a mineral oil such as liquid paraffin. The oily suspensions may contain a thickening agent such as beeswax, hard paraffin or cetyl alcohol. Sweetening agents such as those set forth above, and/or flavoring agents may be added to provide palatable oral preparations. Such suspensions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, such as sweetening, flavoring and coloring agents, may also be present.

Pharmaceutical compositions may also be in the form of oil-in-water emulsions. The oily phase may be a vegetable oil (e.g., olive oil or arachis oil), a mineral oil (e.g., liquid paraffin) or a mixture thereof. Suitable emulsifying agents include naturally-occurring gums (e.g., gum acacia or gum tragacanth), naturally-occurring phosphatides (e.g., soy bean, lecithin, and esters or partial esters derived from fatty acids and hexitol), anhydrides (e.g., sorbitan monoleate) and condensation products of partial esters derived from fatty acids and hexitol with ethylene oxide (e.g., polyoxyethylene sorbitan monoleate). An emulsion may also comprise one or more sweetening and/or flavoring agents.

Syrups and elixirs may be formulated with sweetening agents, such as glycerol, propylene glycol, sorbitol or sucrose. Such formulations may also comprise one or more demulcents, preservatives, flavoring agents and/or coloring agents.

Formulations for topical administration typically comprise a topical vehicle combined with active agent(s), with or without additional optional components. Suitable topical vehicles and additional components are well known in the art, and it will be apparent that the choice of a vehicle will depend on the particular physical form and mode of delivery. Topical vehicles include water; organic solvents such as alcohols (e.g., ethanol or isopropyl alcohol) or glycerin; glycols (e.g., butylene, isoprene or propylene glycol); aliphatic alcohols (e.g., lanolin); mixtures of water and organic solvents and mixtures of organic solvents such as alcohol and glycerin; lipid-based materials such as fatty acids, acylglycerols (including oils, such as mineral oil, and fats of natural or synthetic origin), phosphoglycerides, sphingolipids and waxes; protein-based materials such as collagen and gelatin; silicone-based materials (both non-volatile and volatile); and hydrocarbon-based materials such as microsponges and polymer matrices. A composition may further include one or more components adapted to improve the stability or effectiveness of the applied formulation, such as stabilizing agents, suspending agents, emulsifying agents, viscosity adjusters, gelling agents, preservatives, antioxidants, skin penetration enhancers, moisturizers and sustained release materials. Examples of such components are described in Martindale—The Extra Pharmacopoeia (Pharmaceutical Press, London 1993) and Martin (ed.), Remington's Pharmaceutical Sciences. Formulations may comprise microcapsules, such as hydroxymethylcellulose or gelatin-microcapsules, liposomes, albumin microspheres, microemulsions, nanoparticles or nanocapsules.

A topical formulation may be prepared in a variety of physical forms including, for example, solids, pastes, creams, foams, lotions, gels, powders, aqueous liquids and emulsions. The physical appearance and viscosity of such forms can be governed by the presence and amount of emulsifier(s) and viscosity adjuster(s) present in the formulation. Solids are generally firm and non-pourable and commonly are formulated as bars or sticks, or in particulate form; solids can be opaque or transparent, and optionally can contain solvents, emulsifiers, moisturizers, emollients, fragrances, dyes/colorants, preservatives and other active ingredients that increase or enhance the efficacy of the final product. Creams and lotions are often similar to one another, differing mainly in their viscosity; both lotions and creams may be opaque, translucent or clear and often contain emulsifiers, solvents, and viscosity adjusting agents, as well as moisturizers, emollients, fragrances, dyes/colorants, preservatives and other active ingredients that increase or enhance the efficacy of the final product. Gels can be prepared with a range of viscosities, from thick or high viscosity to thin or low viscosity. These formulations, like those of lotions and creams, may also contain solvents, emulsifiers, moisturizers, emollients, fragrances, dyes/colorants, preservatives and other active ingredients that increase or enhance the efficacy of the final product. Liquids are thinner than creams, lotions, or gels and often do not contain emulsifiers. Liquid topical products often contain solvents, emulsifiers, moisturizers, emollients, fragrances, dyes/colorants, preservatives and other active ingredients that increase or enhance the efficacy of the final product.

Suitable emulsifiers for use in topical formulations include, but are not limited to, ionic emulsifiers, cetearyl alcohol, non-ionic emulsifiers like polyoxyethylene oleyl ether, PEG-40 stearate, ceteareth-12, ceteareth-20, ceteareth-30, ceteareth alcohol, PEG-100 stearate and glyceryl stearate. Suitable viscosity adjusting agents include, but are not limited to, protective colloids or non-ionic gums such as hydroxyethylcellulose, xanthan gum, magnesium aluminum silicate, silica, microcrystalline wax, beeswax, paraffin, and cetyl palmitate. A gel composition may be formed by the addition of a gelling agent such as chitosan, methyl cellulose, ethyl cellulose, polyvinyl alcohol, polyquaterniums, hydroxyethylcellulose, hydtoxypropylcellulose, hydroxypropylmethylcellulose, carbomer or ammoniated glycyrrhizinate. Suitable surfactants include, but are not limited to, nonionic, amphoteric, ionic and anionic surfactants. For example, one or more of dimethicone copolyol, polysorbate 20, polysorbate 40, polysorbate 60, polysorbate 80, lauramide DEA, cocamide DEA, and cocamide MEA, oleyl betaine, cocamidopropyl phosphatidyl PG-dimonium chloride, and ammonium laureth sulfate may be: used within topical formulations. Suitable preservatives include, but are not limited to, antimicrobials such as methylparaben, propylparaben, sorbic acid, benzoic acid, and formaldehyde, as well as physical stabilizers and antioxidants such as vitamin E, sodium ascorbate/ascorbic acid and propyl gallate. Suitable moisturizers include, but are not limited to, lactic acid and other hydroxy acids and their salts, glycerin, propylene glycol, and butylene glycol. Suitable emollients include lanolin alcohol, lanolin, lanolin derivatives, cholesterol, petrolatum, isostearyl neopentanoate and mineral oils. Suitable fragrances and colors include, but are not limited to, FD&C Red No. 40 and FD&C Yellow No. 5. Other suitable additional ingredients that may be included a topical formulation include, but are not limited to, abrasives, absorbents, anti-caking agents, anti-foaming agents, anti-static agents, astringents (e.g., witch hazel, alcohol and herbal extracts such as chamomile extract), binders/excipients, buffering agents, chelating agents, film forming agents, conditioning agents, propellants, opacifying agents, pH adjusters and protectants.

An example of a suitable topical vehicle for formulation of a gel is: hydroxypropylcellulose (2.1%); 70/30 isopropyl alcohol/water (90.9%); propylene glycol (5.1%); and Polysorbate 80 (1.9%). An example of a suitable topical vehicle for formulation as a foam is: cetyl alcohol (1.1%); stearyl alcohol (0.5%; Quaternium 52 (1.0%); propylene glycol (2.0%); Ethanol 95 PGF3 (61.05%); deionized water (30.05%); P75 hydrocarbon propellant (4.30%). All percents are by weight.

Typical modes of delivery for topical compositions include application using the fingers; application using a physical applicator such as a cloth, tissue, swab, stick or brush; spraying (including mist, aerosol or foam spraying); dropper application; sprinkling; soaking; and rinsing. Controlled release vehicles can also be used.

A pharmaceutical composition may be prepared as a sterile injectable aqueous or oleaginous suspension. The modulator, depending on the vehicle and concentration used, can either be suspended or dissolved in the vehicle. Such a composition may be formulated according to the known art using suitable dispersing, wetting agents and/or suspending agents such as those mentioned above. Among the acceptable vehicles and solvents that may be employed are water, 1,3-butanediol, Ringer's solution and isotonic sodium chloride solution. In addition, sterile, fixed oils may be employed as a solvent or suspending medium. For this purpose any bland fixed oil may be employed, including synthetic mono- or diglycerides. In addition, fatty acids such as oleic acid find use in the preparation of injectable compositions, and adjuvants such as local anesthetics, preservatives and/or buffering agents can be dissolved in the vehicle.

Modulators may also be prepared in the form of suppositories (e.g., for rectal administration). Such compositions can be prepared by mixing the drug with a suitable non-irritating excipient that is solid at ordinary temperatures but liquid at the rectal temperature and will therefore melt in the rectum to release the drug. Suitable excipients include, for example, cocoa butter and polyethylene glycols.

Pharmaceutical compositions may be formulated as sustained release formulations (i.e., a formulation such as a capsule that effects a slow release of modulator following administration). Such formulations may generally be prepared using well known technology and administered by, for example, oral, rectal or subcutaneous implantation, or by implantation at the desired target site. Carriers for use within such formulations are biocompatible, and may also be biodegradable; preferably the formulation provides a relatively constant level of modulator release. The amount of modulator contained within a sustained release formulation depends upon, for example, the site of implantation, the rate and expected duration of release and the nature of the condition to be treated or prevented.

In addition to or together with the above modes of administration, a modulator may be conveniently added to food or drinking water (e.g., for administration to non-human animals including companion animals (such as dogs and cats) and livestock). Animal feed and drinking water compositions may be formulated so that the animal takes in an appropriate quantity of the composition along with its diet. It may also be convenient to present the composition as a premix for addition to feed or drinking water.

Modulators are generally administered in a capsaicin receptor modulatory amount (i.e., an amount that achieves a concentration in a body fluid (e.g., blood, plasma, serum, CSF, synovial fluid, lymph, cellular interstitial fluid, tears or urine) that is sufficient to inhibit the binding of vanilloid ligand to VR1 in vitro). A dose is considered to be therapeutically effective if it results in a discernible patient benefit, such as pain relief, as described herein. Preferred systemic doses are no higher than 50 mg per kilogram of body weight per day (e.g., ranging from about 0.001 mg to about 50 mg per kilogram of body weight per day), with oral doses generally being about 5–20 fold higher than intravenous doses (e.g., ranging from 0.01 to 40 mg per kilogram of body weight per day).

The amount of active ingredient that may be combined with the carrier materials to produce a single dosage form will vary depending, for example, upon the patient being treated and the particular mode of administration. Dosage unit forms will generally contain between from about 10 µg to about 500 mg of an active ingredient. Optimal dosages may be established using routine testing, and procedures that are well known in the art.

Pharmaceutical compositions may be packaged for treating conditions responsive to VR1 modulation (e.g., treatment of exposure to vanilloid ligand, pain, itch, obesity or urinary incontinence). Packaged pharmaceutical compositions may include a container holding a therapeutically effective amount of at least one VR1 modulator as described herein and instructions (e.g., labeling) indicating that the contained composition is to be used for treating a condition responsive to VR1 modulation in the patient.

Methods of Use

VR1 modulators provided herein may be used as agonists or (preferably) antagonists of capsaicin receptors in a variety of contexts, both in vitro and in vivo. Within certain aspects, VR1 antagonists may be used to inhibit the binding of vanilloid ligand agonist (such as capsaicin and/or RTX) to capsaicin receptor in vitro or in vivo. In general, such methods comprise the step of contacting a capsaicin receptor with a sufficient amount of one or more quinazolin-4-ylamine analogues, in the presence of vanilloid ligand in aqueous solution and under conditions otherwise suitable for binding of the ligand to capsaicin receptor. The capsaicin receptor may be present in solution or suspension. (e.g., in an isolated membrane or cell preparation), or in a cultured or isolated cell. Within certain embodiments, the capsaicin receptor is expressed by a neuronal cell present in a patient, and the aqueous solution is a body fluid. In general, the amount of quinazolin-4-ylamine analogue(s) contacted with the receptor should yield a concentration in the aqueous solution sufficient to inhibit vanilloid ligand binding to VR1 in vitro as measured, for example, using a binding assay as described in Example 5 and/or a calcium mobilization assay as described in Example 6. Preferably, one or more quinazolin-4-ylamine analogues are administered to an animal in an amount such that the analogue is present in at least one body fluid of the animal at a therapeutically effective concentration that is 100 nanomolar or less, preferably 50 nanomolar or less, 20 nanomolar or less, or 10 nanomolar or less. For example, such compounds may be administered at a dose that is less than 20 mg/kg body weight, preferably less than 5 mg/kg and, in some instances, less than 1 mg/kg.

Also provided herein are methods for modulating, preferably inhibiting, the signal-transducing activity of a capsaicin receptor. Such modulation may be achieved by contacting a capsaicin receptor (either in vitro or in vivo) with an effective amount of one or more VR1 modulators provided herein under conditions suitable for binding of the modulator(s) to the receptor. The receptor may be present in solution or suspension, in a cultured or isolated cell preparation or within a patient. Modulation of signal tranducing activity may be assessed by detecting an effect on calcium ion conductance (also referred to as calcium mobilization or flux). In general, an effective amount of VR1 modulator(s) is an amount sufficient to yield a concentration (in an aqueous solution that is in contact with the receptor) that is sufficient to modulate VR1 signal transducing activity in vitro within a calcium mobilization assay as described in Example 6. VR1 modulator(s) provided herein are preferably administered to a patient (e.g., a human) orally or topically, and are present within at least one body fluid of the animal while modulating VR1 signal-transducing activity. Preferred VR1 modulators for use in such methods modulate VR1 signal-transducing activity in vitro at a concentration of 1 nanomolar or less, preferably 100 picomolar or less, more preferably 20 picomolar or less, and in vivo at a concentration of 100 nanomolar or less in a body fluid such as blood.

The present invention further provides methods for treating conditions responsive to VR1 modulation. Within the context of the present invention, the term "treatment" encompasses both disease-modifying treatment and symptomatic treatment, either of which may be prophylactic (i.e., before the onset of symptoms, in order to prevent, delay or reduce the severity of symptoms) or therapeutic (i.e., after the onset of symptoms, in order to reduce the severity and/or duration of symptoms). A condition is "responsive to VR1 modulation" if it is characterized by inappropriate activity of a capsaicin receptor, regardless of the amount of vanilloid ligand present locally, and/or if modulation of capsaicin receptor activity results in alleviation of the condition or a symptom thereof. Such conditions include, for example, symptoms resulting from exposure to VR1-activating stimuli, pain, respiratory disorders such as asthma and chronic obstructive pulmonary disease, itch, urinary incontinence, cough, hiccup, and obesity, as described in more detail below. Such conditions may be diagnosed and monitored using criteria that have been established in the art. Patients may include humans, domesticated companion animals and livestock, with dosages as described above.

Treatment regimens may vary depending on the compound used and the particular condition to be treated. However, for treatment of most disorders, a frequency of administration of 4 times daily or less is preferred. In general, a dosage regimen of 2 times daily is more preferred, with once a day dosing particularly preferred. For the treatment of acute pain, a single dose that rapidly reaches effective concentrations is desirable. It will be understood, however, that the specific dose level and treatment regimen for any particular patient will depend upon a variety of factors including the activity of the specific compound employed, the age, body weight, general health, sex, diet, time of administration, route of administration, and rate of excretion, drug combination and the severity of the particular disease undergoing therapy. In general, the use of the minimum dose sufficient to provide effective therapy is preferred. Patients may generally be monitored for therapeutic effectiveness using medical or veterinary criteria suitable for the condition being treated or prevented.

Patients experiencing symptoms resulting from exposure to capsaicin receptor-activating stimuli include individuals with burns caused by heat, light, tear gas or acid and those whose mucous membranes are exposed (e.g., via ingestion, inhalation or eye contact) to capsaicin (e.g., from hot peppers or in pepper spray) or a related irritant such as acid, tear gas or air pollutants. The resulting symptoms (which may be treated using compounds provided herein) may include, for example, pain, broncho-constriction and inflammation.

Pain that may be treated using the compounds provided herein may be chronic or acute and includes, but is not limited to, peripheral nerve-mediated pain (especially neuropathic pain). Compounds provided herein may be used in the treatment of, for example, postmastectomy pain syndrome, stump pain, phantom limb pain, oral neuropathic pain, toothache (dental pain), denture pain, postherpetic neuralgia, diabetic neuropathy, reflex sympathetic dystrophy, trigeminal neuralgia, osteoarthritis, rheumatoid arthritis, fibromyalgia, Guillain-Barre syndrome, meralgia paresthetica, burning-mouth syndrome and/or bilateral peripheral neuropathy. Additional neuropathic pain conditions include causalgia (reflex sympathetic dystrophy—RSD, secondary to injury of a peripheral nerve), neuritis (including, for example, sciatic neuritis, peripheral neuritis, polyneuritis, optic neuritis, postfebrile neuritis, migrating neuritis, segmental neuritis and Gombault's neuritis), neuronitis, neuralgias (e.g., those mentioned above, cervicobrachial neuralgia, cranial neuralgia, geniculate neuralgia, glossopharyngial neuralgia, migranous neuralgia, idiopathic neuralgia, intercostals neuralgia, mammary neuralgia, mandibular joint neuralgia, Morton's neuralgia, nasociliary neuralgia, occipital neuralgia, red neuralgia, Sluder's neuralgia, splenopalatine neuralgia, supraorbital neuralgia and vidian neuralgia), surgery-related pain, musculoskeletal pain, AIDS-related neuropathy, MS-related neuropathy, and spinal cord injury-related pain. Headache, including headaches involving peripheral nerve activity, such as sinus, cluster (i.e., migranous neuralgia) and some tension and headaches and migraine, may also be treated as described herein. For example, migraine headaches may be prevented by administration of a compound provided herein as soon as a pre-migrainous aura is experienced by the patient. Further pain conditions that can be treated as described herein include "burning mouth syndrome," labor pains, Charcot's pains, intestinal gas pains, menstrual pain, acute and chronic back pain, hemorrhoidal pain, dyspeptic pains, angina, nerve root pain, homotopic pain and heterotopic pain—including cancer associated pain (e.g., in patients with bone cancer), pain (and inflammation) associated with venom exposure (e.g., due to snake bite, spider bite, or insect sting) and trauma associated pain (e.g., post-surgical pain, pain from cuts, bruises and broken bones, and burn pain). Additional pain conditions that may be treated as described herein include pain associated with inflammatory bowel disease, irritable bowel syndrome and/or inflammatory bowel disease.

Within certain aspects, VR1 antagonists including (but not limited to) those specifically recited herein, may be used for the treatment of mechanical pain. As used herein, the term "mechanical pain" refers to pain other than headache pain that is not neuropathic or a result of exposure to heat, cold or external chemical stimuli. Mechanical pain includes physical trauma (other than thermal or chemical burns or other irritating and/or painful exposures to noxious chemicals) such as post-surgical pain and pain from cuts, bruises and broken bones; toothache, denture pain; nerve root pain; osteoartiritis; rheumatoid arthritis; fibromyalgia; meralgia paresthetica; back pain; cancer-associated pain; angina; carpel tunnel syndrome; and pain resulting from bone fracture, labor, hemorrhoids, intestinal gas, dyspepsia, and menstruation. Any VR1 antagonist that binds to VR1 with a Ki of less than 100 μM and/or inhibits VR1 activity with an $EC_{50}$ of less than or equal to 100 μM (determined as described herein) may be used. Preferably, the VR1 antagonist used is not a capsaicin analogue; particularly preferred VR1 antagonists are those provided herein.

Itching conditions that may be treated include psoriatic pruritis, itch due to hemodialysis, aguagenic pruritus, and itching associated with vulvar vestibulitis, contact dermatitis, insect bites and skin allergies. Urinary incontinence, as used herein, includes detrusor hyperflexia of spinal origin and bladder hypersensitivity, both of which may be treated as described herein. Compounds provided herein may also be used as anti-tussive agents (to prevent, relieve or suppress coughing) and for the treatment of hiccup, and to promote weight loss in an obese patient. Therapeutically effective amounts for use in such methods are generally sufficient to provide detectable relief from the condition being treated.

Within other aspects, VR1 antagonists provided herein may be used within combination therapy for the treatment of conditions involving inflammatory components. Such conditions include, for example, autoimmune disorders and pathologic autoimmune responses known to have an inflammatory component including, but not limited to, arthritis (especially rheumatoid arthritis), psoriasis, Crohn's disease, lupus erythematosus, irritable bowel syndrome, tissue graft rejection, and hyperacute rejection of transplanted organs. Other such conditions include trauma (e.g., injury to the head or spinal cord), cardio- and cerebo-vascular disease and certain infectious diseases.

Within such combination therapy, a VR1 antagonist is adminnistered to a patient along with an anti-inflammatory agent. The VR1 antagonist and anti-inflammatory agent may be present in the same pharmaceutical composition, or may be administered separately in either: order. Anti-inflammatory agents include, for example, non-steroidal anti-inflammatory drugs (NSAIDs), non-specific and cyclooxygenase-2 (COX-2) specific cyclooxygenase enzyme inhibitors, gold compounds, corticosteroids, methotrexate, tumor necrosis factor (TNF) receptor antagonists, anti-TNF alpha antibodies, anti-C5 antibodies, and interleukin-1 (IL-1) receptor antagonists. Examples of NSAIDs include, but are not limited to ibuprofen (e.g., ADVIL™, MOTRIN™), flurbiprofen (ANSAID™), naproxen or naproxen sodium (e.g., NAPROSYN, ANAPROX, ALEVE™), diclofenac (e.g., CATAFLAM™, VOLTAREN™), combinations of diclofenac sodium and misoprostol (e.g., ARTHROTEC™), sulindac (CLINORIL™), oxaprozin (DAYPRO™), diflunisal (DOLOBID™), piroxicam (FELDENE™), indomethacin (INDOCIN™), etodolac (LODINE™), fenoprofen calcium (NALFON™), ketoprofen (e.g., ORUDIS™, ORUVAIL™), sodium nabumetone (RELAFEN™), sulfasalazine (AZULFIDINE™), tolmetin sodium (TOLECTIN™), and hydroxychloroquine (PLAQUENIL™). A particular class of NSAIDs consists of compounds that inhibit cyclooxygenase (COX) enzymes, such as celecoxib (CELEBREX™) and rofecoxib (VIOXX™). NSAIDs further include salicylates such as acetylsalicylic acid or aspirin, sodium salicylate, choline and magnesium salicylates (TRILISATE™), and salsalate (DISALCID™), as well as corticosteroids such as cortisone (CORTONE™ acetate), dexamethasone (e.g., DECADRON™), methylprednisolone (MEDROL™) prednisolone (PRELONE™), prednisolone sodium phosphate (PEDIAPRED™), and prednisone (e.g., PREDNICEN-M™, DELTASONE™, STERAPRED™).

Suitable dosages for VR1 antagonist within such combination therapy are generally as described above. Dosages and methods of administration of anti-inflammatory agents can be found, for example, in the manufacturer's instructions in the *Physician's Desk Reference*. In certain embodiments, the combination administration of a VR1 antagonist with an anti-inflammatory agent results in a reduction of the dosage of the anti-inflammatory agent required to produce a therapeutic effect. Thus, preferably, the dosage of anti-inflammatory agent in a combination or combination treatment method of the invention is less than the maximum dose advised by the manufacturer for administration of the anti-inflammatory agent without combination administration of a VR1 antagonist. More preferably this dosage is less than ¾, even more preferably less than ½, and highly preferably, less than ¼ of the maximum dose, while most preferably the dose is less than 10% of the maximum dose advised by the manufacturer for administration of the anti-inflammatory agent(s) when administered without combination administration of a VR1 antagonist. It will be apparent that the dosage amount of VR1 antagonist component of the combination needed to achieve the desired effect may similarly be affected by the dosage amount and potency of the anti-inflammatory agent component of the combination.

In certain preferred embodiments the combination administration of a VR1 antagonist with an anti-inflammatory agent is accomplished by packaging one or more VR1 antagonists and one or more anti-inflammatory agents in the same package, either in separate containers within the package or preferably as a mixture of one or more VR1 antagonists and one or more anti-inflammatory agents. Preferred mixtures are formulated for oral administration (e.g., as pills, capsules, tablets or the like). Preferably the package comprises a label bearing indicia indicating that the one or more VR1 antagonists and one or more anti-inflammatory agents are to be taken together for the treatment of an inflammatory pain condition. A highly preferred combination is one in which the anti-inflammatory agent(s) include at least one COX-2 specific cyclooxgenase enzyme inhibitor such as valdecoxib (BEXTRA®), lumiracoxib (PREXIGE™), etoricoxib (ARCOXIA®), celecoxib (CELEBREX®) and/or rofecoxib (VIOXX®).

The methods discussed above generally employ modulators that are VR1 antagonists; however, methods are also provided herein that employ modulators that are VR1 agonists. Such modulators may be used, for example, in crowd control (as a substitute for tear gas) or personal protection (e.g., in a spray formulation) or as pharmaceutical agents for the treatment of pain, itch or urinary incontinence via capsaicin receptor desensitization. In general, compounds for use in crowd control or personal protection are formulated and used according to conventional tear gas or pepper spray technology.

Within separate aspects, the present invention provides a variety of non-pharmaceutical in vitro and in vivo uses for the compounds provided herein. For example, such compounds may be labeled and used as probes for the detection and localization of capsaicin receptor (in samples such as cell preparations or tissue sections, preparations or fractions thereof). Compounds may also be used as positive controls in assays for receptor activity, as standards for determining the ability of a candidate agent to bind to capsaicin receptor, or as radiotracers for positron emission tomography (PET) imaging or for single photon emission computerized tomography (SPECT). Such methods can be used to characterize capsaicin receptors in living subjects. For example, a VR1 modulator may be labeled using any of a variety of well known techniques (e.g., radiolabeled with a radicnuclide such as tritium, as described herein), and incubated with a sample for a suitable incubation time (e.g., determined by first assaying a time course of biding). Following incubation, unbound compound is removed (e.g., by washing), and bound compound detected using any method suitable for the label employed (e.g., autoradiography or scintillation counting for radiolabeled compounds; spectroscopic methods may be used to detect luminescent groups and fluorescent groups). As a control, a matched sample containing labeled compound and a greater (e.g., 10-fold greater) amount of unlabeled compound may be processed in the same manner. A greater amount of detectable label remaining in the test sample than in the control indicates the presence of capsaicin receptor in the sample. Detection assays, including receptor autoradiography (receptor mapping) of capsaicin receptor in cultured cells or tissue samples may be performed as described by Kuhar in sections 8.1.1 to 8.1.9 of Current Protocols in Pharmacology (1998) John Wiley & Sons, New York.

Modulators provided herein may also be used within a variety of well known cell separation methods. For example, modulators may be linked to the interior surface of a tissue culture plate or other support, for use as affinity ligands for immobilizing and thereby isolating, capsaicin receptors (e.g., isolating receptor-expressing cells) in vitro. Within one preferred embodiment, a modulator linked to a fluorescent marker, such as fluorescein, is contacted with the cells, which are then analyzed (or isolated) by fluorescence activated cell sorting (FACS).

The following Examples are offered by way of illustration and not by way of limitation. Unless otherwise specified all reagents and solvent are of standard commercial grade and are used without further purification.

EXAMPLES

Example 1

Preparation of Representative Compounds

This Example illustrates the preparation of representative substituted quinazolin-4-ylamine analogues. Mass spectroscopy data shown in this and subsequent Examples is Electrospray MS, obtained in positive ion mode with a 15V cone voltage, using a Micromass Time-of-Flight LCT, equipped with a Waters 600 pump, Waters 996 photodiode array detector, Gilson 215 autosampler, and a Gilson 841 microinjector. MassLynx (Advanced Chemistry Development, Inc; Toronto, Canada) version 3.5 software was used for data collection and analysis. Sample volume of 1 microliter was injected onto a 50×4.6 mm Chromolith SpeedROD C18 column, and eluted using a 2-phase linear gradient at 6 ml/min flow rate. Sample was detected using total absorbance count over the 220–340 nm UV range. The elution conditions were: Mobile Phase A-95/5/0.1 Water/Methanol/TFA; Mobile Phase B-5/95/0.05 Water/Methanol/TFA.

| Gradient- | Time(min) | % B |
|---|---|---|
| | 0 | 10 |
| | 0.5 | 100 |
| | 1.2 | 100 |
| | 1.21 | 10 |

The total run time was 2 minutes inject to inject.

A. (4-Trifluoromethyl-phenyl)-[7-(2-trifluoromethyl-phenyl)-quinazolin-4-yl]-amine (Cmpd 1)

1. 3-Nitro-2'-trifluoromethyl-biphenyl-4-carboxylic acid methyl ester

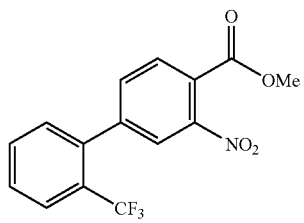

To a solution of 2-(trifluoromethyl)-phenylboronic acid (4.4 g, 0.0232 mol), 2-(dicyclohexylphosphino)biphenyl (111 mg, 0.318 mmol), and potassium phosphate (6.52 g, 0.031 mmol) in toluene, add palladium (II) acetate (36 mg, 0.160 mmol). Purge the reaction mixture for 10 minutes with dry nitrogen and then add 4-chloro-2-nitrobenzoic acid methyl ester. Heat the stirring reaction mixture overnight at 80° C., cool the mixture and filter through celite using ethyl acetate. Concentrate under reduced pressure, take up in fresh ethyl acetate and wash the solution with NaHCO$_3$ (saturated aqueous). Dry the solution (Na$_2$SO$_4$), concentrate under reduced pressure and then filter through a pad of silica gel using ethyl acetate as eluent. Removal of solvent under reduced pressure gives pure 3-nitro-2'-trifluoromethyl-biphenyl-4-carboxylic acid methyl ester as an oil.

2. 3-amino-2'-trifluoromethyl-biphenyl-4-carboxylic acid methyl ester

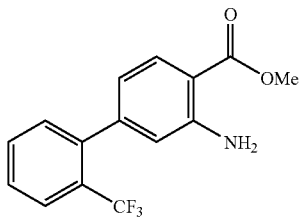

In a Parr apparatus, hydrogenate an ethanolic solution of 3-nitro-2'-trifluoromethyl-biphenyl-4-carboxylic acid methyl ester (5.54 g, 0.0169 mol) under 55 psi of hydrogen using tetrakis(triphenylphosphine)palladium (0) (300 mg). After 18 hours, filter the mixture through celite and concentrate under reduced pressure to give 3-amino-2'-trifluoromethyl-biphenyl-4-carboxylic acid methyl ester as a solid.

3. 7-(2-Trifluoromethyl-phenyl)-3H-quinazolin-4-one

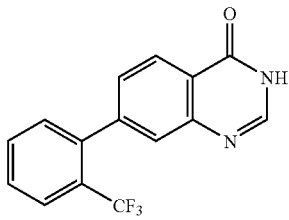

Heat a solution of 3-amino-2'-trifluoromethyl-biphenyl-4-carboxylic-acid methyl ester (5.0 g, 0.0169 mol) and formamidine acetate (2.8 g, 0.0203 mol) in 2-methoxyethanol at reflux for 8 hours. Cool the mixture and concentrate under reduced pressure to give a dark oil. Dissolve the residue in 10% NaOH and wash the aqueous with ether (3×). Bring the aqueous layer to pH 4 using 12N HCl to produce a milky solution. Extract the solution with EtOAc, wash the EtOAc with brine, dry (Na$_2$SO$_4$) and concentrate under reduced pressure to give 7-(2-Trifluoromethyl-phenyl)-3H-quinazolin-4-one as a beige solid.

4. 4-chloro-7-(2-trifluoromethyl-phenyl)-quinazoline

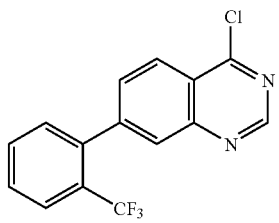

Reflux a solution of 7-(2-Trifluoromethyl-phenyl)-3H-quinazolin-4-one (1.12 g, 0.0039 mol) in POCl$_3$ for 16 hours. Cool the mixture and concentrate under reduced pressure. Partition the residue between saturated aqueous NaHCO$_3$ and EtOAc. Wash the EtOAc layer once with additional NaHCO$_3$, dry it (Na$_2$SO$_4$), and concentrate under reduced pressure to obtain the crude product as a solid. Filter the residue through a 2 inch pad of silica gel (50% EtOAc/Hexanes) and concentrate under reduce pressure to give 4-chloro-7-(2-trifluoromethyl-phenyl)-quinazoline as a pale yellow-brown solid.

5. (4-Trifluoromethyl-phenyl)-[7-(2-trifluoromethyl-phenyl)-quinazolin-4-yl]-amine

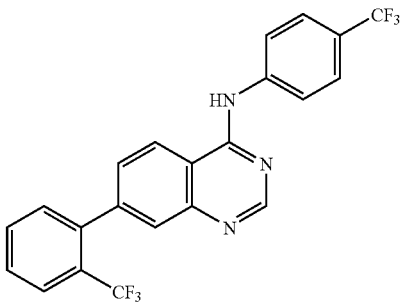

Reflux a solution of 4-chloro-7-(2-trifluoromethyl-phenyl)-quinazoline (258 mg, 0.836 mmol) and 4-(trifluoromethyl)-aniline (269 mg, 1.67 mmol) in isopropyl alcohol for 8 hours. Cool the solution, collect the precipitate via filtration and wash with dry ether (3×) to give pure (4-Trifluoromethyl-phenyl)-[7-(2-trifluoromethyl-phenyl)-quinazolin-4-yl]amine (Cmpd 2) HCl salt. Mass spec. 433.1.

B. (4-tert-Butyl-phenyl)-[7-(2-trifluoromethyl-phenyl)-quinolin-4-yl]-amine (Cmpd 2)

1. 7-(2-Trifluoromethyl-phenyl)-quinolin-4-ol

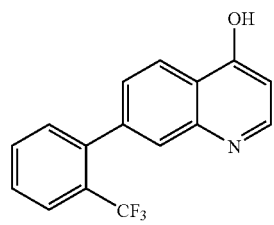

Combine 7-chloroquinolin-4-ol (1000 mg, 5.55 mmol,) 2-(trifluoromethyl)phenylboronic acid (1583 mg, 8.33 mmol) and toluene (50 mL), and bubble nitrogen into the solution for 10 minutes. Add palladium acetate (25 mg, 0.11 mmol), 2-(dicyclohexylphosphino)biphenyl (78 mg, 0.22 mmol), and K$_3$PO$_4$ (2353 mg, 11.1 mmol) and heat at 90° C. for 16 hours. Let cool, add water (25 mL) and EtOAc (50 mL), and remove any insoluble material by filtration. Separate the EtOAc layer, and extract the aqueous layer twice with EtOAc (25 mL each). Combine the EtOAc extracts, dry (Na$_2$SO$_4$), and evaporate. Purify by silica gel chromatography (94% CH2Cl2/5% MeOH/1% NH$_4$OH) to provide 110 mg of 7-(2-Trifluoromethyl-phenyl)-quinolin-4-ol as a white solid.

2. 4-Chloro-7-(2-trifluoromethyl-phenyl)-quinoline

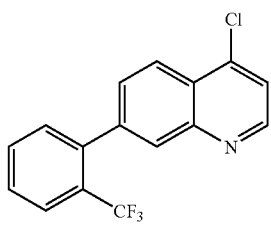

Heat a mixture of 7-(2-trifluoromethyl-phenyl)-quinolin-4-ol (50 mg, 0.17 mmol) in POCl$_3$ (10 mL) at 90° C. for 16 hours. Evaporate the POCl$_3$, and add ice (100 g) followed by careful addition of saturated NaHCO$_3$. Extract with EtOAc, dry (Na$_2$SO$_4$), and evaporate to provide 4-chloro-7-(2-trifluoromethyl-phenyl)-quinoline as a tan solid.

3. (4-tert-Butyl-phenyl)-[7-(2-trifluoromethyl-phenyl)-quinolin-4-yl]-amine

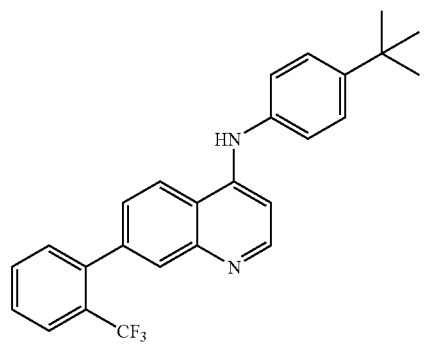

Heat a mixture of 4-chloro-7-(2-trifluoromethyl-phenyl)-quinoline (42 mg, 0.14 mmol) and 4-(tert-butyl)aniline (41 mg, 0.29 mmol) in 2-propanol (10 mL) at reflux for 3 hours. Evaporate the mixture, add 1M NaOH (10 mL), extract twice with EtOAc (10 mL each), dry (Na$_2$SO$_4$), and evaporate to provide the crude product. Purify by silica gel chromatography, eluting with 75% hexane-EtOAc to provide (4-tert-Butyl-phenyl)-[7-(2-trifluoromethyl-phenyl)-quinolin-4-yl]-amine as a white solid. Mass spec. 420.2.

C. (4-tert-Butyl-phenyl)-[7-(2-trifluoromethyl-phenyl)-pyrido[3,2-d]pyrimidin-4-yl]-amine (Cmpd 3)

1. 5-bromo-3-nitropyridine-2-carbonitrile

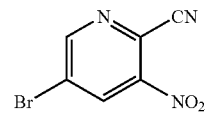

Heat a solution of 2,5-dibromo-3-nitropyridine (1.77 g, 6.3 mmol; Malinowski (1988) *Bull. Soc. Chim. Belg.* 97:51; see also U.S. Pat. No. 5,801,183) and cuprous cyanide (0.60 g, 6.69 mmol) in N,N-dimethylacetamide (25 mL) at 100° C. for 72 hours. After cooling, dilute the mixture with water (25 mL) and extract twice with EtOAc (25 mL each), then wash twice with water (25 mL each). The combined EtOAc extracts are dried (Na$_2$SO$_4$), evaporated, and purified by flash chromatography (50% EtOAc-hexane) to obtain 5-bromo-3-nitropyridine-2-carbonitrile as a pale solid.

2. 3-Amino-5-bromopyridine-2-carbonitrile

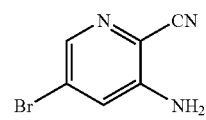

Mix 5-bromo-3-nitropyridine-2-carbonitrile (1.5 g, 5.3 mmol) and SnCl$_2$-dihydrate (5.00 g, 26.3 mmol) in concentrated HCl and allow to stir at room temperature overnight. Work up by adding ice and carefully adding 10 M NaOH until basic. Extract twice with Et$_2$O (200 mL), dry (Na$_2$SO$_4$) and evaporate. Purify by silica gel chromatography (75% hexane-EtOAc) to furnish 3-amino-5-bromopyridine-2-carbonitrile as a pale solid.

3. 7-Bromopyrido[3,2-d]pyrimidin-4-ol

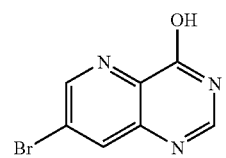

Reflux a mixture of 3-amino-5-bromopyridine-2-carbonitrile (504 mg, 2.00 mmol) and sodium acetate (312 mg, 3.81 mmol) in formic acid (20 mL) for 16 hours. Work up by evaporating to a white solid, and add 3N NaOH (50 mL). Filter off any undissolved material, then re-form the free pyrimidinol by adding concentrated HCl until a pH of 3 is achieved. Collect 7-Bromopyrido[3,2-d]pyrimidin-4-ol and let dry overnight.

4. Bromo-4-chloropyrido[3-2-d]pyrimidine

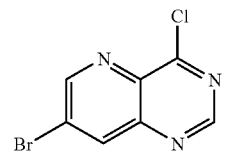

Heat a mixture of 7-Bromopyrido[3,2-d]pyrimidin-4-ol (35 mg, 0.15 mmol) and POCL₃ (10 mL) at 90° C. for 16 hours. Evaporate the POCl₃, and add ice (100 g) followed by careful addition of saturated NaHCO₃. Extract twice with EtOAc, dry (Na₂SO₄), and evaporate to provide bromo-4-chloropyrido[3-2-d]pyrimidine as a white solid.

5. (7-Bromo-pyrido[3,2-d]pyrimidin-4-yl)-4-tert-butyl-phenyl)-amine

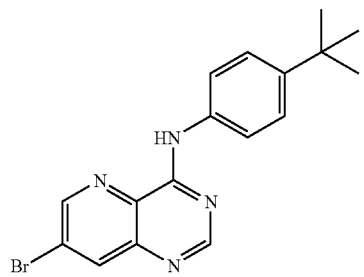

Heat a mixture of bromo-4-chloropyrido[3-2-d]pyrimidine (35 mg, 0.14 mmol) and 4-(tert-butyl)aniline (43 mg, 0.29 mmol) in 2-propanol (10 mL) at reflux for 3 hours. Evaporate the mixture, add 1M NaOH (10 mL), extract twice with EtOAc (10 mL each), dry (Na2SO4), and evaporate to provide the crude product. Purify by silica gel chromatography, eluting with 75% hexane-EtOAc to provide (7-bromo-pyrido[3,2-d]pyridin-4-yl)₄-tert-butyl-phenyl)-amine as a white solid.

6. (4-tert-Butyl-phenyl)-[7-(2-trifluoromethyl-phenyl)-pyrido[3,2-d]pyrimidin-4-yl]-amine

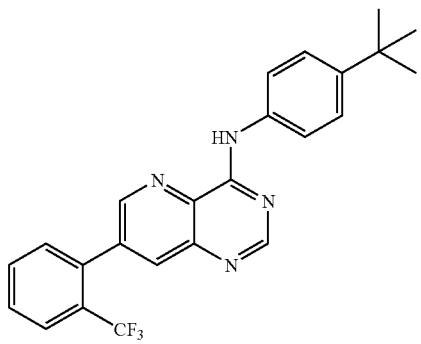

Combine (7-bromo-pyrido[3,2-d]pyrimidin-4-yl)-4-tert-butyl-phenyl)-amine (36 mg, 0.1 mmol), 2-(trifluoromethyl) phenyl-boronic acid (29 mg, 0.15 mmol) in 1,2-dimethoxyethane (10 mL) and bubble nitrogen into the mixture for 10 minutes. Add tetrakis(triphenylphosphine)palladium(0) (12 mg, 0.01 mmol) and 2M Na₂CO₃ (1 mL) and heat at 80° C. for 48 hours. Let the mixture cool to room temperature, dilute with water (10 mL), and extract twice with EtOAc (10 mL each). Dry (Na₂SO₄), evaporate, and purify on a preparative silica gel plate (2000 micron) eluting with 75% hexane-EtOAc to provide (4-tert-butyl-phenyl)-[7-(2-trifluoromethyl-phenyl)-pyrido[3,2-d]pyrimidin-4-yl]-amine as a light yellow solid. Mass spec. 422.2.

D. (4-tert-Butyl-phenyl)-[6-(2-trifluoromethyl-phenyl)-phthalazin-1-yl]-amine (cmpd 4)

1. 4-Bromo-2-dibromomethyl-benzonitrile

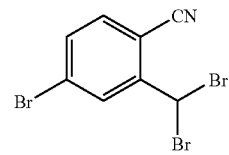

Reflux a mixture of 4-Bromo-2-methyl-benzonitrile (19.6 g, 0.1 mol) and bromine (39.0 g, 0.22 mmol) in carbon tetrachloride (500 mL) using a 500 watt sunlamp for 16 hours. Let cool to room temperature, and filter off succinimide. Evaporate the product fully to provide 4-bromo-2-dibromomethyl-benzonitrile as a yellow powder.

2. 5-Bromo-3-hydroxy-2,3-dihydro-isoindol-1-one

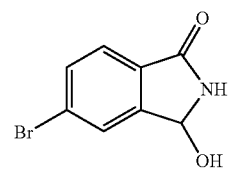

Combine 4-bromo-2-dibromomethyl-benzonitrile (7.0 g, 19.8 mmol) and acetonitrile (150 mL). Drip in a mixture of silver nitrate (7.0 g, 41.2 mmol) in water (40 mL) and reflux the resulting translucent yellow liquid for 72 hours. Evaporate the mixture, and add 1M NaOH (100 mL). Extract twice with EtOAc (100 mL each). Dry the solution (Na₂SO₄), evaporate, and purify by silica gel chromatography (80% hexanes-EtOAc) to obtain 600 mg of 4-bromo-2-formyl-benzonitrile and 1250 mg of 5-bromo-3-hydroxy-2,3-dihydro-isoindol-1-one as a white solid.

3. 6-Bromo-phthalazin-1-ol

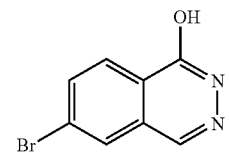

Combine 5-bromo-3-hydroxy-2,3-dihydro-isoindol-1-one (1.0 g, 4.39 mmol) and hydrazine hydrate (10 mL) and allow the suspension to stir at room temperature for 16 hours. Collect 6-Bromo-phthalazin-1-ol as a white solid.

4. 6-Bromo-1-chloro-phthalazine

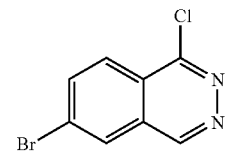

Heat a mixture of 6-Bromo-phthalazin-1-ol (300 mg, 1.33 mmol) in POCl₃ (10 mL) at 90° C. for 2 hours. Evaporate the POCl₃, and add ice (100 g) followed by careful addition of saturated NaHCO₃. Extract with EtOAc, dry (Na₂SO₄), and evaporate to provide 4-chloro-7-(2-trifluoromethyl-phenyl)-quinoline as a white solid.

5. (6-Bromo-phthalazin-1-yl)-(4-tert-butyl-phenyl)-amine

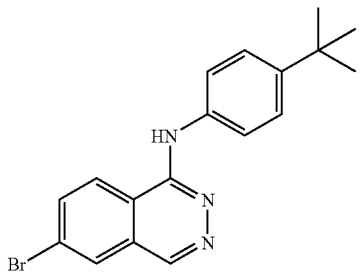

Heat a mixture of 6-bromo-1-chloro-phthalazine (500 mg, 2.05 mmol) and 4-(tert-butyl)aniline (611 mg, 4.10 mmol) in 2-propanol (10 mL) at reflux for 3 hours. Evaporate the mixture, add 1M NaOH (10 mL), extract twice with EtOAc (10 mL each), dry (Na₂SO₄), and evaporate to provide the crude product. Purify by silica gel chromatography, eluting with dichloromethane followed by 95% CH₂Cl₂-MeOH to provide (6-Bromo-phthalazin-1-yl)-(4-tert-butyl-phenyl)-amine as a white solid.

6. (4-tert-Butyl-phenyl)-[6-(2-trifluoromethyl-phenyl)-phthalazin-1-yl]-amine

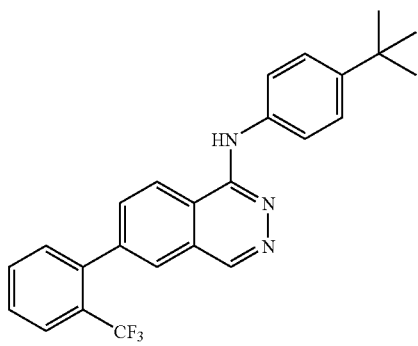

Combine (6-bromo-phthalazin-1-yl)-(4-tert-butyl-phenyl)-amine (60 mg, 0.19 mmol), 2-(trifluoromethyl)phenylboronic acid (50 mg, 0.26 mmol) in 1,2-dimethoxyethane (10 mL) and bubble nitrogen into the mixture for 10 minutes. Add tetrakis(triphenylphosphine)palladium(0) (12 mg, 0.01 mmol) and 2M Na₂CO₃ (1 mL) and heat at 80 C for 48 hours. Let the mixture cool to room temperature, dilute with water (10 mL), and extract twice with EtOAc (10 mL each). Dry (Na₂SO₄), evaporate, and purify on a preparative silica gel plate (2000 micron) eluting with 75% hexane-EtOAc to provide (4-tert-butyl-phenyl)-[6-(2-trifluoromethyl-phenyl)-phthalazin-1-yl]-amine as a straw colored solid. Mass Spec. 421.2.

E. (4-tert-Butyl-phenyl)-[7-(2-trifluoromethyl-phenyl)-pyrido[2,3-d]pyrimidin-4-yl]-amine (cmpds 5 and 6)

1. Oxo-3-phenyl-propionaldehyde

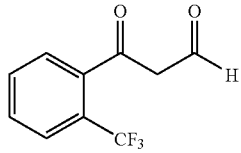

Heat a mixture of toluene and sodium ethoxide (40 mL of a 21% ethanolic solution) to 50° C. Add 2-trifluoromethylacetophenone (20.0 g, 0.11 mol) and ethyl formate (11.8 g, 0.16 mol), and let stir at 65° C. for 12 hours. Allow mixture to cool to room temperature and add 300 mL of diethyl ether. Collect the precipitate to obtain the sodium salt of 3-oxo-3-phenyl-propionaldehyde.

2. 7-(2-Trifluoromethyl-phenyl)-1H-pyrido[2,3-d]pyrimidine-2,4-dione

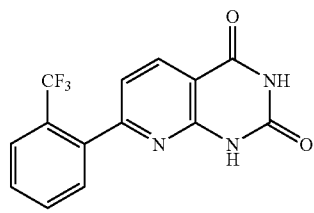

Finely divide the sodium salt of 3-oxo-3-phenyl-propionaldehyde (10.0 g, 0.043 mol) and add 50 mL of 90% phosphoric acid. Let stir until fully dissolved. Separately, similarly dissolve 6-amino-1H-pyrimidine-2,4-dione 5.7 g, 0.043 mol) in 50 mL of 90% phosphoric acid. Combine the 2 solutions and let stir for 12 hours at 100° C. Let the solution cool to room temperature, add 300 mL of water, and collect the product as a sticky solid. Triturate with ether to obtain 7-(2-trifluoromethyl-phenyl)-1H-pyrido[2,3-d]pyrimidine-2,4-dione as a white solid.

3. 2,4-Dichloro-7-(2-trifluoromethyl-phenyl)-pyrido[2,3-d]pyrimidine

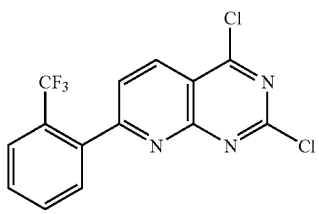

Heat a mixture of 7-(2-Trifluoromethyl-phenyl)-1H-pyrido[2,3-d]pyrimidine-2,4-dione (5.0 g, 0.016 mol) and POCl₃ (100 mL) at 90° C. for 36 hours. Evaporate the POCl₃, and add ice (400 g) followed by careful addition of saturated NaHCO₃. Extract twice with EtOAc, dry (Na₂SO₄), and evaporate to, provide 2,4-Dichloro-7-(2-trifluoromethyl-phenyl)-pyrido[2,3-d]pyrimidine.

4. (4-tert-Butyl-phenyl)-[2-chloro-7-(2-trifluoromethyl-phenyl)-pyrido[2,3-d]pyrimidin-4-yl]-amine (cmpd 5)

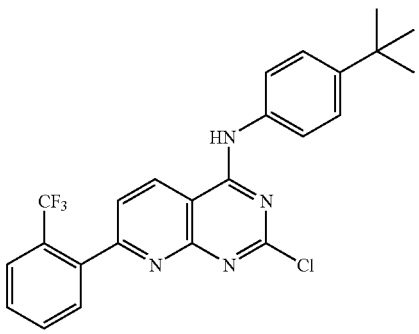

To a mixture of diisopropylethylamine (260 mg, 2.0 mmol) in acetonitrile (5 mL), add t-butylaniline (124 mg, 1.0 mmol) followed by (4-tert-Butyl-phenyl)-[2-chloro-7-(2-trifluoromethyl-phenyl)-pyrido[2,3-d]pyrimidin-4-yl]-amine (310 mg, 1.0 mmol). Heat the mixture to 80° C. for six hours. Evaporate the solvent, and partition between 1M NaOH and EtOAc. Dry the solvent ($Na_2SO_4$) and evaporate. Purify by silica gel chromatography (1:1 hexanes/EtOAc to furnish the monoaniline (4-tert-Butyl-phenyl)-[2-chloro-7-(2-trifluoromethyl-phenyl)-pyrido[2,3-d]pyrimidin-4-yl]-amine as a yellow solid.

5. (4-tert-Butyl-phenyl)-[7-(2-trifluoromethyl-phenyl)-pyrido[2,3-d]pyrimidin-4-yl]-amine (cmpd 6)

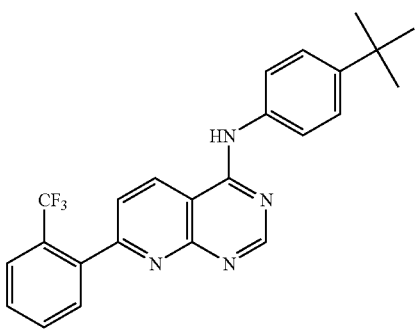

The 2-chloro substituent in (4-tert-Butyl-phenyl)-[2-chloro-7-(2-trifluoromethyl-phenyl)-pyrido[2,3-d]pyrimidin-4-yl]-amine can be removed using a number of reducing conditions known to those skilled in the art of organic synthesis e.g. hydrogenolysis or treatment with aluminum hydride reducing agents (See, e.g., Hudlicky, M. *Reductions in Organic Chemistry*, ACS Monograph 188: 1996).

F. [7-(3-fluoro-pyridin-2-yl)-quinazolin-4-yl]-(5-trifluoromethyl-pyridin-2-yl)-amine (cmpd 7)

1. 7-bromo-4-chloro-quinazoline

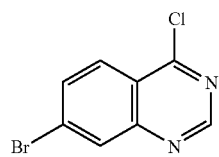

Reflux a solution of 7-bromo-3H-quinazolin-4-one (1.24 g, 0.0055 mol) in $POCl_3$ for 3.5 h. Remove the excess $POCl_3$ under reduced pressure and partition the residue between EtOAc and saturated aqueous $NaHCO_3$. Dry the EtOAc layer and remove the solvent under reduced pressure to give 7-bromo-4-chloro-quinazoline as a yellow solid.

2. (7-bromo-quinazolin-4-yl)-(5-trifluoromethyl-pyridin-2-yl)-amine

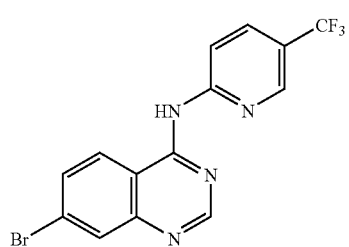

Heat a mixture of 7-bromo-4-chloro-quinazoline (200 mg, 0.821 mmol) and 2-amino-5-trifluoromethyl-pyridine (239 mg, 1.48 mmol) at 230° C. for 2 minutes. Cool and partition the solid residue between EtOAc and 10% NaOH. Dry the EtOAc layer ($Na_2SO_4$), remove the solvent under reduced pressure, and purify via flash chromatography to yield (7-bromo-quinazolin-4-yl)-(5-trifluoromethyl-pyridin-2-yl)-amine as a yellow solid.

3. 3-fluoro-2-tributylstannanyl-pyridine

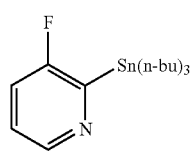

Cool a solution of 2-bromo-3-fluoro-pyridine (542 mg, 3.08 mmol) in dry THF to −78° C. using a dry ice acetone bath. Add n-butyl-lithium (1.6 M in THF, 2.0 mL) to the reaction mixture dropwise via syringe over a 20 minute period. After stirring for 1.5 hours at −78° C., add tributyltin chloride slowly via syringe and remove the cooling bath. After 2 hours, partition the reaction mixture between EtOAc and brine, dry the EtOAc layer ($Na_2SO_4$) and remove the solvents under reduced pressure. Flash chromatography (ether/hexanes) yields 3-fluoro-2-tributylstannanyl-pyridine as a colorless oil.

4. [7-(3-fluoro-pyridin-2-yl)-quinazolin-4-yl]-(5-trifluoromethyl-pyridin-2-yl)-amine

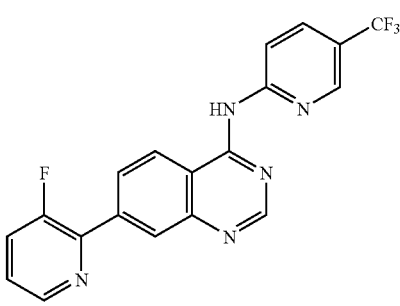

Using procedures analogous to those given above, [7-(3-fluoro-pyridin-2-yl)-quinazolin-4-yl]-(5-trifluoromethyl-pyridin-2-yl)-amine is prepared by coupling (7-bromo-quinazolin-4-yl)-(5-trifluoromethyl-pyridin-2-yl)-amine to 3-fluoro-2-tributylstannanyl-pyridine. Mass spec. 385.1.

G. (4-tert-butyl-phenyl)-(7-pyridin-2-yl-quinazolin-4-yl)-amine (cmpd 8)

1. 4-bromo-2-nitro-benzonitrile

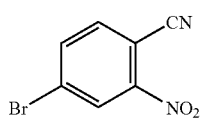

Stir the mixture of 1,4-dibromo-2-nitro-benzene (3.56 mmol) and CuCN (3.74 mmol) in DMA (4 ml) at 100° C. for 5 hours. Cool to room temperature, dilute with EtOAc, filter through celite, wash the organic layer with brine, dry over $Na_2SO_4$, and concentrate under vacuum. Purify the residue by flash chromatography (4:1 hexanes/EtOAc) to give 4-bromo-2-nitro-benzonitrile.

2. 2-amino-4-bromo-benzonitrile

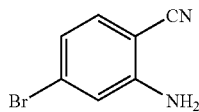

To a suspension of 4-bromo-2-nitro-benzonitrile (2.60 g, 0.0115 mol) in 12N HCl at 0° C., add $SnCl_2$-$2H_2O$ portionwise. As the reaction is stirred vigorously, a white precipitate will form. After 1 h add ice to the reaction vessel followed by 10N NaOH until the solution is basic. Extract the aqueous mixture with ether (2×) and EtOAc (1×) and wash the combined organic layers with brine. Dry the solution ($Na_2SO_4$) and remove the solvents under reduced pressure to give 2-amino-4-bromo-benzonitrile as a beige solid.

3. 7-bromo-3H-quinazolin-4-one

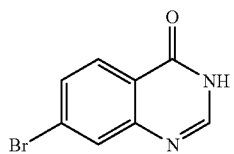

To a solution of 2-amino-4-bromo-benzonitrile (550 mg, 2.79 mmol) in formic acid, add sodium acetate (435 mg, 5.30 mmol) in one portion. Reflux the reaction mixture for 16 h then remove the formic acid under reduced pressure to give a solid. Add 20% aqueous NaOH and stir for 1 hour. Remove the undissolved solids via filtration and acidify the filtrate with 12N HCl to produce a white solid. Collect the solid via filtration and wash it with water (5×) and ether (1×) to give 7-bromo-3H-quinazolin-4-one as an off-white solid.

4. 7-pyridin-2-yl-3H-quinazolin-4-one

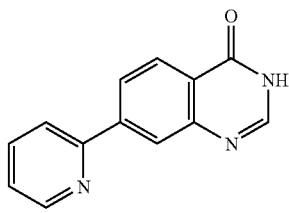

To a solution of 7-bromo-3H-quinazolin-4-one (100 mg, 0.444 mmol) in toluene/dioxane (3:1), add 2-tributylstannanyl-pyridine (162 mg, 0.444 mmol) followed by tetrakis-(triphenylphosphine)-palladium(0) (26 mg, 0.022 mmol). Bubble dry nitrogen through the solution for 10 minutes then heat the stirring solution to 115° C. under a nitrogen atmosphere. After several minutes the reaction mixture becomes homogeneous. After 16 hours, cool the reaction vessel and collect the precipitate via filtration. Wash the solid with 25% EtOAc/hexanes followed by hexanes to give 7-pyridin-2-yl-3H-quinazolin-4-one as a beige solid.

5. (4-tert-butyl-phenyl)-(7-pyridin-2-yl-quinazolin-4-yl)-amine

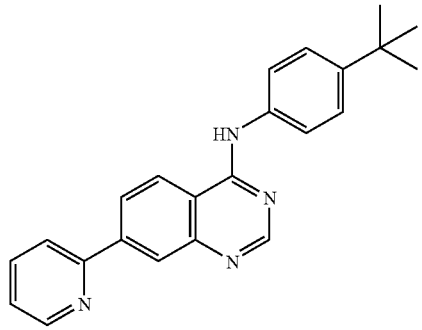

Using procedures analogous to those given above, (4-tert-butyl-phenyl)-(7-pyridin-2-yl-quinazolin-4-yl)-amine is prepared from 4-chloro-7-pyridin-2-yl-quinazoline and 4-tert-butylaniline. Mass spec. 354.2.

H. (4-tert-Butyl-phenyl)-[7-(3-trifluoromethyl-pyridin-2-yl)-quinazolin-4-yl]-amine hydrochloride (cmpd 9)

1. 2-(4-bromo phenyl)-3-(trifluoromethyl)-pyridine

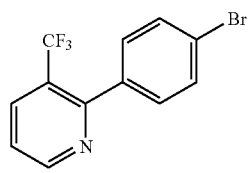

To a de-gassed mixture of 2-bromo-3-(trifluoromethyl)-pyridine (2.26 mmol), 4-bromo-phenylbronic acid (2.49 mmol), and 2M $Na_2CO_3$ (5.65 mmol), in DME (10 mL) under nitrogen add $Pd(PPh_3)_4$ (0.09 mmol). Stir the mixture at 80° C. for overnight, concentrate, extract with EtOAc. Dry over $Na_2SO_4$, concentrate under vacuum, and purify by flash chromatography (4:1 hexanes/EtOAc) to give 2-(4-bromo phenyl)-3-(trifluoromethyl)-pyridine.

2. 2-(4-bromo-3-nitro-phenyl)-3-(trifluoromethyl)-pyridine

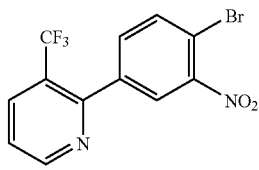

To a solution of 2-(4-bromophenyl)-3-(trifluoromethyl)-pyridine (0.93 mmol) in H₂SO₄ (4 mL) cautiously add fuming HNO₃ (2 ml). Stir the mixture 30 minutes at room temperature. Pour the mixture onto ice-water (20 mL) and collect the precipitate. Dissolve the precipitate in EtOAc and neutralize with saturated NaHCO₃, dry over Na₂SO₄, concentrate under vacuum to obtain 2-(4-bromo-3-nitro-phenyl)-3-(trifluoromethyl)-pyridine.

3. 2-nitro-4-(3-trifluoromethyl-pyridin-2-yl)-benzonitrile

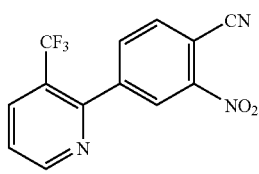

To a solution of 2-(4-bromo-3-nitro-phenyl)-3-(trifluoromethyl)-pyridine (0.55 mmol) in DMA (4 mL) add CuCN (0.60 mmol). Stir the mixture 4 hours at 110° C. Cool to room temperature, dilute with 20 ml of EtOAc, and filter through celite pad. Wash the filtrated with brine, dry over Na₂SO₄, concentrate under vacuum, and purify by flash chromatography (1:1 hexanes/EtOAc) to give 2-nitro-4-(3-trifluoromethyl-pyridin-2-yl)-benzonitrile.

4. 2-amino-4-(3-trifluoromethyl-pyridin-2-yl)-benzo-nitrile

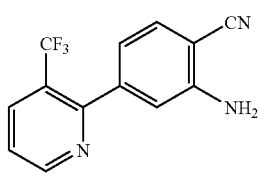

To an ice-water cooled solution of 2-nitro-4-(3-trifluoromethyl-pyridin-2-yl)-benzonitrile (0.44 mmol) in conc. HCl (6 mL) add SnCl₂ (1.457 mmol). Stir the mixture 2 h at room temperature. neutralize with NaOH, extract with EtOAc, dry over Na₂SO₄, and concentrate under vacuum. Purify the residue by flash chromatography (4:1 hexanes/EtOAc) to give 2-amino-4-(3-trifluoromethyl-pyridin-2-yl)-benzo-nitrile.

5. 7-(3-trifluoromethyl-pyridin-2-yl)-quinazolin-4-ol

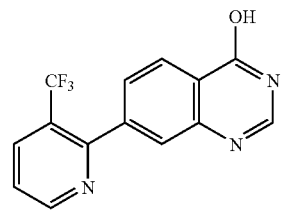

Reflux 2-amino-4-(3-trifluoromethyl-pyridin-2-yl)-benzo-nitrile (0.41 mmol) and NaOAc (1.23 mmol) for 16 h in HCOOH (10 mL). Evaporate the solvent in vacuo, suspend the residue in 20 ml of 20% NaOH, stir for 30 min at room temperature. Filter, extract with EtOAc, dry over Na₂SO₄, and concentrate under vacuum to give 7-(3-trifluoromethyl-pyridin-2-yl)-quinazolin-4-ol.

6. 4-chloro-7-(3-trifluoromethyl-pyridin-2-yl)-quinazoline

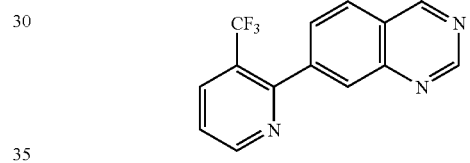

Reflux 7-(3-trifluoromethyl-pyridin-2-yl)-quinazolin-4-ol (0.38 mmol) for 18 hours in POCl₃ (5 mL). Evaporate the solvent in vacuo, then carefully neutralize with saturated NaHCO₃, and extract with EtOAc. Dry over Na₂SO₄, concentrate under vacuum to obtain 4-chloro-7-(3-trifluoromethyl-pyridin-2-yl)-quinazoline.

7. (4-tert-Butyl-phenyl)-[7-(3-trifluoromethyl-pyridin-2-yl)-quinazolin-4-yl]hydrochloride

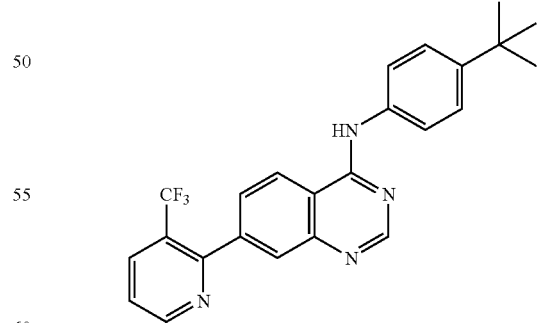

Stir 4-chloro-7-(3-trifluoromethyl-pyridin-2-yl)-quinazoline (0.16 mmol) and 4-tert-butyl-aniline (0.32 mmol) in IPA (4 mL) at 80° C. for 6 hours. Cool the mixture and collect the precipitate to obtain (4-tert-Butyl-phenyl)-[7-(3-trifluoromethyl-pyridin-2-yl)-quinazolin-4-yl] hydrochloride. Mass spec. 422.2.

I. (4-tert-Butylphenyl)-[2-methyl-7-(3-trifluoromethyl-pyridin-2-yl)-quinazolin-4-yl]-amine hydrochloride (cmpd 10)

1. 2-amino-4-(3-trifluoromethyl-pyridin-2-yl)-benzamide

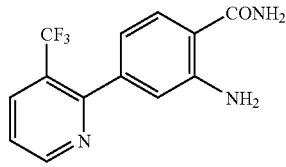

Stir a mixture of 2-amino-4-(3-trifluoromethyl-pyridin-2-yl)-benzo-nitrile (0.50 mmol) in 70% H₂SO₄ (10 ml) at 110° C. for 1 hour. Cool to room temperature, neutralize with NaOH, extract with EtOAc, dry over Na₂SO₄, and concentrate under vacuum. Purify the residue by flash chromatography (3:2 hexanes/EtOAc) to give 2-amino-4-(3-trifluoromethyl-pyridin-2-yl)-benzamide.

2. 2-acetylamino-4-(3-trifluoromethyl-pyridin-2-yl)-benzamide

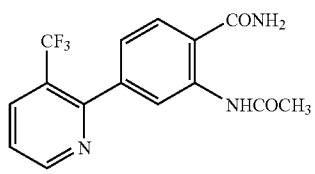

To a solution of 2-amino-4-(3-trifluoromethyl-pyridin-2-yl)-benzamide (0.5 mmol) and pyridine (0.55 mmol) in THF (5 ml) add acetyl chloride (0.55 mmol). Stir the mixture 10 minutes at room temperature. Concentrate under vacuum, extract with EtOAc, wash with brine, dry over Na₂SO₄, and concentrate under vacuum. Triturate with ether to give 2-acetylamino-4-(3-trifluoromethyl-pyridin-2-yl)-benzamide.

3. 2-methyl-7-(3-trifluoromethyl-pyridin-2-yl)-quinazolin-4-ol

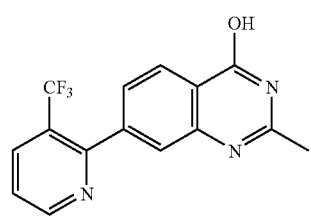

Suspend 2-acetylamino-4-(3-trifluoromethyl-pyridin-2-yl)-benzamide in 20 ml of 20% NaOH, stir for 30 minutes at room temperature. Filter, acidify to pH=6, extract with EtOAc, and concentrate under vacuum to give 2-methyl-7-(3-trifluoromethyl-pyridin-2-yl)-quinazolin-4-ol.

4. 4-chloro-2-methyl-7-(3-trifluoromethyl-pyridin-2-yl)-quinazoline

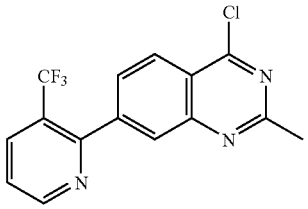

Using procedures analogous to those already described 4-chloro-2-methyl-7-(3-trifluoromethyl-pyridin-2-yl)-quinazoline is prepared from 2-methyl-7-(3-trifluoromethyl-pyridin-2-yl)-quinazolin-4-ol.

5. (4-tert-Butyl-phenyl)-[2-methyl-7-(3-trifluoromethyl-pyridin-2-yl)-quinazolin-4-yl]-amine

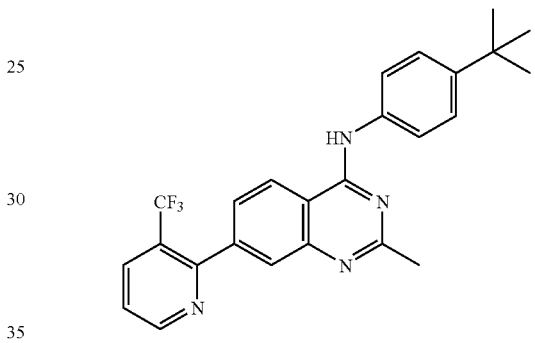

Using procedures analogous to those already described, (4-tert-Butyl-phenyl)-[2-methyl-7-(3-trifluoromethyl-pyridin-2-yl)-quinazolin-4-yl]-amine is prepared by condensing 4-chloro-2-methyl-7-(3-trifluoromethyl-pyridin-2-yl)-quinazoline with 4-tert-butylaniline. Mass spec. 436.2.

J. [7-(3-Methyl-pyridin-2-yl)-quinazolin-4-yl]-(4-trifluoromethyl-phenyl)-amine (cmpd 11)

1. 7-[B(OH)₂]-3H-quinazolin-4-one

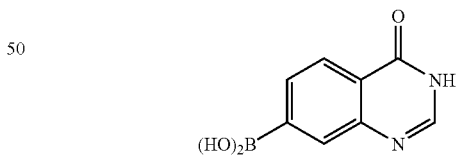

Reflux a mixture of 3-amino-4-carboethoxy-phenylboronic acid (1.46 g, 0.007 mol), prepared according to the procedure of Torssell et. al. (1957) *Arkiv Kemi* 10:497, and formamidine acetate (1.17 g, 0.008 mol) in methoxyethanol for 7 hours. Add an additional equivalent of formamidine acetate and continue to reflux for 16 hours. Cool the dark solution and remove the solvent under reduced pressure. Add ~100 mL of water, stir for 10 minutes, and collect the light gray solid on a sintered glass funnel. Wash the solid with water (3×), dry, and recrystallize from methanol to give 7-[B(OH)₂]-3H-quinazolin-4-one as a white solid.

2. 7-(3-Methyl-pyridin-2-yl)-3H-quinazolin-4-one

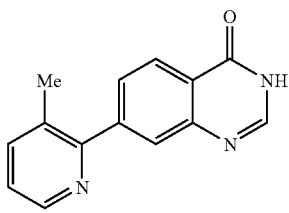

Purge a solution of 7-[B(OH)₂]-3H-quinazolin-4-one (115 mg, 0.605 mmol), 2-bromo-3-methyl-pyridine (103 mg, 0.605 mmol), Na₂CO₃ (0.757 mL, 1.51 mmol, 2M aqueous solution), and DMF (4 mL) with nitrogen for 10 minutes. Add a catalytic amount of tetrakis-(triphenylphosphine)-palladium(0) (35 mg, 0.03 mmol) and heat at 95° C. for 16 hours. Cool the reaction mixture, dilute with water and extract with ethyl acetate. Dry the combined organic layers (Na₂SO₄), concentrate under reduced pressure, and purify the crude product using silica gel chromatography (MeOH/CH₂Cl₂) to give 7-(3-Methyl-pyridin-2-yl)-3H-quinazolin-4-one.

3. [7-(3-Methyl-pyridin-2-yl)-quinazolin-4-yl]-(4-trifluoromethyl-phenyl)-amine

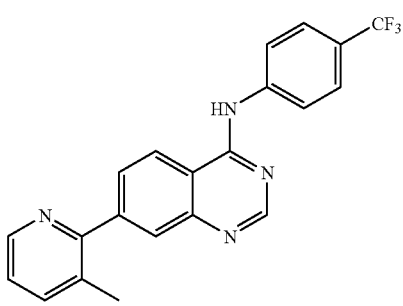

Using procedures analogous to those described above (see, for example, Schemes 1 and 2), [7-(3-Methyl-pyridin-2-yl)-quinazolin-4-yl]-(4-trifluoromethyl-phenyl)-amine is prepared from 7-(3-Methyl-pyridin-2-yl)-3H-quinazolin-4-one in two steps. Mass spec. 380.1.

K. (4-tert-Butyl-phenyl)-[7-(3-trifluoromethyl-pyridin-2-yl)-quinazolin-4-yl]-amine hydrochloride (cmpd 9)

1. 2-p-tolyl-3-trifluoromethyl-pyridine

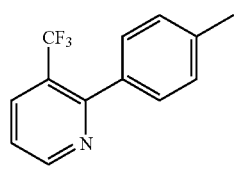

To a de-gassed mixture of 2-chloro-3-(trifluoromethyl)-pyridine (70.1 mmol), p-tolylboronic acid (70.6 mmol), and 2M Na₂CO₃ (175.0 mmol), in DME (200 mL) under nitrogen add Pd(PPh₃)₄ (2.8 mmol). Stir the mixture at 80° C. for overnight, concentrate, extract with EtOAc. Dry over Na₂SO₄, concentrate under vacuum, pass a silica gel pad to give 2-p-tolyl-3-trifluoromethyl-pyridine.

2. 2-(4-methyl-3-nitro-phenyl)-3-(trifluoromethyl)-pyridine

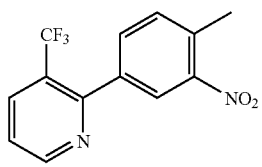

To a solution of 2-p-tolyl-3-trifluoromethyl-pyridine (8.4 mmol) in H₂SO₄ (6 mL) cautiously add fuming HNO₃ (2 ml). Stir the mixture 60 minutes at room temperature. Pour the mixture onto ice-water (30 mL), extract with EtOAc, neutralize with 1 N NaOH, dry over Na₂SO₄, and concentrate under vacuum to obtain 2-(4-methyl-3-nitro-phenyl)-3-(trifluoromethyl)-pyridine.

3. 2-nitro-4-(3-trifluoromethyl-pyridin-2-yl)-benzoic acid

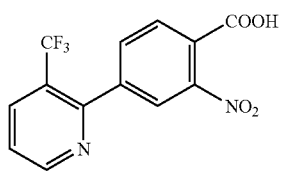

To a solution of 2-(4-methyl-3-nitro-phenyl)-3-(trifluoromethyl)-pyridine (7.1 mmol) in the mixture of pyridine (10 mL) and water (5 ml) add KMnO₄ (25.3 mmol) portionwise. Stir the mixture 4 hours at 110° C. then add another 25.3 mmol of KMnO₄ with 10 ml of water. Stir the mixture at 110° C. for overnight. Cool to room temperature, filter through celite pad. Concentrate the filtrate under vacuum, dilute with water, and wash the aqueous with EtOAc. Neutralize the aqueous with 2 N HCl and collect the precipitate to give 2-nitro-4-(3-trifluoromethyl-pyridin-2-yl)-benzoic acid.

4. 2-amino-4-(3-trifluoromethyl-pyridin-2-yl)-benzoic acid

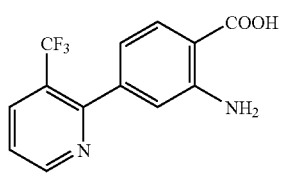

Hydrogenate the solution of 2-nitro-4-(3-trifluoromethyl-pyridin-2-yl)-benzoic acid (3.84 mmol) in 95% EtOH (100 mL) with 10% Pd—C (150 mg) for over night. Filter through a celite pad and concentrate the filtrate to give 2-amino-4-(3-trifluoromethyl-pyridin-2-yl)-benzoic acid.

5. 7-(3-trifluoromethyl-pyridin-2-yl)-quinazolin-4-ol

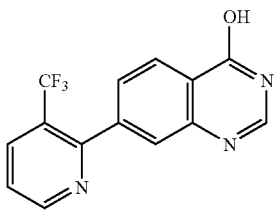

Stir the mixture of 2-amino-4-(3-trifluoromethyl-pyridin-2-yl)-benzoic acid (1.95 mmol) in HCONH$_2$ (10 mL) for 4 hours at 145° C. Cool to room temperature, dilute with 20 ml of water, and collect the precipitate to give 7-(3-trifluoromethyl-pyridin-2-yl)-quinazolin-4-ol.

6. (4-tert-Butyl-phenyl)-[7-(3-trifluoromethyl-pyridin-2-yl)-quinazolin-4-yl]-amine hydrochloride

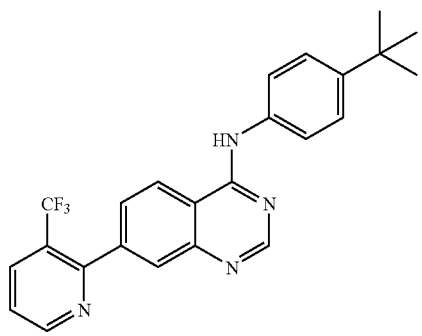

Using procedures analogous to those described above (see, for example, Schemes 1 and 2, (4-tert-Butyl-phenyl)-[7-(3-trifluoromethyl-pyridin-2-yl)-quinazolin-4-yl]-amide hydrochloride is prepared from 7-(3-trifluoromethyl-pyridin-2-yl)-quinazolin-4-ol in two steps. Mass spec. 422.2.

L. [6-(propane-2-sulfonyl)-pyridin-3-yl]-[7-(3-trifluoromethyl-pyridin-2-yl)-quinazolin-4-yl]-amine hydrochloride (cmpd 12)

1. 2-Isopropylsulfanyl-5-nitro-pyridine

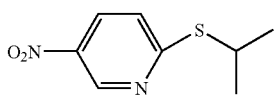

Stir the mixture of 2-mercapto-5-nitropyridine (10.0 mmol) and NaH (14.0 mmol) in DMA (10 ml) at room temperature for 30 minutes. Add 2-iodopropane (11.0 mmol) and stir overnight at room temperature. Dilute with H$_2$O; extract with EtOAc, wash with brine, dry over Na$_2$SO$_4$, and concentrate under vacuum. Purify the residue by flash chromatography (9:1 hexanes/EtOAc) to give 2-isopropyl-sulfanyl-5-nitro-pyridine.

2. 5-Nitro-2-(propane-2-sulfonyl)-pyridine

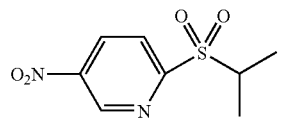

Heat the mixture of 2-isopropyl-sulfanyl-5-nitro-pyridine (3.5 mmol) and KMnO$_4$ (14.1 mmol) in HOAc (15 ml) at 110° C. for overnight. Filter, concentrate the filtrate, and neutralize with NaHCO$_3$. Extract with EtOAc, wash with brine, dry over Na$_2$SO$_4$, and concentrate under vacuum to give 2-(propyl-2-sulfonyl)-5-nitro-pyridine.

3. 6-(Propane-2-sulfonyl)-pyridin-3-ylamine

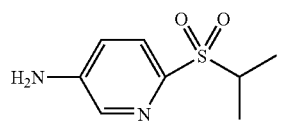

Suspend 2-(propyl-2-sulfonyl)-5-nitro-pyridine (0.44 mmol) in 10 ml of conc. HCl, add SnCl2 dihydrate (1.43 mmol), and stir for 2 hours at room temperature. Neutralize with NaOH. Extract with EtOAc, wash with brine, dry over Na$_2$SO$_4$, and concentrate under vacuum to give 6-(propane-2-sulfonyl)-pyridin-3-ylamine.

4. [6-(propane-2-sulfonyl)-pyridin-3-yl]-[7-(3-trifluoromethyl-pyridin-2-yl)-quinazolin-4-yl]-amine hydrochlorides

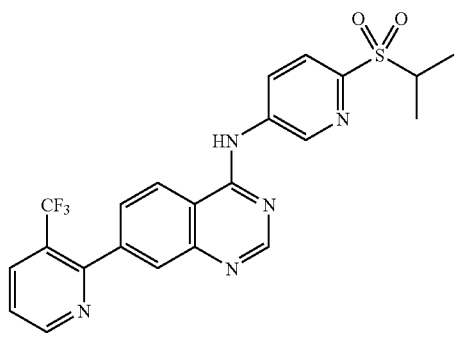

Use the method described in Example 1H.7 to obtain [6-(propane-2-sulfonyl)-pyridin-3-yl]-[7-(3-trifluoromethyl-pyridin-2-yl)-quinazolin-4-yl]-amine hydrochloride. Mass spec. 473.1.

M. Additional Representative Substituted Quinazolin-4-ylamine Analogues

Using routine modifications, the starting materials may be varied and additional steps employed to produce other compounds encompassed by the present invention. Compounds listed in Table II were prepared using the above methods, with readily apparent modifications.

TABLE II

Representative Substituted Quinazoline-4-ylamine Analogues

| Compound | | Name | MS |
|---|---|---|---|
| 13. | | (5-trifluoromethyl-pyridin-2-yl)-[7-(3-trifluoromethyl-pyridin-2-yl)-quinazolin-4-yl]-amine | 435.1 |
| 14. | | (6-trifluoromethyl-pyridin-3-yl)-[7-(3-trifluoromethyl-pyridin-2-yl)-pyrido[3,2-d]pyrimidin-4-yl]-amine | 436.1 |
| 15. | | [2-methyl-7-(3-trifluoromethyl-pyridin-2-yl)-quinazolin-4-yl]-(6-trifluoromethyl-pyridin-3-yl)-amine | 449.1 |
| 16. | | (6-trifluoromethyl-pyridin-3-yl)-[7-(3-trifluoromethyl-pyridin-2-yl)-quinazolin-4-yl]-amine | 435.1 |
| 17. | | (5-chloro-pyridin-2-yl)-[7-(3-trifluoromethyl-pyridin-2-yl)-quinazolin-4-yl]-amine | 336.2 |

TABLE II-continued

Representative Substituted Quinazoline-4-ylamine Analogues

| Compound | Name | MS |
|---|---|---|
| 18. | [2-chloro-7-(2-trifluoromethyl-phenyl)-pyrido[2,3-d]pyrimidin-4-yl]-(6-trifluoromethyl-pyridin-3-yl)-amine | 469.1 |
| 19. | [2-chloro-7-(2-trifluoromethyl-phenyl)-pyrido[2,3-d]pyrimidin-4-yl]-(4-trifluoromethyl-phenyl)-amine | |
| 20. | [7-(2-trifluoromethyl-phenyl)-quinazolin-4-yl]-(5-trifluoromethyl-pyridin-2-yl)-amine | 434.1 |
| 21. | (7-pyridin-2-yl-quinazolin-4-yl)-(5-trifluoromethyl-pyridin-2-yl)-amine | 367.1 |

TABLE II-continued
Representative Substituted Quinazoline-4-ylamine Analogues
| Compound | | Name | MS |
|---|---|---|---|
| 22. | 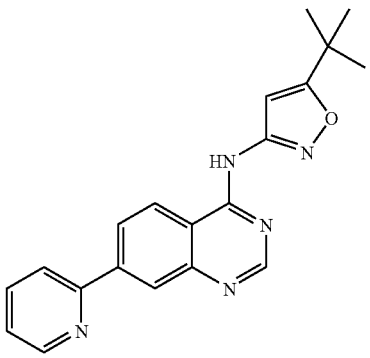 | (5-tert-butyl-isoxazol-3-yl)-(7-2-yl-quinazolin-4-yl)-amine | 345.2 |
| 23. | 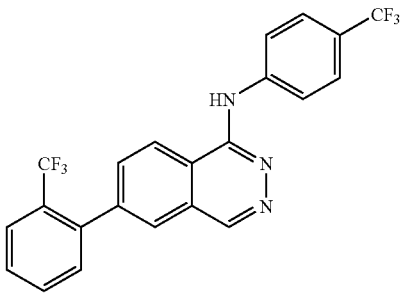 | (4-trifluoromethyl-phenyl)-[6-(2-trifluoromethyl-phenyl)-phthalazin-1-yl]amine | 433.1 |
| 24. | 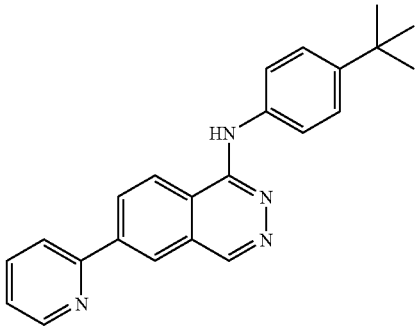 | (4-tert-Butyl-phenyl)-(6-pyridin-2-yl-phthalazin-1-yl)-amine | 354.2 |
| 25. | 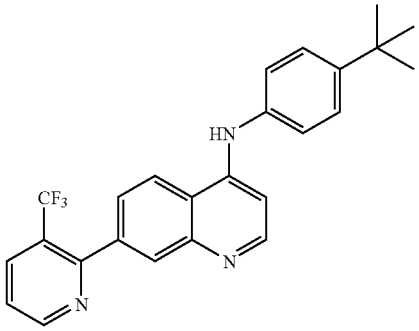 | (4-tert-Butyl-phenyl)-[7-(3-trifluoromethyl-pyridin-2-yl)-quinolin-4-yl]-amine | 421.2 |

TABLE II-continued

Representative Substituted Quinazoline-4-ylamine Analogues

| Compound | Name | MS |
|---|---|---|
| 26. | (4-trifluoromethoxy-phenyl)-7-(3-trifluoromethyl-pyridin-2-yl)-pyrido[3,2-d]pyrimidin-4-yl]-amine | 451.1 |
| 27. | (4-tert-butyl-phenyl)-[7-(2-trifluoromethyl-phenyl)-quinazolin-4-yl]-amine | 421.2 |
| 28. | (4-trifluoromethyl-phenyl)-[7-(2-trifluoromethyl-phenyl)-pyrido[3,2-d]pyrimidin-4-yl]amine | 434.1 |
| 29. | [7-(1-Oxy-3-trifluoromethyl-pyridin-2-yl)-quinazolin-4-yl]-(4-trifluoromethyl-phenyl)-amine | 450.1 |

TABLE II-continued

Representative Substituted Quinazoline-4-ylamine Analogues

| Compound | Name | MS |
|---|---|---|
| 30. | [7-(1-Oxy-pyridin-2-yl)-quinazolin-4-yl]-(4-trifluoromethyl-phenyl)-amine | 382.1 |
| 31. | (4-Trifluoromethyl-phenyl)-[7-(3-trifluoromethyl-pyridin-2-yl)-pyrido[3,2-d]pyrimidin-4-yl]-amine | 435.1 |
| 32. | (4-tert-butyl-phenyl)-[2-methyl-7-(2-trifluoromethyl-phenyl)-quinazolin-4-yl]-amine | 435.2 |
| 33. | [2-methyl-7-(2-trifluoromethyl-phenyl)-quinazolin-4-yl]-(4-trifluoromethyl-phenyl)-amine | 447.1 |

TABLE II-continued

Representative Substituted Quinazoline-4-ylamine Analogues

| Compound | Name | MS |
|---|---|---|
| 34. | (4-tert-butyl-phenyl)-[2-isopropyl-7-(2-trifluoromethyl-phenyl)-quinazolin-4-yl]-amine | 463.2 |
| 35. | $N^2$-isobutyl-$N^4$-(4-trifluoromethyl-phenyl)-7-(2-trifluoromethyl-phenyl)-pyrido[2,3-d]pyrimidine-2,4-diamine | 505.2 |
| 36. | [4-(1,2,2,2-tetrafluoro-1-trifluoromethyl-ethyl)-phenyl-]-[7-(2-trifluoromethyl-phenyl)-quinazolin-4-yl]-amine | 533.1 |
| 37. | (4-isopropyl-3-methyl-phenyl)-[7-(2-trifluoromethyl-phenyl)-pyrido[3,2-d]pyrimidin-4-yl]amine | 422.2 |

TABLE II-continued

Representative Substituted Quinazoline-4-ylamine Analogues

| Compound | | Name | MS |
|---|---|---|---|
| 38. | 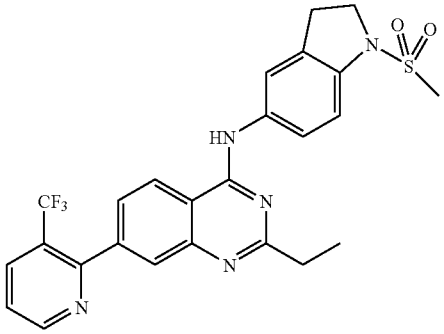 | [2-Ethyl-7-(3-trifluoromethyl-pyridin-2-yl)-quinazolin-4-yl]-(1-methanesulfonyl-2,3-dihydro-1H-indol-5-yl)-amine | 513.1 |
| 39. | 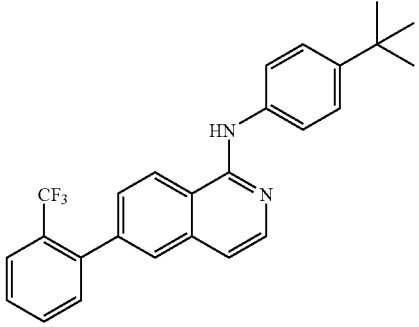 | (4-tert-butyl-phenyl)-[6-(2-trifluoromethyl-phenyl)-isoquinolin-1-yl]-amine | 420.2 |
| 40. | 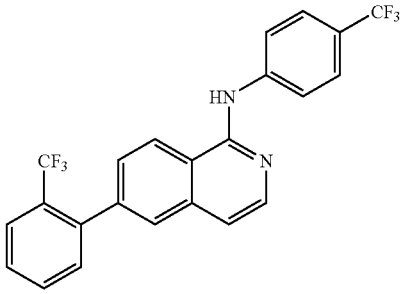 | (4-trifluoromethyl-phenyl)-[6-(2-trifluoromethyl-phenyl)-isoquinolin-1-yl]amine | 432.1 |
| 41. | 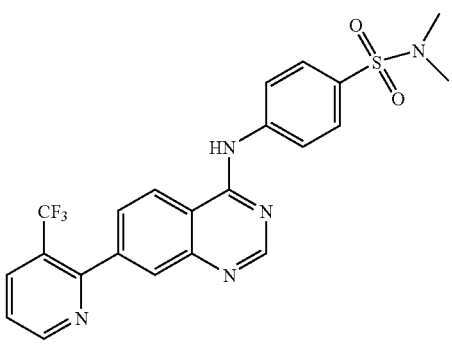 | N,N-dimethyl-4-[7-(3-trifluoromethyl-pyridin-2-yl)-quinazolin-4-ylamino]-benzenesulfonamide | 473.1 |

TABLE II-continued

Representative Substituted Quinazoline-4-ylamine Analogues

| Compound | | Name | MS |
|---|---|---|---|
| 42. | 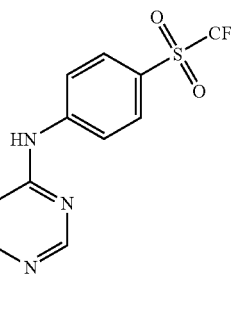 | (4-trifluoromethanesulfonyl-phenyl)-[7-(3-trifluoromethyl-pyridin-2-yl)-quinazolin-4-yl]-amine | 498.1 |
| 43. | 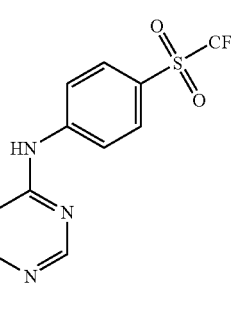 | (4-trifluoromethanesulfonyl-phenyl)-[7-(3-trifluoromethyl-pyridin-2-yl)-pyrido[3,2-d]pyrimidin-4-yl]-amine | 499.1 |
| 44. | 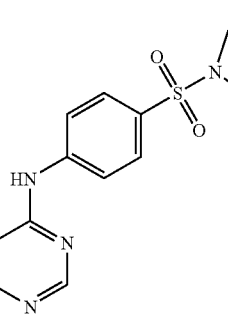 | [4-(pyrrolidine-1-sulfonyl)-phenyl]-[7-(3-trifluoromethyl-pyridin-2-yl)-quinazolin-4-yl]-amine | 499.1 |
| 45. | 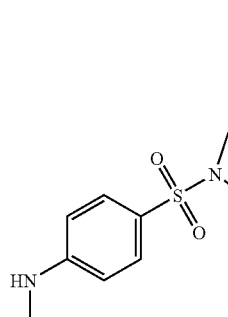 | [4-(3-Dimethylamino-pyrrolidine-1-sulfonyl)-phenyl]-[7-(3-trifluoromethyl-pyridin-2-yl)-quinazolin-4-]-amine | 542.2 |

TABLE II-continued

Representative Substituted Quinazoline-4-ylamine Analogues

| Compound | Name | MS |
|---|---|---|
| 46. | [4-(piperdine-1-sulfonyl)-phenyl]-[7-(3-trifluoromethyl-pyridin-2-yl)-quinazolin-4-yl]-amine | 513.1 |
| 47. | [4-(morpholine-4-sulfonyl)-phenyl]-[7-(3-trifluoromethyl-pyridin-2-yl)-quinazolin-4-yl]-amine | 515.1 |
| 48. | [4-(morpholine-4-sulfonyl)-phenyl]-[7-(3-trifluoromethyl-pyridin-2-yl)-pyrido[3,2-d]pyrimidin-4-yl]-amine | 516.1 |
| 49. | [4-(2-methyl-piperdine-1-sulfonyl)-phenyl]-[7-(3-trifluoromethyl-pyridin-2-yl)-quinazolin-4-yl]-amine | 527.2 |

TABLE II-continued

Representative Substituted Quinazoline-4-ylamine Analogues

| Compound | Name | MS |
|---|---|---|
| 50. | [4-(2,6-Dimethyl-piperidine-1-sulfonyl)-phenyl]-[7-(3-trifluoromethyl-pyridin-2-yl)-quinazolin-4-yl]-amine (chiral) | 541.2 |
| 51. | [4-(2-methyl-pyrrolidine-1-sulfonyl)-phenyl]-[7-(3-trifluoromethyl-pyridin-2-yl)-quinazolin-4-yl]-amine | 513.1 |
| 52. | [4-(2,5-dimethyl-pyrrolidine-1-sulfonyl)-phenyl]-[7-(3-trifluoromethyl-pyridin-2-yl)-quinazolin-4-yl]-amine | 527.2 |

TABLE II-continued

Representative Substituted Quinazoline-4-ylamine Analogues

| Compound | Name | MS |
|---|---|---|
| 53. | [4-(2,6-dimethyl-morpholine-4-sulfonyl)-phenyl]-[7-(3-trifluoromethyl-pyridin-2-yl)-quinazolin-4-yl]-amine | 543.2 |
| 54 | [4-(2-methoxymethyl-pyrrolidine-1-sulfonyl)-phenyl]-[7-(3-trifluoromethyl-pyridin-2-yl)-quinazolin-4-yl]-amine (chiral) | 543.2 |
| 55. | [4-(2-methoxymethyl-pyrrolidine-1-sulfonyl)-phenyl]-[7-(3-trifluoromethyl-pyridin-2-yl)-quinazolin-4-yl]-amine (chiral) | 543.2 |

TABLE II-continued

Representative Substituted Quinazoline-4-ylamine Analogues

| Compound | | Name | MS |
|---|---|---|---|
| 56. | | N,N-diisopropyl-4-[7-(3-trifluoromethyl-pyridin-2-yl)-quinazolin-4-ylamino]-benzenesulfonamide | 529.2 |
| 57. | | N-(2-Hydroxy-1,1-dimethyl-ethyl)-4-[7-(3-trifluoromethyl-pyridin-2-yl)-quinazolin-4-ylamino]-benzenesulfonamide | 517.1 |
| 58. | | | 570.2 |
| 59. | | | 516.1 |

TABLE II-continued

Representative Substituted Quinazoline-4-ylamine Analogues

| Compound | | Name | MS |
|---|---|---|---|
| 60 | 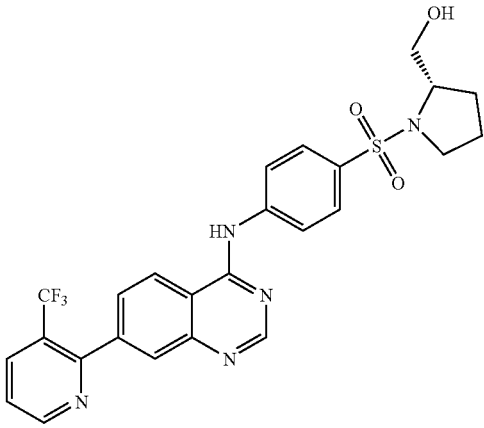 | (1-{4-[7-(3-trifluoromethyl-pyridin-2-yl)-quinazolin-4-ylamino]-benzenesulfonyl}-pyrrolidin-2-yl)-methanol (chiral) | 529.1 |
| 61. | 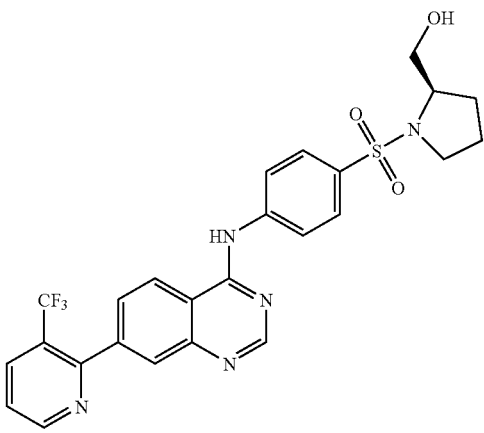 | (1-{4-[7-(3-trifluoromethyl-pyridin-2-yl)-quinazolin-4-ylamino]-benzenesulfonyl}-pyrrolidin-2-yl)-methanol (chiral) | 529.1 |
| 62. | 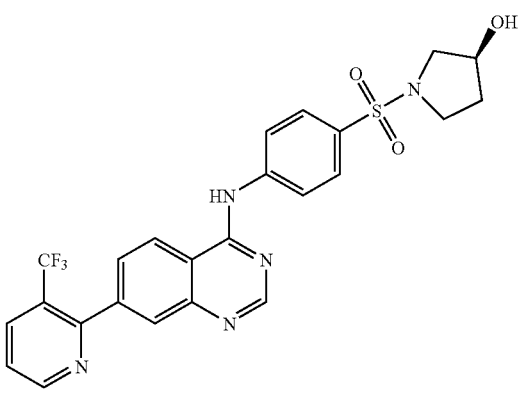 | 1-{4-[7-(3-Trifluoromethyl-pyridin-2-yl)-quinazolin-4-ylamino]-benzenesulfonyl}-pyrrolidin-3-ol (chiral) | 515.1 |
| 63. | 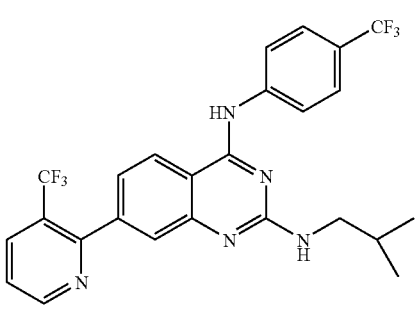 | $N^2$-isobutyl-$N^4$-(4-trifluoromethyl-phenyl)-7-(3-trifluoromethyl-pyridin-2-yl)-quinazoline-2,4-diamine | 505.2 |

TABLE II-continued

Representative Substituted Quinazoline-4-ylamine Analogues

| Compound | | Name | MS |
|---|---|---|---|
| 64. | 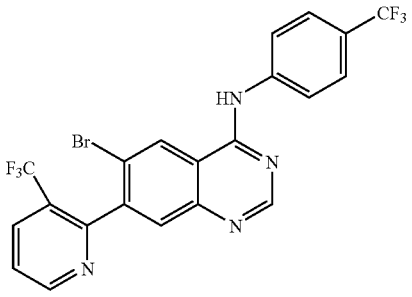 | [6-Bromo-7-(3-trifluoromethyl-pyridin-2-yl)-quinazolin-4-yl]-(4-trifluoromethyl-phenyl)-amine | |
| 65. | 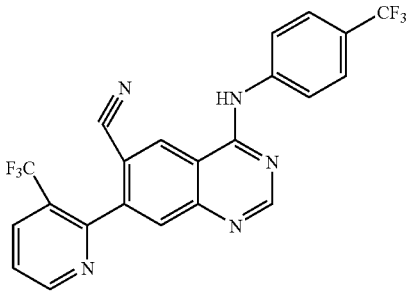 | 4-(4-Trifluoromethyl-phenylamino)-7-(3-trifluoromethyl-pyridin-2-yl)-quinazoline-6-carbonitrile | |
| 66. | 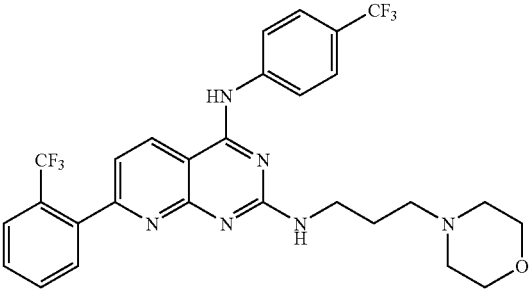 | $N^2$-(3-Morpholin-4-yl-propyl)-$N^4$-(4-trifluoromethyl-phenyl)-7-(2-trifluoromethyl-phenyl)-pyrido[2,3-d]pyrimidine-2,4-diamine | 576.2 |
| 67. | 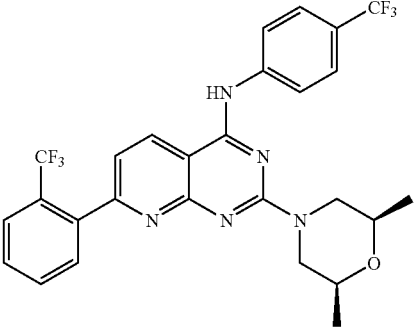 | [2-(2,6-Dimethyl-morpholin-4-yl)-7-(2-trifluoromethyl-phenyl)-pyrido[2,3-d]pyrimidin-4-yl]-(4-trifluoromethyl-phenyl)-amine | 547.2 |

TABLE II-continued

Representative Substituted Quinazoline-4-ylamine Analogues

| Compound | Name | MS |
|---|---|---|
| 68. | [2-(3-Methyl-piperidin-1-yl)-7-(2-trifluoromethyl-phenyl)-pyrido[2,3-d]pyrimidin-4-yl]-(4-trifluoromethyl-phenyl)-amine | 531.2 |
| 69. | (6-Chloro-pyridin-3-yl)-[7-(2-trifluoromethyl-phenyl)-quinazolin-4-yl]-amine | 400.1 |
| 70. | 1,1,1,3,3,3-Hexafluoro-2-{4-[7-(3-trifluoromethyl-pyridin-2-yl)-quinazolin-4-ylamino]-phenyl}-propan-2-ol | 532.1 |
| 71. | (4-Trifluormethoxy-phenyl)-[7-(3-trifluoromethyl-pyridin-2-yl)-quinazolin-4-yl]-amine | 450.1 |

TABLE II-continued

Representative Substituted Quinazoline-4-ylamine Analogues

| Compound | | Name | MS |
|---|---|---|---|
| 72. | 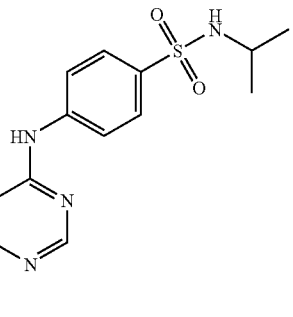 | N-Isopropyl-4-[7-(3-trifluoromethyl-pyridin-2-yl)-quinazolin-4-ylamino]-benzenesulfonamide | 487.1 |
| 73. | 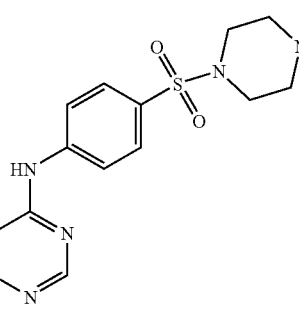 | [4-(4-Methyl-piperazine-1-sulfonyl)-phenyl]-[7-(3-trifluoromethyl-pyridin-2-yl)-quinazolin-4-yl]-amine | 528.2 |
| 74. | 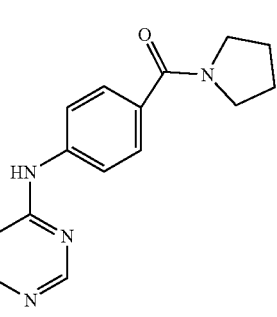 | Pyrrolidin-1-yl-{4-[7-(3-trifluoromethyl-pyridin-2-yl)-quinazolin-4-ylamino]-phenyl}-methanone | 463.2 |
| 75. | 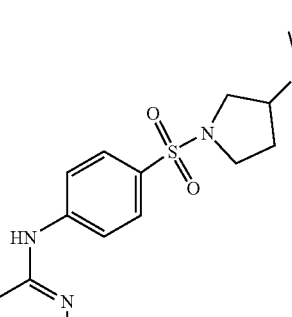 | [4-(3-Dimethylamino-pyrrolidine-1-sulfonyl)-phenyl]-[7-(3-trifluoromethyl-pyridin-2-yl)-quinazolin-4-yl]-amine | |

TABLE II-continued

Representative Substituted Quinazoline-4-ylamine Analogues

| Compound | | Name | MS |
|---|---|---|---|
| 76. | 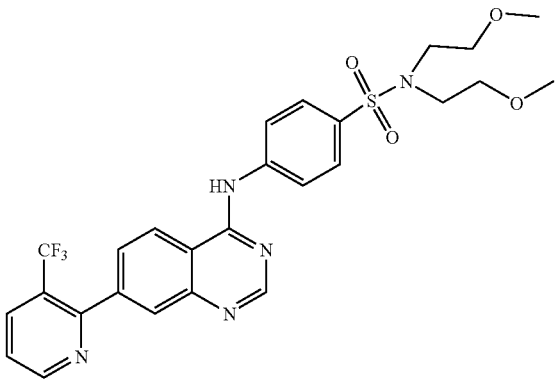 | N,N-Bis-(2-methoxy-ethyl)-4-[7-(3-trifluoromethyl-pyridin-2-yl)-quinazolin-4-ylamino]-benzenesulfonamide | 561.2 |
| 77. | 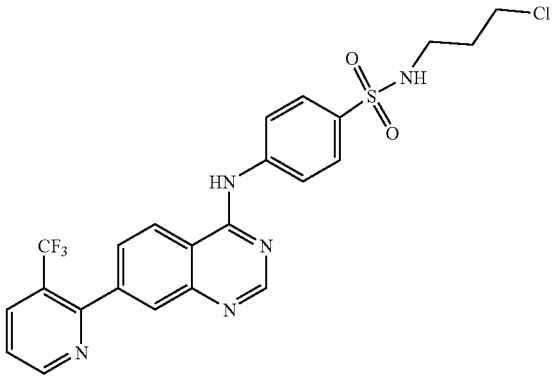 | N-(3-Chloro-propyl)-4-[7-(3-trifluoromethyl-pyridin-2-yl)-quinazolin-4-ylamino]-benzenesulfonamide | 521.1 |
| 78. |  | (4-Methanesulfonyl-phenyl)-[7-(3-trifluoromethyl-pyridin-2-yl)-quinazolin-4-yl]-amine | 444.1 |
| 79. |  | 4[4-(Azetidine-1-sulfonyl)-phenyl]-[7-(3-trifluoromethyl-pyridin-2-yl)-quinazolin-4-yl]-amine | 485.1 |

TABLE II-continued

Representative Substituted Quinazoline-4-ylamine Analogues

| Compound | | Name | MS |
|---|---|---|---|
| 80. |  | [4-(Propane-1-sulfonyl)-phenyl]-[7-(3-trifluoromethyl-pyridin-2-yl)-quinazolin-4-yl]-amine | 472.1 |
| 81. | 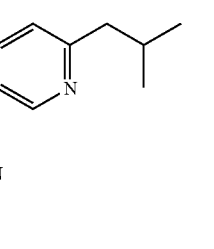 | (6-Isobutyl-pyridin-3-yl)-[7-(3-trifluoromethyl-pyridin-2-yl)-quinazolin-4-yl]-amine | 423.2 |
| 82. | 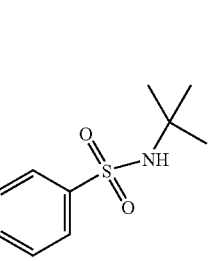 | N-tert-Butyl-4-[7-(3-trifluoromethyl-pyridin-2-yl)-quinazolin-4-ylamino]-benzenesulfonamide | 501.1 |
| 83. |  | [4-(4-Fluoro-piperidine-1-sulfonyl)-phenyl]-[7-(3-trifluoromethyl-pyridin-2-yl)-quinazolin-4-yl]-amine | 531.1 |

TABLE II-continued

Representative Substituted Quinazoline-4-ylamine Analogues

| Compound | | Name | MS |
|---|---|---|---|
| 84. | 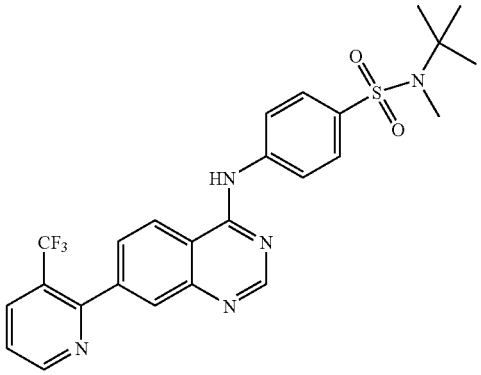 | N-tert-Butyl-N-methyl-4-[7-(3-trifluoromethyl-pyridin-2-yl)-quinazolin-4-ylamino]-benzenesulfonamide | 515.2 |
| 85. | 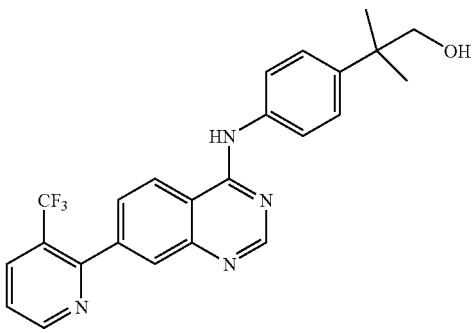 | 2-Methyl-2-{4-[7-(3-trifluoromethyl-pyridin-2-yl)-quinazolin-4-ylamino]-phenyl}-propan-1-ol | 438.2 |
| 86. | 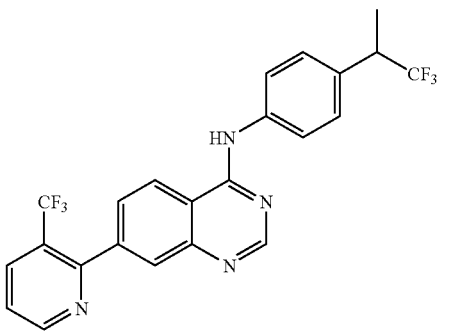 | [4-(2,2,2-Trifluoro-1-methyl-ethyl)-phenyl]-[7-(3-trifluoromethyl-pyridin-2-yl)-quinazolin-4-yl]-amine | 462.1 |
| 87. | 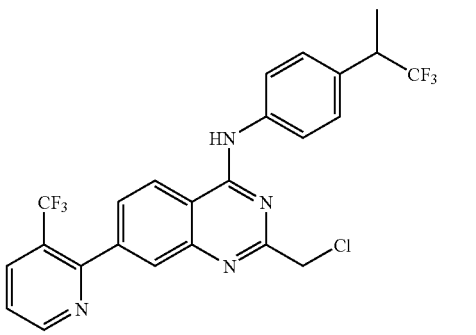 | [2-Chloromethyl-7-(3-trifluoromethyl-pyridin-2-yl)-quinazolin-4-yl]-[4-(2,2,2-trifluoro-1-methyl-ethyl)-phenyl]-amine | 510.1 |

TABLE II-continued

Representative Substituted Quinazoline-4-ylamine Analogues

| Compound | | Name | MS |
|---|---|---|---|
| 88. | 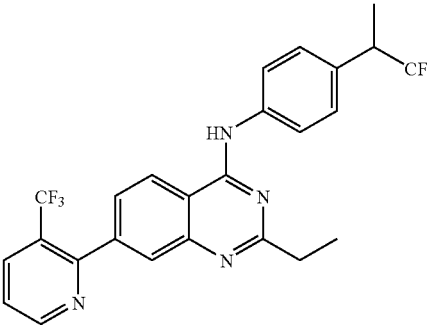 | [2-Ethyl-7-(3-trifluoromethyl-pyridin-2-yl)-quinazolin-4-yl]-[4-(2,2,2-trifluoro-1-methyl-ethyl)-phenyl]-amine | 490.2 |
| 89. | 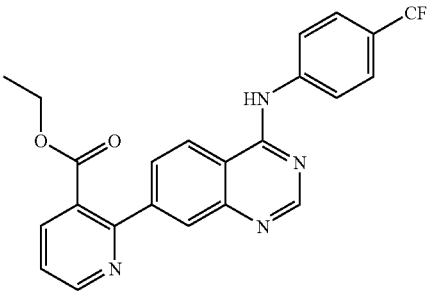 | 2-[4-(4-Trifluoromethyl-phenylamino)-quinazolin-7-yl]-nicotinic acid ethyl ester | |
| 90. | 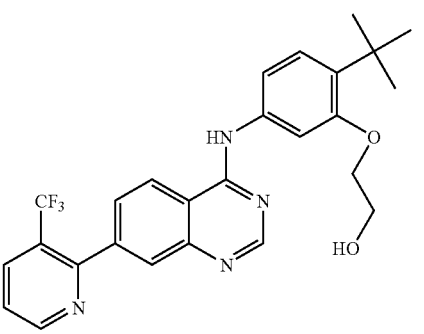 | 2-{2-tert-Butyl-5-[7-(3-trifluoromethyl-pyridin-2-yl)-quinazolin-4-ylamino]-phenoxy}-ethanol | |
| 91. | 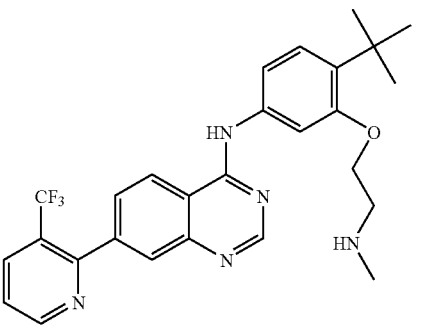 | [4-tert-Butyl-3-(2-methylamino-ethoxy)-phenyl]-[7-(3-trifluoromethyl-pyridin-2-yl)-quinazolin-4-yl]-amine | |

TABLE II-continued

Representative Substituted Quinazoline-4-ylamine Analogues

| Compound | | Name | MS |
|---|---|---|---|
| 92. | 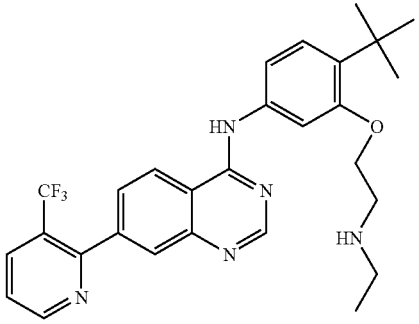 | [4-tert-Butyl-3-(2-ethylamino-ethoxy)-phenyl]-[7-(3-trifluoromethyl-pyridin-2-yl)-quinazolin-4-yl]-amine | |
| 93. | 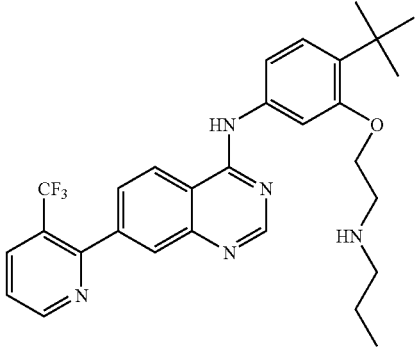 | [4-tert-Butyl-3-(2-propylamino-ethoxy)-phenyl]-[7-(3-trifluoromethyl-pyridin-2-yl)-quinazolin-4-yl]-amine | |
| 94. | 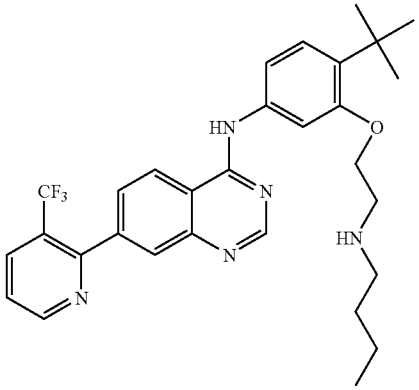 | [4-tert-Butyl-3-(2-butylamino-ethoxy)-phenyl]-[7-(3-trifluoromethyl-pyridin-2-yl)-quinazolin-4-yl]-amine | |
| 95. | 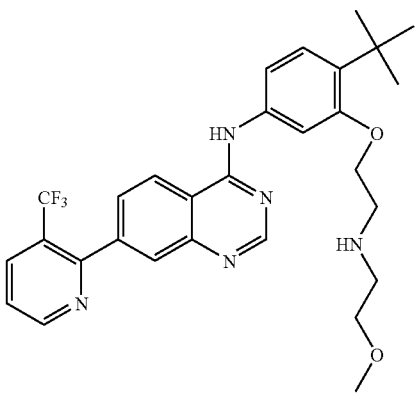 | {4-tert-Butyl-3-[2-(2-methoxy-ethylamino)-ethoxy]-phenyl}-[7-(3-trifluoromethyl-pyridin-2-yl)-quinazolin-4-yl]-amine | |

TABLE II-continued

Representative Substituted Quinazoline-4-ylamine Analogues

| Compound | | Name | MS |
|---|---|---|---|
| 96. | 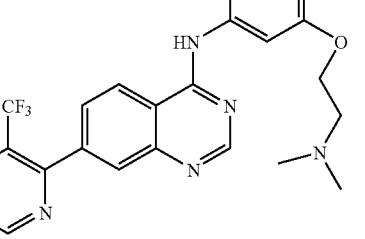 | [4-tert-Butyl-3-(2-dimethylamino-ethoxy)-phenyl]-[7-(3-trifluoromethyl-pyridin-2-yl)-quinazolin-4-yl]-amine | |
| 97. | 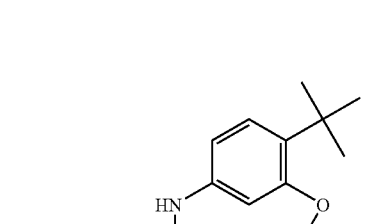 | [4-tert-Butyl-3-(2-diethylamino-ethoxy)-phenyl]-[7-(3-trifluoromethyl-pyridin-2-yl)-quinazolin-4-yl]-amine | |
| 98. | 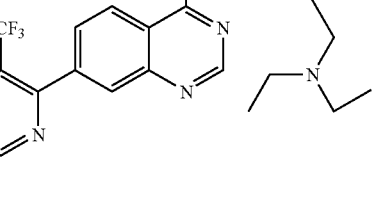 | [4-tert-Butyl-3-(2-pyrrolidin-1-yl-ethoxy)-phenyl]-[7-(3-trifluoromethyl-pyridin-2-yl)-quinazolin-4-yl]-amine | |
| 99. | 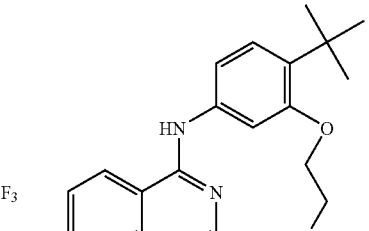 | [4-tert-Butyl-3-(2-piperidin-1-yl-ethoxy)-phenyl]-[7-(3-trifluoromethyl-pyridin-2-yl)-quinazolin-4-yl]-amine | |

TABLE II-continued

Representative Substituted Quinazoline-4-ylamine Analogues

| Compound | | Name | MS |
|---|---|---|---|
| 100. | 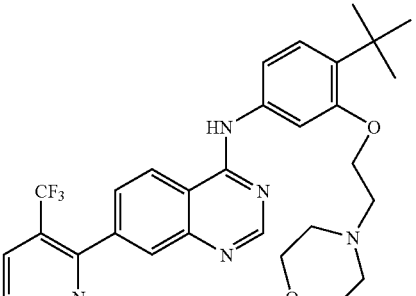 | [4-tert-Butyl-3-(2-morpholin-4-yl-ethoxy)-phenyl]-[7-(3-trifluoromethyl-pyridin-2-yl)-quinazolin-4-yl]-amine | |
| 101. | 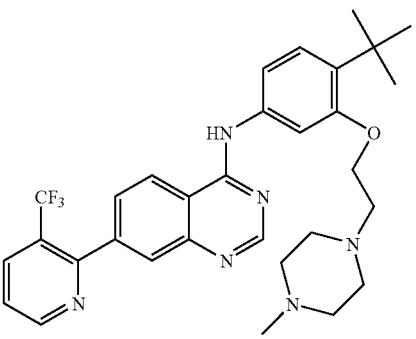 | {4-tert-Butyl-3-[2-(4-methyl-piperazin-1-yl)-ethoxy]-phenyl}-[7-(3-trifluoromethyl-pyridin-2-yl)-quinazolin-4-yl]-amine | |
| 102. | 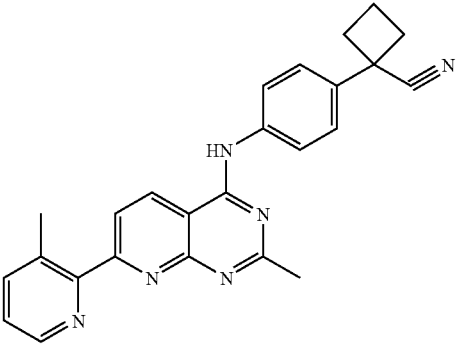 | 1-{4-[2-Methyl-7-(3-methyl-pyridin-2-yl)-pyrido[2,3-d]pyrimidin-4-ylamino]-phenyl}-cyclobutanecarbonitrile | |
| 103. | 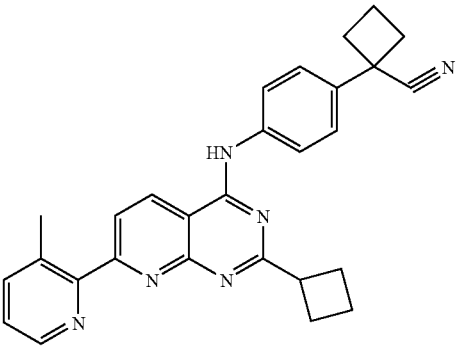 | 1-{4-[2-Cyclobutyl-7-(3-methyl-pyridin-2-yl)-pyrido[2,3-d]pyrimidin-4-ylamino]-phenyl}-cyclobutane carbonitrile | |

TABLE II-continued

Representative Substituted Quinazoline-4-ylamine Analogues

| Compound | Name | MS |
|---|---|---|
| 104. | (4-tert-Butyl-3-vinyl-phenyl)-[7-(3-trifluoromethyl-pyridin-2-yl)-pyrido[3,2-d]pyrimidin-4-yl]-amine | |
| 105. | 3-{2-tert-Butyl-5-[7-(3-trifluoromethyl-pyridin-2-yl)-pyrido[3,2-d]pyrimidin-4-ylamino]-phenoxy}-propan-1-ol | |
| 106. | [4-tert-Butyl-3-(3-methylamino-propoxy)-phenyl]-[7-(3-trifluoromethyl-pyridin-2-yl)-pyrido[3,2-d]pyrimidin-4-yl]-amine | |
| 107. | [4-tert-Butyl-3-(3-ethylamino-propoxy)-phenyl]-[7-(3-trifluoromethyl-pyridin-2-yl)-pyrido[3,2-d]pyrimidin-4-yl]-amine | |

TABLE II-continued

Representative Substituted Quinazoline-4-ylamine Analogues

| Compound | | Name | MS |
|---|---|---|---|
| 108. | 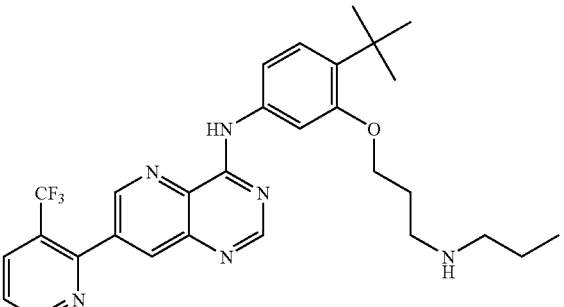 | [4-tert-Butyl-3-(3-propylamino-propoxy)-phenyl]-[7-(3-trifluoromethyl-pyridin-2-yl)-pyrido[3,2-d]pyrimidin-4-yl]-amine | |
| 109. | 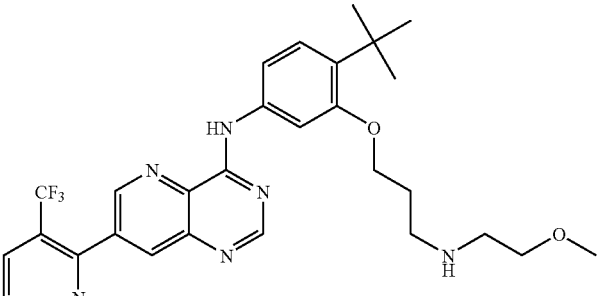 | {4-tert-Butyl-3-[3-(2-methoxy-ethylamino)-propoxy]-phenyl}-[7-(3-trifluoromethyl-pyridin-2-yl)-pyrido[3,2-d]pyrimidin-4-yl]-amine | |
| 110. | 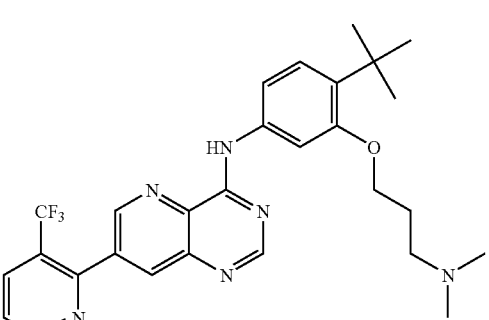 | [4-tert-Butyl-3-(3-dimethylamino-propoxy)-phenyl]-[7-(3-trifluoromethyl-pyridin-2-yl)-pyrido[3,2-d]pyrimidin-4-yl]-amine | |
| 111. | 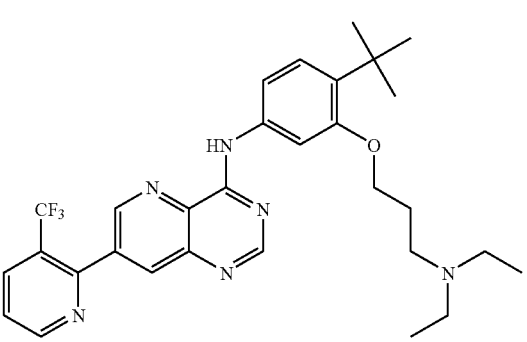 | [4-tert-Butyl-3-(3-diethylamino-propoxy)-phenyl]-[7-(3-trifluoromethyl-pyridin-2-yl)-pyrido[3,2-d]pyrimidin-4-yl]-amine | |

TABLE II-continued

Representative Substituted Quinazoline-4-ylamine Analogues

| Compound | Name | MS |
|---|---|---|
| 112. | [4-tert-Butyl-3-(3-pyrrolidin-1-yl-propoxy)-phenyl]-[7-(3-trifluoromethyl-pyridin-2-yl)-pyrido[3,2-d]pyrimidin-4-yl]-amine | |
| 113. | [4-tert-Butyl-3-(3-piperidin-1-yl-propoxy)-phenyl]-[7-(3-trifluoromethyl-pyridin-2-yl)-pyrido[3,2-d]pyrimidin-4-yl]-amine | |
| 114. | [4-tert-Butyl-3-(3-morpholin-4-yl-propoxy)-phenyl]-[7-(3-trifluoromethyl-pyridin-2-yl)-pyrido[3,2-d]pyrimidin-4-yl]-amine | |
| 115. | [4-tert-Butyl-3-(3-butylamino-propoxy)-phenyl]-[7-(3-trifluoromethyl-pyridin-2-yl)-pyrido[3,2-d]pyrimidin-4-yl]-amine | |

TABLE II-continued

Representative Substituted Quinazoline-4-ylamine Analogues

| Compound | | Name | MS |
|---|---|---|---|
| 116. | | 2-{2-tert-Butyl-5-[7-(3-trifluoromethyl-pyridin-2-yl)-pyrido[3,2-d]pyrimidin-4-ylamino]-phenyl}-ethanol | |
| 117. | | [4-tert-Butyl-3-(2-morpholin-4-yl-ethyl)-phenyl]-[7-(3-trifluoromethyl-pyridin-2-yl)-pyrido[3,2-d]pyrimidin-4-yl]-amine | |
| 118. | | [4-tert-Butyl-3-(2-methylamino-ethyl)-phenyl]-[7-(3-trifluoromethyl-pyridin-2-yl)-pyrido[3,2-d]pyrimidin-4-yl]-amine | |
| 119. | | [4-tert-Butyl-3-(2-piperidin-1-yl-ethyl)-phenyl]-[7-(3-trifluoromethyl-pyridin-2-yl)-pyrido[3,2-d]pyrimidin-4-yl]-amine | |

TABLE II-continued

Representative Substituted Quinazoline-4-ylamine Analogues

| Compound | | Name | MS |
|---|---|---|---|
| 120. | | {4-tert-Butyl-3-[2-(2,6-dimethyl-morpholin-4-yl)-ethyl]-phenyl}-[7-(3-trifluoromethyl-pyridin-2-yl)-pyrido[3,2-d]pyrimidin-4-yl]-amine (cis) | |
| 121. | | (S,S)-{4-tert-Butyl-3-[2-(2,6-dimethyl-morpholin-4-yl)-ethoxy]-phenyl}-[7-(3-trifluoromethyl-pyridin-2-yl)-quinazolin-4-yl]-amine | |
| 122. | | (R,R)-{4-tert-Butyl-3-[2-(2,6-dimethyl-morpholin-4-yl)-ethoxy]-phenyl}-[7-(3-trifluoromethyl-pyridin-2-yl)-quinazolin-4-yl]-amine | |
| 123. | | {4-tert-Butyl-3-[2-(2,6-dimethyl-morpholin-4-yl)-ethoxy]-phenyl}-[7-(3-trifluoromethyl-pyridin-2-yl)-quinazolin-4-yl]-amine (cis) | |

TABLE II-continued

Representative Substituted Quinazoline-4-ylamine Analogues

| Compound | Name | MS |
|---|---|---|
| 124. | 2-{4-[2-Cyclobutyl-7-(3-methyl-pyridin-2-yl)-pyrido[2,3-d]pyrimidin-4-ylamino]-phenyl}-2-methyl-propionitrile | |
| 125. | 2-Methyl-2-{4-[2-methyl-7-(3-methyl-pyridin-2-yl)-pyrido[2,3-d]pyrimidin-4-ylamino]-phenyl}-propionitrile | |
| 126. | N,N-Diethyl-2-{4-[2-methyl-7-(3-methyl-pyridin-2-yl)-pyrido[2,3-d]pyrimidin-4-ylamino]-phenyl}-isobutyramide | |
| 127. | [4-(2-Diethylamino-1,1-dimethyl-ethyl)-phenyl]-[2-methyl-7-(3-methyl-pyridin-2-yl)-pyrido[2,3-d]pyrimidin-4-yl]-amine | |

TABLE II-continued

Representative Substituted Quinazoline-4-ylamine Analogues

| Compound | Name | MS |
|---|---|---|
| 128. | 2-{3-[7-(3-Trifluoromethyl-pyridin-2-yl)-pyrido[3,2-d]pyrimidin-4-ylamino]-phenoxy}-ethanol | |
| 129. | [3-(2-Morpholin-4-yl-ethoxy)-phenyl]-[7-(3-trifluoromethyl-pyridin-2-yl)-pyrido[3,2-d]pyrimidin-4-yl]-amine | |
| 130. | {3-[2-(2,6-Dimethyl-morpholin-4-yl)-ethoxyl-phenyl}-[7-(3-trifluoromethyl-pyridin-2-yl)-pyrido[3,2-d]pyrimidin-4-yl]-amine (cis) | |
| 131. | 2-{2-tert-Butyl-5-[7-(3-trifluoromethyl-pyridin-2-yl)-pyrido[3,2-d]pyrimidin-4-ylamino]-phenoxy}-1-morpholin-4-yl-ethanone | |

TABLE II-continued

Representative Substituted Quinazoline-4-ylamine Analogues

| Compound | Name | MS |
|---|---|---|
| 132. | 2-{2-tert-Butyl-5-[7-(3-trifluoromethyl-pyridin-2-yl)-pyrido[3,2-d]pyrimidin-4-ylamino]-phenoxy}-1-(2,6-dimethyl-morpholin-4-yl)-ethanone (cis) | |
| 133. | [2-Methyl-7-(3-methyl-pyridin-2-yl)-pyrido[2,3-d]pyrimidin-4-yl]-(4-trifluoromethoxy-phenyl)-amine | |
| 134. | (6-tert-Butyl-pyridin-3-yl)-[2-methyl-7-(3-methyl-pyridin-2-yl)-pyrido[2,3-d]pyrimidin-4-yl]-amine | |
| 135. | 2-Methyl-2-{4-[2-methyl-7-(3-trifluoromethyl-pyridin-2-yl)-pyrido[2,3-d]pyrimidin-4-ylamino]-phenyl}-propionitrile | |

TABLE II-continued

Representative Substituted Quinazoline-4-ylamine Analogues

| Compound | | Name | MS |
|---|---|---|---|
| 136. | 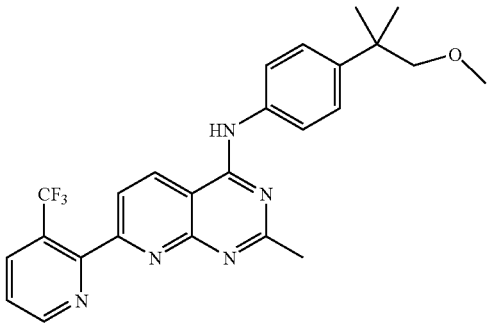 | [4-(2-Methoxy-1,1-dimethyl-ethyl)-phenyl]-[2-methyl-7-(3-trifluoromethyl-pyridin-2-yl)-pyrido[2,3-d]pyrimidin-4-yl]-amine | |
| 137. | 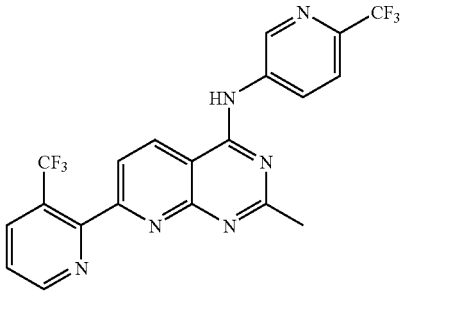 | [2-Methyl-7-(3-trifluoromethyl-pyridin-2-yl)-pyrido[2,3-d]pyrimidin-4-yl]-(6-trifluoromethyl-pyridin-3-yl)-amine | |
| 138. | 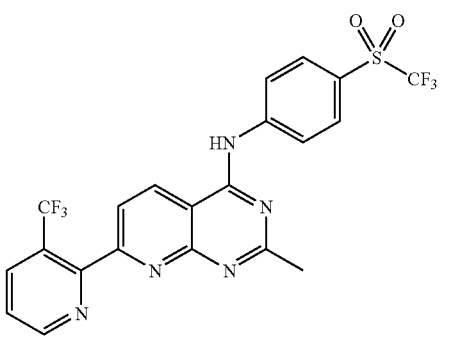 | [2-Methyl-7-(3-trifluoromethyl-pyridin-2-yl)-pyrido[2,3-d]pyrimidin-4-yl]-(4-trifluoromethanesulfonyl-phenyl)-amine | |
| 139. | 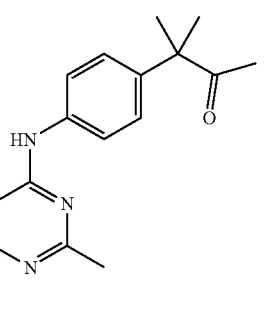 | 3-Methyl-3-{4-[2-methyl-7-(3-trifluoromethyl-pyridin-2-yl)-pyrido[2,3-d]pyrimidin-4-ylamino]-phenyl}-butan-2-one | |

TABLE II-continued

Representative Substituted Quinazoline-4-ylamine Analogues

| Compound | Name | MS |
|---|---|---|
| 140. | 3-Methyl-3-{4-[2-methyl-7-(3-methyl-pyridin-2-yl)-pyrido[2,3-d]pyrimidin-4-ylamino]-phenyl}-butan-2-one | |
| 141. | [4-(1-Methoxy-1-methyl-ethyl)-phenyl]-[2-methyl-7-(3-methyl-pyridin-2-yl)-pyrido[2,3-d]pyrimidin-4-yl]-amine | |
| 142. | (4-Methanesulfonyl-phenyl)-[2-methyl-7-(3-trifluoromethyl-pyridin-2-yl)-pyrido[2,3-d]pyrimidin-4-yl]-amine | |

Other compounds that were prepared are listed in Table III. Abbreviations used are: Ph=phenyl; Py=pyridin; Me=methyl; Et=ethyl; tBu=tert-butyl; thia=(1,3,4)thiadiazol; pyraz=1H-pyrazol; isopr=isopropyl; MeO=methoxy; EtO=ethoxy; PrO=propyloxy; MeA=methylamino; EtA=ethylamino; PrA=propylamino; BuA=butylamino; DMA=dimethylamino; DEA=diethylamino. Variable positions indicated in Table III are as shown on the following structure:

TABLE III

| Cmpd | $Ar_1$ | $Ar_2$ | $R_2$ | MS |
|---|---|---|---|---|
| 143. | 2-$CF_3$-Ph | 4-cyclohexyl-Ph | H | 447.2 |
| 144. | 2-$CF_3$-Ph | 4-$CF_3$-Ph | isopr | 475.1 |

TABLE III-continued

| Cmpd | Ar₁ | Ar₂ | R₂ | MS |
|---|---|---|---|---|
| 145. | 2-CF₃-Ph | 4-tBu-Ph | CF₃ | 489.2 |
| 146. | 2-Cl-Ph | 4-(CF(CF₃)₂)-Ph | H | 499.1 |
| 147. | 2-F-Ph | 4-(CF(CF₃)₂)-Ph | H | 483.1 |
| 148. | 2-MeO-Ph | 4-(CF(CF₃)₂)-Ph | H | 495.1 |
| 149. | 2-CF₃-Ph | 5-tBu-isox-3yl | H | 412.1 |
| 150. | 2-CF₃-Ph | 5-tBu-thia-2yl | H | 429.1 |
| 151. | 2-CF₃-Ph | 5-tBu-pyraz-3yl | H | |
| 152. | 3-CF₃-Py-2yl | 6-CF₃-Py-3yl | —NH-(6-CF₃-Py-3yl) | 595.1 |
| 153. | 3-CF₃-Py-2yl | 6-Me-Py-3yl | H | 381.1 |
| 154. | 3-CF₃-Py-2yl | 5-Cl-Py-2yl | H | |
| 155. | Py-2yl | 4-CF₃-Ph | H | 366.1 |
| 156. | 3-F-Py-2yl | 4-tBu-Ph | H | 372.2 |
| 157. | 3-F-Py-2yl | 4-CF₃-Ph | H | 384.1 |
| 158. | 3-Cl-Py-2yl | 4-tBu-Ph | H | 388.1 |
| 159. | 3-Cl-Py-2yl | 4-CF₃-Ph | H | 400.1 |
| 160. | 3-CF₃-Py-2yl | 4-CF₃-Ph | H | 434.1 |
| 161. | 3-CF₃-Py-2yl | 4-F-Ph | H | 384.1 |
| 162. | 3-CF₃-Py-2yl | 4-Cl-Ph | H | 400.1 |
| 163. | 3-CF₃-Py-2yl | 4-acetyl-Ph | H | 408.1 |
| 164. | 3-CF₃-Py-2yl | 4-cyano-Ph | H | 391.1 |
| 165. | 3-CF₃-Py-2yl | 4-(CF(CF₃)₂)-Ph | H | 534.1 |
| 166. | 3-CF₃-Py-2yl | 4-CF₃-Ph | Me | 448.1 |
| 167. | 3-CF₃-Py-2yl | 4-CF₃-Ph | Cl | |
| 168. | 3-CF₃-Py-2yl | 4-CF₃-Ph | —O—CH₂CH₂OH | 494.1 |
| 169. | 3-CF₃-Py-2yl | 4-CF₃-Ph | —O—CH₂CH₂-DMA | 521.2 |
| 170. | 3-CF₃-Py-2yl | 4-CF₃-Ph | —O—(CH₂)₃-DMA | 535.2 |
| 171. | 3-CF₃-Py-2yl | 4-CF₃-Ph | MeA | 463.1 |
| 172. | 3-CF₃-Py-2yl | 4-CF₃-Ph | DMA | 477.1 |
| 173. | 3-CF₃-Py-2yl | 4-isopr-Ph | H | 408.2 |
| 174. | 3-CF₃-Py-2yl | 6-MeO-Py-3yl | H | 397.1 |
| 175. | 3-CF₃-Py-2yl | 3-Me-4-isopr-Ph | H | 422.2 |
| 176. | 3-MeO-Py-2yl | 4-CF₃-Ph | H | 396.1 |
| 177. | 3-PrO-Py-2yl | 4-CF₃-Ph | H | 424.2 |
| 178. | 3-PrO-Py-2yl | 4-isopr-Ph | H | 398.2 |
| 179. | 2-Cl-Ph | 4-CF₃-Ph | H | 399.1 |
| 180. | 2,4-diCl-Ph | 4-CF₃-Ph | H | 433.0 |
| 181. | 2-Cl-Ph | 4-tBu-Ph | H | 387.2 |
| 182. | 2,4-diCl-Ph | 4-tBu-Ph | H | 421.1 |
| 183. | 3-CF₃-Py-2yl | 4-CF₃-Ph | MeO | |
| 184. | 3-Cl-Py-2yl | 6-CF₃-Py-3yl | H | 401.1 |
| 185. | 2-CF₃-Ph | 4-CF₃-Ph | Morpholin-4yl | 519.1 |
| 186. | 3-CF₃-Py-2yl | 3-MeO-Ph | H | 396.1 |
| 187. | 3-CF₃-Py-2yl | 6-tBu-Py-3yl | H | 423.2 |
| 188. | 3-Cl-Py-2yl | 6-tBu-Py-3yl | H | 389.1 |
| 189. | 3-PrO-Py-2yl | 6-tBu-Py-3yl | H | 413.2 |
| 190. | 3-CF₃-Py-2yl | 4-(isopr-SO₂)-Ph | H | 472.1 |
| 191. | 3-CF₃-Py-2yl | 5-CF₃-Py-2yl | Me | 449.1 |
| 192. | 3-CF₃-Py-2yl | 6-tBu-Py-3yl | Me | 437.2 |
| 193. | 3-CF₃-Py-2yl | 6-CF₃-Py-3yl | CF3 | 503.1 |
| 194. | 3-CF₃-Py-2yl | 6-CF₃-Py-3yl | n-Pr | 477.1 |
| 195. | 3-CF₃-Py-2yl | 6-tBu-Py-3yl | n-Pr | 465.2 |
| 196. | 3-CF₃-Py-2yl | 5-CF₃-Py-2yl | n-Pr | 477.1 |
| 197. | 3-CF₃-Py-2yl | 6-CF₃-Py-3yl | Et | 463.1 |
| 198. | 3-CF₃-Py-2yl | 6-tBu-Py-3yl | Et | |
| 199. | 3-CF₃-Py-2yl | 6-tBu-Py-3yl | CF3 | 491.2 |
| 200. | 3-CF₃-Py-2yl | 4-(tBu-NH-SO₂)-Ph | Me | 515.2 |
| 201. | 3-CF₃-Py-2yl | 6-isopr-Py-3yl | H | 409.2 |
| 202. | 3-CF₃-Py-2yl | 6-isopr-Py-3yl | n-Pr | 451.2 |
| 203. | 3-CF₃-Py-2yl | 6-isopr-Py-3yl | Me | 423.2 |
| 204. | 3-CF₃-Py-2yl | 6-tBu-Py-3yl | —O—(CH₂)CH₂OH | 483.2 |
| 205. | 3-CF₃-Py-2yl | 6-CF₃-Py-3yl | Cl | 469.1 |
| 206. | 3-CF₃-Py-2yl | 6-CF₃-Py-3yl | —N—(CH₂)₂CH(CH₃)₂ | 520.2 |
| 207. | 3-CF₃-Py-2yl | 4-CF₃-Ph | CN | 325.0 |
| 208. | 3-CF₃-Py-2yl | 4-CF₃-Ph | Ph | 510.1 |
| 209. | 3-CF₃-Py-2yl | 5-CF₃-Py-2yl | chloromethyl | 483.1 |
| 210. | 3-CF₃-Py-2yl | 4-CF₃-Ph | chloromethyl | |
| 211. | 3-NO₂-Py-2yl | 6-CF₃-Py-3yl | H | 412.1 |

TABLE III-continued

| Cmpd | Ar₁ | Ar₂ | R₂ | MS |
|---|---|---|---|---|
| 212. | 3-CF₃-Py-2yl | 4-CF₃-Ph | —CH₂SO₂CH₃ | 526.1 |
| 213. | 3-CF₃-Py-2yl | 6-CF₃-Py-3yl | —CH₂SO₂CH₃ | 527.1 |
| 214. | 3-Cl-Py-2yl | 6-CF₃-Py-3yl | Me | 415.1 |
| 215. | 3-CF₃-Py-2yl | 4-(CH₃SO₂)-Ph | H | 445.1 |
| 216. | 2-(CH₃SO₂)-Ph | 4-CF₃-Ph | H | |
| 217. | 2-(CH₃SO₂)-Ph | 6-CF₃-Py-3yl | H | |
| 218. | 3-(DMA-SO₂)-Py-2yl | 4-CF₃-Ph | H | |
| 219. | 2-(CH₃SO₂)-Ph | 4-CF₃-Ph | Me | |
| 220. | 2-(CH₃SO₂)-Ph | 6-CF₃-Py-3yl | Me | |
| 221. | 3-(DMA-SO₂)-Py-2yl | 4-CF₃-Ph | Me | |
| 222. | 3-CF₃-Py-2yl | 4-CF₃-Ph | -(CH₂)₂-S-Me | |
| 223. | 3-CF₃-Py-2yl | 6-CF₃-Py-3yl | -(CH₂)₂-S-Me | |
| 224. | 3-CF₃-Py-2yl | 4-CF₃-Ph | -(CH₂)₂-SO₂-Me | |
| 225. | 3-cyano-Py-2yl | 4-CF₃-Ph | Me | |
| 226. | 3-Cl-Py-2yl | 4-(CF₃SO₂)-Ph | H | 464.0 |
| 227. | 3-CF₃-Py-2yl | 4-CF₃-Ph | -CH2-CN | 473.1 |
| 228. | 3-CH₃-Py-2yl | 4-tBu-Ph | H | 368.2 |
| 229. | 3-CH₃-Py-2yl | 6-CF₃-Py-3yl | H | 381.1 |
| 230. | 3-CH₃-Py-2yl | 4-isopr-Ph | H | 354.2 |
| 231. | 3-CH₃-Py-2yl | 4-Et-Ph | H | 340.2 |

Other compounds that were prepared are listed in Table IV. Abbreviations used are as described above for Table III. Variable positions indicated in Table IV are as shown on the following structure:

TABLE IV

| Cmpd | Ar₁ | Ar₂ | R₂ | MS |
|---|---|---|---|---|
| 232. | 2-CF₃-Ph | 4-CF₃-Ph | —NH-(4-CF₃-Ph) | 593.1 |
| 233. | 2-CF₃-Ph | 4-(CF₃-SO₂)-Ph | Cl | 532.2 |
| 234. | 2-CF₃-Ph | 4-(morpholin-4yl-SO₂)-Ph | Cl | 549.1 |
| 235. | 2-CF₃-Ph | 4-tBu-Ph | —N—CH₂CH(CH₃)₂ | 493.2 |
| 236. | 2-CF₃-Ph | 4-(morpholin-4yl-SO₂)-Ph | —N-CH₂CH(CH₃)₂ | 586.2 |
| 237. | 2-CF₃-Ph | 4-(morpholin-4yl-SO₂)-Ph | —N-isopr | 572.2 |
| 238. | 2-CF₃-Ph | 4-(morpholin-4yl-SO₂)-Ph | —N—(CH₂)₂CH(CH₃)₂ | 600.2 |
| 239. | 2-CF₃-Ph | 4-(morpholin-4yl-SO₂)-Ph | N—(CH₂)₂CH(CH₃)₂ | |
| 240. | 2-CF₃-Ph | 6-CF₃-Py-3yl | H | 435.1 |
| 241. | 2-CF₃-Ph | 5-CF₃-Py-2yl | Cl | 469.1 |
| 242. | 3-Cl-Py-2yl | 4-tBu-Ph | H | 389.1 |
| 243. | 3-Cl-Py-2yl | 4-CF₃-Ph | H | 401.1 |
| 244. | 3-Cl-Py-2yl | 4-[C(CH₃)₂CN]-Ph | H | 400.1 |
| 245. | 3-Cl-Py-2yl | 4-[C(CH₃)₂CH₂OMe]-Ph | H | 419.2 |
| 246. | 3-Cl-Py-2yl | 4-isopr-Ph | H | 375.1 |
| 247. | 3-Cl-Py-2yl | 4-(2-butyl)-Ph | H | 389.1 |
| 248. | 3-Cl-Py-2yl | 4-Cl-Ph | H | 367.0 |
| 249. | 3-Cl-Py-2yl | 3-Me, 4-CF₃-Ph | H | 415.1 |
| 250. | 3-Cl-Py-2yl | 4-[CH(CH₃)(CF₃)]-Ph | H | 429.1 |
| 251. | 3-Cl-Py-2yl | 4-cyclopentyl-Ph | H | 401.1 |
| 252. | 3-Cl-Py-2yl | 4-cyclohexyl-Ph | H | 415.2 |
| 253. | Py-2yl | 4-CF₃-Ph | H | 367.1 |
| 254. | Py-2yl | 4-tBu-Ph | H | 355.2 |
| 255. | Py-2yl | 4-isopr-Ph | H | 341.2 |

TABLE IV-continued

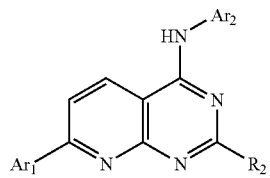

| Cmpd | Ar$_1$ | Ar$_2$ | R$_2$ | MS |
|---|---|---|---|---|
| 256. | Py-2yl | 4-(2-butyl)-Ph | H | 355.2 |
| 257. | Py-2yl | 4-cyclopentyl-Ph | H | 367.2 |
| 258. | Py-2yl | 4-cyclohexyl-Ph | H | 381.2 |
| 259. | 3-Cl-Py-2yl | 6-CF$_3$-Py-3yl | H | 402.1 |
| 260. | 3-Cl-Py-2yl | 4-tBu-Ph | Me | 403.2 |
| 261. | 3-Cl-Py-2yl | 4-isopr-Ph | Me | 389.1 |
| 262. | 3-Cl-Py-2yl | 4-CF$_3$-Ph | Me | 415.1 |
| 263. | 2-Cl-Ph | 4-tBu-Ph | H | 388.1 |
| 264. | 2-Cl-Ph | 4-isopr-Ph | H | 374.1 |
| 265. | 2-Cl-Ph | 4-(2-butyl)-Ph | H | 388.1 |
| 266. | 2-Cl-Ph | 4-CF$_3$-Ph | H | 400.1 |
| 267. | 3-CH$_3$-Py-2yl | 4-tBu-Ph | Me | 383.2 |
| 268. | 3-CH$_3$-Py-2yl | 4-isopr-Ph | Me | 369.2 |
| 269. | 3-CH$_3$-Py-2yl | 4-CF$_3$-Ph | Me | |
| 270. | 3-CH$_3$-Py-2yl | 4-(2-butyl)-Ph | Me | |
| 271. | 3-CH$_3$-Py-2yl | 4-cyclopentyl -Ph | Me | |
| 272. | 3-CF$_3$-Py-2yl | 4-tBu-Ph | Me | |
| 273. | 3-CF$_3$-Py-2yl | 4-isopr-Ph | Me | |
| 274. | 3-CF$_3$-Py-2yl | 4-CF$_3$-Ph | Me | |
| 275. | 3-CH$_3$-Py-2yl | 4-(CH$_3$-SO$_2$)-Ph | Me | |
| 276. | 3-CH$_3$-Py-2yl | 4-(CF$_3$-SO$_2$)-Ph | Me | |
| 277. | 3-CH$_3$-Py-2yl | 6-CF$_3$-Py-3yl | Me | |
| 278. | 3-CF$_3$-Py-2yl | 4-tBu-Ph | H | |
| 279. | 3-CF$_3$-Py-2yl | 4-isopr-Ph | H | |
| 280. | 3-CF$_3$-Py-2yl | 4-CF$_3$-Ph | H | |
| 281. | 3-CF$_3$-Py-2yl | 4-cyclopentyl-Ph | H | |
| 282. | 3-CF$_3$-Py-2yl | 4-(morpholin-4yl-SO$_2$)-Ph | H | |
| 283. | 3-CH$_3$-Py-2yl | 4-(morpholin-4yl-SO$_2$)-Ph | Me | |
| 284. | 3-CH$_3$-Py-2yl | 4-tBu-Ph | cyclobutyl | 423.2 |
| 285. | 3-CH$_3$-Py-2yl | 4-isopr-Ph | cyclobutyl | 409.2 |
| 286. | 3-CH$_3$-Py-2yl | 4-CF$_3$-Ph | cyclobutyl | 435.2 |
| 287. | 3-CH$_3$-Py-2yl | 4-(CF$_3$-SO$_2$)-Ph | cyclobutyl | 499.1 |
| 288. | 3-CH$_3$-Py-2yl | 5-CF$_3$-Py-2yl | cyclobutyl | 436.2 |
| 289. | 3-CH$_3$-Py-2yl | 6-CF$_3$-Py-3yl | cyclobutyl | |

Other compounds that were prepared are listed in Table V. Abbreviations used are as described above for Table III. Variable positions indicated in Table V are as shown on the following structure:

TABLE V

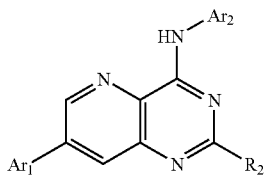

| Cmpd | Ar$_1$ | Ar$_2$ | R$_2$ | MS |
|---|---|---|---|---|
| 290. | 3-CF$_3$-Py-2yl | 4-tBu-Ph | H | .423.2 |
| 291. | 3-CF$_3$-Py-2yl | 4-(tBu-NH-SO$_2$)-Ph | H | 502.1 |
| 292. | 3-CF$_3$-Py-2yl | 6-tBu-Py-3yl | H | 424.2 |
| 293. | 3-CF$_3$-Py-2yl | 4-CF$_3$-Ph | Me | 449.1 |
| 294. | 3-CF$_3$-Py-2yl | 6-CF$_3$-Py-3yl | Me | |
| 295. | 3-CF$_3$-Py-2yl | 5-CF$_3$-Py-2yl | Me | 450.1 |
| 296. | 3-Me-Py-2yl | 4-CF$_3$-Ph | H | 381.1 |
| 297. | 3-Me-Py-2yl | 6-CF$_3$-Py-3yl | H | 382.1 |
| 298. | 3-Me-Py-2yl | 4-tBu-Ph | H | 369.2. |
| 299. | 3-Cl-Py-2yl | 4-CF$_3$-Ph | Me | 415.1 |
| 300. | 3-Cl-Py-2yl | 6-CF$_3$-Py-3yl | Me | 416.1 |

TABLE V-continued

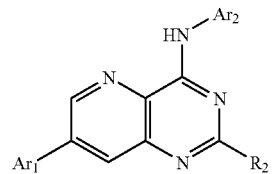

| Cmpd | Ar$_1$ | Ar$_2$ | R$_2$ | MS |
|---|---|---|---|---|
| 301. | 3-Cl-Py-2yl | 4-(CF$_3$SO$_2$)-Ph | Me | 479.0 |
| 302. | 3-Cl-Py-2yl | 4-CF$_3$-Ph | H | 401.1 |
| 303. | 3-Cl-Py-2yl | 6-CF$_3$-Py-3yl | H | 402.1 |
| 304. | 3-Cl-Py-2yl | 4-(CF$_3$SO$_2$)-Ph | H | 465.0 |
| 305. | 3-Cl-Py-2yl | 6-tBu-Py-3yl | Me | 404.2 |
| 306. | 3-Cl-Py-2yl | 4-tBu-Ph | Me | 403.2 |
| 307. | 3-CF$_3$-Py-2yl | 4-isopr-Ph | H | 409.2 |

The Ar1-Matrix, Het-Matrix, and Ar2-Matrix tables below set forth a number of additional representative compounds that may be prepared by methods analogous to those shown above. Compounds can be formed by combining any element from the Het-Matrix with any elements from the Ar1 and Ar2 matrices. For example, the combination of element 111 from the Ar1-Matrix, with element 202 from the Het-matrix, gives the moiety 111202. This moiety is then combined with element 312 from the Ar2-matrix, to form compound 111202312, which is (7-pyridin-yl-quinazolin-4-yl)-(4-trifluoromethyl-phenyl)-amine.
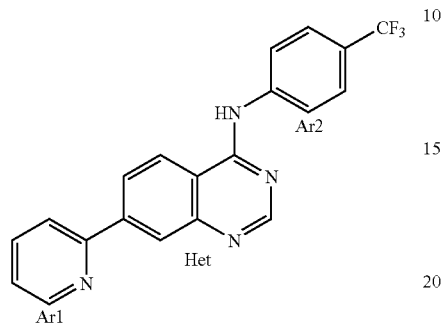
Ar1-Matrix
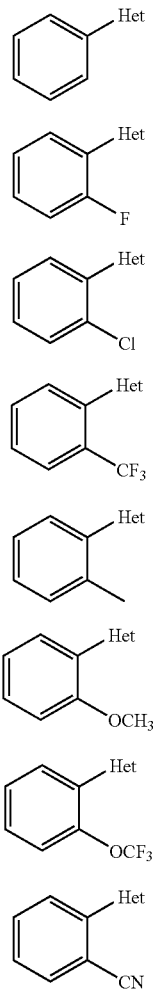
101
102
103
104
105
106
107
108
-continued
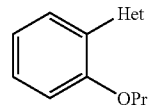 109
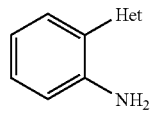 110
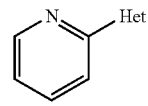 111
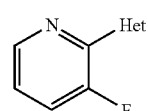 112
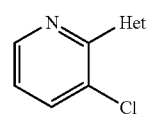 113
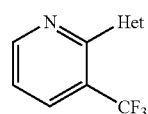 114
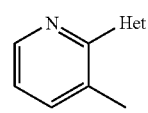 115
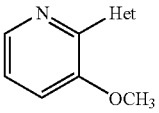 116
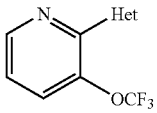 117
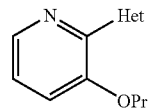 118
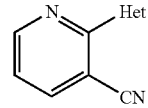 119
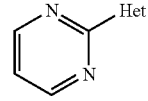 120
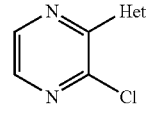 121

-continued
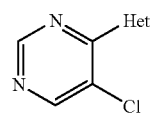 122
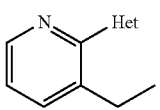 123
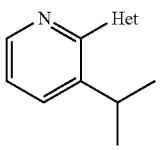 124
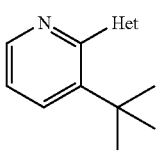 125
Het-Matrix
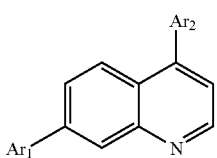 201
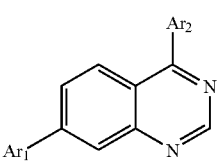 202
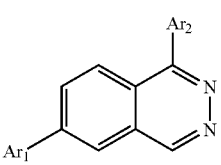 203
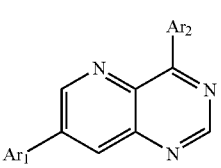 204
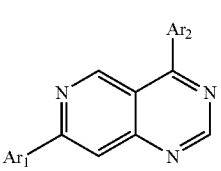 205
-continued
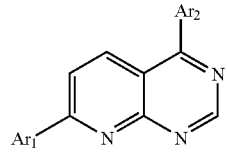 206
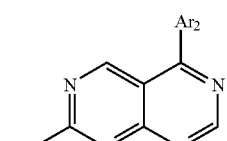 207
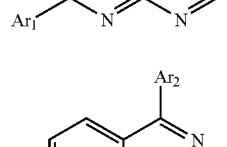 208
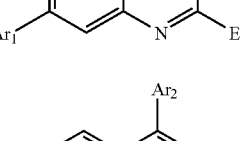 209
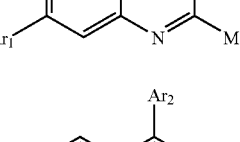 210
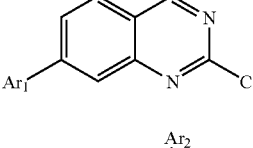 211
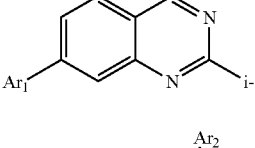 212
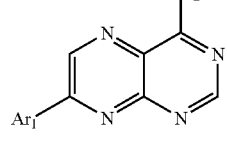 213
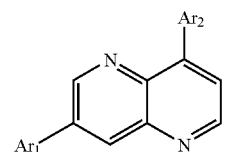 
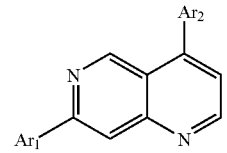 214

-continued
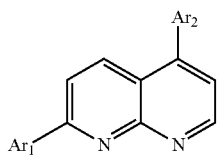
215
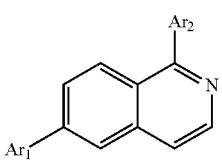
216
Ar2-Matrix
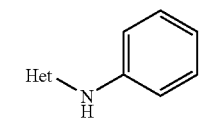
301
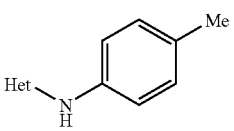
302
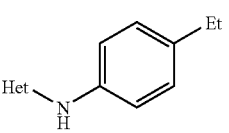
303
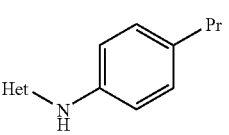
304
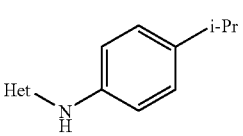
305
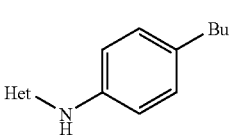
306
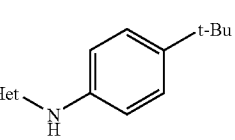
307
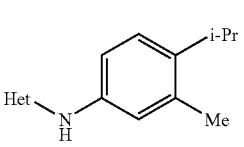
308
-continued
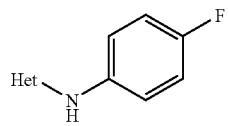
309
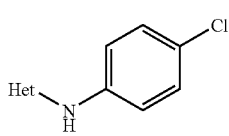
310
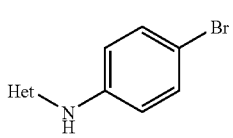
311
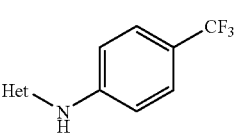
312
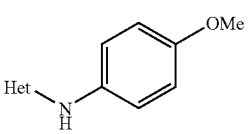
313
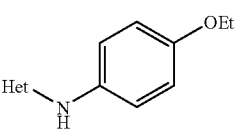
314
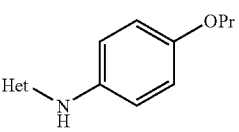
315
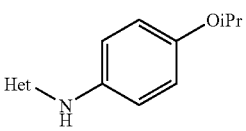
316
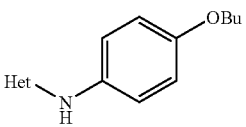
317
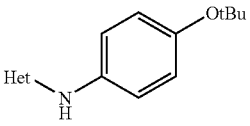
318
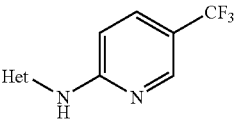
319
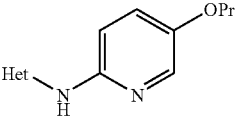
320

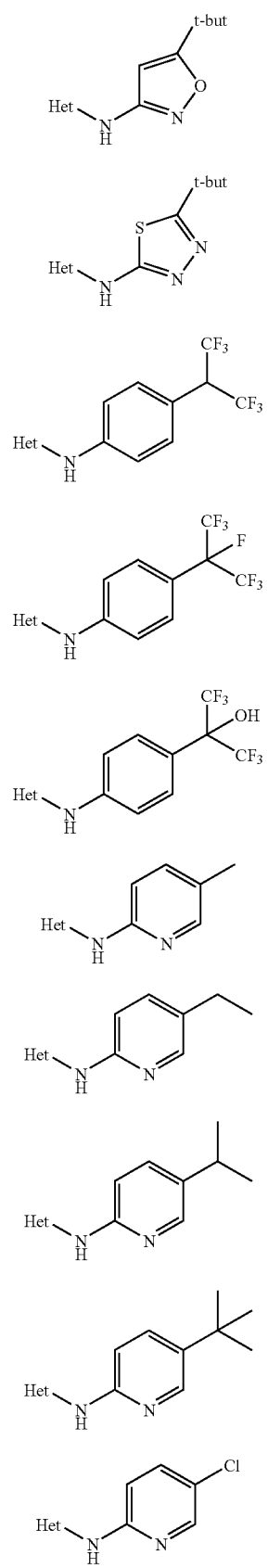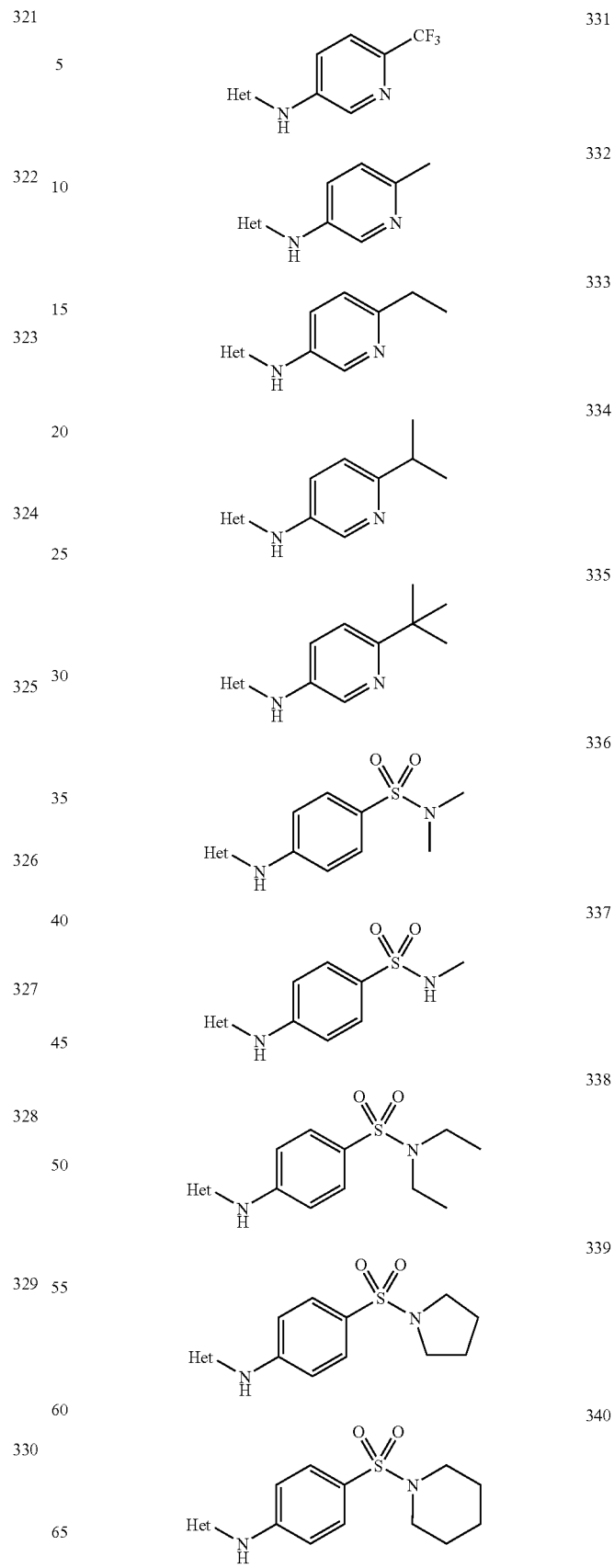

-continued

341

[Structure: Het-NH-phenyl-SO2-morpholine]

Example 2

Preparation of Representative Compounds

This Example illustrates the preparation of representative substituted 2-aminoalkyl-quinazolin-4-ylamine analogues.

A. [2-Pyrrolidin-1-ylmethyl-7-(3-trifluoromethyl-pyridin-2-yl)-quinazolin-4-yl]-(4-trifluoromethyl-phenyl)-amine (cmpd 308)

1. 2-p-tolyl-3-trifluoromethyl-pyridine

[Structure: 3-CF3-2-(p-tolyl)pyridine]

To a de-gassed mixture of 2-chloro-3-(trifluoromethyl)-pyridine (70.1 mmol), p-tolylboronic acid (70.6 mmol), and 2M $Na_2CO_3$ (175.0 mmol), in dimethyl ether (DME; 200 mL) under nitrogen, add $Pd(PPh_3)_4$ (2.8 mmol). Stir the mixture at 80° C. overnight, concentrate, and extract with EtOAc. Dry over $Na_2SO_4$, concentrate under vacuum, and pass through a silica gel pad to give 2-p-tolyl-3-trifluoromethyl-pyridine.

2. 2-(4-methyl-3-nitro-phenyl)-3-(trifluoromethyl)-pyridine

[Structure: 3-CF3-2-(4-methyl-3-nitrophenyl)pyridine]

To a solution of 2-p-tolyl-3-trifluoromethyl-pyridine (8.4 mmol) in $H_2SO_4$ (6 mL) cautiously add fuming $HNO_3$ (2 ml). Stir the mixture for 60 minutes at room temperature. Pour the mixture onto ice-water (30 mL), extract with EtOAc, neutralize with 1 N NaOH, dry over $Na_2SO_4$, and concentrate under vacuum to obtain 2-(4-methyl-3-nitro-phenyl)-3-(trifluoromethyl)-pyridine.

3. 2-nitro-4-(3-trifluoromethyl-pyridin-2-yl)-benzoic acid

[Structure: 3-CF3-pyridin-2-yl substituted benzoic acid with NO2]

To a solution of 2-(4-methyl-3-nitro-phenyl)-3-(trifluoromethyl)-pyridine (7.1 mmol) in a mixture of pyridine (10 mL) and water (5 ml) add $KMnO_4$ (25.3 mmol) portionwise. Stir the mixture for 4 hours at 110° C. then add another 25.3 mmol of $KMnO_4$ with 10 ml of water. Stir the mixture at 110° C. overnight. Cool to room temperature, and filter through celite pad. Concentrate the filtrate under vacuum, dilute with water, and wash the aqueous solution with EtOAc. Neutralize the aqueous solution with 2 N HCl and collect the precipitate to give 2-nitro-4(3-trifluoromethyl-pyridin-2-yl)-benzoic acid.

4. 2-nitro-4-(3-trifluoromethyl-pyridin-2-yl)-benzamide

[Structure: corresponding benzamide with NO2]

Reflux a mixture of 2-amino-4-(3-trifluoromethyl-pyridin-2-yl)-benzoic acid (25 g) with $SOCl_2$ (50 ml) for 4 hours and concentrate. Dissolve the residue in dichloromethane (DCM), cool with ice-water bath, pass $NH_3$ gas through the solution for 30 minutes, and stir for 15 minutes at room temperature. Concentrate and wash with water to give 2-nitro-4-(3-trifluoromethyl-pyridin-2-yl)-benzamide.

5. 2-amino-4-(3-trifluoromethyl-pyridin-2-yl)-benzamide

[Structure: corresponding benzamide with NH2]

Hydrogenate 2-nitro-4-(3-trifluoromethyl-pyridin-2-yl)-benzamide (1.0 g, 0.0032 mol) with 50 psi of $H_2$ and 100 mg of 10% Pd/C in ethanol. After 16 hours, filter the mixture through celite and concentrate under reduced pressure to give 2-amino-4-(3-trifluoromethyl-pyridin-2-yl)-benzamide as a solid.

6. 2-chloromethyl-7-(3-trifluoromethyl-pyridin-2-yl)-3H-quinazolin-4-one

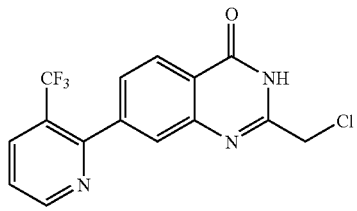

Heat a solution of 2-amino-4-(3-trifluoromethyl-pyridin-2-yl)-benzamide (100 mg, 0.356 mmol) in 2-chloro-1,1,1-trimethoxyethane (bp 138° C.) at 130° C. for 4 hours. Concentrate the mixture under reduced pressure to give 2-chloromethyl-7-(3-trifluoromethyl-pyridin-2-yl)-3H-quinazolin-4-one as an oil which crystallizes on standing.

7. 4-chloro-2-chloromethyl-7-(3-trifluoromethyl-pyridin-2-yl)-quinazoline

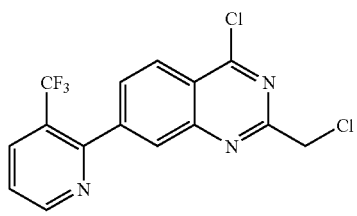

Reflux a mixture of 2-chloromethyl-7-(3-trifluoromethyl-pyridin-2-yl)-3H-quinazolin-4-one (obtained from the reaction above) and POCl$_3$ for 16 hours. Cool the mixture and concentrate under reduced pressure. Partition the residue between EtOAc and saturated NaHCO$_3$ solution. Wash the EtOAc portion with additional NaHCO$_3$ and then dry (Na$_2$SO$_4$) and concentrate under reduced pressure. Filter the brown residue through 2 inches of silica gel (1:1 EtOAc/hexanes eluent) and concentrate under reduced pressure to give 4-chloro-2-chloromethyl-7-(3-trifluoromethyl-pyridin-2-yl)-quinazoline.

8. [2-chloromethyl-7-(3-trifluoromethyl-pyridin-2-yl)-quinazolin-4-yl]-(4-trifluoromethyl-phenyl)-amine

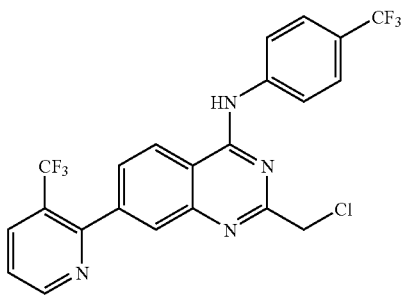

Heat a mixture of 4-chloro-2-chloromethyl-7-(3-trifluoromethyl-pyridin-2-yl)-quinazoline (42 mg, 0.117 mmol) and 4-trifluoromethyl-aniline (19 mg, 0.117 mmol) in isopropyl alcohol (1 mL) at 75° C. for 4 hours. Cool the mixture and wash the precipitate with isopropyl alcohol followed by ether to give [2-chloromethyl-7-(3-trifluoromethyl-pyridin-2-yl)-quinazolin-4-yl]-(4-trifluoromethyl-phenyl)-amine as the mono-HCl salt.

9. [2-Pyrrolidin-1-ylmethyl-7-(3-trifluoromethyl-pyridin-2-yl)-quinazolin-4-yl]-(4-trifluoromethyl-phenyl)-amine

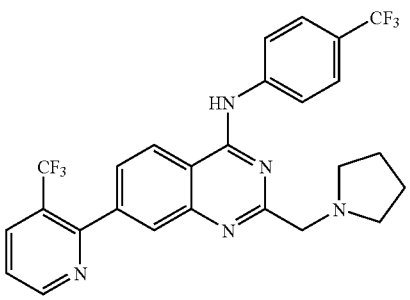

Heat a solution of [2-chloromethyl-7-(3-trifluoromethyl-pyridin-2-yl)-quinazolin-4-yl]-(4-trifluoromethyl-phenyl)-amine HCl (30 mg, 0.058 mmol) in pyrrolidine (1 mL) at 100° C. for 1 hour. Remove the excess pyrrolidine under reduced pressure and partition the residue between EtOAc and 10% NaOH solution. Dry the EtOAc layer (Na$_2$SO$_4$) and concentrate under reduced pressure to give [2-Pyrrolidin-1-ylmethyl-7-(3-trifluoromethyl-pyridin-2-yl)-quinazolin-4-yl]-(4-trifluoromethyl-phenyl)-amine as a foam. Mass Spec 517.2.

B. [2-(2,6-Dimethyl-morpholin-4-ylmethyl)-7-(2-trifluoromethyl-phenyl)-pyrido[4,3-d]pyrimidin-4-yl]-(4-trifluoromethyl-phenyl)-amine (cis) (cmpd 309)

1. 4-Hydroxy-6-(2-trifluoromethyl-phenyl)-nicotinic acid ethyl ester

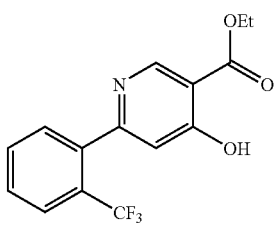

Dissolve Lithium bis(trimethylsilyl)amide (LiHMDS) (34 g, 0.20 mol) in dry THF (150 mL) and cool to −70° C. under N$_2$ atm. Add 4-dimethylamino-3-ethoxy-but-3-en-2-one (15 g, 0.081 mol; see *J. Heterocyclic Chem.* (1987) 24:1669) and 2-(trifluoromethyl)benzoyl chloride (20.0 g, 0.097 mol) in THF (50 mL) into the solution for 10 minutes. Remove the cooling bath and stir for 10 minutes. Add ammonium acetate (10 g) and acetic acid (200 mL) to the reaction mixture and distil THF under reduced pressure. Heat the mixture at 60–65° C. for 18 hours, cool and add water (250 mL) and CH$_2$Cl$_2$ (250 mL). Separate the CH$_2$Cl$_2$ layer, and extract the aqueous layer twice with CH$_2$Cl$_2$ (2×250 mL each). Combine the CH$_2$Cl$_2$ extracts, dry (MgSO$_4$), and evaporate. Purify by silica gel chromatography to provide 4-Hydroxy-6-(2-trifluoromethyl-phenyl)-nicotinic acid ethyl ester as a yellow solid.

2. 4-Chloro-6-(2-trifluoromethyl-phenyl)-nicotinic acid ethyl ester

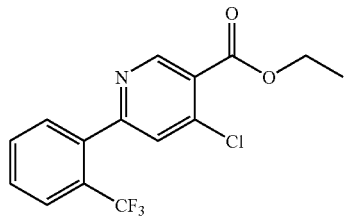

Heat a mixture of 4-Hydroxy-6-(2-trifluoromethyl-phenyl)-nicotinic acid ethyl ester (9.0 g, 0.029 mol) in POCl$_3$ (22 g) at 110° C. for 2 hours. Evaporate the POCl$_3$, and add ice (100 g) followed by careful addition of saturated NaHCO$_3$. Extract with EtOAc, dry (MgSO$_4$), and evaporate to provide 4-chloro-6-(2-trifluoromethyl-phenyl)-nicotinic acid ethyl ester as a brown oil.

3. 4-Amino-6-(2-trifluoromethyl-phenyl)-nicotinamide

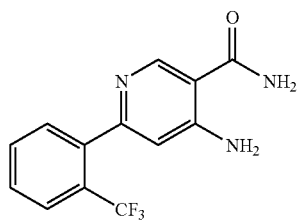

Heat a mixture of 4-Chloro-6-(2-trifluoromethyl-phenyl)-nicotinic acid ethyl ester (5.2 g) and 28% aq. NH$_4$OH (100 mL) in a 350 ml resealable pressure vessel for 60 hours. Cool, extract with EtOAc (3×100 mL each), dry (MgSO$_4$), and evaporate to provide the crude product. Purify by silica gel chromatography to provide 4-amino-6-(2-trifluoromethyl-phenyl)-nicotinamide as a solid.

4. 2-(2,6-Dimethyl-morpholin-4-ylmethyl)-7-(2-trifluoromethyl-phenyl)-pyrido[4,3-d]pyrimidin-4-ol

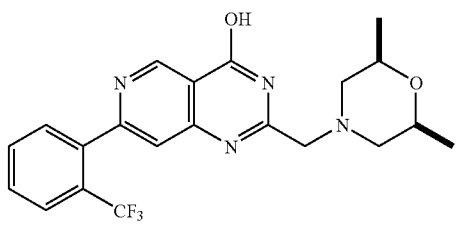

Heat a solution of 4-amino-6-(2-trifluoromethyl-phenyl)-nicotinamide (1 g, 3.5 mmol), 2,6-dimethyl-morpholin-4-yl)-acetic acid ethyl ester (2.85 g, 14 mmol), NaOEt (5.0 eq.) in EtOH (10 mL) for 20 hours. After cooling, concentrate the reaction mixture under reduced pressure, dilute the mixture with water (25 mL) and extract with EtOAc (3×25 mL each), then wash twice with water (25 mL each) and dry with MgSO$_4$. Evaporate, and purify by flash chromatography to obtain 2-(2,6-dimethyl-morpholin-4-ylmethyl)-7-(2-trifluoromethyl-phenyl)-pyrido[4,3-d]-pyrimidin-4-ol.

5. 4-Chloro-2-(2,6-dimethyl-morpholin-4-ylmethyl)-7-(2-trifluoromethyl-phenyl)-pyrido[4,3-d]pyrimidine

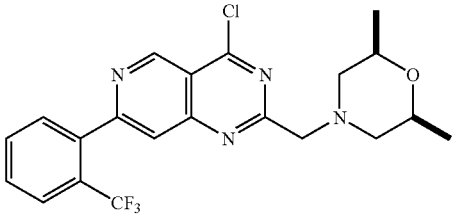

Reflux a mixture of 2-(2,6-dimethyl-morpholin-4-ylmethyl)-7-(2-trifluoromethyl-phenyl)-pyrido[4,3-d]-pyrimidin-4-ol (0.6 g), 2,6-lutidine (0.62 g), and POCl$_3$ (1.1 g) in CHCl$_3$ (15 mL) for 20 hours. Cool the mixture and concentrate under reduced pressure. Partition the residue between EtOAc and saturated NaHCO$_3$ solution. Wash the EtOAc portion with additional NaHCO$_3$ and then dry (Na$_2$SO$_4$) and concentrate under reduced pressure. Filter the brown residue through 2 inches of silica gel (1:1 EtOAc/hexanes eluent) and concentrate under reduced pressure to give 4-chloro-2-(2,6-dimethyl-morpholin-4-ylmethyl)-7-(2-trifluoromethyl-phenyl)-pyrido[4,3-d]pyrimidine.

6. [2-(2,6-Dimethyl-morpholin-4-ylmethyl)-7-(2-trifluoromethyl-phenyl)-pyrido[4,3-d]pyrimidin-4-yl]-(4-trifluoromethyl-phenyl)-amine (cis)

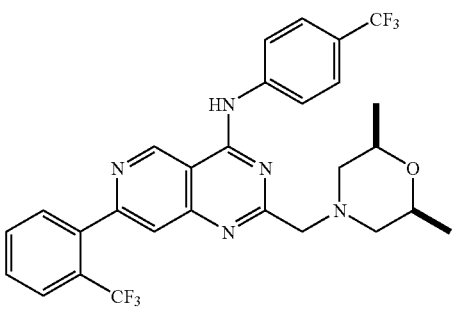

Heat a mixture of 4-chloro-2-(2,6-dimethyl-morpholin-4-ylmethyl)-7-(2-trifluoromethyl-phenyl)-pyrido[4,3-d]pyrimidine (43.7 mg, 0.1 mmol) and 4-trifluoromethyl-aniline (16.1 mg, 0.1 mmol) in AcCN (1 mL) at 80° C. for 24 hours. Cool the mixture and wash the precipitate with ether to give 4-chloro-2-(2,6-dimethyl-morpholin-4-ylmethyl)-7-(2-trifluoromethyl-phenyl)-pyrido[4,3-d]pyrimidine as the mono-HCl salt. Mass Spec 561.2.

C. [2-Morpholin-4-ylmethyl-7-(3-trifluoromethyl-pyridin-2-yl)-pyrido[3,2-a]pyrimidin-4-yl]-(4-trifluoromethyl-phenyl)-amine (cmpd 310)

1. 6'-Methoxy-3-trifluoromethyl-[2,3']bipyridinyl

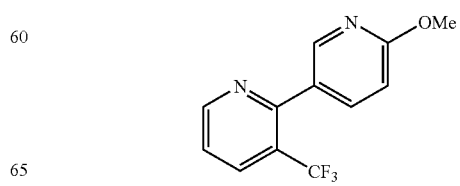

Heat a mixture of 2-chloro-3-trifluoromethylpyridine (37 g, 0.2 mol), 2-methoxypyridine-5-boronic acid (32 g, 0.21 mol), tetrakis(triphenylphosphine) palladium(0) (9 g, 7 mmol) and 2M potassium carbonate (150 mL) in toluene (500 mL) under a nitrogen atmosphere, at 90° C. for 8 hours. Cool the reaction mixture and separate the layers. Extract the aqueous layer with ethyl acetate (2×250 mL) and wash the combined organics with 4M sodium hydroxide (250 mL), water (250 mL), and brine (250 mL). Dry (MgSO$_4$) and concentrate under reduced pressure. Purify the oil by flash chromatography on silica gel (50% ether/50% hexane) to give the title compound (48.2 g, 95%) as a colorless oil.

2. 3-Trifluoromethyl-1'H-[2,3']bipyridinyl-6'-one

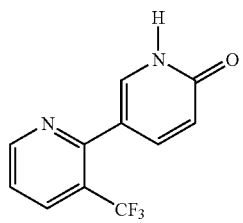

Heat 6'-methoxy-3-trifluoromethyl-[2,3']bipyridinyl (41 g, 0.16 mol) in 30% HBr/AcOH (100 mL) to reflux for 1 hour. Cool the mixture and filter, and wash the precipitate with ether (100 mL). Transfer the precipitate into 10M sodium hydroxide (500 mL) and stir for 1 hour, and treat the solution with hydrochloric acid until the solution is pH 7. Collect the white solid by filtration and air dry to give the title compound (36 g, 93%) as a white solid.

3. 5'-Nitro-3-trifluoromethyl-1'H-[2,3']bipyridinyl-6'-one

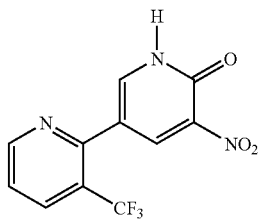

To a solution of 3-trifluoromethyl-1'H-[2,3']bipyridinyl-6'-one (25 g, 0.1 mol) in concentrated sulfuric acid (100 mL) at 0° C., add dropwise a solution of fuming nitric acid (35 mL) and concentrated sulfuric acid (10 mL). Heat the reaction mixture to 70° C. for 1 hour, cool and pour onto ice (500 mL). Filter the mixture and treat the filtrate with 10 M sodium hydroxide until the solution is at pH 4–5. Collect the precipitate by filtration and air dry to give the title compound (26.2 g, 92%) as a white solid.

4. 6'-Chloro-5'-nitro-3-trifluoromethyl-[2,3']bipyridinyl

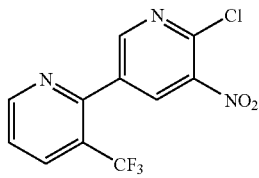

Heat a solution of 5'-nitro-3-trifluoromethyl-1'H-[2,3'] bipyridinyl-6'-one (25 g, 0.088 mol), thionyl chloride (300 mL) and DMF (3 mL) to reflux for 4 hours. Remove the volatiles by rotary evaporation and partition the residue between ethyl acetate (350 mL) and saturated sodium bicarbonate solution (250 mL). Extract the aqueous layer with further ethyl acetate (250 mL) and wash the combined organics with brine (250 mL). Dry (MgSO$_4$) and concentrate under reduced pressure to give the title compound (25 g, 93%) as a yellow oil.

5. 6'-Chloro-3-trifluoromethyl-[2,3']bipyridinyl-5'-ylamine

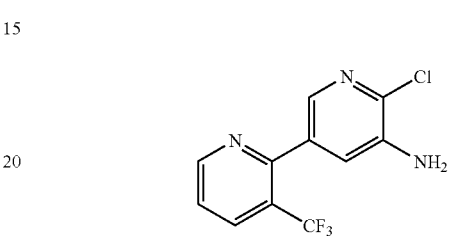

To a solution of 6'-chloro-5'-nitro-3-trifluoromethyl-[2,3'] bipyridinyl (25 g, 0.082 mol) and calcium chloride (11 g, 0.1 mol) in ethanol (300 mL) and water (50 mL), add iron powder (45 g, 0.82 mol). Heat the solution to reflux for 1.5 hours, cool and filter through Celite. Concentrate the mixture under reduced pressure, re-dissolve in ethyl acetate (300 mL) and wash with brine (200 mL). Concentrate the solution under reduced pressure and purify by flash chromatography on silica gel (50/ether/50% hexane) to give the title compound (19 g, 85%) as a pale yellow solid.

6. 3-Amino-5-[3-(trifluoromethyl)(2-pyridyl)]pyridine-2-carboxamide

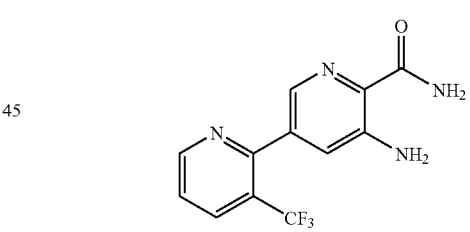

Heat a solution of 6'-chloro-3-trifluoromethyl-[2,3']bipyridinyl-5'-ylamine (25 g, 0.091 mol), zinc cyanide (6.75 g, 0.058 mol), tris[dibenzylidineacetone]di-palladium (also referred to as "pd$_2$(dba)$_3$"; 2.63 g, 2.86 mmol), 1,1'-bis(diphenylphosphino)ferrocene (also referred to as "DPPF"; 3.16 g, 5.72 mmol) in DMF (250 mL) and water (2.5 mL), under a nitrogen atmosphere, at 120° C. for 1 hour. Add water (30 mL) and heat the solution at 120° C. for a further 4 hours to complete the hydrolysis. Cool the reaction to 0° C. and add a solution of saturated ammonium chloride (200 ml), water (200 mL) and concentrated ammonium hydroxide (50 mL). After stirring at 0° C. for 1 hour, filter the yellow precipitate, and wash with water (200 mL) and a 1:1 mixture of ether-hexane (200 mL). Dry the solid in air and then in a vacuum oven to give (23 g, 90%) of the title compound.

7. 2-(Chloromethyl)-7-[3-(trifluoromethyl)(2-pyridyl)]-3-hydropyridino[3,2-d]pyrimidin-4-one

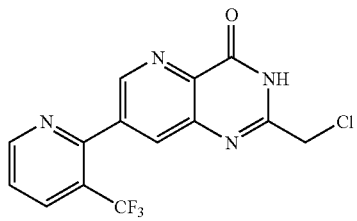

Heat a solution of 3-amino-5-[3-(trifluoromethyl)(2-pyridyl)]pyridine-2-carboxamide (23 g, 81.5 mmol) and 2-chloro-1,1,1-trimethoxyethane (250 mL) at 130° C. for 1 hour. Remove the volatiles by evaporation and triturate the solid (50% ether/50% hexane) to give the title compound as a light brown solid (21 g, 76%).

8. 2-(Morpholin-4-ylmethyl)-7-[3-(trifluoromethyl)(2-pyridyl)]-3-hydropyridino[3,2-d]pyrimidin-4-one

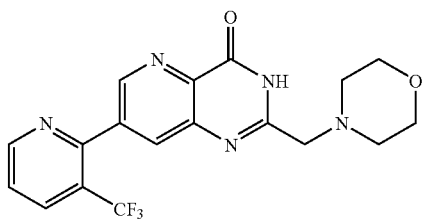

Heat a solution of 2-(chloromethyl)-7-[3-(trifluoromethyl)(2-pyridyl)]-3-hydropyridino[3,2-d]pyrimidin-4-one (20 g, 0.058 mol), morpholine (15.66 g, 0.18 mol) in acetonitrile (500 mL) at 80° C. for 12 hours. Evaporate the solution and partition the residue between ethyl acetate (500 mL) and saturated sodium bicarbonate solution (500 mL). Extract the aqueous layer with further ethyl acetate (250 mL) and wash the combined organics with brine (500 mL). Dry (MgSO$_4$) and concentrate under reduced pressure to give the title compound (18.8 g, 83%) as a brown solid.

9. 4-({4-Chloro-7-[3-(trifluoromethyl)(2-pyridyl)]pyridino[3,2-d]pyrimidin-2-yl}methyl)-methylmorpholine

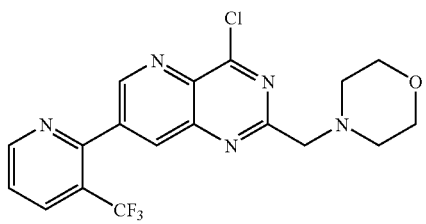

Heat a solution of 2-(morpholin-4-ylmethyl)-7-[3-(trifluoromethyl)(2-pyridyl)]-3-hydropyridino[3,2-d]pyrimidin-4-one (11.73 g, 0.03 mol), POCl$_3$ (13.8 g, 0.09 mol) and 2,6-lutidine (9.63 g, 0.09 mol) in chloroform (500 mL) at 60° C. for 12 hours. Evaporate the solution and partition the residue between ethyl acetate (500 mL) and saturated sodium bicarbonate solution (500 mL). Extract the aqueous layer with further ethyl acetate (250 mL) and wash the combined organics with brine (500 mL). Dry (MgSO$_4$) and concentrate under reduced pressure to give the title compound (11.5 g, 94%) as a brown solid.

10. [2-Morpholin-4-ylmethyl-7(3-trifluoromethyl-pyridin-2-yl)-pyrido[3,2-a]pyrimidin-4-yl]-(4-trifluoromethyl-phenyl)-amine

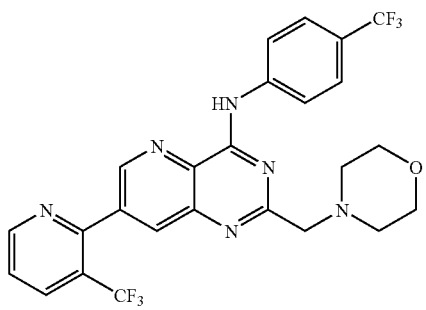

Heat a solution of 4-({4-chloro-7-[3-(trifluoromethyl)(2-pyridyl)]pyridino[3,2-d]pyrimidin-2-yl}methyl)-methylmorpholine (12.2 g, 0.03 mol), 4-(trifluoromethyl)aniline (4.8 g, 0.03 mmol) in acetonitrile (500 mL) at 80° C. for 12 hours. Evaporate the solution and partition the residue between ethyl acetate (500 mL) and saturated sodium bicarbonate solution (500 mL). Extract the aqueous layer with further ethyl acetate (2×250 mL) and wash the combined organics with brine (500 mL). Dry (MgSO$_4$) and concentrate under reduced pressure. Purify the residue by flash chromatography on silica gel (90% ether/10% hexane then 100% ether) to give the title compound (12.5 g, 78%). Mass Spec. 534.2.

D. [2-(2-Pyrrolidin-1-yl-ethyl)-7-(3-trifluoromethyl-pyridiny-2-yl)-quinazolin-4-yl]-(4-trifluoromethyl-phenyl)-amine (cmpd 311)

1. 3-Benzyloxy-propionic acid

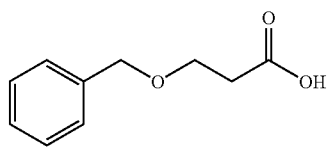

In small portions, add sodium hydride (2.22 g, 60% dispersion in mineral oil, 55.4 mmol) to a cold (0° C.) solution of benzyl alcohol (4.0 g, 37 mmol) in toluene (100 mL). Add ethyl 3-bromopropionate (8.0 g, 44 mmol) dropwise to the mixture, allow the resulting solution to warm to room temperature and stir for 1 hour. Quench the reaction with the addition of water until all bubbling ceases. Dilute the mixture with ethyl acetate (100 mL) and extract with water (100 mL) and brine (100 mL). Dry the organic extract over Na$_2$SO$_4$ and remove the solvent under reduced pressure to yield the crude ester as a clear oil. Dissolve the oil in methanol (20 mL) and 6 N NaOH (20 mL), and stir for 1 hour. Concentrate the mixture (approximately 20 mL) and dilute with water (20 mL). Extract the aqueous mixture once with CH$_2$Cl$_2$ (40 mL). Acidify the aqueous phase with conc. HCl and extract with EtOAc (3×50 mL). Dry the combined EtOAc extracts over Na$_2$SO$_4$. Remove the solvent under reduced pressure to yield the title compound as a clear oil (2.28 g; 34.0%) that solidifies upon standing.

2. 2-(2-Benzyloxy-ethyl)-7-(3-trifluoromethyl-pyridiny-2-yl)-3H-quinazolin-4-one

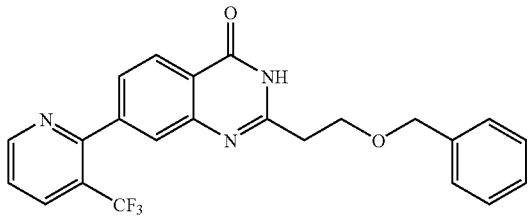

Cool a solution of 3-benzyloxy-propionic acid (1.66 g, 9.19 mmol) in hexanes (40 mL) to 0° C. and add oxalyl chloride (3.50 g, 27.6 mmol) dropwise. After the addition is completed, add DMF (2 drops), and stir the resulting mixture for 1 hour. Remove the solvent under reduced pressure and dissolve the crude acid chloride in dry THF (20 mL). In a separate flask, dissolve 2-amino-4-(3-trifluoromethyl-pyridin-2-yl)-benzamide (2.35 g, 8.37 mmol) in dry THF (40 mL) and pyridine (0.727 g, 9.19 mmol) and cool to 0° C. Add the solution containing the crude acid chloride dropwise to the second solution. Allow the mixture to warm to room temperature and stir for 1 hour. Add a solution of 10% NaOH$_{(aq)}$ (20 mL) to the mixture and stir the solution for 1 hour. Concentrate the mixture (~20 mL), dilute with water (20 mL), and acidify with conc. HCl. Extract the resulting solution with EtOAC (3×50 mL). Wash the combined organic extracts with brine and dry over Na$_2$SO$_4$. Remove the solvent under reduced pressure to yield the title compound as a white solid (3.24 g, 82.9%).

3. 2-(2-(2-Benzyloxy-ethyl)$_4$-chloro-7-(3-trifluoromethyl-pyridiny-2-yl)-quinazoline

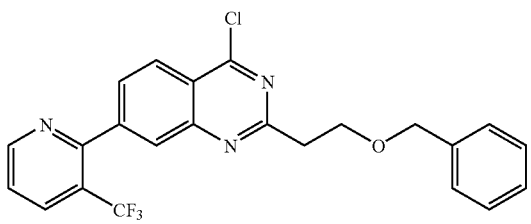

Dissolve 2-(2-benzyloxy-ethyl)-7-(3-trifluoromethyl-pyridiny-2-yl)-3H-quinazolin-4-one (3.24 g, 7.62 mmol) in CHCl$_3$ (40 mL) and 2,6-lutidine (2.45 g, 22.9 mmol). Add phosphorous oxychloride (1.77 mL, 19.0 mmol) dropwise and heat the resulting solution to reflux for 18 hours. Cool the solution and remove the solvent under reduced pressure. Partition the crude residue between EtOAc (200 mL) and saturated NaHCO$_3$ (aq) (200 mL). Remove the organic phase and extract the aqueous phase with EtOAc (200 mL). Combine the two organic extracts, wash with brine (200 mL), and dry over Na$_2$SO$_4$. Remove the solvent to yield the title compound as a light brown solid (2.47 g, 73.1%).

4. [2-(2-Benzyloxy-ethyl)-7-(3-trifluoromethyl-pyridiny-2-yl)-quinazolin-4-yl]-(4-trifluoromethyl-phenyl)-amine

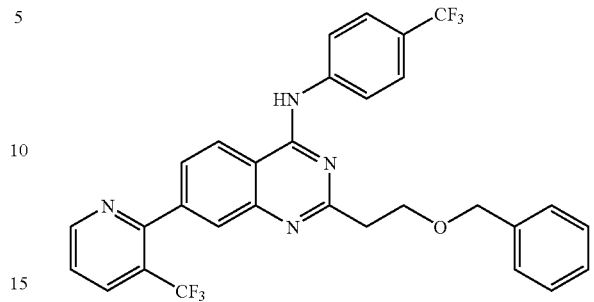

Dissolve 2-(2-benzyloxy-ethyl)-4-chloro-7-(3-trifluoromethyl-pyridiny-2-yl)-quinazoline (2.47 g, 5.57 mmol) into a solution of acetonitrile (50 mL) and 4-trifluoromethyl-aniline (0.986 g, 6.12 mmol). Heat the mixture to 80° C. for 2 hours, to form a white precipitate. Cool the solution in an ice bath and add diethyl ether (25 mL). Filter off the white precipitate and dry in a vacuum oven to yield the title compound as the mono-hydrochloride salt (2.96 g, 87.8%).

5. 2-[4-(4-Trifluoromethyl-phenylamino)-7-(3-trifluoromethyl-pyridin-2-yl)-quinazolin-2-yl]-ethanol

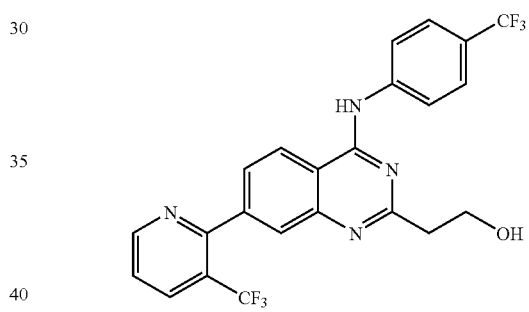

Dissolve [2-(2-benzyloxy-ethyl)-7-(3-trifluoromethyl-pyridiny-2-yl)-quinazolin-4-yl]-(4-trifluoromethyl-phenyl)-amine hydrochloride (2.96 g, 4.89 mmol) in MeOH (150 mL) and add 10% Pd/C (200 mg). Hydrogenate the mixture at 50 p.s.i. at 60° C. for 8 hours. Quickly filter the mixture through Celite and wash the Celite filter cake with hot MeOH (200 mL). Remove the solvent under reduced pressure to yield the mono-hydrochloride salt of title compound as a white solid (1.75 g, 69.5%).

6. [2-(2-Chloro-ethyl)-7-(3-trifluoromethyl-pyridiny-2-yl)-quinazolin-4-yl]-(4-trifluoromethyl-phenyl)-amine

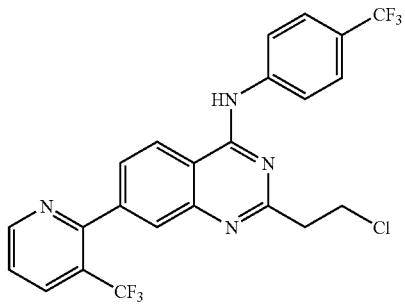

Dissolve 2-[4-(4-trifluoromethyl-phenylamino)-7-(3-trifluoromethyl-pyridin-2-yl)-quinazolin-2-yl]-ethanol hydrochloride (1.54 g, 2.99 mmol) in thionyl chloride (20 mL) and heat to 60° C. for 1 hour. Remove the excess thionyl chloride under reduced pressure and triturate the residue with diethyl ether to yield the mono-hydrochloride salt of the title compound as a light brown solid (1.48 g, 92.8%).

7. [2-(2-Pyrrolidin-1-yl-ethyl)-7-(3-trifluoromethyl-pyridiny-2-yl)-quinazolin-4-yl]-(4-trifluoromethyl-phenyl)-amine

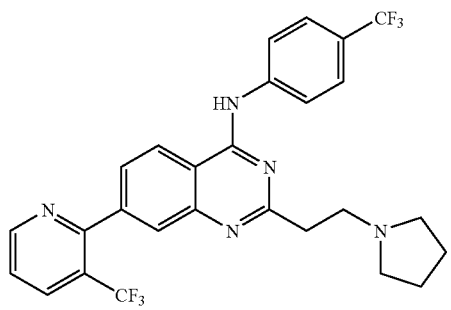

Dissolve [2-(2-chloro-ethyl)-7-(3-trifluoromethyl-pyridiny-2-yl)-quinazolin-4-yl]-(4-trifluoromethyl-phenyl)-amine hydrochloride (20 mg, 0.0375 mmol) in $CH_3CN$/10% diisopropylethylamine (0.187 mL) and add a 0.2 N solution of pyrrolidine in acetonitrile (0.281 mL). Heat the mixture at 70° C. for 18 hours. Remove the solvent under reduced pressure and partition the crude reaction mixture between EtOAc (1 mL) and 1 N (NaOH). Remove the organic extract and extract the aqueous phase again with EtOAc (1 mL). Chromatograph the combined organic extracts through a small pad of silica gel, eluting with acetone to yield the title compound as a light brown solid (18 mg, 90%).

E. [2-(3-morpholin-4-yl-propyl)7-(3-trifluoromethyl-pyridin-2-yl)-quinazolin-4-yl]-(4-trifluoromethyl-phenyl)-amine hydrochloride (cmpd 313)

1. 3-[4-hydroxy-7-(3-trifluoromethyl-pyridin-2-yl)-quinazolin-2-yl]-propionic acid ethyl ester

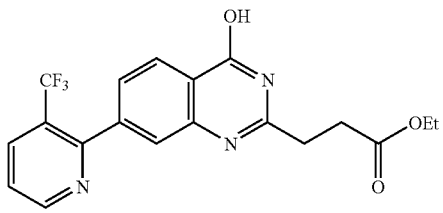

To a solution of 2-amino-4-(3-trifluoromethyl-pyridin-2-yl)-benzamide (0.5 mmol) and pyridine (0.55 mmol) in THF (5 ml), add 3-chlorocarbonyl-propionic acid ethyl ester chloride (0.55 mmol). Stir the mixture for 20 minutes at room temperature, add 20 ml of 21% NaOEt in EtOH, and stir for 30 minutes at 50° C. Concentrate, add water, filter, acidify to pH 6, and collect the precipitate to give 3-[4-hydroxy-7-(3-trifluoromethyl-pyridin-2-yl)quinazolin-2-yl]-propionic acid ethyl ester.

2. 3-[4-chloro-7-(3-trifluoromethyl-pyridin-2-yl)-quinazolin-2-yl]-propionic acid ethyl ester

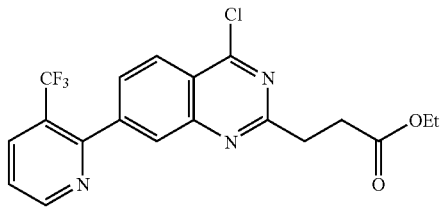

Using procedures analogous to those already described, 3-[4-chloro-7-(3-trifluoromethyl-pyridin-2-yl)-quinazolin-2-yl]-propionic acid ethyl ester is prepared from 3-[4-hydroxy-7-(3-trifluoromethyl-pyridin-2-yl)-quinazolin-2-yl]-propionic acid ethyl ester.

3. 3-[4-(4-trifluoromethyl-phenylamino)-7-(3-trifluoromethyl-pyridin-2-yl)-quinazolin-2-yl]-propionic acid ethyl ester

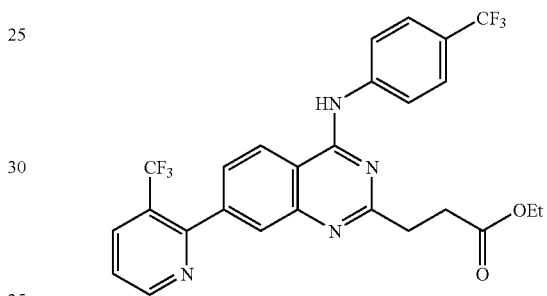

Using procedures analogous to those already described, 3-[4-(4-trifluoromethyl-phenylamino)-7-(3-trifluoromethyl-pyridin-2-yl)-quinazolin-2-yl]-propionic acid ethyl ester is prepared from 3-[4-chloro-7-(3-trifluoromethyl-pyridin-2-yl)-quinazolin-2-yl]-propionic acid ethyl ester.

4. 3-[4-(4-trifluoromethyl-phenylamino)-7-(3-trifluoromethyl-pyridin-2-yl)-quinazolin-2-yl]-propionic acid

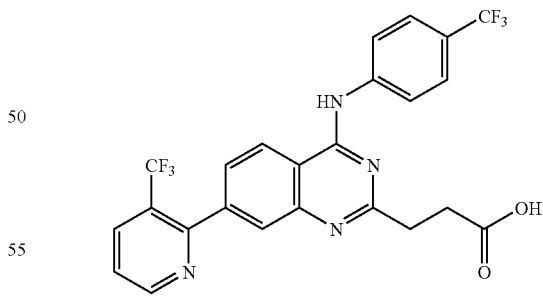

To a mixture of 3-[4-(4-trifluoromethyl-phenylamino)-7-(3-trifluoro-methyl-pyridin-2-yl)-quinazolin-2-yl]-propionic acid ethyl ester (0.5 mmol) in THF (20 ml) and $H_2O$ (20 ml), add LiOH (1.5 mmol). Stir the mixture for 2 hours at 60° C. Concentrate, add water, extract with ether, acidify the aqueous layer to pH 4–5, extract with EtOAc, and concentrate to give 3-[4-(4-trifluoromethyl-phenylamino)-7-(3-trifluoro-methyl-pyridin-2-yl)-quinazolin-2-yl]-propionic acid.

5. 1-morpholin-4-yl-3-[4-(4-trifluoromethyl-phenylamino)-7-(3-trifluoromethyl-pyridin-2-yl)-quinazolin-2-yl]-propan-1-one (cmpd 312)

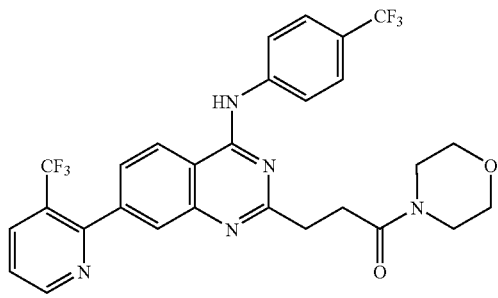

To a solution of 3-[4-(4-trifluoromethyl-phenylamino)-7-(3-trifluoro-methyl-pyridin-2-yl)-quinazolin-2-yl]-propionic acid (0.5 mmol) and triethylamine (0.5 mmol) in DME (10 ml), add benzotriazol-1-yl-oxy-tris(dimethylamino) phosphonium hexafluorophosphate (BOP; 0.5 mmol). Stir the mixture for 18 hours at room temperature, dilute with water, extract with EtOAc, and wash with brine. Concentrate to give 1-morpholin-4-yl-3-[4-(4-trifluoromethyl-phenylamino)-7-(3-trifluoromethyl-pyridin-2-yl)-quinazolin-2-yl]-propan-1-one. Mass Spec. 575.2.

6. [2-(3-morpholin-4-yl-propyl)-7-(3-trifluoromethyl-pyridin-2-yl)-quinazolin-4-yl]-(4-trifluoromethyl-phenyl)-amine hydrochloride (cmpd 313)

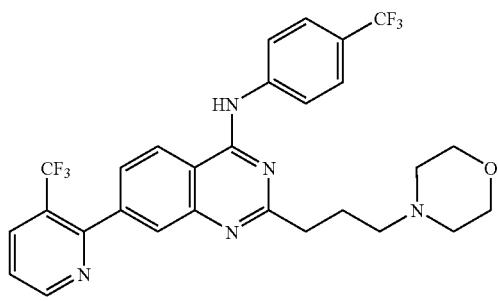

To a solution of 1-morpholin-4-yl-3-[4-(4-trifluoromethyl-phenylamino)-7-(3-trifluoromethyl-pyridin-2-yl)-quinazolin-2-yl]-propan-1-one (0.14 mmol) in THF (20 ml), add LAH (0.67 mmol). Stir the mixture for 6 hours at room temperature, quench with 10% NaOH, extract with EtOAc, dry over $Na_2SO_4$, and add HCl-EtOAc. Collect the precipitate to give [2-(3-morpholin-4-yl-propyl)-7-(3-trifluoromethyl-pyridin-2-yl)-quinazolin-4-yl]-(4-trifluoromethyl-phenyl)-amine hydrochloride. Mass Spec. 561.2.

F. 4-trifluoromethylphenyl-[2-(2,6-dimethylmorphonli-4-ylmethyl)-7-(2-trifluoromethyl phenyl)-quinazolin-4-yl]-amine (cmpd 314)

1. 7-Bromo-2-chloromethyl-3H-quinazolin-4-one

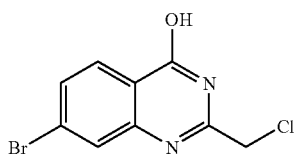

Reflux a solution of 2-amino-4-bromobenzamide (27 g, 0.13 mol; see Joshi and Chaudhari, (1987) *Indian J. Chem., Sect. B*, 26B(6):602–4) in 2-chloro-1,1,1-trimethoxyethane (50 mL) for 30 minutes, during which time a large precipitate appears. Evaporate the mixture fully and triturate with ether to collect 28 g of 7-bromo-2-chloromethyl-3H-quinazolin-4-one as a white solid.

2. 7-Bromo-4-chloro-2-chloromethylquinazoline

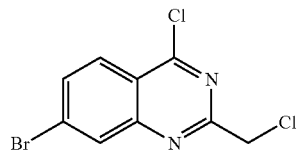

Heat a mixture of 7-bromo-2-chloromethyl-3H-quinazolin-4-one (5 g, 18.2 mmol), 2,6-lutidine (5 g), and phosphorus oxychloride (5 mL) in 1,2-dimethoxyethane (500 mL) at 80° C. for 16 hours. Cool the mixture to room temperature and fully evaporate the mixture, then dilute with ether and wash with water. Dry the solvent ($Na_2SO_4$) and evaporate the ether to obtain 7-bromo-4-chloro-2-chloromethylquinazoline (3.5 g) as a yellow solid.

3. 7-Bromo-2-chloromethylquinazolin-4-yl)-(4-trifluoromethylphenyl)-amine

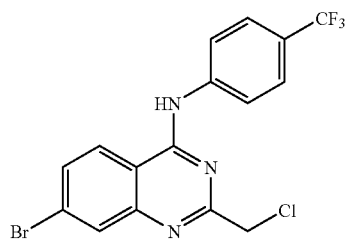

Heat a mixture of 7-bromo-4-chloro-2-chloromethylquinazoline (1168 mg, 4.0 mmol) and 4-(trifluoromethyl) aniline (644 mg, 4.0 mmol) in chloroform (50 mL) at 60° C. for 16 hours. Cool and collect the precipitated product 7-bromo-2-chloromethylquinazolin-4-yl)-(4-trifluoromethylphenyl)-amine (1021 mg) as the HCL salt.

4. [7-Bromo-2-(cis-2,6-dimethylmorpholin-4-ylmethyl)-quinazolin-4-yl]-4-(trifluoromethylphenyl)-amine

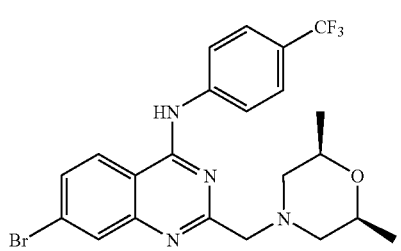

Heat a mixture of 7-bromo-2-chloromethylquinazolin-4-yl)-(4-trifluoromethylphenyl)-amine (416 mg, 1.0 mmol), cis-2,6-dimethylmorpholine (150 mg, 1.3 mmol), and triethylamine (202 mg, 2.0 mmol) in N,N-dimethylacetamide (7 mL) for 1 hour. Cool to room temperature, dilute with EtOAc (50 mL), and wash four times with water (25 mL each). Dry ($Na_2SO_4$) and evaporate. Triturate with ether to give [7-bromo-2-(cis-2,6-dimethylmorpholin-4-ylmethyl)-quinazolin-4-yl]4-(trifluoromethylphenyl)-amine (430 mg) as a yellow solid.

5. [2-(cis-2,6-dimethylmorpholin-4-yloxymethyl)-7-(2-trifluoromethylphenyl)-quinazolin-4-yl]-(4-trifluoromethylphenyl)-amine

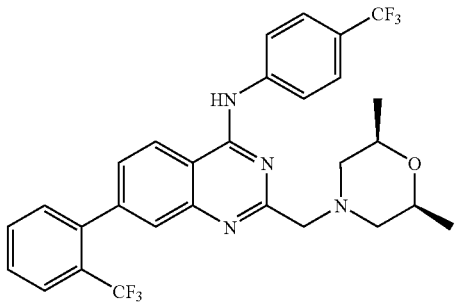

Under nitrogen, heat a mixture of [7-bromo-2-(cis-2,6-dimethylmorpholin-4-ylmethyl)-quinazolin-4-yl]-4-(trifluoromethylphenyl)-amine (75 mg, 0.15 mmol), 2-(trifluoromethylphenyl)boronic acid (45 mg, 0.23 mmol), tetrakis(triphenylphosphine)palladium(0) (21 mg, 0.018 mmol), 2M $Na_2CO_3$ in water (1 mL), and 1,2-dimethoxyethane (5 mL) at 60° C. for 16 hours. Cool the mixture to room temperature, dilute with EtOAc, and wash twice with water (10 mL each). Dry the organic layer ($Na_2SO_4$) and evaporate. Purify by preparative TLC (9:1 $CH_2CL_2$:MeOH) to obtain [2-(cis-2,6-dimethylmorpholin-4-yloxymethyl)-7-(2-trifluoromethylphenyl)-quinazolin-4-yl]-(4-trifluoromethylphenyl)-amine (112 mg) as a yellow solid. Mass Spec. 560.2.

G. [7-(3-Methyl-pyridin-2-yl)-2-pyrrolidin-1-ylmethyl-pyrido[3,2-d]pyrimidin-4-yl]-(4-trifluoromethyl-phenyl)-amine (cmpd 315)

1. 5-Bromo-3-nitropyridine-2-carbonitrile

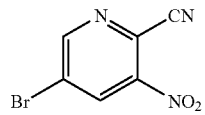

Heat a solution of 2-amino-5-bromo-3-nitropyridine (2.18 g, 10 mmol), cuprous cyanide (1.33 g, 15 mmol) and tert-butylnitrite (2.0 mL, 15 mmol) in acetonitrile (50 mL) to 60° C. for 2 hours. Cool the solution and partition between ethyl acetate (100 mL) and saturated aqueous $NaHCO_3$ (100 mL). Extract the aqueous solution with ethyl acetate (2×50 mL), wash with water (100 mL), brine (100 mL), dry ($MgSO_4$) and evaporate. Purify the solid by flash chromatography on silica gel (25% ether/75% hexane) to obtain the title compound as a pale yellow solid (934 mg, 41%).

2. 5-(3-Methyl(2-pyridyl))-3-nitropyridine-2-carbonitrile

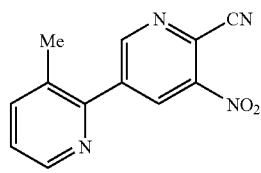

Heat a solution of 5-bromo-3-nitropyridine-2-carbonitrile (228 mg, 1.0 mmol), tetrakis(triphenylphosphine)palladium (0) (15 mg), 3-methyl-2-pyridylzinc bromide (0.5 M in THF, 3 mL, 1.5 mmol) in THF (5 mL) to 60° C. for 2 hours. Cool the solution and partition between ethyl acetate (10 mL) and saturated aqueous $NaHCO_3$ (10 mL), Extract the aqueous solution with ethyl acetate (2×15 mL), wash with water (10 mL), brine (10 mL), dry ($MgSO_4$) and evaporate to obtain the title compound as a pale yellow solid (211 mg, 88%).

3. 3-Amino-5-(3-methyl(2-pyridyl))pyridine-2-carboxamide

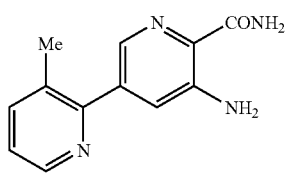

Heat a solution of 5-(3-methyl(2-pyridyl))-3-nitropyridine-2-carbonitrile (1 g, 4.1 mmol), iron (2.3 g, 40 mmol) and calcium chloride (560 mg, 5 mmol) in ethanol (15 mL) and water (4 mL) to reflux for 1 hour. Cool the mixture, filter through Celite and wash with ethyl acetate. Evaporate the filtrate and re-dissolve the residue in ethyl acetate, wash with water and then with brine, dry ($MgSO_4$) and evaporate to obtain the title compound as a pale yellow solid (880 mg, 94%).

4. [7-(3-Methyl-pyridin-2-yl)-2-pyrrolidin-1-ylmethyl-pyrido[3,2-d]pyrimidin-4-yl]-(4-trifluoromethyl-phenyl)-amine

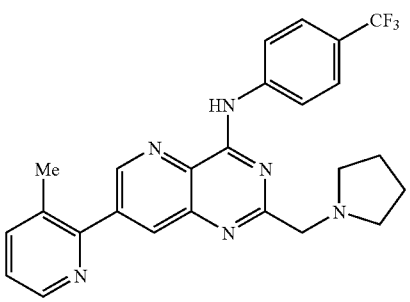

The title compound is prepared from 3-amino-5-(3-methyl(2-pyridyl))pyridine-2-carboxamide in a manner analogous to that used for the preparation of [2-pyrrolidin-1-ylmethyl-7-(3-trifluoromethyl-pyridin-2-yl)-quinazolin-4-yl]-(4-trifluoromethyl-phenyl)-amine (Example 2.A, steps 6 to 9).

H. Additional Representative Substituted 2-Aminoalkyl-Quinazolin-4-ylamine Analogues Those having skill in the art will recognize that the starting materials may be varied and additional steps employed to produce other compounds encompassed by the present invention. Compounds listed in Table VI were prepared using the above methods, with readily apparent modifications.

TABLE VI

Representative Substituted 2-Aminoalkyl-quinazolin-4-ylamine Analogues

| Compound | | | MS |
|---|---|---|---|
| 316. | | (1-{3-[4-(4-Trifluoromethyl-phenylamino)-7-(3-trifluoromethyl-pyridin-2-yl)-quinazolin-2-yl]-propyl}-piperidin-4-yl)-methanol | 589.2 |
| 317. | | (2,6-Dimethyl-morpholin-4-yl)-[4-(4-trifluoromethyl-phenylamino)-7-(3-trifluoromethyl-pyridin-2-yl)-quinazolin-2-yl]-methanone (cis) | |
| 318. | | (4-Cyclopropyl-phenyl)-[2-(2,6-dimethyl-morpholin-4-ylmethyl)-7-(3-trifluoromethyl-pyridin-2-yl)-quinazolin-4-yl]-amine (cis) | |
| 319. | | (4-sec-Butyl-phenyl)-[7-(3-chloro-pyridin-2-yl)-2-(2,6-dimethyl-morpholin-4-ylmethyl)-quinazolin-4-yl]-amine (cis) | |

TABLE VI-continued

Representative Substituted 2-Aminoalkyl-quinazolin-4-ylamine Analogues

| Compound | | MS |
|---|---|---|
| 320. | 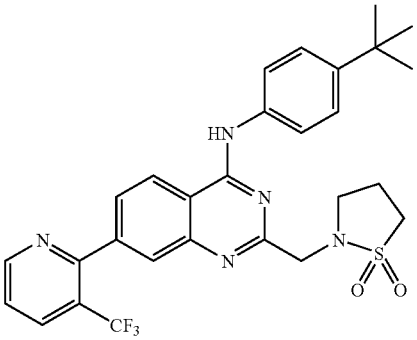 (4-tert-Butyl-phenyl)-[2-(1,1-dioxo-1λ⁶-isothiazolidin-2-ylmethyl)-7-(3-trifluoromethyl-pyridin-2-yl)-quinazolin-4-yl]-amine | |
| 321. | 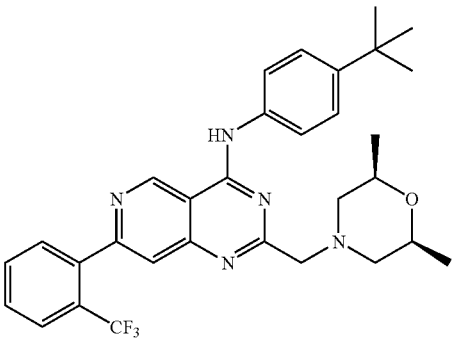 (4-tert-Butyl-phenyl)-[2-(2,6-dimethyl-morpholin-4-ylmethyl)-7-(2-trifluoromethyl-phenyl)-pyrido[4,3-d]pyrimidin-4-yl]-amine (cis) | 549.3 |
| 322. | 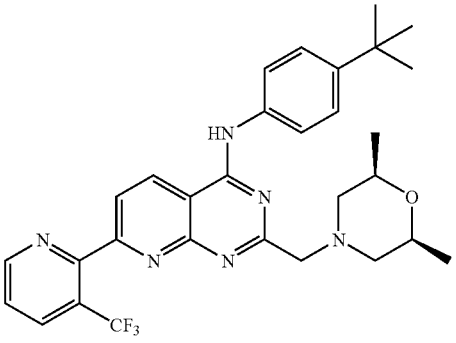 (4-tert-Butyl-phenyl)-[2-(2,6-dimethyl-morpholin-4-ylmethyl)-7-(3-trifluoromethyl-pyridin-2-yl)-pyrido[2,3-d]pyrimidin-4-yl]-amine (cis) | |
| 323. | 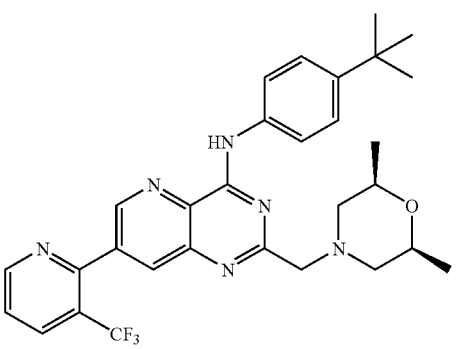 (4-tert-Butyl-phdnyl)-[2-(2,6-dimethyl-morpholin-4-ylmethyl)-7-(3-trifluoromethyl-pyridin-2-yl)-pyrido[3,2-d]pyrimidin-4-yl]-amine (cis) | 550.3 |

TABLE VI-continued

Representative Substituted 2-Aminoalkyl-quinazolin-4-ylamine Analogues

| Compound | | | MS |
|---|---|---|---|
| 324. | | (4-tert-Butyl-phenyl)-[2-(2,6-dimethyl-morpholin-4-ylmethyl)-7-(3-methyl-pyridin-2-yl)-quinazolin-4-yl]-amine (cis) | 495.3 |
| 325. | | (4-tert-Butyl-phenyl)-[2-(2,6-dimethyl-morpholin-4-ylmethyl)-7-(6-methyl-pyridin-2-yl)-quinazolin-4-yl]-amine (cis) | 495.3 |
| 326. | | (4-tert-Butyl-phenyl)-[2-(2,6-dimethyl-morpholin-4-ylmethyl)-7-pyridin-2-yl-quinazolin-4-yl]-amine (cis) | 481.3 |
| 327. | | (4-tert-Butyl-phenyl)-[2-piperidin-1-ylmethyl-7-(3-trifluoromethyl-pyridin-2-yl)-quinazolin-4-yl]-amine | 519.2 |

TABLE VI-continued

Representative Substituted 2-Aminoalkyl-quinazolin-4-ylamine Analogues

| Compound | | MS |
|---|---|---|
| 328. | (4-tert-Butyl-phenyl)-[2-pyrrolidin-1-ylmethyl-7-(3-trifluoromethyl-pyridin-2-yl)-quinazolin-4-yl]-amine | 505.2 |
| 329. | (4-tert-Butyl-phenyl)-[7-(3-chloro-pyridin-2-yl)-2-(2,6-dimethyl-morpholin-4-ylmethyl)-pyrido[3,2-d]pyrimidin-4-yl]-amine (cis) | 516.2 |
| 330. | (4-Trifluoromethyl-phenyl)-[7-(3-trifluoromethyl-pyridin-2-yl)-2-(3,3,5-trimethyl-azepan-1-ylmethyl)-quinazolin-4-yl]-amine | 587.2 |
| 331. | (4-Trifluoromethyl-phenyl)-{7-(3-trifluoromethyl-pyridin-2-yl)-2-[2-(3,3,5-trimethyl-azepan-1-yl)-ethyl]-quinazolin-4-yl}-amine | 601.3 |

TABLE VI-continued

Representative Substituted 2-Aminoalkyl-quinazolin-4-ylamine Analogues

| Compound | | MS |
|---|---|---|
| 332. | (6-tert-Butyl-pyridin-3-yl)-[7-(3-chloro-pyridin-2-yl)-2-(2,6-dimethyl-morpholin-4-ylmethyl)-pyrido[3,2-d]pyrimidin-4-yl]-amine (cis) | 517.2 |
| 333. | (R)-(4-Isopropyl-phenyl)-[2-(2-methyl-morpholin-4-ylmethyl)-7-(3-trifluoromethyl-pyridin-2-yl)-quinazolin-4-yl]amine | |
| 334. | (R)-(4-tert-Butyl-phenyl)-[2-(2-methyl-morpholin-4-ylmethyl)-7-(3-trifluoromethyl-pyridin-2-yl)-quinazolin-4-yl]-amine | |
| 335. | (R)-(4-tert-Butyl-phenyl)-[7-(3-chloro-pyridin-2-yl)-2-(2-methyl-morpholin-4-ylmethyl)-quinazolin-4-yl]-amine | 501.2 |

TABLE VI-continued

Representative Substituted 2-Aminoalkyl-quinazolin-4-ylamine Analogues

| Compound | | MS |
|---|---|---|
| 336. 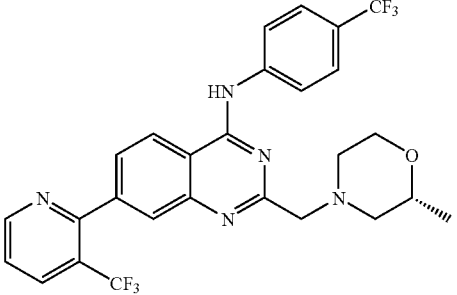 | (R)-[2-(2-Methyl-morpholin-4-ylmethyl)-7-(3-trifluoromethyl-pyridin-2-yl)-quinazolin-4-yl]-(4-trifluoromethyl-phenyl)-amine | |
| 337. 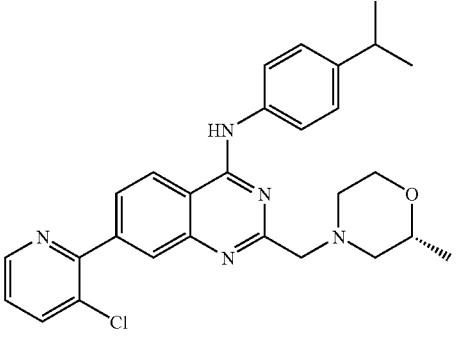 | (R)-[7-(3-Chloro-pyridin-2-yl)-2-(2-methyl-morpholin-4-ylmethyl)-quinazolin-4-yl]-(4-isopropyl-phenyl)-amine | 487.2 |
| 338. 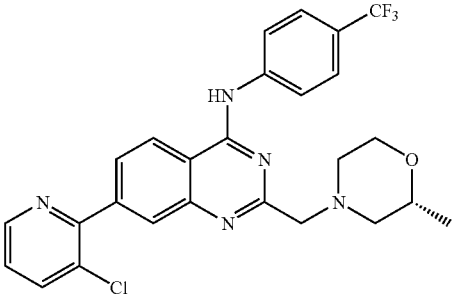 | (R)-[7-(3-Chloro-pyridin-2-yl)-2-(2-methyl-morpholin-4-ylmethyl)-quinazolin-4-yl]-(4-trifluoromethyl-phenyl)-amine | 513.2 |
| 339. 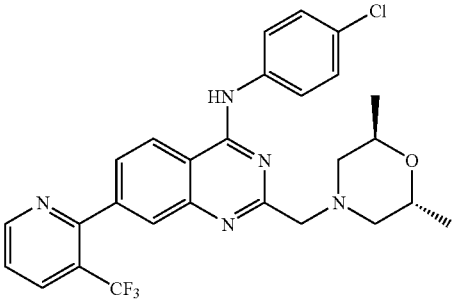 | (R,R)-(4-Chloro-phenyl)-[2-(2,6-dimethyl-morpholin-4-ylmethyl)-7-(3-trifluoromethyl-pyridin-2-yl)-quinazolin-4-yl]-amine | 527.2 |

TABLE VI-continued

Representative Substituted 2-Aminoalkyl-quinazolin-4-ylamine Analogues

| Compound | | | MS |
|---|---|---|---|
| 340. | 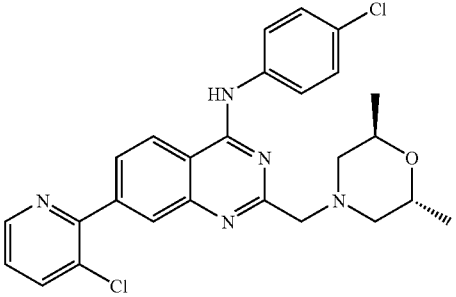 | (R,R)-(4-Chloro-phenyl)-[7-(3-chloro-pyridin-2-yl)-2-(2,6-dimethyl-morpholin-4-ylmethyl)-quinazolin-4-yl]-amine | 493.1 |
| 341. | 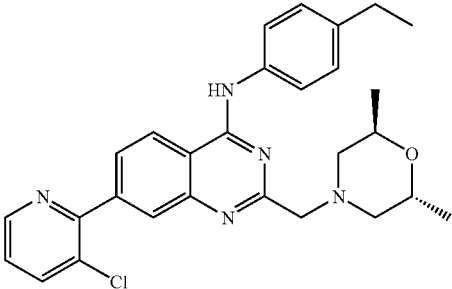 | (R,R)-(4-Ethyl-phenyl)-[7-(3-chloro-pyridin-2-yl)-2-(2,6-dimethyl-morpholin-4-ylmethyl)-quinazolin-4-yl]-amine | 487.2 |
| 342. | 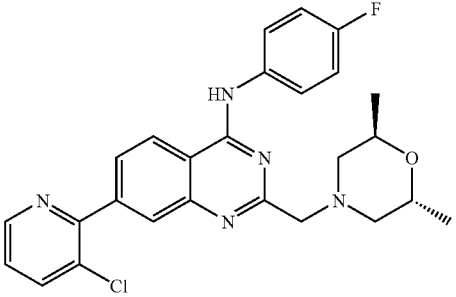 | (R,R)-(4-Fluoro-phenyl)-[7-(3-chloro-pyridin-2-yl)-2-(2,6-dimethyl-morpholin-4-ylmethyl)-quinazolin-4-yl]-amine | 477.2 |
| 343. | 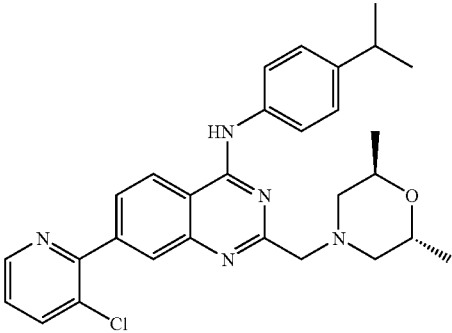 | (R,R)-(4-Isopropyl-phenyl)-[7-(3-chloro-pyridin-2-yl)-2-(2,6-dimethyl-morpholin-4-ylmethyl)-quinazolin-4-yl]-amine | 501.2 |

TABLE VI-continued

Representative Substituted 2-Aminoalkyl-quinazolin-4-ylamine Analogues

| Compound | | MS |
|---|---|---|
| 344. | (R,R)-(4-tert-Butyl-phenyl)-[7-(3-chloro-pyridin-2-yl)-2-(2,6-dimethyl-morpholin-4-ylmethyl)-quinazolin-4-yl]-amine | 515.2 |
| 345. | (R,R)-(6-tert-Butyl-pyridin-3-yl)-[2-(2,6-dimethyl-morpholin-4-ylmethyl)-7-(3-trifluoromethyl-pyridin-2-yl)-quinazolin-4-yl]-amine | 550.3 |
| 346. | (R,R)-(6-tert-Butyl-pyridin-3-yl)-[7-(3-chloro-pyridin-2-yl)-2-(2,6-dimethyl-morpholin-4-ylmethyl)-quinazolin-4-yl]-amine | 516.2 |
| 347. | (R,R)-[2-(2,6-Dimethyl-morpholin-4-ylmethyl)-7-(3-trifluoromethyl-pyridin-2-yl)-quinazolin-4-yl]-(4-trifluoromethyl-phenyl)-amine | 561.2 |

TABLE VI-continued

Representative Substituted 2-Aminoalkyl-quinazolin-4-ylamine Analogues

| Compound | | | MS |
|---|---|---|---|
| 348. | 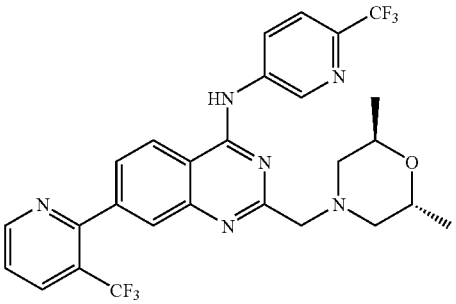 | (R,R)-[2-(2,6-Dimethyl-morpholin-4-ylmethyl)-7-(3-trifluoromethyl-pyridin-2-yl)-quinazolin-4-yl]-(6-trifluoromethyl-pyridin-3-yl)-amine | 562.2 |
| 349. | 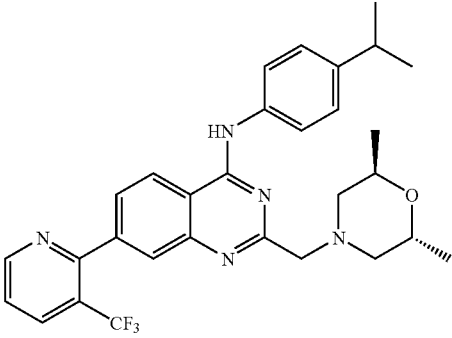 | (R,R)-[2-(2,6-Dimethyl-morpholin-4-ylmethyl)-7-(3-trifluoromethyl-pyridin-2-yl)-quinazolin-4-yl]-(4-isopropyl-phenyl)-amine | 535.3 |
| 350. | 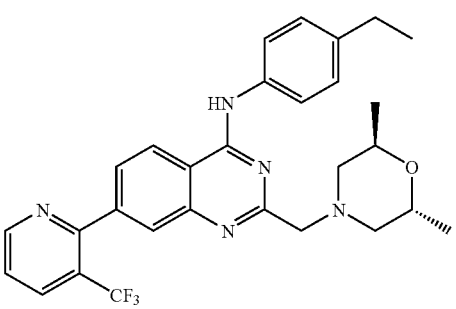 | (R,R)-[2-(2,6-Dimethyl-morpholin-4-ylmethyl)-7-(3-trifluoromethyl-pyridin-2-yl)-quinazolin-4-yl]-(4-ethyl-phenyl)-amine | 521.2 |
| 351. | 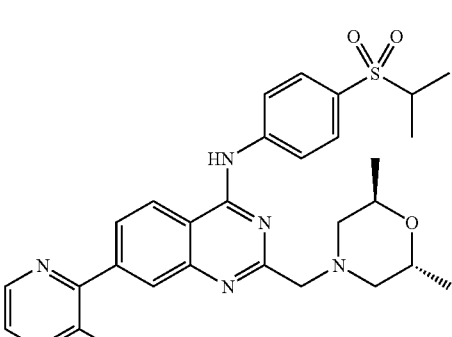 | (R,R)-[2-(2,6-Dimethyl-morpholin-4-ylmethyl)-7-(3-trifluoromethyl-pyridin-2-yl)-quinazolin-4-yl]-[4-(propane-2-sulfonyl)-phenyl]-amine | 599.2 |

TABLE VI-continued

Representative Substituted 2-Aminoalkyl-quinazolin-4-ylamine Analogues

| Compound | | MS |
|---|---|---|
| 352. 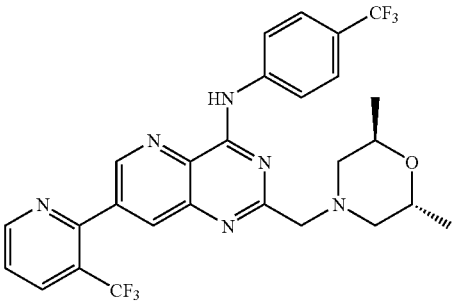 | (R,R)-[2-(2,6-Dimethyl-morpholin-4-ylmethyl)-7-(3-trifluoromethyl-pyridin-2-yl)-pyrido[3,2-d]pyrimidin-4-yl]-(4-trifluoromethyl-phenyl)-amine | 562.2 |
| 353. 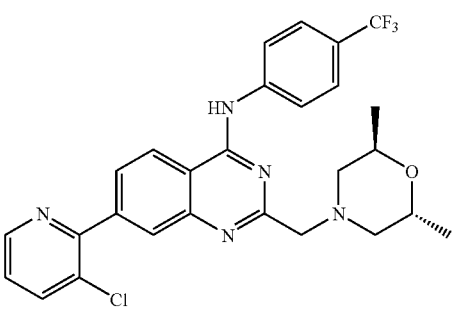 | (R,R)-[7-(3-Chloro-pyridin-2-yl)-2-(2,6-dimethyl-morpholin-4-ylmethyl)-quinazolin-4-yl]-(4-trifluoromethyl-phenyl)-amine | 527.2 |
| 354. 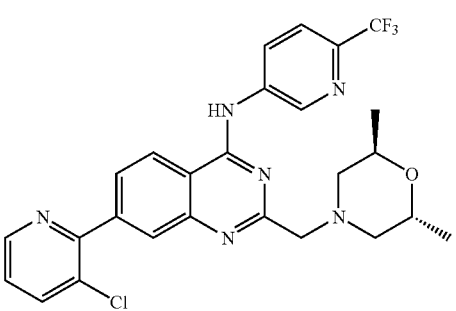 | (R,R)-[7-(3-Chloro-pyridin-2-yl)-2-(2,6-dimethyl-morpholin-4-ylmethyl)-quinazolin-4-yl]-(6-trifluoromethyl-pyridin-3-yl)-amine | 528.2 |
| 355. 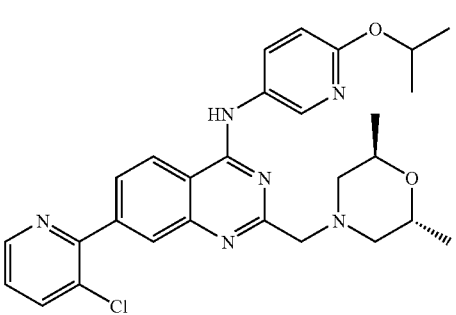 | (R,R)-[7-(3-Chloro-pyridin-2-yl)-2-(2,6-dimethyl-morpholin-4-ylmethyl)-quinazolin-4-yl]-(6-isopropoxy-pyridin-3-yl)-amine | 518.2 |

TABLE VI-continued

Representative Substituted 2-Aminoalkyl-quinazolin-4-ylamine Analogues

| Compound | | | MS |
|---|---|---|---|
| 356. | 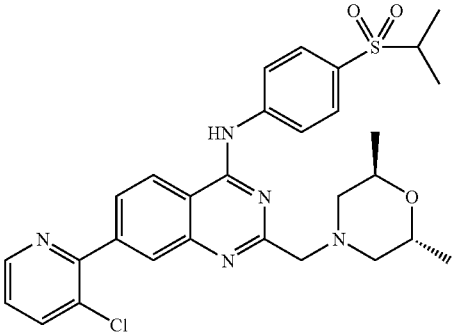 | (R,R)-[7-(3-Chloro-pyridin-2-yl)-2-(2,6-dimethyl-morpholin-4-ylmethyl)-quinazolin-4-yl]-[4-(propane-2-sulfonyl)-phenyl]-amine | 565.2 |
| 357. | 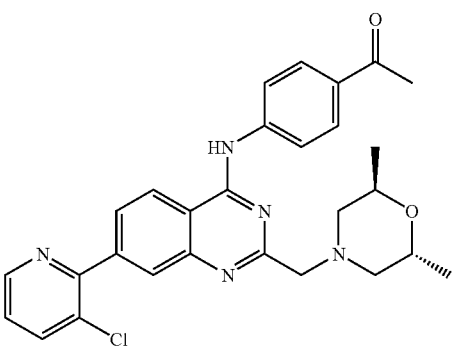 | (R,R)-1-{4-[7-(3-Chloro-pyridin-2-yl)-2-(2,6-dimethyl-morpholin-4-ylmethyl)-quinazolin-4-ylamino]-phenyl}-ethanone | 501.2 |
| 358. | 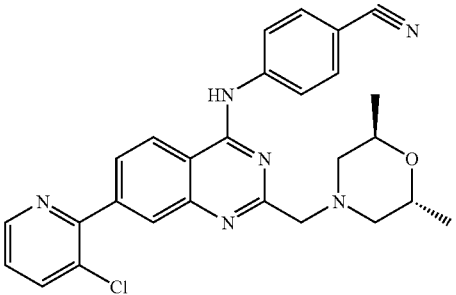 | (R,R)-4-[7-(3-Chloro-pyridin-2-yl)-2-(2,6-dimethyl-morpholin-4-ylmethyl)-quinazolin-4-ylamino]-benzonitrile | 484.2 |
| 359. | 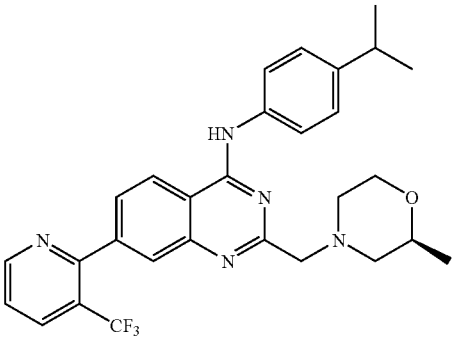 | (S)-(4-Isopropyl-phenyl)-[2-(2-methyl-morpholin-4-ylmethyl)-7-(3-trifluoromethyl-pyridin-2-yl)-quinazolin-4-yl]-amine | |

TABLE VI-continued

Representative Substituted 2-Aminoalkyl-quinazolin-4-ylamine Analogues

| Compound | | MS |
|---|---|---|
| 360. | 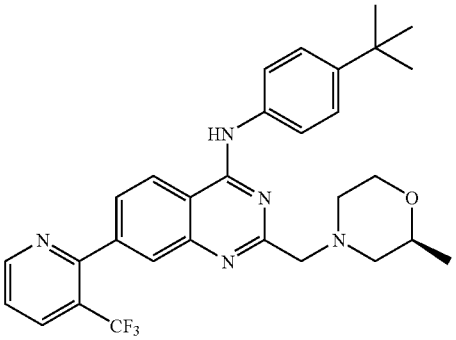 | (S)-(4-tert-Butyl-phenyl)-[2-(2-methyl-morpholin-4-ylmethyl)-7-(3-trifluoromethyl-pyridin-2-yl)-quinazolin-4-yl]-amine | |
| 361. | 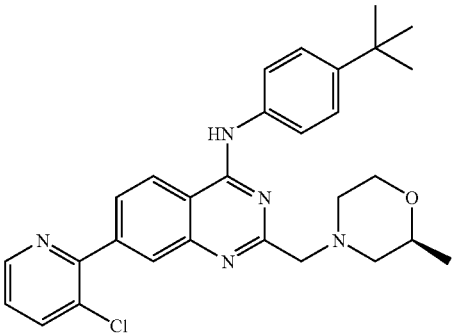 | (S)-(4-tert-Butyl-phenyl)-[7-(3-chloro-pyridin-2-yl)-2-(2-methyl-morpholin-4-ylmethyl)-quinazolin-4-yl]-amine | 501.2 |
| 362. | 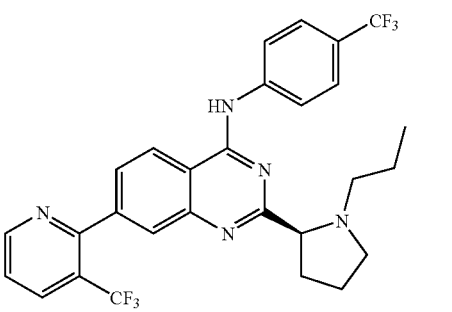 | (S)-[2-(1-Propyl-pyrrolidin-2-yl)-7-(3-trifluoromethyl-pyridin-2-yl)-quinazolin-4-yl]-(4-trifluoromethyl-phenyl)-amine | |
| 363. | 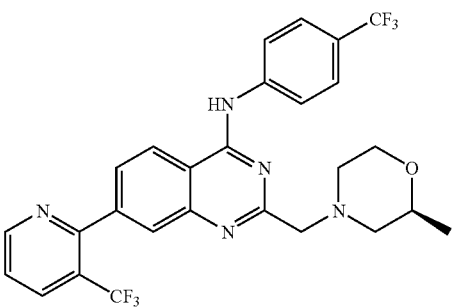 | (S)-[2-(2-Methyl-morpholin-4-ylmethyl)-7-(3-trifluoromethyl-pyridin-2-yl)-quinazolin-4-yl]-(4-trifluoromethyl-phenyl)-amine | |

TABLE VI-continued

Representative Substituted 2-Aminoalkyl-quinazolin-4-ylamine Analogues

| Compound | | | MS |
|---|---|---|---|
| 364. | 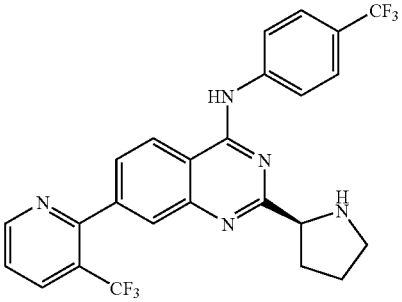 | (S)-[2-Pyrrolidin-2-yl-7-(3-trifluoromethyl-pyridin-2-yl)-quinazolin-4-yl]-(4-trifluoromethyl-phenyl)-amine | |
| 365. | 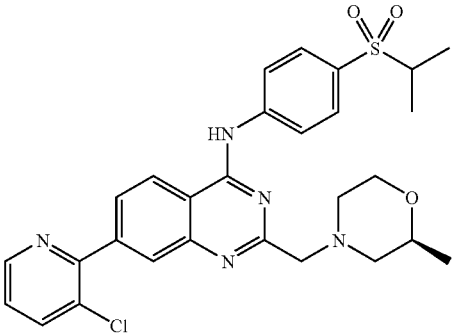 | (S)-[7-(3-Chloro-pyridin-2-yl)-2-(2-methyl-morpholin-4-ylmethyl)-quinazolin-4-yl]-[4-(propane-2-sulfonyl)-phenyl]-amine | 551.2 |
| 366. | 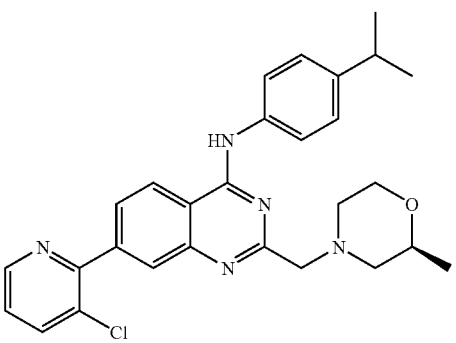 | (S)-[7-(3-Chloro-pyridin-2-yl)-2-(2-methyl-morpholin-4-ylmethyl)-quinazolin-4-yl]-(4-isopropyl-phenyl)-amine | 487.2 |
| 367. | 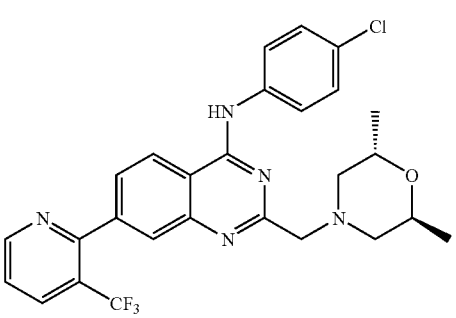 | (S,S)-(4-Chloro-phenyl)-[2-(2,6-dimethyl-morpholin-4-ylmethyl)-7-(3-trifluoromethyl-pyridin-2-yl)-quinazolin-4-yl]-amine | 527.2 |

TABLE VI-continued

Representative Substituted 2-Aminoalkyl-quinazolin-4-ylamine Analogues

| Compound | | | MS |
|---|---|---|---|
| 368. | 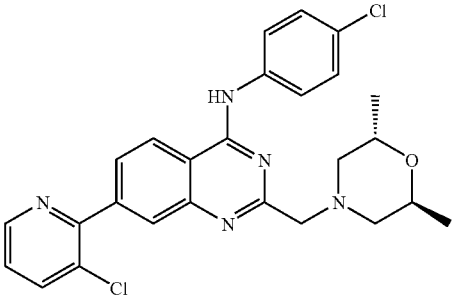 | (S,S)-(4-Chloro-phenyl)-[7-(3-chloro-pyridin-2-yl)-2-(2,6-dimethyl-morpholin-4-ylmethyl)-quinazolin-4-yl]-amine | 493.1 |
| 369. | 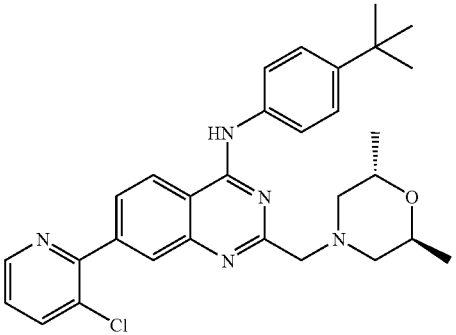 | (S,S)-(4-tert-Butyl-phenyl)-[7-(3-chloro-pyridin-2-yl)-2-(2,6-dimethyl-morpholin-4-ylmethyl)-quinazolin-4-yl]-amine | 515.2 |
| 370. | 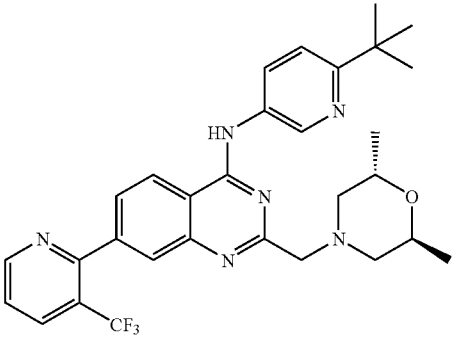 | (S,S)-(6-tert-Butyl-pyridin-3-yl)-[2-(2,6-dimethyl-morpholin-4-ylmethyl)-7-(3-trifluoromethyl-pyridin-2-yl)-quinazolin-4-yl]-amine | 550.3 |
| 371. | 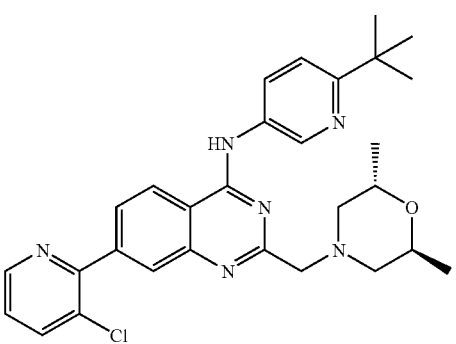 | (S,S)-(6-tert-Butyl-pyridin-3-yl)-[7-(3-chloro-pyridin-2-yl)-2-(2,6-dimethyl-morpholin-4-ylmethyl)-quinazolin-4-yl]-amine | 516.2 |

TABLE VI-continued

Representative Substituted 2-Aminoalkyl-quinazolin-4-ylamine Analogues

| Compound | | MS |
|---|---|---|
| 372. | (S,S)-[2-(2,6-Dimethyl-morpholin-4-ylmethyl)-7-(3-trifluoromethyl-pyridin-2-yl)-quinolin-4-yl]-(4-trifluoromethyl-phenyl)-amine | |
| 373. | (S,S)-[2-(2,6-Dimethyl-morpholin-4-ylmethyl)-7-(3-trifluoromethyl-pyridin-2-yl)-quinazolin-4-yl]-(6-trifluoromethyl-pyridin-3-yl)-amine | 562.2 |
| 374. | (S,S)-[2-(2,6-Dimethyl-morpholin-4-ylmethyl)-7-(3-trifluoromethyl-pyridin-2-yl)-quinazolin-4-yl]-(4-isopropyl-phenyl)-amine | 535.3 |
| 375. | (S,S)-[2-(2,6-Dimethyl-morpholin-4-ylmethyl)-7-(3-trifluoromethyl-pyridin-2-yl)-quinazolin-4-yl]-(4-ethyl-phenyl)-amine | 521.2 |

TABLE VI-continued

Representative Substituted 2-Aminoalkyl-quinazolin-4-ylamine Analogues

| Compound | | | MS |
|---|---|---|---|
| 376. | 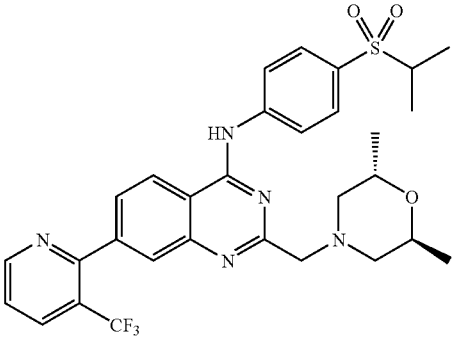 | (S,S)-[2-(2,6-Dimethyl-morpholin-4-ylmethyl)-7-(3-trifluoromethyl-pyridin-2-yl)-quinazolin-4-yl]-[4-(propane-2-sulfonyl)-phenyl]-amine | 599.2 |
| 377. | 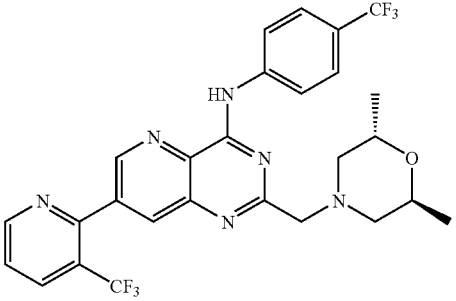 | (S,S)-[2-(2,6-Dimethyl-morpholin-4-ylmethyl)-7-(3-trifluoromethyl-pyridin-2-yl)-pyrido[3,2-d]pyrimidin-4-yl]-(4-trifluoromethyl-phenyl)-amine | 562.2 |
| 378. | 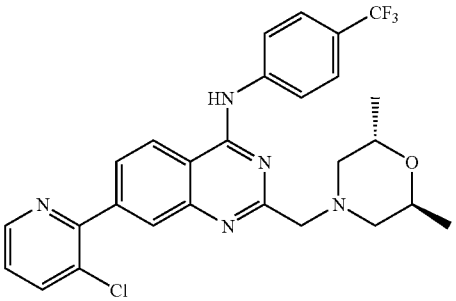 | (S,S)-[7-(3-Chloro-pyridin-2-yl)-2-(2,6-dimethyl-morpholin-4-ylmethyl)-quinazolin-4-yl]-(4-trifluoromethyl-phenyl)-amine | 527.2 |
| 379. | 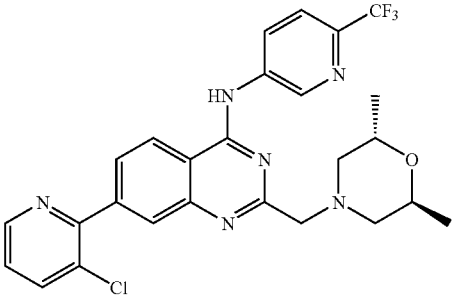 | (S,S)-[7-(3-Chloro-pyridin-2-yl)-2-(2,6-dimethyl-morpholin-4-ylmethyl)-quinazolin-4-yl]-(6-trifluoromethyl-pyridin-3-yl)-amine | 528.2 |

TABLE VI-continued

Representative Substituted 2-Aminoalkyl-quinazolin-4-ylamine Analogues

| Compound | | | MS |
|---|---|---|---|
| 380. | 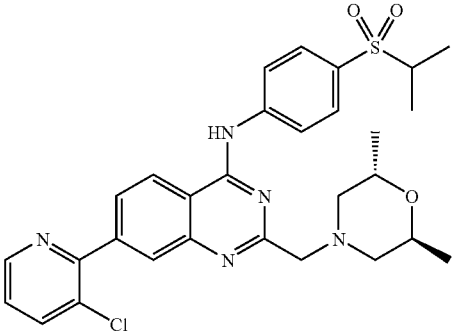 | (S,S)-[7-(3-Chloro-pyridin-2-yl)-2-(2,6-dimethyl-morpholin-4-ylmethyl)-quinazolin-4-yl]-[4-(propane-2-sulfonyl)-phenyl]-amine | 565.2 |
| 381. | 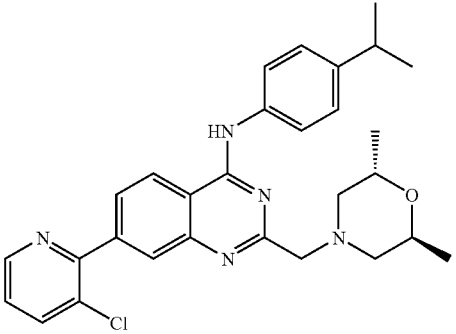 | (S,S)-[7-(3-Chloro-pyridin-2-yl)-2-(2,6-dimethyl-morpholin-4-ylmethyl)-quinazolin-4-yl]-(4-isopropyl-phenyl)-amine | 501.2 |
| 382. | 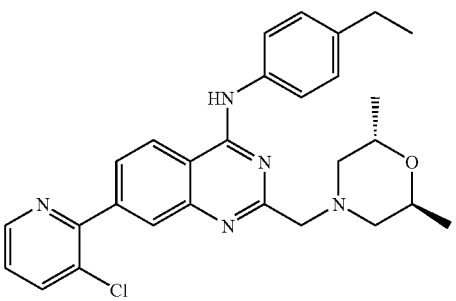 | (S,S)-[7-(3-Chloro-pyridin-2-yl)-2-(2,6-dimethyl-morpholin-4-ylmethyl)-quinazolin-4-yl]-(4-ethyl-phenyl)-amine | 487.2 |
| 383. | 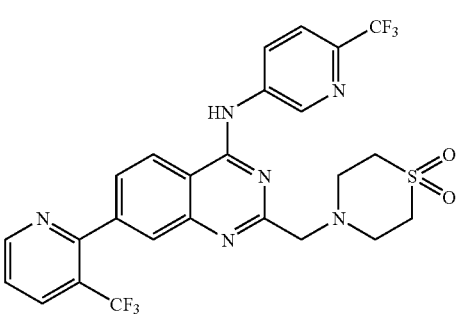 | [2-(1,1-Dioxo-1$\lambda^6$-thiomorpholin-4-ylmethyl)-7-(3-trifluoromethyl-pyridin-2-yl)-quinazolin-4-]-(6-trifluoromethyl-pyridin-3-yl)-amine | 582.1 |

TABLE VI-continued

Representative Substituted 2-Aminoalkyl-quinazolin-4-ylamine Analogues

| Compound | | | MS |
|---|---|---|---|
| 384. | 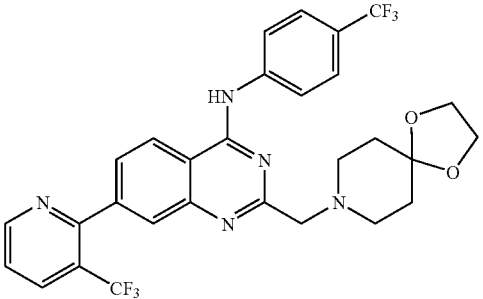 | [2-(1,4-Dioxa-8-aza-spiro[4.5]dec-8-ylmethyl)-7-(3-trifluoromethyl-pyridin-2-yl)-quinazolin-4-yl]-(4-trifluoromethyl-phenyl)-amine | 589.2 |
| 385. | 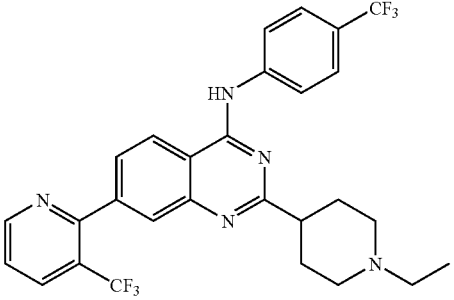 | [2-(1-Ethyl-piperidin-4-yl)-7-(3-trifluoromethyl-pyridin-2-yl)-quinazolin-4-yl]-(4-trifluoromethyl-phenyl)-amine | |
| 386. | 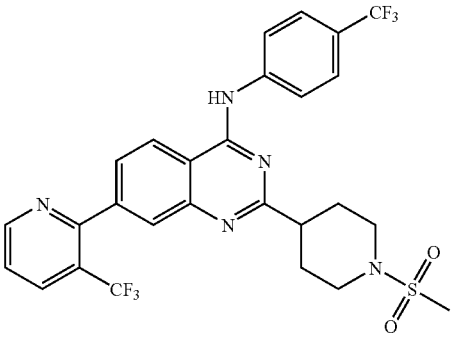 | [2-(1-Methanesulfonyl-piperidin-4-yl)-7-(3-trifluoromethyl-pyridin-2-yl)-quinazolin-4-yl]-(4-trifluoromethyl-phenyl)-amine | |
| 387. | 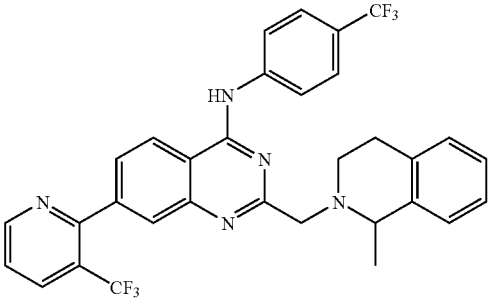 | [2-(1-Methyl-3,4-dihydro-1H-isoquinolin-2-ylmethyl)-7-(3-trifluoromethyl-pyridin-2-yl)-quinazolin-4-yl]-(4-trifluoromethyl-phenyl)-amine | 593.2 |

TABLE VI-continued

Representative Substituted 2-Aminoalkyl-quinazolin-4-ylamine Analogues

| Compound | | MS |
|---|---|---|
| 388. | [2-(1-Propyl-piperidin-4-yl)-7-(3-trifluoromethyl-pyridin-2-yl)-quinazolin-4-yl]-(4-trifluoromethyl-phenyl)-amine | |
| 389. | [2-(1-Pyridin-4-ylmethyl-piperidin-4-yl)-7-(3-trifluoromethyl-pyridin-2-yl)-quinazolin-4-yl]-(4-trifluoromethyl-phenyl)-amine | |
| 390. | [2-(2,6-Dimethyl-morpholin-4-ylmethyl)-7-(2-methoxy-phenyl)-quinazolin-4-yl]-(4-trifluoromethyl-phenyl)-amine (cis) | |
| 391. | [2-(2,6-Dimethyl-morpholin-4-ylmethyl)-7-(3-methyl-pyridin-2-yl)-pyrido[3,2-d]pyrimidin-4-yl]-(4-trifluoromethyl-phenyl)-amine (cis) | 508.2 |
| 392. | [2-(2,6-Dimethyl-morpholin-4-ylmethyl)-7-(3-methyl-pyridin-2-yl)-quinazolin-4-yl]-(4-trifluoromethyl-phenyl)-amine (cis) | 507.2 |

TABLE VI-continued

Representative Substituted 2-Aminoalkyl-quinazolin-4-ylamine Analogues

| Compound | | | MS |
|---|---|---|---|
| 393. | 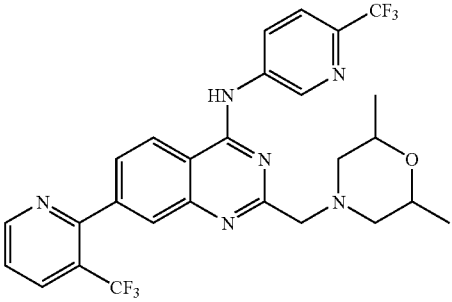 | [2-(2,6-Dimethyl-morpholin-4-ylmethyl)-7-(3-trifluoromethyl-pyridin-2-yl)-quinazolin-4-yl]-(6-trifluoromethyl-pyridin-3-yl)-amine | 562.2 |
| 394. | 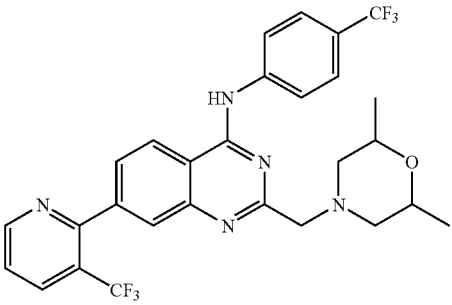 | [2-(2,6-Dimethyl-morpholin-4-ylmethyl)-7-(3-trifluoromethyl-pyridin-2-yl)-quinazolin-4-yl]-(4-trifluoromethyl-phenyl)-amine | 561.2 |
| 395. | 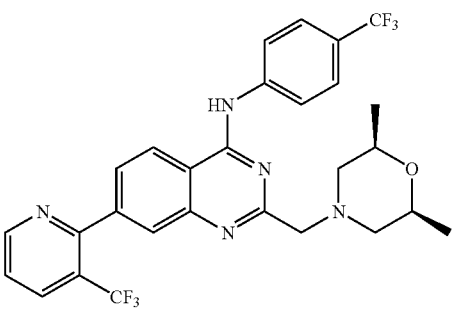 | [2-(2,6-Dimethyl-morpholin-4-ylmethyl)-7-(3-trifluoromethyl-pyridin-2-yl)-quinazolin-4-yl]-(4-trifluoromethyl-phenyl)-amine (cis) | 561.2 |
| 396. | 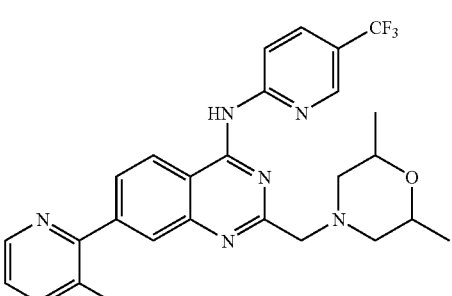 | [2-(2,6-Dimethyl-morpholin-4-ylmethyl)-7-(3-trifluoromethyl-pyridin-2-yl)-quinazolin-4-yl]-(5-trifluoromethyl-pyridin-2-yl)-amine | 562.2 |

TABLE VI-continued

Representative Substituted 2-Aminoalkyl-quinazolin-4-ylamine Analogues

| Compound | | | MS |
|---|---|---|---|
| 397. | 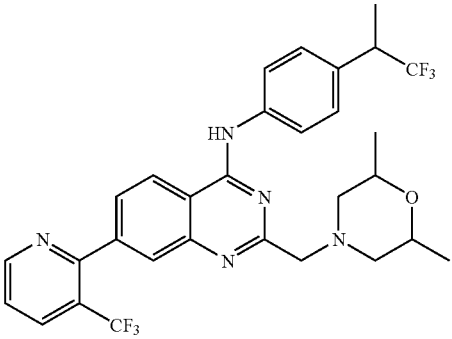 | [2-(2,6-Dimethyl-morpholin-4-ylmethyl)-7-(3-trifluoromethyl-pyridin-2-yl)-quinazolin-4-yl]-[4-(2,2,2-trifluoro-1-methyl-ethyl)-phenyl]-amine | 589.2 |
| 398. | 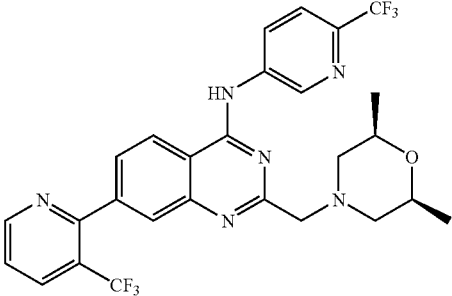 | [2-(2,6-Dimethyl-morpholin-4-ylmethyl)-7-(3-trifluoromethyl-pyridin-2-yl)-quinazolin-4-yl]-(6-trifluoromethyl-pyridin-3-yl)-amine (cis) | 562.2 |
| 399. | 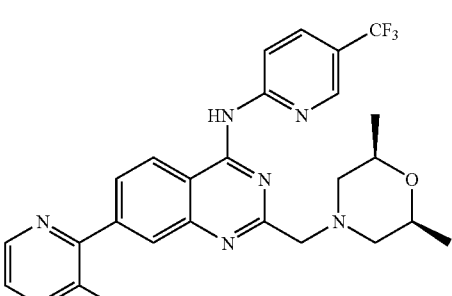 | [2-(2,6-Dimethyl-morpholin-4-ylmethyl)-7-(3-trifluoromethyl-pyridin-2-yl)-quinazolin-4-yl]-(5-trifluoromethyl-pyridin-2-yl)-amine (cis) | 562.2 |
| 400. | 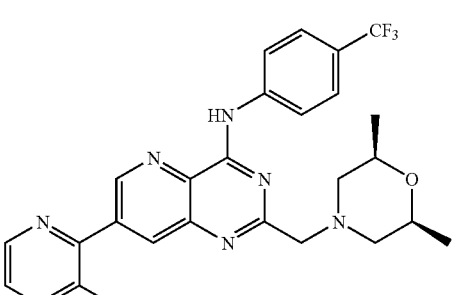 | [2-(2,6-Dimethyl-morpholin-4-ylmethyl)-7-(3-trifluoromethyl-pyridin-2-yl)-pyrido[3,2-d]pyrimidin-4-yl]-(4-trifluoromethyl-phenyl)-amine (cis) | 562.2 |

TABLE VI-continued

Representative Substituted 2-Aminoalkyl-quinazolin-4-ylamine Analogues

| Compound | | MS |
|---|---|---|
| 401. | [2-(2,6-Dimethyl-morpholin-4-ylmethyl)-7-(3-trifluoromethyl-pyridin-2-yl)-pyrido[3,2-d]pyrimidin-4-yl]-(6-trifluoromethyl-pyridin-3-yl)-amine (cis) | 563.2 |
| 402. | [2-(2,6-Dimethyl-morpholin-4-ylmethyl)-7-(3-trifluoromethyl-pyridin-2-yl)-quinazolin-4-yl]-(4-trifluoromethanesulfonyl-phenyl)-amine | 625.2 |
| 403. | [2-(2,6-Dimethyl-morpholin-4-ylmethyl)-7-(3-trifluoromethyl-pyridin-2-yl)-quinazolin-4-yl]-(4-trifluoromethanesulfonyl-phenyl)-amine (cis) | 625.2 |
| 404. | [2-(2,6-Dimethyl-morpholin-4-ylmethyl)-7-(3-trifluoromethyl-pyridin-2-yl)-pyrido[3,2-d]pyrimidin-4-yl]-(4-methanesulfonyl-phenyl)-amine (cis) | 572.2 |

TABLE VI-continued

Representative Substituted 2-Aminoalkyl-quinazolin-4-ylamine Analogues

| Compound | | | MS |
|---|---|---|---|
| 405. | 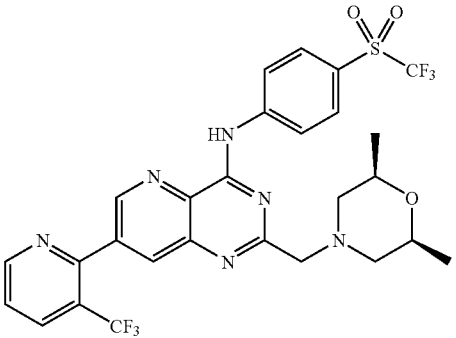 | [2-(2,6-Dimethyl-morpholin-4-ylmethyl)-7-(3-trifluoromethyl-pyridin-2-yl)-pyrido[3,2-d]pyrimidin-4-yl]-(4-trifluoromethanesulfonyl-phenyl)-amine (cis) | |
| 406. | 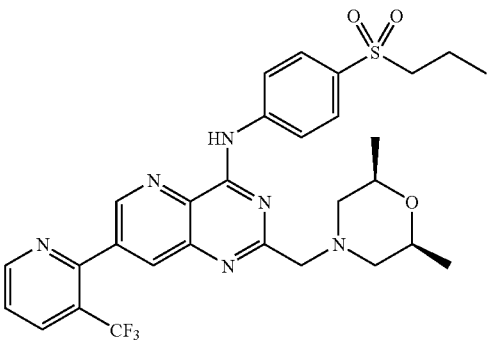 | [2-(2,6-Dimethyl-morpholin-4-ylmethyl)-7-(3-trifluoromethyl-pyridin-2-yl)-pyrido[3,2-d]pyrimidin-4-yl]-[4-(propane-1-sulfonyl)-phenyl]-amine (cis) | 600.2 |
| 407. | 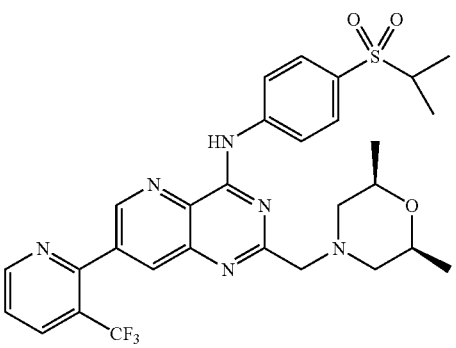 | [2-(2,6-Dimethyl-morpholin-4-ylmethyl)-7-(3-trifluoromethyl-pyridin-2-yl)-pyrido[3,2-d]pyrimidin-4-yl]-[4-(propane-2-sulfonyl)-phenyl]-amine (cis) | 600.2 |
| 408. | 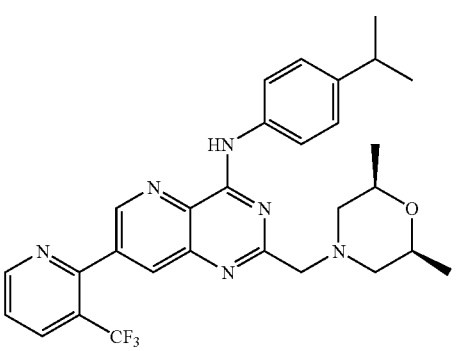 | [2-(2,6-Dimethyl-morpholin-4-ylmethyl)-7-(3-trifluoromethyl-pyridin-2-yl)-pyrido[3,2-d]pyrimidin-4-yl]-(4-isopropyl-phenyl)-amine (cis) | 536.3 |

TABLE VI-continued

Representative Substituted 2-Aminoalkyl-quinazolin-4-ylamine Analogues

| Compound | | MS |
|---|---|---|
| 409. | [2-(2,6-Dimethyl-morpholin-4-ylmethyl)-7-(3-trifluoromethyl-pyridin-2-yl)-pyrido[3,2-d]pyrimidin-isopropyl-phenyl)-amine (cis) | |
| 410. | [2-(2,6-Dimethyl-morpholin-4-ylmethyl)-7-pyridin-2-yl-quinazolin-4-yl]-(4-trifluoromethyl-phenyl)-amine (cis) | 493.2 |
| 411. | [2-(2-Ethyl-piperidin-1-ylethyl)-7-(3-trifluoromethyl-pyridin-2-yl)-quinazolin-4-yl]-(4-trifluoromethyl-phenyl)-amine | 573.2 |
| 412. | [2-(2-Ethyl-piperidin-1-ylmethyl)-7-(3-trifluoromethyl-pyridin-2-yl)-quinazolin-4-yl]-(4-trifluoromethyl-phenyl)-amine | 559.2 |

TABLE VI-continued

Representative Substituted 2-Aminoalkyl-quinazolin-4-ylamine Analogues

| Compound | | | MS |
|---|---|---|---|
| 413. | 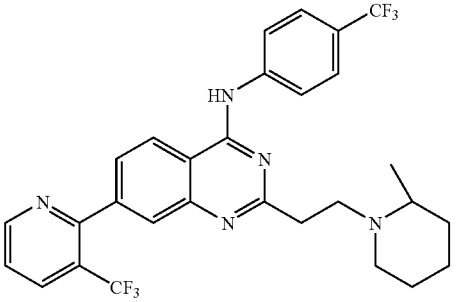 | [2-(2-Methyl-piperidin-1-ylethyl)-7-(3-trifluoromethyl-pyridin-2-yl)-quinazolin-4-yl]-(4-trifluoromethyl-phenyl)-amine | 559.2 |
| 414. | 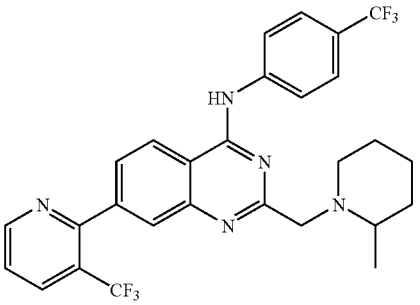 | [2-(2-Methyl-piperidin-1-ylmethyl)-7-(3-trifluoromethyl-pyridin-2-yl)-quinazolin-4-yl]-(4-trifluoromethyl-phenyl)-amine | 545.2 |
| 415. | 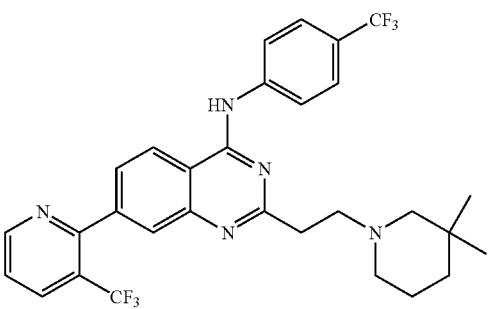 | [2-(3,3-Dimethyl-piperidin-1-ylethyl)-7-(3-trifluoromethyl-pyridin-2-yl)-quinazolin-4-yl]-(4-trifluoromethyl-phenyl)-amine | 573.2 |
| 416. | 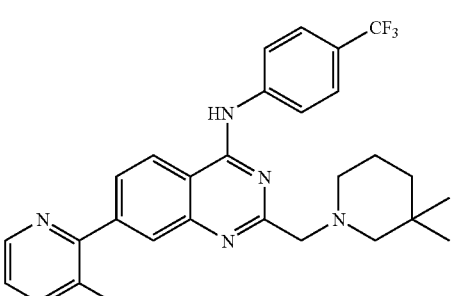 | [2-(3,3-Dimethyl-piperidin-1-ylmethyl)-7-(3-trifluoromethyl-pyridin-2-yl)-quinazolin-4-yl]-(4-trifluoromethyl-phenyl)-amine | 559.2 |

TABLE VI-continued

Representative Substituted 2-Aminoalkyl-quinazolin-4-ylamine Analogues

| Compound | | | MS |
|---|---|---|---|
| 417. | 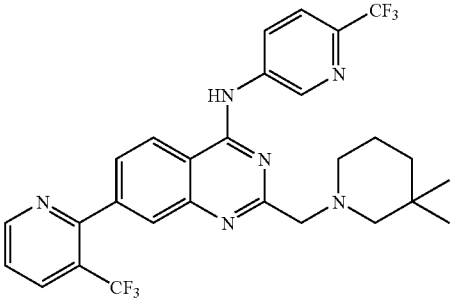 | [2-(3,3-Dimethyl-piperidin-1-ylmethyl)-7-(3-trifluoromethyl-pyridin-2-yl)-quinazolin-4-yl]-(6-trifluoromethyl-pyridin-3-yl)-amine | 560.2 |
| 418. | 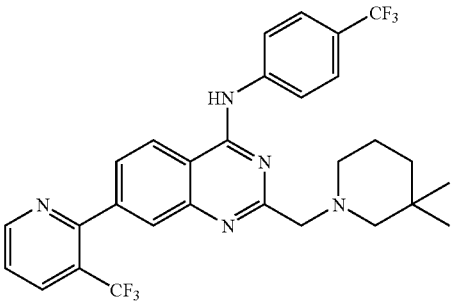 | [2-(3,3-Dimethyl-piperidin-1-ylmethyl)-7-(3-trifluoromethyl-pyridin-2-yl)-quinazolin-4-yl]-(4-trifluoromethyl-phenyl)-amine | 559.2 |
| 419. | 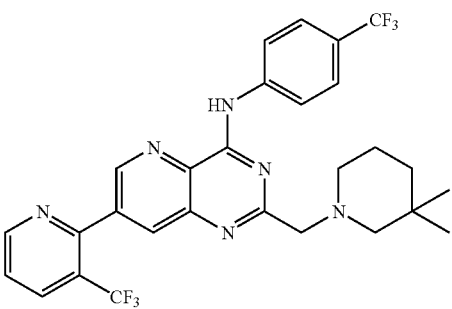 | [2-(3,3-Dimethyl-piperidin-1-ylmethyl)-7-(3-trifluoromethyl-pyridin-2-yl)-pyrido[3,2-d]pyrimidin-4-yl]-(4-trifluoromethyl-phenyl)-amine | 560.2 |
| 420. | 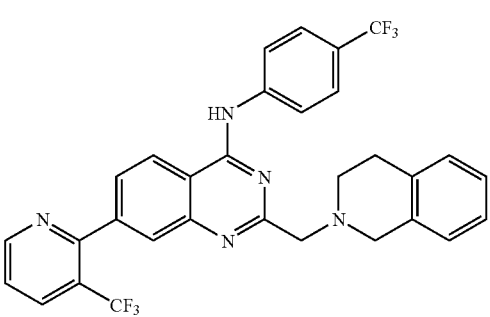 | [2-(3,4-Dihydro-1H-isoquinolin-2-ylmethyl)-7-(3-trifluoromethyl-pyridin-2-yl)-quinazolin-4-yl]-(4-trifluoromethyl-phenyl)-amine | 579.2 |

TABLE VI-continued

Representative Substituted 2-Aminoalkyl-quinazolin-4-ylamine Analogues

| Compound | | | MS |
|---|---|---|---|
| 421. | 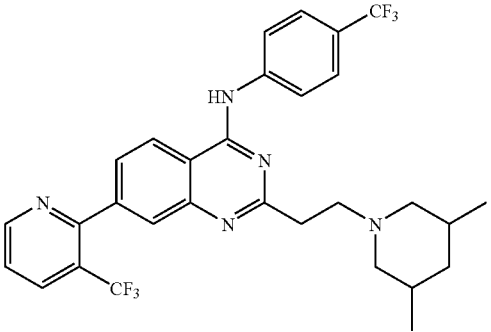 | [2-(3,5-Dimethyl-piperidin-1-ylethyl)-7-(3-trifluoromethyl-pyridin-2-yl)-quinazolin-4-yl]-(4-trifluoromethyl-phenyl)-amine | 573.2 |
| 422. | 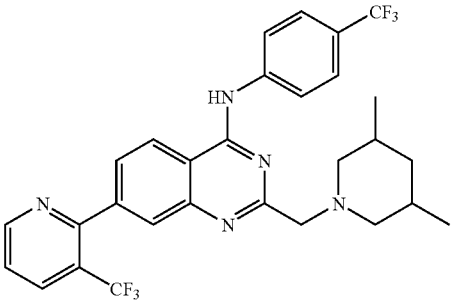 | [2-(3,5-Dimethyl-piperidin-1-ylmethyl)-7-(3-trifluoromethyl-pyridin-2-yl)-quinazolin-4-yl]-(4-trifluoromethyl-phenyl)-amine | 559.2 |
| 423. | 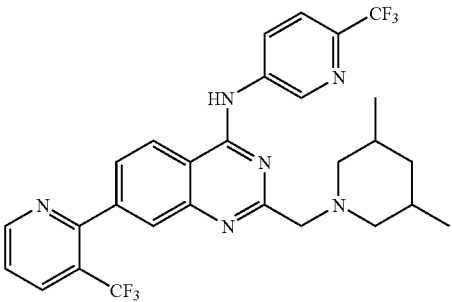 | [2-(3,5-Dimethyl-piperidin-1-ylmethyl)-7-(3-trifluoromethyl-pyridin-2-yl)-quinazolin-4-yl]-(6-trifluoromethyl-pyridin-3-yl)-amine | 560.2 |
| 424. | 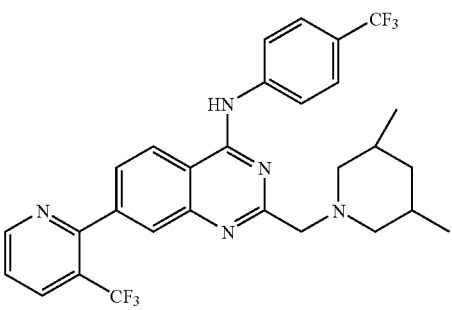 | [2-(3,5-Dimethyl-piperidin-1-ylmethyl)-7-(3-trifluoromethyl-pyridin-2-yl)-quinazolin-4-yl]-(4-trifluoromethyl-phenyl)-amine | 559.2 |

TABLE VI-continued

Representative Substituted 2-Aminoalkyl-quinazolin-4-ylamine Analogues

| Compound | | | MS |
|---|---|---|---|
| 425. | | [2-(3,5-Dimethyl-piperidin-1-ylmethyl)-7-(3-trifluoromethyl-pyridin-2-yl)-pyrido[3,2-d]pyrimidin-4-yl]-(4-trifluoromethyl-phenyl)-amine (cis) | 560.2 |
| 426. | | [2-(3-Hydroxy-piperidin-1-ylethyl)-7-(3-trifluoromethyl-pyridin-2-yl)-quinazolin-4-yl]-(4-trifluoromethyl-phenyl)-amine | 561.2 |
| 427. | | [2-(3-Methoxy-piperidin-1-ylethyl)-7-(3-trifluoromethyl-pyridin-2-yl)-quinazolin-4-yl]-(4-trifluoromethyl-phenyl)-amine | 575.2 |
| 428. | | [2-(3-Methyl-piperidin-1-ylethyl)-7-(3-trifluoromethyl-pyridin-2-yl)-quinazolin-4-yl]-(4-trifluoromethyl-phenyl)-amine | 559.2 |

TABLE VI-continued

Representative Substituted 2-Aminoalkyl-quinazolin-4-ylamine Analogues

| Compound | | | MS |
|---|---|---|---|
| 429. | 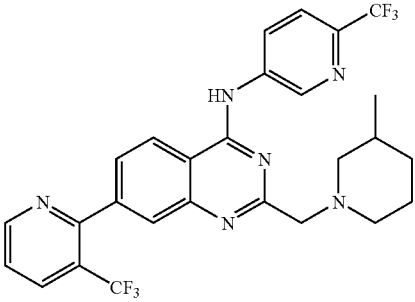 | [2-(3-Methyl-piperidin-1-ylmethyl)-7-(3-trifluoromethyl-pyridin-2-yl)-quinazolin-4-yl]-(6-trifluoromethyl-pyridin-3-yl)-amine | 546.2 |
| 430. | 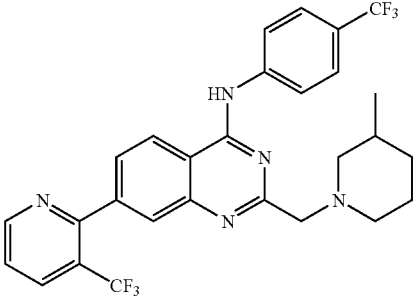 | [2-(3-Methyl-piperidin-1-ylmethyl)-7-(3-trifluoromethyl-pyridin-2-yl)-quinazolin-4-yl]-(4-trifluoromethyl-phenyl)-amine | 545.2 |
| 431. | 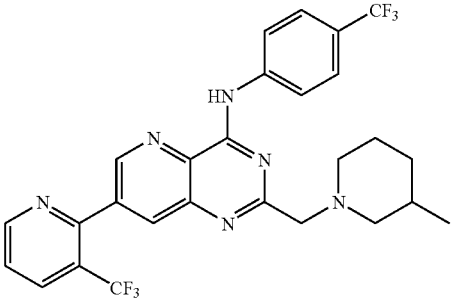 | [2-(3-Methyl-piperidin-1-ylmethyl)-7-(3-trifluoromethyl-pyridin-2-yl)-pyrido[3,2-d]pyrimidin-4-yl]-(4-trifluoromethyl-phenyl)-amine | 546.2 |
| 432. | 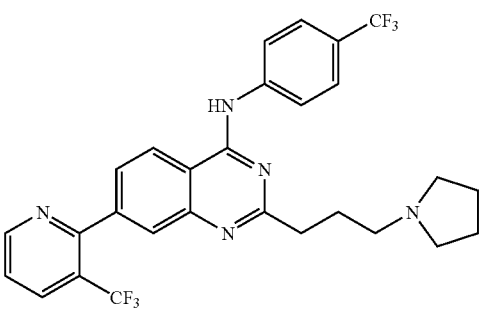 | [2-(3-Pyrrolidin-1-yl-propyl)-7-(3-trifluoromethyl-pyridin-2-yl)-quinazolin-4-yl]-(4-trifluoromethyl-phenyl)-amine | 545.2 |

TABLE VI-continued

Representative Substituted 2-Aminoalkyl-quinazolin-4-ylamine Analogues

| Compound | | | MS |
|---|---|---|---|
| 433. | 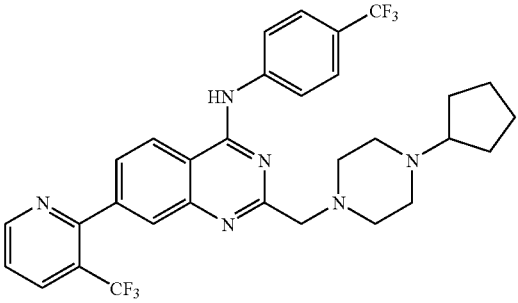 | [2-(4-Cyclopentyl-piperazin-1-ylmethyl)-7-(3-trifluoromethyl-pyridin-2-yl)-quinazolin-4-yl]-(4-trifluoromethyl-phenyl)-amine | 600.2 |
| 434. | 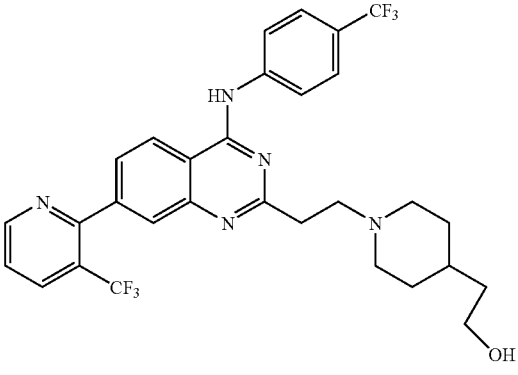 | [2-(4-Ethoxy-piperidin-1-ylethyl)-7-(3-trifluoromethyl-pyridin-2-yl)-quinazolin-4-yl]-(4-trifluoromethyl-phenyl)-amine | 589.2 |
| 435. | 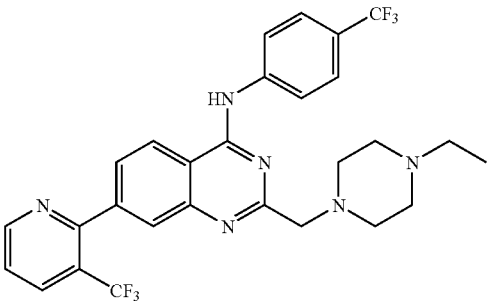 | [2-(4-Ethyl-piperazin-1-ylmethyl)-7-(3-trifluoromethyl-pyridin-2-yl)-quinazolin-4-ylI -(4-trifluoromethyl-phenyl)-amine | 560.2 |
| 436. | 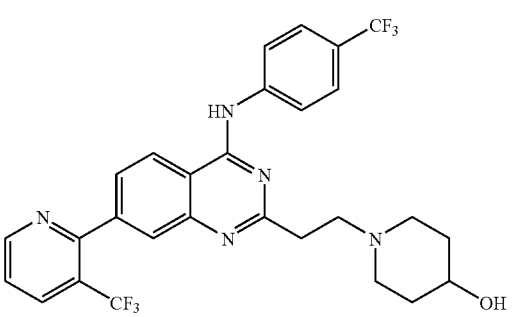 | [2-(4-Hydroxy-piperidin-1-ylethyl)-7-(3-trifluoromethyl-pyridin-2-yl)-quinazolin-4-yl]-(4-trifluoromethyl-phenyl)-amine | 561.2 |

TABLE VI-continued

Representative Substituted 2-Aminoalkyl-quinazolin-4-ylamine Analogues

| Compound | | MS |
|---|---|---|
| 437. | [2-(4-Isopropyl-piperazin-1-ylmethyl)-7-(3-trifluoromethyl-pyridin-2-yl)-quinazolin-4-yl]-(4-trifluoromethyl-phenyl)-amine | 574.2 |
| 438. | [2-(4-Methoxy-piperidin-1-ylethyl)-7-(3-trifluoromethyl-pyridin-2-yl)-quinazolin-4-yl]-(4-trifluoromethyl-phenyl)-amine | 575.2 |
| 439. | [2-(4-Methyl-[1,4]diazepan-1-ylmethyl)-7-(3-trifluoromethyl-pyridin-2-yl)-quinazolin-4-yl]-(4-trifluoromethyl-phenyl)-amine | |
| 440. | [2-(4-Methyl-piperazin-1-ylmethyl)-7-(3-trifluoromethyl-pyridin-2-yl)-quinazolin-4-yl]-(5-trifluoromethyl-pyridin-2-yl)-amine | 547.2 |

TABLE VI-continued

Representative Substituted 2-Aminoalkyl-quinazolin-4-ylamine Analogues

| Compound | | | MS |
|---|---|---|---|
| 441. | 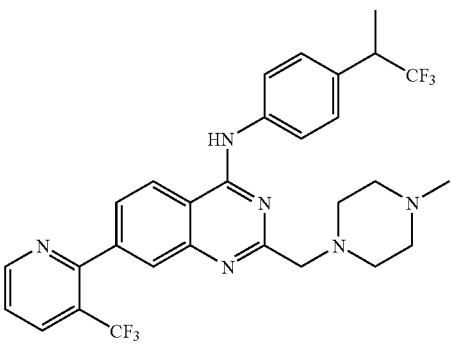 | [2-(4-Methyl-piperazin-1-ylmethyl)-7-(3-trifluoromethyl-pyridin-2-yl)-quinazolin-4-yl]-[4-(2,2,2-trifluoro-1-methyl-ethyl)-phenyl]-amine | 574.2 |
| 442. | 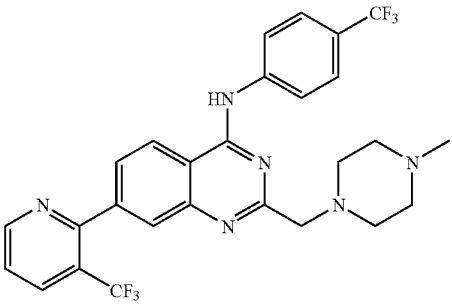 | [2-(4-Methyl-piperazin-1-ylmethyl)-7-(3-trifluoromethyl-pyridin-2-yl)-quinazolin-4-yl]-(4-trifluoromethyl-phenyl)-amine | 546.2 |
| 443. | 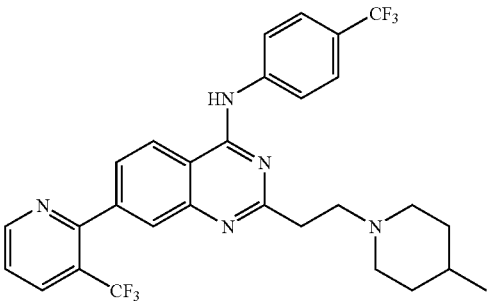 | [2-(4-Methyl-piperidin-1-ylethyl)-7-(3-trifluoromethyl-pyridin-2-yl)-quinazolin-4-yl]-(4-trifluoromethyl-phenyl)-amine | 559.2 |
| 444. | 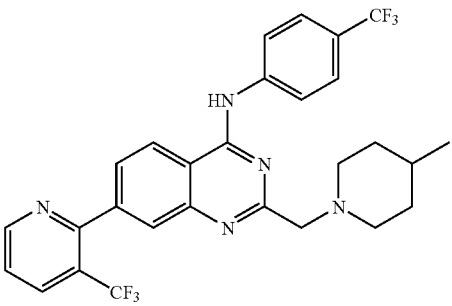 | [2-(4-Methyl-piperidin-1-ylmethyl)-7-(3-trifluoromethyl-pyridin-2-yl)-quinazolin-4-yl]-(4-trifluoromethyl-phenyl)-amine | 545.2 |

TABLE VI-continued

Representative Substituted 2-Aminoalkyl-quinazolin-4-ylamine Analogues

| Compound | | | MS |
|---|---|---|---|
| 445. | 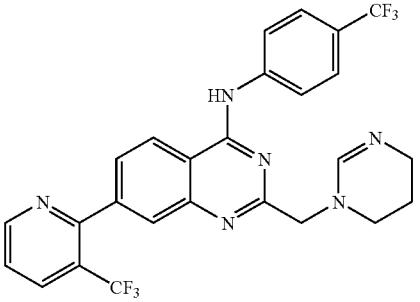 | [2-(5,6-Dihydro-4H-pyrimidin-1-ylmethyl)-7-(3-trifluoromethyl-pyridin-2-yl)-quinazolin-4-yl]-(4-trifluoromethyl-phenyl)-amine | 530.2 |
| 446. | 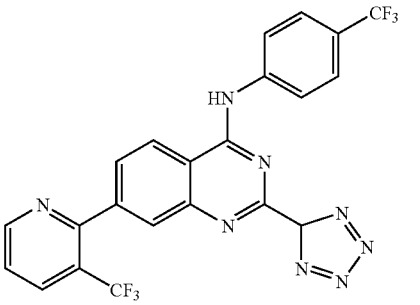 | [2-(5H-Tetrazol-5-yl)-7-(3-trifluoromethyl-pyridin-2-yl)-quinazolin-4-yl]-(4-trifluoromethyl-phenyl)-amine | 502.1 |
| 447. | 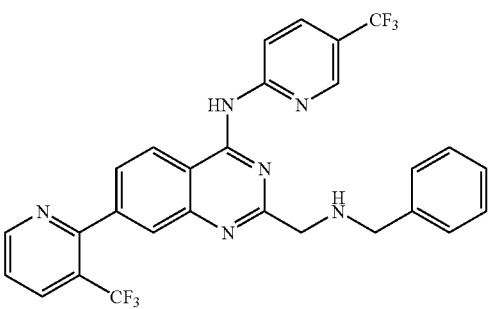 | [2-(Benzylamino-methyl)-7-(3-trifluoromethyl-pyridin-2-yl)-quinazolin-4-yl]-(5-trifluoromethyl-pyridin-2-yl)-amine | 554.2 |
| 448. | 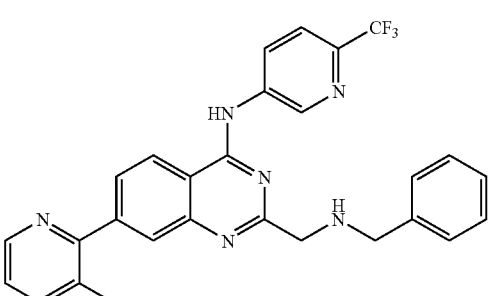 | [2-(Benzylamino-methyl)-7-(3-trifluoromethyl-pyridin-2-yl)-quinazolin-4-yl]-(6-trifluoromethyl-pyridin-3-yl)-amine | 554.2 |

TABLE VI-continued

Representative Substituted 2-Aminoalkyl-quinazolin-4-ylamine Analogues

| Compound | | | MS |
|---|---|---|---|
| 449. | 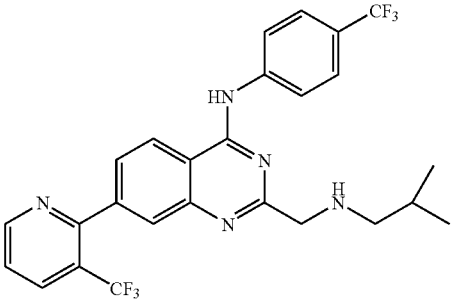 | [2-(Isobutylamino-methyl)-7-(3-trifluoromethyl-pyridin-2-yl)-quinazolin-4-yl]-(4-trifluoromethyl-phenyl)-amine | 519.2 |
| 450. | 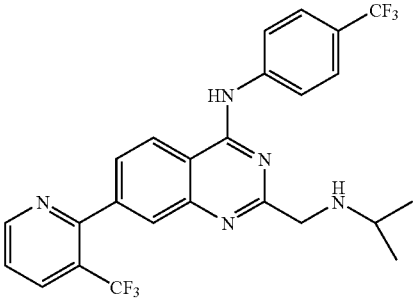 | [2-(Isopropylamino-methyl)-7-(3-trifluoromethyl-pyridin-2-yl)-quinazolin-4-yl]-(4-trifluoromethyl-phenyl)-amine | 505.2 |
| 451. | 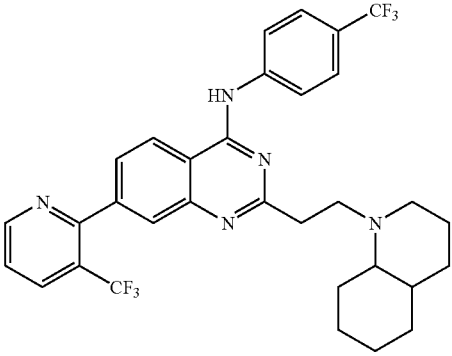 | [2-(Octahydro-quinolin-1-ylethyl)-7-(3-trifluoromethyl-pyridin-2-yl)-quinazolin-4-yl]-(4-trifluoromethyl-phenyl)-amine | 599.2 |
| 452. | 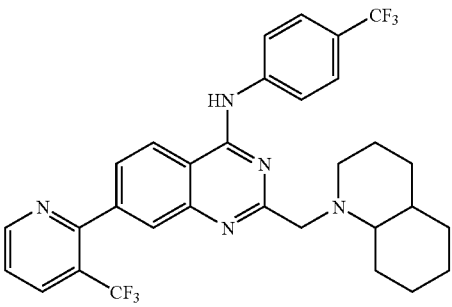 | [2-(Octahydro-quinolin-1-ylmethyl)-7-(3-trifluoromethyl-pyridin-2-yl)-quinazolin-4-yl]-(4-trifluoromethyl-phenyl)-amine | 585.2 |

TABLE VI-continued

Representative Substituted 2-Aminoalkyl-quinazolin-4-ylamine Analogues

| Compound | | | MS |
|---|---|---|---|
| 453. | 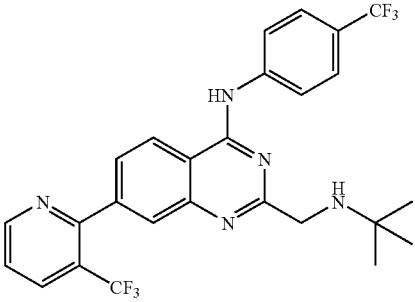 | [2-(tert-Butylamino-methyl)-7-(3-trifluoromethyl-pyridin-2-yl)-quinazolin-4-yl]-(4-trifluoromethyl-phenyl)-amine | 519.2 |
| 454. | 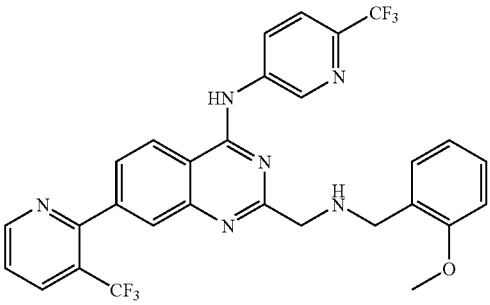 | [2-[(2-Methoxy-benzylamino)-methyl]-7-(3-trifluoromethyl-pyridin-2-yl)-quinazolin-4-yl]-(6-trifluoromethyl-pyridin-3-yl)-amine | 584.2 |
| 455. | 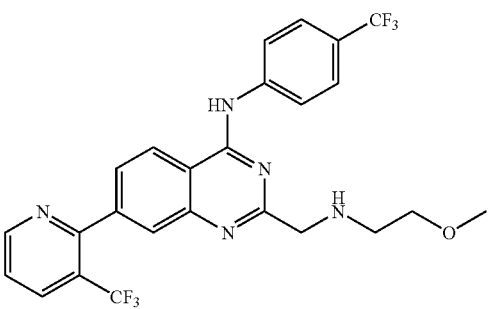 | [2-[(2-Methoxy-ethylamino)-methyl]-7-(3-trifluoromethyl-pyridin-2-yl)-quinazolin-4-yl]-(4-trifluoromethyl-phenyl)-amine | 521.2 |
| 456. | 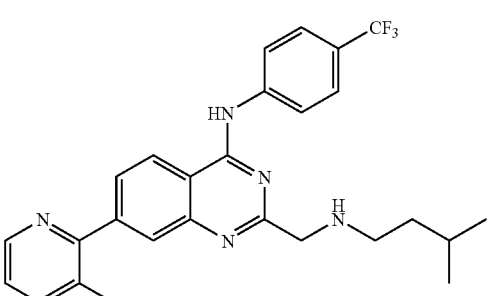 | [2-[(3-Methyl-butylamino)-methyl]-7-(3-trifluoromethyl-pyridin-2-yl)-quinazolin-4-yl]-(4-trifluoromethyl-phenyl)-amine | 533.2 |

TABLE VI-continued

Representative Substituted 2-Aminoalkyl-quinazolin-4-ylamine Analogues

| Compound | | | MS |
|---|---|---|---|
| 457. | 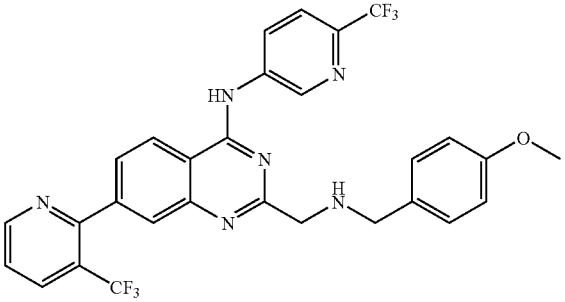 | [2-[(4-Methoxy-benzylamino)-methyl]-7-(3-trifluoromethyl-pyridin-2-yl)-quinazolin-4-yl]-(6-trifluoromethyl-pyridin-3-yl)-amine | 584.2 |
| 458. | 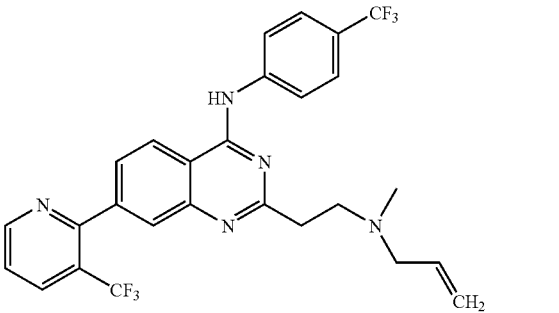 | [2-[(Allyl-methyl-amino)-ethyl]-7-(3-trifluoromethyl-pyridin-2-yl)-quinazolin-4-yl]-(4-trifluoromethyl-phenyl)-amine | 531.2 |
| 459. | 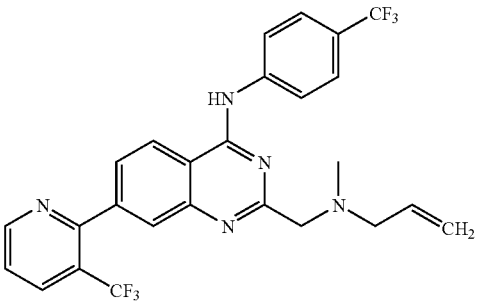 | [2-[(Allyl-methyl-amino)-methyl]-7-(3-trifluoromethyl-pyridin-2-yl)-quinazolin-4-yl]-(4-trifluoromethyl-phenyl)-amine | 517.2 |
| 460. | 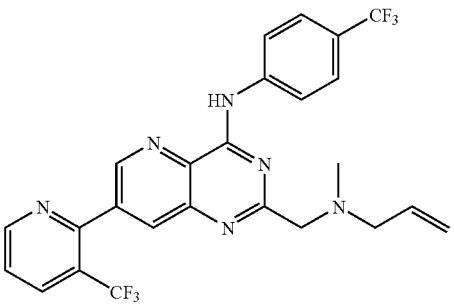 | [2-[(Allyl-methyl-amino)-methyl]-7-(3-trifluoromethyl-pyridin-2-yl)-pyrido[3,2-d]pyrimidin-4-yl]-(4-trifluoromethyl-phenyl)-amine | 518.2 |

TABLE VI-continued

Representative Substituted 2-Aminoalkyl-quinazolin-4-ylamine Analogues

| Compound | | | MS |
|---|---|---|---|
| 461. | 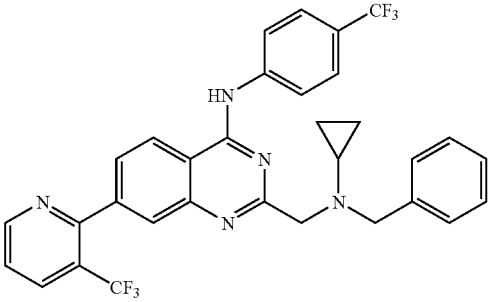 | [2-[(Benzyl-cyclopropyl-amino)-methyl]-7-(3-trifluoromethyl-pyridin-2-yl)-quinazolin-4-yl]-(4-trifluoromethyl-phenyl)-amine | 593.2 |
| 462. | 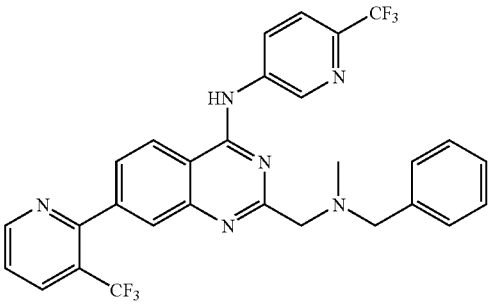 | [2-[(Benzyl-methyl-amino)-methyl]-7-(3-trifluoromethyl-pyridin-2-yl)-quinazolin-4-yl]-(6-trifluoromethyl-pyridin-3-yl)-amine | 568.2 |
| 463. | 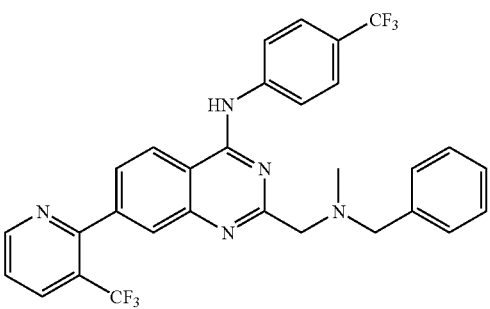 | [2-[(Benzyl-methyl-amino)-methyl]-7-(3-trifluoromethyl-pyridin-2-yl)-quinazolin-4-yl]-(4-trifluoromethyl-phenyl)-amine | 567.2 |
| 464. | 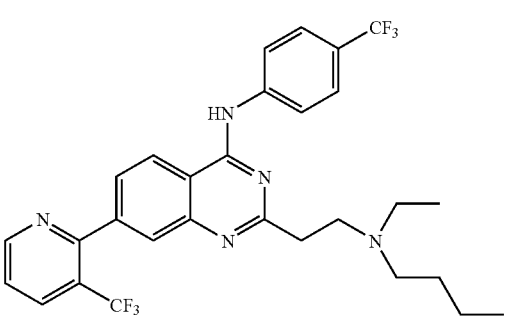 | [2-[(Butyl-ethyl-amino)-ethyl]-7-(3-trifluoromethyl-pyridin-2-yl)-quinazolin-4-yl]-(4-trifluoromethyl-phenyl)-amine | 561.2 |

TABLE VI-continued

Representative Substituted 2-Aminoalkyl-quinazolin-4-ylamine Analogues

| Compound | | | MS |
|---|---|---|---|
| 465. | 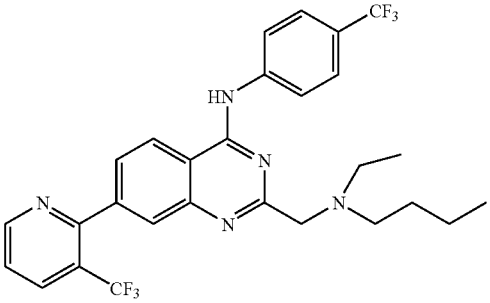 | [2-[(Butyl-ethyl-amino)-methyl]-7-(3-trifluoromethyl-pyridin-2-yl)-quinazolin-4-yl]-(4-trifluoromethyl-phenyl)-amine | 547.2 |
| 466. | 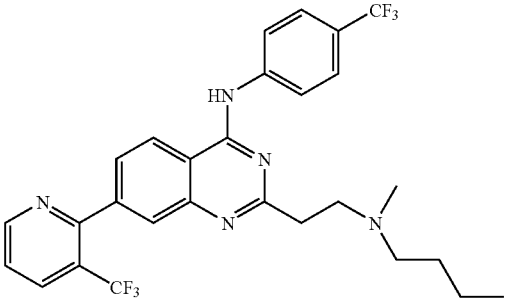 | [2-[(Butyl-methyl-amino)-ethyl]-7-(3-trifluoromethyl-pyridin-2-yl)-quinazolin-4-yl]-(4-trifluoromethyl-phenyl)-amine | 547.2 |
| 467. | 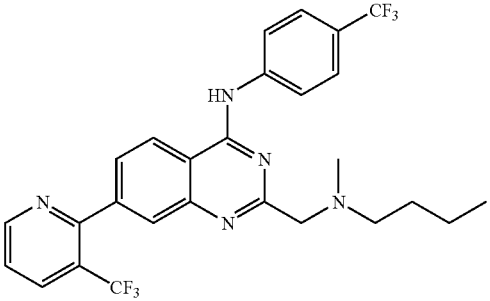 | [2-[(Butyl-methyl-amino)-methyl]-7-(3-trifluoromethyl-pyridin-2-yl)-quinazolin-4-yl]-(4-trifluoromethyl-phenyl)-amine | 533.2 |
| 468. | 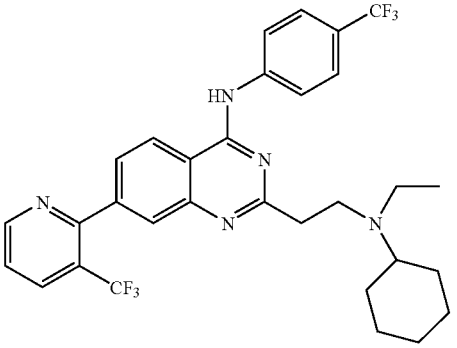 | [2-[(Cyclohexyl-ethyl-amino)-ethyl]-7-(3-trifluoromethyl-pyridin-2-yl)-quinazolin-4-yl]-(4-trifluoromethyl-phenyl)-amine | 587.2 |

TABLE VI-continued

Representative Substituted 2-Aminoalkyl-quinazolin-4-ylamine Analogues

| Compound | | MS |
|---|---|---|
| 469. 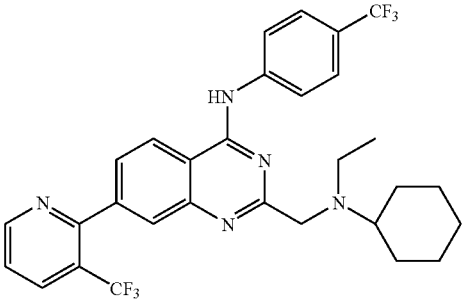 | [2-[(Cyclohexyl-ethyl-amino)-methyl]-7-(3-trifluoromethyl-pyridin-2-yl)-quinazolin-4-yl]-(4-trifluoromethyl-phenyl)-amine | 573.2 |
| 470. 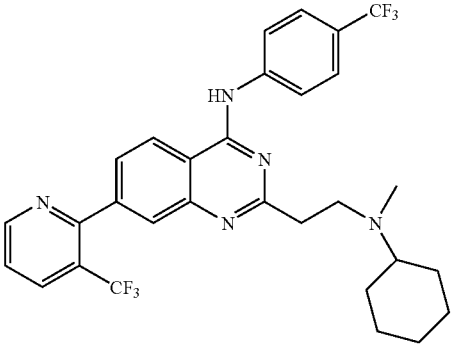 | [2-[(Cyclohexyl-methyl-amino)-ethyl]-7-(3-trifluoromethyl-pyridin-2-yl)-quinazolin-4-yl]-(4-trifluoromethyl-phenyl)-amine | 573.2 |
| 471. 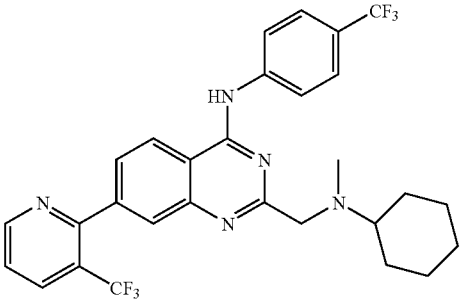 | [2-[(Cyclohexyl-methyl-amino)-methyl]-7-(3-trifluoromethyl-pyridin-2-yl)-quinazolin-4-yl]-(4-trifluoromethyl-phenyl)-amine | 559.2 |
| 472. 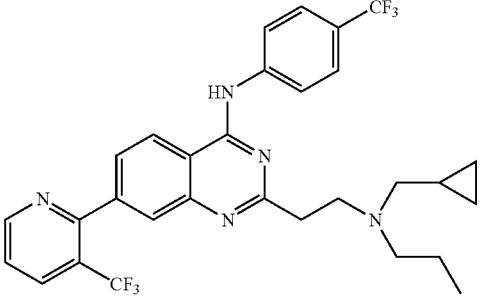 | [2-[(Cyclopropylmethyl-propyl-amino)-ethyl]-7-(3-trifluoromethyl-pridin-2-yl)-quinazolin-4-yl]-(4-trifluoromethyl-phenyl)-amine | 573.2 |

TABLE VI-continued

Representative Substituted 2-Aminoalkyl-quinazolin-4-ylamine Analogues

| Compound | | | MS |
|---|---|---|---|
| 473. | 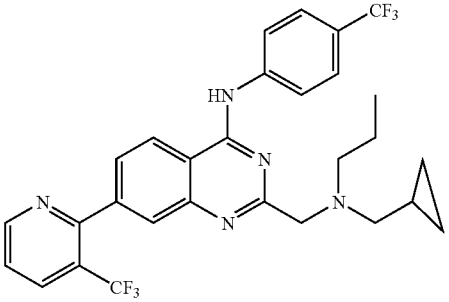 | [2-[(Cyclopropylmethyl-propyl-amino)-methyl]-7-(3-trifluoromethyl-pyridin-2-yl)-quinazohn-4-yl]-(4-trifluoromethyl-phenyl)-amine | 559.2 |
| 474. | 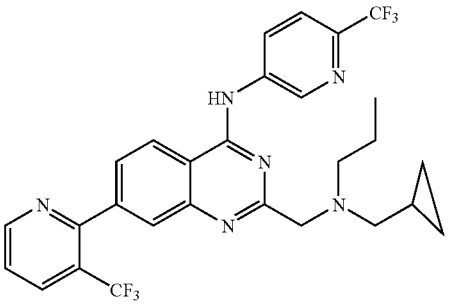 | [2-[(Cyclopropylmethyl-propyl-amino)-methyl]-7-(3-trifluoromethyl-pyridin-2-yl)-quinazolin-4-yl]-(6-trifluoromethyl-pyridin-3-yl)-amine | 560.2 |
| 475. | 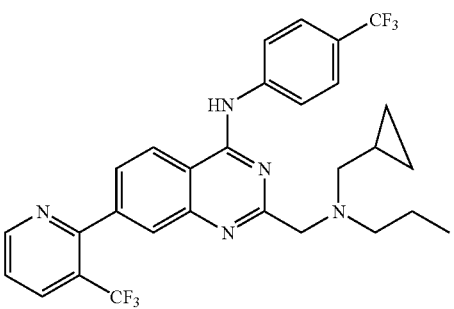 | [2-[(Cyclopropylmethyl-propyl-amino)-methyl]-7-(3-trifluoromethyl-pyridin-2-yl)-quinazolin-4-yl]-(4-trifluoromethyl-phenyl)-amine | 559.2 |
| 476. | 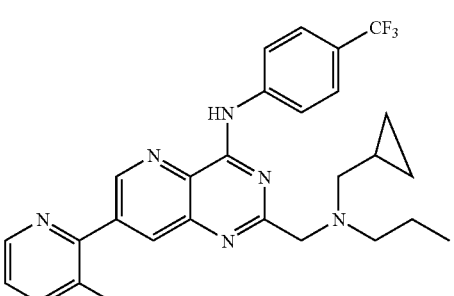 | [2-[(Cyclopropylmethyl-propyl-amino)-methyl]-7-(3-trifluoromethyl-pyridin-2-yl)-pyrido[3,2-d]pyrimidin-4-yl]-(4-trifluoromethyl-phenyl)-amine | 560.2 |

TABLE VI-continued

Representative Substituted 2-Aminoalkyl-quinazolin-4-ylamine Analogues

| Compound | | MS |
|---|---|---|
| 477. 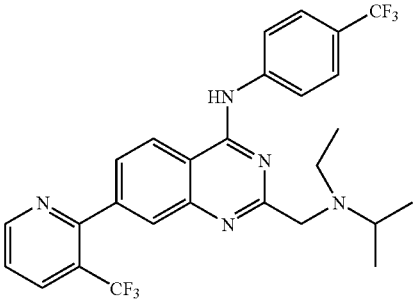 | [2-[(Ethyl-isopropyl-amino)-methyl]-7-(3-trifluoromethyl-pyridin-2-yl)-quinazolin-4-yl]-(4-trifluoromethyl-phenyl)-amine | 533.2 |
| 478. 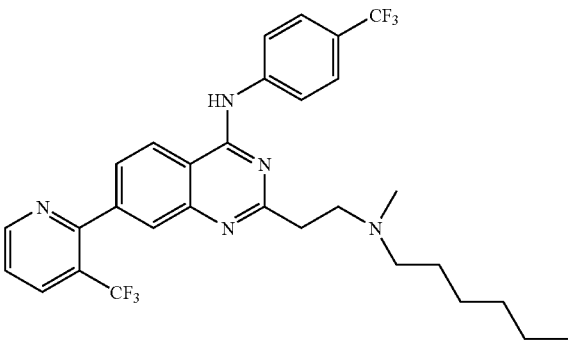 | [2-[(Hexyl-methyl-amino)-ethyl]-7-(3-trifluoromethyl-pyridin-2-yl)-quinazolin-4-yl]-(4-trifluoromethyl-phenyl)-amine | 575.2 |
| 479. 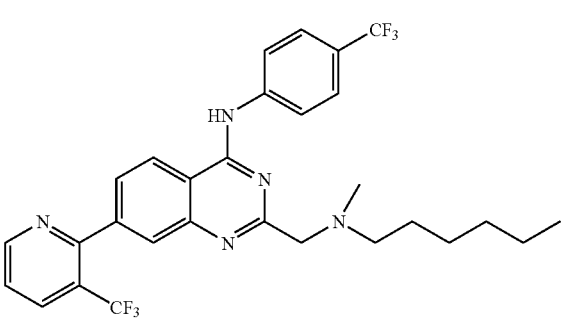 | [2-[(Hexyl-methyl-amino)-methyl]-7-(3-trifluoromethyl-pyridin-2-yl)-quinazolin-4-yl]-(4-trifluoromethyl-phenyl)-amine | 561.2 |
| 480. 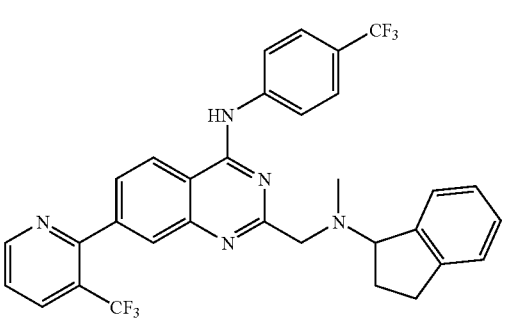 | [2-[(Indan-1-yl-methyl-amino)-methyl]-7-(3-trifluoromethyl-pyridin-2-yl)-quinazolin-4-yl]-(4-trifluoromethyl-phenyl)-amine | 593.2 |

TABLE VI-continued

Representative Substituted 2-Aminoalkyl-quinazolin-4-ylamine Analogues

| Compound | | | MS |
|---|---|---|---|
| 481. | 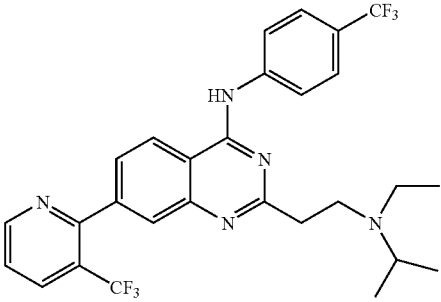 | [2-[(Isopropyl-ethyl-amino)-ethyl]-7-(3-trifluoromethyl-pyridin-2-yl)-quinazolin-4-yl]-(4-trifluoromethyl-phenyl)-amine | 547.2 |
| 482. | 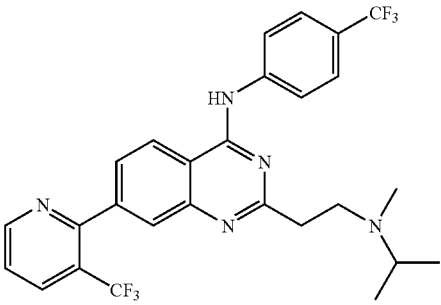 | [2-[(Isopropyl-methyl-amino)-ethyl]-7-(3-trifluoromethyl-pyridin-2-yl)-quinazolin-4-yl]-(4-trifluoromethyl-phenyl)-amine | 533.2 |
| 483. | 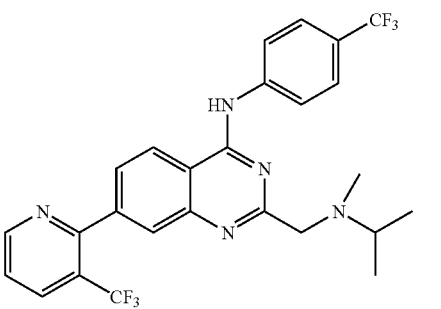 | [2-[(Isopropyl-methyl-amino)-methyl]-7-(3-trifluoromethyl-pyridin-2-yl)-quinazolin-4-yl]-(4-trifluoromethyl-phenyl)-amine | 519.2 |
| 484. | 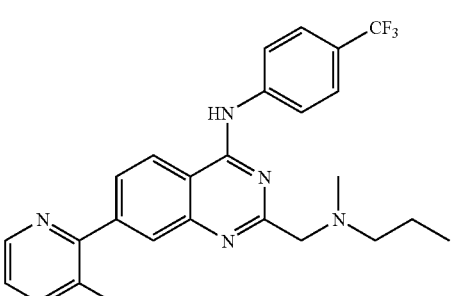 | [2-[(Methyl-propyl-amino)-methyl]-7-(3-trifluoromethyl-pyridin-2-yl)-quinazolin-4-yl]-(4-trifluoromethyl-phenyl)-amine | 519.2 |

TABLE VI-continued

Representative Substituted 2-Aminoalkyl-quinazolin-4-ylamine Analogues

| Compound | | | MS |
|---|---|---|---|
| 485. | 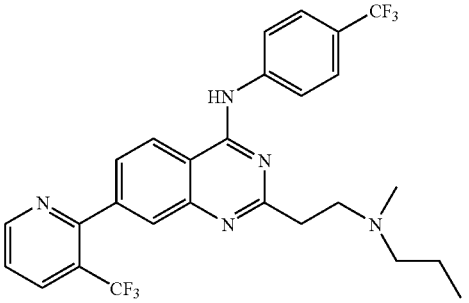 | [2-[(Propyl-methyl-amino)-ethyl]-7-(3-trifluoromethyl-pyridin-2-yl)-quinazolin-4-yl]-(4-trifluoromethyl-phenyl)-amine | 533.2 |
| 486. | 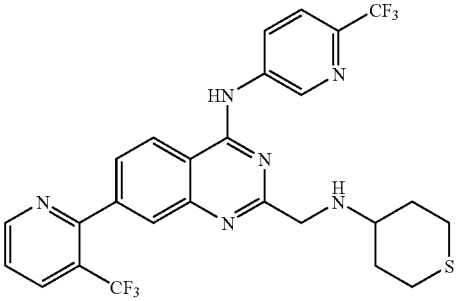 | [2-[(Tetrahydro-thiopyran-4-ylamino)-methyl]-7-(3-trifluoromethyl-pyridin-2-yl)-quinazolin-4-yl]-(6-trifluoromethyl-pyridin-3-yl)-amine | 564.2 |
| 487. | 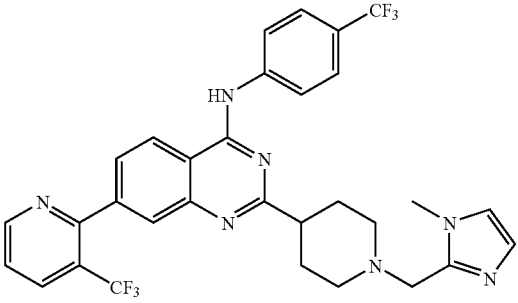 | [2-[1-(1-Methyl-1H-imidazol-2-ylmethyl)-piperidin-4-yl]-7-(3-trifluoromethyl-pyridin-2-yl)-quinazolin-4-yl]-(4-trifluoromethyl-phenyl)-amine | |
| 488. | 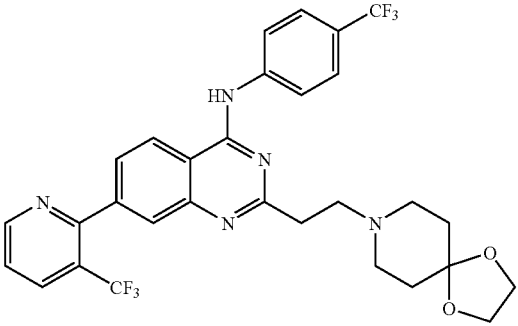 | [2-[2-(1,4-Dioxa-8-aza-spiro[4.5]dec-8-yl)-ethyl]-7-(3-trifluoromethyl-pyridin-2-yl)-quinazolin4-yl]-(4-trifluoromethyl-phenyl)-amine | 603.2 |

TABLE VI-continued

Representative Substituted 2-Aminoalkyl-quinazolin-4-ylamine Analogues

| Compound | | | MS |
|---|---|---|---|
| 489. | 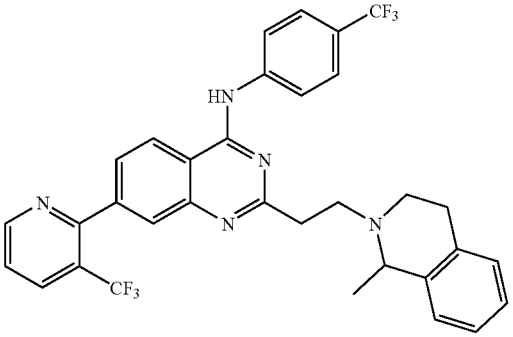 | [2-[2-(1-Methyl-3,4-dihydro-1H-isoquinolin-2-yl)-ethyl]-7-(3-trifluoromethyl-pyridin-2-yl)-quinazolin-4-yl]-(4-trifluoromethyl-phenyl)-amine | 607.2 |
| 490. | 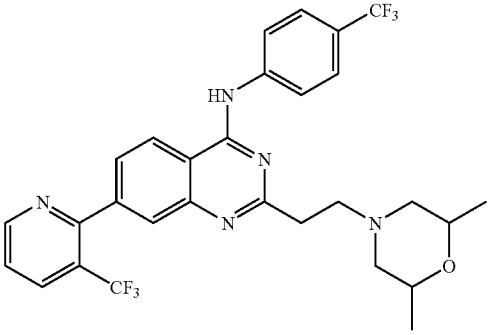 | [2-[2-(2,6-Dimethyl-morpholin-4-yl)-ethyl]-7-(3-trifluoromethyl-pyridin-2-yl)-quinazolin-4-yl]-(4-trifluoromethyl-phenyl)-amine | |
| 491. | 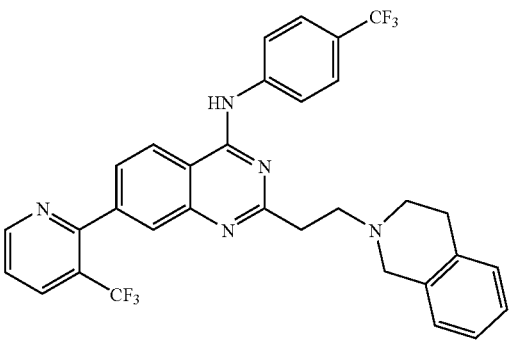 | [2-[2-(3,4-Dihydro-1H-isoquinolin-2-yl)-ethyl]-7-(3-trifluoromethyl-pyridin-2-yl)-quinazolin-4-yl]-(4-trifluoromethyl-phenyl)-amine | 593.2 |
| 492. | 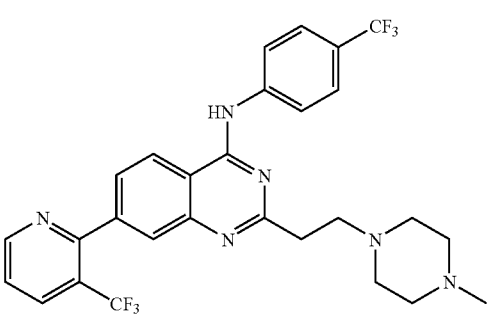 | [2-[2-(4-Methyl-piperazin-1-yl)-ethyl]-7-(3-trifluoromethyl-pyridin-2-yl)-quinazolin-4-yl]-(4-trifluoromethyl-phenyl)-amine | 560.2 |

TABLE VI-continued

Representative Substituted 2-Aminoalkyl-quinazolin-4-ylamine Analogues

| Compound | | | MS |
|---|---|---|---|
| 493. | 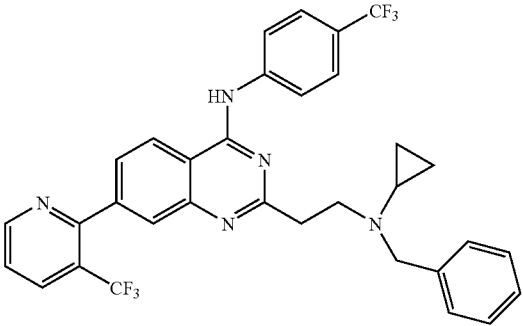 | [2-[2-(Benzyl-cyclopropyl-amino)-ethyl]-7-(3-trifluoromethyl-pyridin-2-yl)-quinazolin-4-yl]-(4-trifluoromethyl-phenyl)-amine | 607.2 |
| 494. | 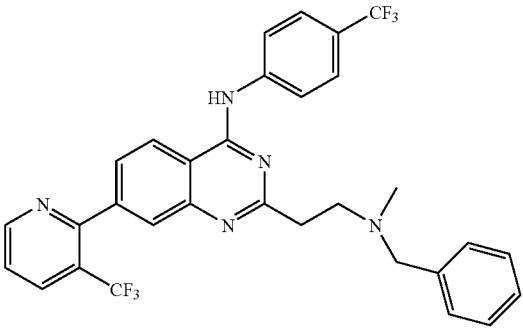 | [2-[2-(Benzyl-methyl-amino)-ethyl]-7-(3-trifluoromethyl-pyridin-2-yl)-quinazolin-4-yl]-(4-trifluoromethyl-phenyl)-amine | 581.2 |
| 495. | 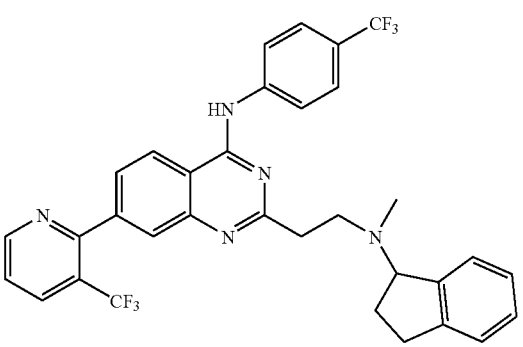 | [2-[2-(Indan-1-yl-methyl-amino)-ethyl]-7-(3-trifluoromethyl-pyridin-2-yl)-quinazolin-4-yl]-(4-trifluoromethyl-phenyl)-amine | 607.2 |
| 496. | 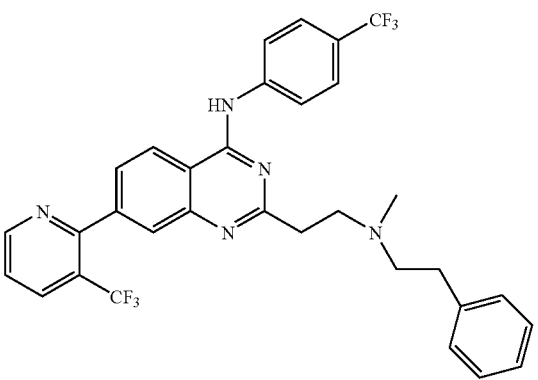 | [2-[2-(Methyl-phenethyl-amino)-ethyl]-7-(3-trifluoromethyl-pyridin-2-yl)-quinazolin-4-yl]-(4-trifluoromethyl-phenyl)-amine | 595.2 |

TABLE VI-continued

Representative Substituted 2-Aminoalkyl-quinazolin-4-ylamine Analogues

| Compound | | | MS |
|---|---|---|---|
| 497. | 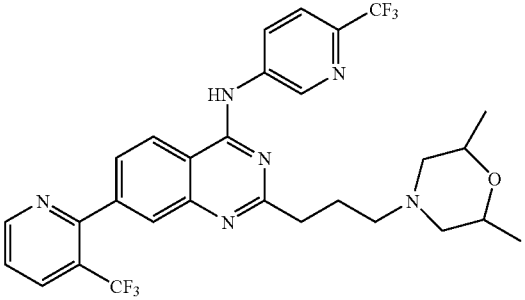 | [2-[3-(2,6-Dimethyl-morpholin-4-yl)-propyl]-7-(3-trifluoromethyl-pyridin-2-yl)-quinazolin-4-yl]-(6-trifluoromethyl-pyridin-3-yl)-amine | 590.2 |
| 498. | 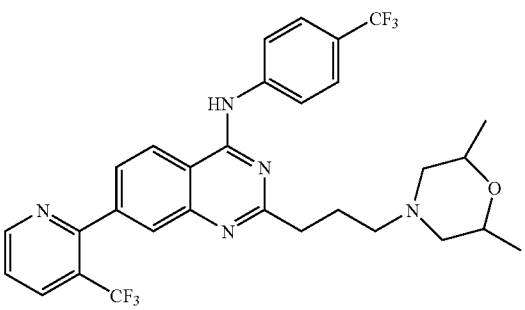 | [2-[3-(2,6-Dimethyl-morpholin-4-yl)-propyl]-7-(3 -trifluoromethyl-pyridin-2-yl)-quinazolin-4-yl]-(4-trifluoromethyl-phenyl)-amine | 589.2 |
| 499. | 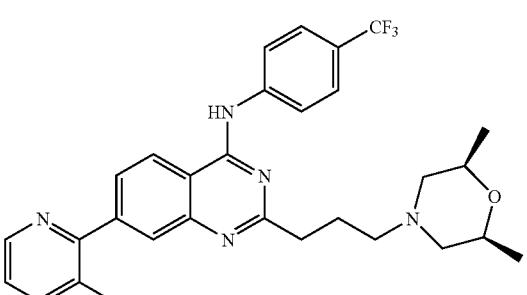 | [2-[3-(2,6-Dimethyl-morpholin-4-yl)-propyl]-7-(3-trifluoromethyl-pyridin-2-yl)-quinazolin-4-yl]-(4-trifluoromethyl-phenyl)-amine (cis) | 589.2 |
| 500. | 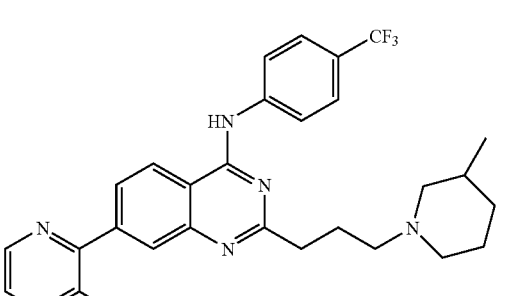 | [2-[3-(3-Methyl-piperidin-1-yl)-propyl]-7-(3-trifluoromethyl-pyridin-2-yl)-quinazolin-4-yl]-(4-trifluoromethyl-phenyl)-amine | 573.2 |

TABLE VI-continued

Representative Substituted 2-Aminoalkyl-quinazolin-4-ylamine Analogues

| Compound | | | MS |
|---|---|---|---|
| 501. | 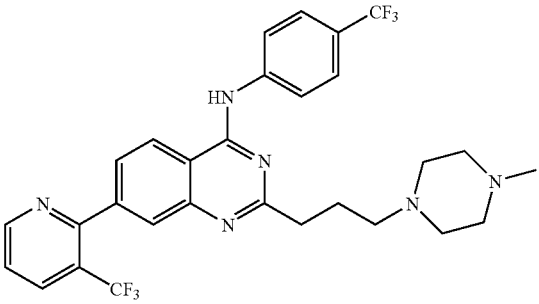 | [2-[3-(4-Methyl-piperazin-1-yl)-propyl]-7-(3-trifluoromethyl-pyridin-2-yl)-quinazolin-4-yl]-(4-trifluoromethyl-phenyl)-amine | 574.2 |
| 502. | 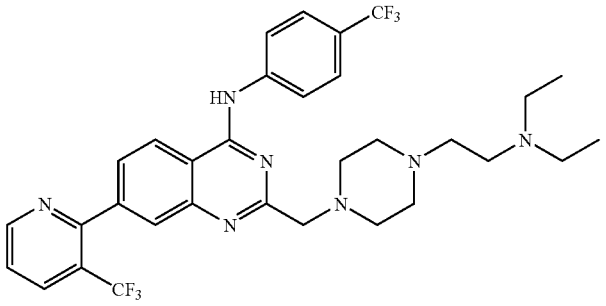 | [2-[4-(2-Diethylamino-ethyl)-piperazin-1-ylmethyl]-7-(3-trifluoromethyl-pyridin-2-yl)-quinazolin-4-yl]-(4-trifluoromethyl-phenyl)-amine | 631.3 |
| 503. | 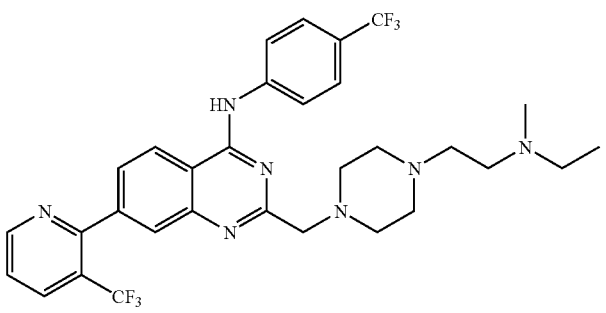 | [2-[4-(2-Dimethylamino-ethyl)-piperazin-1-ylmethyl]-7-(3-trifluoromethyl-pyridin-2-yl)-quinazolin-4-yl]-(4-trifluoromethyl-phenyl)-amine | 603.3 |
| 504. | 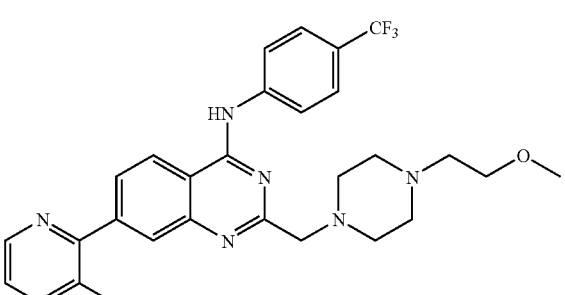 | [2-[4-(2-Methoxy-ethyl)-piperazin-1-ylmethyl]-7-(3-trifluoromethyl-pyridin-2-yl)-quinazolin-4-yl]-(4-trifluoromethyl-phenyl)-amine | 590.2 |

TABLE VI-continued

Representative Substituted 2-Aminoalkyl-quinazolin-4-ylamine Analogues

| Compound | | | MS |
|---|---|---|---|
| 505. | 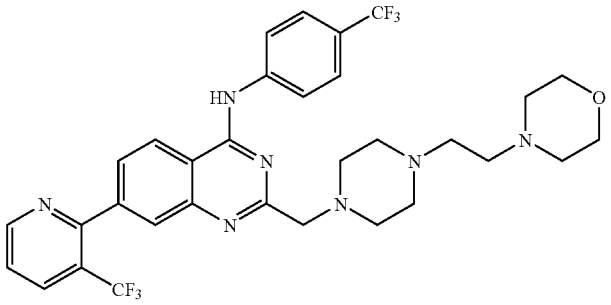 | [2-[4-(2-Morpholin-4-yl-ethyl)-piperazin-1-ylmethyl]-7-(3-trifluoromethyl-pyridin-2-yl)-quinazolin-4-yl]-(4-trifluoromethyl-phenyl)-amine | 645.3 |
| 506. | 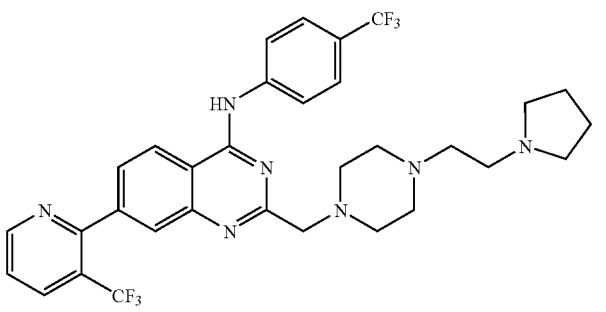 | [2-[4-(2-Pyrrolidin-1-yl-ethyl)-piperazin-1-ylmethyl]-7-(3-quinazolin-4-yl]-(4-trifluoromethyl-phenyl)-amine | 629.3 |
| 507. | 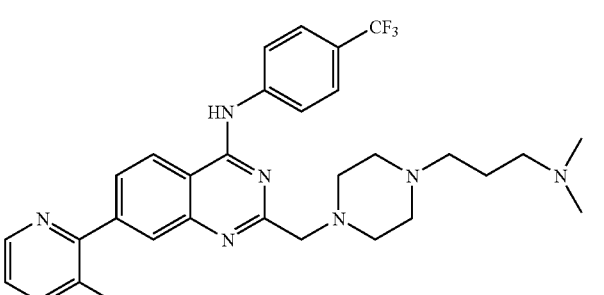 | [2-[4-(3-Dimethylamino-propyl)-piperazin-1-ylmethyl]-7-(3-trifluoromethyl-pyridin-2-yl)-quinazolin-4-yl]-(4-trifluoromethyl-phenyl)-amine | 617.3 |
| 508. | 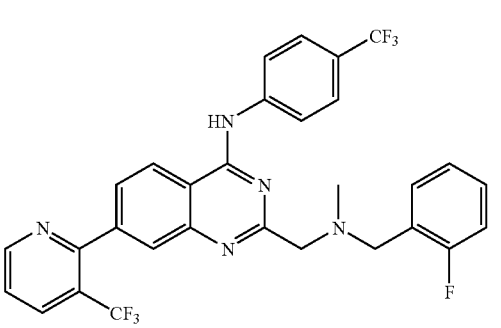 | [2-{[(2-Fluoro-benzyl)-methyl-amino]-methyl}-7-(3-trifluoromethyl-pyridin-2-yl)-quinazolin-4-yl]-(4-trifluoromethyl-phenyl)-amine | 585.2 |

TABLE VI-continued

Representative Substituted 2-Aminoalkyl-quinazolin-4-ylamine Analogues

| Compound | | | MS |
|---|---|---|---|
| 509. | 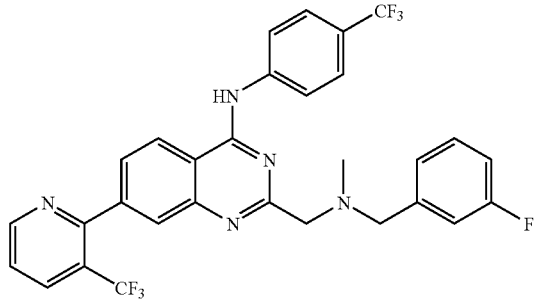 | [2-{[(3-Fluoro-benzyl)-methyl-amino]-methyl}-7-(3-trifluoromethyl-pyridin-2-yl)-quinazolin-4-yl]-(4-trifluoromethyl-phenyl)-amine | 585.2 |
| 510. | 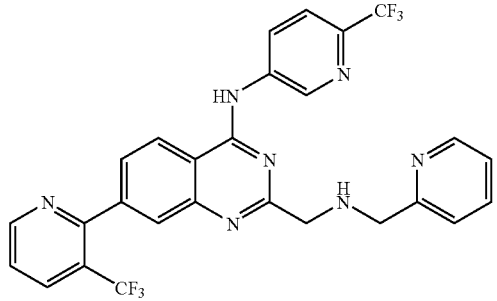 | [2-{[(Pyridin-2-ylmethyl)-amino]-methyl}-7-(3-trifluoromethyl-pyridin-2-yl)-quinazolin-4-yl]-(6-trifluoromethyl-pyridin-3-yl)-amine | 555.2 |
| 511. | 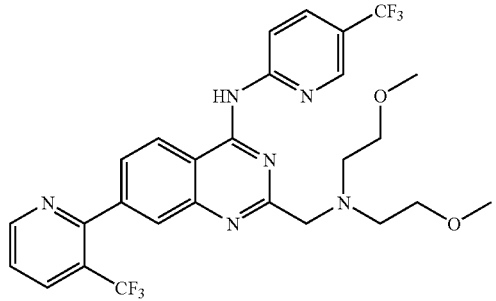 | [2-{[Bis-(2-methoxy-ethyl)-amino]-methyl}-7-(3-trifluoromethyl-pyridin-2-yl)-quinazolin-4-yl]-(5-trifluoromethyl-pyridin-2-yl)-amine | 580.2 |
| 512. | 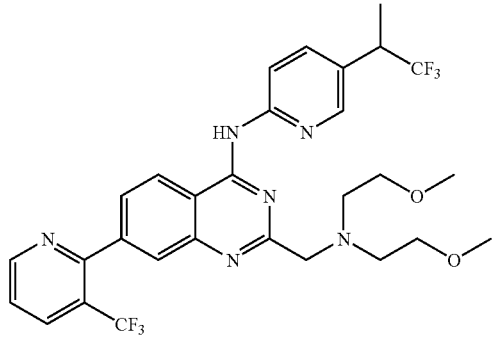 | [2-{[Bis-(2-methoxy-ethyl)-amino]-methyl}-7-(3-trifluoromethyl-pyridin-2-yl)-quinazolin-4-yl]-[4-(2,2,2-trifluoro-1-methyl-ethyl)-phenyl]-amine | 607.2 |

TABLE VI-continued

Representative Substituted 2-Aminoalkyl-quinazolin-4-ylamine Analogues

| Compound | | | MS |
|---|---|---|---|
| 513. | | [2-{[Bis-(2-methoxy-ethyl)-amino]-methyl}-7-(3-trifluoromethyl-pyridin-2-yl)-quinazolin-4-yl]-(4-trifluoromethyl-phenyl)-amine | 579.2 |
| 514. | | [2-{[Bis-(2-methoxy-ethyl)-amino]-methyl}-7-(3-trifluoromethyl-pyridin-2-yl)-pyrido[3,2-d]pyrimidin-4-yl]-(4-trifluoromethyl-phenyl)-amine | 580.2 |
| 515. | | [2-{[Ethyl-(2-methyl-allyl)-amino]-methyl}-7-(3-trifluoromethyl-pyridin-2-yl)-quinazolin-4-yl]-(4-trifluoromethyl-phenyl)-amine | 545.2 |
| 516. | | [2-{[Ethyl-(2-methyl-allyl)-amino]-methyl}-7-(3-trifluoromethyl-pyridin-2-yl)-pyrido[3,2-d]pyrimidin-4-yl]-(4-trifluoromethyl-phenyl)-amine | 546.2 |

TABLE VI-continued

Representative Substituted 2-Aminoalkyl-quinazolin-4-ylamine Analogues

| Compound | | MS |
|---|---|---|
| 517. 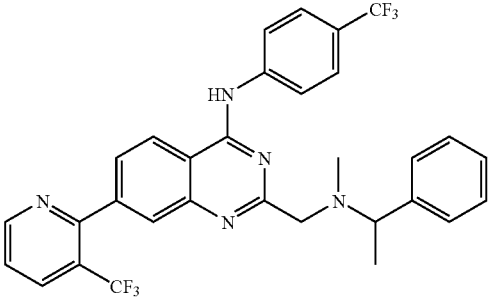 | [2-{[Methyl-(1-phenyl-ethyl)-amino]-methyl}-7-(3-trifluoromethyl-pyridin-2-yl)-quinazolin-4-yl]-(4-trifluoromethyl-phenyl)-amine | 581.2 |
| 518. 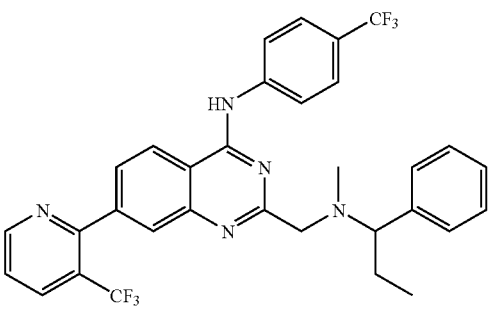 | [2-{[Methyl-(1-phenyl-propyl)-amino]-methyl}-7-(3-trifluoromethyl-pyridin-2-yl)-quinazolin-4-yl]-(4-trifluoromethyl-phenyl)-amine | 595.2 |
| 519. 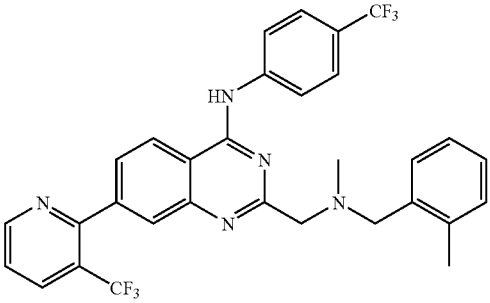 | [2-{[Methyl-(2-methyl-benzyl)-amino]-methyl}-7-(3-trifluoromethyl-pyridin-2-yl)-quinazolin-4-yl]-(4-trifluoromethyl-phenyl)-amine | 581.2 |
| 520. 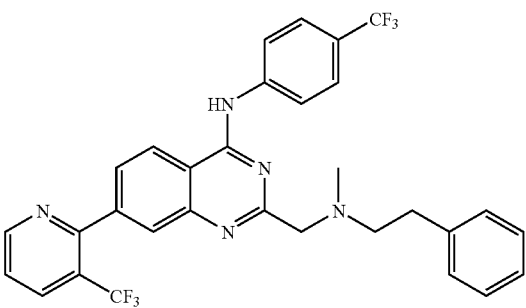 | [2-{[Methyl-(2-phenyl-ethyl)-amino]-methyl}-7-(3-trifluoromethyl-pyridin-2-yl)-quinazolin-4-yl]-(4-trifluoromethyl-phenyl)-amine | 581.2 |

TABLE VI-continued

Representative Substituted 2-Aminoalkyl-quinazolin-4-ylamine Analogues

| Compound | | | MS |
|---|---|---|---|
| 521. | 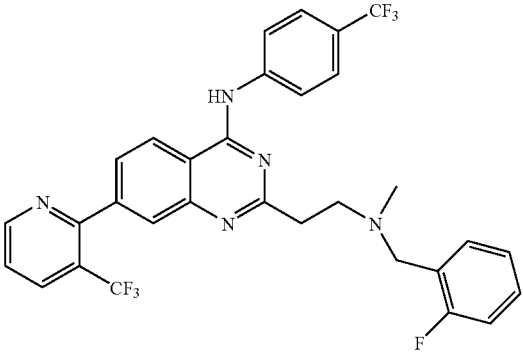 | [2-{2-[(2-Fluoro-benzyl)-methyl-amino]-ethyl}-7-(3-trifluoromethyl-pyridin-2-yl)-quinazolin-4-yl]-(4-trifluoromethyl-phenyl)-amine | 599.2 |
| 522. | 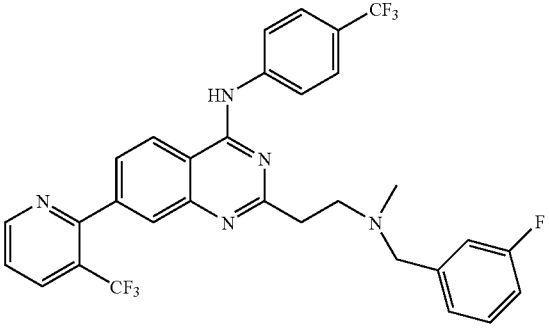 | [2-{2-[(3-Fluoro-benzyl)-methyl-amino]-ethyl}-7-(3-trifluoromethyl-pyridin-2-yl)-quinazolin-4-yl]-(4-trifluoromethyl-phenyl)-amine | 599.2 |
| 523. | 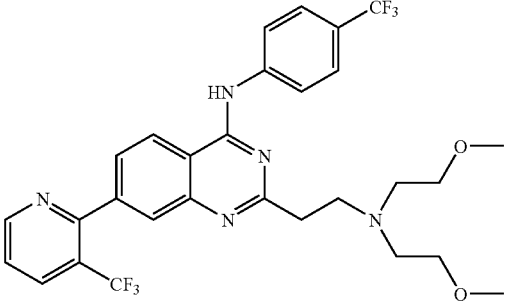 | [2-{2-[Bis-(2-methoxy-ethyl)-amino]-ethyl}-7-(3-trifluoromethyl-pyridin-2-yl)-quinazolin-4-yl]-(4-trifluoromethyl-phenyl)-amine | 593.2 |
| 524. | 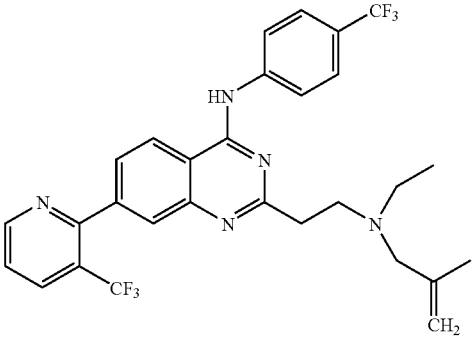 | [2-{2-[Ethyl-(2-methyl-allyl)-amino]-ethyl}-7-(3-trifluoromethyl-pyridin-2-yl)-quinazolin-4-yl]-(4-trifluoromethyl-phenyl)-amine | 559.2 |

TABLE VI-continued

Representative Substituted 2-Aminoalkyl-quinazolin-4-ylamine Analogues

| Compound | | | MS |
|---|---|---|---|
| 525. | 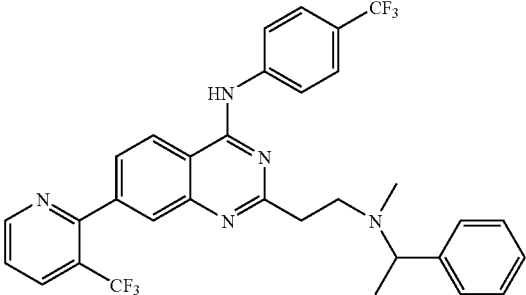 | [2-{2-[Methyl-(1-phenyl-ethyl)-amino]-ethyl}-7-(3-trifluoromethyl-pyridin-2-yl)-quinazolin-4-yl]-(4-trifluoromethyl-phenyl)-amine | 595.2 |
| 526. | 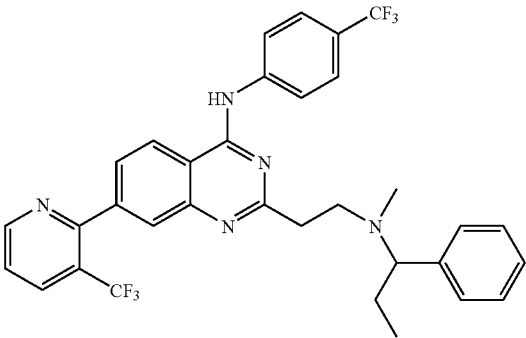 | [2-{2-[Methyl-(1-phenyl-propyl)-amino]-ethyl}-7-(3-trifluoromethyl-pyridin-2-yl)-quinazolin-4-yl]-(4-trifluoromethyl-phenyl)-amine | 609.2 |
| 527. | 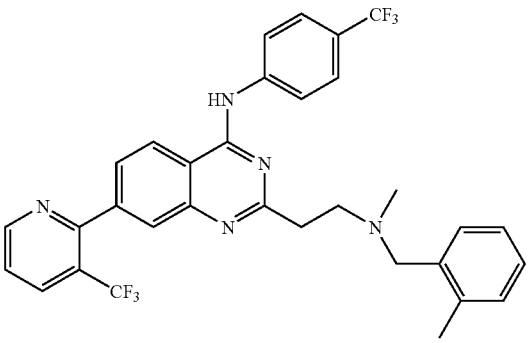 | [2-{2-[Methyl-(2-methyl-benzyl)-amino]-ethyl}-7-(3-trifluoromethyl-pyridin-2-yl)-quinazolin-4-yl]-(4-trifluoromethyl-phenyl)-amine | 595.2 |
| 528. | 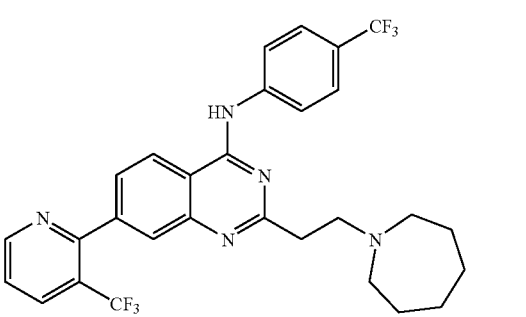 | [2-Azepan-1-ylethyl-7-(3-trifluoromethyl-pyridin-2-yl)-quinazolin-4-yl]-(4-trifluoromethyl-phenyl)-amine | 559.2 |

TABLE VI-continued

Representative Substituted 2-Aminoalkyl-quinazolin-4-ylamine Analogues

| Compound | | | MS |
|---|---|---|---|
| 529. | 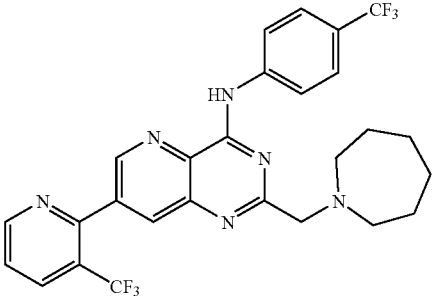 | [2-Azepan-1-ylmethyl-7-(3-trifluoromethyl-pyridin-2-yl)-pyrido[3,2-d]pyrimidin-4-yl]-(4-trifluoromethyl-phenyl)-amine | 546.2 |
| 530. | 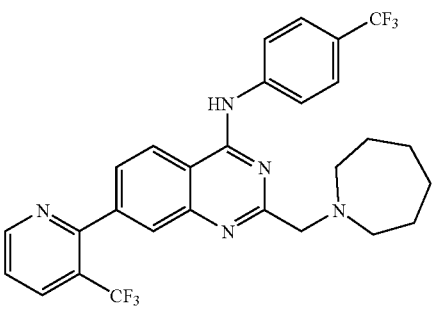 | [2-Azepan-1-ylmethyl-7-(3-trifluoromethyl-pyridin-2-yl)-quinazolin-4-yl]-(4-trifluoromethyl-phenyl)-amine | 545.2 |
| 531. | 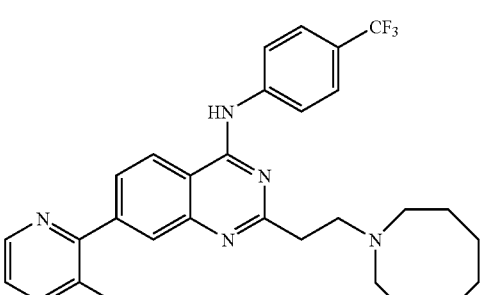 | [2-Azocan-1-ylethyl-7-(3-trifluoromethyl-pyridin-2-yl)-quinazolin-4-yl]-(4-trifluoromethyl-phenyl)-amine | 573.2 |
| 532. | 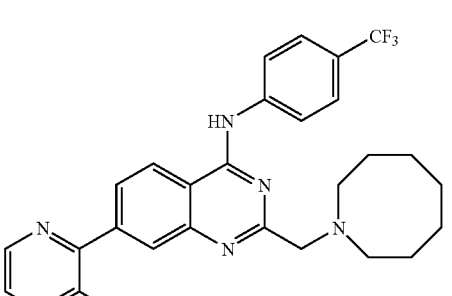 | [2-Azocan-1-ylmethyl-7-(3-trifluoromethyl-pyridin-2-yl)-quinazolin-4-yl]-(4-trifluoromethyl-phenyl)-amine | 559.2 |

TABLE VI-continued

Representative Substituted 2-Aminoalkyl-quinazolin-4-ylamine Analogues

| Compound | | | MS |
|---|---|---|---|
| 533. | 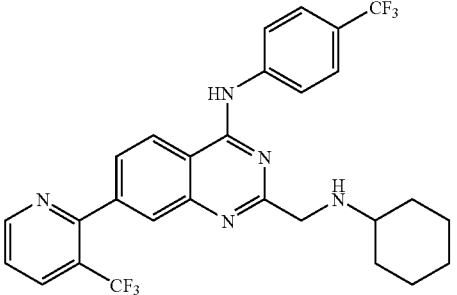 | [2-Cyclohexylaminomethyl-7-(3-trifluoromethyl-pyridin-2-yl)-quinazolin-4-yl]-(4-trifluoromethyl-phenyl)-amine | 545.2 |
| 534. | 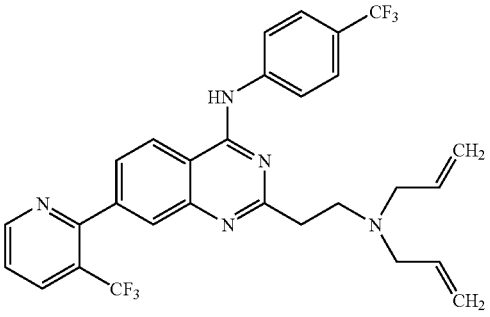 | [2-Diallylaminoethyl-7-(3-trifluoromethyl-pyridin-2-yl)-quinazolin-4-yl]-(4-trifluoromethyl-phenyl)-amine | 557.2 |
| 535. | 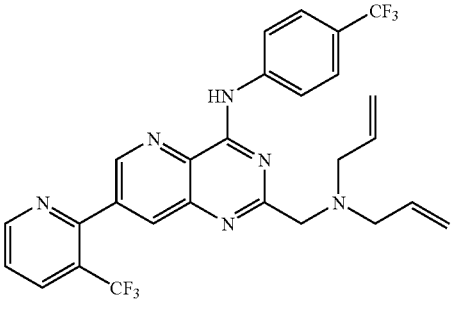 | [2-Diallylaminomethyl-7-(3-trifluoromethyl-pyridin-2-yl)-pyrido[3,2-d]pyrimidin-4-yl]-(4-trifluoromethyl-phenyl)-amine | 544.2 |
| 536. | 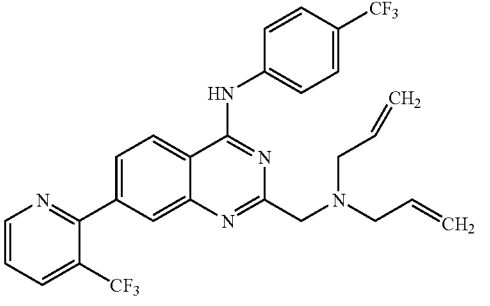 | [2-Diallylaminomethyl-7-(3-trifluoromethyl-pyridin-2-yl)-quinazolin-4-yl]-(4-trifluoromethyl-phenyl)-amine | 543.2 |

TABLE VI-continued

Representative Substituted 2-Aminoalkyl-quinazolin-4-ylamine Analogues

| Compound | | | MS |
|---|---|---|---|
| 537. | 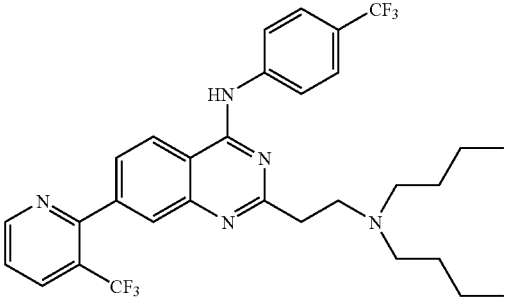 | [2-Dibutylaminoethyl-7-(3-trifluoromethyl-pyridin-2-yl)-quinazolin-4-yl]-(4-trifluoromethyl-phenyl)-amine | 589.3 |
| 538. | 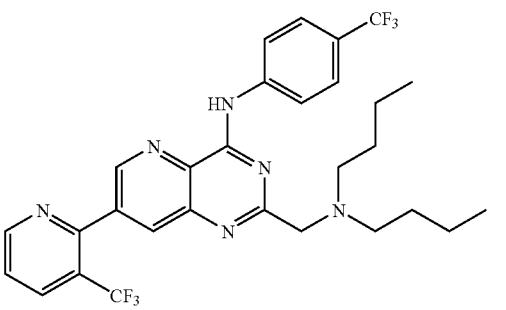 | [2-Dibutylaminomethyl-7-(3-trifluoromethyl-pyridin-2-yl)-pyrido[3,2-d]pyrimidin-4-yl]-(4-trifluoromethyl-phenyl)-amine | 576.2 |
| 539. | 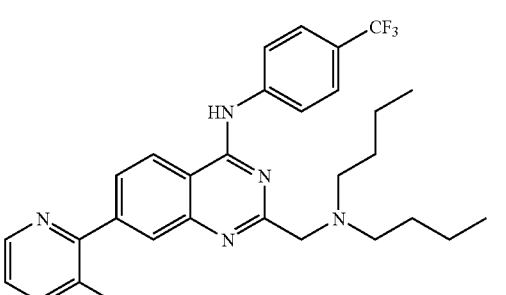 | [2-Dibutylaminomethyl-7-(3-trifluoromethyl-pyridin-2-yl)-quinazolin-4-yl]-(4-trifluoromethyl-phenyl)-amine | 575.2 |
| 540. | 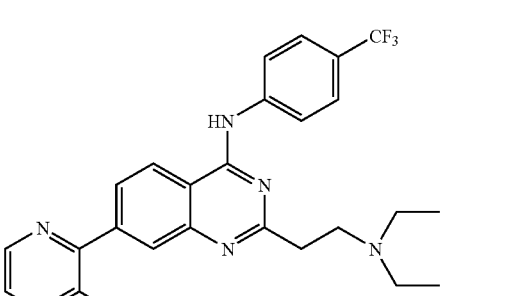 | [2-Diethylaminoethyl-7-(3-trifluoromethyl-pyridin-2-yl)-quinazolin-4-yl]-(4-trifluoromethyl-phenyl)-amine | 533.2 |

TABLE VI-continued

Representative Substituted 2-Aminoalkyl-quinazolin-4-ylamine Analogues

| Compound | | | MS |
|---|---|---|---|
| 541. | 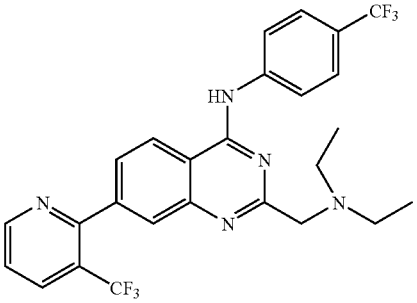 | [2-Diethylaminomethyl-7-(3-trifluoromethyl-pyridin-2-yl)-quinazolin-4-yl]-(4-trifluoromethyl-phenyl)-amine | 519.2 |
| 542. | 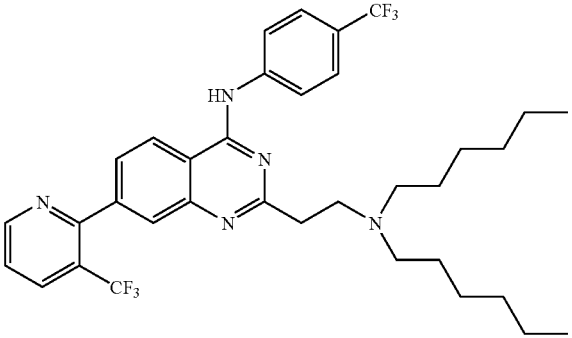 | [2-Dihexylaminoethyl-7-(3-trifluoromethyl-pyridin-2-yl)-quinazolin-4-yl]-(4-trifluoromethyl-phenyl)-amine | 645.3 |
| 543. | 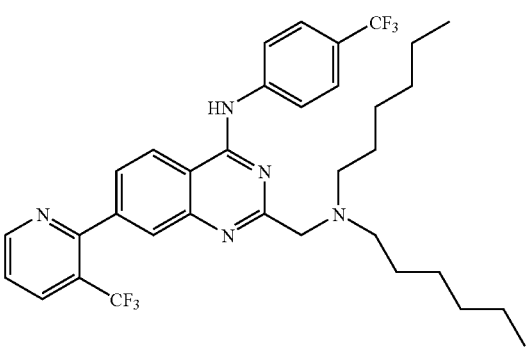 | [2-Dihexylaminomethyl-7-(3-trifluoromethyl-pyridin-2-yl)-quinazolin-4-yl]-(4-trifluoromethyl-phenyl)-amine | 631.3 |
| 544. | 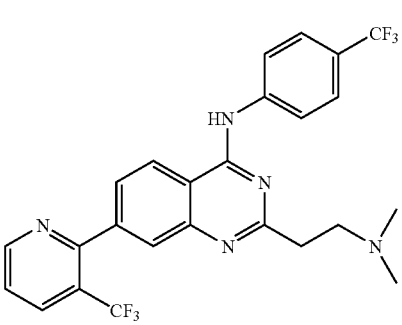 | [2-Dimethylaminoethyl-7-(3-trifluoromethyl-pyridin-2-yl)-quinazolin-4-yl]-(4-trifluoromethyl-phenyl)-amine | |

TABLE VI-continued

Representative Substituted 2-Aminoalkyl-quinazolin-4-ylamine Analogues

| Compound | | | MS |
|---|---|---|---|
| 545. | 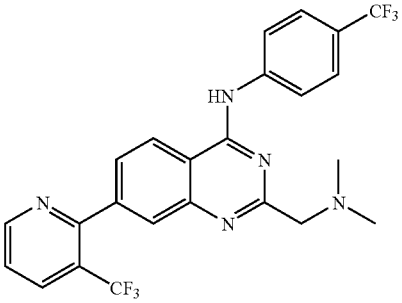 | [2-Dimethylaminomethyl-7-(3-trifluoromethyl-pyridin-2-yl)-quinazolin-4-yl]-(4-trifluoromethyl-phenyl)-amine | 491.2 |
| 546. | 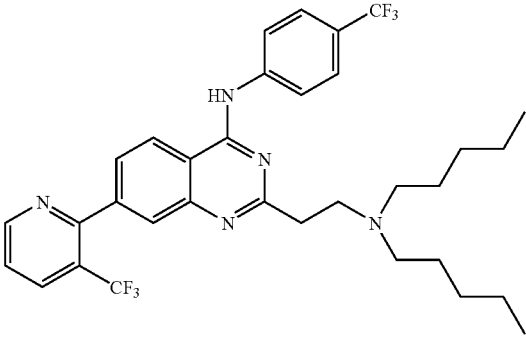 | [2-Dipentylaminoethyl-7-(3-trifluoromethyl-pyridin-2-yl)-quinazolin-4-yl]-(4-trifluoromethyl-phenyl)-amine | 617.3 |
| 547. | 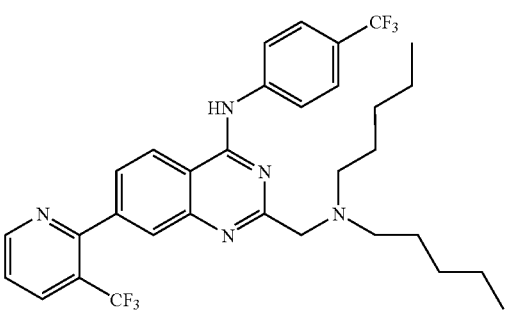 | [2-Dipentylaminomethyl-7-(3-trifluoromethyl-pyridin-2-yl)-quinazolin-4-yl]-(4-trifluoromethyl-phenyl)-amine | 603.3 |
| 548. | 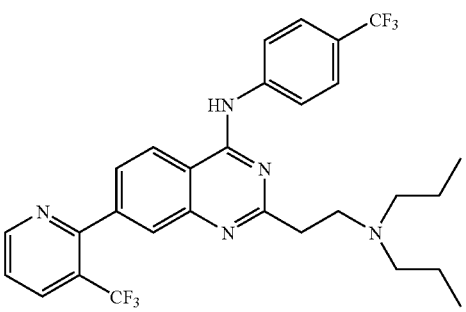 | [2-Dipropylaminoethyl-7-(3-trifluoromethyl-pyridin-2-yl)-quinazolin-4-yl]-(4-trifluoromethyl-phenyl)-amine | 561.2 |

TABLE VI-continued

Representative Substituted 2-Aminoalkyl-quinazolin-4-ylamine Analogues

| Compound | | MS |
|---|---|---|
| 549. 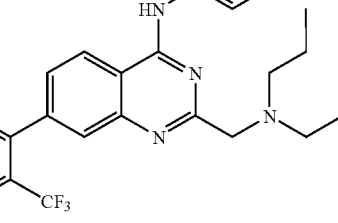 | [2-Dipropylaminomethyl-7-(3-trifluoromethyl-pyridin-2-yl)-pyrido[3,2-d]pyrimidin-4-yl]-(4-trifluoromethyl-phenyl)-amine | 548.2 |
| 550. 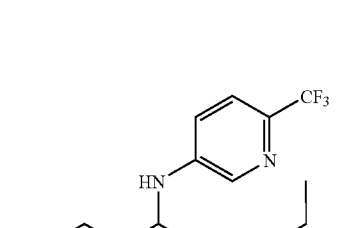 | [2-Dipropylaminomethyl-7-(3-trifluoromethyl-pyridin-2-yl)-quinazolin-4-yl]-(6-trifluoromethyl-pyridin-3-yl)-amine | 548.2 |
| 551. 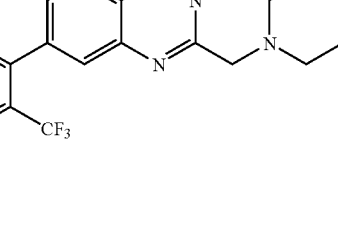 | [2-Dipropylaminomethyl-7-(3-trifluoromethyl-pyridin-2-yl)-quinazolin-4-yl]-(4-trifluoromethyl-phenyl)-amine | 547.2 |
| 552. 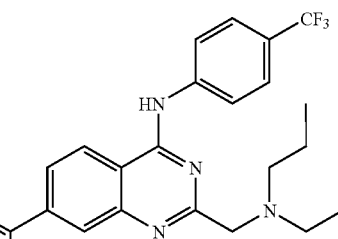 | [2-Ethylaminomethyl-7-(3-trifluoromethyl-pyridin-2-yl)-quinazolin-4-yl]-(4-trifluoromethyl-phenyl)-amine | 491.2 |

TABLE VI-continued

Representative Substituted 2-Aminoalkyl-quinazolin-4-ylamine Analogues

| Compound | | | MS |
|---|---|---|---|
| 553. | 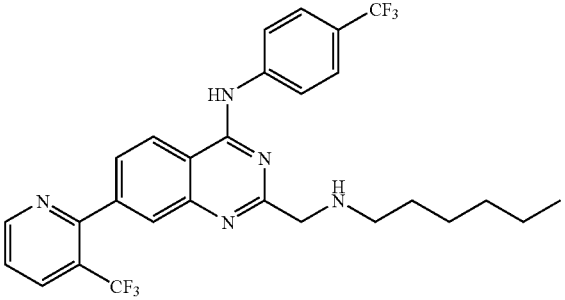 | [2-Hexylaminomethyl-7-(3-trifluoromethyl-pyridin-2-yl)-quinazolin-4-yl]-(4-trifluoromethyl-phenyl)-amine | 547.2 |
| 554. | 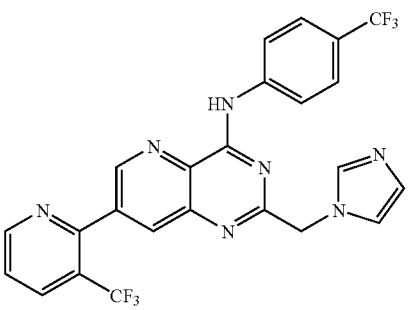 | [2-Imidazol-1-ylmethyl-7-(3-trifluoromethyl-pyridin-2-yl)-pyrido[3,2-d]pyrimidin-4-yl]-(4-trifluoromethyl-phenyl)-amine | |
| 555. | 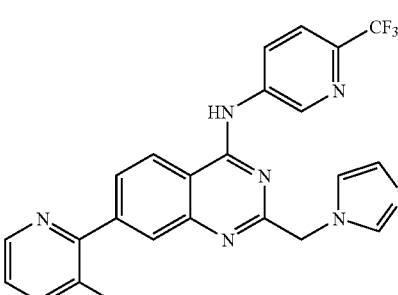 | [2-Imidazol-1-ylmethyl-7-(3-trifluoromethyl-pyridin-2-yl)-quinazolin-4-yl]-(6-trifluoromethyl-pyridin-3-yl)-amine | 515.1 |
| 556. | 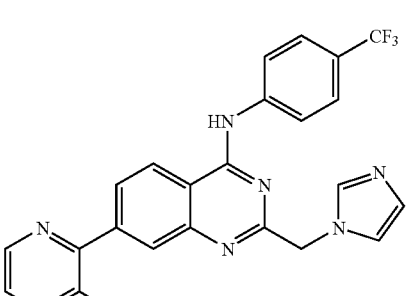 | [2-Imidazol-1-ylmethyl-7-(3-trifluoromethyl-pyridin-2-yl)-quinazolin-4-yl]-(4-trifluoromethyl-phenyl)-amine | |

TABLE VI-continued

Representative Substituted 2-Aminoalkyl-quinazolin-4-ylamine Analogues

| Compound | | MS |
|---|---|---|
| 557. 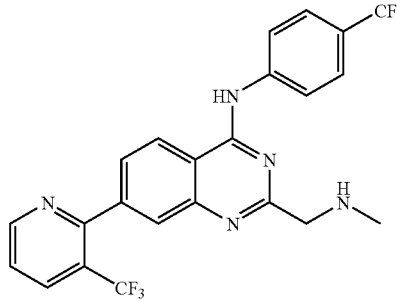 | [2-Methylaminomethyl-7-(3-trifluoromethyl-pyridin-2-yl)-quinazolin-4-yl]-(4-trifluoromethyl-phenyl)-amine | 477.1 |
| 558. 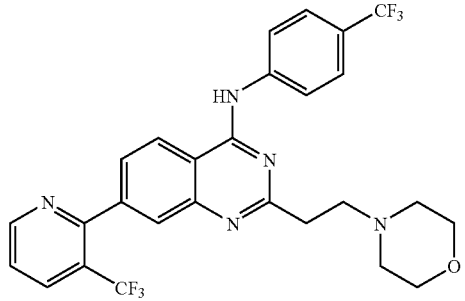 | [2-Morpholin-4-ylethyl-7-(3-trifluoromethyl-pyridin-2-yl)-quinazolin-4-yl]-(4-trifluoromethyl-phenyl)-amine | 547.2 |
| 559. 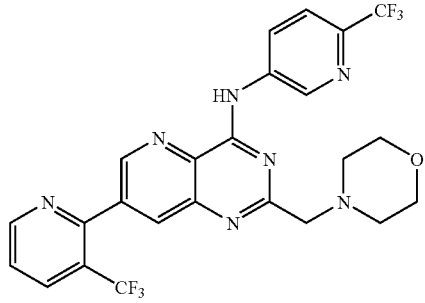 | [2-Morpholin-4-ylmethyl-7-(3-trifluoromethyl-pyridin-2-yl)-pyrido[3,2-d]pyrimidin-4-yl]-(6-trifluoromethyl-pyridin-3-yl)-amine | 535.2 |
| 560. 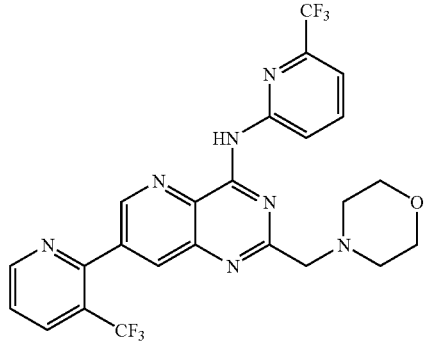 | [2-Morpholin-4-ylmethyl-7-(3-trifluoromethyl-pyridin-2-yl)-pyrido[3,2-d]pyrimidin-4-yl]-(6-trifluoromethyl-pyridin-2-yl)-amine | 535.2 |

TABLE VI-continued

Representative Substituted 2-Aminoalkyl-quinazolin-4-ylamine Analogues

| Compound | | | MS |
|---|---|---|---|
| 561. | 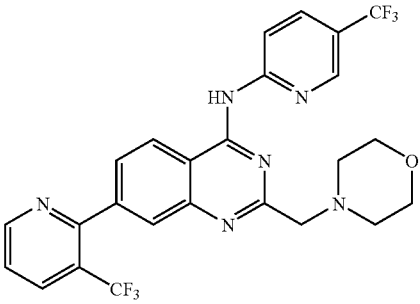 | [2-Morpholin-4-ylmethyl-7-(3-trifluoromethyl-pyridin-2-yl)-quinazolin-4-yl]-(5-trifluoromethyl-pyridin-2-yl)-amine | 534.2 |
| 562. | 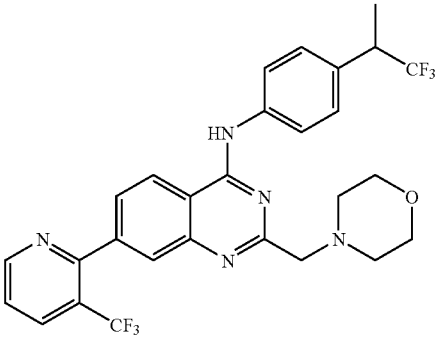 | [2-Morpholin-4-ylmethyl-7-(3-trifluoromethyl-pyridin-2-yl)-quinazolin-4-yl]-[4-(2,2,2-trifluoro-1-methyl-ethyl)-phenyl]-amine | 561.2 |
| 563. | 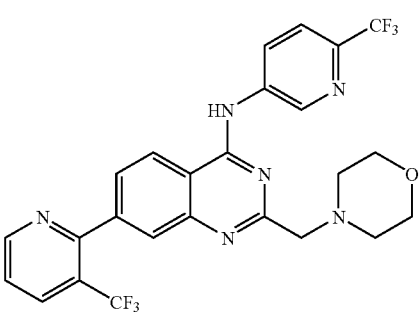 | [2-Morpholin-4-ylmethyl-7-(3-trifluoromethyl-pyridin-2-yl)-quinazolin-4-yl]-(6-trifluoromethyl-pyridin-3-yl)-amine | 534.2 |
| 564. | 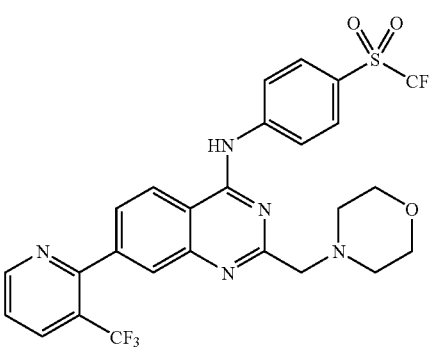 | [2-Morpholin-4-ylmethyl-7-(3-trifluoromethyl-pyridin-2-yl)-quinazolin-4-yl]-(4-trifluoromethanesulfonyl-phenyl)-amine | 597.1 |

TABLE VI-continued

Representative Substituted 2-Aminoalkyl-quinazolin-4-ylamine Analogues

| Compound | | | MS |
|---|---|---|---|
| 565. | 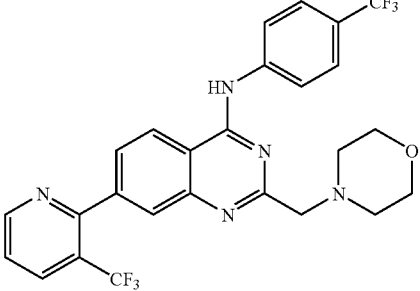 | [2-Morpholin-4-ylmethyl-7-(3-trifluoromethyl-pyridin-2-yl)-quinazolin-4-yl]-(4-trifluoromethyl-phenyl)-amine | 533.2 |
| 566. | 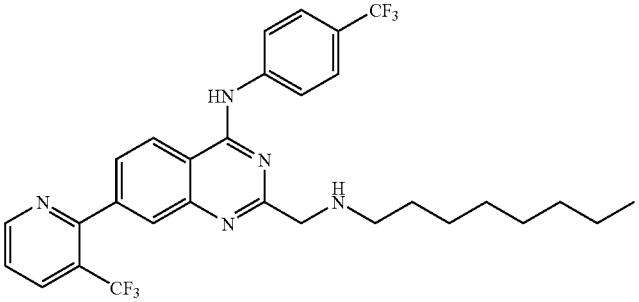 | [2-Octylaminomethyl-7-(3-trifluoromethyl-pyridin-2-yl)-quinazolin-4-yl]-(4-trifluoromethyl-phenyl)-amine | 575.2 |
| 567. | 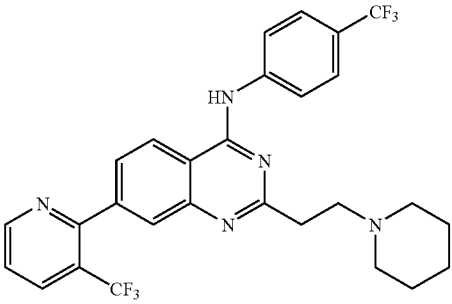 | [2-Piperidin-1-ylethyl-7-(3-trifluoromethyl-pyridin-2-yl)-quinazolin-4-yl]-(4-trifluoromethyl-phenyl)-amine | 545.2 |
| 568. | 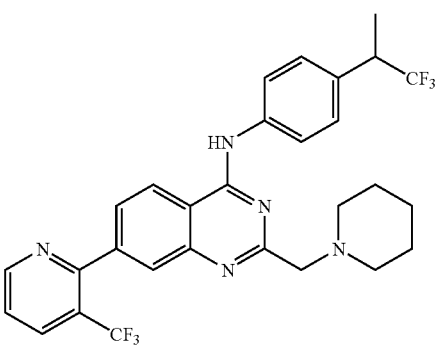 | [2-Piperidin-1-ylmethyl-7-(3-trifluoromethyl-pyridin-2-yl)-quinazolin-4-yl]-[4-(2,2,2-trifluoro-1-methyl-ethyl)-phenyl]-amine | 559.2 |

TABLE VI-continued

Representative Substituted 2-Aminoalkyl-quinazolin-4-ylamine Analogues

| Compound | | | MS |
|---|---|---|---|
| 569. | 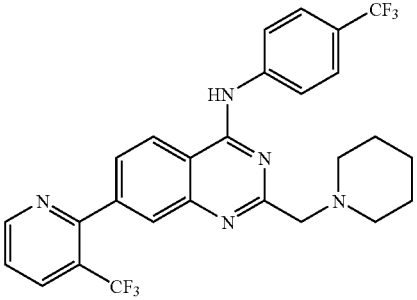 | [2-Piperidin-1-ylmethyl-7-(3-trifluoromethyl-pyridin-2-yl)-quinazolin-4-yl]-(4-trifluoromethyl-phenyl)-amine | 531.2 |
| 570. | 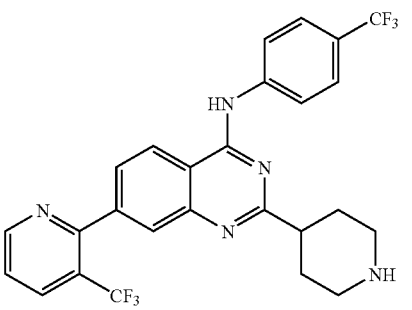 | [2-Piperidin-4-yl-7-(3-trifluoromethyl-pyridin-2-yl)-quinazolin-4-yl]-(4-trifluoromethyl-phenyl)-amine | |
| 571. | 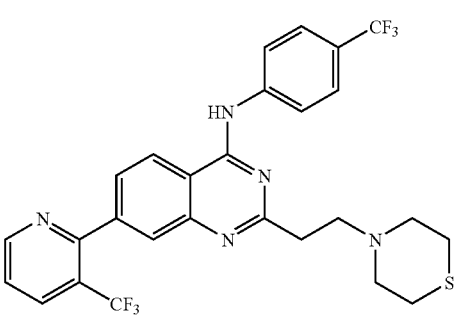 | [2-Thiomorpholin-4-ylethyl-7-(3-trifluoromethyl-pyridin-2-yl)-quinazolin-4-yl]-(4-trifluoromethyl-phenyl)-amine | 563.2 |
| 572. | 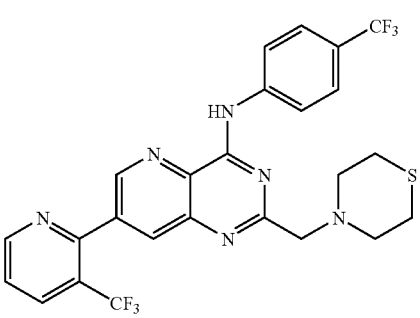 | [2-Thiomorpholin-4-ylmethyl-7-(3-trifluoromethyl-pyridin-2-yl)-pyrido[3,2-d]pyrimidin-4-yl]-(4-trifluoromethyl-phenyl)-amine | 550.1 |

TABLE VI-continued

Representative Substituted 2-Aminoalkyl-quinazolin-4-ylamine Analogues

| Compound | | | MS |
|---|---|---|---|
| 573. | 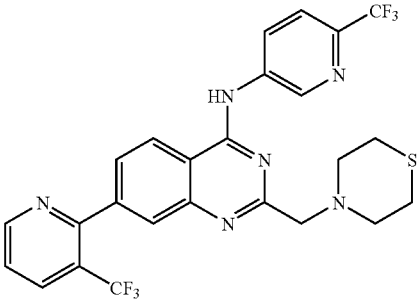 | [2-Thiomorpholin-4-ylmethyl-7-(3-trifluoromethyl-pyridin-2-yl)-quinazolin-4-yl]-(6-trifluoromethyl-pyridin-3-yl)-amine | 550.1 |
| 574. | 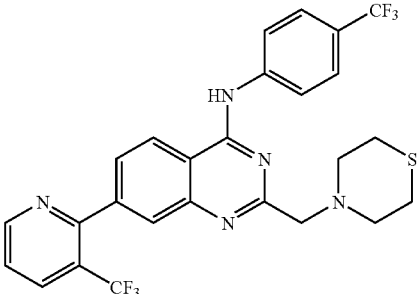 | [2-Thiomorpholin-4-ylmethyl-7-(3-trifluoromethyl-pyridin-2-yl)-quinazolin-4-yl]-(4-trifluoromethyl-phenyl)-amine | 549.1 |
| 575. | 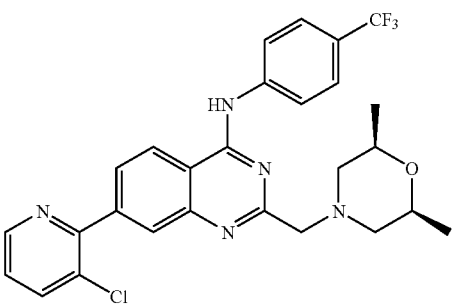 | [7-(3-Chloro-pyridin-2-yl)-2-(2,6-dimethyl-morpholin-4-yl-methyl)-quinazolin-4-yl]-(4-trifluoromethyl-phenyl)-amine (cis) | 527.2 |
| 576. | 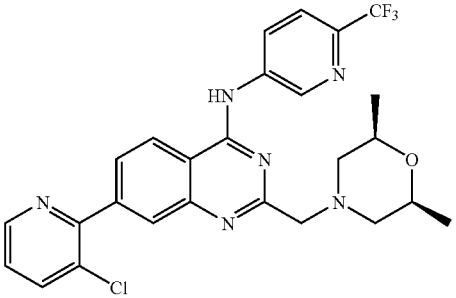 | [7-(3-Chloro-pyridin-2-yl)-2-(2,6-dimethyl-morpholin-4-ylmethyl)-quinazolin-4-yl]-(6-trifluoromethyl-pyridin-3-yl)-amine (cis) | 528.2 |

TABLE VI-continued

Representative Substituted 2-Aminoalkyl-quinazolin-4-ylamine Analogues

| Compound | | | MS |
|---|---|---|---|
| 577. | 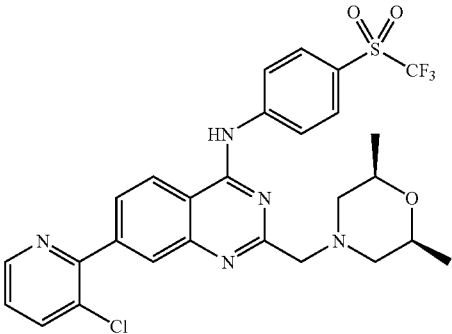 | [7-(3-Chloro-pyridin-2-yl)-2-(2,6-dimethyl-morpholin-4-ylmethyl)-quinazolin-4-yl]-(4-trifluoromethanesulfonyl-phenyl)-amine (cis) | 591.1 |
| 578. | 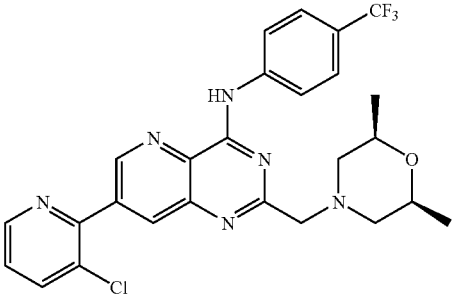 | [7-(3-Chloro-pyridin-2-yl)-2-(2,6-dimethyl-morpholin-4-ylmethyl)-pyrido[3,2-d]pyrimidin4-yl]-(4-trifluoromethyl-phenyl)-amine (cis) | 528.2 |
| 579. | 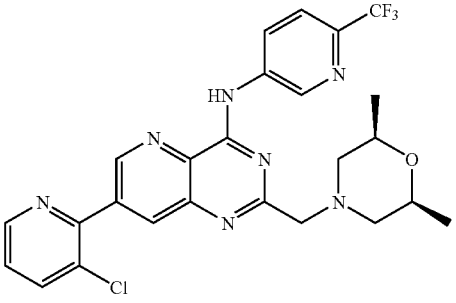 | [7-(3-Chloro-pyridin-2-yl)-2-(2,6-dimethyl-morpholin-4-ylmethyl)-pyrido[3,2-d]pyrimidin-4-yl]-(6-trifluoromethyl-pyridin-3-yl)-amine (cis) | 529.2 |
| 580. | 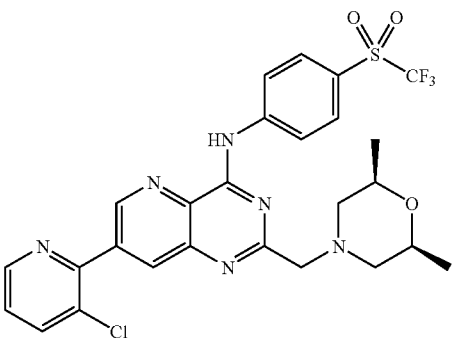 | [7-(3-Chloro-pyridin-2-yl)-2-(2,6-dimethyl-morpholin-4-ylmethyl)-pyrido[3,2-d]pyrimidin-4-yl]-(4-trifluoromethanesulfonyl-phenyl)-amine (cis) | 592.1 |

TABLE VI-continued

Representative Substituted 2-Aminoalkyl-quinazolin-4-ylamine Analogues

| Compound | | MS |
|---|---|---|
| 581. | [7-(3-Chloro-pyridin-2-yl)-2-(2,6-dimethyl-morpholin-4-ylmethyl)-quinazolin-4-yl]-(4-isopropyl-phenyl)-amine (cis) | |
| 582. | [7-(3-Chloro-pyridin-2-yl)-2-(3,5-dimethyl-piperazin-1-ylmethyl)-quinazolin-4-yl]-(4-trifluoromethyl-phenyl)-amine | 526.2 |
| 583. | [7-(3-Chloro-pyridin-2-yl)-2-imidazol-1-ylmethyl-pyrido[3,2-d]pyrimidin-4-yl]-(4-trifluoromethyl-phenyl)-amine | |
| 584. | {1-[4-(4-Trifluoromethyl-phenylamino)-7-(3-trifluoromethyl-pyridin-2-yl)-quinazolin-2-ylmethyl]-piperidin-4-yl}-methanol | 561.2 |

TABLE VI-continued

Representative Substituted 2-Aminoalkyl-quinazolin-4-ylamine Analogues

| Compound | | | MS |
|---|---|---|---|
| 585. | 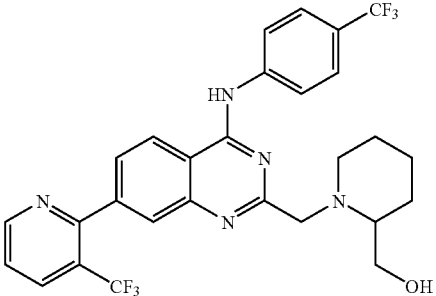 | {1-[4-(4-Trifluoromethyl-phenylamino)-7-(3-trifluoromethyl-pyridin-2-yl)-quinazolin-2-ylmethyl]-piperidin-2-yl}-methanol | 561.2 |
| 586. | 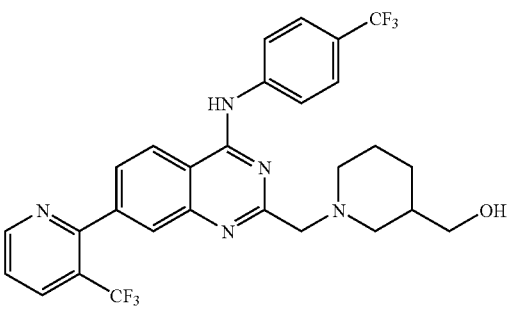 | {1-[4-(4-Trifluoromethyl-phenylamino)-7-(3-trifluoromethyl-pyridin-2-yl)-quinazolin-2-ylmethyl]-piperidin-3-yl}-methanol | 561.2 |
| 587. | 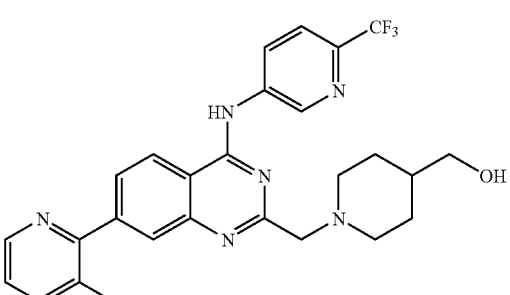 | {1-[7-(3-Trifluoromethyl-pyridin-2-yl)-4-(6-trifluoromethyl-pyridin-3-ylamino)-quinazolin-2-ylmethyl]-piperidin-4-yl}-methanol | 562.2 |
| 588. | 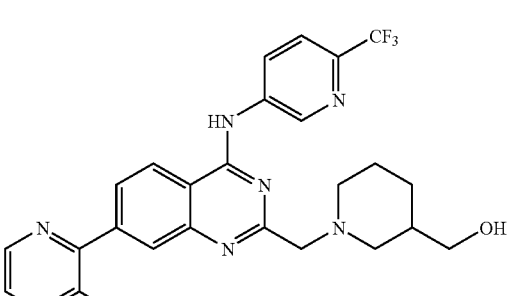 | {1-[7-(3-Trifluoromethyl-pyridin-2-yl)-4-(6-trifluoromethyl-pyridin-3-ylamino)-quinazolin-2-ylmethyl]-piperidin-3-yl}-methanol | 562.2 |

TABLE VI-continued

Representative Substituted 2-Aminoalkyl-quinazolin-4-ylamine Analogues

| Compound | | | MS |
|---|---|---|---|
| 589. | 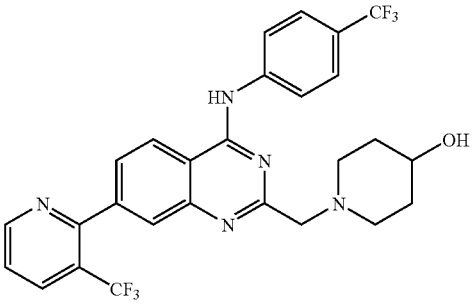 | 1-[4-(4-Trifluoromethyl-phenylamino)-7-(3-trifluoromethyl-pyridin-2-yl)-quinazolin-2-ylmethyl]-piperidin-4-ol | 547.2 |
| 590. | 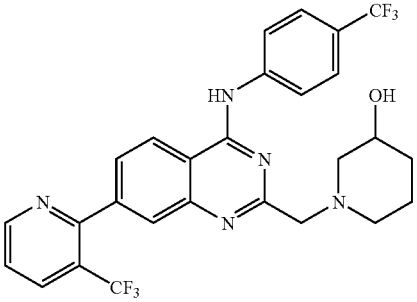 | 1-[4-(4-Trifluoromethyl-phenylamino)-7-(3-trifluoromethyl-pyridin-2-yl)-quinazolin-2-ylmethyl]-piperidin-3-ol | 547.2 |
| 591. | 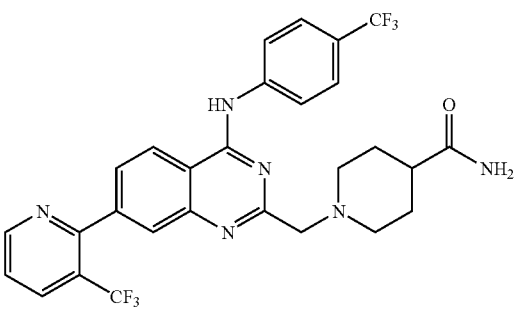 | 1-[4-(4-Trifluoromethyl-phenylamino)-7-(3-trifluoromethyl-pyridin-2-yl)-quinazolin-2-ylmethyl]-piperidine-4-carboxylic acid amide | 574.2 |
| 592. | 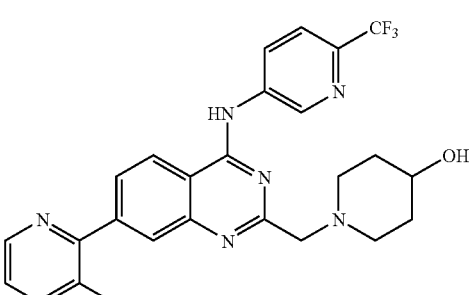 | 1-[7-(3-Trifluoromethyl-pyridin-2-yl)-4-(6-trifluoromethyl-pyridin-3-ylamino)-quinazolin-2-ylmethyl]-piperidin-4-ol | 548.2 |

TABLE VI-continued

Representative Substituted 2-Aminoalkyl-quinazolin-4-ylamine Analogues

| Compound | | | MS |
|---|---|---|---|
| 593. | 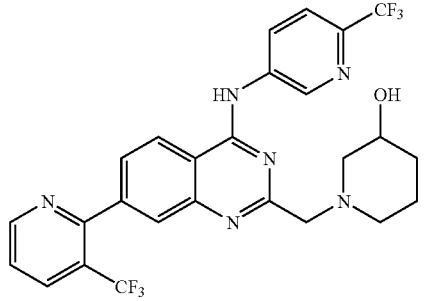 | 1-[7-(3-Trifluoromethyl-pyridin-2-yl)-4-(6-trifluoromethyl-pyridin-3-ylamino)-quinazolin-2-ylmethyl]-piperidin-3-ol | 548.2 |
| 594. | 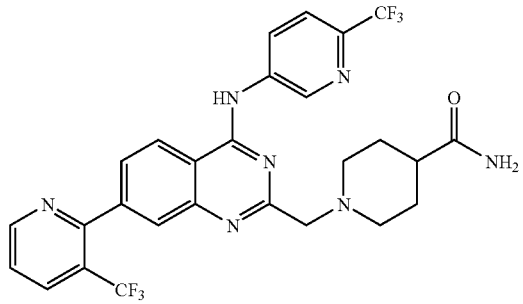 | 1-[7-(3-Trifluoromethyl-pyridin-2-yl)-4-(6-trifluoromethyl-pyridin-3-ylamino)-quinazolin-2-ylmethyl]-piperidine-4-carboxylic acid amide | 575.2 |
| 595. | 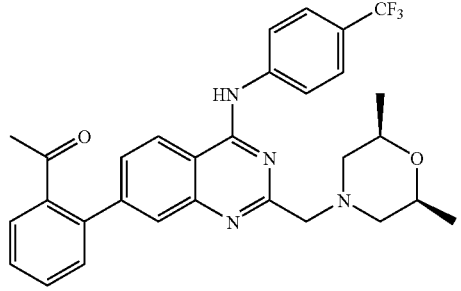 | 1-{2-[2-(2,6-Dimethyl-morpholin-4-ylmethyl)-4-(4-trifluoromethyl-phenylamino)-quinazolin-7-yl]-phenyl}-ethanone (cis) | |
| 596. | 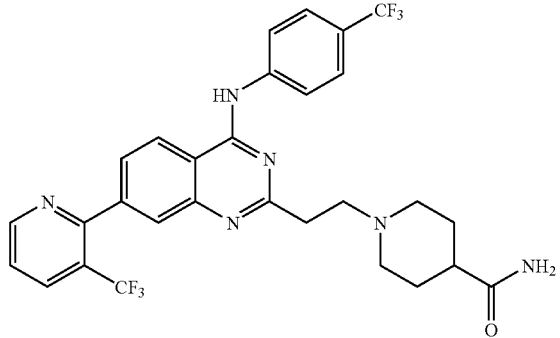 | 1-{2-[4-(4-Trifluoromethyl-phenylamino)-7-(3-trifluoromethyl-pyridin-2-yl)-quinazolin-2-yl]-ethyl}-piperidine-4-carboxylic acid amide | 588.2 |

TABLE VI-continued

Representative Substituted 2-Aminoalkyl-quinazolin-4-ylamine Analogues

| Compound | | | MS |
|---|---|---|---|
| 597. | 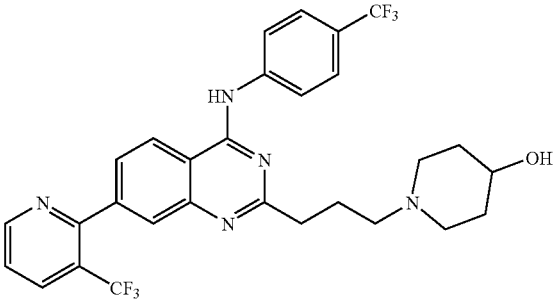 | 1-{3-[4-(4-Trifluoromethyl-phenylamino)-7-(3-trifluoromethyl-pyridin-2-yl)-quinazolin-2-yl]-propyl-piperidin-4-ol | 575.2 |
| 598. | 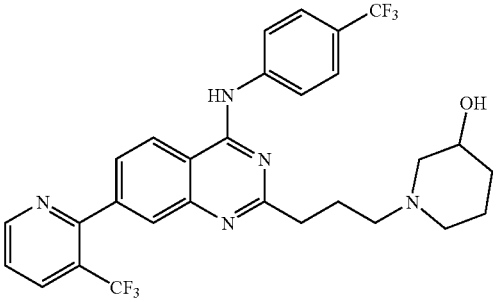 | 1-{3-[4-(4-Trifluoromethyl-phenylamino)-7-(3-trifluoromethyl-pyridin-2-yl)-quinazolin-2-yl]-propyl}piperidin-3-ol | 575.2 |
| 599. | 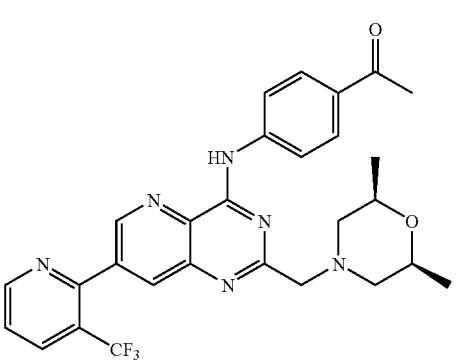 | 1-{4-[2-(2,6-Dimethyl-morpholin-4-ylmethyl)-7-(3-trifluoromethyl-pyridin-2-yl)-pyrido[3,2-d]pyrimidin-4-ylamino]-phenyl}-ethanone (cis) | |
| 600. | 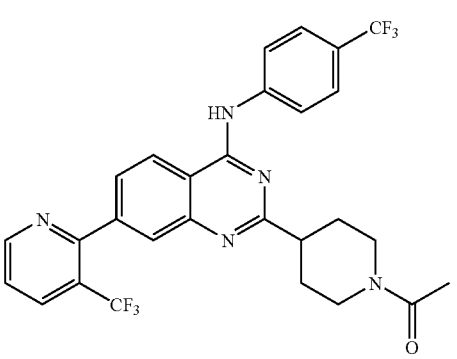 | 1-{4-[4-(4-Trifluoromethyl-phenylamino)-7-(3-trifluoromethyl-pyridin-2-yl)-quinazolin-2-yl]-piperidin-1-yl I -ethanone | |

TABLE VI-continued

Representative Substituted 2-Aminoalkyl-quinazolin-4-ylamine Analogues

| Compound | | MS |
|---|---|---|
| 601. | 1-{4-[4-(4-Trifluoromethyl-phenylamino)-7-(3-trifluoromethyl-pyridin-2-yl)-quinazolin-2-yl]-piperidin-1-yl}-propan-1-one | |
| 602. | 1-{4-[7-(3-Trifluoromethyl-pyridin-2-yl)-4-(6-trifluoromethyl-pyridin-3-ylamino)-quinazolin-2-ylmethyl]-piperazin-1-yl}-ethanone | 575.2 |
| 603. | 1-Pyrrolidin-1-yl-3-[4-(4-trifluoromethyl-phenylamino)-7-(3-trifluoromethyl-pyridin-2-yl)-quinazolin-2-yl]-propan-1-one | 559.2 |
| 604. | 2-(1-{3-[4-(4-Trifluoromethyl-phenylamino)-7-(3-trifluoromethyl-pyridin-2-yl)-quinazolin-2-yl]-propyl}-piperidin-4-yl)-ethanol | 603.2 |

TABLE VI-continued

Representative Substituted 2-Aminoalkyl-quinazolin-4-ylamine Analogues

| Compound | | | MS |
|---|---|---|---|
| 605. | 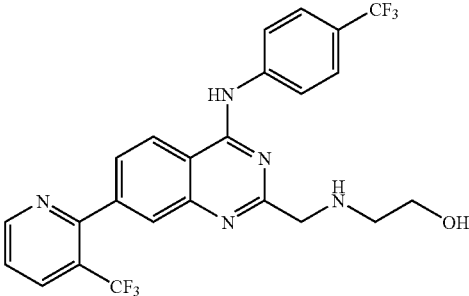 | 2-{[4-(4-Trifluoromethyl-phenylamino)-7-(3-trifluoromethyl-pyridin-2-yl)-quinazolin-2-ylmethyl]-amino}-ethanol | 507.1 |
| 606. | 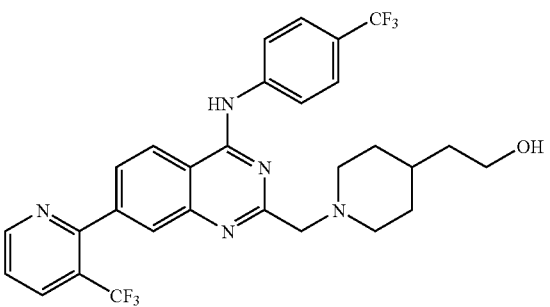 | 2-{1-[4-(4-Trifluoromethyl-phenylamino)-7-(3-trifluoromethyl-pyridin-2-yl)-quinazolin-2-ylmethyl]-piperidin-4-yl}-ethanol | 575.2 |
| 607. | 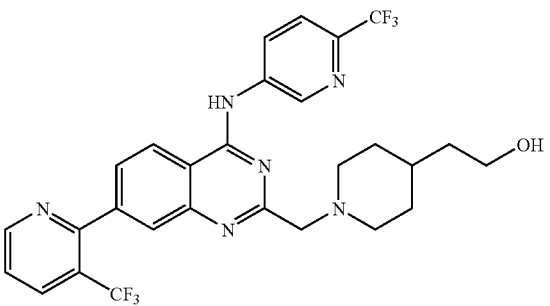 | 2-}-[7-(3-Trifluoromethyl-pyridin-2-yl)-4-(6-trifluoromethyl-pyridin-3-ylamino)-quinazolin-2-ylmethyl]-piperidin-4-yl}-ethanol | 576.2 |
| 608. | 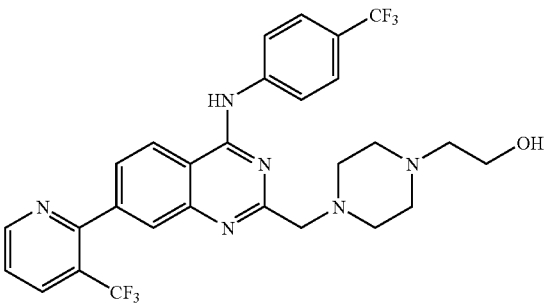 | 2-{4-[4-(4-Trifluoromethyl-phenylamino)-7-(3-trifluoromethyl-pyridin-2-yl)-quinazolin-2-ylmethyl]-piperazin-1-yl}-ethanol | 576.2 |

TABLE VI-continued

Representative Substituted 2-Aminoalkyl-quinazolin-4-ylamine Analogues

| Compound | | | MS |
|---|---|---|---|
| 609. | 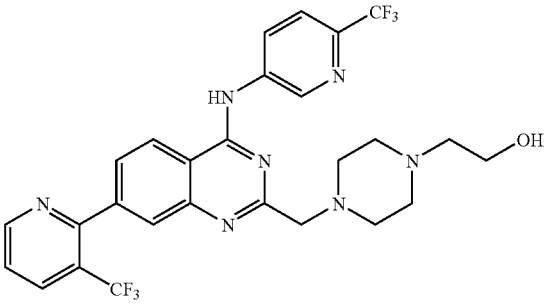 | 2-{4-[7-(3-Trifluoromethyl-pyridin-2-yl)-4-(6-trifluoromethyl-pyridin-3-ylamino)-quinazolin-2-ylmethyl]-piperazin-1-yl}-ethanol | 577.2 |
| 610. | 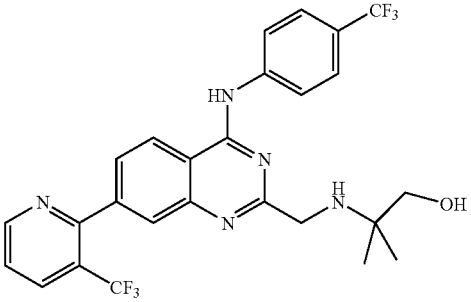 | 2-Methyl-2-{[4-(4-trifluoromethyl-phenylamino)-7-(3-trifluoromethyl-pyridin-2-yl)-quinazolin-2-ylmethyl]-amino}-propan-1-ol | |
| 611. | 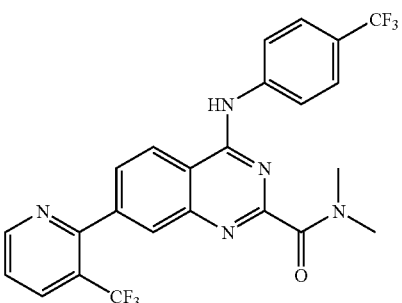 | 4-(4-Trifluoromethyl-phenylamino)-7-(3-trifluoromethyl-pyridin-2-yl)-quinazoline-2-carboxylic acid dimethylamide | |
| 612. | 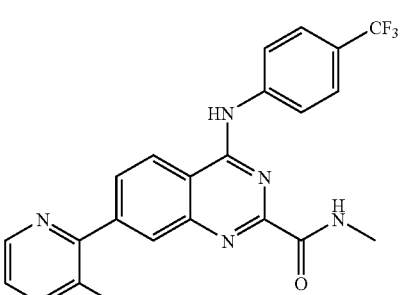 | 4-(4-Trifluoromethyl-phenylamino)-7-(3-trifluoromethyl-pyridin-2-yl)-quinazoline-2-carboxylic acid methylamide | |

TABLE VI-continued

Representative Substituted 2-Aminoalkyl-quinazolin-4-ylamine Analogues

| Compound | | MS |
|---|---|---|
| 613. | 4-(4-Trifluoromethyl-phenylamino)-7-(3-trifluoromethyl-pyriclin-2-yl)-quinazoline-2-carboxylic acid (2-dimethylamino-ethyl)-amide | |
| 614. | 4-(4-Trifluoromethyl-phenylamino)-7-(3-trifluoromethyl-pyriclin-2-yl)-quinazoline-2-carboxylic acid (2-morpholin-4-yl-ethyl)-amide | |
| 615. | 4-{2-[4-(4-Trifluoromethyl-phenylamino)-7-(3-trifluoromethyl-pyridin-2-yl)-quinazolin-2-yl]-ethyl}-piperazine-1-carbaldehyde | 574.2 |
| 616. | N,N,N'-Trimethyl-N'-[4-(4-trifluoromethyl-phenylamino)-7-(3-trifluoromethyl-pyridin-2-yl)-quinazolin-2-ylmethyl]-propane-1,3-diamine | |

TABLE VI-continued

Representative Substituted 2-Aminoalkyl-quinazolin-4-ylamine Analogues

| Compound | | | MS |
|---|---|---|---|
| 617. | | N-[4-(4-Trifluoromethyl-phenylamino)-7-(3-trifluoromethyl-pyridin-2-yl)-quinazolin-2-ylmethyl]-methanesulfonamide | 541.1 |
| 618. | | [2-Dimethylaminomethyl-7-(3-methyl-pyridin-2-yl)-quinazolin-4-yl]-(4-isopropyl-phenyl)-amine | 411.2 |
| 619. | | (4-Isopropyl-phenyl)-[7-(3-methyl-pyridin-2-yl)-2-morpholin-4-ylmethyl-quinazolin-4-yl]-amine | 453.3 |
| 620. | | (4-Isopropyl-phenyl)-[7-(3-methyl-pyridin-2-yl)-2-thiomorpholin-4-ylmethyl-quinazolin-4-yl]-amine | 469.2 |

TABLE VI-continued

Representative Substituted 2-Aminoalkyl-quinazolin-4-ylamine Analogues

| Compound | | | MS |
|---|---|---|---|
| 621. | 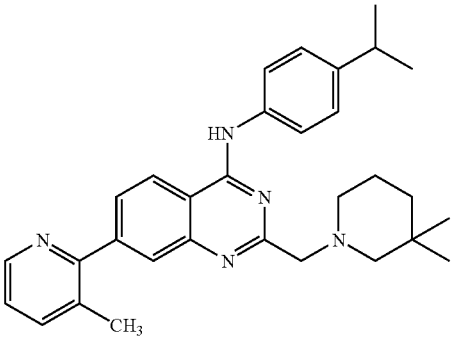 | [2-(3,3-Dimethyl-piperidin-1-ylmethyl)-7-(3-methyl-pyridin-2-yl)-quinazolin-4-yl]-(4-isopropyl-phenyl)-amine | 479.3 |
| 622. | 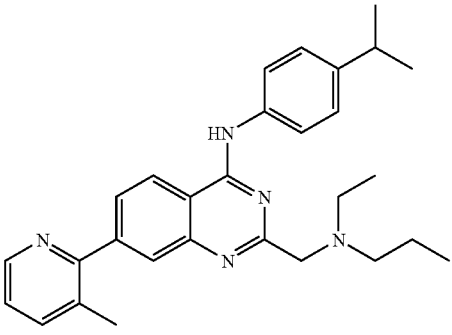 | [2-[(Ethyl-propyl-amino)-methyl]-7-(3-methyl-pyridin-2-yl)-quinazolin-4-yl]-(4-isopropyl-phenyl)-amine | 439.3 |
| 623. | 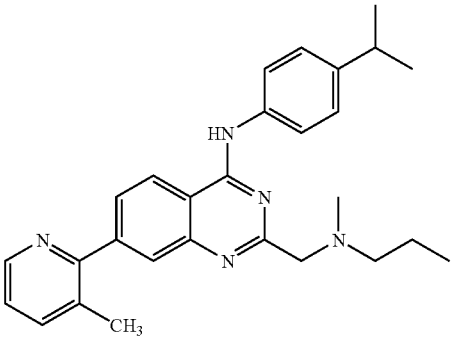 | (4-Isopropyl-phenyl)-[2-[(methyl-propyl-amino)-methyl]-7-(3-methyl-pyridin-2-yl)-quinazolin-4-yl]-amine | 439.3 |
| 624. | 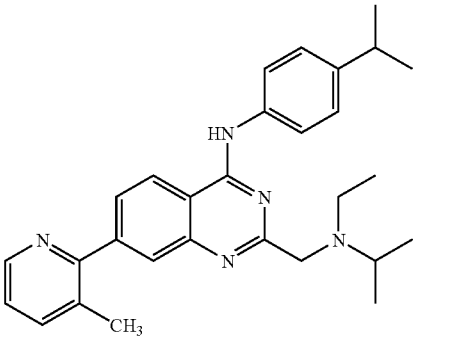 | [2-[(Ethyl-isopropyl-amino)-methyl]-7-(3-methyl-pyridin-2-yl)-quinazolin-4-yl]-(4-isopropyl-phenyl)-amine | 453.3 |

TABLE VI-continued

Representative Substituted 2-Aminoalkyl-quinazolin-4-ylamine Analogues

| Compound | | | MS |
|---|---|---|---|
| 625. | 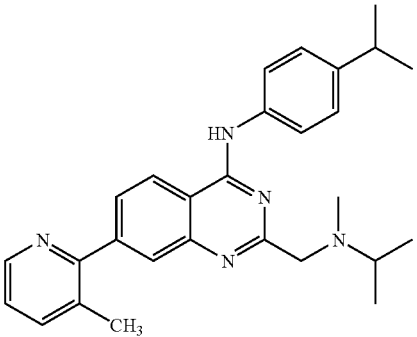 | [2-[(Isopropyl-methyl-amino)-methyl]-7-(3-methyl-pyridin-2-yl)-quinazolin-4-yl]-(4-isopropyl-phenyl)-amine | 439.3 |
| 626. | 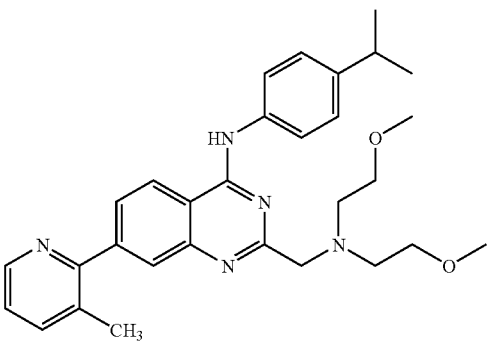 | [2-{[Bis-(2-methoxy-ethyl)-amino]-methyl}-7-(3-methyl-pyridin-2-yl)-quinazolin-4-yl]-(4-isopropyl-phenyl)-amine | 499.3 |
| 627. | 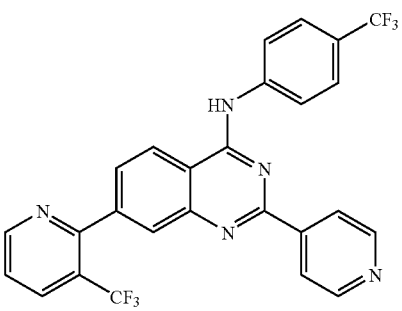 | [2-Pyridin-4-yl-7-(3-trifluoromethyl-pyridin-2-yl)-quinazolin-4-yl]-(4-trifluoromethyl-phenyl)-amine | 511.1 |
| 628. | 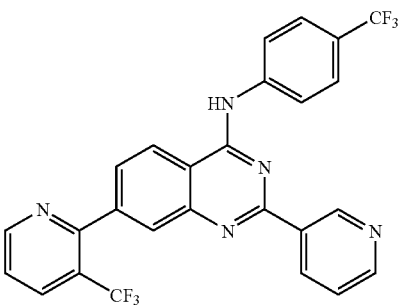 | [2-Pyridin-3-yl-7-(3-trifluoromethyl-pyridin-2-yl)-quinazolin-4-yl]-(4-trifluoromethyl-phenyl)-amine | 511.1 |

TABLE VI-continued

Representative Substituted 2-Aminoalkyl-quinazolin-4-ylamine Analogues

| Compound | | MS |
|---|---|---|
| 629. | 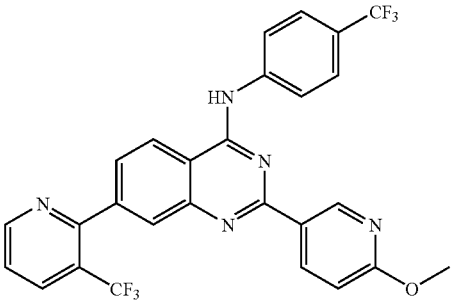 [2-(6-Methoxy-pyridin-3-yl)-7-(3-trifluoromethyl-pyridin-2-yl)-quinazolin-4-yl]-(4-trifluoromethyl-phenyl)-amine | 541.1 |
| 630. | 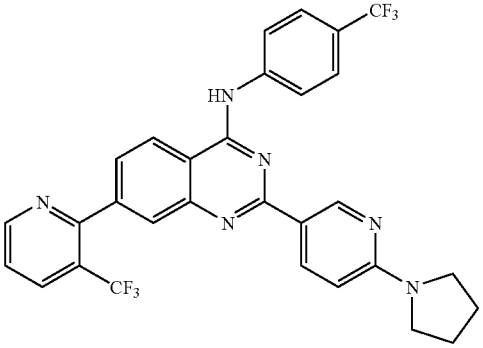 [2-(6-Pyrrolidin-1-yl-pyridin-3-yl)-7-(3-trifluoromethyl-pyridin-2-yl)-quinazolin-4-yl]-(4-trifluoromethyl-phenyl)-amine | 580.2 |
| 631. | 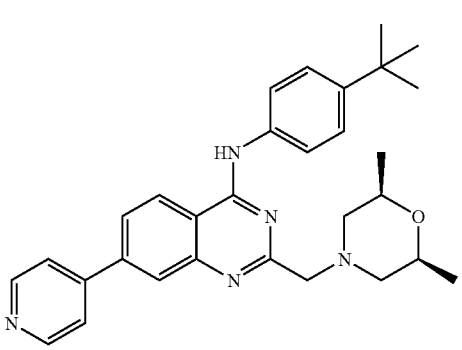 (4-tert-Butyl-phenyl)-[2-(2,6-dimethyl-morpholin-4-ylmethyl)-7-pyridin-4-yl-quinazolin-4-yl]-amine (cis) | 481.3 |
| 632. | 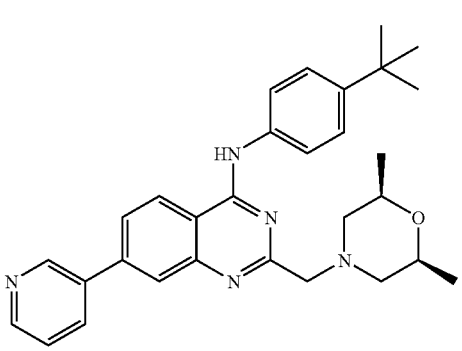 (4-tert-Butyl-phenyl)-[2-(2,6-dimethyl-morpholin-4-ylmethyl)-7-pyridin-3-yl-quinazolin-4-yl]-amine (cis) | 481.3 |

TABLE VI-continued

Representative Substituted 2-Aminoalkyl-quinazolin-4-ylamine Analogues

| Compound | | MS |
|---|---|---|
| 633. | 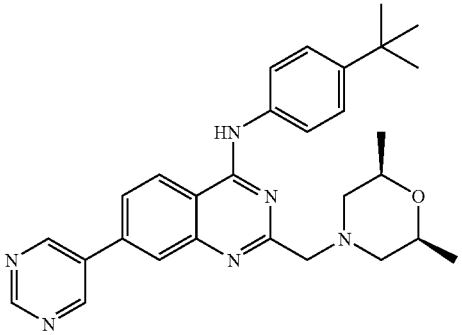 | (4-tert-Butyl-phenyl)-[2-(2,6-dimethyl-morpholin-4-ylmethyl)-7-pyrimidin-5-yl-quinazolin-4-yl]-amine (cis) |
| 634. | 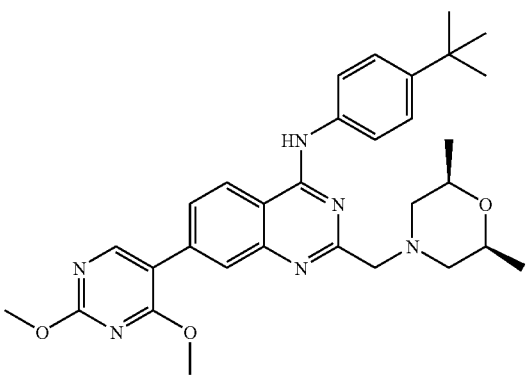 | (4-tert-Butyl-phenyl)-[7-(2,4-dimethoxy-pyrimidin-5-yl)-2-(2,6-dimethyl-morpholin-4-ylmethyl)-quinazolin-4-yl]-amine (cis) |
| 635. | 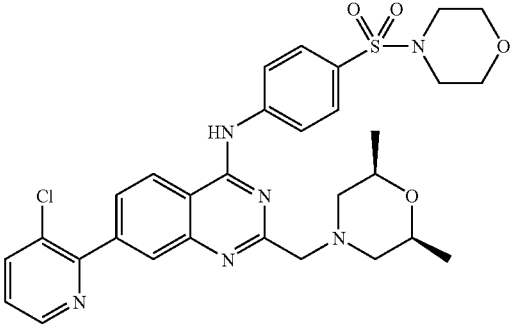 | [7-(3-Chloro-pyridin-2-yl)-2-(2,6-dimethyl-morpholin-4-ylmethyl)-pyrido[3,2-d]pyrimidin-4-yl]-[4-(morpholine-4-sulfonyl)-phenyl]-amine |
| 636. | 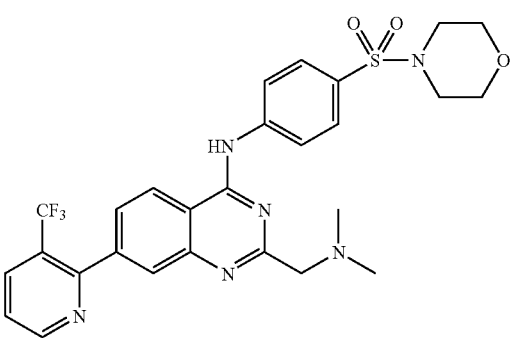 | [2-Dimethylaminomethyl-7-(3-trifluoromethyl-pyridin-2-yl)-quinazolin-4-yl]-[4-(morpholine-4-sulfonyl)-phenyl]-amine |

TABLE VI-continued

Representative Substituted 2-Aminoalkyl-quinazolin-4-ylamine Analogues

| Compound | | MS |
|---|---|---|
| 637. | 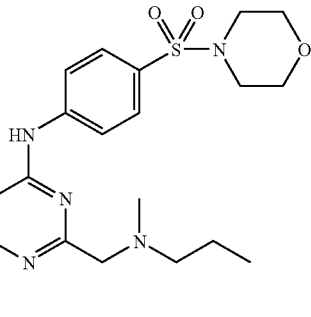 | [2-[-Methyl-propyl-amino)-methyl]-7-(3-trifluoromethyl-pyridin-2-yl)-quinazolin-4-yl]-[4-(morpholine-4-sulfonyl)-phenyl]-amine |
| 638. | 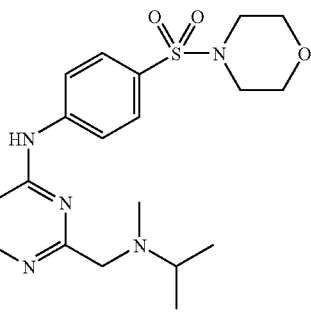 | [2-[(Isopropyl-methyl-amino)-methyl]-7-(3-trifluoromethyl-pyridin-2-yl)-quinazolin-4-yl]-[4-(morpholine-4-sulfonyl)-phenyl]-amine |
| 639. | 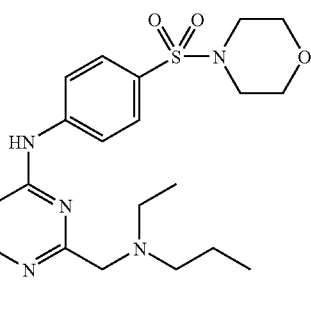 | [2-[(Ethyl-propyl-amino)-methyl]-7-(3-trifluoromethyl-pyridin-2-yl)-quinazolin-4-yl]-[4-(morpholine-4-sulfonyl)-phenyl]-amine |
| 640. | 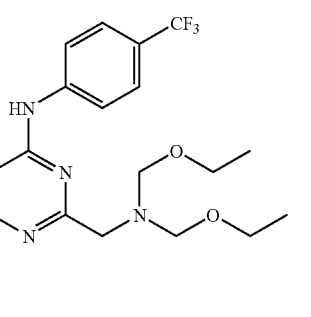 | [2-[(Bis-ethoxymethyl-amino)-methyl]-7-(3-methyl-pyridin-2-yl)-quinazolin-4-yl]-(4-trifluoromethyl-phenyl)-amine |

TABLE VI-continued

Representative Substituted 2-Aminoalkyl-quinazolin-4-ylamine Analogues

| Compound | | MS |
|---|---|---|
| 641. 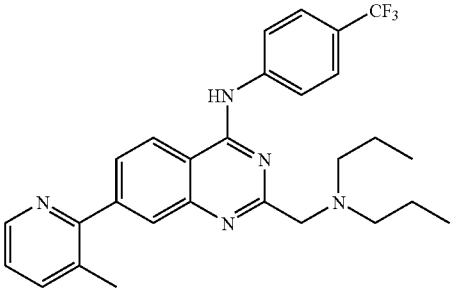 | [2-Dipropylaminomethyl-7-(3-methyl-pyridin-2-yl)-quinazolin-4-yl]-(4-trifluoromethyl-phenyl)-amine | |
| 642. 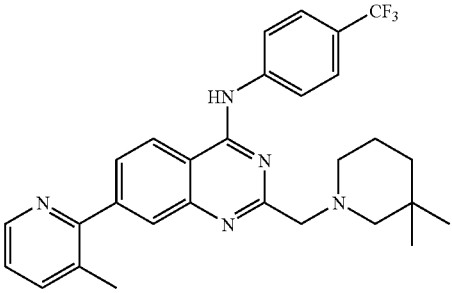 | [2-(3,3-Dimethyl-piperidin-1-ylmethyl)-7-(3-methyl-pyridin-2-yl)-quinazolin-4-yl]-(4-trifluoromethyl-phenyl)-amine | |
| 643. 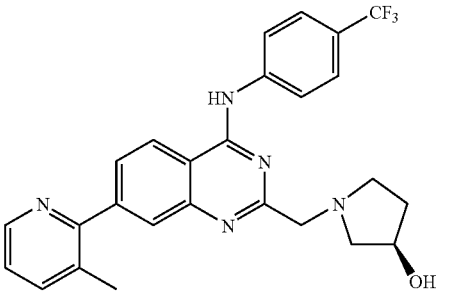 | 1-[7-(3-Methyl-pyridin-2-yl)-4-(4-trifluoromethyl-phenylamino)-quinazolin-2-ylmethyl]-pyrrolidin-3-ol (chiral) | |
| 644. 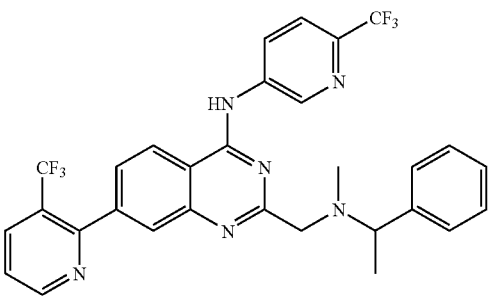 | [2-{[Methyl-(1-phenyl-ethyl)-amino]-methyl}-7-(3-trifluoromethyl-pyridin-2-yl)-quinazolin-4-yl]-(6-trifluoromethyl-pyridin-3-yl)-amine | |
| 645. 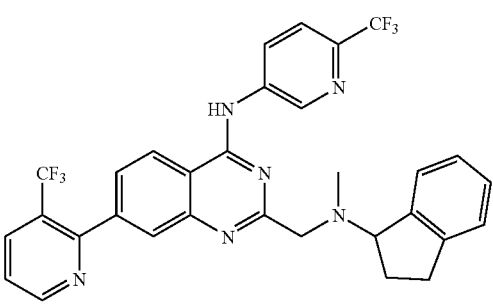 | [2-[(Indan-1-yl-methyl-amino)-methyl]-7-(3-trifluoromethyl-pyridin-2-yl)-quinazolin-4-yl]-(6-trifluoromethyl-pyridin-3-yl)-amine | |

TABLE VI-continued

Representative Substituted 2-Aminoalkyl-quinazolin-4-ylamine Analogues

| Compound | | MS |
|---|---|---|
| 646. | 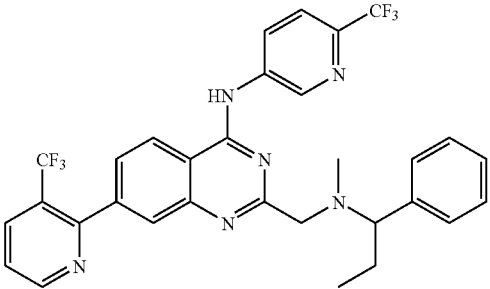 [2-{[Methyl-(1-phenyl-propyl)-amino]-methyl}-7-(3-trifluoromethyl-pyridin-2-yl)-quinazolin-4-yl]-(6-trifluoromethyl-pyridin-3-yl)-amine | |
| 647. | 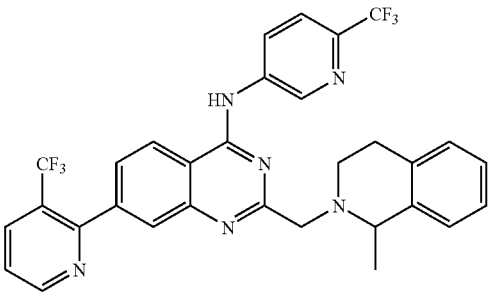 [2-(1-Methyl-3,4-dihydro-1H-isoquinolin-2-ylmethyl)-7-(3-trifluoromethyl-pyridin-2-yl)-quinazolin-4-yl]-(6-trifluoromethyl-pyridin-3-yl)-amine | |
| 648. | 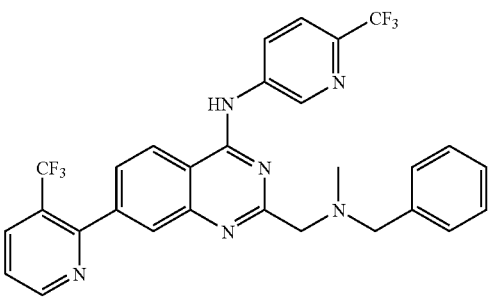 [2-[(Benzyl-methyl-amino)-methyl]-7-(3-trifluoromethyl-pyridin-2-yl)-quinazolin-4-yl]-(6-trifluoromethyl-pyridin-3-yl)-amine | |
| 649. | 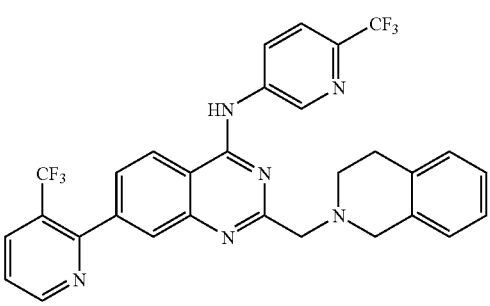 [2-(3,4-Dihydro-1H-isoquinolin-2-ylmethyl)-7-(3-trifluoromethyl-pyridin-2-yl)-quinazolin-4-yl]-(6-trifluoromethyl-pyridin-3-yl)-amine | |
| 650. | 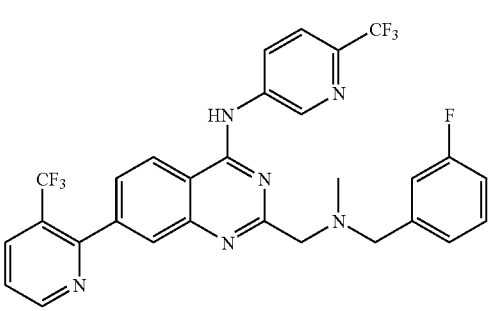 [2-{[(3-Fluoro-benzyl)-methyl-amino]-methyl}-7-(3-trifluoromethyl-pyridin-2-yl)-quinazolin-4-yl]-(6-trifluoromethyl-pyridin-3-yl)-amine | |

TABLE VI-continued

Representative Substituted 2-Aminoalkyl-quinazolin-4-ylamine Analogues

| Compound | | MS |
|---|---|---|
| 651. | 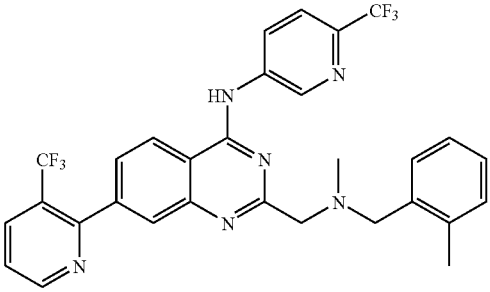 [2-{[Methyl-(2-methyl-benzyl)-amino]-methyl}-7-(3-trifluoromethyl-pyridin-2-yl)-quinazolin-4-yl]-(6-trifluoromethyl-pyridin-3-yl)-amine | |
| 652. | 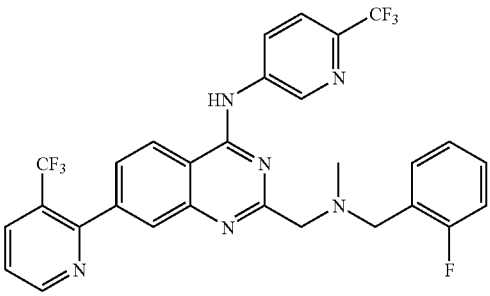 [2-{[(2-Fluoro-benzyl)-methyl-amino]-methyl}-7-(3-trifluoromethyl-pyridin-2-yl)-quinazolin-4-yl]-(6-trifluoromethyl-pyridin-3-yl)-amine | |
| 653. | 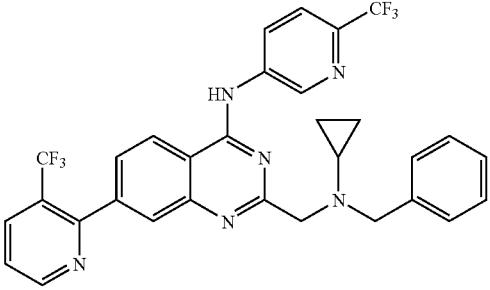 [2-[(Benzyl-cyclopropyl-amino)-methyl]-7-(3-trifluoromethyl-pyridin-2-yl)-quinazolin-4-yl]-(6-trifluoromethyl-pyridin-3-yl)-amine | |
| 654. | 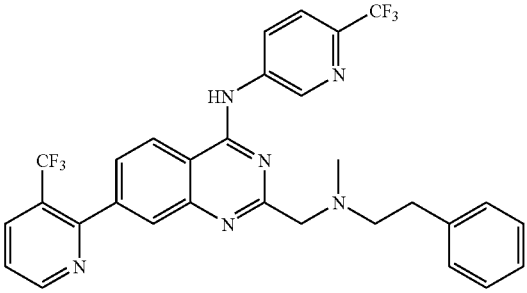 [2-[(Methyl-phenethyl-amino)-methyl]-7-(3-trifluoromethyl-pyridin-2-yl)-quinazolin-4-yl]-(6-trifluoromethyl-pyridin-3-yl)-amine | |
| 655. | 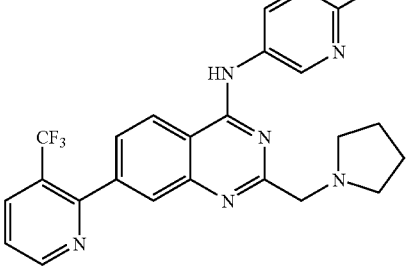 [2-Pyrrolidin-1-ylmethyl-7-(3-trifluoromethyl-pyridin-2-yl)-quinazolin-4-yl]-(6-trifluoromethyl-pyridin-3-yl)-amine | |

TABLE VI-continued

Representative Substituted 2-Aminoalkyl-quinazolin-4-ylamine Analogues

| Compound | | MS |
|---|---|---|
| 656. | | [2-Piperidin-1-ylmethyl-7-(3-trifluoromethyl-pyridin-2-yl)-quinazolin-4-yl]-(6-trifluoromethyl-pyridin-3-yl)-amine |
| 657. | | [2-(4-Methyl-piperidin-1-ylmethyl)-7-(3-trifluoromethyl-pyridin-2-yl)-quinazolin-4-yl]-(6-trifluoromethyl-pyridin-3-yl)-amine |
| 658. | | [2-Azepan-1-ylmethyl-7-(3-trifluoromethyl-pyridin-2-yl)-quinazolin-4-yl]-(6-trifluoromethyl-pyridin-3-yl)-amine |
| 659. | | [2-Azocan-1-ylmethyl-7-(3-trifluoromethyl-pyridin-2-yl)-quinazolin-4-yl]-(6-trifluoromethyl-pyridin-3-yl)-amine |
| 660. | | (6-Trifluoromethyl-pyridin-3-yl)-[7-(3-trifluoromethyl-pyridin-2-yl)-2-(3,3,5-trimethyl-azepan-1-ylmethyl)-quinazolin-4-yl]-amine |

TABLE VI-continued

Representative Substituted 2-Aminoalkyl-quinazolin-4-ylamine Analogues

| Compound | | MS |
|---|---|---|
| 661. | | [2-(1,4-Dioxa-8-aza-spiro[4.5]dec-8-ylmethyl)-7-(3-trifluoromethyl-pyridin-2-yl)-quinazolin-4-yl]-(6-trifluoromethyl-pyridin-3-yl)-amine |
| 662. | | [2-(Octahydro-quinolin-1-ylmethyl)-7-(3-trifluoromethyl-pyridin-2-yl)-quinazolin-4-yl]-(6-trifluoromethyl-pyridin-3-yl)-amine |
| 663. | | [2-Dimethylaminomethyl-7-(3-trifluoromethyl-pyridin-2-yl)-quinazolin-4-yl]-(6-trifluoromethyl-pyridin-3-yl)-amine |
| 664. | | [2-[(Allyl-methyl-amino)-methyl]-7-(3-trifluoromethyl-pyridin-2-yl)-quinazolin-4-yl]-(6-trifluoromethyl-pyridin-3-yl)-amine |
| 665. | | [2-Diethylaminomethyl-7-(3-trifluoromethyl-pyridin-2-yl)-quinazolin-4-yl]-(6-trifluoromethyl-pyridin-3-yl)-amine |

TABLE VI-continued

Representative Substituted 2-Aminoalkyl-quinazolin-4-ylamine Analogues

| Compound | | MS |
|---|---|---|
| 666. | | [2-[(Methyl-propyl-amino)-methyl]-7-(3-trifluoromethyl-pyridin-2-yl)-quinazolin-4-yl]-(6-trifluoromethyl-pyridin-3-yl)-amine |
| 667. | | [2-[(Butyl-methyl-amino)-methyl]-7-(3-trifluoromethyl-pyridin-2-yl)-quinazolin-4-yl]-(6-trifluoromethyl-pyridin-3-yl)-amine |
| 668. | | [2-[(Ethyl-isopropyl-amino)-methyl]-7-(3-trifluoromethyl-pyridin-2-yl)-quinazolin-4-yl]-(6-trifluoromethyl-pyridin-3-yl)-amine |
| 669. | | [2-Diallylaminomethyl-7-(3-trifluoromethyl-pyridin-2-yl)-quinazolin-4-yl]-(6-trifluoromethyl-pyridin-3-yl)-amine |
| 670. | | [2-Dipropylaminomethyl-7-(3-trifluoromethyl-pyridin-2-yl)-quinazolin-4-yl]-(6-trifluoromethyl-pyridin-3-yl)-amine |

TABLE VI-continued

Representative Substituted 2-Aminoalkyl-quinazolin-4-ylamine Analogues

| Compound | | MS |
|---|---|---|
| 671. 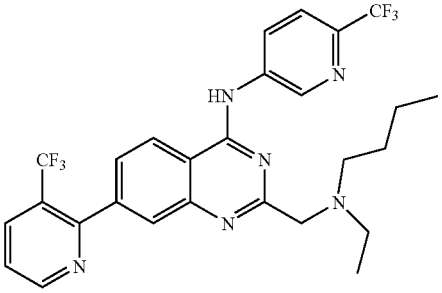 | [2-[(Butyl-ethyl-amino)-methyl]-7-(-3-trifluoromethyl-pyridin-2-yl)-quinazolin-4-yl]-(6-trifluoromethyl-pyridin-3-yl)-amine | |
| 672. 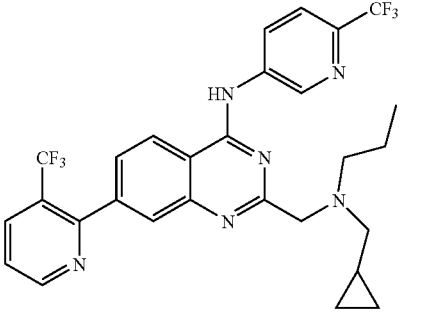 | [2-[(Cyclopropylmethyl-propyl-amino)-methyl]-7-(3-trifluoromethyl-pyridin-2-yl)-quinazolin-4-yl]-(6-trifluoromethyl-pyridin-3-yl)-amine | |
| 673. 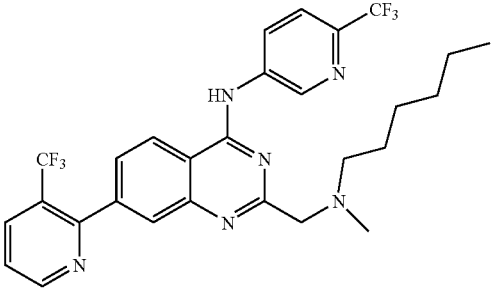 | [2-[(Hexyl-methyl-amino)-methyl]-7-(3-trifluoromethyl-pyridin-2-yl)-quinazolin-4-yl]-(6-trifluoromethyl-pyridin-3-yl)-amine | |

| Compound | Name | MS |
|---|---|---|
| 674. 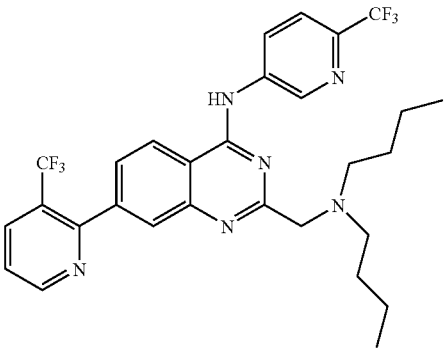 | [2-Dibutylaminomethyl-7-(3-trifluoromethyl-pyridin-2-yl)-quinazolin-4-yl]-(6-tritluoromethyl-pyridin-3-yl)-amine | |

| Compound | | Name | MS |
|---|---|---|---|
| 675. | | [2-[(Isopropyl-methyl-amino)-methyl]-7-(3-trifluoromethyl-pyridin-2-yl)-quinazolin-4-yl]-(6-trifluoromethyl-pyridin-3-yl)-amine | |
| 676. | | [2-(2-Methyl-piperidin-1-ylmethyl)-7-(3-trifluoromethyl-pyridin-2-yl)-quinazolin-4-yl]-(6-trifluoromethyl-pyridin-3-yl)-amine | |
| 677. | | [2-{[Ethyl-(2-methyl-allyl)-amino]-methyl}]-7-(3-trifluoromethyl-pyndin-2-yl)-quinazolin-4-yl]-(6-trifluoromethyl-pyridin-3-yl)-amine | |
| 678. | | [2-[(Cyclohexyl-methyl-amino)-methyl]-7-(3-trifluoromethyl-pyridin-2-yl)-quinazolin-4-yl]-(6-trifluoromethyl-pyridin-3-yl)-amine | |
| 679. | | [2-(2-Ethyl-piperidin-1-ylmethyl)-7-(3-trifluoromethyl-pyridin-2-yl)-quinazolin-4-yl]-(6-trifluoromethyl-pyridin-3-yl)-amine | |

| Compound | | Name | MS |
|---|---|---|---|
| 680. | (structure) | [2-](Cyclohexyl-ethyl-amino)-methyl]-7-(3-trifluoromethyl-pyridin-2-yl)-quinazolin-4-yl]-(6-trifluoromethyl-pyridin-3-yl)-amine | |
| 681. | (structure) | [2-{[Bis-(2-methoxy-ethyl)-amino]-methyl}-7-(3-trifluoromethyl-pyridin-2-yl)-quinazolin-4-yl]-(6-trifluoromethyl-pyridin-3-yl)-amine | |
| 682. | (structure) | [2-Dipentylaminomethyl-7-(3-trifluoromethyl-pyridin-2-yl)-quinazolin-4-yl]-(6-trifluoromethyl-pyridin-3-yl)-amine | |
| 683. | (structure) | [2-Dihexylaminomethyl-7-(3-trifluoromethyl-pyridin-2-yl)-quinazolin-4-yl]-(6-trifluoromethyl-pyridin-3-yl)-amine | |

-continued

| Compound | | Name | MS |
|---|---|---|---|
| 684. | | [2-(3,5-Dimethyl-piperidin-1-ylmethyl)-7-(3-trifluoromethyl-pyridin-2-yl)-quinazolin-4-yl]-(6-trifluoromethyl-pyridin-3-yl)-anime | |
| 685. | | {1-[7-(3-Methyl-pyridin-2-yl)-4-(4-trifluoromethyl-phenylamino)-quinazolin-2-ylmethyl]-pyrrolidin-3-yl}-methanol (chiral) | |
| 686. | | {1-[7-(3-Methyl-pyridin-2-yl)-4-(4-trifluoromethyl-phenylamino)-quinazolin-2-ylmethyl]-pyrrolidin-3-yl}-methanol (chiral) | |
| 687. | | [2-(2,6-Dimethyl-morpholin-4-ylmethyl)-7-(3-methyl-pyridin-2-yl)-pyrido[2,3-d]pyrimidin-4-yl]-(4-trifluoromethyl-phenyl)-amine | |
| 688. | | [2-Azetidin-3-yl-7-(3-methyl-pyridin-2-yl)-pyrido[2,3-d]pyrimidin-4-yl]-(4-trifluoromethyl-phenyl)-amine | |

-continued

| Compound | | Name | MS |
|---|---|---|---|
| 689. | 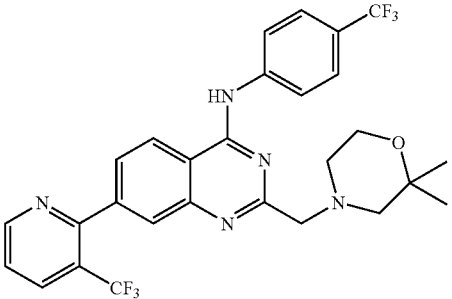 | [2-(2,2-Dimethyl-morpholin-4-ylmethyl)-7-(3-trifluoromethyl-trifluoromethyl-phenyl)-amine | |
| 690. | 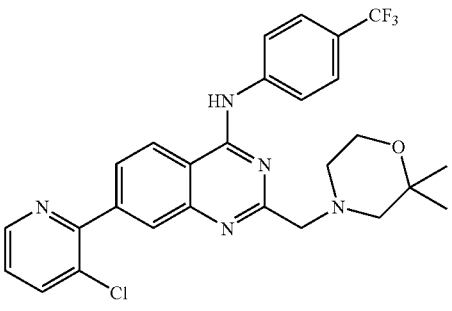 | [7-(3-Chloro-pyridin-2-yl)-2-(2,2-dimethyl-morpholin-4-ylmethyl)-quinazolin-4-yl]-(4-trifluoromethyl-phenyl)-amine | |
| 691. | 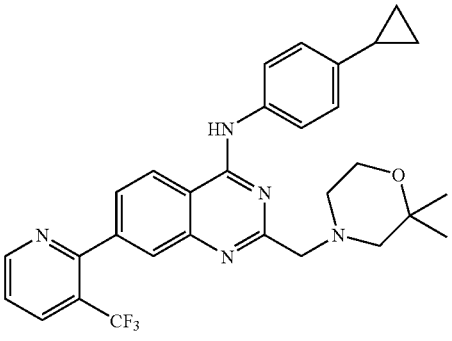 | (4-Cyclopropyl-phenyl)-[2-(2,2-dimethyl-morpholin-4-ylmethyl)-7-(3-trifluoromethyl-pyridin-2-yl)-quinazolin-4-yl]-amine | |
| 692. | 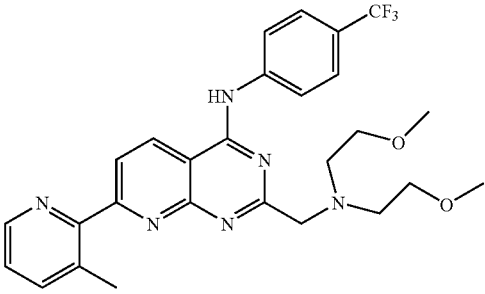 | [2-(2,2-Dimethyl-morpholin-4-ylmethyl)-7-(3-trifluoromethyl-pyridin-2-yl)-pyrido[3,2-d]pyrimidin-4-yl]-(4-trifluorohiethyl-phenyl)-amine | |
| 693. | 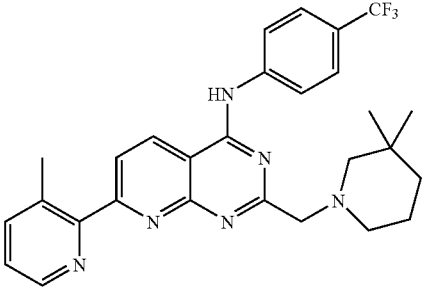 | [2-{[Bis-(2-methoxy-ethyl)-amino]-methyl}-7-(3-methyl-pyridin-2-yl)-pyrido[2,3-d]pyrimidin-4-yl]-(4-trifluoromethyl-phenyl)-amine | |

-continued

| Compound | | Name | MS |
|---|---|---|---|
| 694. | 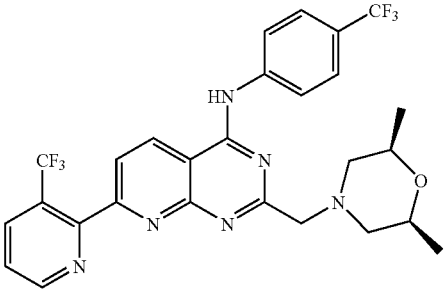 | [2-(3,3-Dimethyl-piperidin-1-ylmethyl)-7-(3-methyl-pyridin-2-yl)-pyrido[2,3-d]pyrimidin-4-yl]-(4-trifluoromethyl-phenyl)-amine | |
| 695. | 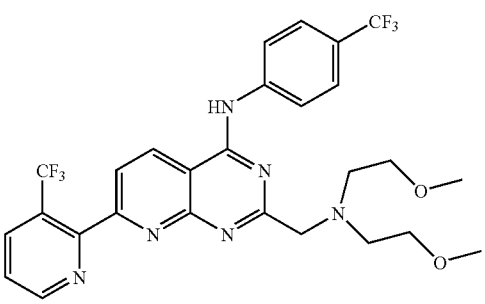 | [2-(2,6-Dimethyl-morpholin-4-ylmethyl)-7-(3-trifluoromethyl-pyridin-2-yl)-pyrido[2,3-d]pyrimidin-4-yl]-(4-trifluoromethyl-phenyl)-amine | |
| 696. | 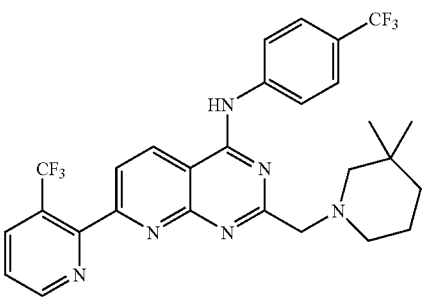 | [2-{[Bis-(2-methoxy-ethyl)-amino]-methyl}-7-(3-trifluoromethyl-pyridin-2-yl)-pyrido[2,3-d]pyrimidin-4-yl]-(4-trifluoromethyl-phenyl)-amine | |
| 697. | 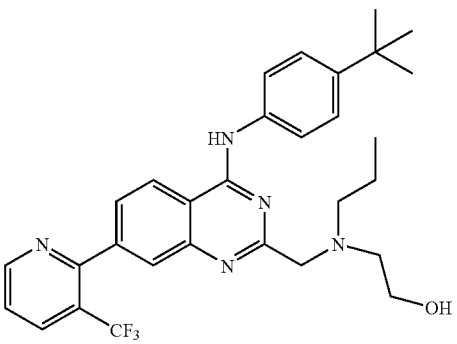 | [2-(3,3-Dimethyl-piperidin-1-ylmethyl)-7-(3-trifluoromethyl-pyridin-2-yl)-pyrido[2,3-d]pyrimidin-4-yl]-(4-trifluoromethyl-phenyl)-amine | |

| Compound | | Name | MS |
|---|---|---|---|
| 698. | (structure) | 2-{[4-(4-tert-Butyl-phenylamino)-7-(3-trifluoromethyl-pyridin-2-yl)-quinazolin-2-ylmethyl]-propyl-amino}-ethanol | |
| 699. | (structure) | {1-[4-(4-tert-Butyl-phenylamino)-7-(3-trifluoromethyl-pyridin-2-yl)-quinazolin-2-ylmethyl]-pyrrolidin-2-yl}-methanol | |
| 700. | (structure) | [2-(1,1-Dioxo-1$\lambda^6$-[1,2]thiazinan-2-ylmethyl)-7-(3-trifluoromethyl-pyridin-2-yl)-quinazolin-4-yl]-(4-trifluoromethyl-phenyl)-amine | |

EXAMPLE 3

Preparation of Representative Compounds

This Example illustrates the preparation of representative substituted 2-hydroxyalkyl-quinazolin-4-ylamine analogues.

A. [2-Isopropoxymethyl-7-(3-trifluoromethyl-pyridin-2-yl)-quinazolin-4-yl]-(4-trifluoromethyl-phenyl)-amine ester (compound 701)

4. 2-p-tolyl-3-trifluoromethyl-pyridine

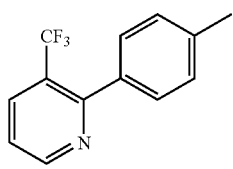

To a de-gassed mixture of 2-chloro-3-(trifluoromethyl)-pyridine (70.1 mmol), p-tolylboronic acid (70.6 mmol), and 2M Na$_2$CO$_3$ (175.0 mmol), in dimethyl ether (DME; 200 mL) under nitrogen add Pd(PPh$_3$)$_4$ (2.8 mmol). Stir the mixture at 80° C. overnight, concentrate, and extract with EtOAc. Dry over Na$_2$SO$_4$, concentrate under vacuum, and pass through a silica gel pad to give 2-p-tolyl-3-trifluoromethyl-pyridine.

5. 2-(4-methyl-3-nitro-phenyl)-3-(trifluoromethyl)-pyridine

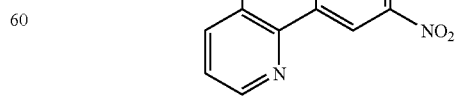

To a solution of 2-p-tolyl-3-trifluoromethyl-pyridine (8.4 mmol) in H$_2$SO$_4$ (6 mL) cautiously add fuming HNO$_3$ (2 ml). Stir the mixture for 60 minutes at room temperature.

Pour the mixture onto ice-water (30 mL), extract with EtOAc, neutralize with 1 N NaOH, dry over Na₂SO₄, and concentrate under vacuum to obtain 2-(4-methyl-3-nitrophenyl)-3-(trifluoromethyl)-pyridine.

6. 2-nitro-4-(3-trifluoromethyl-pyridin-2-yl)-benzoic acid

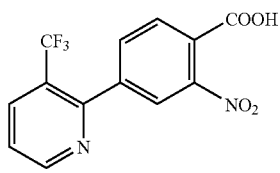

To a solution of 2-(4-methyl-3-nitro-phenyl)-3-(trifluoromethyl)-pyridine (7.1 mmol) in a mixture of pyridine (10 mL) and water (5 ml), add KMnO₄ (25.3 mmol) portionwise. Stir the mixture for 4 hours at 110° C., and then add another 25.3 mmol of KMnO₄ with 10 ml of water. Stir the mixture at 110° C. over night. Cool to room temperature, and filter through celite pad. Concentrate the filtrate under vacuum, dilute with water, and wash the aqueous solution with EtOAc. Neutralize the aqueous solution with 2 N HCl and collect the precipitate to give 2-nitro-4(3-trifluoromethyl-pyridin-2-yl)-benzoic acid.

4. 2-nitro-4-(3-trifluoromethyl-pyridin-2-yl)-benzamide

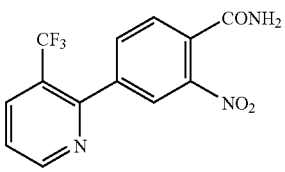

Reflux a mixture of 2-amino-4-(3-trifluoromethyl-pyridin-2-yl)-benzoic acid (25 g) with SOCl₂ (50 ml) for 4 hours and concentrate. Dissolve the residue in dichloromethane (DCM), cool with ice-water bath, pass NH₃ gas through the solution for 30 minutes, and stir for 15 minutes at room temperature. Concentrate and wash with water to give 2-nitro-4-(3-trifluoromethyl-pyridin-2-yl)-benzamide.

5. 2-amino-4-(3-trifluoromethyl-pyridin-2-yl)-benzamide

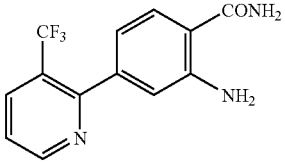

Hydrogenate 2-nitro-4-(3-trifluoromethyl-pyridin-2-yl)-benzamide (1.0 g, 0.0032 mol) with 5.0 psi of H₂ and 100 mg of 10% Pd/C in ethanol. After 16 hours, filter the mixture through celite and concentrate under reduced pressure to give 2-amino-4-(3-trifluoromethyl-pyridin-2-yl)-benzamide as a solid.

6. 2-chloromethyl-7-(3-trifluoromethyl-pyridin-2-yl)-3H-quinazolin-4-one

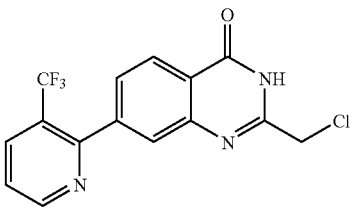

Heat a solution of 2-amino-4-(3-trifluoromethyl-pyridin-2-yl)-benzamide (100 mg, 0.356 mmol) in 2-chloro-1,1,1-trimethoxyethane (bp 138° C.) at 130° C. for 4 hours. Concentrate the mixture under reduced pressure to give 2-chloromethyl-7-(3-trifluoromethyl-pyridin-2-yl)-3H-quinazolin-4-one as an oil which crystallizes on standing.

7. 4-chloro-2-chloromethyl-7-(3-trifluoromethyl-pyridin-2-yl)-quinazoline

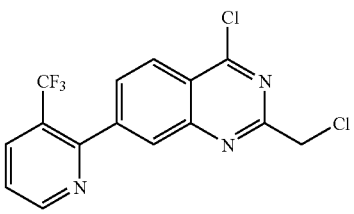

Reflux a mixture of 2-chloromethyl-7-(3-trifluoromethyl-pyridin-2-yl)-3H-quinazolin-4-one (obtained from the reaction above) and POCl₃ for 16 hours. Cool the mixture and concentrate under reduced pressure. Partition the residue between EtOAc and saturated NaHCO₃ solution. Wash the EtOAc portion with additional NaHCO₃ and then dry (Na₂SO₄) and concentrate under reduced pressure. Filter the brown residue through 2 inches of silica gel (1:1 EtOAc/hexanes eluent) and concentrate under reduced pressure to give 4-chloro-2-chloromethyl-7-(3-trifluoromethyl-pyridin-2-yl)quinazoline.

8. [2-chloromethyl-7-(3-trifluoromethyl-pyridin-2-yl)-quinazolin-4-yl]-(4-trifluoromethyl-phenyl)-amine

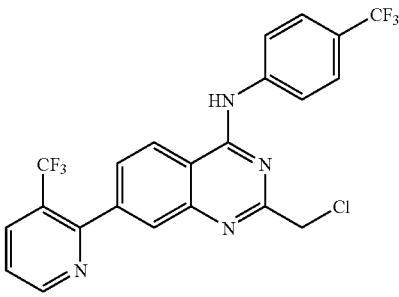

Heat a mixture of 4-chloro-2-chloromethyl-7-(3-trifluoromethyl-pyridin-2-yl)-quinazoline (42 mg, 0.117 mmol) and 4-trifluoromethyl-aniline (19 mg, 0.117 mmol) in isopropyl alcohol (1 mL) at 75° C. for 4 hours. Cool the mixture and wash the precipitate with isopropyl alcohol followed by ether to give [2-chloromethyl-7-(3-trifluoromethyl-pyridin-2-yl)-quinazolin-4-yl]-(4-trifluoromethyl-phenyl)-amine as the mono-HCl salt.

9. [2-Isopropoxymethyl-7-(3-trifluoromethyl-pyridin-2-yl)-quinazolin-4-yl]-(4-trifluoromethyl-phenyl)-amine

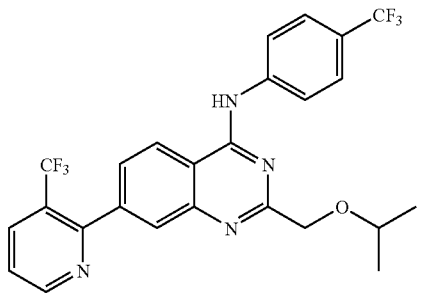

To a suspension of [2-chloromethyl-7-(3-trifluoromethyl-pyridin-2-yl)-quinazolin-4-yl]-(4-trifluoromethyl-phenyl)-amine hydrochloride (1.9 g, 0.0037 mol) in dry isopropanol (100 mL), add 20 equivalents of NaO-i-Pr (prepared from Na and isopropanol). Stir the pale yellow mixture at 60° C. for 5 hours, cool and evaporate the solvent under reduced pressure. Partition the residue between ethyl acetate and water and wash the organic layer with water (1×). Dry the organic layer (Na$_2$SO$_4$) and concentrate to give [2-isopropoxymethyl-7-(3-trifluoromethyl-pyridin-2-yl)-quinazolin-4-yl]-(4-trifluoromethyl-phenyl)-amine as a foam.

B. 2-[4-(4-Trifluoromethyl-phenylamino)-7-(3-trifluoromethyl-pyridin-2-yl)-quinazolin-2-yl]-ethanol (compound 702)

1. 3-Benzyloxy-propionic acid

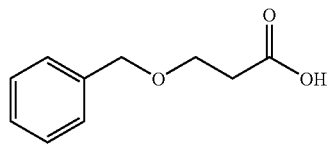

Add sodium hydride (2.22 g, 60% dispersion in mineral oil, 55.4 mmol) in small portions to a cold (0° C.) solution of benzyl alcohol (4.0 g, 37 mmol) in toluene (100 mL). Add ethyl 3-bromopropionate (8.0 g, 44 mmol) dropwise to the mixture, allow the resulting solution to warm to room temperature and stir for 1 hour. Quench the reaction with the addition of water until all bubbling ceases. Dilute the mixture with ethyl acetate (100 mL) and extract with water (100 mL) and brine (100 mL). Dry the organic extract over Na$_2$SO$_4$ and remove the solvent under reduced pressure to yield the crude ester as a clear oil. Dissolve the oil in methanol (20 mL) and 6 N NaOH (20 mL), stir for 1 hour, concentrate the mixture (~20 mL) and dilute with water (20 mL). Extract the aqueous mixture once with CH$_2$Cl$_2$ (40 mL). Acidify the aqueous phase with conc. HCl, extract with EtOAc (3×50 mL), and dry the combined EtOAc extracts over Na$_2$SO$_4$. Remove the solvent under reduced pressure to yield the title compound as a clear oil (2.28 g, 34.0%) that solidifies upon standing.

2. 2-(2-Benzyloxy-ethyl)-7-(3-trifluoromethyl-pyridiny-2-yl)-3H-quinazolin-4-one

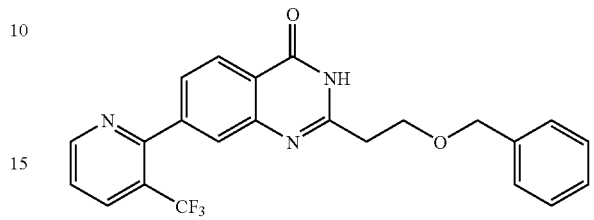

Cool a solution of 3-benzyloxy-propionic acid (1.66 g, 9.19 mmol) in hexanes (40 mL) to 0° C. and add oxalyl chloride (3.50 g, 27.6 mmol) dropwise. After the addition is completed, add DMF (2 drops) and stir the resulting mixture for 1 hour. Remove the solvent under reduced pressure and dissolve the crude acid chloride in dry THF (20 mL). In a separate flask, dissolve 2-amino-4-(3-trifluoromethyl-pyridin-2-yl)-benzamide (2.35 g, 8.37 mmol) in dry THF (40 mL) and pyridine (0.727 g, 9.19 mmol) and cool to 0° C. Add the solution containing the crude acid chloride dropwise to the second solution. Allow the mixture to warm to room temperature and stir for 1 hour. Add a solution of 10% NaOH$_{(aq)}$ (20 mL) to the mixture and stir the solution for 1 hour. Concentrate the mixture (~20 mL), dilute with water (20 mL), and acidify with conc. HCl. Extract the resulting solution with EtOAC (3×50 mL). Wash the combined organic extracts with brine and dry over Na$_2$SO$_4$. Remove the solvent under reduced pressure to yield the title compound as a white solid (3.24 g, 82.9%).

3. 2-(2-Benzyloxy-ethyl)4-chloro-7-(3-trifluoromethyl-pyridiny-2-yl)-quinazoline

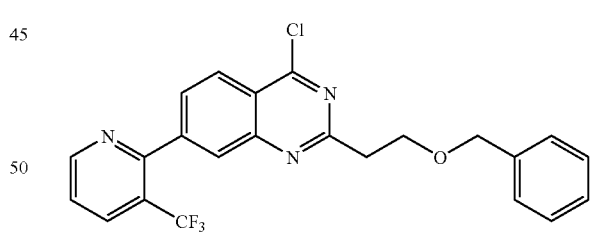

Dissolve 2-(2-Benzyloxy-ethyl)-7-(3-trifluoromethyl-pyridiny-2-yl)-3H-quinazolin-4-one (3.24 g, 7.62 mmol) in CHCl$_3$ (40 mL) and 2,6-lutidine (2.45 g, 22.9 mmol). Add phosphorous oxychloride (1.77 mL, 19.0 mmol) dropwise and heat the resulting solution to reflux for 18 hours. Cool the solution and remove the solvent under reduced pressure. Partition the crude residue between EtOAc (200 mL) and saturated NaHCO$_3$$_{(aq)}$ (200 mL). Remove the organic phase and extract the aqueous phase with EtOAc (200 mL). Combine the two organic extracts, wash with brine (200 mL), and dry over Na$_2$SO$_4$. Remove the solvent to yield the title compound as a light brown solid (2.47 g, 73.1%).

4. [2-(2-Benzyloxy-ethyl)-7-(3-trifluoromethyl-pyridiny-2-yl)-quinazolin-4-yl]-(4-trifluoromethyl-phenyl)-amine

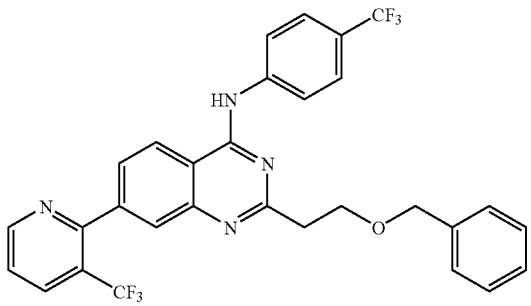

Dissolve 2-(2-Benzyloxy-ethyl)-4-chloro-7-(3-trifluoromethyl-pyridiny-2-yl)-quinazoline (2.47 g, 5.57 mmol) in a solution of acetonitrile (50 mL) and 4-trifluoromethyl-aniline (0.986 g, 6.12 mmol). Heat the mixture to 80° C. for 2 hours. A white precipitate forms. Cool the solution in an ice bath and add diethyl ether (25 mL). Filter off the white precipitate and dry in a vacuum oven to yield the title compound as the mono-hydrochloride salt (2.96 g, 87.8%).

5. 2-[4-(4-Trifluoromethyl-phenylamino)-7-(3-trifluoromethyl-pyridin-2-yl)-quinazolin-2-yl]-ethanol

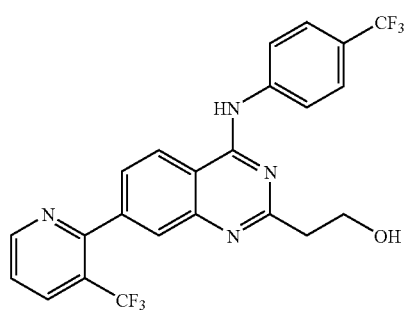

Dissolve [2-(2-Benzyloxy-ethyl)-7-(3-trifluoromethyl-pyridiny-2-yl)-quinazolin-4-yl]-(4-trifluoromethyl-phenyl)-amine hydrochloride (2.96 g, 4.89 mmol) in MeOH (150 mL) and add 10% Pd/C (200 mg). Hydrogenate the mixture at 50 p.s.i. at 60° C. for 8 hours. Quickly filter the mixture through Celite and wash the Celite filter cake with hot MeOH (200 mL). Remove the solvent under reduced pressure to yield the mono-hydrochloride salt of title compound as a white solid (1.75 g, 69.5%). Mass Spec. 478.1.

C. [2-(2-methoxy-ethyl)-7-(3-trifluoromethyl-pyridin-2-yl)-quinazolin-4-yl]-(4-trifluoromethyl-phenyl)-amine (compound 703)

1. 2-(2-methoxy-ethyl)-7-(3-trifluoromethyl-pyridin-2-yl)-quinazolin-4-ol

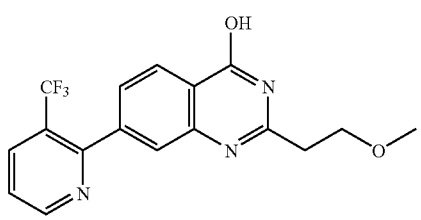

To a solution of 2-amino-4-(3-trifluoromethyl-pyridin-2-yl)-benzamide (3.56 mmol) and pyridine (3.91 mmol) in THF (20 ml), add 4-methoxy-butyryl chloride (3.91 mmol). Stir the mixture 20 minutes at room temperature, add 20 ml of 20% NaOH, stir for 60 minutes at 50° C. Concentrate, add water, filter, acidify to pH=6, collect the precipitate to obtain 2-(3-benzyloxy-propyl)7-(3-trifluoromethyl-pyridin-2-yl)-quinazolin-4-ol.

2. 2-(2-methoxy-ethyl)-4-chloro-7-(3-trifluoromethyl-pyridin-2-yl)-quinazoline

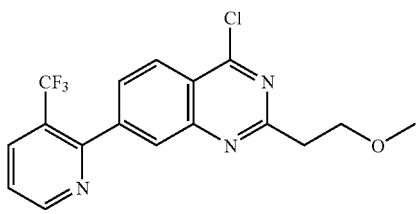

Using procedures analogous to those already described, 2-(2-methoxy-ethyl)4-chloro-7-(3-trifluoromethyl-pyridin-2-yl)-quinazoline is prepared from 2-(2-methoxy-ethyl)-7-(3-trifluoromethyl-pyridin-2-yl)-quinazolin-4-ol.

3. [2-(2-methoxy-ethyl)-7-(3-trifluoromethyl-pyridin-2-yl)-quinazolin-4-yl]-(4-trifluoromethyl-phenyl)-amine

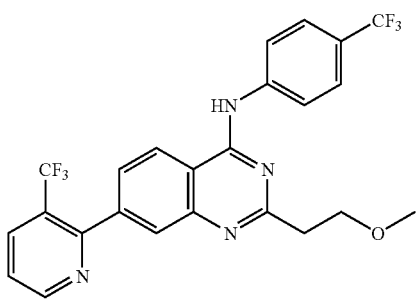

Using procedures analogous to those already described, [2-(2-methoxy-ethyl)-7-(3-trifluoromethyl-pyridin-2-yl)-quinazolin-4-yl]-(4-trifluoromethyl-phenyl)-amine is prepared from 2-(2-methoxy-ethyl)-4-chloro-7-(3-trifluoro-methyl-pyridin-2-yl)-quinazoline. Mass Spec. 492.1.

D. 3-[4-(4-trifluoromethyl-phenylamino)-7-(3-trifluoro-methyl-pyridin-2-yl)-quinazolin-2-yl]-propan-1-ol (Compound 704)

1. 2-(3-benzyloxy-propyl)-7-(3-trifluoromethyl-pyridin-2-yl)-quinazolin-4-ol

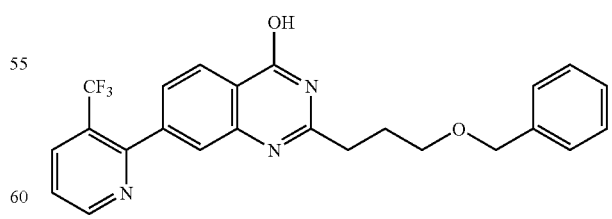

To a solution of 2-amino-4-(3-trifluoromethyl-pyridin-2-yl)-benzamide (3.56 mmol), and pyridine (3.91 mmol) in THF (20 ml) add 4-benzyloxy-butyryl chloride (3.91 mmol). Stir the mixture 20 minutes at room temperature, add 20 ml of 20% NaOH, stir for 60 minutes at 50° C. Concentrate, add water, filter, acidify to pH=6, collect the precipitate to obtain 2-(3-benzyloxy-propyl)-7-(3-trifluoromethyl-pyridin-2-yl)-quinazolin-4-ol.

2. 2-(3-benzyloxy-propyl)-4-chloro-7-(3-trifluoromethyl-pyridin-2-yl)-quinazoline

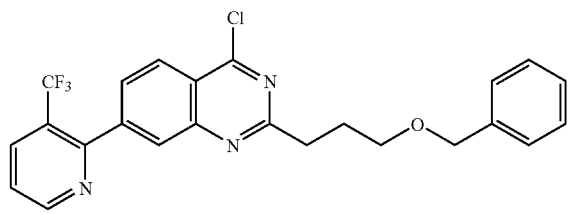

Using procedures analogous to those already described 2-(3-benzyloxy-propyl)-4-chloro-7 (3-trifluoromethyl-pyridin-2-yl)-quinazoline can be prepared from 2-(3-benzyloxy-propyl)-7-(3-trifluoromethyl-pyridin-2-yl)-quinazolin-4-ol.

3. [2-(3-benzyloxy-propyl)-7-(3-trifluoromethyl-pyridin-2-yl)-quinazolin-4-yl]-(4-trifluoromethyl-phenyl)-amine

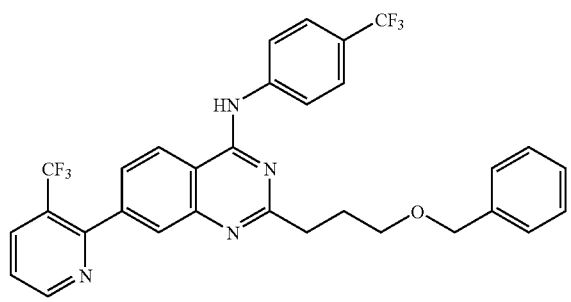

Using procedures analogous to those already described, [2-(3-benzyloxy-propyl)-7-(3-trifluoromethyl-pyridin-2-yl)-quinazolin-4-yl]-(4-trifluoromethyl-phenyl)-amine is prepared from 2-(3-benzyloxy-propyl)-4-chloro-7-(3-trifluoromethyl-pyridin-2-yl)-quinazoline.

4. 3-[4-(4-trifluoromethyl-phenylamino)-7-(3=trifluoromethyl-pyridin-2-yl)-quinazolin-2-yl]-propan-1-ol

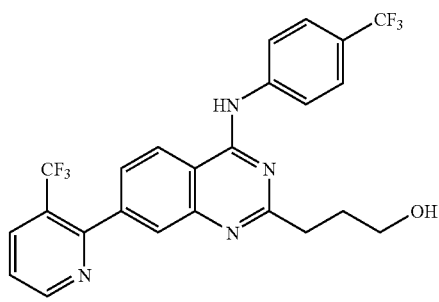

Hydrogenate the mixture of 2-(3-benzyloxy-propyl)-4-chloro-7-(3-trifluoromethyl-pyridin-2-yl)-quinazoline (0.5 mmol) and 10% Pd—C in EtOH (100 ml) at 50 psi for 30 hours. Filter, concentrate, and chromatograph to give 3-[4-(4-trifluoromethyl-phenylamino)-7-(3-trifluoro-methyl-pyridin-2-yl)-quinazolin-2-yl]-propan-1-ol. Mass Spec. 492.1.

E. 7-(3-trifluoromethyl-pyridin-2-yl)-2-methoxymethyl-pyrido[3,2-d]pyrimidin-4-yl]-(4-trifluoromethyl-phenyl)-amine (compound 705)

1. 6'-Methoxy-3-trifluoromethyl-[2,3']bipyridinyl

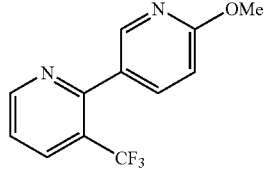

Heat a mixture of 2-chloro-3-trifluoromethylpyridine (37 g, 0.2 mol), 2-methoxypyridine-5-boronic acid (32 g, 0.21 mol), tetrakis(triphenylphosphine)palladium(0) (9 g, 7 mmol) and 2M potassium carbonate (150 mL) in toluene (500 mL) under a nitrogen atmosphere at 90° C. for 8 hours. Cool the reaction mixture and separate the layers. Extract the aqueous layer with ethyl acetate (2×250 mL) and wash the combined organics with 4M sodium hydroxide (250 mL), water (250 mL), and brine (250 mL). Dry (MgSO$_4$) and concentrate under reduced pressure. Purify the resulting oil by flash chromatography on silica gel (50% ether/50% hexane) to give the title compound (48.2 g, 95%) as a colorless oil.

2. 3-Trifluoromethyl-1'H-[2,3']bipyridinyl-6'-one

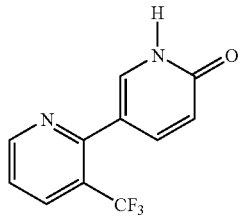

Heat 6'-Methoxy-3-trifluoromethyl-[2,3']bipyridinyl (41 g, 0.16 mol) in 30% HBr/AcOH (100 mL) to reflux for 1 hour. Cool the mixture, filter and wash the precipitate with ether (100 mL). Transfer the precipitate into 10M sodium hydroxide (500 mL) and stir for 1 hour. Treat the solution with hydrochloric acid until the solution is pH 7. Collect the white solid by filtration and air dry to give the title compound (36 g, 93%) as a white solid.

3. 5'-Nitro-3-trifluoromethyl-1'H-[2,3']bipyridinyl-6'-one

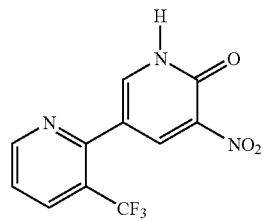

To a solution of 3-trifluoromethyl-1'H-[2,3']bipyridinyl-6'-one (25 g, 0.1 mol) in concentrated sulfuric acid (100 mL) at 0° C., add dropwise a solution of fuming nitric acid (35 mL) and concentrated sulfuric acid (10 mL). Heat the reaction mixture to 70° C. for 1 hour, cool and pour onto ice (500 mL). Filter the mixture and treat the filtrate with 10 M sodium hydroxide until the solution is at pH 4–5. Collect the precipitate by filtration and air dry to give the title compound (26.2 g, 92%) as a white solid.

4. 6'-Chloro-5'-nitro-3-trifluoromethyl-[2,3']bipyridinyl

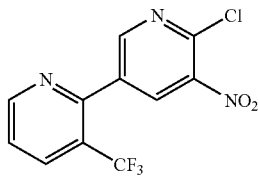

Heat a solution of 5'-nitro-3-trifluoromethyl-1'H-[2,3'] bipyridinyl-6'-one (25 g, 0.088 mol), thionyl chloride (300 mL) and DMF (3 mL) to reflux for 4 hours. Remove the volatiles by rotary evaporation and partition the residue between ethyl acetate (350 mL) and saturated sodium bicarbonate solution (250 mL). Extract the aqueous layer with further ethyl acetate (250 mL) and wash the combined organics with brine (250 mL). Dry (MgSO$_4$) and concentrate under reduced pressure to give the title compound (25 g, 93%) as a yellow oil.

5. 6'-Chloro-3-trifluoromethyl-[2,3']bipyridinyl-5'-ylamine

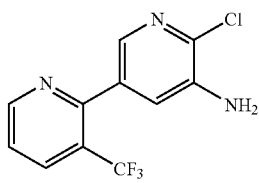

To a solution of 6'-chloro-5'-nitro-3-trifluoromethyl-[2,3'] bipyridinyl (25 g, 0.082 mol) and calcium chloride (11 g, 0.1 mol) in ethanol (300 mL) and water (50 mL), add iron powder (45 g, 0.82 mol). Heat the solution to reflux for 1.5 hours, cool and filter through Celite. Concentrate the mixture under reduced pressure, re-dissolve in ethyl acetate (300 mL) and wash with brine (200 mL). Concentrate the solution under reduced pressure and purify by flash chromatography on silica gel (50% ether/50% hexane) to give the title compound (19 g, 85%) as a pale yellow solid.

6. 3-Amino-5-[3-(trifluoromethyl)(2-pyridyl)]pyridine-2-carboxamide

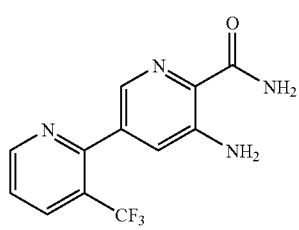

Heat a solution of 6'-chloro-3-trifluoromethyl-[2,3']bipyridinyl-5'-ylamine (25 g, 0.091 mol), zinc cyanide (6.75 g, 0.058 mol), tris[dibenzylidineacetone]di-palladium (pd$_2$(dba)$_3$; 2.63 g, 2.86 mmol), and 1,1'-bis(diphenylphosphino)ferrocene (DPPF; 3.16 g, 5.72 mmol) in DMF (250 mL) and water (2.5 mL), under a nitrogen atmosphere, at 120° C. for 1 hour. Add water (30 mL) and heat the solution at 120° C. for a further 4 hours to complete the hydrolysis. Cool the reaction to 0° C. and add a solution of saturated ammonium chloride (200 ml), water (200 mL) and concentrated ammonium hydroxide (50 mL). After stirring at 0° C. for 1 hour, filter the yellow precipitate, and wash with water (200 mL) and a 1:1 mixture of ether-hexane (200 mL). Air dry the solid, and then dry in a vacuum oven to give (23 g, 90%) of the title compound.

7. 2-(Chloromethyl)-7-[3-(trifluoromethyl)(2-pyridyl)]-3-hydropyridino[3,2-d]pyrimidin-4-one

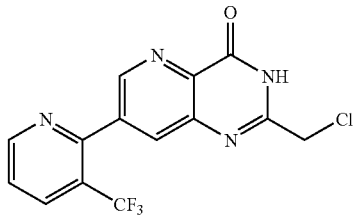

Heat a solution of 3-amino-5-[3-(trifluoromethyl)(2-pyridyl)]pyridine-2-carboxamide (23 g, 81.5 mmol) and 2-chloro 1,1,1-trimethoxyethane (250 mL) at 130° C. for 1 hour. Remove the volatiles by evaporation and triturate the solid (50% ether/50% hexane) to give the title compound as a light brown solid (21 g, 76%).

8. 4-Chloro-2-chloromethyl-7-(3-chloro-pyridin-2-yl)-pyrido[3,2-d]pyrimidine

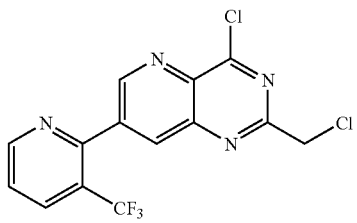

Heat a solution of 2-(chloromethyl)-7-[3-(trifluoromethyl)(2-pyridyl)]-3-hydropyridino[3,2-d]pyrimidin-4-one (2.49 g, 7.31 mmol), phosphorous oxychloride (10 mL), 2,6-lutidine (2.13 mL, 18.3 mmol) and toluene to reflux for 8 hours. Remove the solvent and partition the crude residue between EtOAc (150 mL) and H$_2$O (150 mL). Remove the organic phase and extract the aqueous phase with EtOAc (150 mL). Combine the organic extractions, wash with saturated NaHCO$_3$(aq) (150 mL) and brine (150 mL), and dry over Na$_2$SO$_4$. Remove the solvent to yield the title compound as a light brown solid (2.30 g, 87.6%).

9. [2-(2-Chloromethyl)-7-(3-trifluoromethyl-pyridiny-2-yl)-quinazolin-4-yl]-(4-trifluoromethyl-phenyl)-amine

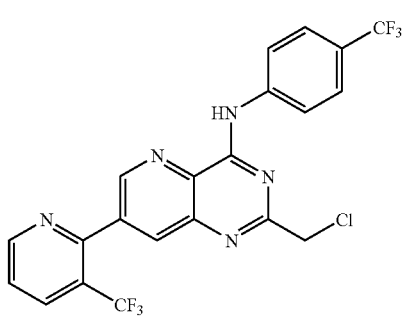

Dissolve 4-Chloro-2-chloro-methyl-7-(3-chloro-pyridin-2-yl)-pyrido[3,2-d]pyrimidine (2.30 g, 6.40 mmol) in a solution of acetonitrile (20 mL) and 4-trifluoromethyl aniline (1.13 g, 7.04 mmol). Heat the mixture at 80° C. for 18 hours. Cool the mixture to 0° C. and dilute with diethyl ether (20 mL). The mono-hydrochloride salt of the title compound forms a light brown precipitate (2.85 g 85.6%), which is removed by filtration and dried in a vacuum oven.

10. 7-(3-trifluoromethyl-pyridin-2-yl)-2-methoxymethyl-pyrido[3,2-d]pyrimidin-4-yl]-(4-trifluoromethyl-phenyl)-amine

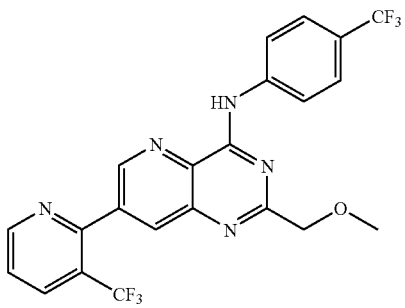

Treat [2-(2-Chloromethyl)-7-(3-trifluoromethyl-pyridiny-2-yl)-quinazolin-4-yl]-(4-trifluoromethyl-phenyl)-amine with NaOMe as described in Example 1.A-9 above. This affords 7-(3-trifluoromethyl-pyridin-2-yl)-2-methoxymethyl-pyrido[3,2-d]pyrimidin-4-yl]-(4-trifluoromethyl-phenyl)-amine as a solid. Mass Spec. 479.1.

F. 7-(3-methyl-pyridin-2-yl)-2-methoxymethyl-pyrido[3,2-d]pyrimidin-4-yl]-(4-trifluoromethyl-phenyl)-amine (compound 706)

1. 5-Bromo-3-nitropyridine-2-carbonitrile

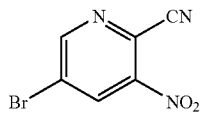

Heat a solution of 2-amino-5-bromo-3-nitropyridine (2.18 g, 10 mmol), cuprous cyanide (1.33 g, 15 mmol) and tert-butylnitrite (2.0 mL, 15 mmol) in acetonitrile (50 mL) at 60° C. for 2 hours. Cool the solution and partitioned between ethyl acetate (100 mL) and saturated aqueous NaHCO₃ (100 mL). Extract the aqueous layer with ethyl acetate (2×50 mL), wash with water (100 mL) and brine (100 mL), dry (MgSO₄) and evaporate. Purify the solid by flash chromatography on silica gel (25% ether/75% hexane) to give the title compound as a pale yellow solid (934 mg, 41%).

4. 5-(3-Methyl(2-pyridyl))-3-nitropyridine-2-carbonitrile

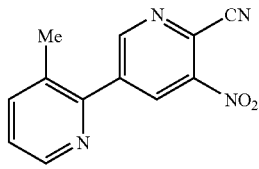

Heat a solution of 5-bromo-3-nitropyridine-2-carbonitrile (228 mg, 1.0 mmol), tetrakis(triphenylphosphine)palladium (0) (15 mg), 3-methyl-2-pyridylzinc bromide (0.5 M in THF, 3 mL, 1.5 mmol) in THF (5 mL) at 60° C. for 2 hours. Cool the solution and partition between ethyl acetate (10 mL) and saturated aqueous NaHCO₃ (10 mL). Extract the aqueous layer with ethyl acetate (2×15 mL), wash with water (10 mL) and brine (10 mL), dry (MgSO₄) and evaporate to give the title compound as a pale yellow solid (211 mg, 88%).

5. 3-Amino-5-(3-methyl(2-pyridyl))pyridine-2-carboxamide

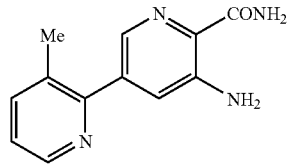

Heat a solution of 5-(3-methyl(2-pyridyl))-3-nitropyridine-2-carbonitrile (1 g, 4.1 mmol), iron (2.3 g, 40 mmol) and calcium chloride (560 mg, 5 mmol) in ethanol (15 mL) and water (4 mL) to reflux for 1 hour. Cool the mixture, filter through Celite and wash with ethyl acetate. Evaporate the filtrate and re-dissolve the residue in ethyl acetate. Wash with water and brine, dry (MgSO₄) and evaporate to give the title compound as a pale yellow solid (880 mg, 94%).

4. 7-(3-methyl-pyridin-2-yl)-2-methoxymethyl-pyrido[3,2-d]pyrimidin-4-yl]-(4-trifluoromethyl-phenyl)-amine

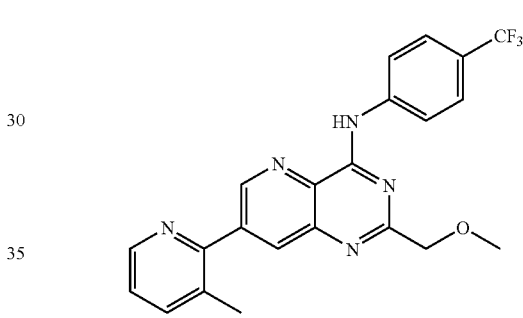

The title compound is prepared from 5'-amino-3-methyl-[2,3']bipyridinyl-6'-carboxylic acid amide using procedures analogous to those described in examples A, B, D, E, G and H.

G. 7-(3-trifluoromethyl-pyridin-2-yl)-2-methoxymethyl-pyrido[3,2-d]pyrimidin-4-yl]-(4-trifluoromethyl-phenyl)-amine (compound 707)

1. 7-(3-trifluoromethyl-pyridin-2-yl)-2-methoxymethyl-3H-pyrido[3,2-d]pyrimidin-4-one

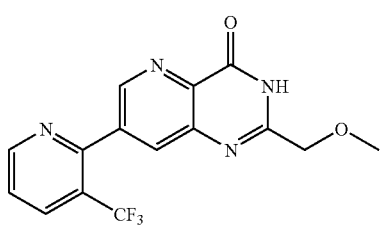

Treat a solution of 3-amino-5-[3-(chloro-pyridin-2-yl)]pyridine-2-carboxamide (340 mg, 1.21 mmol) in THF (5 mL) and pyridine (0.11 mL) with methoxy-acetyl chloride (0.11 mL, 144 mg, 1.33 mmol). Stir the mixture for 3 hours at room temperature. Then, add 5 N NaOH (10 mL) and stir the solution for an additional 18 hours. Concentrate the solution (~5 mL) and acidify with conc. HCl. Extract the aqueous mixture with EtOAc (3×25 mL), and dry the combined organic extracts over Na$_2$SO$_4$. Remove the solvent under reduced pressure to yield the title compound as a white solid.

2. 4-Chloro-7-(3-trifluoromethyl-pyridin-2-yl)-2-methoxymethyl-pyrido[3,2-d]pyrimidine

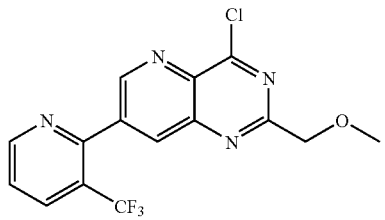

Dissolve 7-(3-trifluoromethyl-pyridin-2-yl)-2-methoxymethyl-3H-pyrido[3,2-d]pyrimidin-4-one (276 mg, 0.822 mmol) in CHCl$_3$ (25 mL) and 2,6-lutidine (294 mg, 2.74 mmol). Add phosphorous oxycloride (0.255 mL, 2.74 mmol) dropwise and heat the resulting solution to reflux for 24 hours. Cool the solution and remove the solvent under reduced pressure. Partition the crude residue between EtOAc (50 mL) and saturated NaHCO$_3$ $_{(aq)}$ (50 mL). Remove the organic phase and extract the aqueous phase with additional EtOAc (50 mL). Combine the two organic extracts, wash with brine (100 mL), and dry over Na$_2$SO$_4$. Remove the solvent to yield the title compound as a light brown solid.

3. 7-(3-trifluoromethyl-pyridin-2-yl)-2-methoxymethyl-pyrido[3,2-d]pyrimidin-4-yl]-(4-trifluoromethyl-phenyl)-amine

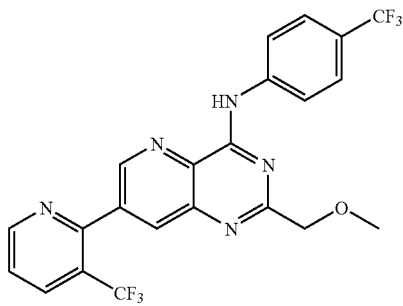

Dissolve 4-Chloro-7-(3-trifluoromethyl-pyridin-2-yl)-2-methoxymethyl-pyrido[3,2-d]pyrimidine (30 mg, 0.0934 mmol) into a solution of acetonitrile (3 mL) and 4-trifluoromethyl-aniline (18.0 mg, 0.112 mmol). Heat the mixture to 80° C. for 16 hours. Cool the reaction mixture in an ice bath and add diethyl ether (3 mL). Filter off the off-white precipitate and dry in a vacuum oven to yield the title compound as the mono-hydrochloride salt. Mass Spec. 479.1.

H. [7-(3-Chloro-pyridin-2-yl)-2-methoxymethyl-pyrido[2,3-d]pyrimidin-4-yl]-(4-trifluoromethyl-phenyl)-amine (compound 708)

1. 2-Acetyl-3-chloropyridine

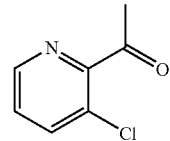

Dissolve 3-chloro-2-cyanopyridine (10.0 g, 0.072 mol, Chem. Pharm. Bull. (1985) 33:565–571) in anhydrous THF (200 mL) under N$_2$ atmosphere and cool in an ice bath. Add drop wise 3.0 M MeMgI in diethyl ether (48 ml, 0.14 mol) to the reaction mixture and stir in an ice bath for 2 hours. Pour the reaction mixture over ice cold water, acidify the mixture with 2.0 N aq. HCl to pH 2 to 3. Extract the reaction mixture with EtOAc (3×100 mL) and dry over anhydrous MgSO$_4$. Filter, concentrate under vacuum and then filter through a pad of silica gel using 20% ethyl acetate/hexane as eluent. Removal of solvent under reduced pressure gives pure 2-acetyl-3-chloropyridine as oil.

2. 1-(3-Chloro-pyridin-2-yl)-3-dimethylaminopropenone

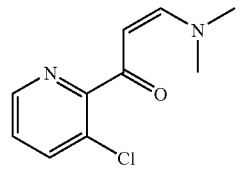

Heat 2-acetyl-3-chloropyridine (0.77 g, 5.0 mmol) with N,N-dimethylformamide dimetylacetal (3.0 g) at 105° C. for 20 hours. Concentrate under reduced pressure to give 1-(3-chloro-pyridin-2-yl)-3-dimethylaminopropenone as oil.

3. 2-Amino-4-(3-chloro-pyridin-2-yl)-benzonitrile

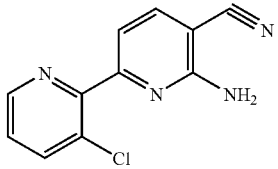

Heat a solution of 1-(3-Chloro-pyridin-2-yl)-3-dimethylaminopropenone (1.05 g, 5 mmol), 3-amino-3-methoxyacrylonitrile hydrochloride (1.35 g, 10 mmol) and ammonium acetate (2.2 g, 15.0 mmol) in ethanol (25 mL) at reflux for 20 hours. Cool the mixture and concentrate under reduced pressure to give dark oil. Dissolve the residue in EtOAc/water (100 mL). Extract the aqueous solution with EtOAc, wash the EtOAc with brine, dry (MgSO$_4$) and concentrate under reduced pressure to give 2-amino-4-(3-chloro-pyridin-2-yl)-benzonitrile as a brown solid.

4. 6-Amino-3'-chloro-[2,2']bipyridinyl-5-carboxylic acid amide

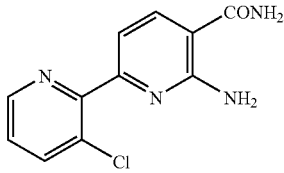

Cool concentrated sulfuric acid (10 mL) in an ice bath under nitrogen atmosphere. Add in portions 2-amino-4-(3-chloro-pyridin-2-yl)-benzonitrile (1.0 g, 4.3 mmol) over a period of 15 minutes. Stir at room temperature overnight. Pour the reaction mixture over ice, adjust the pH to 10 using 10 N aq. NaOH, filter the solid, wash the solid with water and dry under vacuum to give 6-amino-3'-chloro-[2,2']bipyridinyl-5-carboxylic acid amide as a yellow solid.

5. 7-(3-Chloro-pyridin-2-yl)-2-methoxymethyl-3H-pyrido[2,3-d]pyrimidin-4-one

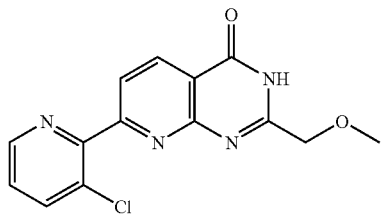

Dissolve 6-amino-3'-chloro-[2,2']bipyridinyl-5-carboxylic acid amide (0.5 g, 2.02 mmol) in anhydrous THF (10 mL) under $N_2$ atmosphere. Add drop wise pyridine (0.36 g, 4.04 mmol) and methoxyacetyl chloride (0.48 g, 4.04 mmol) to the reaction mixture and stir at room temperature overnight. Add 10% aq. NaOH (10 mL) and reflux for 4 hours. Concentrate in vacuum, adjust the pH to 6.0 using AcOH, collect the solid by filtration and dry under vacuum to give 7-(3-chloro-pyridin-2-yl)-2-methoxymethyl-3H-pyrido[2,3-d]pyrimidin-4-one as a white solid.

6. 4-Chloro-7-(3-chloro-pyridin-2-yl)-2-methoxymethyl-pyrido[2,3-d]pyrimidine

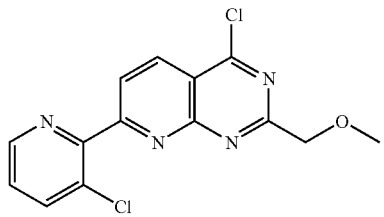

Reflux a mixture of 7-(3-chloro-pyridin-2-yl)-2-methoxymethyl-3H-pyrido[2,3-d]pyrimidin-4-one (0.25 g), 2,6-lutidine (0.44 g), and $POCl_3$ (0.51 g) in $CHCl_3$ (5 mL) for 20 hours. Cool the mixture and concentrate under reduced pressure. Partition the residue between EtOAc and saturated $NaHCO_3$ solution. Wash the EtOAc portion with additional $NaHCO_3$ and then dry ($Na_2SO_4$) and concentrate under reduced pressure. Filter the brown residue through 2 inches of silica gel (1:1 EtOAc/hexanes eluent) and concentrate under reduced pressure to give 4-chloro-7-(3-chloro-pyridin-2-yl)-2-methoxymethyl-pyrido[2,3-d]pyrimidine.

7. [7-(3-Chloro-pyridin-2-yl)-2-methoxymethyl-pyrido[2,3-d]pyrimidin-4-yl]-(4-trifluoromethyl-phenyl)-amine

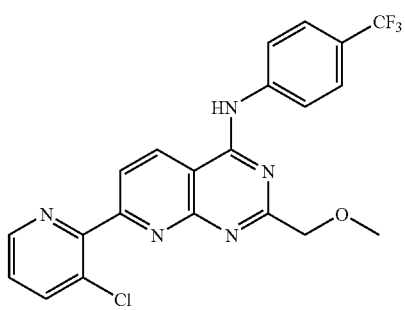

Heat a mixture of 4-chloro-7-(3-chloro-pyridin-2-yl)-2-methoxymethyl-pyrido[2,3-d]pyrimidine (0.1 mmol) and 4-trifluoromethyl-aniline (16.1 mg, 0.1 mmol) in AcCN (1 mL) at 80° C. for 24 hours. Cool the mixture and wash the precipitate with ether to give [7-(3-chloro-pyridin-2-yl)-2-methoxymethyl-pyrido[2,3-d]pyrimidin-4-yl]-(4-trifluoromethyl-phenyl)-amine as the mono-HCl salt. Mass Spec. 445.1.

I. [2-Methoxymethyl-7-(3-methylpyridin-2-yl)-quinazolin-4-yl)-(4-trifluoromethylphenyl)-amine (compound 709)

1. 7-bromo-2-methoxymethylquinazolin-4-yl)-(4-trifluoromethylphenyl)-amine

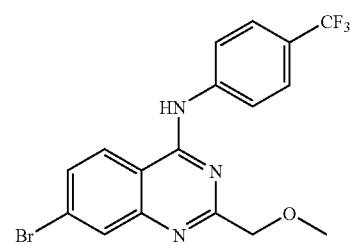

Heat a mixture of 7-bromo-2-chloromethylquinazolin-4-yl)-(4-trifluoromethylphenyl)-amine (from Example C, 200 mg, 0.48 mmol), 4.4M sodium methoxide in methanol (2.4 mL), and methanol (1 mL) to 60° C. for 4 hours. Cool to room temperature and evaporate the mixture. Dilute with EtOAc (10 mL) and wash 2x with water (10 mL each). Dry the organic layer ($Na_2SO_4$) and evaporate. Purify by preparative TLC (3:1 hexanes:EtOAc) to obtain 2-methoxymethyl-7-pyridin-4-yl-quinazolin-4-yl)-(4-trifluoromethylphenyl)-amine (225 mg) as a yellow solid.

2. [2-Methoxymethyl-7-(3-methylpyridin-2-yl)-quinazolin-4-yl]-(4-trifluoromethylphenyl)-amine

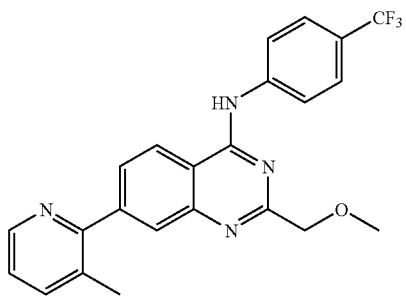

Heat a mixture of 2-methoxymethyl-7-pyridin-4-yl-quinazolin-4-yl)-(4-trifluoromethylphenyl)-amine (100 mg, 0.243 mmol), 3-methyl-2-pyridylzinc bromide (1 mL of a 0.5M THF solution), tetrakis(triphenylphosphinepalladium (0) (50 mg, 0.043 mmol) in 1,2-dimethoxymethane (5 mL) for 3 hours at 80° C. under nitrogen. Cool to room temperature and dilute with EtOAc (10 mL). Wash with water (2×10 mL) and dry the organic layer ($Na_2SO_4$) and evaporate. Purify by preparative TLC to obtain [2-methoxymethyl-7-(3-methylpyridin-2-yl)-quinazolin-4-yl]-(4-trifluoromethylphenyl)-amine (38 mg) as an off-white solid.

J. Additional Representative Substituted 2-Hydroxyalkyl-Quinazolin-4-ylamine Analogues Compounds listed in Table VII were prepared using the above methods, with readily apparent modifications.

TABLE VII

Representative Substituted 2-Hydroxyalkyl-quinazolin-4-ylamine Analogues

| Compound | | Name | MS |
|---|---|---|---|
| 710. | | (1-Methanesulfonyl-2,3-dihydro-1H-indol-5-yl)-[2-methoxymethyl-7-(3-trifluoromethyl-pyridin-2-yl)-quinazolin-4-yl]-amine | 529.1 |
| 711. | | (2,6-Dimethyl-morpholin-4-yl)-(1-{4-[2-methoxymethyl-7-(3-trifluoromethyl-pyridin-2-yl)-pyrido[2,3-d]pyrimidin-4-ylamino]-phenyl}-cyclobutyl)-methanone | |
| 712. | | (4-Cyclohexyl-phenyl)-[2-trifluoromethyl-pyridin-2-yl)-pyridin-2-yl)-pyrido[3,2-d]pyrimidin-4-yl]-amine | 493.2 |

TABLE VII-continued

Representative Substituted 2-Hydroxyalkyl-quinazolin-4-ylamine Analogues

| Compound | Name | MS |
|---|---|---|
| 713. | (4-Cyclopentyl-phenyl)-[2-methoxymethyl-7-(3-trifluoromethyl-pyridin-2-yl)-pyrido[2,3-d]pyrimidin-4-yl]-amine | |
| 714. | (4-Cyclopropyl-phenyl)-[2-methoxymethyl-7-(3-trifluoromethyl-pyridin-2-yl)-quinazolin-4-yl]-amine | 450.2 |
| 715. | (4-Ethyl-phenyl)-[2-methoxymethyl-7-(3-trifluoromethyl-pyridin-2-yl)-pyrido[3,2-d]pyrimidin-4-yl[-amine | 439.2 |
| 716. | (4-Isopropyl-phenyl)-[2-(2-methoxy-ethyl)-7-(3-trifluoromethyl-pyridin-2-yl)-quinazolin-4-yl]-amine | 466.2 |

TABLE VII-continued

Representative Substituted 2-Hydroxyalkyl-quinazolin-4-ylamine Analogues

| Compound | Name | MS |
| --- | --- | --- |
| 717. | (4-Isopropyl-phenyl)-[2-(tetrahydro-pyran-4-yloxymethyl)-7-(3-trifluoromethyl-pyridin-2-yl)-quinazolin-4-yl]-amine | 522.2 |
| 718. | (4-Isopropyl-phenyl)-[2-methoxymethyl-7-(3-methyl-pyridin-2-yl)-pyrido[2,3-d]pyrimidin-4-yl]-amine | 399.2 |
| 719. | (4-Isopropyl-phenyl)-[2-methoxymethyl-7-(3-methyl-pyridin-2-yl)-quinazolin-4yl]-amine | 398.2 |
| 720. | (4-Isopropyl-phenyl)-[2-methoxymethyl-7-(3-trifluoromethyl-pyridin-2-yl)-pyrido[3,2-d]pyrimidin-4-yl]-amine | 453.2 |

TABLE VII-continued

Representative Substituted 2-Hydroxyalkyl-quinazolin-4-ylamine Analogues

| Compound | | Name | MS |
|---|---|---|---|
| 721. | | (4-Isopropyl-phenyl)-[2-methoxymethyl-7-(3-trifluoromethyl-pyridin-2-yl)-quinazolin-4-yl]-amine | 452.2 |
| 722. | | (4-Isopropyl-phenyl)-[2-methoxymethyl-7-(3-trifluoromethyl-pyridin-2-yl)-pyrido[2,3-d]pyrimidin-4-yl]-amine | |
| 723. | | (4-Isopropyl-phenyl)-[7-(3-methyl-pyridin-2-yl)-2-(tetrahydro-pyran-4-yloxymethyl)-quinazolin-4-yl]-amine | 468.3 |
| 724. | | (4-Methanesulfonyl-phenyl)-[2-methoxymethyl-7-(3-trifluoromethyl-pyridin-2-yl)-quinazolin-4-yl]-amine | 488.1 |

TABLE VII-continued

Representative Substituted 2-Hydroxyalkyl-quinazolin-4-ylamine Analogues

| Compound | | Name | MS |
|---|---|---|---|
| 725. | | (4-Methanesulfonyl-phenyl)-[2-methoxymethyl-7-(3-trifluoromethyl-pyridin-2-yl)-pyrido[2,3-d]pyrimidin-4-yl]-amine | |
| 726. | | (4-sec-Butyl-phenyl)-[2-methoxymethyl-7-(3-methyl-pyridin-2-yl)-pyrido[2,3-d]pyrimidin-4-yl]-amine | 413.2 |
| 727. | | (4-sec-Butyl-phenyl)-[2-methoxymethyl-7-(3-trifluoromethyl-pyridin-2-yl)-pyrido[2,3-d]pyrimidin-4-yl]-amine | |
| 728. | | (4-sec-Butyl-phenyl)-[7-(3-chloro-pyridin-2-yl)-2-(2-methoxy-ethoxymethyl)-pyrido[2,3-d]pyrimidin-4-yl]-amine | 477.2 |

TABLE VII-continued

Representative Substituted 2-Hydroxyalkyl-quinazolin-4-ylamine Analogues

| Compound | | Name | MS |
|---|---|---|---|
| 729. | 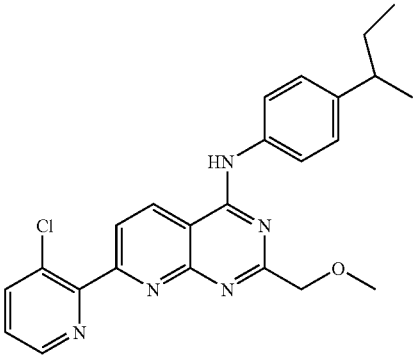 | (4-sec-Butyl-phenyl)-[7-(3-chloro-pyridin-2-yl)-2-methoxymethyl-pyrido[2,3-d]pyrimidin-4-yl]-amine | 433.2 |
| 730. | 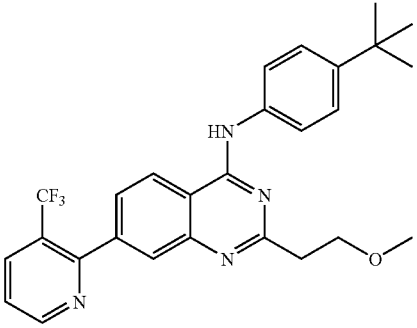 | (4-tert-Butyl-phenyl)-[2-(2-methoxy-ethyl)-7-(3-trifluoromethyl-pyridin-2-yl)-quinazolin-4-yl]-amine | 480.2 |
| 731. | 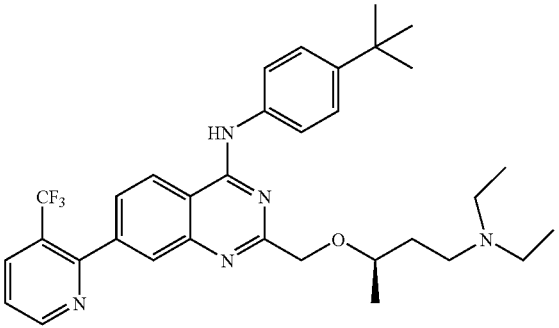 | (4-tert-Butyl-phenyl)-[2-(3-diethylamino-1-methyl-propoxymethyl)-7-(3-trifluoromethyl-pyridin-2-yl)-quinazolin-4-yl]-amine | |
| 732. | 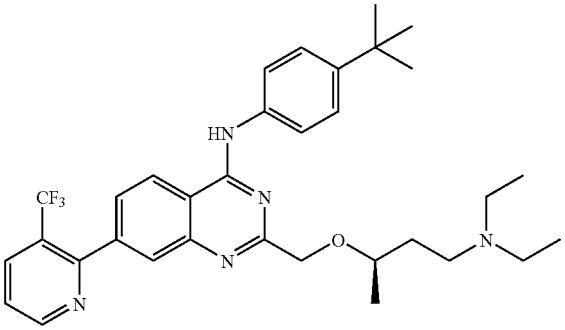 | (4-tert-Butyl-phenyl)-[2-(3-diethylamino-1-methyl-propoxymethyl)-7-(3-trifluoromethyl-pyridin-2-yl)-quinazolin-4-yl]-amine | 579.3 |

TABLE VII-continued

Representative Substituted 2-Hydroxyalkyl-quinazolin-4-ylamine Analogues

| Compound | | Name | MS |
|---|---|---|---|
| 733. | | (4-tert-Butyl-phenyl)-[2-(3-diethylamino-propoxymethyl)-7-(3-trifluoromethyl-pyridin-2-yl)-quinazolin-4-yl]-amine | 565.3 |
| 734. | | (4-tert-Butyl-phenyl)-[2-(3-dimethylamino-propoxymethyl)-7-(3-trifluoromethyl-pyridin-2-yl)-quinazolin-4-yl]-amine | 537.3 |
| 735. | | (4-tert-Butyl-phenyl)-[2-(3-morpholin-4-yl-propoxymethyl)-7-(3-trifluoromethyl-pyridin-2-yl)-quinazolin-4-yl]-amine | 579.3 |
| 736. | | (4-tert-Butyl-phenyl)-[2-(4-dimethylamino-butoxymethyl)-7-(3-trifluoromethyl-pyridin-2-yl)-quinazolin-4-yl]-amine | |

TABLE VII-continued

Representative Substituted 2-Hydroxyalkyl-quinazolin-4-ylamine Analogues

| Compound | Name | MS |
|---|---|---|
| 737. | (4-tert-Butyl-phenyl)-[2-(4-trifluoromethyl-pyridin-2-yl)-quinazolin-4-yl]-amine | |
| 738. | (4-tert-Butyl-phenyl)-[2-isobutoxymethyl-7-(3-methyl-pyridin-2-yl)-pyrido[2,3-d]pyrimidin-4-yl]-amine | |
| 739. | (4-tert-Butyl-phenyl)-[2-isobutoxymethyl-7-(3-trifluoromethyl-pyridin-2-yl)-pyrido[2,3-d]pyrimidin-4-yl]-amine | |
| 740. | (4-tert-Butyl-phenyl)-[2-methoxymethyl-7-(3-methyl-pyridin-2-yl)-pyrido[2,3-d]pyrimidin-4-yl]-amine | 413.2 |

TABLE VII-continued

Representative Substituted 2-Hydroxyalkyl-quinazolin-4-ylamine Analogues

| Compound | | Name | MS |
|---|---|---|---|
| 741. | 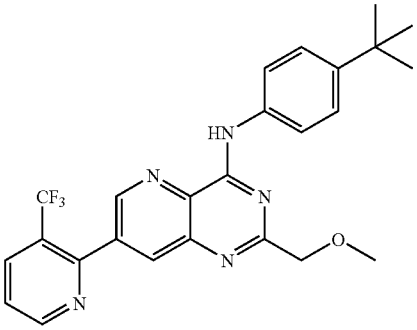 | (4-tert-Butyl-phenyl)-[2-methoxymethyl-7-(3-trifluoromethyl-pyridin-2-yl)-pyrido[3,2-d]pyrimidin-4-yl]-amine | 467.2 |
| 742. | 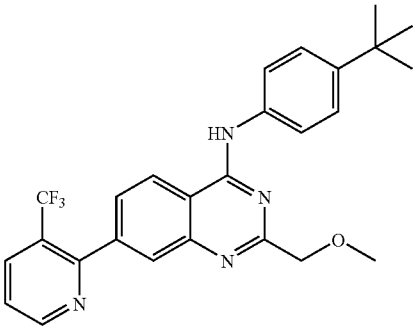 | (4-tert-Butyl-phenyl)-[2-methoxymethyl-7-(3-trifluoromethyl-pyridin-2-yl)-quinazolin-4-yl]-amine | 466.2 |
| 743. | 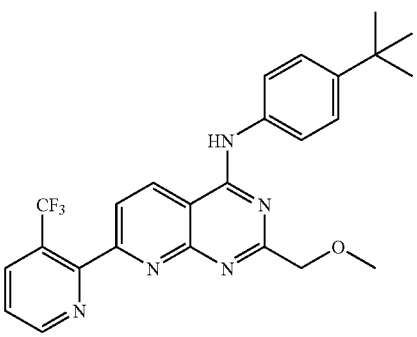 | (4-tert-Butyl-phenyl)-[2-methoxymethyl-7-(3-trifluoromethyl-pyridin-2-yl)-pyrido[2,3-d]pyrimidin-4-yl]-amine | |
| 744. | 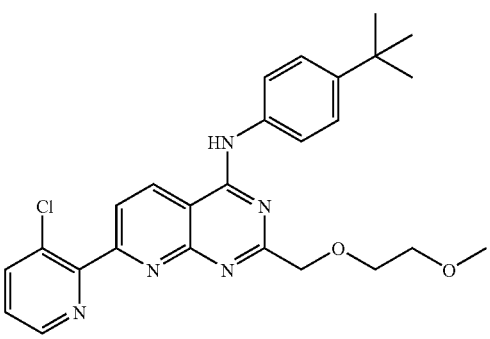 | (4-tert-Butyl-phenyl)-[7-(3-chloro-pyridin-2-yl)-2-(2-methoxy-ethoxymethyl)-pyrido[2,3-d]pyrimidin-4-yl]-amine | |

TABLE VII-continued

Representative Substituted 2-Hydroxyalkyl-quinazolin-4-ylamine Analogues

| Compound | | Name | MS |
|---|---|---|---|
| 745. | | (4-tert-Butyl-phenyl)-[7-(3-chloro-pyridin-2-yl)-2-ethoxymethyl-pyrido[2,3-d]pyrimidin-4-yl]-amine | |
| 746. | | (4-tert-Butyl-phenyl)-[7-(3-chloro-pyridin-2-yl)-2-ethoxymethyl-quinazolin-4-yl]-amine | 446.2 |
| 747. | | (4-tert-Butyl-phenyl)-[7-(3-chloro-pyridin-2-yl)-2-methoxymethyl-pyrido[2,3-d]pyrimidin-4-yl]-amine | 433.2 |
| 748. | | (4-tert-Butyl-phenyl)-[7-(3-chloro-pyridin-2-yl)-2-methoxymethyl-pyrido[3,2-d]pyrimidin-4-yl]-amine | 433.2 |

TABLE VII-continued

Representative Substituted 2-Hydroxyalkyl-quinazolin-4-ylamine Analogues

| Compound | Name | MS |
|---|---|---|
| 749. | (4-tert-Butyl-phenyl)-[7-(3-chloro-pyridin-2-yl)-2-methoxymethyl-quinazolin-4-yl]-amine | 432.2 |
| 750. | (6-tert-Butyl-pyridin-3-yl)-[2-(2-methoxy-ethyl)-7-(3-trifluoromethyl-pyridin-2-yl)-quinazolin-4-yl]-amine | 481.2 |
| 751. | (6-tert-Butyl-pyridin-3-yl)-[2-isobutoxymethyl-7-(3-methyl-pyridin-2-yl)-pyrido[2,3-d]pyrimidin-4-yl]-amine | |
| 752. | (6-tert-Butyl-pyridin-3-yl)-[2-isobutoxymethyl-7-(3-trifluoromethyl-pyridin-2-yl)-pyrido[2,3-d]pyrimidin-4-yl]-amine | |

TABLE VII-continued

Representative Substituted 2-Hydroxyalkyl-quinazolin-4-ylamine Analogues

| Compound | | Name | MS |
|---|---|---|---|
| 753. | | (6-tert-Butyl-pyridin-3-yl)-[2-methoxymethyl-7-(3-methyl-pyridin-2-yl)-pyrido[2,3-d]pyrimidin-4-yl]-amine | |
| 754. | | (6-tert-Butyl-pyridin-3-yl)-[2-methoxymethyl-7-(3-trifluoromethyl-pyridin-2-yl)-quinazolin-4-yl]-amine | 467.2 |
| 755. | | (6-tert-Butyl-pyridin-3-yl)-[2-methoxymethyl-7-(3-trifluoromethyl-pyridin-2-yl)-pyrido[2,3-d]pyrimidin-4-yl]-amine | |
| 756. | | (6-tert-Butyl-pyridin-3-yl)-[7-(3-chloro-pyridin-2-yl)-2-ethoxymethyl-quinazolin-4-yl]-amine | 447.2 |

TABLE VII-continued

Representative Substituted 2-Hydroxyalkyl-quinazolin-4-ylamine Analogues

| Compound | Name | MS |
|---|---|---|
| 757. | (6-tert-Butyl-pyridin-3-yl)-[7-(3-chloro-pyridin-2-yl)-2-isobutoxymethyl-pyrido[2,3-d]pyrimidin-4-yl]-amine | |
| 758. | (6-tert-Butyl-pyridin-3-yl)-[7-(3-chloro-pyridin-2-yl)-2-methoxymethyl-quinazolin-4-yl]-amine | 433.2 |
| 759. | (6-tert-Butyl-pyridin-3-yl)-[7-(3-chloro-pyridin-2-yl)-2-methoxymethyl-pyrido[2,3-d]pyrimidin-4-yl]-amine | |
| 760. | [2-(1-Methyl-piperidin-4-yloxymethyl)-7-(3-trifluoromethyl-pyridin-2-yl)-quinazolin-4-yl]-(6-trifluoromethyl-pyridin-3-yl)-amine | 562.2 |

TABLE VII-continued

Representative Substituted 2-Hydroxyalkyl-quinazolin-4-ylamine Analogues

| Compound | | Name | MS |
|---|---|---|---|
| 761. | 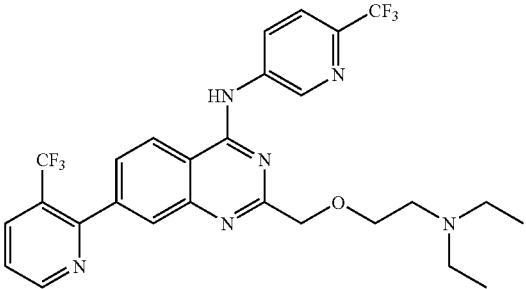 | [2-(2-Diethylamino-ethoxymethyl)-7-(3-trifluoromethyl-pyridin-2-yl)-quinazolin-4-yl]-(6-trifluoromethyl-pyridin-3-yl)-amine | 564.2 |
| 762. | 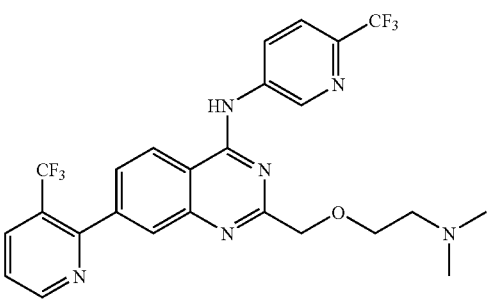 | [2-(2-Dimethylamino-ethoxymethyl)-7-(3-trifluoromethyl-pyridin-2-yl)-quinazolin-4-yl]-(4-trifluoromethyl-phenyl)-amine | 535.2 |
| 763. | 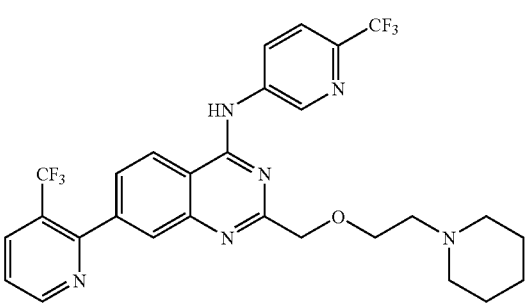 | [2-(2-Piperidin-1-yl-ethoxymethyl)-7-(3-trifluoromethyl-pyridin-2-yl)-quinazolin-4-yl]-(6-trifluoromethyl-pyridin-3-yl)-amine | 576.2 |
| 764. | 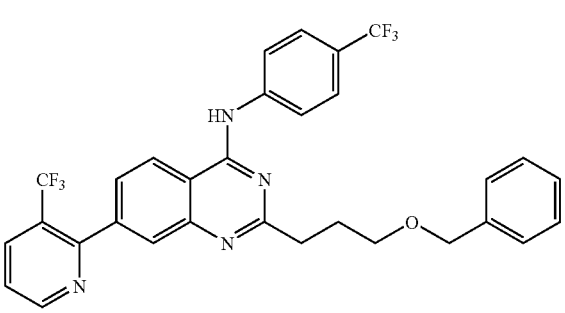 | [2-(3-Benzyloxy-propyl)-7-(3-trifluoromethyl-pyridin-2-yl)-quinazolin-4-yl]-(4-trifluoromethyl-phenyl)-amine | 582.2 |
| 765. | 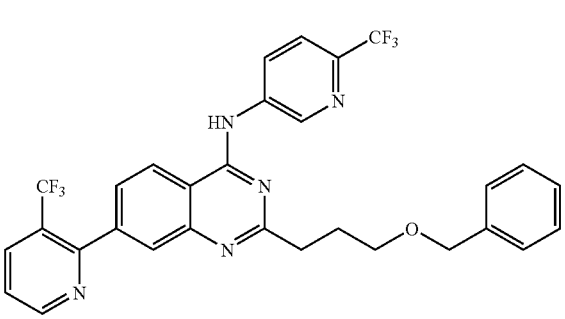 | [2-(3-Benzyloxy-propyl)-7-(3-trifluoromethyl-pyridin-2-yl)-quinazolin-4-yl]-(6-trifluoromethyl-pyridin-3-yl)-amine | 583.2 |

TABLE VII-continued

Representative Substituted 2-Hydroxyalkyl-quinazolin-4-ylamine Analogues

| Compound | | Name | MS |
|---|---|---|---|
| 766. | | [2-(3-Benzyloxy-propyl)-7-(3-trifluoromethyl-pyridin-2-yl)-quinazolin-4-yl]-(6-tert-butyl-pyridin-3-yl)-amine | 571.3 |
| 767. | | [2-(3-Diethylamino-propoxymethyl)-7-(3-trifluoromethyl-pyridin-2-yl)-quinazolin-4-yl]-(4-trifluoromethyl-phenyl)-amine | 577.2 |
| 768. | | [2-(3-Dimethylamino-2,2-dimethyl-propoxymethyl)-7-(3-trifluoromethyl-pyridin-2-yl)-quinazolin-4-yl]-(4-trifluoromethyl-phenyl)-amine | 577.2 |
| 769. | | [2-(3-Dimethylamino-propoxymethyl)-7-(3-trifluoromethyl-pyridin-2-yl)-quinazolin-4-yl]-(4-trifluoromethyl-phenyl)-amine | 549.2 |
| 770. | | [2-(Pyridin-3-ylmethoxymethyl)-7-(3-trifluoromethyl-pyridin-2-yl)-quinazolin-4-yl]-(6-trifluoromethyl-pyridin-3-yl)-amine | 556.1 |

TABLE VII-continued

Representative Substituted 2-Hydroxyalkyl-quinazolin-4-ylamine Analogues

| Compound | | Name | MS |
|---|---|---|---|
| 771. | 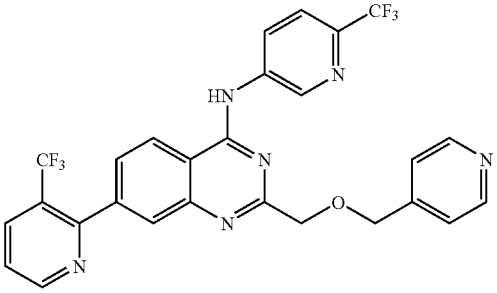 | [2-(Pyridin-4-ylmethoxymethyl)-7-(3-trifluoromethyl-pyridin-2-yl)-quinazolin-4-yl]-(6-trifluoromethyl-pyridin-3-yl)-amine | 556.1 |
| 772. | 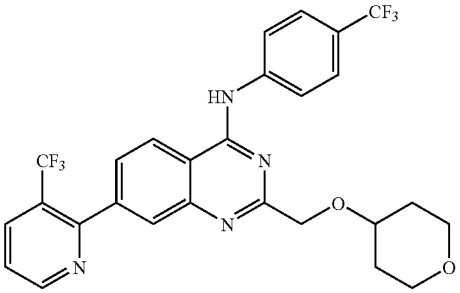 | [2-(Tetrahydro-pyran-4-yloxymethyl)-7-(3-trifluoromethyl-pyridin-2-yl)-quinazolin-4-yl]-(4-trifluoromethyl-phenyl)-amine | 548.2 |
| 773. | 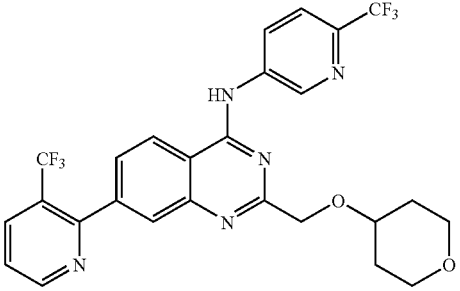 | [2-(Tetrahydro-pyran-4-yloxymethyl)-7-(3-trifluoromethyl-pyridin-2-yl)-quinazolin-4-yl]-(6-trifluoromethyl-pyridin-3-yl)-amine | 549.2 |
| 774. | 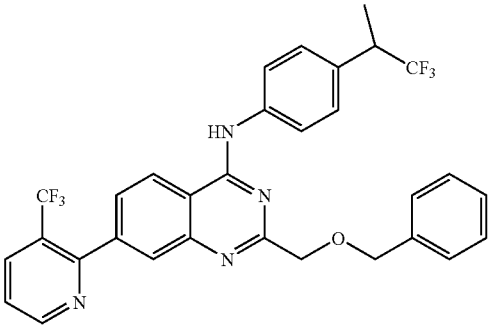 | [2-Benzyloxymethyl-7-(3-trifluoromethyl-pyridin-2-yl)-quinazolin-4-yl]-[4-(2,2,2-trifluoro-1-methyl-ethyl)-phenyl]-amine | 582.2 |

TABLE VII-continued

Representative Substituted 2-Hydroxyalkyl-quinazolin-4-ylamine Analogues

| Compound | | Name | MS |
|---|---|---|---|
| 775. | 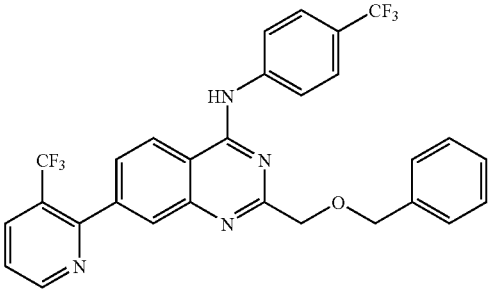 | [2-Benzyloxymethyl-7-(3-trifluoromethyl-pyridin-2-yl)-quinazolin-4-yl]-(4-trifluoromethyl-phenyl)-amine | 554.2 |
| 776. | 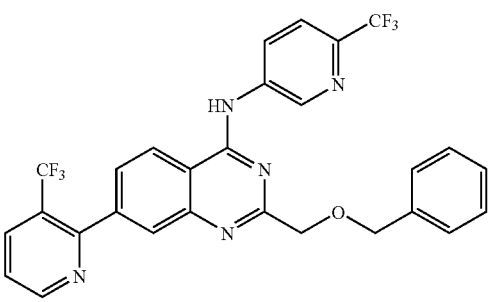 | [2-Benzyloxymethyl-7-(3-trifluoromethyl-pyridin-2-yl)-quinazolin-4-yl]-(6-trifluoromethyl-pyridin-3-yl)-amine | 555.1 |
| 777. | 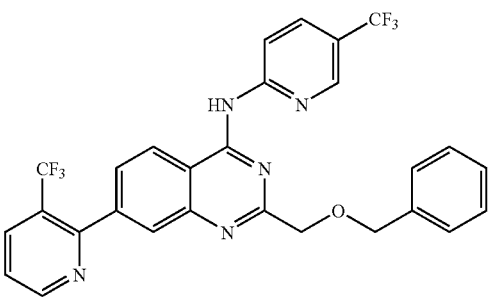 | [2-Benzyloxymethyl-7-(3-trifluoromethyl-pyridin-2-yl)-quinazolin-4-yl]-(5-trifluoromethyl-pyridin-2-yl)-amine | 555.1 |
| 778. | 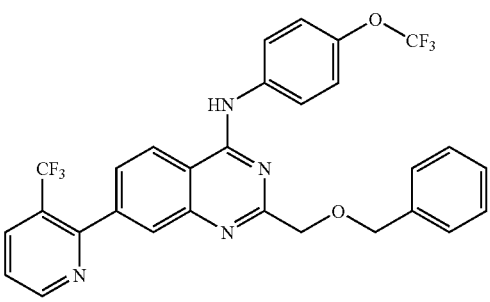 | [2-Benzyloxymethyl-7-(3-trifluoromethyl-pyridin-2-yl)-quinazolin-4-yl]-(4-trifluoromethoxy-phenyl)-amine | 570.1 |
| 779. | 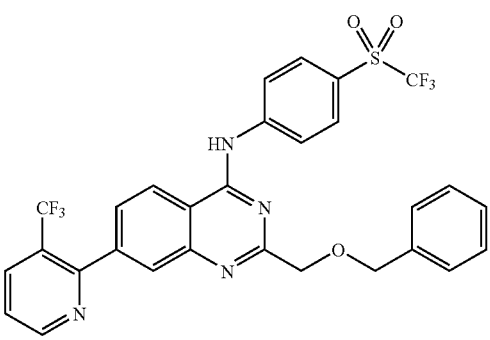 | [2-Benzyloxymethyl-7-(3-trifluoromethyl-pyridin-2-yl)-quinazolin-4-yl]-(4-trifluoromethanesulfonyl-phenyl)-amine | 618.1 |

TABLE VII-continued

Representative Substituted 2-Hydroxyalkyl-quinazolin-4-ylamine Analogues

| Compound | | Name | MS |
|---|---|---|---|
| 780. | 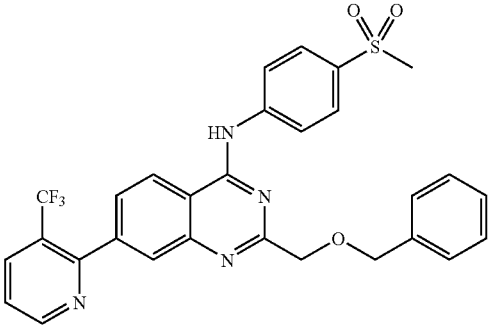 | [2-Benzyloxymethyl-7-(3-trifluoromethyl-pyridin-2-yl)-quinazolin-4-yl]-(4-methanesulfonyl-phenyl)-amine | 564.1 |
| 781. | 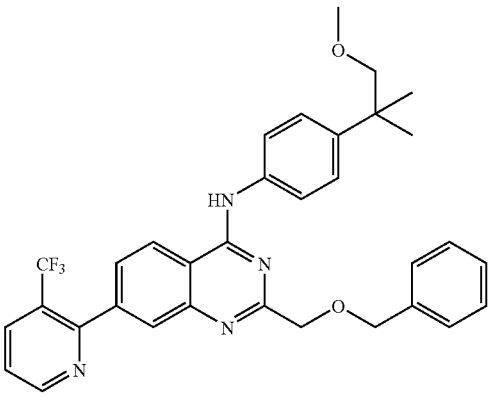 | [2-Benzyloxymethyl-7-(3-trifluoromethyl-pyridin-2-yl)-quinazolin-4-yl]-[4-(2-methoxy-1,1-dimethyl-ethyl)-phenyl]-amine | 572.2 |
| 782. | 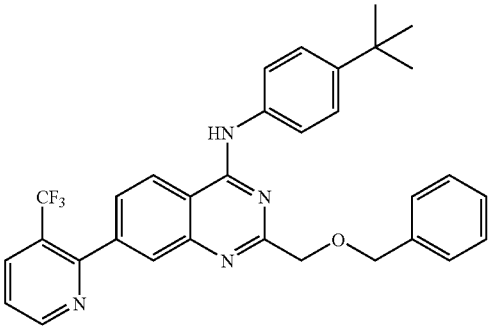 | [2-Benzyloxymethyl-7-(3-trifluoromethyl-pyridin-2-yl)-quinazolin-4-yl]-(4-tert-butyl-phenyl)-amine | 542.2 |
| 783. | 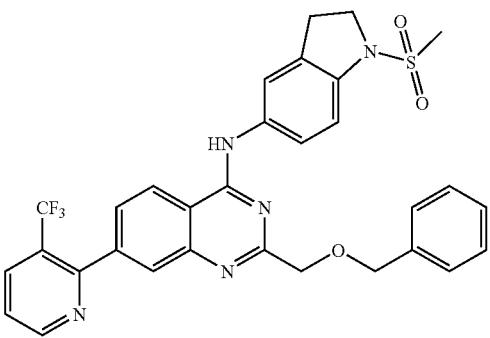 | [2-Benzyloxymethyl-7-(3-trifluoromethyl-pyridin-2-yl)-quinazolin-4-yl]-(1-methanesulfonyl-2,3-dihydro-1H-indol-5-yl)-amine | 605.2 |

TABLE VII-continued

Representative Substituted 2-Hydroxyalkyl-quinazolin-4-ylamine Analogues

| Compound | | Name | MS |
|---|---|---|---|
| 784. | 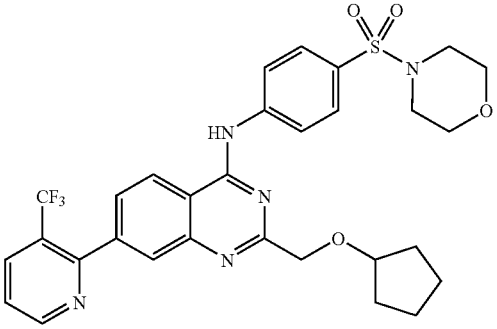 | [2-Cyclopentyloxymethyl-7-(3-trifluoromethyl-pyridin-2-yl)-quinazolin-4-yl]-[4-(morpholine-4-sulfonyl)-phenyl]-amine | |
| 785. | 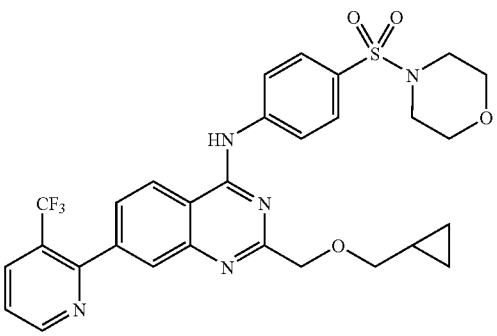 | [2-Cyclopropylmethoxymethyl-7-(3-trifluoromethyl-pyridin-2-yl)-quinazolin-4-yl]-[4-(morpholine-4-sulfonyl)-phenyl]-amine | |
| 786. | 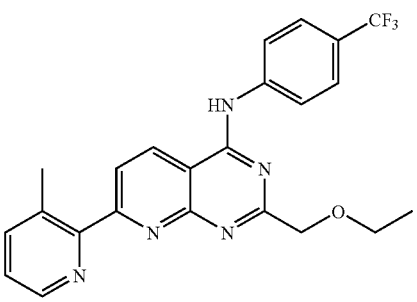 | [2-Ethoxymethyl-7-(3-methyl-pyridin-2-yl)-pyrido[2,3-d]pyrimidin-4-yl]-(4-trifluoromethyl-phenyl)-amine | 412.2 |
| 787. | 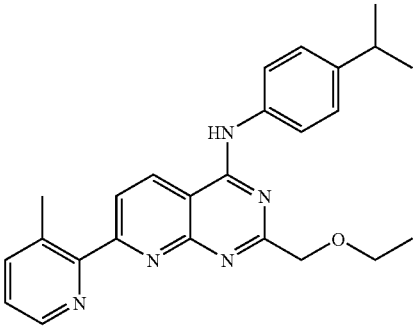 | [2-Ethoxymethyl-7-(3-methyl-pyridin-2-yl)-pyrido[2,3-d]pyrimidin-4-yl]-(4-isopropyl-phenyl)-amine | 438.2 |

TABLE VII-continued

Representative Substituted 2-Hydroxyalkyl-quinazolin-4-ylamine Analogues

| Compound | | Name | MS |
|---|---|---|---|
| 788. | 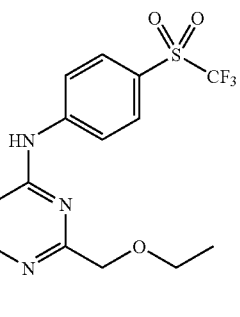 | [2-Ethoxymethyl-7-(3-methyl-pyridin-2-yl)-pyrido[2,3-d]pyrimidin-4-yl]-(4-trifluoromethanesulfonyl-phenyl)-amine | 492.1 |
| 789. | 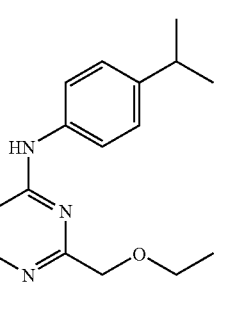 | [2-Ethoxymethyl-7-(3-methyl-pyridin-2-yl)-quinazolin-4-yl]-(4-isopropyl-2-yl)-quinazolin-4-yl]-(4-isopropyl- | |
| 790. | 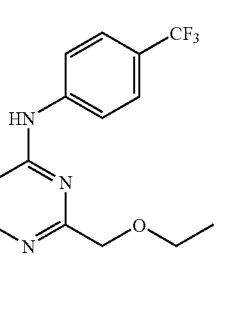 | [2-Ethoxymethyl-7-(3-methyl-pyridin-2-yl)-quinazolin-4-yl]-(4-trifluoromethyl-phenyl)-amine | |
| 791. | 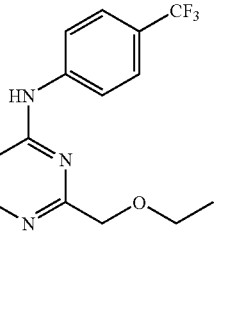 | [2-Ethoxymethyl-7-(3-trifluoromethyl-pyridin-2-yl)-pyrido[2,3-d pyrimidin-4-yl]-(4-trifluoromethyl-phenyl)-amine | |

TABLE VII-continued

Representative Substituted 2-Hydroxyalkyl-quinazolin-4-ylamine Analogues

| Compound | | Name | MS |
|---|---|---|---|
| 792. | | [2-Ethoxymethyl-7-(3-trifluoromethyl-pyridin-2-yl)-pyrido[2,3-d]pyrimidin-4-yl]-(6-pyridin-3-yl)-amine | |
| 793. | | [2-Ethoxymethyl-7-(3-trifluoromethyl-pyridin-2-yl)-quinazolin-4-yl]-(4-trifluoromethyl-phenyl)-amine | |
| 794. | | [2-Ethoxymethyl-7-(3-trifluoromethyl-pyridin-2-yl)-quinazolin-4-yl]-[4-(morpholine-4-sulfonyl)-phenyl]-amine | |
| 795. | | [2-Ethoxymethyl-7-(3-trifluoromethyl-pyridin-2-yl)-quinazolin-4-yl]-(6-trifluoromethyl-pyridin-3-yl)-amine | |

TABLE VII-continued

Representative Substituted 2-Hydroxyalkyl-quinazolin-4-ylamine Analogues

| Compound | | Name | MS |
|---|---|---|---|
| 796. | | [2-Isobutoxymethyl-7-(3-methyl-pyridin-2-yl)-pyrido[2,3-d]pyrimidin-4-yl]-(4-isopropyl-phenyl)-amine | |
| 797. | | [2-Isobutoxymethyl-7-(3-methyl-pyridin-2-yl)-pyrido[2,3-d]pyrimidin-4-yl]-(4-trifluoromethyl-phenyl)-amine | |
| 798. | | [2-Isobutoxymethyl-7-(3-methyl-pyridin-2-yl)-pyrido[2,3-d]pyrimidin-4-yl]-(3-methyl-4-trifluoromethyl-phenyl)-amine | |
| 799. | | [2-Isobutoxymethyl-7-(3-methyl-pyridin-2-yl)-pyrido[2,3-d]pyrimidin-4-yl]-(4-trifluoromethoxy-phenyl)-amine | |

TABLE VII-continued

Representative Substituted 2-Hydroxyalkyl-quinazolin-4-ylamine Analogues

| Compound | Name | MS |
|---|---|---|
| 800. | [2-Isobutoxymethyl-7-(3-methyl-pyridin-2-yl)-pyrido[2,3-d]pyrimidin-4-yl]-[4-(2-methoxy-1,1-dimethyl ethyl)-phenyl]-amine | |
| 801. | [2-Isobutoxymethyl-7-(3-methyl-pyridin-2-yl)-pyrido[2,3-d]pyrimidin-4-yl]-(4-methanesulfonyl-phenyl)-amine | |
| 802. | [2-Isobutoxymethyl-7-(3-trifluoromethyl-pyridin-2-yl)-pyrido[2,3-d]pyrimidin-4-yl]-(4-isopropyl-phenyl)-amine | |
| 803. | [2-Isobutoxymethyl-7-(3-trifluoromethyl-pyridin-2-yl)-pyrido[2,3-d]pyrimidin-4-yl]-(4-trifluoromethyl-phenyl)-amine | |

TABLE VII-continued

Representative Substituted 2-Hydroxyalkyl-quinazolin-4-ylamine Analogues

| Compound | | Name | MS |
|---|---|---|---|
| 804. | | [2-Isobutoxymethyl-7-(3-trifluoromethyl-pyridin-2-yl)-pyrido[2,3-d]pyrimidin-4-yl]-(6-trifluoromethyl-pyridin-3-yl)-amine | |
| 805. | | [2-Isobutoxymethyl-7-(3-trifluoromethyl-pyridin-2-yl)-pyrido[2,3-d]pyrimidin-4-yl]-(3-methyl-4-trifluoromethyl-phenyl)-amine | |
| 806. | | [2-Isobutoxymethyl-7-(3-trifluoromethyl-pyridin-2-yl)-pyrido[2,3-d]pyrimidin-4-yl]-(4-trifluoromethanesulfonyl-phenyl)-amine | |
| 807. | | [2-Isobutoxymethyl-7-(3-trifluoromethyl-pyridin-2-yl)-pyrido[2,3-d]pyrimidin-4-yl]-(4-trifluoromethoxy-phenyl)-amine | |

TABLE VII-continued

Representative Substituted 2-Hydroxyalkyl-quinazolin-4-ylamine Analogues

| Compound | | Name | MS |
|---|---|---|---|
| 808. | 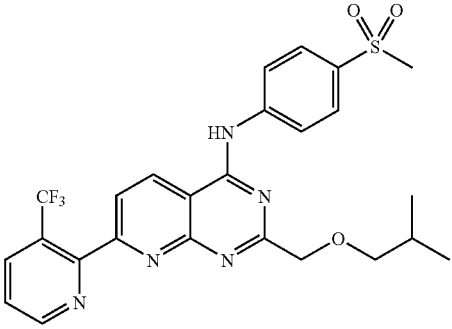 | [2-Isobutoxymethyl-7-(3-trifluoromethyl-pyridin-2-yl)-pyrido[2,3-d]pyrimidin-4-yl]-(4-methanesulfonyl-phenyl)-amine | |
| 809. | 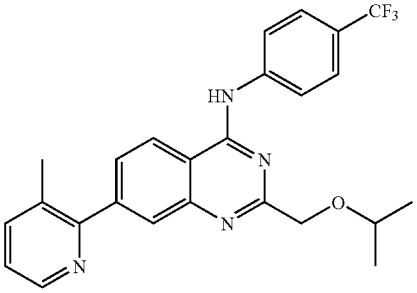 | [2-Isopropoxymethyl-7-(3-methyl-pyridin-2-yl)-quinazolin-4-yl]-(4-trifluoromethyl-phenyl)-amine | 452.2 |
| 810. | 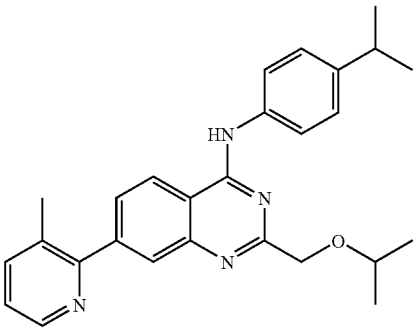 | [2-Isopropoxymethyl-7-(3-methyl-pyridin-2-yl)-quinazolin-4-yl]-(4-isopropyl-phenyl)-amine | |
| 811. | 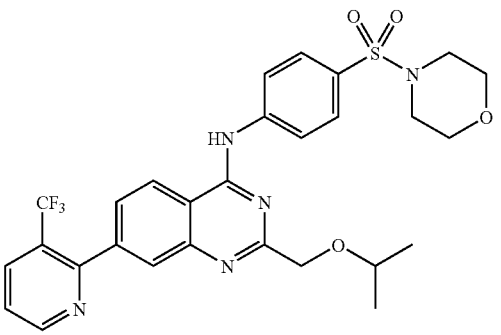 | [2-Isopropoxymethyl-7-(3-trifluoromethyl-pyridin-2-yl)-sulfonyl)-phenyl]-amine | |

TABLE VII-continued

Representative Substituted 2-Hydroxyalkyl-quinazolin-4-ylamine Analogues

| Compound | Name | MS |
|---|---|---|
| 812. | [2-Isopropoxymethyl-7-(3-trifluoromethyl-pyridin-2-yl)-quinazolin-4-yl]-(6-trifluoromethyl-pyridin-3-yl)-amine | 507.1 |
| 813. | [2-Methoxymethyl-7-(3-methyl-pyridin-2-yl)-pyrido[2,3-d]pyrimidin-4-yl]-(4-trifluoromethyl-phenyl)-amine | |
| 814. | [2-Methoxymethyl-7-(3-methyl-pyridin-2-yl)-pyrido[2,3-d]pyrimidin-4-yl]-(6-trifluoromethyl-pyridin-3-yl)-amine | 425.1 |
| 815. | [2-Methoxymethyl-7-(3-methyl-pyridin-2-yl)-pyrido[2,3-d]pyrimidin-4-yl]-(4-trifluoromethanesulfonyl-phenyl)-amine | |
| 816. | [2-Methoxymethyl-7-(3-methyl-pyridin-2-yl)-pyrido[2,3-d]pyrimidin-4-yl]-(4-trifluoromethoxy-phenyl)-amine | |

TABLE VII-continued

Representative Substituted 2-Hydroxyalkyl-quinazolin-4-ylamine Analogues

| Compound | | Name | MS |
|---|---|---|---|
| 817. | 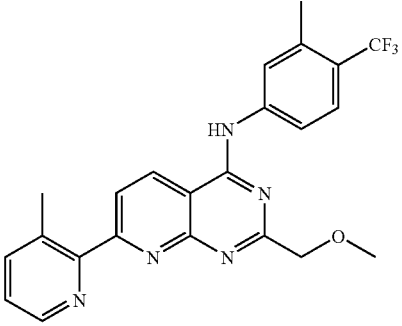 | [2-Methoxymethyl-7-(3-methyl-pyridin-2-yl)-pyrido[2,3-d]pyrimidin-4-yl]-(3-methyl-4-trifluoromethyl-phenyl)-amine | |
| 818. | 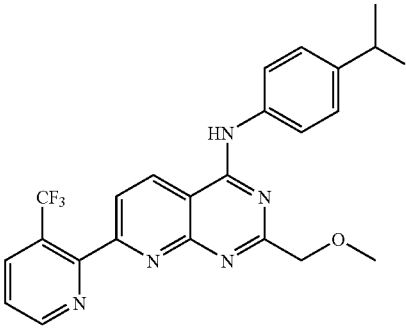 | [2-Methoxymethyl-7-(3-trifluoromethyl-pyridin-2-yl)-pyrido[2,3-d]pyrimidin-4-yl]-[4-(2,2,2-trifluoro-1-methyl-ethyl)-phenyl]-amine | |
| 819. | 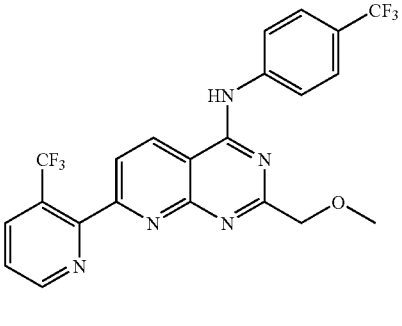 | [2-Methoxymethyl-7-(3-trifluoromethyl-pyridin-2-yl)-pyrido[2,3-d]pyrimidin-4-yl]-(4-trifluoromethyl-phenyl)-amine | |
| 820. | 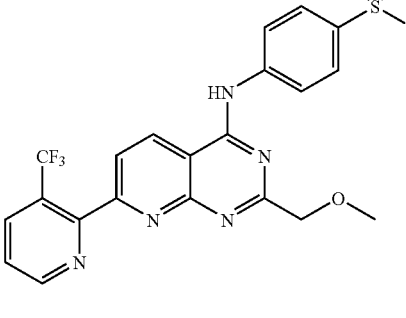 | [2-Methoxymethyl-7-(3-trifluoromethyl-pyridin-2-yl)-pyrido[2,3-d]pyrimidin-4-yl]-(4-trifluoromethanesulfonyl-phenyl)-amine | |

TABLE VII-continued

Representative Substituted 2-Hydroxyalkyl-quinazolin-4-ylamine Analogues

| Compound | | Name | MS |
|---|---|---|---|
| 821. | 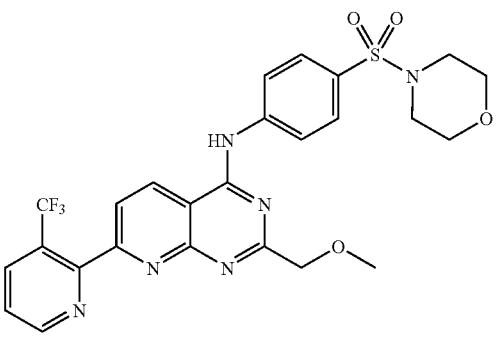 | [2-Methoxymethyl-7-(3-trifluoromethyl-pyridin-2-yl)-pyrido[2,3-d]pyrimidin-4-yl]-[4-(morpholine-4-sulfonyl)-phenyl]-amine | |
| 822. | 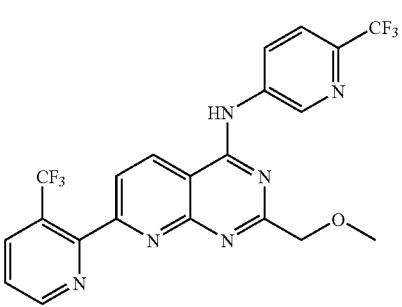 | [2-Methoxymethyl-7-(3-trifluoromethyl-pyridin-2-yl)-pyrido[2,3-d]pyrimidin-4-yl]-(6-trifluoromethyl-pyridin-3-yl)-amine | |
| 823. | 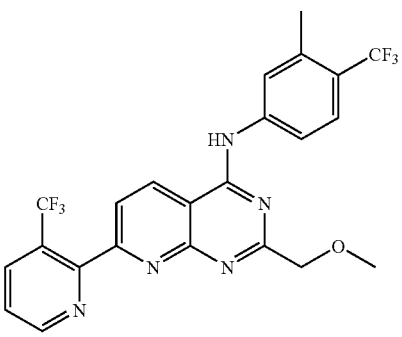 | [2-Methoxymethyl-7-(3-trifluoromethyl-pyridin-2-yl)-pyrido[2,3-d]pyrimidin-4-yl]-(3-methyl-4-trifluoromethyl-phenyl)-amine | |
| 824. | 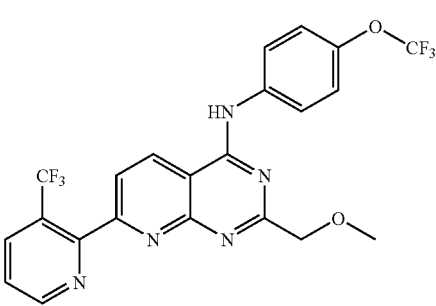 | [2-Methoxymethyl-7-(3-trifluoromethyl-pyridin-2-yl)-pyrido[2,3-d]pyrimidin-4-yl]-(4-trifluoromethoxy-phenyl)-amine | |

TABLE VII-continued

Representative Substituted 2-Hydroxyalkyl-quinazolin-4-ylamine Analogues

| Compound | Name | MS |
|---|---|---|
| 825. | [2-Methoxymethyl-7-(3-trifluoromethyl-pyridin-2-yl)-pyrido[3,2-d]pyrimidin-4-yl]-(6-trifluoromethyl-pyridin-3-yl)-amine | 480.1 |
| 826. | [2-Methoxymethyl-7-(3-trifluoromethyl-pyridin-2-yl)-pyrido[3,2-d]pyrimidin-4-yl]-(4-morpholin-4-yl-phenyl)-amine | 496.2 |
| 827. | [2-Methoxymethyl-7-(3-trifluoromethyl-pyridin-2-yl)-quinazolin-4-yl]-(4-trifluoromethyl-phenyl)-amine | 478.1 |
| 828. | [2-Methoxymethyl-7-(3-trifluoromethyl-pyridin-2-yl)-quinazolin-4-yl]-(6-trifluoromethyl-pyridin-3-yl)-amine | 479.1 |

TABLE VII-continued

Representative Substituted 2-Hydroxyalkyl-quinazolin-4-ylamine Analogues

| Compound | | Name | MS |
|---|---|---|---|
| 829. | 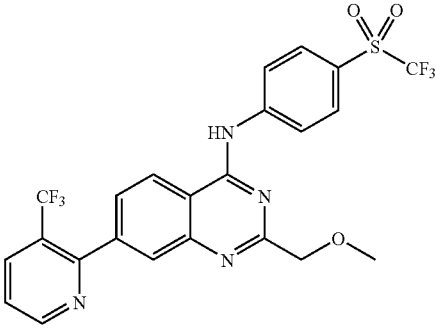 | [2-Methoxymethyl-7-(3-trifluoromethyl-pyridin-2-yl)-quinazolin-4-yl]-(4-trifluoromethanesulfonyl-phenyl)-amine | 542.1 |
| 830. | 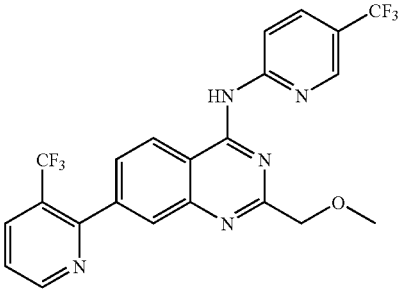 | [2-Methoxymethyl-7-(3-trifluoromethyl-pyridin-2-yl)-quinazolin-4-yl]-(5-trifluoromethyl-pyridin-2-yl)-amine | 479.1 |
| 831. | 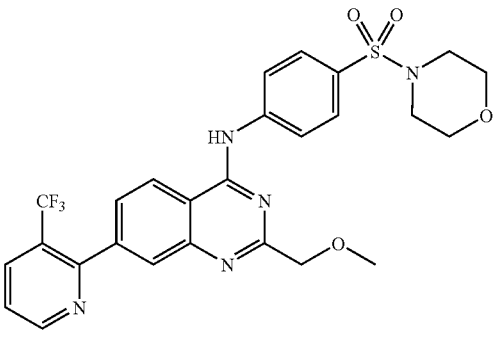 | [2-Methoxymethyl-7-(3-trifluoromethyl-pyridin-2-yl)-quinazolin-4-yl]-[4-(morpholine-4-sulfonyl)-phenyl]-amine | |
| 832. | 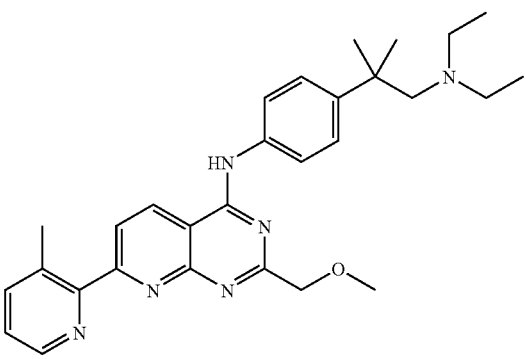 | [4-(2-Diethylamino-1,1-dimethyl-ethyl)-phenyl]-[2-methoxymethyl-7-(3-methyl-pyridin-2-yl)-pyrido[2,3-d]pyrimidin-4-yl]-amine | |

TABLE VII-continued

Representative Substituted 2-Hydroxyalkyl-quinazolin-4-ylamine Analogues

| Compound | | Name | MS |
|---|---|---|---|
| 833. | 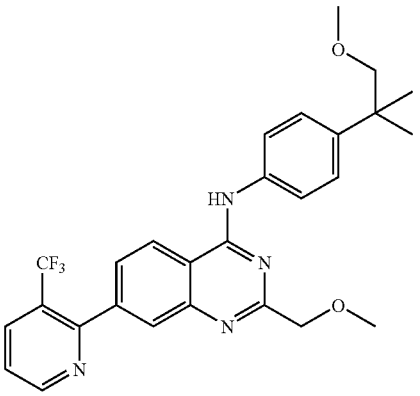 | [4-(2-Methoxy-1,1-dimethyl-ethyl)-phenyl]-[2-methoxymethyl-7-(3-trifluoromethyl-pyridin-2-yl)-quilazolin-4-yl]-amine | 496.2 |
| 834. | 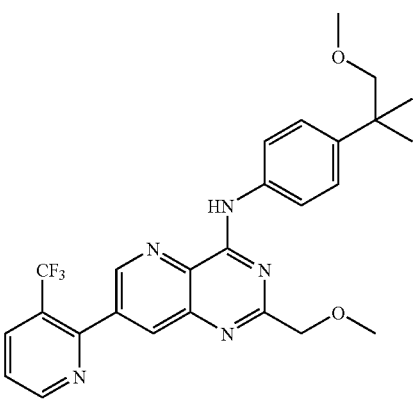 | [4-(2-Methoxy-1,1-dimethyl-ethyl)-phenyl]-[2-methoxymethyl-7-(3-trifluoromethyl-pyridin-2-yl)-pyrido-[3,2-d]pyrimidin-4-yl]-amine | 497.2 |
| 835. | 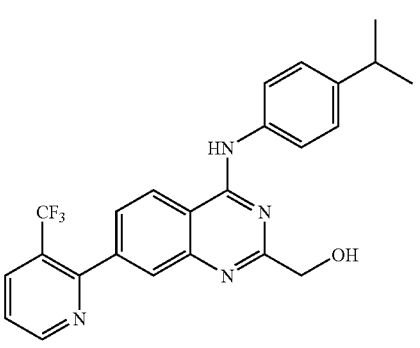 | [4-(4-Isopropyl-phenylamino)-7-(3-trifluoromethyl-pyridin-2-yl)-quinazolin-2-yl]-methanol | 438.2 |
| 836. | 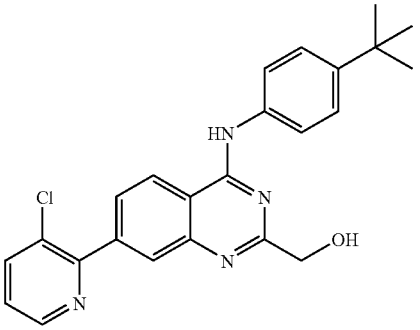 | [4-(4-tert-Butyl-phenylamino)-7-(3-chloro-pyridin-2-yl)-quinazolin-2-yl]-methanol | 418.2 |

TABLE VII-continued

Representative Substituted 2-Hydroxyalkyl-quinazolin-4-ylamine Analogues

| Compound | | Name | MS |
|---|---|---|---|
| 837. | 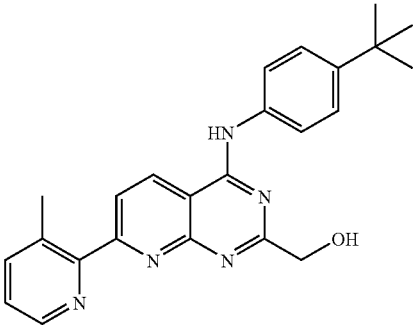 | [4-(4-tert-Butyl-phenylamino)-7-(3-methyl-pyridin-2-yl)-pyrido[2,3d]pyrimidin-2-yl]-methanol | |
| 838. | 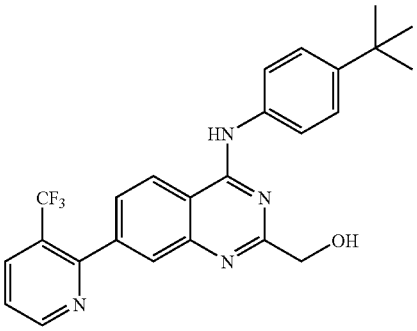 | [4-(4-tert-Butyl-phenylamino)-7-(3-trifluoromethyl-pyridin-2-yl)-quinazolin-2-yl]-methanol | 452.2 |
| 839. | 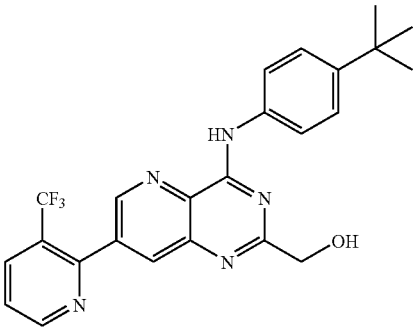 | [4-(4-tert-Butyl-phenylamino)-7-(3-trifluoromethyl-pyridin-2-yl)-pyrido[3,2-d]pyrimidin-2-yl]-methanol | |
| 840. | 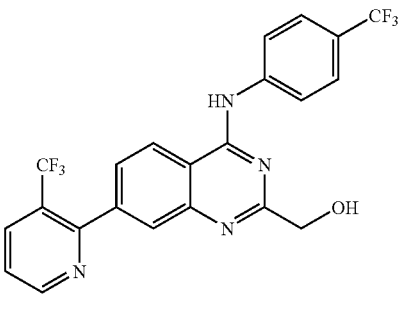 | [4-(4-Trifluoromethyl-phenylanuno)-7-(3-trifluoromethyl-pyridin-2-yl)-quinazolin-2-yl]-methanol | 464.1 |

TABLE VII-continued

Representative Substituted 2-Hydroxyalkyl-quinazolin-4-ylamine Analogues

| Compound | Name | MS |
|---|---|---|
| 841. | [4-(4-Trifluoromethyl-phenylamino)-7-(3-trifluoromethyl-pyridin-2-yl)-pyrido[3,2-d]pyrimidin-2-yl]-methanol | 465.1 |
| 842. | [4-(4-Trifluoromethyl-phenylamino)-7-(3-trifluoromethyl-pyridin-2-yl)-pyrido[2,3-d]pyrimidin-2-yl]-methanol | |
| 843. | [4-(Morpholine-4-sulfonyl)-phenyl]-[2-(tetrahydro-pyran-4-yloxymethyl)-7-(3-trifluoromethyl-pyridin-2-yl)-quinazolin-4-yl]-amine | |
| 844. | [4-[4-(Piperidine-1-sulfonyl)-phenylamino]-7-(3-trifluoromethyl-pyridin-2-yl)-quinazolin-2-yl]-methanol | |

TABLE VII-continued

Representative Substituted 2-Hydroxyalkyl-quinazolin-4-ylamine Analogues

| Compound | | Name | MS |
|---|---|---|---|
| 845. | 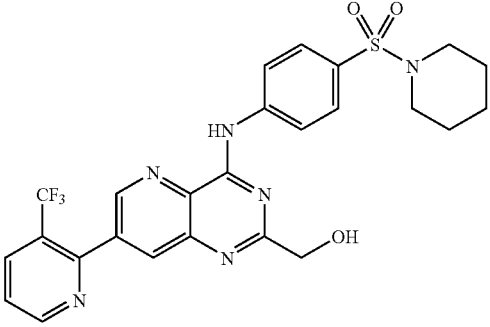 | [4-[4-(Piperidine-1-sulfonyl)-phenylamino]-7-(3-trifluoromethyl-pyridin-2-yl)-pyrido[3,2-d]pyrimidin-2-yl]-methanol | |
| 846. | 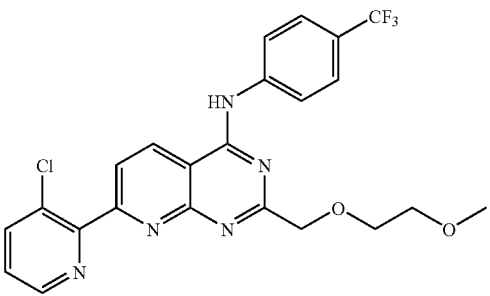 | [7-(3-Chloro-pyridin-2-yl)-2-(2-methoxy-ethoxymethyl)-pyrido[2,3-d]pyrimidin-4-yl]-(4-trifluoromethyl-phenyl)-amine | |
| 847. | 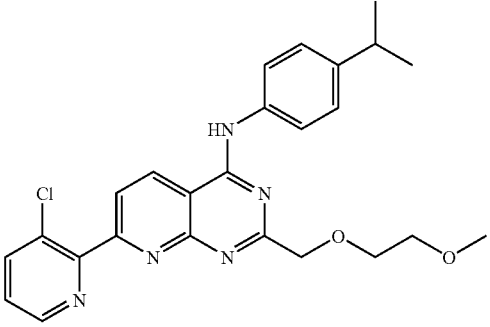 | [7-(3-Chloro-pyridin-2-yl)-2-(2-methoxy-ethoxymethyl)-pyrido[2,3-d]pyrimidin-4-yl]-(4-isopropyl-phenyl)-amine | 463.2 |
| 848. | 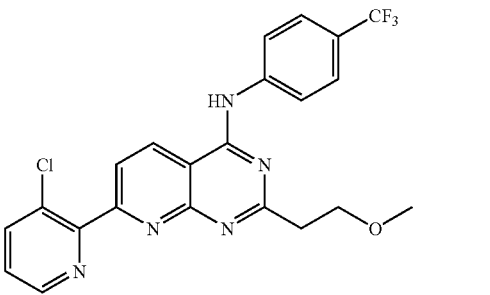 | [7-(3-Chloro-pyridin-2-yl)-2-(2-methoxy-ethyl)-pyrido[2,3-d]pyrimidin-4-yl]-(4-trifluoromethyl-phenyl)-amine | |

TABLE VII-continued

Representative Substituted 2-Hydroxyalkyl-quinazolin-4-ylamine Analogues

| Compound | Name | MS |
|---|---|---|
| 849. | [7-(3-Chloro-pyridin-2-yl)-2-(tetrahydro-pyran-4-yloxymethyl)-quinazolin-4-yl]-(4-trifluoromethyl-phenyl)-amine | 514.1 |
| 850. | [7-(3-Chloro-pyridin-2-yl)-2-(tetrahydro-pyran-4-yloxymethyl)-quinazolin-4-yl]-(4-isopropyl-phenyl)-amine | 488.2 |
| 851. | [7-(3-Chloro-pyridin-2-yl)-2-ethoxymethyl-pyrido[2,3-d]pyrimidin-4-yl]-(4-isopropyl-phenyl)-amine | |
| 852. | [7-(3-Chloro-pyridin-2-yl)-2-ethoxymethyl-pyrido[2,3-d]pyrimidin-4-yl]-(4-trifluoromethyl-phenyl)-amine | |

TABLE VII-continued

Representative Substituted 2-Hydroxyalkyl-quinazolin-4-ylamine Analogues

| Compound | | Name | MS |
|---|---|---|---|
| 853. | | [7-(3-Chloro-pyridin-2-yl)-2-ethoxymethyl-pyrido[2,3-d]pyrimidin-4-yl]-(4-trifluoromethanesulfonyl-phenyl)-amine | |
| 854. | | [7-(3-Chloro-pyridin-2-yl)-2-ethoxymethyl-pyrido[2,3-d]pyrimidin-4-yl]-[4-(2,2,2-trifluoro-1-methyl-ethyl)-phenyl]-amine | |
| 855. | | [7-(3-Chloro-pyridin-2-yl)-2-ethoxymethyl-pyrido[2,3-d]pyrimidin-4-yl]-(4-cyclopentyl-phenyl)-amine | |
| 856. | | [7-(3-Chloro-pyridin-2-yl)-2-ethoxymethyl-pyrido[2,3-d]pyrimidin-4-yl]-(6-trifluoromethyl-pyridin-3-yl)-amine | |

TABLE VII-continued

Representative Substituted 2-Hydroxyalkyl-quinazolin-4-ylamine Analogues

| Compound | | Name | MS |
|---|---|---|---|
| 857. | 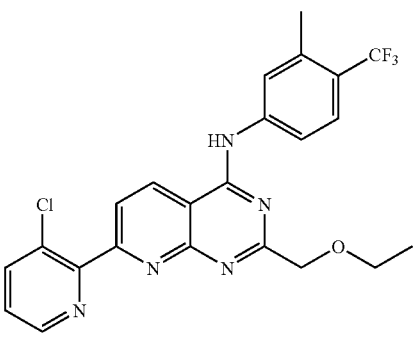 | [7-(3-Chloro-pyridin-2-yl)-2-ethoxymethyl-pyrido[2,3-d]pyrimidin-4-yl]-(3-methyl-4-trifluoromethyl-phenyl)-amine | |
| 858. | 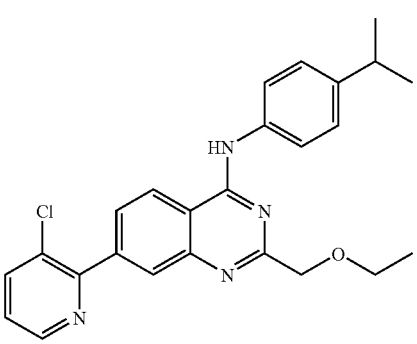 | [7-(3-Chloro-pyridin-2-yl)-2-ethoxymethyl-quinazolin-4-yl]-(4-isopropyl-phenyl)-amine | 432.2 |
| 859. | 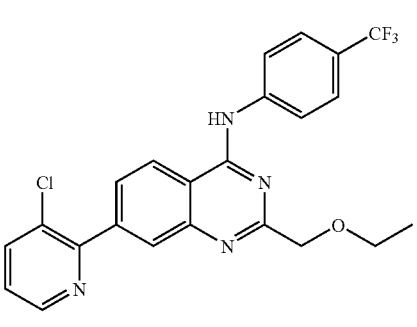 | [7-(3-Chloro-pyridin-2-yl)-2-ethoxymethyl-quinazolin-4-yl]-(4-trifluoromethyl-phenyl)-amine | 458.1 |
| 860. | 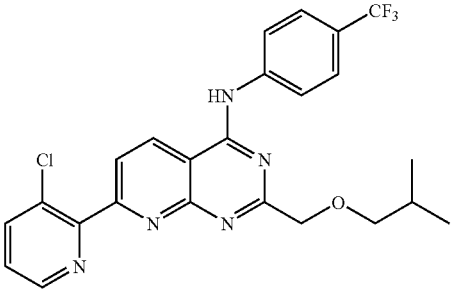 | [7-(3-Chloro-pyridin-2-yl)-2-isobutoxymethyl-pyrido[2,3-d]pyrimidin-4-yl]-(4-trifluoromethyl-phenyl)-amine | |

TABLE VII-continued

Representative Substituted 2-Hydroxyalkyl-quinazolin-4-ylamine Analogues

| Compound | | Name | MS |
|---|---|---|---|
| 861. | 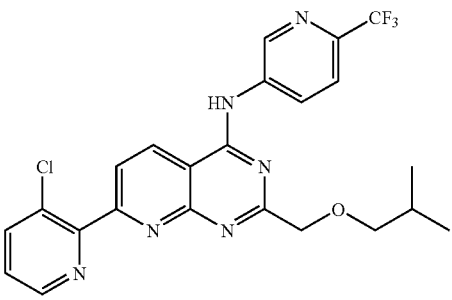 | [7-(3-Chloro-pyridin-2-yl)-2-isobutoxymethyl-pyrido[2,3-d]pyrimidin-4-yl]-(6-trifluoromethyl-pyridin-3-yl)-amine | |
| 862. | 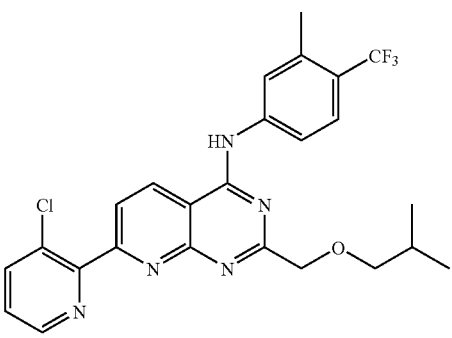 | [7-(3-Chloro-pyridin-2-yl)-2-isobutoxymethyl-pyrido[2,3-d]pyrimidin-4-yl]-(3-methyl-4-trifluoromethyl-phenyl)-amine | |
| 863. | 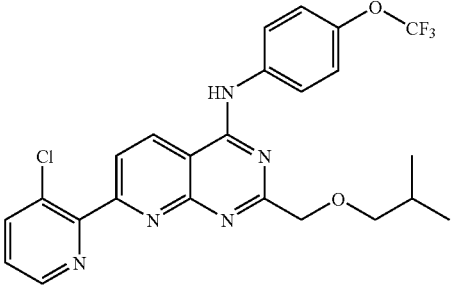 | [7-(3-Chloro-pyridin-2-yl)-2-isobutoxymethyl-pyrido[2,3-d]pyrimidin-4-yl]-(4-trifluoromethoxy-phenyl-amine | |
| 864. | 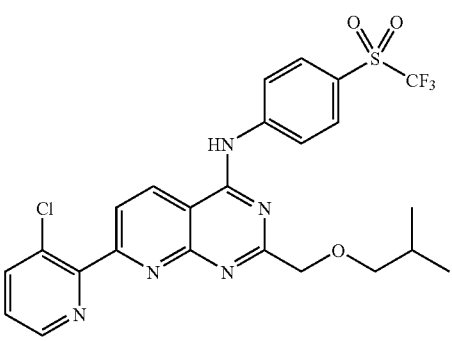 | [7-(3-Chloro-pyridin-2-yl)-2-isobutoxymethyl-pyrido[2,3-trifluoromethanesulfonyl-phenyl)-amine | |

TABLE VII-continued

Representative Substituted 2-Hydroxyalkyl-quinazolin-4-ylamine Analogues

| Compound | | Name | MS |
|---|---|---|---|
| 865. | | [7-(3-Chloro-pyridin-2-yl)-2-isobutoxymethyl-pyrido[2,3-d]pyrimidin-4-yl]-(4-methanesulfonyl-phenyl)-amine | |
| 866. | | [7-(3-Chloro-pyridin-2-yl)-2-methoxymethyl-pyrido[2,3-d]pyrimidin-4-yl]-(4-isopropyl-phenyl)-amine | 419.2 |
| 867. | | [7-(3-Chloro-pyridin-2-yl)-2-methoxymethyl-pyrido[2,3-d]pyrimidin-4-yl]-[4-(2-methoxy-1,1-dimethyl-ethyl)-phenyl]-amine | 463.2 |
| 868. | | [7-(3-Chloro-pyridin-2-yl)-2-methoxymethyl-pyrido[2,3-d]pyrimidin-4-yl]-(4-trifluoromethoxy-phenyl)-amine | |

TABLE VII-continued

Representative Substituted 2-Hydroxyalkyl-quinazolin-4-ylamine Analogues

| Compound | | Name | MS |
|---|---|---|---|
| 869. | 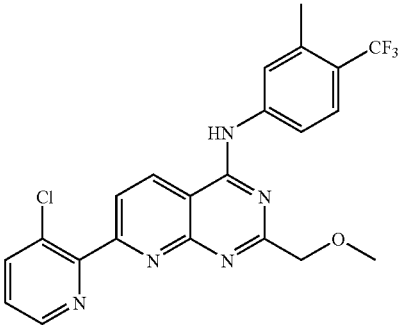 | [7-(3-Chloro-pyridin-2-yl)-2-methoxymethyl-pyrido[2,3-d]pyrimidin-4-yl]-(3-methyl-4-trifluoromethyl-phenyl)-amine | |
| 870. | 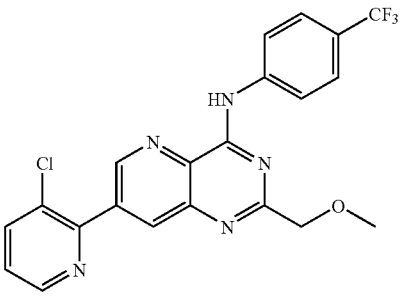 | [7-(3-Chloro-pyridin-2-yl)-2-methoxymethyl-pyrido[3,2-d]pyrimidin-4-yl]-(4-trifluoromethyl-phenyl)-amine | 445.1 |
| 871. | 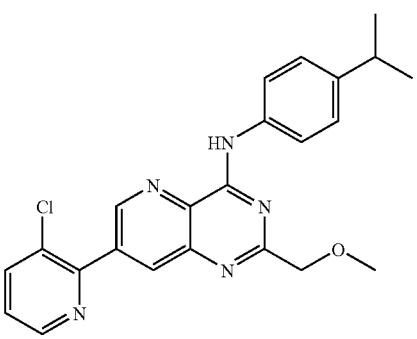 | [7-(3-Chloro-pyridin-2-yl)-2-d]pyrimidin-4-yl]-(4-isopropyl-methoxymethyl-pyrido[3,2-phenyl)-amine | 419.2 |
| 872. | 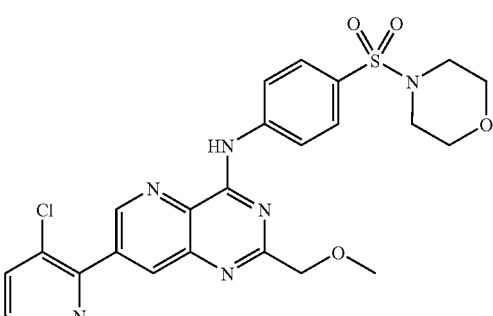 | [7-(3-Chloro-pyridin-2-yl)-2-methoxymethyl-pyrido[3,2-sulfonyl)-phenyl]-amine | 526.1 |

TABLE VII-continued

Representative Substituted 2-Hydroxyalkyl-quinazolin-4-ylamine Analogues

| Compound | | Name | MS |
|---|---|---|---|
| 873. | | [7-(3-Chloro-pyridin-2-yl)-2-methoxymethyl-quinazolin-4-yl]-(4-isopropyl-phenyl)-amine | 418.2 |
| 874. | | [7-(3-Chloro-pyridin-2-yl)-2-methoxymethyl-quinazolin-4-yl]-(4-trifluoromethyl-phenyl)-amine | 444.1 |
| 875. | | [7-(3-Chloro-pyridin-2-yl)-4-(4-isopropyl-phenylamino)-quinazolin-2-yl]-methanol | 404.1 |
| 876. | | [7-(3-Chloro-pyridin-2-yl)-4-(4-trifluoromethyl-phenylamino)-pyrido[3,2-d]pyrimidin-2-yl]-methanol | 431.1 |

TABLE VII-continued

Representative Substituted 2-Hydroxyalkyl-quinazolin-4-ylamine Analogues

| Compound | Name | MS |
|---|---|---|
| 877. | [7-(3-Methyl-pyridin-2-yl)-2-(tetrahydro-furan-3-yl)-pyrido[2,3-d]pyrimidin-4-yl]-(4-trifluoromethyl-phenyl)-amine | |
| 878. | [7-(3-Methyl-pyridin-2-yl)-2-(tetrahydro-pyran-4-yloxymethyl)-quinazolin-4-yl]-(4-trifluoromethyl-phenyl)-amine | 494.2 |
| 879. | [7-(3-Methyl-pyridin-2-yl)-4-(4-trifluoromethyl-phenylamino)-pyrido[2,3-d]pyrimidin-2-yl]-methanol | 411.1 |
| 880. | [7-(3-Trifluoromethyl-pyridin-2-yl)-4-(6-trifluoromethyl-pyridin-3-ylamino)-quinazolin-2-yl]-methanol | 465.1 |

TABLE VII-continued

Representative Substituted 2-Hydroxyalkyl-quinazolin-4-ylamine Analogues

| Compound | | Name | MS |
|---|---|---|---|
| 881. | 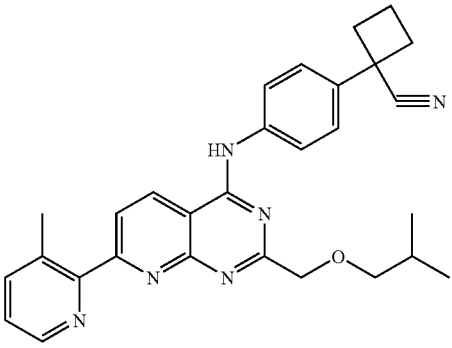 | 1-{4-[2-Isobutoxymethyl-7-(3-methyl-pyridin-2-yl)-pyrido[2,3-d]pyrimidin-4-ylamino]-phenyl}-cyclobutanecarbonitrile | |
| 882. | 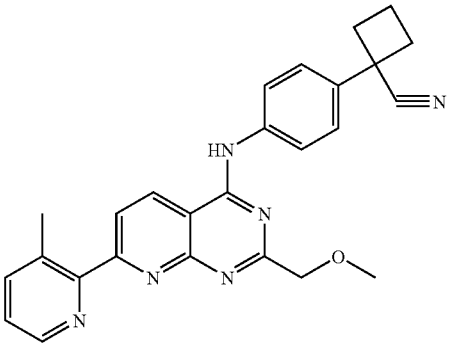 | 1-{4-[2-Methoxymethyl-7-(3-methyl-pyridin-2-yl)-pyrido[2,3-d]pyrimidin-4-ylamino]-phenyl}-cyclobutanecarbonitrile | 436.2 |
| 883. | 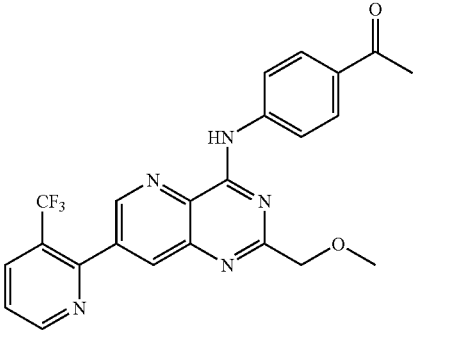 | 1-{4-[2-Methoxymethyl-7-(3-trifluoromethyl-pyridin-2-yl)-pyrido[3,2-d]pyrimidin-4-ylamino]-phenyl}-ethanone | 453.1 |
| 884. | 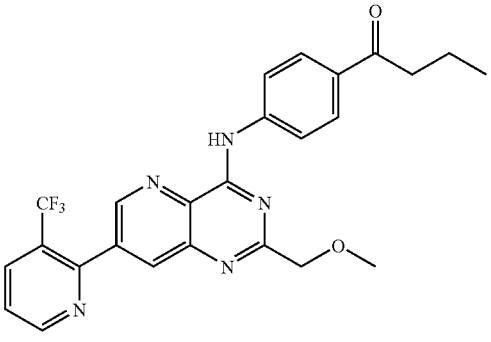 | 1-{4-[2-Methoxymethyl-7-(3-trifluoromethyl-pyridin-2-yl)-pyrido[3,2-d]pyrimidin-4-ylamino]-phenyl}-butan-1-one | 481.2 |

TABLE VII-continued

Representative Substituted 2-Hydroxyalkyl-quinazolin-4-ylamine Analogues

| Compound | Name | MS |
|---|---|---|
| 885. | 1-{4-[7-(3-Chloro-pyridin-2-yl)-2-ethoxymethyl-pyrido[2,3-d]pyrimidin-4-ylaniino]-phenyl}-cyclobutanecarbonitrile | |
| 886. | 1-Dimethylamino-3-[4-(4-trifluoromethyl-phenylamino)-7-(3-trifluoromethyl-pyridin-2-yl)-quinazolin-2-ylmethoxy]-propan-2-ol | |
| 887. | 2-[4-(4-tert-Butyl-phenylamino)-7-(3-trifluoromethyl-pyridin-2-yl)-quinazolin-2-yl]-2-methyl-propan-1-ol | |
| 888. | 2-{4-[2-Benzyloxymethyl-7-(3-trifluoromethyl-pyridin-2-yl)-quinazolin-4-ylaniino]-phenyl}-2-methyl-propionitrile | 553.2 |

TABLE VII-continued

Representative Substituted 2-Hydroxyalkyl-quinazolin-4-ylamine Analogues

| Compound | | Name | MS |
|---|---|---|---|
| 889. | 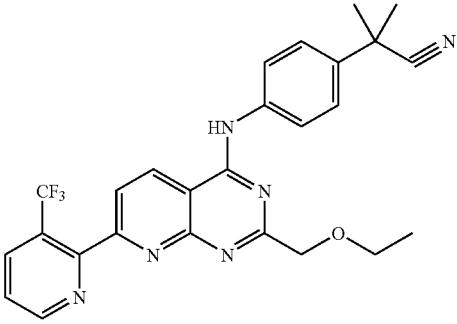 | 2-{4-[2-Ethoxymethyl-7-(3-trifluoromethyl-pyridin-2-yl)-pyrido[2,3-d]pyrimidin-4-ylamino]-phenyl}-2-methyl-propionitrile | |
| 890. | 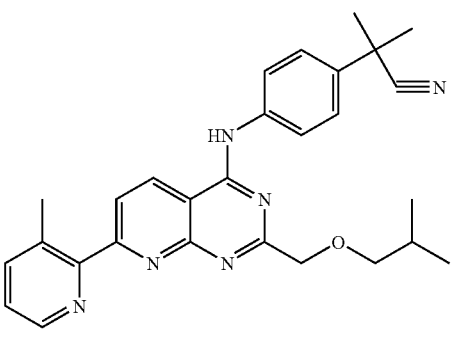 | 2-{4-[2-Isobutoxymethyl-7-(3-methyl-pyridin-2-yl)-pyrido[2,3-d]pyrimidin-4-ylamino]-phenyl}-2-methyl-propionitrile | |
| 891. | 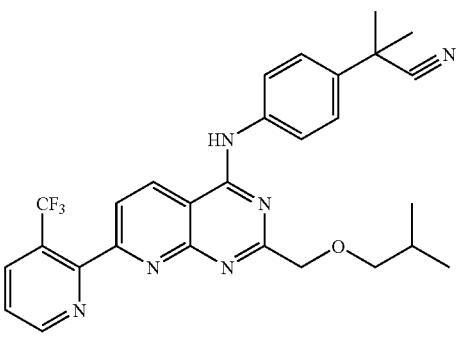 | 2-{4-[2-Isobutoxymethyl-7-(3-trifluoromethyl-pyridin-2-yl)-pyrido[2,3-d]pyrimidin-4-ylamino]-phenyl}-2-methyl-propionitrile | |
| 892. | 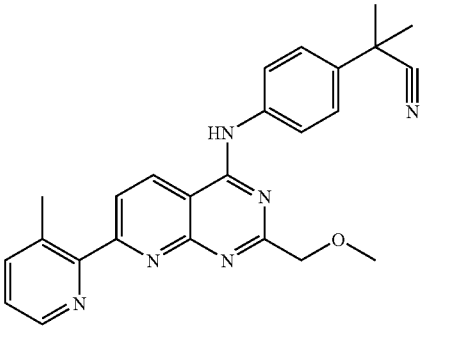 | 2-{4-[2-Methoxymethyl-7-(3-methyl-pyridin-2-yl)-pyrido[2,3-d]pyrimidin-4-ylamino]-phenyl}-2-methyl-propionitrile | 424.2 |

TABLE VII-continued

Representative Substituted 2-Hydroxyalkyl-quinazolin-4-ylamine Analogues

| Compound | | Name | MS |
|---|---|---|---|
| 893. | 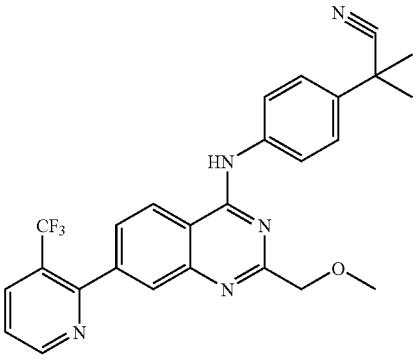 | 2-{4-[2-Methoxymethyl-7-(3-trifluoromethyl-pyridin-2-yl)-quinazolin-4-ylamino]-phenyl}-2-methyl-propionitrile | 477.2 |
| 894. | 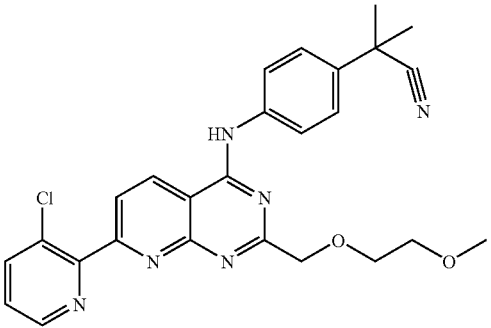 | 2-{4-[7-(3-Chloro-pyridin-2-yl)-2-(2-methoxy-ethoxymethyl)-pyrido[2,3-d]pyrimidin-4-ylamino]-phenyl}-2-methyl-propionitrile | 488.2 |
| 895. | 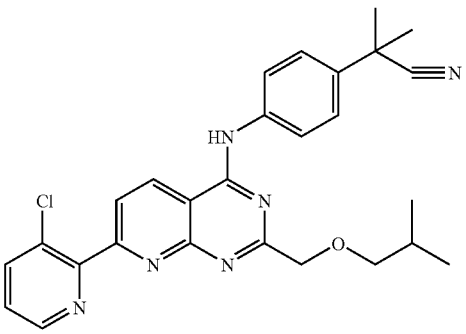 | 2-{4-[7-(3-Chloro-pyridin-2-yl)-2-isobutoxymethyl-pyrido[2,3-d]pyrimidin-4-ylamino]-phenyl}-2-methyl-propionitrile | |
| 896. | 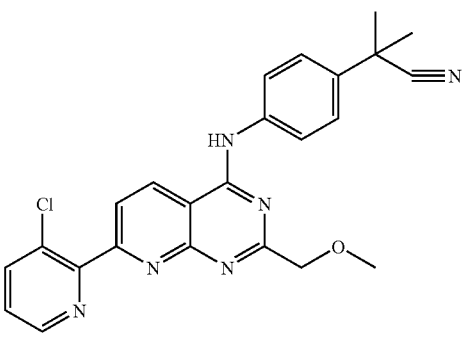 | 2-{4-[7-(3-Chloro-pyridin-2-yl)-2-methoxymethyl-pyrido[2,3-d]pyrimidin-4-ylamino]-phenyl}-2-methyl-propionitrile | 444.1 |

TABLE VII-continued

Representative Substituted 2-Hydroxyalkyl-quinazolin-4-ylamine Analogues

| Compound | | Name | MS |
|---|---|---|---|
| 897. | | 2-Methyl-2-[4-(4-trifluoromethyl-phenylamino)-7-(3-trifluoromethyl-pyridin-2-yl)-quinazolin-2-yl]-propan-1-ol | |
| 898. | | 2-Methyl-2-{4-[7-(3-methyl-pyridin-2-yl)-2-(tetrahydro-furan-3-yl)-pyrido[2,3-d]pyrimidin-4-ylamino]-phenyl}-propionitrile | |
| 899. | | 3-[4-(6-tert-Butyl-pyridin-3-ylamino)-7-(3-trifluoromethyl-pyridin-2-yl)-quinazolin-2-yl]-propan-1-ol | 481.2 |
| 900. | | 3-[7-(3-Trifluoromethyl-pyridin-2-yl)-4-(6-trifluoromethyl-pyridin-3-ylamino-quinazolin-2-yl]-propan-1-ol | 493.1 |

TABLE VII-continued

Representative Substituted 2-Hydroxyalkyl-quinazolin-4-ylamine Analogues

| Compound | | Name | MS |
|---|---|---|---|
| 901. | 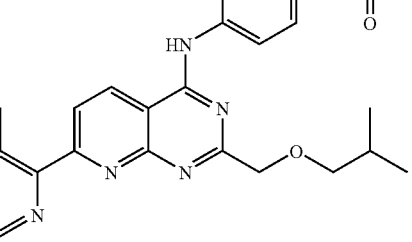 | 3-{4-[2-Isobutoxymethyl-7-(3-methyl-pyridin-2-yl)-pyrido[2,3-d]pyrimidin-4-ylamino]-phenyl}-3-methyl-butan-2-one | |
| 902. | 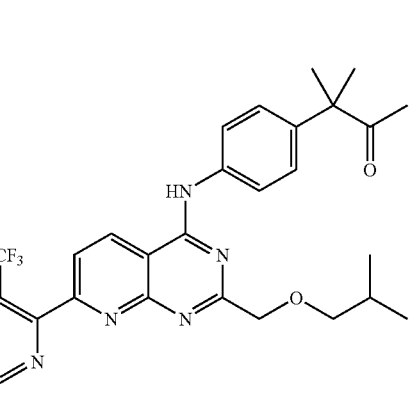 | 3-{4-[2-Isobutoxymethyl-7-(3-trifluoromethyl-pyridin-2-yl)-pyrido[2,3-d]pyrimidin-4-ylamino]-phenyl}-3-methyl-butan-2-one | |
| 903. | 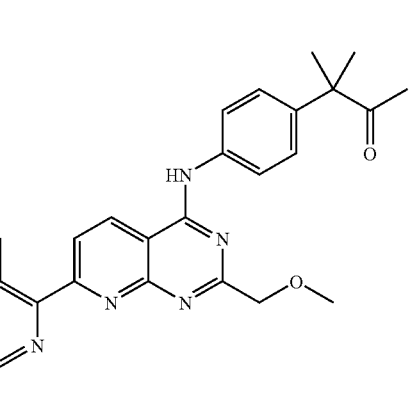 | 3-{4-[2-Methoxymethyl-7-(3-methyl-pyridin-2-yl)-pyrido[2,3-d]pynmidin-4-ylamino]-phenyl}-3-methyl-butan-2-one | |
| 904. | 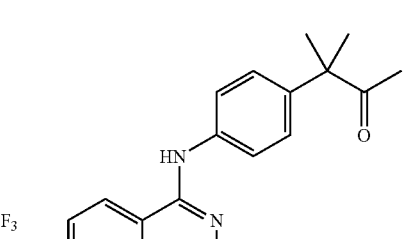 | 3-{4-[2-Methoxymethyl-7-(3-trifluoromethyl-pyridin-2-yl)-pyrido[2,3-d]pyrimidin-4-ylamino]-phenyl}-3-methyl-butan-2-one | |

TABLE VII-continued

Representative Substituted 2-Hydroxyalkyl-quinazolin-4-ylamine Analogues

| Compound | Name | MS |
|---|---|---|
| 905. | 3-{4-[7-(3-Chloro-pyridin-2-yl)-2-isobutoxymethyl-pyrido[2,3-d]pyrimidin-4-ylamino]-phenyl}-3-methyl-butan-2-one | |
| 906. | 3-{4-[7-(3-Chloro-pyridin-2-yl)-2-methoxymethyl-pyrido[2,3-d]pyrimidin-4-ylamino]-phenyl}-3-methyl-butan-2-one | |
| 907. | 4-[2-Benzyloxymethyl-7-(3-trifluoromethyl-pyridin-2-yl)-quinazolin-4-ylamino]-N-tert-butyl-benzenesulfonamide | 621.2 |
| 908. | 4-[2-Methoxymethyl-7-(3-trifluoromethyl-pyridin-2-yl)-pyrido[3,2-d]pyrimidin-4-ylamino]-benzonitrile | 436.1 |

TABLE VII-continued

Representative Substituted 2-Hydroxyalkyl-quinazolin-4-ylamine Analogues

| Compound | | Name | MS |
|---|---|---|---|
| 909. | 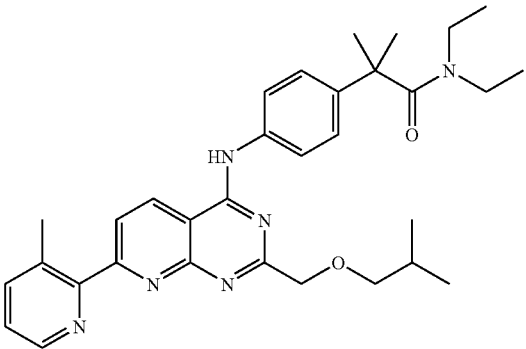 | N,N-Diethyl-2-{4-[2-isobutoxymethyl-7-(3-methyl-pyridin-2-yl)-pyrido[2,3-d]pyrimidin-4-ylamino]-phenyl}-isobutyramide | |
| 910. | 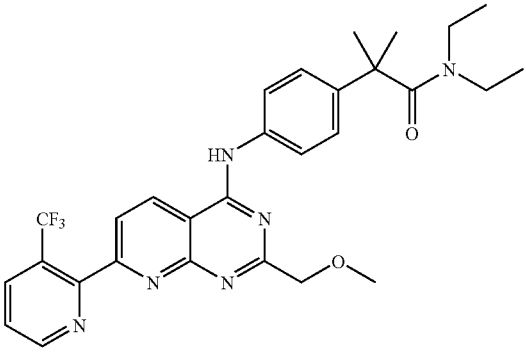 | N,N-Diethyl-2-{4-[2-methoxymethyl-7-(3-trifluoromethyl-pyridin-2-yl)-pyrido[2,3-d]pyrimidin-4-ylamino]-phenyl}-isobutyramide | |
| 911. | 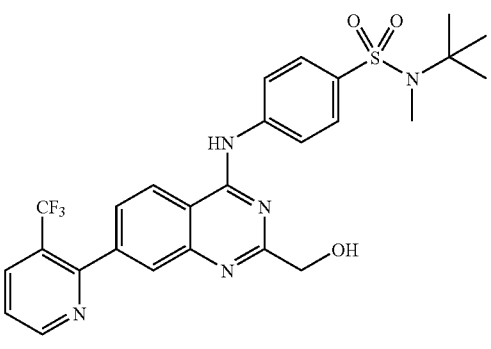 | N-tert-Butyl-4-[2-hydroxymethyl-7-(3-trifluoromethyl-pyridin-2-yl)-quinazolin-4-ylamino]-N-methyl-benzenesulfonamide | |
| 912. | 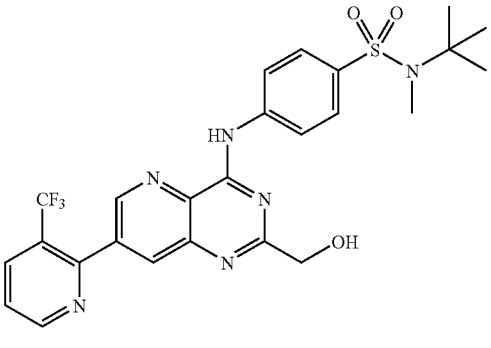 | N-tert-Butyl-4-[2-hydroxymethyl-7-(3-trifluoromethyl-pyridin-2-yl)-pyrido[3,2-d]pyrimidin-4-ylamino]-N-methyl-benzenesulfonamide | |

TABLE VII-continued

Representative Substituted 2-Hydroxyalkyl-quinazolin-4-ylamine Analogues

| Compound | | Name | MS |
|---|---|---|---|
| 913. | 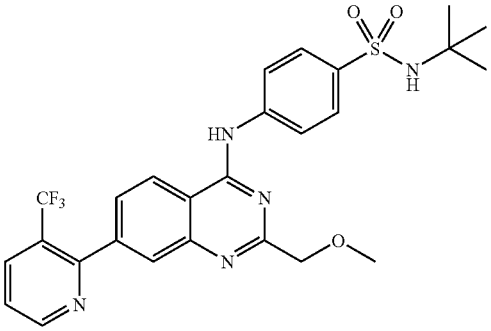 | N-tert-Butyl-4-[2-methoxymethyl-7-(3-trifluoromethyl-pyridin-2-yl)-quinazolin-4-ylamino]-benzenesulfonamide | 545.2 |

Example 4

VR1-Transfected Cells and Membrane Preparations

This Example illustrates the preparation of VR1-transfected cells and VR1-containing membrane preparations for use in capsaicin binding assays (Example 5).

A cDNA encoding full length human capsaicin receptor (SEQ ID NO:1, 2 or 3 of U.S. Pat. No. 6,482,611) was subcloned in the plasmid pBK-CMV (Stratagene, La Jolla, Calif.) for recombinant expression in mammalian cells.

Human embryonic kidney (HEK293) cells were transfected with the pBK-CMV expression construct encoding the full length human capsaicin receptor using standard methods. The transfected cells were selected for two weeks in media containing G418 (400 µg/ml) to obtain a pool of stably transfected cells. Independent clones were isolated from this pool by limiting dilution to obtain clonal stable cell lines for use in subsequent experiments.

For radioligand binding experiments, cells were seeded in T175 cell culture flasks in media without antibiotics and grown to approximately 90% confluency. The flasks were then washed with PBS and harvested in PBS containing 5 mM EDTA. The cells were pelleted by gentle centrifugation and stored at −80° C. until assayed.

Previously frozen cells were disrupted with the aid of a tissue homogenizer in ice-cold HEPES homogenization buffer (5 mM KCl 5, 5.8 mM NaCl, 0.75 mM $CaCl_2$, 2 mM $MgCl_2$, 320 mM sucrose, and 10 mM HEPES pH 7.4). Tissue homogenates were first centrifuged for 10 minutes at 1000×g (4° C.) to remove the nuclear fraction and debris, and then the supernatant from the first centrifugation is further centrifuged for 30 minutes at 35,000×g (4° C.) to obtain a partially purified membrane fraction. Membranes were resuspended in the HEPES homogenization buffer prior to the assay. An aliquot of this membrane homogenate is used to determine protein concentration via the Bradford method (BIO-RAD Protein Assay Kit, #500-0001, BIO-RAD, Hercules, Calif.).

Example 5

Capsaicin Receptor Binding Assay

This Example illustrates a representative assay of capsaicin receptor binding that may be used to determine the binding affinity of compounds for the capsaicin (VR1) receptor.

Binding studies with [$^3$H] Resiniferatoxin (RTX) are carried out essentially as described by Szallasi and Blumberg (1992) *J. Pharmacol. Exp. Ter.* 262: 883–888. In this protocol, non-specific RTX binding is reduced by adding bovine alpha, acid glycoprotein (100 µg per tube) after the binding reaction has been terminated.

[$^3$H] RTX (37 Ci/mmol) is synthesized by and obtained from the Chemical Synthesis and Analysis Laboratory, National Cancer Institute-Frederick Cancer Research and Development Center, Frederick, Md. [$^3$H] RTX may also be obtained from commercial vendors (e.g., Amersham Pharmacia Biotech, Inc.; Piscataway, N.J.).

The membrane homogenate of Example 4 is centrifuged as before and resuspended to a protein concentration of 333 µg/ml in homogenization buffer. Binding assay mixtures are set up on ice and contained [$^3$H]RTX (specific activity 2200 mCi/ml), 2 µl non-radioactive test compound, 0.25 mg/ml bovine serum albumin (Cohn fraction V), and $5\times10^4$–$1\times10^5$ VR1-transfected cells. The final volume is adjusted to 500 µl (for competition binding assays) or 1,000 µl (for saturation binding assays) with the ice-cold HEPES homogenization buffer solution (pH 7.4) described above. Non-specific binding is defined as that occurring in the presence of 1 µM non-radioactive RTX (Alexis Corp.; San Diego, Calif.). For saturation binding, [3H]RTX is added in the concentration range of 7–1,000 pM, using 1 to 2 dilutions. Typically 11 concentration points are collected per saturation binding curve.

Competition binding assays are performed in the presence of 60 pM [$^3$H]RTX and various concentrations of test compound. The binding reactions are initiated by transferring the assay mixtures into a 37° C. water bath and are terminated following a 60 minute incubation period by cooling the tubes on ice. Membrane-bound RTX is separated from free, as well as any alpha$_1$-acid glycoprotein-bound RTX, by filtration onto WALLAC glass fiber filters (PERKIN-ELMER, Gaithersburg, Md.) which were pre-soaked with 1.0% PEI (polyethyleneimine) for 2 hours prior to use.

Filters are allowed to dry overnight then counted in a WALLAC 1205 BETA PLATE counter after addition of WALLAC BETA SCINT scintillation fluid.

Equilibrium binding parameters are determined by fitting the allosteric Hill equation to the measured values with the aid of the computer program FIT P (Biosoft, Ferguson, Mo.) as described by Szallasi, et al. (1993) *J. Pharmacol. Exp. Ther.* 266:678–683. Compounds provided herein generally exhibit $K_i$ values for capsaicin receptor of less than 4 µM, preferably less than 1 µM, 100 nM, 50 nM, 25 nM, 10 nM or 1 nM in this assay.

Example 6

Calcium Mobilization Assay

This Example illustrates a representative calcium mobilization assay for use in monitoring the response of cells expressing capsaicin receptor to capsaicin and other vanilloid ligands of the capsaicin receptor, as well as for evaluating test compounds for agonist and antagonist activity.

Cells transfected with expression plasmids (as described in Example 4) and thereby expressing human capsaicin receptor are seeded and grown to 70–90% confluency in FALCON black-walled, clear-bottomed 96-well plates (#3904, BECTON-DICKINSON, Franklin Lakes, N.J.). The culture medium is emptied from the 96 well plates and FLUO-3 AM calcium sensitive dye (Molecular Probes, Eugene, Oreg.) is added to each well (dye solution: 1 mg FLUO-3 AM, 440 µL DMSO and 440 µl 20% pluronic acid in DMSO, diluted 1:250 in Krebs-Ringer HEPES (KRH) buffer (25 mM HEPES, 5 mM KCl, 0.96 mM $NaH_2PO_4$, 1 mM $MgSO_4$, 2 mM $CaCl_2$, 5 mM glucose, 1 mM probenecid, pH 7.4), 50 µl diluted solution per well). Plates are covered with aluminum foil and incubated at 37° C. for 1–2 hours in an environment containing 5% $CO_2$. After the incubation, the dye is emptied from the plates, and the cells are washed once with KRH buffer, and resuspended in KRH buffer.

Agonist (e.g., olvanil, capsaicin, or RTX)-induced calcium mobilization is monitored using either FLUOROSKAN ASCENT (Labsystems, Franklin, Mass.) or FLIPR (fluorometric imaging plate reader system, Molecular Devices, Sunnyvale, Calif.) instruments. Varying concentrations of the antagonists ruthenium red or capsazepine (RBI; Natick, Mass.) are added to cells concurrently with agonist (e.g., 25–50 nM capsaicin). For agonist-induced calcium responses, data obtained between 30 and 60 seconds after agonist application are used to generate the $IC_{50}$ values. KALEIDAGRAPH software (Synergy Software, Reading, Pa.) is used to fit the data to the equation:

$$y=a*(1/(1+(b/x)^c))$$

to determine the $IC_{50}$ for the response. In this equation, y is the maximum fluorescence signal, x is the concentration of the agonist or antagonist, a is the $E_{max}$, b corresponds to the $IC_{50}$ value and c is the Hill coefficient.

To measure the ability of a test compound to antagonize (inhibit) the response of cells expressing capsaicin receptors to capsaicin or other vanilloid agonist, the $IC_{50}$ of capsaicin is first determined. An additional 20 µl of KRH buffer and 1 µl DMSO is added to each well of cells, prepared as described above. 100 µl capsaicin in KRH buffer is automatically transferred by the FLIPR instrument to each well. An 8-point concentration response curve, with final capsaicin concentrations of 1 nM to 3 µM, is used to determine capsaicin $IC_{50}$.

Test compounds are dissolved in DMSO, diluted in 20 µl KRH buffer so that the final concentration of test compounds in the assay well is between 1 µM and 5 µM, and added to cells prepared as described above. The 96 well plates containing prepared cells and test compounds are incubated in the dark, at room temperature for 0.5 to 6 hours. It is important that the incubation not continue beyond 6 hours. Just prior to determining the fluorescence response, 100 µl capsaicin in KRH buffer at twice the $IC_{50}$ concentration determined from the concentration response curve is automatically added by the FLIPR instrument to each well of the 96 well plate for a final sample volume of 200 µl and a final capsaicin concentration equal to the $EC_{50}$. The final concentration of test compounds in the assay wells is between 1 µM and 5 µM. Typically cells exposed to one $IC_{50}$ of capsaicin exhibit a fluorescence response of about 10,000 Relative Fluorescence Units. Antagonists of the capsaicin receptor decrease this response by at least about 20%, preferably by at least about 50%, and most preferably by at least 80% as compared to matched control. The concentration of antagonist required to provide a 50% decrease is the $IC_{50}$ for the antagonist, and is preferably below 1 micromolar, 100 nanomolar, 10 nanomolar or 1 nanomolar.

The ability of a compound to act as an agonist of the capsaicin receptor is determined by measuring the fluorescence response of cells expressing capsaicin receptors, using the methods described above, in the absence of capsaicin, RTX, or other known capsaicin receptor agonists. Compounds that cause cells to exhibit fluorescence above background are capsaicin receptor agonists. Certain preferred compounds of the present invention are antagonists that are essentially free of agonist activity as demonstrated by the absence of detectable agonist activity in such an assay at compound concentrations below 4 nM, more preferably at concentrations below 10 µM and most preferably at concentrations less than or equal to 100 µM.

Example 7

Microsomal In Vitro Half-Life

This Example illustrates the evaluation of compound half-life values ($t_{1/2}$ values) using a representative liver microsomal half-life assay.

Pooled human liver microsomes are obtained from XenoTech LLC, 3800 Cambridge St. Kansas City, Kans. 66103 (catalog # H0610). Such liver microsomes may also be obtained from In Vitro Technologies (Baltimore, Md.) or Tissue Transformation Technologies (Edison, N.J.). Six test reactions are prepared, each containing 25 µl microsomes, 5 µl of a 100 µM solution of test compound, and 399 µl 0.1 M phosphate buffer (19 mL 0.1 M $NaH_2PO_4$, 81 mL 0.1M $Na_2HPO_4$, adjusted to pH 7.4 with $H_3PO_4$). A seventh reaction is prepared as a positive control containing 25 µl microsomes, 399 µl 0.1 M phosphate buffer, and 5, µl of a 100 µM solution of a compound with known metabolic properties (e.g., DIAZEPAM or CLOZAPENE). Reactions are preincubated at 39° C. for 10 minutes.

CoFactor Mixture is prepared by diluting 16.2 mg NADP and 45.4 mg Glucose-6-phosphate in 4 mL 100 mM $MgCl_2$. Glucose-6-phosphate dehydrogenase solution is prepared by diluting 214.3 µl glucose-6-phosphate dehydrogenase suspension (Boehringer-Manheim catalog no. 0737224, distributed by Roche Molecular Biochemicals, Indianapolis, Ind.) into 1285.7 µl distilled water. 71 µl Starting Reaction Mixture (3 mL CoFactor Mixture; 1.2 mL Glucose-6-phosphate dehydrogenase solution) is added to 5 of the 6 test reactions and to the positive control. 71 μl 100 mM MgCl$_2$ is added to the sixth test reaction, which is used as a negative control. At each time point (0, 1, 3, 5, and 10 minutes), 75 μl of each reaction mix is pipetted into a well of a 96-well deep-well plate containing 75 μl ice-cold acetonitrile. Samples are vortexed and centrifuged 10 minutes at 3500 rpm (Sorval T 6000D centrifuge, H1000B rotor). 75 μl of supernatant from each reaction is transferred to a well of a 96-well plate containing 150 μl of a 0.5 μM solution of a compound with a known LCMS profile (internal standard) per well. LCMS analysis of each sample is carried out and the amount of unmetabolized test compound is measured as AUC, compound concentration vs. time is plotted, and the $t_{1/2}$ value of the test compound is extrapolated.

Preferred compounds of the present invention exhibit in vitro $t_{1/2}$ values of greater than 10 minutes and less than 4 hours, preferably between 30 minutes and 1 hour, in human liver microsomes.

Example 8

MDCK Toxicity Assay

This Example illustrates the evaluation of compound toxicity using a Madin Darby canine kidney (MDCK) cell cytotoxicity assay.

1 μL of test compound is added to each well of a clear bottom 96-well plate (PACKARD, Meriden, Conn.) to give final concentration of compound in the assay of 10 micromolar, 100 micromolar or 200 micromolar. Solvent without test compound is added to control wells.

MDCK cells, ATCC no. CCL-34 (American Type Culture Collection, Manassas, Va.), are maintained in sterile conditions following the instructions in the ATCC production information sheet. Confluent MDCK cells are trypsinized, harvested, and diluted to a concentration of 0.1×10$^6$ cells/ml with warm (37° C.) medium (VITACELL Minimum Essential Medium Eagle, ATCC catalog # 30-2003). 100 μL of diluted cells is added to each well, except for five standard curve control wells that contain 100 μL of warm medium without cells. The plate is then incubated at 37° C. under 95% O$_2$, 5% CO$_2$ for 2 hours with constant shaking. After incubation, 50 μL of mammalian cell lysis solution is added per well, the wells are covered with PACKARD TOPSEAL stickers, and plates are shaken at approximately 700 rpm on a suitable shaker for 2 minutes.

Compounds causing toxicity will decrease ATP production, relative to untreated cells. The PACKARD, (Meriden, Conn.) ATP-LITE-M Luminescent ATP detection kit, product no. 6016941, is generally used according to the manufacturer's instructions to measure ATP production in treated and untreated MDCK cells. PACKARD ATP LITE-M reagents are allowed to equilibrate to room temperature. Once equilibrated, the lyophilized substrate solution is reconstituted in 5.5 mls of substrate buffer solution (from kit). Lyophilized ATP standard solution is reconstituted in deionized water to give a 10 mM stock. For the five control wells, 10 μL of serially diluted PACKARD standard is added to each of the standard curve control wells to yield a final concentration in each subsequent well of 200 nM, 100 nM, 50 nM, 25 nM and 12.5 nM. PACKARD substrate solution (50 μL) is added to all wells, which are then covered, and the plates are shaken at approximately 700 rpm on a suitable shaker for 2 minutes. A white PACKARD sticker is attached to the bottom of each plate and samples are dark adapted by wrapping plates in foil and placing in the dark for 10 minutes. Luminescence is then measured at 22° C. using a luminescence counter (e.g., PACKARD TOPCOUNT Microplate Scintillation and Luminescence Counter or TECAN SPECTRAFLUOR PLUS), and ATP levels calculated from the standard curve. ATP levels in cells treated with test compound(s) are compared to the levels determined for untreated cells. Cells treated with 10 μM of a preferred test compound exhibit ATP levels that are at least 80%, preferably at least 90%, of the untreated cells. When a 100 μM concentration of the test compound is used, cells treated with preferred test compounds exhibit ATP levels that are at least 50%, preferably at least 80%, of the ATP levels detected in untreated cells.

Example 9

Dorsal Root Ganglion Cell Assay

This Example illustrates a representative dorsal root ganglian cell assay for evaluating VR1 antagonist activity of a compound.

DRG are dissected from neonatal rats, dissociated and cultured using standard methods (Aguayo and White (1992) *Brain Research* 570:61–67). After 48 hour incubation, cells are washed once and incubated for 30–60 minutes with the calcium sensitive dye Fluo 4 AM (2.5–10 ug/ml; TefLabs, Austin, Tex.). Cells are then washed once, and various concentrations of compound is added to the cells. Addition of capsaicin to the cells results in a VR1-dependent increase in intracellular calcium levels which is monitored by a change in Fluo-4 fluorescence with a fluorometer. Data are collected for 60–180 seconds to determine the maximum fluorescent signal. Fluorescent signal is then plotted as a function of compound concentration to identify the concentration required to achieve a 50% inhibition of the capsaicin-activated response, or IC$_{50}$. Antagonists of the capsaicin receptor preferably have an IC$_{50}$ below 1 micromolar, 100 nanomolar, 10 nanomolar or 1 nanomolar.

Example 10

Animal Models for Determining Pain Relief

This Example illustrates representative methods for assessing the degree of pain relief provided by a compound.

A. Pain Relief Testing

The following methods may be used to assess pain relief.

Mechanical Allodynia

Mechanical allodynia (an abnormal response to an innocuous stimulus) is assessed essentially as described by Chaplan et al. (1994) *J. Neurosci. Methods* 53:55–63 and Tal and Eliav (1998) *Pain* 64(3):511–518. A series of von Frey filaments of varying rigidity (typically 8–14 filaments in a series) are applied to the plantar surface of the hind paw with just enough force to bend the filament. The filaments are held in this position for no more than three seconds or until a positive allodynic response is displayed by the rat. A positive allodynic response consists of lifting the affected paw followed immediately by licking or shaking of the paw. The order and frequency with which the individual filaments are applied are determined by using Dixon up-down method. Testing is initiated with the middle hair of the series with subsequent filaments being applied in consecutive fashion, ascending or descending, depending on whether a negative or positive response, respectively, is obtained with the initial filament.

Compounds are effective in reversing or preventing mechanical allodynia-like symptoms if rats treated with such compounds require stimulation with a Von Frey filament of higher rigidity strength to provoke a positive allodynic response as compared to control untreated or vehicle treated rats. Alternatively, or in addition, testing of an animal in chronic pain may be done before and after compound administration. In such an assay, an effective compound results in an increase in the rigidity of the filament needed to induce a response after treatment, as compared to the filament that induces a response before treatment or in an animal that is also in chronic pain but is left untreated or is treated with vehicle. Test compounds are administered before or after onset of pain. When a test compound is administered after pain onset, testing is performed 10 minutes to three hours after administration.

Mechanical Hyperalgesia

Mechanical hyperalgesia (an exaggerated response to painful stimulus) is tested essentially as described by Koch et al. (1996) *Analgesia* 2(3):157–164. Rats are placed in individual compartments of a cage with a warmed, perforated metal floor. Hind paw withdrawal duration (i.e., the amount of time for which the animal holds its paw up before placing it back on the floor) is measured after a mild pinprick to the plantar surface of either hind paw.

Compounds produce a reduction in mechanical hyperalgesia if there is a statistically significant decrease in the duration of hindpaw withdrawal. Test compound may be administered before or after onset of pain. For compounds administered after pain onset, testing is performed 10 minutes to three hours after administration.

Thermal Hyperalgesia

Thermal hyperalgesia (an exaggerated response to noxious thermal stimulus) is measured essentially as described by Hargreaves et al. (1988) *Pain*. 32(1):77–88. Briefly, a constant radiant heat source is applied the animals' plantar surface of either hind paw. The time to withdrawal (i.e., the amount of time that heat is applied before the animal moves its paw), otherwise described as thermal threshold or latency, determines the animal's hind paw sensitivity to heat.

Compounds produce a reduction in thermal hyperalgesia if there is a statistically significant increase in the time to hindpaw withdrawal (i.e., the thermal threshold to response or latency is increased). Test compound may be administered before or after onset of pain. For compounds administered after pain onset, testing is performed 10 minutes to three hours after administration.

B. Pain Models

Pain may be induced using any of the following methods, to allow testing of analgesic efficacy of a compound. In general, compounds provided herein result in a statistically significant reduction in pain as determined by at least one of the previously described testing methods, using male SD rats and at least one of the following models.

Acute Inflammatory Pain Model

Acute inflammatory pain is induced using the carrageenan model essentially as described by Field et al. (1997) *Br. J. Pharmacol*. 121(8):1513–1522. 100–200 µl of 1–2% carrageenan solution is injected into the rats' hind paw. Three to four hours following injection, the animals' sensitivity to thermal and mechanical stimuli is tested using the methods described above. A test compound (0.01 to 50 mg/kg) is administered to the animal, prior to testing, or prior to injection of carrageenan. The compound can be administered orally or through any parenteral route, or topically on the paw. Compounds that relieve pain in this model result in a statistically significant reduction in mechanical allodynia and/or thermal hyperalgesia.

Chronic Inflammatory Pain Model

Chronic inflammatory pain is induced using one of the following protocols:

1. Essentially as described by Bertorelli et al. (1999) *Br. J. Pharmacol*. 128(6):1252–1258, and Stein et al. (1998) *Pharmacol. Biochem. Behav*. 31(2):455–51, 200 µl Complete Freund's Adjuvant (0.1 mg heat killed and dried *M. Tuberculosis*) is injected to the rats' hind paw: 100 µl into the dorsal surface and 100 µl into the plantar surface.
2. Essentially as described by Abbadie et al. (1994) *J. Neurosci*. 14(10):5865–5871 rats are injected with 150 µl of CFA (1.5 mg) in the tibio-tarsal joint.

Prior to injection with CFA in either protocol, an individual baseline sensitivity to mechanical and thermal stimulation of the animals' hind paws is obtained for each experimental animal.

Following injection of CFA, rats are tested for thermal hyperalgesia, mechanical allodynia and mechanical hyperalgesia as described above. To verify the development of symptoms, rats are tested on days 5, 6, and 7 following CFA injection. On day 7, animals are treated with a test compound, morphine or vehicle. An oral dose of morphine of 1–5 mg/kg is suitable as positive control. Typically, a dose of 0.01–50 mg/kg of test compound is used. Compounds can be administered as a single bolus prior to testing or once or twice or three times daily, for several days prior to testing. Drugs are administered orally or through any parenteral route, or applied topically to the animal.

Results are expressed as Percent Maximum Potential Efficacy (MPE). 0% MPE is defined as analgesic effect of vehicle, 100% MPE is defined as an animal's return to pre-CFA baseline sensitivity. Compounds that relieve pain in this model result in a MPE of at least 30%.

Chronic Neuropathic Pain Model

Chronic neuropathic pain is induced using the chronic constriction injury (CCI) to the rat's sciatic nerve essentially as described by Bennett and Xie (1988) *Pain* 33:87–107. Rats are anesthetized (e.g. with an intraperitoneal dose of 50–65 mg/kg pentobarbital with additional doses administered as needed). The lateral aspect of each hind limb is shaved and disinfected. Using aseptic technique, an incision is made on the lateral aspect of the hind limb at the mid thigh level. The biceps femoris is bluntly dissected and the sciatic nerve is exposed. On one hind limb of each animal, four loosely tied ligatures are made around the sciatic nerve approximately 1–2 mm apart. On the other side the sciatic nerve is not ligated and is not manipulated. The muscle is closed with continuous pattern and the skin is closed with wound clips or sutures. Rats are assessed for mechanical allodynia, mechanical hyperalgesia and thermal hyperalgesia as described above.

Compounds that relieve pain in this model result in a statistically significant reduction in mechanical allodynia, mechanical hyperalgesia and/or thermal hyperalgesia when administered (0.01–50 mg/kg, orally, parenterally or topically) immediately prior to testing as a single bolus, or for several days: once or twice or three times daily prior to testing.

From the foregoing it will be appreciated that, although specific embodiments of the invention have been described herein for purposes of illustration, various modifications may be made without deviating from the spirit and scope of the invention. Accordingly, the invention is not limited except as by the appended claims.

What is claimed is:

1. A compound of the formula:

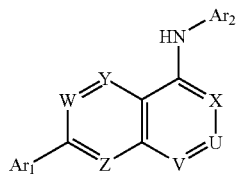

or a pharmaceutically acceptable salt thereof, wherein:
V and X are N;
W, Y and Z are each independently $CR_1$;
U is $CR_2$;
$R_1$ is independently selected at each occurrence from hydrogen, halogen, hydroxy, amino, $C_1$–$C_8$alkyl, halo$C_1$–$C_8$alkyl, $C_1$–$C_8$alkoxy, halo$C_1$–$C_8$alkoxy and mono- and di-($C_1$–$C_8$alkyl)amino;
$R_2$ is: (i) hydrogen, halogen or cyano;
(ii) $C_2$–$C_8$alkanoyl or $C_3$–$C_8$alkanone, each of which is unsubstituted or substituted with from 1 to 9 substituents independently selected from $R_d$; or
(iii) a group of the formula —$R_c$-M-A-$R_y$, wherein:
$R_c$ is $C_0$–$C_3$alkyl;
M is a bond, S, $SO_2$, $(C=O)_pN(R_z)$, $N(R_z)(C=O)_p$, $SO_2N(R_z)$, or $N(R_z)SO_2$, wherein p is 0 or 1;
A is a bond or $C_1$–$C_8$alkyl, optionally substituted with from 1 to 3 substituents independently selected from $R_d$; and
$R_y$ and $R_z$, if present, are:
(a) independently hydrogen, $C_1$–$C_8$alkyl, $C_3$–$C_8$alkanone, $C_2$–$C_8$alkenyl, a 4- to 10-membered carbocycle, or joined to $R_c$ to form a 4- to 10-membered carbocycle, wherein each $R_y$ and $R_z$ is independently unsubstituted or substituted with from 1 to 9 substituents independently selected from $R_d$; or
(b) joined to form a 4- to 10-membered heterocycle that is unsubstituted or substituted with from 1 to 9 substituents independently selected from $R_d$;
wherein $R_d$ is independently selected at each occurrence from hydroxy, halogen, amino, aminocarbonyl, cyano, nitro, $C_1$–$C_8$alkyl, $C_1$–$C_8$alkylthio, hydroxy$C_1$–$C_8$alkyl, halo$C_1$–$C_8$alkyl, phenyl, phenyl($C_1$–$C_8$alkyl), mono-and di-($C_1$–$C_6$alkyl)amino, $(SO_2)C_1$–$C_8$alkyl, 5- to 7-membered heterocycle and (5- to 7-membered heterocycle)($C_1$–$C_8$alkyl);
$Ar_2$ is a 5- to 7-membered aromatic heterocycle, optionally substituted with from 1 to 3 substituents independently selected from groups of the formula $LR_a$;
$Ar_1$ is a 5- to 10-membered aromatic carbocycle or heterocycle, optionally substituted with from 1 to 3 substituents independently selected from groups of the formula $LR_a$;
L is independently selected at each occurrence from a bond, —O—, —C(=O)—, —OC(=O)—, —C(=O)—O—, —O—C(=O)O—, —S(O)$_m$—, —NR$_x$—, —C(=O)NHR$_x$—, —NHR$_x$C(=O)—, —NR$_x$S(O)$_m$—, —S(O)$_m$NR$_x$— and —N[S(O)$_m$R$_x$]S(O)$_m$—; wherein m is independently selected at each occurrence from 0, 1 and 2; and $R_x$ is independently selected at each occurrence from hydrogen and $C_1$–$C_8$alkyl;
$R_a$ is independently selected at each occurrence from:
(i) hydrogen, halogen, cyano and nitro; and
(ii) $C_1$–$C_8$alkyl, $C_2$–$C_8$alkenyl, $C_2$–$C_8$alkynyl, $C_2$–$C_8$alkyl ether, 3- to 10-membered heterocycles, mono- and di-($C_1$–$C_8$alkyl)amino and (3- to 10-membered heterocycle)$C_1$–$C_6$alkyl, each of which is unsubstituted or substituted with from 1 to 9 substituents independently selected from $R_b$; and
$R_b$ is independently chosen at each occurrence from hydroxy, halogen, amino, aminocarbonyl, cyano, nitro, $C_1$–$C_8$alkyl, $C_1$–$C_8$alkoxy, $C_1$–$C_8$alkylthio, $C_2$–$C_8$alkyl ether, hydroxy$C_1$–$C_8$alkyl, halo$C_1$–$C_8$alkyl, phenyl, phenyl($C_1$–$C_8$alkyl), mono- and di-($C_1$–$C_6$alkyl)amino, $(SO_2)C_1$–$C_8$alkyl, 5- to 7-membered heterocycle and (5- to 7-membered heterocycle)($C_1$–$C_8$alkyl).

2. A compound or salt according to claim 1, wherein W, Y and Z are each CH.

3. A compound or salt according to claim 1, wherein $Ar_2$ is selected from pyridyl, pyridazinyl, pyrimidinyl, pyrazinyl, pyrrolyl, imidazolyl, pyrazolyl, oxazolyl, isoxazolyl, thiazolyl, isothiazolyl and thiadiazolyl, each of which is unsubstituted or substituted with 1 or 2 substituents selected from halogen, cyano, $C_1$–$C_6$alkyl, halo$C_1$–$C_6$alkyl, hydroxy$C_1$–$C_6$alkyl, $C_2$–$C_6$alkyl ether, $C_1$–$C_6$alkanoyl, amino, mono- and di-($C_1$–$C_6$alkyl)amino.

4. A compound or salt according to claim 1, wherein $Ar_2$ is pyridyl, isoxazolyl, thiadiazolyl or pyrazolyl, each of which is unsubstituted or substituted with halogen, $C_1$–$C_4$alkyl or halo$C_1$–$C_4$alkyl.

5. A compound according to claim 1, wherein $Ar_1$ is phenyl or pyridyl, each of which is optionally substituted with halogen, $C_1$–$C_6$alkyl, halo$C_1$–$C_6$alkyl, $C_1$–$C_6$alkoxy or halo$C_1$–$C_6$alkoxy.

6. A compound according to claim 1, wherein $R_2$ is:
(i) hydrogen or halogen; or
(ii) $C_1$–$C_6$alkyl, which is unsubstituted or substituted with from 1 to 4 substituents independently chosen from halogen, cyano, hydroxy, amino, mono- and di-($C_1$–$C_6$alkyl)amino, $C_1$–$C_6$alkyl, and halo$C_1$–$C_6$alkyl.

7. A compound or salt according to claim 6, wherein $Ar_1$ and $Ar_2$ are each pyridyl, substituted with 1 substituent independently chosen from halogen, $C_1$–$C_4$alkyl, $C_1$–$C_4$haloalkyl, and $C_1$–$C_4$alkoxy.

8. A compound or salt according to claim 1, wherein the compound is selected from: [7-(3-fluoro-pyridin-2-yl)-quinazolin-4-yl]-( 5-trifluoromethyl-pyridin-2-yl )-amine; [6-(propane-2-sulfonyl)-pyridin-3-yl]-[7-(3-trifluoromethyl-pyridin-2-yl )-quinazolin-4-yl]-amine hydrochloride; (5-tert-butyl-isoxazol-3-yl )-( 7-pyridin-2-yl-quinazolin-4-yl)-amine; (5-trifluoromethyl-pyridin-2-yl)-[7-( 3-trifluoromethyl-pyridin-2-yl )-quinazolin-4-yl]-amine; (6-Chloro-pyridin-3-yl)-[7-( 2-trifluoromethyl-phenyl)-quinazolin-4-yl]-amine; (6-Isobutyl-pyridin-3-yl)-[7-(3-trifluoromethyl-pyridin-2-yl)-quinazolin-4-yl]-amine; (6-trifluoromethyl-pyridin-3-yl)-[7-(3-trifluoromethyl-pyridin-2-yl)-quinazolin-4-yl]-amine; (7-pyridin-2-yl-quinazolin-4-yl)-(5-trifluoromethyl-pyridin-2-yl)-amine; [2-methyl-7-(3-trifluoromethyl-pyridin-2-yl)-quinazolin-4-yl]-6-trifluoromethyl-pyridin-3-yl)-amine; [7-(2-trifluoromethyl-phenyl)-quinazolin-4-yl]-(5-trifluoromethyl-pyridin-2-yl)-amine; (6-Trifluoromethyl-pyridin-3-yl)-[7-(3-trifluoromethyl-pyridin-2-yl)-2-(3,3,5-trimethyl-azepan-1-ylmethyl)-quinazolin-4-yl]-amine; (R,R)-(6-tert-Butylpyridin-3-yl)-[2-(2,6-dimethyl-morpholin-4-ylmethyl)-7-(3-trifluoromethyl-pyridin-2-yl)-quinazolin-4-yl]-amine; (R,R)-(6-tert-Butyl-pyridin-3-yl)-[7-(3-chloro-pyridin-2-yl)-2-(2,6-dimethyl-morpholin-4-ylmethyl)-quinazolin-4-yl]-amine; (R,R)-[2-(2,6-Dimethyl-morpholin-4-ylmethyl)-7-(3-trifluoromethyl-pyridin-2-yl)-quinazolin-4-yl]-(6-trifluoromethyl-pyridin-3-yl)-amine; (R,R)-[7-(3-Chloro-pyridin-2-yl)-2-(2,6-dimethyl-morpholin-4-ylmethyl)-quinazolin-4-yl]-(6-trifluoromethyl-pyridin-3-yl)-amine; (R,R)-[7-(3-Chloro-pyridin-2-yl)-2-(2,6-dimethyl-morpholin-4-ylmethyl)-quinazolin-4-yl]-(6-isopropoxy-pyridin-3-yl)-amine; (S,S)-(6-tert-Butyl-pyridin-3-yl)-[2-(2,6-dimethyl-morpholin-4-ylmethyl)-7-(3-trifluoromethyl-pyridin-2-yl)-quinazolin-4-yl]-amine; (S,S)-(6-tert-Butyl-pyridin-3-yl)-[7-(3-chloro-pyridin-2-yl)-2-(2,6-dimethyl-morpholin-4-ylmethyl)-quinazolin-4-yl]-amine; (S,S)-[2-(2,6-Dimethyl-morpholin-4-ylmethyl)-7-(3-trifluoromethyl-pyridin-2-yl)-quinazolin-4-yl]-(6-trifluoromethyl-pyridin-3-yl)-amine; (S,S)-[7-(3-Chloro-pyridin-2-yl)-2-(2,6-dimethyl-morpholin-4-ylmethyl)-quinazolin-4-yl]-(6-trifluoromethyl-pyridin-3-yl)-amine; [2-(1,1-Dioxo-1$\lambda^6$-thiomorpholin-4-ylmethyl)-7-(3-trifluoromethyl-pyridin-2-yl)-quinazolin-4-yl]-(6-trifluoromethyl-pyridin-3-yl)-amine; [2-(1,4-Dioxa-8-aza-spiro[4.5]dec-8-ylmethyl)-7-(3-trifluoromethyl-pyridin-2-yl)-quinazolin-4-yl]-(6-trifluoromethyl-pyridin-3-yl)-amine; [2-(1-Methyl-3,4-dihydro-1H-isoquinolin-2-ylmethyl)-7-(3-trifluoromethyl-pyridin-2-yl)-quinazolin-4-yl]-(6-trifluoromethyl-pyridin-3-yl)-amine; [2-(2,6-Dimethyl-morpholin-4-ylmethyl)-7-(3-trifluoromethyl-pyridin-2-yl)-quinazolin-4-yl]-(5-trifluoromethyl-pyridin-2-yl)-amine; [2-(2,6-Dimethyl-morpholin-4-ylmethyl)-7-(3-trifluoromethyl-pyridin-2-yl)-quinazolin-4-yl]-(6-trifluoromethyl-pyridin-3-yl)-amine (cis); [2-(2,6-Dimethyl-morpholin-4-ylmethyl)-7-(3-trifluoromethyl-pyridin-2-yl)-quinazolin-4-yl]-(5-trifluoromethyl-pyridin-2-yl)-amine (cis); [2-(2-Ethyl-piperidin-1-ylmethyl)-7-(3-trifluoromethyl-pyridin-2-yl)-quinazolin-4-yl]-(6-trifluoromethyl-pyridin-3-yl)-amine; [2-(2-Methyl-piperidin-1-ylmethyl)-7-(3-trifluoromethyl-pyridin-2-yl)-quinazolin-4-yl]-(6-trifluoromethyl-pyridin-3-yl)-amine; [2-(3,3-Dimethyl-piperidin-1-ylmethyl)-7-(3-trifluoromethyl-pyridin-2-yl)-quinazolin-4-yl]-(6-trifluoromethyl-pyridin-3-yl)-amine; [2-(3,4-Dihydro-1H-isoquinolin-2-ylmethyl)-7-(3-trifluoromethyl-pyridin-2-yl)-quinazolin-4-yl]-(6-trifluoromethyl-pyridin-3-yl)-amine; [2-(3,5-Dimethyl-piperidin-1-ylmethyl)-7-(3-trifluoromethyl-pyridin-2-yl)-quinazolin-4-yl]-(6-trifluoromethyl-pyridin-3-yl)-amine; [2-(3,5-Dimethyl-piperidin-1-ylmethyl)-7-(3-trifluoromethyl-pyridin-2-yl)-quinazolin-4-yl]-(6-trifluoromethyl-pyridin-3-yl)-amine; [2-(3-Methyl-piperidin-1-ylmethyl)-7-(3-trifluoromethyl-pyridin-2-yl)-quinazolin-4-yl]-(6-trifluoromethyl-pyridin-3-yl)-amine; [2-(4-Methyl-piperazin-1-ylmethyl)-7-(3-trifluoromethyl-pyridin-2-yl)-quinazolin-4-yl]-(5trifluoromethyl-pyridin-2-yl)-amine; [2-(4-Methyl-piperidin-1-ylmethyl)-7-(3-trifluoromethyl-pyridin-2-yl)-quinazolin-4-yl]-(6-trifluoromethyl-pyridin-3-yl)-amine; [2-(Benzylamino-methyl)-7-(3-trifluoromethyl-pyridin-2-yl)-quinazolin-4-yl]-(5-trifluoromethyl-pyridin 2-yl)-quinazolin-4-yl]-(6-trifluoromethyl-pyridin-3-yl)-amine; [2-(Octahydro-quinolin-1-ylmethyl)-7-(3-trifluoromethyl-pyridin-2-yl)-quinazolin-4-yl]-(6-trifluoromethyl-pyridin-3-yl)-amine; [2-[(2-Methoxy-benzylamino)-methyl]-7-(3-trifluoromethyl-pyridin-2-yl)-quinazolin-4-yl]-(6-trifluoromethyl-pyridin-3-yl)-amine; [2-[(4-Methoxy-benzylamino)-methyl]-7-(3-trifluoromethyl-pyridin-2-yl)-quinazolin-4-yl]-(6-trifluoromethyl-pyridin-3-yl)-amine; [2-[(Allyl-methyl-amino)-methyl]-7-(3-trifluoromethyl-pyridin-2-yl)-quinazolin-4-yl]-(6-trifluoromethyl-pyridin-3-yl)-amine; [2-[(Benzyl-cyclopropyl-amino)-methyl]-7-(3-trifluoromethyl-pyridin-2-yl)-quinazolin-4-yl]-(6-trifluoromethy 3-yl)-amine; [2-[(Benzyl-methyl-amino)-methyl]-7-(3-trifluoromethyl-pyridin-2-yl)-quinazolin-4-yl]-(6-trifluoromethyl-pyridin-3-yl)-amine; [2-[(Benzyl-methyl-amino)-methyl]-7-(3-trifluoromethyl-pyridin-2-yl)-quinazolin-4-yl]-(6-trifluoromethyl-pyridin-3-yl)-amine; [2-[(Butyl-ethyl-amino)-methyl]-7-(3-trifluoromethyl-pyridin-2-yl)-quinazolin-4-yl]-(6-trifluoromethyl-pyridin-3-yl)-amine; [2-[(Butyl-methyl-amino)-methyl]-7-(3-trifluoromethyl-pyridin-2-yl)-quinazolin-4-yl]-(6-trifluoromethyl-pyridin-3-yl)-amine; [2-[(Cyclohexyl-ethyl-amino)-methyl]-7-(3-trifluoromethyl-pyridin-2-yl)-quinazolin-4-yl]-(6-trifluoromethyl-pyridin-3-yl)-amine; [2-[(Cyclohexyl-methyl-amino)-methyl]-7-(3-trifluoromethyl-pyridin-2-yl)-quinazolin-4-yl]-(6-trifluoromethyl-pyridin-3-yl)-amine; [2-[(Cyclopropylmethyl-propyl-amino)-methyl]-7-(3-trifluoromethyl-pyridin-2-yl)-quinazolin-4-yl]-(6-trifluoromethyl-pyridin-3-yl)-amine; [2-[(Cyclopropylmethyl-propyl-amino)-methyl]-7-(3-trifluoromethyl-pyridin-2-yl)-quinazolin-4-yl]-(6-trifluoromethyl-pyridin-3-yl)-amine; [2-[(Ethyl-isopropyl-amino)-methyl]-7-(3-trifluoromethyl-pyridin-2-yl)-quinazolin-4-yl]-(6-trifluoromethyl-pyridin-3-yl)-amine; [2-[(Hexyl-methyl-amino)-methyl]-7-(3-trifluoromethyl-pyridin-2-yl)-quinazolin-4-yl]-(6-trifluoromethyl-pyridin-3-yl)-amine; [2-[(Indan-1-yl-methyl-amino)-methyl]-7-(3-trifluoromethyl-pyridin-2-yl)-quinazolin-4-yl]-(6-trifluoromethyl-pyridin-3-yl)-amine; [2-[(Isopropyl-methyl-amino)-methyl]-7-(3-trifluoromethyl-pyridin-2-yl)-quinazolin-4-yl]-(6-trifluoromethyl-pyridin-3-yl)-amine; [2-[(Methyl-phenethyl-amino)-methyl]-7-(3-trifluoromethyl-pyridin-2-yl)-quinazolin-4-yl]-(6-trifluoromethyl-pyridin-3-yl)-amine; [2-[(Methyl-propyl-amino)-methyl]-7-(3-trifluoromethyl-pyridin-2-yl)-quinazolin-4-yl]-(6-trifluoromethyl-pyridin-3-yl)-amine; [2-[(Tetrahydro-thiopyran-4-ylamino)-methyl]-7-(3-trifluoromethyl-pyridin-2-yl)-quinazolin-4-yl]-(6-trifluoromethyl-pyridin-3-yl)-amine; [2-[3-(2,6-Dimethyl-morpholin-4-yl)-propyl]-7-(3-trifluoromethyl-pyridin-2-yl)-quinazolin-4-yl]-(6-trifluoromethyl-pyridin-3-yl)-amine; [2-{[(2-Fluoro-benzyl)-methyl-amino]-methyl}-7-(3-trifluoromethyl-pyridin-2-yl)-quinazolin-4-yl]-(6-trifluoromethyl-pyridin-3-yl)-amine; [2-{[(3-Fluoro-benzyl)-methyl-amino]-methyl}-7-(3-trifluoromethyl-pyridi 2-yl)-quinazolin-4-yl]-(6-trifluoromethyl-pyridin-3-yl)-amine; [2-{[(Pyridin-2-ylmethyl)-amino]-methyl}-7-(3-trifluoromethyl-pyridin-2-yl)-quinazolin-4-yl]-(6-trifluoromethyl-pyridin-3-yl)-amine; [2-{[Bis-(2-methoxy-ethyl)-amino]-methyl}-7-(3-trifluoromethyl-pyridin-2-yl)-quinazolin-4-yl]-(5-trifluoromethyl-pyridin-2-yl)-amine; [2-{[Bis-(2-methoxy-ethyl)-amino]-methyl}-7-(3-trifluoromethyl-pyridin-2-yl)-quinazolin-4-yl]-(6-trifluoromethyl-pyridin-3-yl)-amine; [2-{[Ethyl-(2-methyl-allyl)-amino]-methyl}-7-(3-trifluoromethyl-pyridin-2-yl)-quinazolin-4-yl]-(6-trifluoromethyl-pyridin-3-yl)-amine; [2-{[Methyl-(1-phenyl-ethyl)-amino]-methyl}-7-(3-trifluoromethyl-pyridin-2-yl)-quinazolin-4-yl]-(6-trifluoromethyl-pyridin-3-yl)-amine; [2-{[Methyl-(1-phenyl-propyl)-amino]-methyl}-7-(3-trifluoromethyl-pyridin-2-yl)-quinazolin-4-yl]-(6-trifluoromethyl-pyridin-3-yl)-amine; [2-{[Methyl-(2-methyl-benzyl)-amino]-methyl}-7-(3-trifluoromethyl-pyridin-2-yl)-quinazolin-4-yl]-(6-trifluoromethyl-pyridin-3-yl)-amine; [2-Azepan-1-ylmethyl-7-(3-trifluoromethyl-pyridin-2-yl)-quinazolin-4-yl]-(6-trifluoromethyl-pyridin-3-yl)-amine; [2-Azocan-1- ylmethyl-7-(3-trifluoromethyl-pyridin-2-yl)-quinazolin-4-yl]-(6-trifluoromethyl-pyridin-3-yl)-amine; [2-Diallylaminomethyl-7-(3-trifluoromethyl-pyridin-2-yl)-quinazolin-4-yl]-(6-trifluoromethyl-pyridin-3-yl)-amine; [2-Dibutylaminomethyl-7-(3-trifluoromethyl-pyridin-2-yl)-quinazolin-4-yl]-(6-trifluoromethyl-pyridin-3-yl)-amine; [2-Diethylaminomethyl-7-(3-trifluoromethyl-pyridin-2-yl)-quinazolin-4-yl]-(6-trifluoromethyl-pyridin-3-yl)-amine; [2-Dihexylaminomethyl-7-(3-trifluoromethyl-pyridin-2-yl)-quinazolin-4-yl]-(6-trifluoromethyl-pyridin-3-yl)-amine; [2-Dimethylaminomethyl-7-(3-trifluoromethyl-pyridin-2-yl)-quinazolin-4-yl]-(6-trifluoromethyl-pyridin-3-yl)-amine; [2-Dimethylaminomethyl-7-(3-trifluoromethyl-pyridin-2-yl)-quinazolin-4-yl]-(6-trifluoromethyl-pyridin-3-yl)-amine; [2-Dipentylaminomethyl-7-(3-trifluoromethyl-pyridin-2-yl)-quinazolin-4-yl]-(6-trifluoromethyl-pyridin-3-yl)-amine; [2-Dipropylaminomethyl-7-(3-trifluoromethyl-pyridin-2-yl)-quinazolin-4-yl]-(6-trifluoromethyl-pyridin-3-yl)-amine; [2-Dipropylaminomethyl-7-(3-trifluoromethyl-pyridin-2-yl)-quinazolin-4-yl]-(6-trifluoromethyl-pyridin-3-yl)-amine; [2-Imidazol-1-ylmethyl-7-(3-trifluoromethyl-pyridin-2-yl)-quinazolin-4-yl]-(6-trifluoromethyl-pyridin-3-yl)-amine; [2-Morpholin-4-ylmethyl-7-(3-trifluoromethyl-pyridin-2-yl)-quinazolin-4-yl]-(5-trifluoromethyl-pyridin-2-yl)-amine; [2-Morpholin-4-ylmethyl-7-(3-trifluoromethyl-pyridin-2-yl)-quinazolin-4-yl]-[4-(2,2,2-trifluoro-1-methyl-ethyl)-phenyl]-amine; [2-Morpholin-4-ylmethyl-7-(3-trifluoromethyl-pyridin-2-yl)-quinazolin-4-yl]-(6-trifluoromethyl-pyridin-3-yl)-amine; [2-Piperidin-1-ylmethyl-7-(3-trifluoromethyl-pyridin-2-yl)-quinazolin-4-yl]-(6-trifluoromethyl-pyridin-3-yl)-amine; [2-Pyrrolidin-1-ylmethyl-7-(3-trifluoromethyl-pyridin-2-yl)-quinazolin-4-yl]-(6-trifluoromethyl-pyridin-3-yl)-amine; [2-Thiomorpholin-4-ylmethyl-7-(3-trifluoromethyl-pyridin-2-yl)-quinazolin-4-yl]-(6-trifluoromethyl-pyridin-3-yl)-amine; [7-(3-Chloro-pyridin-2-yl)-2-(2,6-dimethyl-morpholin-4-ylmethyl)-quinazolin-4-yl]-(6-trifluoromethyl-pyridin-3-yl)-amine(cis); {1-[7-(3-Trifluoromethyl-pyridin-2-yl)-4-(6-trifluoromethyl-pyridin-3-ylamino)-quinazolin-2-ylmethyl]-piperidin-4-yl}-methanol; {1-[7-(3-Trifluoromethyl-pyridin-2-yl)-4-(6-trifluoromethyl-pyridin-3-ylamino)-quinazolin-2-ylmethyl]-piperidin-3-yl}-methanol; 1-[7-(3-Trifluoromethyl-pyridin-2-yl)-4-(6-trifluoromethyl-pyridin-3-ylamino)-quina 2-yl)-4-(6-trifluoromethyl-pyridin-3-ylamino)-quinazolin-2-ylmethyl]-piperidin-3-ol; 1-[7-(3-Trifluoromethyl-pyridin-2-yl)-4-(6-trifluoromethyl-pyridin-3-ylamino)-quinazolin-2-ylmethyl]-piperidine-4-carboxylic acid amide; 1-{4-[7-(3-Trifluoromethyl-pyridin-2-yl)-4-(6-trifluoromethyl-pyridin-3-ylamino)-quinazolin-2-ylmethyl]-piperazin-1-yl}-ethanone; 2-{1-[7-(3-Trifluoromethyl-pyridin-2-yl)-4-(6-trifluoromethyl-pyridin-3-ylamino)-quinazolin-2-ylmethyl]-piperidin-4-yl}-ethanol; 2-{4-[7-(3-Trifluoromethyl-pyridin-2-yl)-4-(6-trifluoromethyl-pyridin-3-ylamino)-quinazolin-2-ylmethyl]-piperazin-1-yl}-ethanol; (6-tert-Butyl-pyridin-3-yl)-[2-(2-methoxy-ethyl)-7-(3-trifluoromethyl-pyrid 2-yl)-quinazolin-4-yl]-amine; (6-tert-Butyl-pyridin-3-yl)-[2-methoxymethyl-7-(3-trifluoromethyl-pyridin-2-yl)-quinazolin-4-yl]-amine; (6-tert-Butyl-pyridin-3-yl)-[7-(3-chloro-pyridin-2-yl)-2-ethoxymethyl-quinazolin-4-yl]1-amine; (6-tert-Butyl-pyridin-3-yl)-[7-(3-chloro-pyridin-2-yl)-2-methoxymethyl-quinazolin-4-yl]-amine; [2-(1-Methyl-piperidin-4-yloxymethyl)-7-(3-trifluoromethyl-pyridin-2-yl)-quinazolin-4-yl]-(6-trifluoromethyl-pyridin-3-yl)-amine; [2-(2-Diethylamino-ethoxymethyl)-7-(3-trifluoromethyl-pyridin-2-yl)-quinazolin-4-yl]-(6-trifluoromethyl-pyridin-3-yl)-amine; [2-(2-Piperidin-1-yl-ethoxymethyl)-7-(3-trifluoromethyl-pyridin-2-yl)-quinazolin-4-yl]-(6-trifluoromethyl-pyridin-3-yl)-amine; [2-(3-Benzyloxy-propyl)-7-(3-trifluoromethyl-pyridin-2-yl)-quinazolin-4-yl]-(6-trifluoromethyl-pyridin-3-yl)-amine; [2-(3-Benzyloxy-propyl)-7-(3-trifluoromethyl-pyridin-2-yl)-quinazolin-4-yl]-(6-tert-butyl-pyridin-3-yl)-amine; [2-(Pyridin-3-ylmethoxymethyl)-7-(3-trifluoromethyl-pyridin-2-yl)-quinazolin-4-yl]-(6-trifluoromethyl-pyridin-3-yl)-amine; [2-(Pyridin-4-ylmethoxymethyl)-7-(3-trifluoromethyl-pyridin-2-yl)-quinazolin-4-yl]-(6-trifluoromethyl-pyridin-3-yl)-amine; [2-(Tetrahydro-pyran-4-yloxymethyl)-7-(3-trifluoromethyl-pyridin-2-yl)-quinazolin-4-yl]-(6-trifluoromethyl-pyridin-3-yl)-amine; [2-Benzyloxymethyl-7-(3-trifluoromethyl-pyridin-2-yl)-quinazolin-4-yl]-(6-trifluoromethyl-pyridin-3-yl)-amine; [2-Benzyloxymethyl-7-(3-trifluoromethyl-pyridin-2-yl)-quinazolin-4-yl]-(5-trifluoromethyl-pyridin-2-yl)-amine; [2-Isopropoxymethyl-7-(3-trifluoromethyl-pyridin-2-yl)-quinazolin-4-yl]-(6-trifluoromethyl-pyridin-3-yl)-amine; [2-Methoxymethyl-7-(3-trifluoromethyl-pyridin-2-yl)-quinazolin-4-yl]-(6-trifluoromethyl-pyridin-3-yl)-amine; [2-Methoxymethyl-7-(3-trifluoromethyl-pyridin-2-yl)-quinazolin-4-yl]-(5-trifluoromethyl-pyridin-2-yl)-amine; [7-(3-Trifluoromethyl-pyridin-2-yl)-4-(6-trifluoromethyl-pyridin-3-ylamino)-quinazolin-2-yl]-methanol; and 3-[7-(3-Trifluoromethyl-pyridin-2-yl)-4-(6-trifluoromethyl-pyridin-3-ylamino)-quinazolin-2-yl]-propan-1-ol.

9. A compound of the formula:

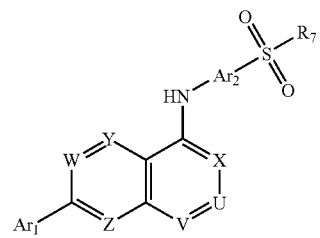

or a pharmaceutically acceptable salt thereof, wherein:

V and X are N;

W, Y and Z are each independently $CR_1$;

U is $CR_2$;

$R_1$ is independently selected at each occurrence from hydrogen, halogen, hydroxy, amino, $C_1$–$C_8$alkyl, halo$C_1$–$C_8$alkyl, $C_1$–$C_8$alkoxy, halo$C_1$–$C_8$alkoxy and mono- and di-($C_1$–$C_8$alkyl)amino;

$R_2$ is: (i) hydrogen, halogen or cyano;

(ii) $C_2$–$C_8$alkanoyl or $C_3$–$C_8$alkanone, each of which is unsubstituted or substituted with from 1 to 9 substituents independently selected from $R_d$; or (iii) a group of the formula —$R_c$-M-A-$R_y$, wherein:

$R_c$ is $C_0$–$C_3$alkyl;

M is a bond, S, $SO_2$, $(C=O)_pN(R_z)$, $N(R_z)(C=O)_p$, $SO_2N(R_z)$, or $N(R_z)SO_2$, wherein p is 0 or 1;

A is a bond or $C_1$–$C_8$alkyl, optionally substituted with from 1 to 3 substituents independently selected from $R_d$; and $R_y$ and $R_z$, if present, are:

(a) independently hydrogen, $C_1$–$C_8$alkyl, $C_3$–$C_8$alkanone, $C_2$–$C_8$alkenyl, a 4- to 10-membered carbocycle, or joined to $R_c$ to form a 4- to 10-membered carbocycle, wherein each $R_y$ and R$_z$ is independently unsubstituted or substituted with from 1 to 9 substituents independently selected from R$_d$; or (b) joined to form a 4- to 10-membered heterocycle that is unsubstituted or substituted with from 1 to 9 substituents independently selected from R$_d$;

wherein R$_d$ is independently selected at each occurrence from hydroxy, halogen, amino, aminocarbonyl, cyano, nitro, C$_1$–C$_8$alkyl, C$_1$–C$_8$alkylthio, hydroxyC$_1$–C$_8$alkyl, haloC$_1$–C$_8$alkyl, phenyl, phenyl(C$_1$–C$_8$alkyl), mono-and di-(C$_1$–C$_6$alkyl)amino, (SO$_2$)C$_1$–C$_8$alkyl, 5- to 7-membered heterocycle and (5- to 7-membered heterocycle)(C$_1$–C$_8$alkyl);

Ar$_1$ and Ar$_2$ are independently chosen from phenyl and 5- and 6-membered aromatic heterocycles, optionally substituted with from 1 to 3 substituents independently selected from groups of the formula LR$_a$;

L is independently selected at each occurrence from a bond, —O—, —C(=O)—, —OC(=O)—, —C(=O)O—, —O—C(=O)O—, —S(O)$_m$, —NR$_x$—, —C(=O)NHR$_x$—, —NHR$_x$C(=O)—, —NR$_x$S(O)$_m$—, —S(O)$_m$NR$_x$— and —N[S(O)$_m$R$_x$]S(O)$_m$—; wherein m is independently selected at each occurrence from 0, 1 and 2; and R$_x$ is independently selected at each occurrence from hydrogen and C$_1$–C$_8$alkyl;

R$_a$ is independently selected at each occurrence from:
(i) hydrogen, halogen, cyano and nitro; and
(ii) C$_1$–C$_8$alkyl, C$_2$–C$_8$alkenyl, C$_2$–C$_8$alkynyl, C$_2$–C$_8$alkyl ether, 3- to 10-membered heterocycles, mono- and di-(C$_1$–C$_8$alkyl)amino and (3- to 10-membered heterocycle)C$_1$–C$_6$alkyl, each of which is unsubstituted or substituted with from 1 to 9 substituents independently selected from R$_b$;

R$_b$ is independently chosen at each occurrence from hydroxy, halogen, amino, aminocarbonyl, cyano, nitro, C$_1$–C$_8$alkyl, C$_1$–C$_8$alkoxy, C$_1$–C$_8$alkylthio, C$_2$–C$_8$alkyl ether, hydroxyC$_1$–C$_8$alkyl, haloC$_1$–C$_8$alkyl, phenyl, phenyl(C$_1$–C$_8$alkyl), mono- and di-(C$_1$–C$_6$alkyl)amino, (SO$_2$)C$_1$–C$_8$alkyl, 5- to 7-membered heterocycle and (5- to 7-membered heterocycle)(C$_1$–C$_8$alkyl); and R$_7$ is C$_1$–C$_8$alkyl, C$_2$–C$_8$alkenyl, C$_2$–C$_8$alkynyl, mono- or di(C$_1$–C$_8$alkyl)amino or a 3- to 10-membered heterocycle, each of which is optionally substituted with from 1 to 5 substituents independently selected from hydroxy, halogen, C$_1$–C$_6$alkyl, C$_1$–C$_8$alkoxy, C$_2$–C$_8$alkyl ether, haloC$_1$–C$_8$alkyl and haloC$_1$–C$_8$alkoxy.

10. A compound or salt according to claim 9, wherein W, Y and Z are each CH.

11. A compound or salt according to claim 9, wherein Ar$_2$ is phenyl or pyridyl, each of which is optionally substituted with 1 or 2 substituents selected from halogen, cyano, C$_1$–C$_6$alkyl and haloC$_1$–C$_6$alkyl.

12. A compound or salt according to claim 9, wherein Ar$_2$ is phenyl, optionally substituted with halogen, C$_1$–C$_4$alkyl or haloC$_1$–C$_4$alkyl.

13. A compound or salt according to claim 9, wherein Ar$_1$ is phenyl or pyridyl, each of which is optionally substituted with from 1 to 3 substituents independently selected from halogen, C$_1$–C$_6$alkyl, haloC$_1$–C$_6$alkyl, C$_1$–C$_6$alkoxy or haloC$_1$–C$_6$alkoxy.

14. A compound or salt according to claim 9, wherein R$_2$ is
(i) hydrogen or halogen; or
(ii) C$_1$–C$_6$alkyl which is unsubstituted or substituted with from 1 to 4 substituents independently chosen from halogen, cyano, hydroxy, amino, mono- and di-(C$_1$–C$_6$alkyl)amino, C$_1$–C$_6$alkyl and haloC$_1$–C$_6$alkyl.

15. A compound or salt according to claim 9, wherein R$_7$ is attached directly to the SO$_2$ via a nitrogen atom.

16. A compound or salt according to claim 15, wherein R$_7$ is amino, mono- or di(C$_1$–C$_6$alkyl)amino, morpholinyl, piperidinyl, piperazinyl or pyrrolidinyl, each of which is unsubstituted or substituted with from 1 to 3 substituents independently chosen from halogen, C$_1$–C$_6$alkyl and haloC$_1$–C$_6$alkyl.

17. A compound or salt according to claim 9, wherein R$_7$ is C$_1$–C$_6$alkyl, haloC$_1$–C$_6$alkyl, morpholinyl, piperidinyl, piperazinyl or pyrrolidinyl, optionally substituted with from 1 to 5 substituents independently selected from C$_1$–C$_6$alkyl, C$_1$–C$_6$alkoxy, C$_2$–C$_6$alkyl ether, haloC$_1$–C$_6$alkyl and haloC$_1$–C$_6$alkoxy.

18. A compound or salt according to claim 9, wherein the compound is selected from: [6-(propane-2-sulfonyl)-pyridin-3-yl]-[7-(3-trifluoromethyl-pyridin-2-yl)-quinazolin-4-yl]-amine hydrochloride; (1-{4-[7-(3-trifluoromethyl-pyridin-2-yl)-quinazolin-4-ylamino]-benzenesulfonyl}-pyrrolidin-2-yl)-methanol(chiral); (1-{4-[7-(3-trifluoromethyl-pyridin-2-yl)-quinazolin-4-ylamino]-benzenesulfonyl}-pyrrolidin-2-yl)-methanol(chiral); (4-Methanesulfonyl-phenyl)-[7-(3-trifluoromethyl-pyridin-2-yl)-quinazolin-4-yl]-amine; (4-trifluoromethanesulfonyl-phenyl)-[7-(3-trifluoromethyl-pyridin-2-yl)-quinazolin-4-yl]-amine; [4-(2,5-dimethyl-pyrrolidine-1-sulfonyl)-phenyl]-[7-(3trifluoromethyl-pyridin-2-yl)-quinazolin-4-yl]-amine; [4-(2,6-dimethyl-morpholine-4-sulfonyl)-phenyl]-[7-(3-trifluoromethyl-pyridin-2-yl)-quinazolin-4-yl]-amine; [4-(2,6-Dimethyl-piperidine-1-sulfonyl)-pheny 4-yl]-amine(chiral); [4-(2-methoxymethyl-pyrrolidine-1-sulfonyl)-phenyl]-[7-(3-trifluoromethyl-pyridin-2-yl)-quinazolin-4-yl]-amine(chiral); [4-(2-methoxymethyl-pyrrolidine-1-sulfonyl)-phenyl]-[7-(3-trifluoromethyl-pyridin-2-yl)-quinazolin-4-yl]-amine (chiral); [4-(2-methyl-piperdine-1-sulfonyl)-phenyl]-[7-(3-trifluoromethyl-pyridin-2-yl)-quinazolin-4-yl]-amine; [4-(2-methyl-pyrrolidine-1-sulfonyl)-phenyl]-[7-(3-trifluoromethyl-pyridin-2-yl)-quinazolin-4-yl]-amine; [4-(3-Dimethylamino-pyrrolidine-1-sulfonyl)-phenyl]-[7-(3-trifluoromethyl-pyridin-2-yl)-quinazolin-4-yl]-amine; [4-(3-Dimethylamino-pyrrolidine-1-sulfonyl)-phenyl]-[7-(3-trifluoromethyl-pyridin-2-yl)-quinazolin-4-yl]-amine; [4-(4-Fluoro-piperidine-1-sulfonyl)-phenyl]-[7-(3-trifluoromethyl-pyridin-2-yl)-quinazolin-4-yl]-amine; [4-(4-Methyl-piperazine-1-sulfonyl)-phenyl]-[7-(3-trifluoromethyl-pyridin-2-yl)-quinazolin-4-yl]-amine; [4-(morpholine-4-sulfonyl)-phenyl]-[7-(3-trifluoromethyl-pyridin-2-yl)-quinazolin-4-yl]-amine; [4-(piperdine-1-sulfonyl)-phenyl]-[7-(3-trifluoromethyl-pyridin-2-yl)-quinazolin-4-yl]-amine; [4-(Propane-1-sulfonyl)-phenyl]-[7-(3-trifluoromethyl-pyridin-2-yl)-quinazolin-4-yl]-amine; [4-(pyrrolidine-1-sulfonyl)-phenyl]-[7-(3-trifluoromethyl-pyridin-2-yl)-quinazolin-4-yl]-amine; 1-{4-[7-(3-Trifluoromethyl-pyridin-2-yl)-quinazolin-4-ylamino]-benzenesulfonyl}-pyrrolidin-3-ol(chiral); 4[4-(Azetidine-1-sulfonyl)-phenyl]-[7-(3-trifluoromethyl-pyridin-2-yl)-quinazolin-4-yl]-amineN-(2-Hydroxy-1,1-dimethyl-ethyl)-4-[7-(3-trifluoromethyl-pyridin-2-yl)-quinazolin-4-ylamino]-benzenesulfonamide; N-(3-Chloro-propyl)-4-[7-

(3-trifluoromethyl-pyridin-2-yl)-quinazolin-4-ylamino]-benzenesulfonamide; N,N-Bis-(2-methoxy-ethyl)-4-[7-(3-trifluoromethyl-pyridin-2-yl)-quinazolin-4-ylamino]-benzenesulfonamide; N,N-diisopropyl-4-[7-(3-trifluoromethyl-pyridin-2-yl)-quinazolin-4-ylamino]-benzenesulfonamide; N,N-dimethyl-4-[7-(3-trifluoromethyl-pyridin-2-yl)-quinazolin-4-ylamino]-benzenesulfonamide; N-Isopropyl-4-[7-(3-trifluoromethyl-pyridin-2-yl)-quinazolin-4-ylamino]-benzenesulfonamide; N-tert-Butyl-4-[7-(3-trifluoromethyl-pyridin-2-yl)-quinazolin-4-ylamino]-benzenesulfonamide; N-tert-Butyl-N-methyl-4-[7-(3-trifluoromethyl-pyridin-2-yl)-quinazolin-4-ylamino]-benzenesulfonamide; (R,R)-[2-(2,6-Dimethyl-morpholin-4-ylmethyl)-7-(3-trifluoromethyl-pyridin-2-yl)-quinazolin-4-yl]-[4-(propane-2-sulfonyl)-phenyl]-amine; (R,R)-[7-(3-Chloro-pyridin-2-yl)-2-(2,6-dimethyl-morpholin-4-ylmethyl)-quinazolin-4-yl]-[4-(propane-2-sulfonyl)-phenyl]-amine; (S)-[7-(3-Chloro-pyridin-2-yl)-2-(2-methyl-morpholin-4-ylmethyl)-quinazolin-4-yl-]-[4-(propane-2-sulfonyl)-phenyl]-amine; (S,S)-[2-(2,6-Dimethyl-morpholin-4-ylmethyl)-7-(3-trifluoromethyl-pyridin-2-yl)-quinazolin-4-yl]-[4-(propane-2-sulfonyl)-phenyl]-amine; (S,S)-[7-(3-Chloro-pyridin-2-yl)-2-(2,6-dimethyl-morpholin-4-ylmethyl)-quinazolin-4-yl]-[4-(propane-2-sulfonyl)-phenyl]-amine; [2-(2,6-Dimethyl-morpholin-4-ylmethyl)-7-(3-trifluoromethyl-pyridin-2-yl)-quinazolin-4-yl]-(4-trifluoromethanesulfonyl-phenyl)-amine; [2-(2,6-Dimethyl-morpholin-4-ylmethyl)-7-(3-trifluoromethyl-pyridin-2-yl)-quinazolin-4-yl]-(4-trifluoromethanesulfonyl-phenyl)-amine(cis); [2-[(Ethyl-propyl-amino)-methyl]-7-(3-trifluoromethyl-pyridin-2-yl)-quinazolin-4-yl]-[4-(morpholine-4-sulfonyl)-phenyl]-amine; [2-[(Isopropyl-methyl-amino)-methyl]-7-(3-trifluoromethyl-pyridin-2-yl)-quinazolin-4-yl]-[4-(morpholine-4-sulfonyl)-phenyl]-amine; [2-[(Methyl-propyl-amino)-methyl]-7-(3-trifluoromethyl-pyridin-2-yl)-quinazolin-4-yl]-[4-(morpholine-4-sulfonyl)-phenyl]-amine; [2-Dimethylaminomethyl-7-(3-trifluoromethyl-pyridin-2-yl)-quinazolin-4-yl]-[4-(morpholine-4-sulfonyl)-phenyl]-amine; [2-Morpholin-4-ylmethyl-7-(3-trifluoromethyl-pyridin-2-yl)-quinazolin-4-yl]-(4-trifluoromethanesulfonyl-phenyl)-amine; [7-(3-Chloro-pyridin-2-yl)-2-(2,6-dimethyl-morpholin-4-ylmethyl)-quinazolin-4-yl]-(4-trifluoromethanesulfonyl-phenyl)-amine(cis); (4-Methanesulfonyl-phenyl)-[2-methoxymethyl-7-(3-trifluoromethyl-pyridin-2-yl)-quinazolin-4-yl]-amine; [2-Benzyloxymethyl-7-(3-trifluoromethyl-pyridin-2-yl)-quinazolin-4-yl]-(4-trifluoromethanesulfonyl-phenyl)-amine; [2-Benzyloxymethyl-7-(3-trifluoromethyl-pyridin-2-yl)-quinazolin-4-yl]-(4-methanesulfonyl-phenyl)-amine; [2-Benzyloxymethyl-7-(3-trifluoromethyl-pyridin-2-yl)-quinazolin-4-yl]-(1-methanesulfonyl-2,3-dihydro-1H-indol-5-yl)-amine; [2-Cyclopentyloxymethyl-7-(3-trifluoromethyl-pyridin-2-yl)-quinazolin-4-yl]-[4-(morpholine-4-sulfonyl)-phenyl]-amine; [2-Cyclopropylmethoxymethyl-7-(3-trifluoromethyl-pyridin-2-yl)-quinazolin-4-yl]-[4-(morpholine-4-sulfonyl)-phenyl]-amine; [2-Ethoxymethyl-7-(3-trifluoromethyl-pyridin-2-yl)-quinazolin)-4-yl]-[4-(morpholine-4-sulfonyl)-phenyl]-amine; [2-Isopropoxymethyl-7-(3-trifluoromethyl-pyridin-2-yl)-quinazolin-4-yl]-[4-(morpholine-4-sulfonyl)-phenyl]-amine; [2-Methoxymethyl-7-(3-trifluoromethyl-pyridin-2-yl)-quinazolin-4-yl]-(4-trifluoromethanesulfonyl-phenyl)-amine; [2-Methoxymethyl-7-(3-trifluoromethyl-pyridin-2-yl)-quinazolin-4-yl]-[4-(morpholine-4-sulfonyl)-phenyl]-amine; [4-(Morpholine-4-sulfonyl)-phenyl]-[2-(tetrahydro-pyran-4-yloxymethyl)-7-(3-trifluoromethyl-pyridin-2-yl)-quinazolin-4-yl]-amine; [4-[4-(Piperidine-1-sulfonyl)-phenylamino]-7-(3-trifluoromethyl-pyridin-2-yl)-quinazolin-2-yl]-methanol; 4-[2-Benzyloxymethyl-7-(3-trifluoromethyl-pyridin-2-yl)-quinazolin-4-ylamino]-N-tert-butyl-benzenesulfonamide; N-tert-Butyl-4-[2-hydroxymethyl-7-(3-trifluoromethyl-pyridin-2-yl)-quinazolin-4-ylamino]-N-methyl-benzenesulfonamide; and N-tert-Butyl-4-[2-methoxymethyl-7-(3-trifluoromethyl-pyridin-2-yl)-quinazolin-4-ylamino]-benzenesulfonamide.

19. A compound or salt according to claim 1 wherein the compound has an $IC_{50}$ value of 100 nanomolar or less in a capsaicin receptor calcium mobilization assay.

20. A compound or salt according to claim 9 wherein the compound or salt has an $IC_{50}$ value of 100 nanomolar or less in a capsaicin receptor calcium mobilization assay.

21. A compound or salt according to claim 1 wherein the compound or salt has an $IC_{50}$ value of 10 nanomolar or less in a capsaicin receptor calcium mobilization assay.

22. A compound or salt according to claim 9 wherein the compound or salt has an $IC_{50}$ value of 10 nanomolar or less in a capsaicin receptor calcium mobilization assay.

23. A compound or salt according to claim 1 wherein the compound or salt has an $IC_{50}$ value of 1 nanomolar or less in a capsaicin receptor calcium mobilization assay.

24. A compound or salt according to claim 9 wherein the compound or salt has an $IC_{50}$ value of 1 nanomolar or less in a capsaicin receptor calcium mobilization assay.

25. A pharmaceutical composition, comprising at least one compound or salt according to claim 1 in combination with a physiologically acceptable carrier or excipient.

26. A pharmaceutical composition, comprising at least one compound or salt according to claim 9 in combination with a physiologically acceptable carrier or excipient.

27. A pharmaceutical composition according to claim 25 wherein the composition is formulated as an injectible fluid, an aerosol, a cream, a gel, a pill, a capsule, a syrup or a transdermal patch.

28. A pharmaceutical composition according to claim 26 wherein the composition is formulated as an injectible fluid, an aerosol, a cream, a gel, a pill, a capsule, a syrup or a transdermal patch.

29. A method for reducing calcium conductance of a cellular capsaicin receptor, comprising contacting a cell expressing a capsaicin receptor with at least one compound or salt of the formula:

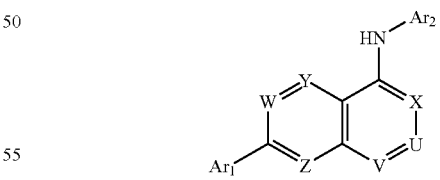

wherein:

V and X are N;

W, Y and Z are each independently $CR_1$;

U is $CR_2$;

$R_1$ is independently selected at each occurrence from hydrogen, halogen, hydroxy, cyano, amino, $C_1$–$C_8$alkyl, halo$C_1$–$C_8$alkyl, $C_1$–$C_8$alkoxy, halo$C_1$–$C_8$alkoxy and mono- and di-($C_1$–$C_8$alkyl)amino;

$R_2$ is: (i) hydrogen, halogen or cyano;
(ii) $C_2$–$C_8$alkanoyl or $C_3$–$C_8$alkanone, each of which is unsubstituted or substituted with from 1 to 9 substituents independently selected from $R_d$; or
(iii) a group of the formula —$R_c$-M-A-$R_y$, wherein:
$R_c$ is $C_0$–$C_3$alkyl;
M is a bond, N($R_z$), S, $SO_2$, (C=O)$_p$N($R_z$), N($R_z$)(C=O)$_p$, $SO_2$N($R_z$), or N($R_z$)$SO_2$, wherein p is 0 or 1;
A is a bond or $C_1$–$C_8$alkyl, optionally substituted with from 1 to 3 substituents independently selected from $R_d$; and
$R_y$ and $R_z$, if present, are:
(a) independently hydrogen, $C_1$–$C_8$alkyl, $C_2$–$C_8$alkenyl, $C_2$–$C_8$alkynyl, $C_6$–$C_{10}$aryl$C_0$–$C_8$alkyl, a 4- to 10-membered carbocycle, or joined to $R_c$ to form a 4- to 10-membered carbocycle, wherein each $R_y$ and $R_z$ is independently unsubstituted or substituted with from 1 to 9 substituents independently selected from $R_d$; or
(b) joined to form a 4- to 10-membered heterocycle that is unsubstituted or substituted with from 1 to 9 substituents independently selected from $R_d$;
wherein $R_d$ is independently selected at each occurrence from hydroxy, halogen, amino, aminocarbonyl, cyano, nitro, $C_1$–$C_8$alkyl, $C_1$–$C_8$alkylthio, hydroxy$C_1$–$C_8$alkyl, halo$C_1$–$C_8$alkyl, phenyl, phenyl($C_1$–$C_8$alkyl), mono-and di-($C_1$–$C_6$alkyl)amino, ($SO_2$)$C_1$–$C_8$alkyl, 5- to 7-membered heterocycle and (5- to 7-membered heterocycle)($C_1$–$C_8$alkyl);
$Ar_1$ and $Ar_2$ are independently selected from 5- to 10-membered aromatic carbocycles and heterocycles, each of which is unsubstituted or substituted with from 1 to 3 substituents independently selected from groups of the formula $LR_a$;
L is independently selected at each occurrence from a bond, —O—, —C(=O)—, —OC(=O)—, —C(=O) O—, —O—C(=O)O—, —S(O)$_m$—, —NR$_x$—, —C(=O)NHR$_x$—, —NHR$_x$C(=O)—, —NR$_x$S(O)$_m$—, —S (O)$_m$NR$_x$— and —N[S(O)$_m$R$_x$]S(O)$_m$—; wherein m is independently selected at each occurrence from 0, 1 and 2; and R$_x$ is independently selected at each occurrence from hydrogen and $C_1$–$C_8$alkyl;
$R_a$ is independently selected at each occurrence from:
(i) hydrogen, halogen, cyano and nitro; and
(ii) $C_1$–$C_8$alkyl, $C_2$–$C_8$alkenyl, $C_2$–$C_8$alkynyl, $C_2$–$C_8$alkyl ether, 3- to 10-membered heterocycles, mono- and di-($C_1$–$C_8$alkyl)amino and (3- to 10-membered heterocycle)$C_1$–$C_6$alkyl, each of which is unsubstituted or substituted with from 1 to 9 substituents independently selected from $R_b$; and
$R_b$ is independently chosen at each occurrence from hydroxy, halogen, amino, aminocarbonyl, cyano, nitro, $C_1$–$C_8$alkyl, $C_1$–$C_8$alkoxy, $C_1$–$C_8$alkylthio, $C_2$–$C_8$alkyl ether, hydroxy$C_1$–$C_8$alkyl, halo$C_1$–$C_8$alkyl, phenyl, phenyl($C_1$–$C_8$alkyl), mono-and di-($C_1$–$C_6$alkyl)amino, ($SO_2$)$C_1$–$C_8$alkyl, 5- to 7-membered heterocycle and (5- to 7-membered heterocycle)($C_1$–$C_8$alkyl);
and thereby reducing calcium conductance of the capsaicin receptor.

30. A method according to claim 29, wherein the compound or salt is a compound of the formula:

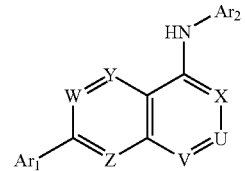

or a pharmaceutically acceptable salt thereof, wherein:
V and X are N;
W, Y and Z are each independently $CR_1$;
U is $CR_2$;
$R_1$ is independently selected at each occurrence from hydrogen, halogen, hydroxy, amino, $C_1$–$C_8$alkyl, halo$C_1$–$C_8$alkyl, $C_1$–$C_8$alkoxy, halo$C_1$–$C_8$alkoxy and mono- and di- ($C_1$–$C_8$alkyl)amino:
$R_2$ is: (i) hydrogen, halogen or cyano:
(ii) $C_2$–$C_8$alkanoyl or $C_3$–$C_8$alkanone, each of which is unsubstituted of substituted with from 1 to 9 substitutents independently selected from $R_d$: or
(iii) a group of the formula —$R_c$—M-A-$R_y$, wherein:
$R_c$ is $C_0$–$C_3$alkyl;
M is a bond, S, $SO_2$, (C=O)$_p$N($R_z$), N($R_z$)(C=O)$_p$, $SO_2$N($R_z$), or N($R_z$)$SO_2$, wherein p is 0 or 1;
A is a bond or $C_1$–$C_8$alkyl, optionally substituted with from 1 to 3 substituents independently selected from $R_d$; and
$R_y$ and $R_z$, if present, are:
(a) independently hydrogen, $C_1$–$C_8$alkyl, $C_3$–$C_8$alkanone, $C_2$–$C_8$alkenyl, a 4- to 10-membered carbocycle, or joined to $R_c$ to form a 4- to 10- membered carbocycle, wherein each $R_y$ and $R_z$ is independently unsubstituted or substituted with from 1 to 9 substituents independently selected from $R_d$; or
wherein $R_d$ is independently selected at each occurrence from hydroxy, halogen, amino, aminocarbonyl, cyano, nitro, $C_1$–$C_8$alkyl, $C_1$–$C_8$alkylthio, hydroxy$C_1$–$C_8$alkyl, halo$C_1$–$C_8$alkyl, phenyl, phenyl($C_1$–$C_8$alkyl), mono-and di-($C_1$–$C_6$alkyl)amino, ($SO_2$)$C_1$$C_8$alkyl, 5- to 7-membered heterocycle and (5- to 7-membered heterocycle) ($C_1$–$C_8$alkyl);
$Ar_2$ is a 5- to 7-membered aromatic heterocycle, optionally substituted with from 1 to 3 substituents independently selected from groups of the formula $LR_a$;
$Ar_1$ is a 5- to 10-membered aromatic carbocycle or heterocycle, optionally substituted with from 1to 3 substituents independently selected from groups of the formula $LR_a$;
L is independently selected at each occurrence from a bond, —O—, —C(=O)—, —OC(=O)—, —C(=O) O—, —O—C(=O)O—, —S(O)$_m$—, —NR$_x$—, —C(=O)NHR$_x$—, —NHR$_x$C(=O)—, —NR$_x$S(O)$_m$—, —S (O)$_m$NR$_x$—and —N[S(O)$_m$R$_x$]S(O)$_m$—; wherein m is independently selected at each occurrence from 0, 1 and 2; and R$_x$ is independently selected at each occurrence from hydrogen and $C_1$—$C_8$alkyl;

$R_a$ is independently selected at each occurrence from:
(i) hydrogen, halogen, cyano and nitro; and
(ii) $C_1$—$C_8$alkyl, $C_2$—$C_8$alkenyl, $C_2$—$C_8$alkynyl, $C_2$—$C_8$alkyl ether, 3- to 10-membered heterocycles, mono- and di-($C_1$—$C_8$alkyl)amino and (3- to 10-membered heterocycle)$C_1$—$C_8$alkyl, each of which is unsubstituted or substituted with from 1 to 9 substituents independently selected from $R_b$; and $R_b$ is independently chosen at each occurrence from hydroxy, halogen, amino, aminocarbonyl, cyano, nitro, $C_1$—$C_8$alkyl, $C_1$—$C_8$alkoxy, $C_1$—$C_1$—$C_8$alkylthio, $C_2$—$C_8$alkyl ether, hydroxy$C_1$—$C_8$alkyl, halo$C_1$—$C_8$alkyl, phenyl, phenyl($C_1$—$C_8$alkyl), mono-and-di-($C_1$—$C_8$alkyl)amino, $(SO_2)C_1$—$C_8$alkyl, 5- to 7-membered heterocycle and (5- to 7-membered heterocycle)($C_1$-$C_8$alkyl).

31. A method according to claim 29, wherein the compound or salt is a compound of the formula:

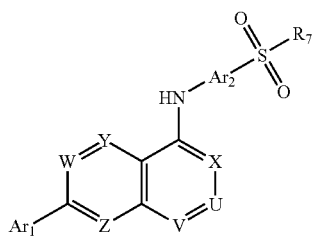

or a pharmaceutically acceptable salt thereof, wherein:
V and X are N;
W, Y and Z are each independently $CR_1$;
U is $CR_2$;
$R_1$ is independently selected at each occurrence from hydrogen, halogen, hydroxy, amino, $C_1$—$C_8$alkyl, halo$C_1$—$C_8$alkyl, $C_1$—$C_8$alkoxy, halo$C_1$—$C_8$alkoxy and mono- and di-($C_1$—$C_8$alkyl) amino;
$R_2$ is: (i) hydrogen, halogen or cyano;
(ii) $C_2$—$C_8$alkanoyl or $C_3$—$C_8$alkanone, each of which is unsubstituted or substituted with from 1 to 9 substituents independently selected from $R_d$; or
(iii) a group of the formula –$R_c$—M-A-$R_y$, wherein:
$R_c$ is $C_0$—$C_3$alkyl;
M is a bond, S, $SO_2$, $(C=O)_pN(R_z)$, $_{N(Rz)}(C=O)_p$, $SO_2N(R_z)$, or $N(R_z)SO_2$, wherein p is 0 or 1;
A is a bond or $C_1$—$C_8$alkyl, optionally substituted with from 1 to 3 substituents independently selected from $R_d$; and
$R_y$ and $R_z$, if present, are:
(a) independently hydrogen, $C_1$—$C_8$alkyl, $C_3$—$C_8$alkanone, $C_2$—$C_8$alkenyl, a 4- to 10-membered carbocycle, or joined to $R_c$ to form a 4- to 10-membered carbocycle, wherein each $R_y$ and $R_z$ is independently unsubstituted or substituted with from 1 to 9 substituents independently selected from $R_d$; or
(b) joined to form a 4- to 10-membered heterocycle that is unsubstitued or substituted with from 1 to 9 substituents independently selected from $R_d$;
wherein $R_d$ is independently selected at each occurrence from hydroxy, halogen, amino, aminocarbonyl, cyano, nitro, $C_1$—$C_8$alkyl, $C_1$—$C_8$alkylthio, hydroxy$C_1$—$C_8$alkyl, halo$C_1$—$C_8$alkyl, phenyl, phenyl($C_1$—$C_8$alkyl), mono-and di-($C_1$—$C_6$alkyl)amino, $(SO_2)C_1$—$C_8$alkyl, 5- to 7-membered heterocycle and (5- to 7-membered heterocycle)($C_1$—$C_8$alkyl);

$Ar_1$ and $Ar_2$ are independently chosen from phenyl and 5- and 6-membered aromatic heterocycles, optionally substituted with from 1to 3 substituents independently selected from groups of the formula $LR_a$;

L is independently selected at each occurrence from a bond, —O—, —C(=O)—, —OC(=O)—, —C(=O) O—, —O—C(=))O—, —S(O)$_m$—, —NR$_x$—, —C(=O)NHR$_x$—, —NHR$_x$C(=O)—, —NR$_x$S(O)$_m$—, —S (O)$_m$NR$_x$— and —N[S(O)$_m$R$_x$]S (O)$_m$—; wherein m is independently selected at each occurrence from 0, 1 and 2; and $R_x$ is independently selected at each occurrence from hydrogen and $C_1$—$C_8$alkyl;

$R_a$ is independently selected at each occurrence from:
(i) hydrogen, halogen, cyano and nitro; and
(ii) $C_1$—$C_8$alkyl, $C_2$—$C_8$alkenyl, $C_2$—$C_8$alkynyl, $C_2$—$C_8$alkyl ether, 3- to 10membered heterocycles, mono- and di-($C_1$—$C_8$alkyl)amino and (3- to 10-membered heterocycle)$C_1$—$C_6$alkyl, each of which is unsubstituted or substituted with from 1 to 9 substituents independently selected from $R_b$;

$R_b$ is independently chosen at each occurrence from hydroxy, halogen, amino, aminocarbonyl, cyano, nitro, $C_1$—$C_8$alkyl, $C_1$—$C_8$alkoxy, $C_1$—$C_8$alkylthio, $C_2$—$C_8$alkyl ether, hydroxy$C_1$—$C_8$alkyl, halo$C_1$—$C_8$alkyl, phenyl, phenyl($C_1$—$C_8$alkyl), mono-and di-($C_1$—$C_6$alkyl)amino, $(SO_2)C_1$—$C_8$alkyl, 5- to 7-membered heterocycle and (5- to 7- membered heterocycle) and (5- to 7-membered heterocycle)($C_1$—$C_8$alkyl); and $R_7$ is $C_1$—$C_8$alkyl, $C_2$—$C_8$alkenyl, $C_2$—$C_8$alkynyl, mono- or di($C_1$—$C_8$alkyl)amino or a 3- to 10- membered heterocycle, each of which is optionally substituted with from 1 to 5 substituents independently selected from hydroxy, halogen, $C_1$—$C_6$alkyl, $C_1$—$C_8$alkoxy, $C_2$—$C_8$alkyl ether, halo$C_1$—$C_8$alkyl and halo$C_1$—$C_8$alkoxy.

32. A method according to claim 29, wherein the cell is a neuronal cell that is contacted in vivo in an animal.

33. A method according to claim 32, wherein during contact the compound or salt is present within a body fluid of the animal.

34. A method according to claim 33, wherein the compound or salt is present in the blood of the animal at a concentration of 100 nanomolar or less.

35. A method according to claim 32, wherein the animal is a human.

36. A method according to claim 32, wherein the compound or salt is administered orally.

37. A method for inhibiting binding of vanilloid ligand to a capsaicin receptor in vitro, the method comprising contacting capsaicin receptor with at least one compound or salt of the formula:

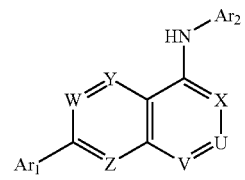

wherein:
V and X are N;
W, Y and Z are each independently $CR_1$;
U is $CR_2$;
$R_1$ is independently selected at each occurrence from hydrogen, halogen, hydroxy, cyano, amino, $C_1$–$C_8$alkyl, halo$C_1$–$C_8$alkyl, $C_1$–$C_8$alkoxy, halo$C_1$–$C_8$alkoxy and mono- and di-($C_1$–$C_8$alkyl) amino;
$R_2$ is: (i) hydrogen, halogen or cyano;
  (ii) $C_2$–$C_8$alkanoyl or $C_3$–$C_8$alkanone, each of which is unsubstituted or substituted with from 1 to 9 substituents independently selected from $R_d$; or
  (iii) a group of the formula —$R_c$-M-A-$R_y$, wherein:
    $R_c$ is $C_0$–$C_3$alkyl;
    M is a bond, $N(R_z)$, S, $SO_2$, $(C=O)_pN(R_z)$, $N(R_z)(C=O)_p$, $SO_2N(R_z)$, or $N(R_z)SO_2$, wherein p is 0 or 1;
    A is a bond or $C_1$–$C_8$alkyl, optionally substituted with from 1 to 3 substituents independently selected from $R_d$; and
    $R_y$ and $R_z$, if present, are:
      (a) independently hydrogen, $C_1$–$C_8$alkyl, $C_2$–$C_8$alkenyl, $C_2$–$C_8$alkynyl, $C_6$–$C_{10}$aryl$C_0$–$C_8$alkyl, a 4- to 10-membered carbocycle, or joined to $R_c$ to form a 4- to 10-membered carbocycle, wherein each $R_y$ and $R_z$ is independently unsubstituted or substituted with from 1 to 9 substituents independently selected from $R_d$; or
      (b) joined to form a 4- to 10-membered heterocycle that is unsubstituted or substituted with from 1 to 9 substituents independently selected from $R_d$;
    wherein $R_d$ is independently selected at each occurrence from hydroxy, halogen, amino, aminocarbonyl, cyano, nitro, $C_1$–$C_8$alkyl, $C_1$–$C_8$alkylthio, hydroxy$C_1$–$C_8$alkyl, halo$C_1$–$C_8$alkyl, phenyl, phenyl($C_1$–$C_8$alkyl), mono- and di-($C_1$–$C_6$alkyl) amino, $(SO_2)C_1$–$C_8$alkyl, 5- to 7-membered heterocycle and (5- to 7-membered heterocycle)($C_1$–$C_8$alkyl);
$Ar_1$ and $Ar_2$ are independently selected from 5- to 10-membered aromatic carbocycles and heterocycles, each of which is unsubstituted or substituted with from 1 to 3 substituents independently selected from groups of the formula $LR_a$;
L is independently selected at each occurrence from a bond, —O—, —C(=O)—, —OC(=O)—, —C(=O)O—, —O—C(=O)O—, —S(O)$_m$—, —$NR_x$—, —C(=O)$NHR_x$—, —$NHR_xC(=O)$—, —$NR_xS(O)_m$—, —S(O)$_mNR_x$— and —N[S(O)$_mR_x$]S(O)$_m$—; wherein m is independently selected at each occurrence from 0, 1 and 2; and $R_x$ is independently selected at each occurrence from hydrogen and $C_1$–$C_8$alkyl;
$R_a$ is independently selected at each occurrence from:
  (i) hydrogen, halogen, cyano and nitro; and
  (ii) $C_1$–$C_8$alkyl, $C_2$–$C_8$alkenyl, $C_2$–$C_8$alkynyl, $C_2$–$C_8$alkyl ether, 3- to 10-membered heterocycles, mono- and di-($C_1$–$C_8$alkyl)amino and (3- to 10-membered heterocycle)$C_1$–$C_6$alkyl, each of which is unsubstituted or substituted with from 1 to 9 substituents independently selected from $R_b$; and
$R_b$ is independently chosen at each occurrence from hydroxy, halogen, amino, aminocarbonyl, cyano, nitro, $C_1$–$C_8$alkyl, $C_1$–$C_8$alkoxy, $C_1$–$C_8$alkylthio, $C_2$–$C_8$alkyl ether, hydroxy$C_1$–$C_8$alkyl, halo$C_1$–$C_8$alkyl, phenyl, phenyl($C_1$–$C_8$alkyl), mono- and di-($C_1$–$C_6$alkyl)amino, $(SO_2)C_1$–$C_8$alkyl, 5- to 7-membered heterocycle and (5- to 7-membered heterocycle)($C_1$–$C_8$alkyl);
under conditions and in an amount sufficient to detectably inhibit vanilloid ligand binding to capsaicin receptor.

38. A method according to claim 37, wherein the compound or salt is a compound of the formula:

or a pharmaceutically acceptable salt thereof, wherein:
V and X are N;
W, Y and Z are each independently $CR_1$;
U is $CR_2$;
$R_1$ is independently selected at each occurrence from hydrogen, halogen, hydroxy, amino, $C_1$–$C_8$alkyl, halo$C_1$–$C_8$alkyl, $C_1$–$C_8$alkoxy, halo$C_1$–$C_8$alkoxy and mono- and di-($C_1$–$C_8$alkyl) amino;
$R_2$ is: (i) hydrogen, halogen or cyano;
  (ii) $C_2$–$C_8$alkanoyl or $C_3$–$C_8$alkanone, each of which is unsubstituted or substituted with from 1 to 9 substituents independently selected from $R_d$; or
  (iii) a group of the formula —$R_c$-M-A-$R_y$, wherein:
    $R_c$ is $C_0$–$C_3$alkyl;
    M is a bond, S, $SO_2$, $(C=O)_pN(R_z)$, $N(R_z)(C=O)_p$, $SO_2N(R_z)$, or $N(R_z)SO_2$, wherein p is 0 or 1;
    A is a bond or $C_1$–$C_8$alkyl, optionally substituted with from 1 to 3 substituents independently selected from $R_d$; and
    $R_y$ and $R_z$, if present, are:
      (a) independently hydrogen, $C_1$–$C_8$alkyl, $C_3$–$C_8$alkanone, $C_2$–$C_8$alkenyl, a 4- to 10-membered carbocycle, or joined to $R_c$ to form a 4- to 10-membered carbocycle, wherein each $R_y$ and $R_z$ is independently unsubstituted or substituted with from 1 to 9 substituents independently selected from $R_d$; or
      (b) joined to form a 4- to 10-membered heterocycle that is unsubstituted or substituted with from 1 to 9 substituents independently selected from $R_d$;
    wherein $R_d$ is independently selected at each occurrence from hydroxy, halogen, amino, aminocarbonyl, cyano, nitro, $C_1$–$C_8$alkyl, $C_1$–$C_8$alkylthio, hydroxy$C_1$–$C_8$alkyl, halo$C_1$–$C_8$alkyl, phenyl, phenyl($C_1$–$C_8$alkyl), mono- and di-($C_1$–$C_6$alkyl) amino, $(SO_2)C_1$–$C_8$alkyl, 5- to 7-membered heterocycle and (5- to 7-membered heterocycle)($C_1$–$C_8$alkyl);
$Ar_2$ is a 5- to 7-membered aromatic heterocycle, optionally substituted with from 1 to 3 substituents independently selected from groups of the formula $LR_a$;
$Ar_1$ is a 5- to 10-membered aromatic carbocycle or heterocycle, optionally substituted with from 1 to 3 substituents independently selected from groups of the formula $LR_a$;
L is independently selected at each occurrence from a bond, —O—, —C(=O)—, —OC(=O)—, —C(=O)O—, —O—C(=O)O—, —S(O)$_m$—, —NR$_x$—, —C(=O)NHR$_x$—, —NHR$_x$C(=O)—, —NR$_x$S(O)$_m$—, —S(O)$_m$NR$_x$— and —N[S(O)$_m$R$_x$]S(O)$_m$—; wherein m is independently selected at each occurrence from 0, 1 and 2; and R$_x$ is independently selected at each occurrence from hydrogen and C$_1$–C$_8$alkyl;

R$_a$ is independently selected at each occurrence from:
(i) hydrogen, halogen, cyano and nitro; and
(ii) C$_1$–C$_8$alkyl, C$_2$–C$_8$alkenyl, C$_2$–C$_8$alkynyl, C$_2$–C$_8$alkyl ether, 3- to 10-membered heterocycles, mono- and di-(C$_1$–C$_8$alkyl)amino and (3- to 10-membered heterocycle)C$_1$–C$_6$alkyl, each of which is unsubstituted or substituted with from 1 to 9 substituents independently selected from R$_b$; and R$_b$ is independently chosen at each occurrence from hydroxy, halogen, amino, aminocarbonyl, cyano, nitro, C$_1$–C$_8$alkyl, C$_1$–C$_8$alkoxy, C$_1$–C$_8$alkylthio, C$_2$–C$_8$alkyl ether, hydroxyC$_1$–C$_8$alkyl, haloC$_1$–C$_8$alkyl, phenyl, phenyl(C$_1$–C$_8$alkyl), mono- and di-(C$_1$–C$_6$alkyl)amino, (SO$_2$)C$_1$–C$_8$alkyl, 5- to 7-membered heterocycle and (5- to 7-membered heterocycle)(C$_1$–C$_8$alkyl).

39. A method according to claim 37, wherein the compound or salt is a compound of the formula:

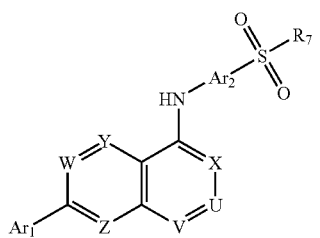

or a pharmaceutically acceptable salt thereof, wherein:
V and X are N;
W, Y and Z are each independently CR$_1$;
U is CR$_2$;
R$_1$ is independently selected at each occurrence from hydrogen, halogen, hydroxy, amino, C$_1$–C$_8$alkyl, haloC$_1$–C$_8$alkyl, C$_1$–C$_8$alkoxy, haloC$_1$–C$_8$alkoxy and mono- and di-(C$_1$–C$_8$alkyl) amino;
R$_2$ is: (i) hydrogen, halogen or cyano;
(ii) C$_2$–C$_8$alkanoyl or C$_3$–C$_8$alkanone, each of which is unsubstituted or substituted with from 1 to 9 substituents independently selected from R$_d$; or
(iii) a group of the formula —R$_c$-M-A-R$_y$, wherein:
R$_c$ is C$_0$–C$_3$alkyl;
M is a bond, N(R$_z$), S, SO$_2$, (C=O)$_p$N(R$_z$), N(R$_z$)(C=O)$_p$, SO$_2$N(R$_z$), or N(R$_z$)SO$_2$, wherein p is 0 or 1;
A is a bond or C$_1$–C$_8$alkyl, optionally substituted with from 1 to 3 substituents independently selected from R$_d$; and
R$_y$ and R$_z$, if present, are:
(a) independently hydrogen, C$_1$–C$_8$alkyl, C$_3$–C$_8$alkanone, C$_2$–C$_8$alkenyl, a 4- to 10-membered carbocycle, or joined to R$_c$ to form a 4- to 10-membered carbocycle, wherein each R$_y$ and R$_z$ is independently unsubstituted or substituted with from 1 to 9 substituents independently selected from R$_d$; or (b) joined to form a 4- to 10-membered heterocycle that is unsubstituted or substituted with from 1 to 9 substituents independently selected from R$_d$;
wherein R$_d$ is independently selected at each occurrence from hydroxy, halogen, amino, aminocarbonyl, cyano, nitro, C$_1$–C$_8$alkyl, C$_1$–C$_8$alkylthio, hydroxyC$_1$–C$_8$alkyl, haloC$_1$–C$_8$alkyl, phenyl, phenyl(C$_1$–C$_8$alkyl), mono- and di-(C$_1$–C$_6$alkyl)amino, (SO$_2$)C$_1$–C$_8$alkyl, 5- to 7-membered heterocycle and (5- to 7-membered heterocycle)(C$_1$–C$_8$alkyl);

Ar$_1$ and Ar$_2$ are independently chosen from phenyl and 5- and 6-membered aromatic heterocycles, optionally substituted with from 1 to 3 substituents independently selected from groups of the formula LR$_a$;

L is independently selected at each occurrence from a bond, —O—, —C(=O)—, —OC(=O)—, —C(=O)O—, —O—C(=O)O—, —S(O)$_m$—, —NR$_x$—, —C(=O)NHR$_x$—, —NHR$_x$C(=O)—, —NR$_x$S(O)$_m$—, —S(O)$_m$NR$_x$— and —N[S(O)$_m$R$_x$]S(O)$_m$—; wherein m is independently selected at each occurrence from 0, 1 and 2; and R$_x$ is independently selected at each occurrence from hydrogen and C$_1$–C$_8$alkyl;

R$_a$ is independently selected at each occurrence from:
(i) hydrogen, halogen, cyano and nitro; and
(ii) C$_1$–C$_8$alkyl, C$_2$–C$_8$alkenyl, C$_2$–C$_8$alkynyl, C$_2$–C$_8$alkyl ether, 3- to 10-membered heterocycles, mono- and di-(C$_1$–C$_8$alkyl)amino and (3- to 10-membered heterocycle)C$_1$–C$_6$alkyl, each of which is unsubstituted or substituted with from 1 to 9 substituents independently selected from R$_b$;

R$_b$ is independently chosen at each occurrence from hydroxy, halogen, amino, aminocarbonyl, cyano, nitro, C$_1$–C$_8$alkyl, C$_1$–C$_8$alkoxy, C$_1$–C$_8$alkylthio, C$_2$–C$_8$alkyl ether, hydroxyC$_1$–C$_8$alkyl, haloC$_1$–C$_8$alkyl, phenyl, phenyl(C$_1$–C$_8$alkyl), mono- and di-(C$_1$–C$_6$alkyl)amino, (SO$_2$)C$_1$–C$_8$alkyl, 5- to 7-membered heterocycle and (5- to 7-membered heterocycle)(C$_1$–C$_8$alkyl); and R$_7$ is C$_1$–C$_8$alkyl, C$_2$–C$_8$alkenyl, C$_2$–C$_8$alkynyl, mono- or di(C$_1$–C$_8$alkyl)amino or a 3- to 10-membered heterocycle, each of which is optionally substituted with from 1 to 5 substituents independently selected from hydroxy, halogen, C$_1$–C$_6$alky, C$_1$–C$_8$alkoxy, C$_2$–C$_8$alkyl ether, haloC$_1$–C$_8$alkyl and haloC$_1$–C$_8$alkoxy.

40. A method for treating a condition responsive to capsaicin receptor modulation in a patient, wherein the condition is selected from exposure to capsaicin, pain, asthma, chronic obstructive pulmonary disease, itch, urinary incontinence, and cough, the method comprising administering to the patient a pharmaceutical composition comprising a capsaicin receptor modulatory amount of at least one compound or salt of the formula:

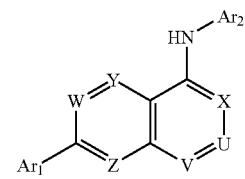

wherein:
V and X are N:
W, Y and Z are each independently CR$_1$;
U is CR$_2$
R$_1$ is independently selected at each occurrence from hydrogen, halogen, hydroxy, cyano, amino, C$_1$–C$_8$alkyl, haloC$_1$–C$_8$alkyl, C$_1$–C$_8$alkoxy, haloC$_1$–C$_8$alkoxy and mono- and di-(C$_1$–C$_8$alkyl)amino;
R$_2$ is: (i) hydrogen, halogen or cyano;
  (ii) C$_2$–C$_8$alkanoyl or C$_3$–C$_8$alkanone, each of which is unsubstituted or substituted with from 1 to 9 substituents independently selected from R$_d$; or
  (iii) a group of the formula —R$_c$-M-A-R$_y$, wherein:
    R$_c$ is C$_0$–C$_3$alkyl;
    M is a bond, N(R$_z$), S, SO$_2$, (C=O)$_p$N(R$_z$), N(R$_z$)(C=O)$_p$, SO$_2$N(R$_z$), or N(R$_z$)SO$_2$, wherein p is 0 or 1;
    A is a bond or C$_1$–C$_8$alkyl, optionally substituted with from 1 to 3 substituents independently selected from R$_d$; and
    R$_y$ and R$_z$, if present, are:
      (a) independently hydrogen, C$_1$–C$_8$alkyl, C$_2$–C$_8$alkenyl, C$_2$–C$_8$alkynyl, C$_6$–C$_{10}$arylC$_0$–C$_8$alkyl, a 4- to 10-membered carbocycle, or joined to R$_c$ to form a 4- to 10-membered carbocycle, wherein each R$_y$ and R$_z$ is independently unsubstituted or substituted with from 1 to 9 substituents independently selected from R$_d$; or
      (b) joined to form a 4- to 10-membered heterocycle that is unsubstituted or substituted with from 1 to 9 substituents independently selected from R$_d$;
    wherein R$_d$ is independently selected at each occurrence from hydroxy, halogen, amino, aminocarbonyl, cyano, nitro, C$_1$–C$_8$alkyl, C$_1$–C$_8$alkylthio, hydroxyC$_1$–C$_8$alkyl, haloC$_1$–C$_8$alkyl, phenyl, phenyl(C$_1$–C$_8$alkyl), mono- and di-(C$_1$–C$_6$alkyl)amino, (SO$_2$)C$_1$–C$_8$alkyl, 5- to 7-membered heterocycle and (5- to 7-membered heterocycle)(C$_1$–C$_8$alkyl);
Ar$_1$ and Ar$_2$ are independently selected from 5- to 10-membered aromatic carbocycles and heterocycles, each of which is unsubstituted or substituted with from 1 to 3 substituents independently selected from groups of the formula LR$_a$;
L is independently selected at each occurrence from a bond, —O—, —C(=O)—, —OC(=O)—, —C(=O)O—, —O—C(=O)O—, —S(O)$_m$—, —NR$_x$—, —C(=O)NHR$_x$—, —NHR$_x$C(=O)—, —NR$_x$S(O)$_m$—, —S(O)$_m$NR$_x$— and —N[S(O)$_m$R$_x$]S(O)$_m$—; wherein m is independently selected at each occurrence from 0, 1 and 2; and R$_x$ is independently selected at each occurrence from hydrogen and C$_1$–C$_8$alkyl;
R$_a$ is independently selected at each occurrence from:
  (i) hydrogen, halogen, cyano and nitro; and
  (ii) C$_1$–C$_8$alkyl, C$_2$–C$_8$alkenyl, C$_2$–C$_8$alkynyl, C$_2$–C$_8$alkyl ether, 3- to 10-membered heterocycles, mono- and di-(C$_1$–C$_8$alkyl)amino and (3- to 10-membered heterocycle)C$_1$–C$_6$alkyl, each of which is unsubstituted or substituted with from 1 to 9 substituents independently selected from R$_b$; and
R$_b$ is independently chosen at each occurrence from hydroxy, halogen, amino, aminocarbonyl, cyano, nitro, C$_1$–C$_8$alkyl, C$_1$–C$_8$alkoxy, C$_1$–C$_8$alkylthio, C$_2$–C$_8$alkyl ether, hydroxyC$_1$–C$_8$alkyl, haloC$_1$–C$_8$alkyl, phenyl, phenyl(C$_1$–C$_8$alkyl), mono- and di-(C$_1$–C$_6$alkyl)amino, (SO$_2$)C$_1$–C$_8$alkyl, 5- to 7-membered heterocycle and (5- to 7-membered heterocycle)(C$_1$–C$_8$alkyl); and a physiologically acceptable carrier or excipient;
wherein the compound or salt is a capsaicin receptor antagonist and has an IC$_{50}$ value of 1 micromolar or less in a VR1-mediated calcium mobilization assay;
and thereby alleviating the condition in the patient.

41. A method according to claim 40, wherein the compound or salt is a compound of the formula:

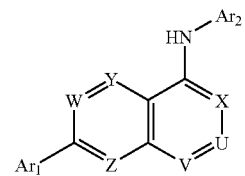

or a pharmaceutically acceptable salt thereof, wherein:
V and X are N;
W, Y and Z are each independently CR$_1$;
U is CR$_2$;
R$_1$ is independently selected at each occurrence from hydrogen, halogen, hydroxy, amino, C$_1$–C$_8$alkyl, haloC$_1$–C$_8$alkyl, C$_1$–C$_8$alkoxy, haloC$_1$–C$_8$alkoxy and mono- and di-(C$_1$–C$_8$alkyl)amino;
R$_2$ is: (i) hydrogen, halogen or cyano;
  (ii) C$_2$–C$_8$alkanoyl or C$_3$–C$_8$alkanone, each of which is unsubstituted or substituted with from 1 to 9 substituents independently selected from R$_d$; or
  (iii) a group of the formula —R$_c$-M-A-R$_y$, wherein:
    R$_c$ is C$_0$–C$_3$alkyl;
    M is a bond, S, SO$_2$, (C=O)$_p$N(R$_z$), N(R$_z$)(C=O)$_p$, SO$_2$N(R$_z$), or N(R$_z$)SO$_2$, wherein p is 0 or 1;
    A is a bond or C$_1$–C$_8$alkyl, optionally substituted with from 1 to 3 substituents independently selected from R$_d$; and
    R$_y$ and R$_z$, if present, are:
      (a) independently hydrogen, C$_1$–C$_8$alkyl, C$_3$–C$_8$alkanone, C$_2$–C$_8$alkenyl, a 4- to 10-membered carbocycle, or joined to R$_c$ to form a 4- to 10-membered carbocycle, wherein each R$_y$ and R$_z$ is independently unsubstituted or substituted with from 1 to 9 substituents independently selected from R$_d$; or
      (b) joined to form a 4- to 10-membered heterocycle that is unsubstituted or substituted with from 1 to 9 substituents independently selected from R$_d$;
    wherein R$_d$ is independently selected at each occurrence from hydroxy, halogen, amino, aminocarbonyl, cyano, nitro, C$_1$–C$_8$alkyl, C$_1$–C$_8$alkylthio, hydroxyC$_1$–C$_8$alkyl, haloC$_1$–C$_8$alkyl, phenyl, phenyl(C$_1$–C$_8$alkyl), mono- and di-(C$_1$–C$_6$alkyl)amino, (SO$_2$)C$_1$–C$_8$alkyl, 5- to 7-membered heterocycle and (5- to 7-membered heterocycle)(C$_1$–C$_8$alkyl);
Ar$_2$ is a 5- to 7-membered aromatic heterocycle, optionally substituted with from 1 to 3 substituents independently selected from groups of the formula LR$_a$;

Ar$_1$ is a 5- to 10-membered aromatic carbocycle or heterocycle, optionally substituted with from 1 to 3 substituents independently selected from groups of the formula LR$_a$;

L is independently selected at each occurrence from a bond, —O—, —C(=O)—, —OC(=O)—, —C(=O)O—, —O—C(=O)O—, —S(O)$_m$—, —NR$_x$—, —C(=O)NHR$_x$—, —NHR$_x$C(=O)—, —NR$_x$S(O)$_m$—, —S(O)$_m$NR$_x$— and —N[S(O)$_m$R$_x$]S(O)$_m$—; wherein m is independently selected at each occurrence from 0, 1 and 2; and R$_x$ is independently selected at each occurrence from hydrogen and C$_1$–C$_8$alkyl;

R$_a$ is independently selected at each occurrence from:
(i) hydrogen, halogen, cyano and nitro; and
(ii) C$_1$–C$_8$alkyl, C$_2$–C$_8$alkenyl, C$_2$–C$_8$alkynyl, C$_2$–C$_8$alkyl ether, 3- to 10-membered heterocycles, mono- and di-(C$_1$–C$_8$alkyl)amino and (3- to 10-membered heterocycle)C$_1$–C$_6$alkyl, each of which is unsubstituted or substituted with from 1 to 9 substituents independently selected from R$_b$; and R$_b$ is independently chosen at each occurrence from hydroxy, halogen, amino, aminocarbonyl, cyano, nitro, C$_1$–C$_8$alkyl, C$_1$–C$_8$alkoxy, C$_1$–C$_8$alkylthio, C$_2$–C$_8$alkyl ether, hydroxyC$_1$–C$_8$alkyl, haloC$_1$–C$_8$alkyl, phenyl, phenyl(C$_1$–C$_8$alkyl), mono- and di-(C$_1$–C$_6$alkyl)amino, (SO$_2$)C$_1$–C$_8$alkyl, 5- to 7-membered heterocycle and (5- to 7-membered heterocycle)(C$_1$–C$_8$alkyl).

42. A method according to claim 40, wherein the compound or salt is a compound of the formula:

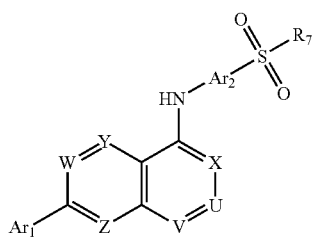

or a pharmaceutically acceptable salt thereof, wherein:
V and X are N;
W, Y and Z are each independently CR$_1$;
U is CR$_2$;
R$_1$ is independently selected at each occurrence from hydrogen, halogen, hydroxy, amino, C$_1$–C$_8$alkyl, haloC$_1$–C$_8$alkyl, C$_1$–C$_8$alkoxy, haloC$_1$–C$_8$alkoxy and mono- and di-(C$_1$–C$_8$alkyl)amino;
R$_2$ is: (i) hydrogen, halogen or cyano;
(ii) C$_2$–C$_8$alkanoyl or C$_3$–C$_8$alkanone, each of which is unsubstituted or substituted with from 1 to 9 substituents independently selected from R$_d$; or
(iii) a group of the formula —R$_c$-M-A-R$_y$, wherein:
R$_c$ is C$_0$–C$_3$alkyl;
M is a bond, S, SO$_2$, (C=O)$_p$N(R$_z$), N(R$_z$)(C=O)$_p$, SO$_2$N(R$_z$), or N(R$_z$)SO$_2$, wherein p is 0 or 1;
A is a bond or C$_1$–C$_8$alkyl, optionally substituted with from 1 to 3 substituents independently selected from R$_d$; and R$_y$ and R$_z$, if present, are:
(a) independently hydrogen, C$_1$–C$_8$alkyl, C$_3$–C$_8$alkanone, C$_2$–C$_8$alkenyl, a 4- to 10-membered carbocycle, or joined to R$_c$ to form a 4- to 10-membered carbocycle, wherein each R$_y$ and R$_z$ is independently unsubstituted or substituted with from 1 to 9 substituents independently selected from R$_d$; or
(b) joined to form a 4- to 10-membered heterocycle that is unsubstituted or substituted with from 1 to 9 substituents independently selected from R$_d$;

wherein R$_d$ is independently selected at each occurrence from hydroxy, halogen, amino, aminocarbonyl, cyano, nitro, C$_1$–C$_8$alkyl, C$_1$–C$_8$alkylthio, hydroxyC$_1$–C$_8$alkyl, haloC$_1$–C$_8$alkyl, phenyl, phenyl(C$_1$–C$_8$alkyl), mono- and di-(C$_1$–C$_6$alkyl)amino, (SO$_2$)C$_1$–C$_8$alkyl, 5- to 7-membered heterocycle and (5- to 7-membered heterocycle)(C$_1$–C$_8$alkyl);

Ar$_1$ and Ar$_2$ are independently chosen from phenyl and 5- and 6-membered aromatic heterocycles, optionally substituted with from 1 to 3 substituents independently selected from groups of the formula LR$_a$;

L is independently selected at each occurrence from a bond, —O—, —C(=O)—, —OC(=O)—, —C(=O)O—, —O—C(=O)O—, —S(O)$_m$—, —NR$_x$—, —C(=O)NHR$_x$—, —NHR$_x$C(=O)—, —NR$_x$S(O)$_m$—, —S(O)$_m$NR$_x$— and —N[S(O)$_m$R$_x$]S(O)$_m$—; wherein m is independently selected at each occurrence from 0, 1 and 2; and R$_x$ is independently selected at each occurrence from hydrogen and C$_1$–C$_8$alkyl;

R$_a$ is independently selected at each occurrence from:
(i) hydrogen, halogen, cyano and nitro; and
(ii) C$_1$–C$_8$alkyl, C$_2$–C$_8$alkenyl, C$_2$–C$_8$alkynyl, C$_2$–C$_8$alkyl ether, 3- to 10-membered heterocycles, mono- and di-(C$_1$–C$_8$alkyl)amino and (3- to 10-membered heterocycle)C$_1$–C$_6$alkyl, each of which is unsubstituted or substituted with from 1 to 9 substituents independently selected from R$_b$;

R$_b$ is independently chosen at each occurrence from hydroxy, halogen, amino, aminocarbonyl, cyano, nitro, C$_1$–C$_8$alkyl, C$_1$–C$_8$alkoxy, C$_1$–C$_8$alkylthio, C$_2$–C$_8$alkyl ether, hydroxyC$_1$–C$_8$alkyl, haloC$_1$–C$_8$alkyl, phenyl, phenyl(C$_1$–C$_8$alkyl), mono- and di-(C$_1$–C$_6$alkyl)amino, (SO$_2$)C$_1$–C$_8$alkyl, 5- to 7-membered heterocycle and (5- to 7-membered heterocycle)(C$_1$–C$_8$alkyl); and R$_7$ is C$_1$–C$_8$alkyl, C$_2$–C$_8$alkenyl, C$_2$–C$_8$alkynyl, mono- or di(C$_1$–C$_8$alkyl)amino or a 3- to 10-membered heterocycle, each of which is optionally substituted with from 1 to 5 substituents independently selected from hydroxy, halogen, C$_1$–C$_6$alky, C$_1$–C$_8$alkoxy, C$_2$–C$_8$alkyl ether, haloC$_1$–C$_8$alkyl and haloC$_1$–C$_8$alkoxy.

43. A method according to claim 40, wherein the compound or salt is present in the blood of the animal at a concentration of 100 nanomolar or less.

44. A method according to claim 40, wherein the condition is treating asthma or chronic obstructive pulmonary disease.

45. A method for treating pain in a patient, comprising administering to a patient suffering from pain a capsaicin receptor modulatory amount of at least one compound or salt of the formula:

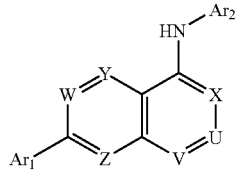

wherein:
V and X are N;
W, Y and Z are each independently $CR_1$;
U is $CR_2$;
$R_1$ is independently selected at each occurrence from hydrogen, halogen, hydroxy, cyano, amino, $C_1$–$C_8$alkyl, halo$C_1$–$C_8$alkyl, $C_1$–$C_8$alkoxy, halo$C_1$–$C_8$alkoxy and mono- and di-($C_1$–$C_8$alkyl)amino;
$R_2$ is: (i) hydrogen, halogen or cyano;
  (ii) $C_2$–$C_8$alkanoyl or $C_3$–$C_8$alkanone, each of which is unsubstituted or substituted with from 1 to 9 substituents independently selected from $R_d$; or
  (iii) a group of the formula —$R_c$-M-A-$R_y$, wherein:
    $R_c$ is $C_0$–$C_3$alkyl;
    M is a bond, N($R_z$), S, $SO_2$, (C=O)$_p$N($R_z$), N($R_z$)(C=O)$_p$, $SO_2$N($R_z$), or N($R_z$)$SO_2$, wherein p is 0 or 1;
    A is a bond or $C_1$–$C_8$alkyl, optionally substituted with from 1 to 3 substituents independently selected from $R_d$; and
    $R_y$ and $R_z$, if present, are:
      (a) independently hydrogen, $C_1$–$C_8$alkyl, $C_2$–$C_8$alkenyl, $C_2$–$C_8$alkynyl, $C_6$–$C_{10}$aryl$C_0$–$C_8$alkyl, a 4- to 10-membered carbocycle, or joined to $R_c$ to form a 4- to 10-membered carbocycle, wherein each $R_y$ and $R_z$ is independently unsubstituted or substituted with from 1 to 9 substituents independently selected from $R_d$; or
      (b) joined to form a 4- to 10-membered heterocycle that is unsubstituted or substituted with from 1 to 9 substituents independently selected from $R_d$;
    wherein $R_d$ is independently selected at each occurrence from hydroxy, halogen, amino, aminocarbonyl, cyano, nitro, $C_1$–$C_8$alkyl, $C_1$–$C_8$alkylthio, hydroxy$C_1$–$C_8$alkyl, halo$C_1$–$C_8$alkyl, phenyl, phenyl($C_1$–$C_8$alkyl), mono- and di-($C_1$–$C_6$alkyl)amino, $(SO_2)C_1$–$C_8$alkyl, 5-to 7-membered heterocycle and (5- to 7-membered heterocycle)($C_1$–$C_8$alkyl);
$Ar_1$ and $Ar_2$ are independently selected from 5- to 10-membered aromatic carbocycles and heterocycles, each of which is unsubstituted or substituted with from 1 to 3 substituents independently selected from groups of the formula $LR_a$;
L is independently selected at each occurrence from a bond, —O—, —C(=O)—, —OC(=O)—, —C(=O)O—, —O—C(=O)O—, —S(O)$_m$—, —NR$_x$—, —C(=O)NHR$_x$—, —NHR$_x$C(=O)—, —NR$_x$S(O)$_m$—, —S(O)$_m$NR$_x$— and —N[S(O)$_m$R$_x$]S(O)$_m$—; wherein m is independently selected at each occurrence from 0, 1 and 2; and $R_x$ is independently selected at each occurrence from hydrogen and $C_1$–$C_8$alkyl;
$R_a$ is independently selected at each occurrence from:
  (i) hydrogen, halogen, cyano and nitro; and
  (ii) $C_1$–$C_8$alkyl, $C_2$–$C_8$alkenyl, $C_2$–$C_8$alkynyl, $C_2$–$C_8$alkyl ether, 3- to 10-membered heterocycles, mono- and di-($C_1$–$C_8$alkyl)amino and (3- to 10-membered heterocycle)$C_1$–$C_6$alkyl, each of which is unsubstituted or substituted with from 1 to 9 substituents independently selected from $R_b$; and
$R_b$ is independently chosen at each occurrence from hydroxy, halogen, amino, aminocarbonyl, cyano, nitro, $C_1$–$C_8$alkyl, $C_1$–$C_8$alkoxy, $C_1$–$C_8$alkylthio, $C_2$–$C_8$alkyl ether, hydroxy$C_1$–$C_8$alkyl, halo$C_1$–$C_8$alkyl, phenyl, phenyl($C_1$–$C_8$alkyl), mono- and di-($C_1$–$C_6$alkyl)amino, $(SO_2)C_1$–$C_8$alkyl, 5- to 7-membered heterocycle and (5- to 7-membered heterocycle)($C_1$–$C_8$alkyl);
and thereby alleviating pain in the patient.

46. A method according to claim 45, wherein the compound or salt is a compound of the formula:

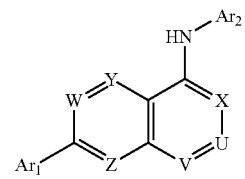

or a pharmaceutically acceptable salt thereof, wherein:
V and X are N;
W, Y and Z are each independently $CR_1$;
U is $CR_2$;
$R_1$ is independently selected at each occurrence from hydrogen, halogen, hydroxy, amino, $C_1$–$C_8$alkyl, halo$C_1$–$C_8$alkyl, $C_1$–$C_8$alkoxy, halo$C_1$–$C_8$alkoxy and mono- and di-($C_1$–$C_8$alkyl)amino;
$R_2$ is: (i) hydrogen, halogen or cyano;
  (ii) $C_2$–$C_8$alkanoyl or $C_3$–$C_8$alkanone, each of which is unsubstituted or substituted with from 1 to 9 substituents independently selected from $R_d$; or
  (iii) a group of the formula —$R_c$-M-A-$R_y$, wherein:
    $R_c$ is $C_0$–$C_3$alkyl;
    M is a bond, S, $SO_2$, (C=O)$_p$N($R_z$), N($R_z$)(C=O)$_p$, $SO_2$N($R_z$), or N($R_z$)$SO_2$, wherein p is 0 or 1;
    A is a bond or $C_1$–$C_8$alkyl, optionally substituted with from 1 to 3 substituents independently selected from $R_d$; and
    $R_y$ and $R_z$, if present, are:
      (a) independently hydrogen, $C_1$–$C_8$alkyl, $C_3$–$C_8$alkanone, $C_2$–$C_8$alkenyl, a 4- to 10-membered carbocycle, or joined to $R_c$ to form a 4- to 10-membered carbocycle, wherein each $R_y$ and $R_z$ is independently unsubstituted or substituted with from 1 to 9 substituents independently selected from $R_d$; or
      (b) joined to form a 4- to 10-membered heterocycle that is unsubstituted or substituted with from 1 to 9 substituents independently selected from $R_d$;
    wherein $R_d$ is independently selected at each occurrence from hydroxy, halogen, amino, aminocarbonyl, cyano, nitro, $C_1$–$C_8$alkyl, $C_1$–$C_8$alkylthio, hydroxy$C_1$–$C_8$alkyl, halo$C_1$–$C_8$alkyl, phenyl, phenyl($C_1$–$C_8$alkyl), mono- and di-($C_1$–$C_6$alkyl) amino, $(SO_2)C_1$–$C_8$alkyl, 5- to 7-membered heterocycle and (5- to 7-membered heterocycle) ($C_1$–$C_8$alkyl);

$Ar_2$ is a 5- to 7-membered aromatic heterocycle, optionally substituted with from 1 to 3 substituents independently selected from groups of the formula $LR_a$;

$Ar_1$ is a 5- to 10-membered aromatic carbocycle or heterocycle, optionally substituted with from 1 to 3 substituents independently selected from groups of the formula $LR_a$;

L is independently selected at each occurrence from a bond, —O—, —C(=O)—, —OC(=O)—, —C(=O)O—, —O—C(=O)O—, —S(O)$_m$—, —NR$_x$—, —C(=O)NHR$_x$—, —NHR$_x$C(=O)—, —NR$_x$S(O)$_m$—, —S(O)$_m$NR$_x$— and —N[S(O)$_m$R$_x$]S(O)$_m$—; wherein m is independently selected at each occurrence from 0, 1 and 2; and $R_x$ is independently selected at each occurrence from hydrogen and $C_1$–$C_8$alkyl;

$R_a$ is independently selected at each occurrence from:
(i) hydrogen, halogen, cyano and nitro; and
(ii) $C_1$–$C_8$alkyl, $C_2$–$C_8$alkenyl, $C_2$–$C_8$alkynyl, $C_2$–$C_8$alkyl ether, 3- to 10-membered heterocycles, mono- and di-($C_1$–$C_8$alkyl)amino and (3- to 10-membered heterocycle)$C_1$–$C_6$alkyl, each of which is unsubstituted or substituted with from 1 to 9 substituents independently selected from $R_b$; and $R_b$ is independently chosen at each occurrence from hydroxy, halogen, amino, aminocarbonyl, cyano, nitro, $C_1$–$C_8$alkyl, $C_1$–$C_8$alkoxy, $C_1$–$C_8$alkylthio, $C_2$–$C_8$alkyl ether, hydroxy$C_1$–$C_8$alkyl, halo$C_1$–$C_8$alkyl, phenyl, phenyl($C_1$–$C_8$alkyl), mono- and di-($C_1$–$C_6$alkyl)amino, $(SO_2)C_1$–$C_8$alkyl, 5- to 7-membered heterocycle and (5- to 7-membered heterocycle)($C_1$–$C_8$alkyl).

47. A method according to claim 45, wherein the compound or salt is a compound of the formula:

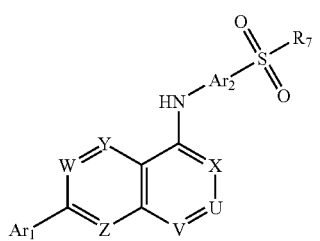

or a pharmaceutically acceptable salt thereof, wherein:
V and X are N;
W, Y and Z are each independently $CR_1$;
U is $CR_2$;
$R_1$ is independently selected at each occurrence from hydrogen, halogen, hydroxy, amino, $C_1$–$C_8$alkyl, halo$C_1$–$C_8$alkyl, $C_1$–$C_8$alkoxy, halo$C_1$–$C_8$alkoxy and mono- and di-($C_1$–$C_8$alkyl)amino;
$R_2$ is: (i) hydrogen, halogen or cyano;
(ii) $C_2$–$C_8$alkanoyl or $C_3$–$C_8$alkanone, each of which is unsubstituted or substituted with from 1 to 9 substituents independently selected from $R_d$; or (iii) a group of the formula —$R_c$-M-A-$R_y$, wherein:
$R_c$ is $C_0$–$C_3$alkyl;
M is a bond, S, $SO_2$, (C=O)$_p$N($R_z$), N($R_z$)(C=O)$_p$, $SO_2$N($R_z$), or N($R_z$)$SO_2$, wherein p is 0 or 1;
A is a bond or $C_1$–$C_8$alkyl, optionally substituted with from 1 to 3 substituents independently selected from $R_d$; and
$R_y$ and $R_z$, if present, are:
(a) independently hydrogen, $C_1$–$C_8$alkyl, $C_3$–$C_8$alkanone, $C_2$–$C_8$alkenyl, a 4- to 10-membered carbocycle, or joined to $R_c$ to form a 4- to 10-membered carbocycle, wherein each $R_y$ and $R_z$ is independently unsubstituted or substituted with from 1 to 9 substituents independently selected from $R_d$; or
(b) joined to form a 4- to 10-membered heterocycle that is unsubstituted or substituted with from 1 to 9 substituents independently selected from $R_d$;
wherein $R_d$ is independently selected at each occurrence from hydroxy, halogen, amino, aminocarbonyl, cyano, nitro, $C_1$–$C_8$alkyl, $C_1$–$C_8$alkylthio, hydroxy$C_1$–$C_8$alkyl, halo$C_1$–$C_8$alkyl, phenyl, phenyl($C_1$–$C_8$alkyl), mono- and di-($C_1$–$C_6$alkyl)amino, $(SO_2)C_1$–$C_8$alkyl, 5- to 7-membered heterocycle and (5- to 7-membered heterocycle) ($C_1$–$C_8$alkyl);

$Ar_1$ and $Ar_2$ are independently chosen from phenyl and 5- and 6-membered aromatic heterocycles, optionally substituted with from 1 to 3 substituents independently selected from groups of the formula $LR_a$;

L is independently selected at each occurrence from a bond, —O—, —C(=O)—, —OC(=O)—, —C(=O)O—, —O—C(=O)O—, —S(O)$_m$—, —NR$_x$—, —C(=O)NHR$_x$—, —NHR$_x$C(=O)—, —NR$_x$S(O)$_m$—, —S(O)$_m$NR$_x$— and —N[S(O)$_m$R$_x$]S(O)$_m$—; wherein m is independently selected at each occurrence from 0, 1 and 2; and $R_x$ is independently selected at each occurrence from hydrogen and $C_1$–$C_8$alkyl;

$R_a$ is independently selected at each occurrence from:
(i) hydrogen, halogen, cyano and nitro; and
(ii) $C_1$–$C_8$alkyl, $C_2$–$C_8$alkenyl, $C_2$–$C_8$alkynyl, $C_2$–$C_8$alkyl ether, 3- to 10-membered heterocycles, mono- and di-($C_1$–$C_8$alkyl)amino and (3- to 10-membered heterocycle)$C_1$–$C_6$alkyl, each of which is unsubstituted or substituted with from 1 to 9 substituents independently selected from $R_b$; and $R_b$ is independently chosen at each occurrence from hydroxy, halogen, amino, aminocarbonyl, cyano, nitro, $C_1$–$C_8$alkyl, $C_1$–$C_8$alkoxy, $C_1$–$C_8$alkylthio, $C_2$–$C_8$alkyl ether, hydroxy$C_1$–$C_8$alkyl, halo$C_1$–$C_8$alkyl, phenyl, phenyl($C_1$–$C_8$alkyl), mono- and di-($C_1$–$C_6$alkyl)amino, $(SO_2)C_1$–$C_8$alkyl, 5- to 7-membered heterocycle and (5- to 7-membered heterocycle)($C_1$–$C_8$alkyl); and $R_7$ is $C_1$–$C_8$alkyl, $C_2$–$C_8$alkenyl, $C_2$–$C_8$alkynyl, mono- or di($C_1$–$C_8$alkyl)amino or a 3- to 10-membered heterocycle, each of which is optionally substituted with from 1 to 5 substituents independently selected from hydroxy, halogen, $C_1$–$C_6$alky, $C_1$–$C_8$alkoxy, $C_2$–$C_8$alkyl ether, halo$C_1$–$C_8$alkyl and halo$C_1$–$C_8$alkoxy.

48. A method according to claim 45, wherein the compound or salt is present in the blood of the animal at a concentration of 100 nanomolar or less.

49. A method according to claim 45, wherein the patient is suffering from neuropathic pain.

50. A method according to claim 45, wherein the pain is associated with a condition selected from: postmastectomy pain syndrome, stump pain, phantom limb pain, oral neuropathic pain, toothache, postherpetic neuralgia, diabetic neuropathy, reflex sympathetic dystrophy, trigeminal neuralgia, osteoarthritis, rheumatoid arthritis, fibromyalgia, Guillain-Barre syndrome, meralgia paresthetica, burning-mouth syndrome, bilateral peripheral neuropathy, causalgia, neuritis, neuronitis, neuralgia, AIDS-related neuropathy, MS-related neuropathy, spinal cord injury-related pain, surgery-related pain, musculoskeletal pain, back pain, headache, migraine, angina, labor, hemorrhoids, dyspepsia, Charcot's pains, intestinal gas, menstruation, cancer, venom exposure, irritable bowel syndrome, inflammatory bowel disease, and/or trauma.

51. A method according to claim 45, wherein the patient is a human.

52. A method for treating itch in a patient, comprising administering to a patient a capsaicin receptor modulatory amount of a compound or salt of the formula:

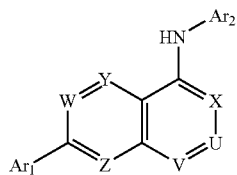

wherein:
V and X are N:
W, Y and Z are each independently $CR_1$;
U is $CR_2$;
$R_1$ is independently selected at each occurrence from hydrogen, halogen, hydroxy, cyano, amino, $C_1$–$C_8$alkyl, halo$C_1$–$C_8$alkyl, $C_1$–$C_8$alkoxy, halo$C_1$–$C_8$alkoxy and mono- and di-($C_1$–$C_8$alkyl)amino;
$R_2$ is: (i) hydrogen, halogen or cyano;
  (ii) $C_2$–$C_8$alkanoyl or $C_3$–$C_8$alkanone, each of which is unsubstituted or substituted with from 1 to 9 substituents independently selected from $R_d$; or
  (iii) a group of the formula —$R_c$-M-A-$R_y$, wherein:
    $R_c$ is $C_0$–$C_3$alkyl;
    M is a bond, $N(R_z)$, S, $SO_2$, $(C=O)_pN(R_z)$, $N(R_z)(C=O)_p$, $SO_2N(R_z)$, or $N(R_z)SO_2$, wherein p is 0 or 1;
    A is a bond or $C_1$–$C_8$alkyl, optionally substituted with from 1 to 3 substituents independently selected from $R_d$; and
    $R_y$ and $R_z$, if present, are:
      (a) independently hydrogen, $C_1$–$C_8$alkyl, $C_2$–$C_8$alkenyl, $C_2$–$C_8$alkynyl, $C_6$–$C_{10}$aryl$C_0$–$C_8$alkyl, a 4- to 10-membered carbocycle, or joined to $R_c$ to form a 4- to 10-membered carbocycle, wherein each $R_y$ and $R_z$ is independently unsubstituted or substituted with from 1 to 9 substituents independently selected from $R_d$; or
      (b) joined to form a 4- to 10-membered heterocycle that is unsubstituted or substituted with from 1 to 9 substituents independently selected from $R_d$;

wherein $R_d$ is independently selected at each occurrence from hydroxy, halogen, amino, aminocarbonyl, cyano, nitro, $C_1$–$C_8$alkyl, $C_1$–$C_8$alkylthio, hydroxy$C_1$–$C_8$alkyl, halo$C_1$–$C_8$alkyl, phenyl, phenyl($C_1$–$C_8$alkyl), mono- and di-($C_1$–$C_6$alkyl)amino, $(SO_2)C_1$–$C_8$alkyl, 5- to 7-membered heterocycle and (5- to 7-membered heterocycle)($C_1$–$C_8$alkyl);

$Ar_1$ and $Ar_2$ are independently selected from 5- to 10-membered aromatic carbocycles and heterocycles, each of which is unsubstituted or substituted with from 1 to 3 substituents independently selected from groups of the formula $LR_a$;

L is independently selected at each occurrence from a bond, —O—, —C(=O)—, —OC(=O)—, —C(=O)O—, —O—C(=O)O—, —S(O)$_m$—, —$NR_x$—, —C(=O)$NHR_x$—, —$NHR_xC$(=O)—, —$NR_xS(O)_m$—, —$S(O)_mNR_x$— and —N[S(O)$_m$R$_x$]S(O)$_m$—; wherein m is independently selected at each occurrence from 0, 1 and 2; and $R_x$ is independently selected at each occurrence from hydrogen and $C_1$–$C_8$alkyl;

$R_a$ is independently selected at each occurrence from:
  (i) hydrogen, halogen, cyano and nitro; and
  (ii) $C_1$–$C_8$alkyl, $C_2$–$C_8$alkenyl, $C_2$–$C_8$alkynyl, $C_2$–$C_8$alkyl ether, 3- to 10-membered heterocycles, mono- and di-($C_1$–$C_8$alkyl)amino and (3- to 10-membered heterocycle)$C_1$–$C_6$alkyl, each of which is unsubstituted or substituted with from 1 to 9 substituents independently selected from $R_b$; and $R_b$ is independently chosen at each occurrence from hydroxy, halogen, amino, aminocarbonyl, cyano, nitro, $C_1$–$C_8$alkyl, $C_1$–$C_8$alkoxy, $C_1$–$C_8$alkylthio, $C_2$–$C_8$alkyl ether, hydroxy$C_1$–$C_8$alkyl, halo$C_1$–$C_8$alkyl, phenyl, phenyl($C_1$–$C_8$alkyl), mono- and di-($C_1$–$C_6$alkyl)amino, $(SO_2)C_1$–$C_8$alkyl, 5- to 7-membered heterocycle and (5- to 7-membered heterocycle)($C_1$–$C_8$alkyl);

and thereby alleviating itch in the patient.

53. A method according to claim 52, wherein the compound or salt is a compound of the formula:

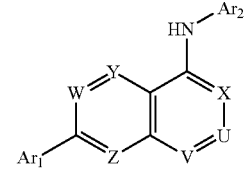

or a pharmaceutically acceptable salt thereof, wherein:
V and X are N;
W, Y and Z are each independently $CR_1$;
U is $CR_2$;
$R_1$ is independently selected at each occurrence from hydrogen, halogen, hydroxy, amino, $C_1$–$C_8$alkyl, halo$C_1$–$C_8$alkyl, $C_1$–$C_8$alkoxy, halo$C_1$–$C_8$alkoxy and mono- and di-($C_1$–$C_8$alkyl)amino;
$R_2$ is: (i) hydrogen, halogen or cyano;
  (ii) $C_2$–$C_8$alkanoyl or $C_3$–$C_8$alkanone, each of which is unsubstituted or substituted with from 1 to 9 substituents independently selected from $R_d$; or (iii) a group of the formula —$R_c$-M-A-$R_y$, wherein:

$R_c$ is $C_0$–$C_3$alkyl;

M is a bond, S, $SO_2$, (C=O)$_p$N($R_z$), N($R_z$)(C=O)$_p$, $SO_2$N($R_z$), or N($R_z$)$SO_2$, wherein p is 0 or 1;

A is a bond or $C_1$–$C_8$alkyl, optionally substituted with from 1 to 3 substituents independently selected from $R_d$; and $R_y$ and $R_z$, if present, are:

(a) independently hydrogen, $C_1$–$C_8$alkyl, $C_3$–$C_8$alkanone, $C_2$–$C_8$alkenyl, a 4- to 10-membered carbocycle, or joined to $R_c$ to form a 4- to 10-membered carbocycle, wherein each $R_y$ and $R_z$ is independently unsubstituted or substituted with from 1 to 9 substituents independently selected from $R_d$; or (b) joined to form a 4- to 10-membered heterocycle that is unsubstituted or substituted with from 1 to 9 substituents independently selected from $R_d$;

wherein $R_d$ is independently selected at each occurrence from hydroxy, halogen, amino, aminocarbonyl, cyano, nitro, $C_1$–$C_8$alkyl, $C_1$–$C_8$alkylthio, hydroxy$C_1$–$C_8$alkyl, halo$C_1$–$C_8$alkyl, phenyl, phenyl($C_1$–$C_8$alkyl), mono- and di-($C_1$–$C_6$alkyl)amino, ($SO_2$)$C_1$–$C_8$alkyl, 5- to 7-membered heterocycle and (5- to 7-membered heterocycle)($C_1$–$C_8$alkyl);

$Ar_2$ is a 5- to 7-membered aromatic heterocycle, optionally substituted with from 1 to 3 substituents independently selected from groups of the formula L$R_a$;

$Ar_1$ is a 5- to 10-membered aromatic carbocycle or heterocycle, optionally substituted with from 1 to 3 substituents independently selected from groups of the formula L$R_a$;

L is independently selected at each occurrence from a bond, —O—, —C(=O)—, —OC(=O)—, —C(=O)O—, —O—C(=O)O—, —S(O)$_m$—, —N$R_x$—, —C(=O)NH$R_x$—, —NH$R_x$C(=O)—, —N$R_x$S(O)$_m$—, —S(O)$_m$N$R_x$— and —N[S(O)$_m$$R_x$]S(O)$_m$—; wherein m is independently selected at each occurrence from 0, 1 and 2; and $R_x$ is independently selected at each occurrence from hydrogen and $C_1$–$C_8$alkyl;

$R_a$ is independently selected at each occurrence from:

(i) hydrogen, halogen, cyano and nitro; and (ii) $C_1$–$C_8$alkyl, $C_2$–$C_8$alkenyl, $C_2$–$C_8$alkynyl, $C_2$–$C_8$alkyl ether, 3- to 10-membered heterocycles, mono- and di-($C_1$–$C_8$alkyl)amino and (3- to 10-membered heterocycle)$C_1$–$C_6$alkyl, each of which is unsubstituted or substituted with from 1 to 9 substituents independently selected from $R_b$; and $R_b$ is independently chosen at each occurrence from hydroxy, halogen, amino, aminocarbonyl, cyano, nitro, $C_1$–$C_8$alkyl, $C_1$–$C_8$alkoxy, $C_1$–$C_8$alkylthio, $C_2$–$C_8$alkyl ether, hydroxy$C_1$–$C_8$alkyl, halo$C_1$–$C_8$alkyl, phenyl, phenyl($C_1$–$C_8$alkyl), mono- and di-($C_1$–$C_6$alkyl)amino, ($SO_2$)$C_1$–$C_8$alkyl, 5- to 7-membered heterocycle and (5- to 7-membered heterocycle)($C_1$–$C_8$alkyl).

54. A method according to claim 52, wherein the compound or salt is a compound of the formula:

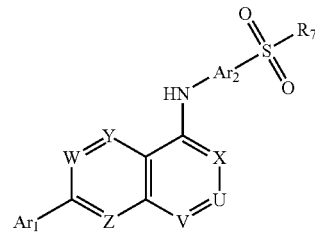

or a pharmaceutically acceptable salt thereof, wherein:

V and X are N;

W, Y and Z are each independently $CR_1$;

U is $CR_2$;

$R_1$ is independently selected at each occurrence from hydrogen, halogen, hydroxy, amino, $C_1$–$C_8$alkyl, halo$C_1$–$C_8$alkyl, $C_1$–$C_8$alkoxy, halo$C_1$–$C_8$alkoxy and mono- and di-($C_1$–$C_8$alkyl)amino;

$R_2$ is: (i) hydrogen, halogen or cyano;

(ii) $C_2$–$C_8$alkanoyl or $C_3$–$C_8$alkanone, each of which is unsubstituted or substituted with from 1 to 9 substituents independently selected from $R_d$; or (iii) a group of the formula —$R_c$-M-A-$R_y$, wherein:

$R_c$ is $C_0$–$C_3$alkyl;

M is a bond, N($R_z$), S, $SO_2$, (C=O)$_p$N($R_z$), N($R_z$)(C=O)$_p$, $SO_2$N($R_z$), or N($R_z$)$SO_2$, wherein p is 0 or 1;

A is a bond or $C_1$–$C_8$alkyl, optionally substituted with from 1 to 3 substituents independently selected from $R_d$; and $R_y$ and $R_z$, if present, are:

(a) independently hydrogen, $C_1$–$C_8$alkyl, $C_3$–$C_8$alkanone, $C_2$–$C_8$alkenyl, a 4- to 10-membered carbocycle, or joined to $R_c$ to form a 4- to 10-membered carbocycle, wherein each $R_y$ and $R_z$ is independently unsubstituted or substituted with from 1 to 9 substituents independently selected from $R_d$; or (b) joined to form a 4- to 10-membered heterocycle that is unsubstituted or substituted with from 1 to 9 substituents independently selected from $R_d$;

wherein $R_d$ is independently selected at each occurrence from hydroxy, halogen, amino, aminocarbonyl, cyano, nitro, $C_1$–$C_8$alkyl, $C_1$–$C_8$alkylthio, hydroxy$C_1$–$C_8$alkyl, halo$C_1$–$C_8$alkyl, phenyl, phenyl($C_1$–$C_8$alkyl), mono- and di-($C_1$–$C_6$alkyl)amino, ($SO_2$)$C_1$–$C_8$alkyl, 5- to 7-membered heterocycle and (5- to 7-membered heterocycle)($C_1$–$C_8$alkyl);

$Ar_1$ and $Ar_2$ are independently chosen from phenyl and 5- and 6-membered aromatic heterocycles, optionally substituted with from 1 to 3 substituents independently selected from groups of the formula L$R_a$;

L is independently selected at each occurrence from a bond, —O—, —C(=O)—, —OC(=O)—, —C(=O)O—, —O—C(=O)O—, —S(O)$_m$—, —N$R_x$—, —C(=O)NH$R_x$—, —NH$R_x$C(=O)—, —N$R_x$S(O)$_m$—, —S(O)$_m$N$R_x$— and —N[S(O)$_m$$R_x$]S(O)$_m$—; wherein m is independently selected at each occurrence from 0, 1 and 2; and $R_x$ is independently selected at each occurrence from hydrogen and $C_1$–$C_8$alkyl;

$R_a$ is independently selected at each occurrence from:
(i) hydrogen, halogen, cyano and nitro; and
(ii) $C_1$–$C_8$alkyl, $C_2$–$C_8$alkenyl, $C_2$–$C_8$alkynyl, $C_2$–$C_8$alkyl ether, 3- to 10-membered heterocycles, mono- and di-($C_1$–$C_8$alkyl)amino and (3- to 10-membered heterocycle)$C_1$–$C_6$alkyl, each of which is unsubstituted or substituted with from 1 to 9 substituents independently selected from $R_b$;

$R_b$ is independently chosen at each occurrence from hydroxy, halogen, amino, aminocarbonyl, cyano, nitro, $C_1$–$C_8$alkyl, $C_1$–$C_8$alkoxy, $C_1$–$C_8$alkylthio, $C_2$–$C_8$alkyl ether, hydroxy$C_1$–$C_8$alkyl, halo$C_1$–$C_8$alkyl, phenyl, phenyl($C_1$–$C_8$alkyl), mono- and di-($C_1$–$C_6$alkyl)amino, $(SO_2)C_1$–$C_8$alkyl, 5- to 7-membered heterocycle and (5- to 7-membered heterocycle)($C_1$–$C_8$alkyl); and $R_7$ is $C_1$–$C_8$alkyl, $C_2$–$C_8$alkenyl, $C_2$–$C_8$alkynyl, mono- or di($C_1$–$C_8$alkyl)amino or a 3- to 10-membered heterocycle, each of which is optionally substituted with from 1 to 5 substituents independently selected from hydroxy, halogen, $C_1$–$C_6$alkyl, $C_1$–$C_8$alkoxy, $C_2$–$C_8$alkyl ether, halo$C_1$–$C_8$alkyl and halo$C_1$–$C_8$alkoxy.

55. A method for treating cough or hiccup in a patient, comprising administering to a patient a capsaicin receptor modulatory amount of a compound or salt of the formula:

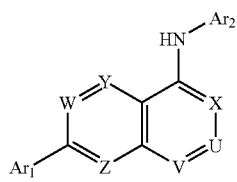

wherein:
V and X are N:
W, Y and Z are each independently $CR_1$;
U is $CR_2$;
$R_1$ is independently selected at each occurrence from hydrogen, halogen, hydroxy, cyano, amino, $C_1$–$C_8$alkyl, halo$C_1$–$C_8$alkyl, $C_1$–$C_8$alkoxy, halo$C_1$–$C_8$alkoxy and mono- and di-($C_1$–$C_8$alkyl)amino;
$R_2$ is: (i) hydrogen, halogen or cyano;
(ii) $C_2$–$C_8$alkanoyl or $C_3$–$C_8$alkanone, each of which is unsubstituted or substituted with from 1 to 9 substituents independently selected from $R_d$; or
(iii) a group of the formula —$R_c$-M-A-$R_y$, wherein:
$R_c$ is $C_0$–$C_3$alkyl;
M is a bond, $N(R_z)$, S, $SO_2$, $(C=O)_pN(R_z)$, $N(R_z)(C=O)_p$, $SO_2N(R_z)$, or $N(R_z)SO_2$, wherein p is 0 or 1;
A is a bond or $C_1$–$C_8$alkyl, optionally substituted with from 1 to 3 substituents independently selected from $R_d$; and
$R_y$ and $R_z$, if present, are:
(a) independently hydrogen, $C_1$–$C_8$alkyl, $C_2$–$C_8$alkenyl, $C_2$–$C_8$alkynyl, $C_6$–$C_{10}$aryl$C_0$–$C_8$alkyl, a 4- to 10-membered carbocycle, or joined to $R_c$ to form a 4- to 10-membered carbocycle, wherein each $R_y$ and $R_z$ is independently unsubstituted or substituted with from 1 to 9 substituents independently selected from $R_d$; or
(b) joined to form a 4- to 10-membered heterocycle that is unsubstituted or substituted with from 1 to 9 substituents independently selected from $R_d$;
wherein $R_d$ is independently selected at each occurrence from hydroxy, halogen, amino, aminocarbonyl, cyano, nitro, $C_1$–$C_8$alkyl, $C_1$–$C_8$alkylthio, hydroxy$C_1$–$C_8$alkyl, halo$C_1$–$C_8$alkyl, phenyl, phenyl($C_1$–$C_8$alkyl), mono- and di-($C_1$–$C_6$alkyl)amino, $(SO_2)C_1$–$C_8$alkyl, 5- to 7-membered heterocycle and (5- to 7-membered heterocycle)($C_1$–$C_8$alkyl);

$Ar_1$ and $Ar_2$ are independently selected from 5- to 10-membered aromatic carbocycles and heterocycles, each of which is unsubstituted or substituted with from 1 to 3 substituents independently selected from groups of the formula $LR_a$;

L is independently selected at each occurrence from a bond, —O—, —C(=O)—, —OC(=O)—, —C(=O)O—, —O—C(=O)O—, —S(O)$_m$—, —$NR_x$—, —C(=O)$NHR_x$—, —$NHR_xC(=O)$—, —$NR_xS(O)_m$—, —$S(O)_mNR_x$— and —$N[S(O)_mR_x]S(O)_m$—; wherein m is independently selected at each occurrence from 0, 1 and 2; and $R_x$ is independently selected at each occurrence from hydrogen and $C_1$–$C_8$alkyl;

$R_a$ is independently selected at each occurrence from:
(i) hydrogen, halogen, cyano and nitro; and
(ii) $C_1$–$C_8$alkyl, $C_2$–$C_8$alkenyl, $C_2$–$C_8$alkynyl, $C_2$–$C_8$alkyl ether, 3- to 10-membered heterocycles, mono- and di-($C_1$–$C_8$alkyl)amino and (3- to 10-membered heterocycle)$C_1$–$C_6$alkyl, each of which is unsubstituted or substituted with from 1 to 9 substituents independently selected from $R_b$; and $R_b$ is independently chosen at each occurrence from hydroxy, halogen, amino, aminocarbonyl, cyano, nitro, $C_1$–$C_8$alkyl, $C_1$–$C_8$alkoxy, $C_1$–$C_8$alkylthio, $C_2$–$C_8$alkyl ether, hydroxy$C_1$–$C_8$alkyl, halo$C_1$–$C_8$alkyl, phenyl, phenyl($C_1$–$C_8$alkyl), mono- and di-($C_1$–$C_6$alkyl)amino, $(SO_2)C_1$–$C_8$alkyl, 5- to 7-membered heterocycle and (5- to 7-membered heterocycle)($C_1$–$C_8$alkyl);

and thereby alleviating cough or hiccup in the patient.

56. A method according to claim 55, wherein the compound or salt is a compound of the formula:

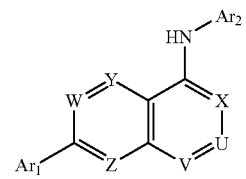

or a pharmaceutically acceptable salt thereof, wherein:
V and X are N;
W, Y and Z are each independently $CR_1$;
U is $CR_2$;
$R_1$ is independently selected at each occurrence from hydrogen, halogen, hydroxy, amino, $C_1$–$C_8$alkyl, halo$C_1$–$C_8$alkyl, $C_1$–$C_8$alkoxy, halo$C_1$–$C_8$alkoxy and mono- and di-($C_1$–$C_8$alkyl)amino;

$R_2$ is: (i) hydrogen, halogen or cyano;
(ii) $C_2$–$C_8$alkanoyl or $C_3$–$C_8$alkanone, each of which is unsubstituted or substituted with from 1 to 9 substituents independently selected from $R_d$; or
(iii) a group of the formula —$R_c$-M-A-$R_y$, wherein:
$R_c$ is $C_0$–$C_3$alkyl;
M is a bond, S, $SO_2$, $(C=O)_p N(R_z)$, $N(R_z)(C=O)_p$, $SO_2 N(R_z)$, or $N(R_z)SO_2$, wherein p is 0 or 1;
A is a bond or $C_1$–$C_8$alkyl, optionally substituted with from 1 to 3 substituents independently selected from $R_d$; and
$R_y$ and $R_z$, if present, are:
(a) independently hydrogen, $C_1$–$C_8$alkyl, $C_3$–$C_8$alkanone, $C_2$–$C_8$alkenyl, a 4- to 10-membered carbocycle, or joined to $R_c$ to form a 4- to 10-membered carbocycle, wherein each $R_y$ and $R_z$ is independently unsubstituted or substituted with from 1 to 9 substituents independently selected from $R_d$; or
(b) joined to form a 4- to 10-membered heterocycle that is unsubstituted or substituted with from 1 to 9 substituents independently selected from $R_d$;
wherein $R_d$ is independently selected at each occurrence from hydroxy, halogen, amino, aminocarbonyl, cyano, nitro, $C_1$–$C_8$alkyl, $C_1$–$C_8$alkylthio, hydroxy$C_1$–$C_8$alkyl, halo$C_1$–$C_8$alkyl, phenyl, phenyl($C_1$–$C_8$alkyl), mono- and di-($C_1$–$C_6$alkyl)amino, $(SO_2)C_1$–$C_8$alkyl, 5- to 7-membered heterocycle and (5- to 7-membered heterocycle)($C_1$–$C_8$alkyl);
$Ar_2$ is a 5- to 7-membered aromatic heterocycle, optionally substituted with from 1 to 3 substituents independently selected from groups of the formula $LR_a$;
$Ar_1$ is a 5- to 10-membered aromatic carbocycle or heterocycle, optionally substituted with from 1 to 3 substituents independently selected from groups of the formula $LR_a$;
L is independently selected at each occurrence from a bond, —O—, —C(=O)—, —OC(=O)—, —C(=O)O—, —O—C(=O)O—, —S(O)$_m$—, —NR$_x$—, —C(=O)NHR$_x$—, —NHR$_x$C(=O)—, —NR$_x$S(O)$_m$—, —S(O)$_m$NR$_x$— and —N[S(O)$_m$R$_x$]S(O)$_m$—; wherein m is independently selected at each occurrence from 0, 1 and 2; and $R_x$ is independently selected at each occurrence from hydrogen and $C_1$–$C_8$alkyl;
$R_a$ is independently selected at each occurrence from:
(i) hydrogen, halogen, cyano and nitro; and
(ii) $C_1$–$C_8$alkyl, $C_2$–$C_8$alkenyl, $C_2$–$C_8$alkynyl, $C_2$–$C_8$alkyl ether, 3- to 10-membered heterocycles, mono- and di-($C_1$–$C_8$alkyl)amino and (3- to 10-membered heterocycle)$C_1$–$C_6$alkyl, each of which is unsubstituted or substituted with from 1 to 9 substituents independently selected from $R_b$; and
$R_b$ is independently chosen at each occurrence from hydroxy, halogen, amino, aminocarbonyl, cyano, nitro, $C_1$–$C_8$alkyl, $C_1$–$C_8$alkoxy, $C_1$–$C_8$alkylthio, $C_2$–$C_8$alkyl ether, hydroxy$C_1$–$C_8$alkyl, halo$C_1$–$C_8$alkyl, phenyl, phenyl($C_1$–$C_8$alkyl), mono- and di-($C_1$–$C_6$alkyl)amino, $(SO_2)C_1$–$C_8$alkyl, 5- to 7-membered heterocycle and (5- to 7-membered heterocycle)($C_1$–$C_8$alkyl).

57. A method according to claim 55, wherein the compound or salt is a compound of the formula:

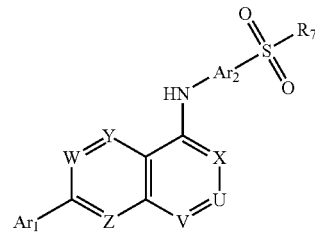

or a pharmaceutically acceptable salt thereof, wherein:
V and X are N;
W, Y and Z are each independently $CR_1$;
U is $CR_2$;
$R_1$ is independently selected at each occurrence from hydrogen, halogen, hydroxy, amino, $C_1$–$C_8$alkyl, halo$C_1$–$C_8$alkyl, $C_1$–$C_8$alkoxy, halo$C_1$–$C_8$alkoxy and mono- and di-($C_1$–$C_8$alkyl)amino;
$R_2$ is: (i) hydrogen, halogen or cyano;
(ii) $C_2$–$C_8$alkanoyl or $C_3$–$C_8$alkanone, each of which is unsubstituted or substituted with from 1 to 9 substituents independently selected from $R_d$; or
(iii) a group of the formula —$R_c$-M-A-$R_y$, wherein:
$R_c$ is $C_0$–$C_3$alkyl;
M is a bond, S, $SO_2$, $(C=O)_p N(R_z)$, $N(R_z)(C=O)_p$, $SO_2 N(R_z)$, or $N(R_z)SO_2$, wherein p is 0 or 1;
A is a bond or $C_1$–$C_8$alkyl, optionally substituted with from 1 to 3 substituents independently selected from $R_d$; and
$R_y$ and $R_z$, if present, are:
(a) independently hydrogen, $C_1$–$C_8$alkyl, $C_3$–$C_8$alkanone, $C_2$–$C_8$alkenyl, a 4- to 10-membered carbocycle, or joined to $R_c$ to form a 4- to 10-membered carbocycle, wherein each $R_y$ and $R_z$ is independently unsubstituted or substituted with from 1 to 9 substituents independently selected from $R_d$; or
(b) joined to form a 4- to 10-membered heterocycle that is unsubstituted or substituted with from 1 to 9 substituents independently selected from $R_d$;
wherein $R_d$ is independently selected at each occurrence from hydroxy, halogen, amino, aminocarbonyl, cyano, nitro, $C_1$–$C_8$alkyl, $C_1$–$C_8$alkylthio, hydroxy$C_1$–$C_8$alkyl, halo$C_1$–$C_8$alkyl, phenyl, phenyl($C_1$–$C_8$alkyl), mono- and di-($C_1$–$C_6$alkyl)amino, $(SO_2)C_1$–$C_8$alkyl, 5- to 7-membered heterocycle and (5- to 7-membered heterocycle)($C_1$–$C_8$alkyl);
$Ar_1$ and $Ar_2$ are independently chosen from phenyl and 5- and 6-membered aromatic heterocycles, optionally substituted with from 1 to 3 substituents independently selected from groups of the formula $LR_a$;
L is independently selected at each occurrence from a bond, —O—, —C(=O)—, —OC(=O)—, —C(=O)O—, —O—C(=O)O—, —S(O)$_m$—, —NR$_x$—, —C(=O)NHR$_x$—, —NHR$_x$C(=O)—, —NR$_x$S(O)$_m$—, —S(O)$_m$NR$_x$— and —N[S(O)$_m$R$_x$]S(O)$_m$—; wherein m is independently selected at each occurrence from 0, 1 and 2; and $R_x$ is independently selected at each occurrence from hydrogen and $C_1$–$C_8$alkyl;

$R_a$ is independently selected at each occurrence from:
(i) hydrogen, halogen, cyano and nitro; and
(ii) $C_1$–$C_8$alkyl, $C_2$–$C_8$alkenyl, $C_2$–$C_8$alkynyl, $C_2$–$C_8$alkyl ether, 3- to 10-membered heterocycles, mono- and di-($C_1$–$C_8$alkyl)amino and (3- to 10-membered heterocycle)$C_1$–$C_6$alkyl, each of which is unsubstituted or substituted with from 1 to 9 substituents independently selected from $R_b$;

$R_b$ is independently chosen at each occurrence from hydroxy, halogen, amino, aminocarbonyl, cyano, nitro, $C_1$–$C_8$alkyl, $C_1$–$C_8$alkoxy, $C_1$–$C_8$alkylthio, $C_2$–$C_8$alkyl ether, hydroxy$C_1$–$C_8$alkyl, halo$C_1$–$C_8$alkyl, phenyl, phenyl($C_1$–$C_8$alkyl), mono- and di-($C_1$–$C_6$alkyl)amino, ($SO_2$)$C_1$–$C_8$alkyl, 5- to 7-membered heterocycle and (5- to 7-membered heterocycle)($C_1$–$C_8$alkyl); and $R_7$ is $C_1$–$C_8$alkyl, $C_2$–$C_8$alkenyl, $C_2$–$C_8$alkynyl, mono- or di($C_1$–$C_8$alkyl)amino or a 3- to 10-membered heterocycle, each of which is optionally substituted with from 1 to 5 substituents independently selected from hydroxy, halogen, $C_1$–$C_6$alky, $C_1$–$C_8$alkoxy, $C_2$–$C_8$alkyl ether, halo$C_1$–$C_8$alkyl and halo$C_1$–$C_8$alkoxy.

58. A compound or salt according to claim 1, wherein the heterocyclic group is substituted with from 1 to 4 substituents independently selected from methyl and ethyl.

* * * * *